US010329270B2

(12) United States Patent
Qiu et al.

(10) Patent No.: US 10,329,270 B2
(45) Date of Patent: *Jun. 25, 2019

(54) HETEROARYL COMPOUNDS AS BTK INHIBITORS AND USES THEREOF

(71) Applicant: Merck Patent GmbH, Darmstadt (DE)

(72) Inventors: Hui Qiu, Acton, MA (US); Richard D. Caldwell, Melrose, MA (US); Constantin Neagu, Belmont, MA (US); Igor Mochalkin, San Diego, CA (US); Lesley Liu-Bujalski, Bedford, MA (US); Reinaldo Jones, Lowell, MA (US); Devon Tate, Bedford, MA (US); Theresa L. Johnson, Salem, MA (US); Anna Gardberg, Arlington, MA (US)

(73) Assignee: Merck Patent GmbH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/029,420

(22) PCT Filed: Oct. 21, 2014

(86) PCT No.: PCT/US2014/061455
§ 371 (c)(1),
(2) Date: Apr. 14, 2016

(87) PCT Pub. No.: WO2015/061247
PCT Pub. Date: Apr. 30, 2015

(65) Prior Publication Data
US 2016/0264548 A1 Sep. 15, 2016

Related U.S. Application Data

(60) Provisional application No. 61/893,613, filed on Oct. 21, 2013.

(51) Int. Cl.
*C07D 401/14* (2006.01)
*C07F 5/02* (2006.01)
*C07D 213/82* (2006.01)
*C07D 401/04* (2006.01)
*C07D 409/04* (2006.01)
*C07D 405/04* (2006.01)
*C07D 413/14* (2006.01)
*C07D 401/12* (2006.01)
*C07D 403/12* (2006.01)
*C07D 403/04* (2006.01)
*C07D 405/14* (2006.01)
*C07D 495/04* (2006.01)
*C07D 239/47* (2006.01)
*C07D 487/08* (2006.01)
*C07D 487/10* (2006.01)
(Continued)

(52) U.S. Cl.
CPC ......... *C07D 401/04* (2013.01); *A61K 9/0019* (2013.01); *A61K 9/0043* (2013.01); *A61K 9/0048* (2013.01); *A61K 9/0078* (2013.01); *A61K 9/02* (2013.01); *A61K 9/06* (2013.01); *A61K 9/08* (2013.01); *A61K 9/1688* (2013.01); *A61K 9/19* (2013.01); *A61K 9/2018* (2013.01); *A61K 9/2059* (2013.01); *A61K 9/286* (2013.01); *A61K 9/2826* (2013.01); *A61K 47/06* (2013.01); *A61K 47/186* (2013.01); *C07D 213/81* (2013.01); *C07D 213/82* (2013.01); *C07D 239/47* (2013.01); *C07D 239/48* (2013.01); *C07D 401/12* (2013.01); *C07D 401/14* (2013.01); *C07D 403/04* (2013.01); *C07D 403/12* (2013.01); *C07D 405/04* (2013.01); *C07D 405/14* (2013.01); *C07D 407/04* (2013.01); *C07D 409/04* (2013.01); *C07D 413/04* (2013.01); *C07D 413/06* (2013.01); *C07D 413/14* (2013.01); *C07D 451/02* (2013.01); *C07D 471/08* (2013.01); *C07D 487/04* (2013.01); *C07D 487/08* (2013.01); *C07D 487/10* (2013.01); *C07D 495/04* (2013.01); *C07F 5/022* (2013.01)

(58) Field of Classification Search
CPC .. C07D 401/04; C07D 487/08; C07D 471/08; C07D 213/82; C07D 451/02; C07D 405/04; C07D 401/14; C07D 495/04; C07D 239/47; C07D 405/14; C07D 413/14; C07D 487/10; C07F 5/022; A61K 9/19
See application file for complete search history.

(56) References Cited

U.S. PATENT DOCUMENTS 4,650,750 A    3/1987   Giese
4,709,016 A   11/1987   Giese
(Continued)

FOREIGN PATENT DOCUMENTS

EP     1184376 A1    3/2002
EP     1518855 A1    3/2005
(Continued)

OTHER PUBLICATIONS

Baskin et al., Proc. Natl. Acad. Sci. USA, 2007, 104:16793-16797.
(Continued)

*Primary Examiner* — Sarah Pihonak
*Assistant Examiner* — Jason Deck
(74) *Attorney, Agent, or Firm* — Grüneberg and Myers PLLC

(57) ABSTRACT

The present invention relates to pyridine, pyrimidine, pyrazine, and pyridazine compounds, and pharmaceutically acceptable compositions thereof, useful as BTK inhibitors.

3 Claims, No Drawings

(51) Int. Cl.

| | |
|---|---|
| C07D 487/04 | (2006.01) |
| C07D 239/48 | (2006.01) |
| C07D 471/08 | (2006.01) |
| C07D 451/02 | (2006.01) |
| C07D 213/81 | (2006.01) |
| C07D 407/04 | (2006.01) |
| C07D 413/04 | (2006.01) |
| C07D 413/06 | (2006.01) |
| A61K 9/00 | (2006.01) |
| A61K 47/06 | (2006.01) |
| A61K 47/18 | (2017.01) |
| A61K 9/02 | (2006.01) |
| A61K 9/06 | (2006.01) |
| A61K 9/08 | (2006.01) |
| A61K 9/16 | (2006.01) |
| A61K 9/19 | (2006.01) |
| A61K 9/20 | (2006.01) |
| A61K 9/28 | (2006.01) |

(56) References Cited

U.S. PATENT DOCUMENTS

| | | | |
|---|---|---|---|
| 5,360,819 | A | 11/1994 | Giese |
| 5,516,931 | A | 5/1996 | Giese |
| 5,602,273 | A | 2/1997 | Giese |
| 5,604,104 | A | 2/1997 | Giese |
| 5,610,020 | A | 3/1997 | Giese |
| 5,650,270 | A | 7/1997 | Giese |
| 7,994,204 | B2 | 8/2011 | Ono et al. |
| 2007/0049578 | A1 * | 3/2007 | Edwards ............ C07D 213/74 514/218 |
| 2010/0216793 | A1 | 8/2010 | Alberati |
| 2010/0249092 | A1 | 9/2010 | Singh et al. |

FOREIGN PATENT DOCUMENTS

| | | |
|---|---|---|
| EP | 2133331 A1 | 12/2009 |
| EP | 2428508 A1 | 3/2012 |
| WO | 2008009458 A1 | 1/2008 |
| WO | 2009051822 A1 | 4/2009 |
| WO | 2009131687 A2 | 10/2009 |
| WO | 2009145856 A1 | 12/2009 |
| WO | 2009158571 A1 | 12/2009 |
| WO | 2010007756 A1 | 1/2010 |
| WO | 2010144647 A1 | 12/2010 |
| WO | 2012041872 A1 | 4/2012 |
| WO | 2012135801 A1 | 10/2012 |
| WO | 2012170976 A2 | 12/2012 |
| WO | 2012171337 A1 | 12/2012 |
| WO | 2013014448 A1 | 1/2013 |
| WO | 2013030665 A1 | 3/2013 |
| WO | 2013060098 A1 | 5/2013 |
| WO | 2013108754 A1 | 7/2013 |
| WO | 2013144180 A1 | 10/2013 |
| WO | WO-2013144180 A1 * | 10/2013 ........... C07D 213/74 |
| WO | 2013169401 A1 | 11/2013 |
| WO | 2014124230 A2 | 8/2014 |
| WO | 2015039613 A1 | 3/2015 |
| WO | 2015048662 A2 | 4/2015 |
| WO | WO 2015048662 A2 * | 4/2015 ........... C07D 401/14 |

OTHER PUBLICATIONS

Berge et al., J. Pharmaceutical Sciences, 1977, 66(1):1-19.
Delvare et al. ACS Combinatorial Science, 2011, 13(5): 449-452.
Ellmeier et al., J. Exp. Med. 2000, 192(11):1611-1623.
Feldhahn et al., J. Exp. Med., 2005, 201(11):1837-1852.
Foster, Adv. Drug Res., 1985, 14:1-40.
Gillette et al., Biochemistry, 1994, 33(10):2927-2937.
Hanzlik et al., J. Org. Chem., 1990, 55(13):3992-3997.
Horwood et al., J Exp Med, 2003, 197(12)1603-1611.
Hunter T., Cell, 1987, 50(5):823-829.
Islam and Smith, Immunol. Rev., 2000, 178:49-63.
Iwaki et al., J. Biol. Chem., 2005, 280(48):40261-40270.
Jansson and Holmdahl, Clin. Exp. Immunol.,1993, 94:459-465.
Jarman et al., Carcinogenesis, 1995, 16(4):683-688.
Kawakami et al., Journal of Leukocyte Biology, 1999, 65:286-290.
Khan et al., Immunity, 1995, 3:283-299.
Lindvall et al., Immunol. Rev., 2005, 203:200-215.
Mao et al. Bioorganic & Medicinal Chemistry, 2013, 21(11): 3090-3104.
Pan et al., Chem. Med Chem., 2007, 2:58-61.
Phillips et al. Journal of Medicinal Chemistry, American Chemical Society. 1999, 42(10): 1749-1756.
Rastetter et al., Annu Rev Med, 2004, 55:477-503.
Reider et al., J. Org. Chem., 1987, 52:3326-3334.
Rosen et al., New Eng. J. Med., 1995, 333(7):431-440.
Rostovtsev et al., Angew. Chem. Int. Ed. 2002, 41:2596-99.
Smith M.B. and March J., "March's Advanced Organic Chemistry", 5th Ed., Ed., John Wiley & Sons, New York, 2001.
Sorrell Thomas Organic Chemistry University Science Books, Sausalito, 1999.
Sun et al., Bioconjugate Chem., 2006, 17(1):52-57.
Vassilev et al., J. Biol. Chem., 1999, 274(3):1646-1656.
Vihinen et al., Frontiers in Bioscience, 2000, 5:d917-928.
CAS Registry No. 1356569-14-6—Registry (STN) [online], Entered STN: Feb. 14, 2012, Searching date: Apr. 19, 2018.

* cited by examiner

HETEROARYL COMPOUNDS AS BTK INHIBITORS AND USES THEREOF

RELATED APPLICATION

This application claims the benefit of U.S. Provisional application 61/893,613, filed on Oct. 21, 2013, the contents of which are incorporated in its entirety by reference.

TECHNICAL FIELD OF THE INVENTION

The present invention relates to pyridine, pyrimidine, pyrazine, and pyridazine compounds that are useful as inhibitors of Bruton's Tyrosine Kinase (BTK). The invention also provides pharmaceutically acceptable compositions comprising compounds of the present invention and methods of using said compositions in the treatment of various disorders.

BACKGROUND OF THE INVENTION

Protein kinases constitute one of the largest families of human enzymes and regulate many different signaling processes by adding phosphate groups to proteins (T. Hunter, Cell 1987 50:823-829). Specifically, tyrosine kinases phosphorylate proteins on the phenolic moiety of tyrosine residues. The tyrosine kinase family includes members that control cell growth, migration, and differentiation. Abnormal kinase activity has been implicated in a variety of human diseases including cancers, autoimmune and inflammatory diseases. Since protein kinases are among the key regulators of cell signaling, they provide a target to modulate cellular function with small molecular kinase inhibitors and thus make good drug targets. In addition to treatment of kinase-mediated disease processes, selective and efficacious inhibitors of kinase activity are also useful for investigation of cell signaling processes and identification of other cellular targets of therapeutic interest.

There is good evidence that B-cells play a key role in the pathogenesis of autoimmune and/or inflammatory disease. Protein-based therapeutics that deplete B cells such as Rituxan are effective against autoantibody-driven inflammatory diseases such as rheumatoid arthritis (Rastetter et al. Annu Rev Med 2004 55:477). Therefore inhibitors of the protein kinases that play a role in B-cell activation should be useful therapeutics for B-cell mediated disease pathology, such as autoantibody production.

Signaling through the B-cell receptor (BCR) controls a range of B-cell responses including proliferation and differentiation into mature antibody producing cells. The BCR is a key regulatory point for B-cell activity and aberrant signaling can cause deregulated B-cell proliferation and formation of pathogenic autoantibodies that lead to multiple autoimmune and/or inflammatory diseases. Bruton's Tyrosine Kinase (BTK) is a non-BCR associated kinase that is membrane proximal and immediately downstream from BCR. Lack of BTK has been shown to block BCR signaling and therefore inhibition of BTK could be a useful therapeutic approach to block B-cell mediated disease processes. Also, BTK has been reported to play a role in apoptosis (Islam and Smith Immunol. Rev. 2000 178:49,) and thus BTK inhibitors would be useful for the treatment of certain B-cell lymphomas and leukemias (Feldhahn et al. J. Exp. Med. 2005 201:1837).

BTK is a member of the Tec family of tyrosine kinases, and has been shown to be a critical regulator of early B-cell development and mature B-cell activation and survival (Khan et al. Immunity 1995 3:283; Ellmeier et al. J. Exp. Med. 2000 192:1611). Mutation of BTK in humans leads to the condition X-linked agammaglobulinemia (XLA) (reviewed in Rosen et al. New Eng. J. Med. 1995 333:431 and Lindvall et al. Immunol. Rev. 2005 203:200). These patients are immunocompromised and show impaired maturation of B-cells, decreased immunoglobulin and peripheral B-cell levels, diminished T-cell independent immune responses as well as attenuated calcium mobilization following BCR stimulation.

Evidence for a role for BTK in autoimmune and inflammatory diseases has also been provided by BTK-deficient mouse models. In preclinical murine models of systemic lupus erythematosus (SLE), BTK-deficient mice show marked amelioration of disease progression. In addition, BTK-deficient mice are resistant to collagen-induced arthritis (Jansson and Holmdahl Clin. Exp. Immunol. 1993 94:459). A selective BTK inhibitor has demonstrated dose-dependent efficacy in a mouse arthritis model (Z. Pan et al., Chem. Med Chem. 2007 2:58-61).

BTK is also expressed by cells other than B-cells that may be involved in disease processes. BTK is key component of Fc-gamma signaling in myeloid cells. For example, BTK is expressed by mast cells and BTK-deficient bone marrow derived mast cells demonstrate impaired antigen induced degranulation (Iwaki et al. J. Biol. Chem. 2005 280:40261). This shows BTK could be useful to treat pathological mast cells responses such as allergy and asthma. Also monocytes from XLA patients, in which BTK activity is absent, show decreased TNF alpha production following stimulation (Horwood et al. J Exp Med 197:1603, 2003). Therefore TNF alpha mediated inflammation could be modulated by small molecular BTK inhibitors.

SUMMARY OF THE INVENTION

It has now been found that compounds of this invention, and pharmaceutically acceptable compositions thereof, are effective as inhibitors of BTK. Such compounds have general formula I:

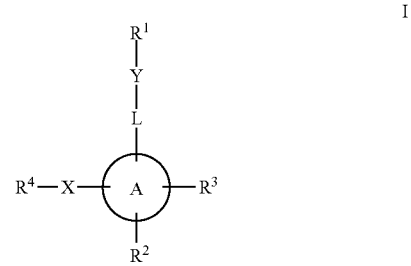

or a pharmaceutically acceptable salt thereof, wherein each of $R^1$, $R^2$, $R^3$, $R^4$, X, Y, and L, is as defined and described in embodiments herein.

Compounds of the present invention, and pharmaceutically acceptable compositions thereof, are useful for treating a variety of diseases, disorders or conditions, associated with BTK. Such diseases, disorders, or conditions include those described herein.

DETAILED DESCRIPTION OF CERTAIN EMBODIMENTS

1. General Description of Compounds of the Invention

In certain aspects, the present invention provides for inhibitors of BTK. In some embodiments, such compounds include those of the formulae described herein, or a pharmaceutically acceptable salt thereof, wherein each variable is as defined and described herein.

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Exemplary aliphatic groups are linear or branched, substituted or unsubstituted $C_1$-$C_8$ alkyl, $C_2$-$C_8$ alkenyl, $C_2$-$C_8$ alkynyl groups and hybrids thereof such as (cycloalkyl)alkyl, (cycloalkenyl)alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, or phosphorus (including, any oxidized form of nitrogen, sulfur, or phosphorus; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl", "aralkoxy", or "aryloxyalkyl", refers to monocyclic and bicyclic ring systems having a total of five to fourteen ring members, wherein at least one ring in the system is aromatic and wherein each ring in the system contains three to seven ring members. The term "aryl" is used interchangeably with the term "aryl ring". In certain embodiments of the present invention, "aryl" refers to an aromatic ring system. Exemplary aryl groups are phenyl, biphenyl, naphthyl, anthracyl and the like, which optionally includes one or more substituents. Also included within the scope of the term "aryl", as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group is optionally mono- or bicyclic. The term "heteroaryl" is used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen is N (as in 3,4-dihydro-2H-pyrrolyl), NH (as in pyrrolidinyl), or $^{+}$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group is optionally mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, certain compounds of the invention contain "optionally substituted" moieties. In general, the term "substituted", whether preceded by the term "optionally" or not, means that one or more hydrogens of the designated moiety are replaced with a suitable substituent. "Substituted" applies to one or more hydrogens that are either explicit or implicit from the structure (e.g.,

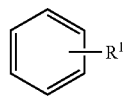

refers to at least

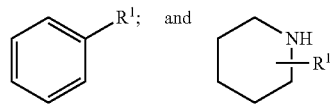

refers to at least

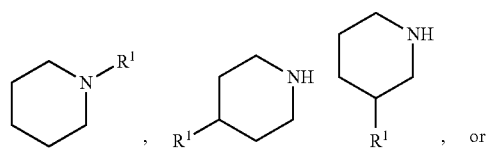

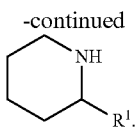

Unless otherwise indicated, an "optionally substituted" group has a suitable substituent at each substitutable position of the group, and when more than one position in any given structure is substituted with more than one substituent selected from a specified group, the substituent is either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently deuterium; halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which are optionally substituted with R°; —(CH$_2$)$_{0-4}$O(CH$_2$)$_{0-1}$Ph which is optionally substituted with R°; —CH=CHPh, which is optionally substituted with R°; —(CH$_2$)$_{0-4}$O(CH$_2$)$_{0-1}$-pyridyl which is optionally substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°N(R°)C(O)NR°$_2$; —N(R°N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR°, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched)alkylene)C(O)O—N(R°)$_2$, wherein each R° is optionally substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which is optionally substituted as defined below.

Suitable monovalent substituents on R° (or the ring formed by taking two independent occurrences of R° together with their intervening atoms), are independently deuterium, halogen, —(CH$_2$)$_{0-2}$R$^{\bullet}$, -(halo$^{\bullet}$*), —(CH$_2$)$_{0-2}$OH$^{\bullet}$, —(CH$_2$)$_{0-2}$OR$^{\bullet}$, —(CH$_2$)$_{0-2}$CH(OR$^{\bullet}$)$_2$; —O(haloR$^{\bullet}$), —CN, —N$_3$, —(CH$_2$)$_{0-2}$C(O)R$^{\bullet}$, —(CH$_2$)$_{0-2}$C(O)OH, —(CH$_2$)$_{0-2}$C(O)OR$^{\bullet}$, —(CH$_2$)$_{0-2}$SR$^{\bullet}$, (CH$_2$)$_{0-2}$SH, —(CH$_2$)$_{0-2}$NH$_2$, —(CH$_2$)$_{0-2}$NHR$^{\bullet}$, —(CH$_2$)$_{0-2}$NR$^{\bullet}$$_2$, —NO$_2$, —SiR$^{\bullet}$$_3$, —OSiR$^{\bullet}$$_3$, —C(O)SR$^{\bullet}$, —(C$_{1-4}$ straight or branched alkylene)C(O)OR$^{\bullet}$, or —SSR$^{\bullet}$ wherein each R$^{\bullet}$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R°$ include =O and =S.

Suitable divalent substituents on a saturated carbon atom of an "optionally substituted" group include the following: =O, =S, =$NNR^*_2$, =$NNHC(O)R^*$, =$NNHC(O)OR^*$, =$NNHS(O)_2R^*$, =$NR^*$, =$NOR^*$, —$O(C(R^*_2))_{2-3}O$—, or —$S(C(R^*_2))_{2-3}S$—, wherein each independent occurrence of $R^*$ is selected from hydrogen, $C_{1-6}$ aliphatic which is substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —$O(CR^*_2)_{2-3}O$—, wherein each independent occurrence of $R^*$ is selected from hydrogen, $C_{1-6}$ aliphatic which is optionally substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, —$R^•$, -(halo$R^•$), —OH, —$OR^•$, —O(halo$R^•$), —CN, —C(O)OH, —C(O)$OR^•$, —$NH_2$, —$NHR^•$, —$NR^•_2$, or —$NO_2$, wherein each $R^•$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —$R^†$, —$NR^†_2$, —$C(O)R^†$, —$C(O)OR^†$, —$C(O)C(O)R^†$, —$C(O)CH_2C(O)R^†$, —$S(O)_2R^†$, —$S(O)_2NR^†_2$, —$C(S)NR^†_2$, —$C(NH)NR^†_2$, or —$N(R^†)S(O)_2R^†$; wherein each $R^†$ is independently hydrogen, $C_{1-6}$ aliphatic which is optionally substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^†$ are independently halogen, —$R^•$, -(halo$R^•$), —OH, —$OR^•$, —O(halo$R^•$), —CN, —C(O)OH, —C(O)$OR^•$, —$NH_2$, —$NHR^•$, —$NR^•_2$, or —$NO_2$, wherein each $R^•$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

In certain embodiments, the terms "optionally substituted", "optionally substituted alkyl," "optionally substituted "optionally substituted alkenyl," "optionally substituted alkynyl", "optionally substituted carbocyclic," "optionally substituted aryl", "optionally substituted heteroaryl," "optionally substituted heterocyclic," and any other optionally substituted group as used herein, refer to groups that are substituted or unsubstituted by independent replacement of one, two, or three or more of the hydrogen atoms thereon with typical substituents including, but not limited to:

—F, —Cl, —Br, —I, deuterium,

—OH, protected hydroxy, alkoxy, oxo, thiooxo,

—$NO_2$, —CN, $CF_3$, $N_3$,

—$NH_2$, protected amino, —NH alkyl, —NH alkenyl, —NH alkynyl, —NH cycloalkyl, —NH-aryl, —NH-heteroaryl, —NH-heterocyclic, -dialkylamino, -diarylamino, -diheteroarylamino, —O— alkyl, —O— alkenyl, —O— alkynyl, —O—cycloalkyl, —O-aryl, —O-heteroaryl, —O-heterocyclic, —C(O)— alkyl, —C(O)— alkenyl, —C(O)— alkynyl, —C(O)— carbocyclyl, —C(O)-aryl, —C(O)— heteroaryl, —C(O)-heterocyclyl, —$CONH_2$, —CONH— alkyl, —CONH— alkenyl, —CONH— alkynyl, —CONH-carbocyclyl, —CONH-aryl, —CONH-heteroaryl, —CONH-heterocyclyl, —$OCO_2$— alkyl, —$OCO_2$— alkenyl, —$OCO_2$— alkynyl, —$OCO_2$— carbocyclyl, —$OCO_2$-aryl, —$OCO_2$-heteroaryl, —$OCO_2$-heterocyclyl, —$OCONH_2$, —OCONH— alkyl, —OCONH— alkenyl, —OCONH— alkynyl, —OCONH— carbocyclyl, —OCONH— aryl, —OCONH— heteroaryl, —OCONH— heterocyclyl, —NHC(O)— alkyl, —NHC(O)— alkenyl, —NHC(O)— alkynyl, —NHC(O)— carbocyclyl, —NHC(O)-aryl, —NHC(O)-heteroaryl, —NHC(O)-heterocyclyl, —$NHCO_2$— alkyl, —$NHCO_2$— alkenyl, —$NHCO_2$— alkynyl, —$NHCO_2$-carbocyclyl, —$NHCO_2$— aryl, —$NHCO_2$— heteroaryl, —$NHCO_2$-heterocyclyl, —NHC(O)$NH_2$, —NHC(O)NH— alkyl, —NHC(O)NH— alkenyl, —NHC(O)NH— alkenyl, —NHC(O)NH— carbocyclyl, —NHC(O)NH-aryl, —NHC(O)NH-heteroaryl, —NHC(O)NH— heterocyclyl, NHC(S)$NH_2$, —NHC(S)NH— alkyl, —NHC(S)NH— alkenyl, —NHC(S)NH— alkynyl, —NHC(S)NH— carbocyclyl, —NHC(S)NH— aryl, —NHC(S)NH-heteroaryl, —NHC(S)NH-heterocyclyl, —NHC(NH)$NH_2$, —NHC(NH)NH— alkyl, —NHC(NH)NH-alkenyl, —NHC(NH)NH— alkenyl, —NHC(NH)NH— carbocyclyl, —NHC(NH)NH-aryl, —NHC(NH)NH-heteroaryl, —NHC(NH)NH— heterocyclyl, —NHC(NH)— alkyl, —NHC(NH)— alkenyl, —NHC(NH)— alkenyl, —NHC(NH)-carbocyclyl, —NHC(NH)-aryl, —NHC(NH)-heteroaryl, —NHC(NH)-heterocyclyl, —C(NH)NH— alkyl, —C(NH)NH— alkenyl, —C(NH)NH— alkynyl, —C(NH)NH— carbocyclyl, —C(NH)NH-aryl, —C(NH)NH-heteroaryl, —C(NH)NH-heterocyclyl, —S(O)— alkyl, —S(O)— alkenyl, —S(O)— alkynyl, —S(O)— carbocyclyl, —S(O)-aryl, —S(O)-heteroaryl, —S(O)-heterocyclyl —$SO_2NH_2$, —$SO_2NH$— alkyl, —$SO_2NH$— alkenyl, —$SO_2NH$— alkynyl, —$SO_2NH$— carbocyclyl, —$SO_2NH$— aryl, —$SO_2NH$— heteroaryl, —$SO_2NH$— heterocyclyl, —$NHSO_2$— alkyl, —$NHSO_2$— alkenyl, —$NHSO_2$— alkynyl, —$NHSO_2$— carbocyclyl, —$NHSO_2$-aryl, —$NHSO_2$-heteroaryl, —$NHSO_2$-heterocyclyl,

—$CH_2NH_2$, —$CH_2SO_2CH_3$,

-mono-, di-, or tri-alkyl silyl,

-alkyl, -alkenyl, -alkynyl, -aryl, -arylalkyl, -heteroaryl, -heteroarylalkyl, -heterocycloalkyl, -cycloalkyl, -carbocyclic, -heterocyclic, polyalkoxyalkyl, polyalkoxy, -methoxymethoxy, -methoxyethoxy, —SH, —S— alkyl, —S— alkenyl, —S— alkynyl, —S— carbocyclyl, —S-aryl, —S-heteroaryl, —S-heterocyclyl, or methylthiomethyl.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}\text{ alkyl})_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. In some embodiments, the group comprises one or more deuterium atoms.

There is furthermore intended that a compound of the formula I includes isotope-labeled forms thereof. An isotope-labeled form of a compound of the formula I is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of the formula I by well-known methods include isotopes of hydrogen, carbon, nitrogen, oxygen, phos-phorus, fluo-rine and chlorine, for example $^{2}H$, $^{3}H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. A compound of the formula I, a prodrug, thereof or a pharmaceutically acceptable salt of either which contains one or more of the above-mentioned isotopes and/or other isotopes of other atoms is intended to be part of the present invention. An isotope-labeled compound of the formula I can be used in a number of beneficial ways. For example, an isotope-labeled compound of the formula I into which, for example, a radioisotope, such as $^{3}H$ or $^{14}C$, has been incorporated, is suitable for medicament and/or substrate tissue distribution assays. These radioisotopes, i.e. tritium ($^{3}H$) and carbon-14 ($^{14}C$), are particularly preferred owing to simple preparation and excellent detectability. Incorporation of heavier isotopes, for example deuterium ($^{2}H$), into a compound of the formula I has therapeutic advantages owing to the higher metabolic stability of this isotope-labeled compound. Higher metabolic stability translates directly into an increased in vivo half-life or lower dosages, which under most circumstances would represent a preferred embodiment of the present invention. An isotope-labeled compound of the formula I can usually be prepared by carrying out the procedures disclosed in the synthesis schemes and the related description, in the example part and in the preparation part in the present text, replacing a non-isotope-labeled reactant by a readily available isotope-labeled reactant.

Deuterium ($^{2}H$) can also be incorporated into a compound of the formula I for the purpose in order to manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D=2-7$ are typical. If this rate difference is successfully applied to a com-pound of the formula I that is susceptible to oxidation, the profile of this compound in vivo can be drastically modified and result in improved pharmacokinetic properties.

When discovering and developing therapeutic agents, the person skilled in the art is able to optimize pharmacokinetic parameters while retaining desirable in vitro properties. It is reasonable to assume that many compounds with poor pharmacokinetic profiles are susceptible to oxidative metabolism. In vitro liver microsomal assays currently available provide valuable information on the course of oxidative metabolism of this type, which in turn permits the rational design of deuterated compounds of the formula I with improved stability through resistance to such oxidative metabolism. Significant improvements in the pharmacokinetic profiles of compounds of the formula I are thereby obtained, and can be expressed quantitatively in terms of increases in the in vivo half-life (t/2), concentration at maximum therapeutic effect ($C_{max}$), area under the dose response curve (AUC), and F; and in terms of reduced clearance, dose and materials costs.

The following is intended to illustrate the above: a compound of the formula I which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favorable and accurate determination of the extent of the extent to which the improvement in resistance to oxidative metabolism has improved. In this way, it is determined that the half-life of the parent compound can be extended by up to 100% as the result of deuterium-hydrogen exchange of this type.

Deuterium-hydrogen exchange in a compound of the formula I can also be used to achieve a favorable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1993.

As used herein, the term "modulator" is defined as a compound that binds to and/or inhibits the target with measurable affinity. In certain embodiments, a modulator has an $IC_{50}$ and/or binding constant of less about 50 µM, less than about 1 µM, less than about 500 nM, less than about 100 nM, or less than about 10 nM.

The terms "measurable affinity" and "measurably inhibit," as used herein, means a measurable change in BTK activity between a sample comprising a compound of the present invention, or composition thereof, and BTK, and an equivalent sample comprising BTK, in the absence of said compound, or composition thereof.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

3. Description of Exemplary Compounds

According to one aspect, the present invention provides a compound of formula I,

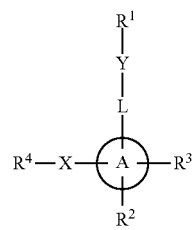

or a pharmaceutically acceptable salt thereof, wherein:
Ring A is a 6-membered heteroaryl ring having 1 or 2 nitrogens, selected from pyridine, pyrazine, pyridazine, and pyrimidine;
$R^2$ is selected from —R, halogen, -haloalkyl, —OR, —SR, —CN, —$NO_2$, —$SO_2R$, —SOR, —C(O)R, —$CO_2R$, —C(O)N(R)$_2$, —NRC(O)R, —NRC(O)N(R)$_2$, —NRSO$_2$R, or —N(R)$_2$;
$R^3$ is selected from —R, halogen, -haloalkyl, —OR, —SR, —CN, —$NO_2$, —$SO_2R$, —SOR, —C(O)R, —$CO_2R$, —C(O)N(R)$_2$, —NRC(O)R, —NRC(O)N(R)$_2$, —NRSO$_2$R, or —N(R)$_2$;
wherein at least one of $R^2$ or $R^3$ is —C(O)N(R)$_2$, or CN;
each R is independently hydrogen, $C_{1-6}$ aliphatic, $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted; or
two R groups on the same atom are taken together with the atom to which they are attached to form a $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;
L is a divalent group selected from $C_{1-6}$ aliphatic, $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, and a 5-6 membered monocyclic heteroaryl ring having 1-4 heteroatoms independently selected from nitrogen, oxygen, or sulfur; each of which is optionally substituted; or L is a divalent group selected from $C_{1-6}$ aliphatic-$C_{3-10}$ aryl, $C_{1-6}$ aliphatic-3-8 membered saturated or partially unsaturated carbocyclic ring, $C_{1-6}$ aliphatic-3-7 membered heterocylic ring having 1-4 heteroatoms independently selected from nitrogen, oxygen, or sulfur, and a $C_{1-6}$ aliphatic-5-6 membered monocyclic heteroaryl ring having 1-4 heteroatoms independently selected from nitrogen, oxygen, or sulfur; each of which is optionally substituted;
Y is O, S, $SO_2$, SO, C(O), $CO_2$, C(O)N(R), —NRC(O), —NRC(O)N(R), —NRSO$_2$, or N(R); or Y is absent;
$R^1$ is $C_{1-6}$ aliphatic, $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;

X is O, S, SO$_2$, SO, C(O), CO$_2$, C(O)N(R), —NRC(O), —NRC(O)N(R), —NRSO$_2$, or N(R); or X is absent; and R$^4$ is hydrogen, C$_{1-6}$ aliphatic, C$_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted; or X—R$^4$ is absent.

In certain embodiments, the present invention provides a compound of formula I-a, I-b, I-c, or I-d

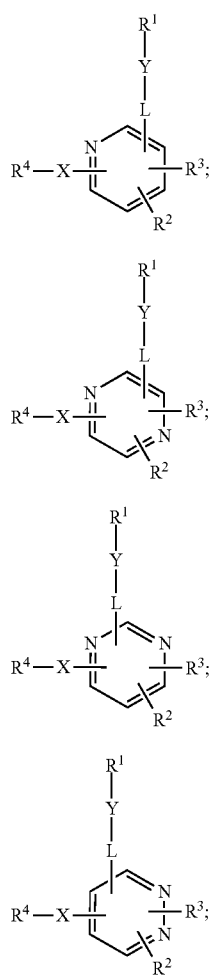

or a pharmaceutically acceptable salt thereof, wherein each of R$^1$, R$^2$, R$^3$, R$^4$, X, L and Y is as defined above and described in embodiments, classes and subclasses above and herein, singly or in combination.

In certain embodiments of any of the formulae herein, R$^2$ is hydrogen, halogen, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$. In certain embodiments, R$^2$ is halogen, —OR, —SR, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$. In certain embodiments, R$^2$ is halogen, —C(O)R, —CO$_2$R, —C(O)N (R)$_2$, —NRC(O)R, —NRC(O)N(R)$_2$, or —NRSO$_2$R. In certain embodiments, R$^2$ is halogen or —C(O)N(R)$_2$.

In certain embodiments of any of the formulae herein, R$^2$ is F or —C(O)NH$_2$. In certain embodiments, R$^2$ is F. In certain embodiments, R$^2$ is —C(O)NH$_2$. In certain embodiments, R$^2$ is —CN.

In certain embodiments of any of the formulae herein, R$^2$ is hydrogen.

In certain embodiments of any of the formulae herein, R$^3$ is hydrogen, halogen, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$. In certain embodiments, R$^3$ is halogen, —OR, —SR, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$. In certain embodiments, R$^3$ is halogen, —C(O)R, —CO$_2$R, —C(O)N (R)$_2$, —NRC(O)R, —NRC(O)N(R)$_2$, or —NRSO$_2$R. In certain embodiments, R$^3$ is halogen or —C(O)N(R)$_2$.

In certain embodiments of any of the formulae herein, R$^3$ is NH$_2$, Cl, F or —C(O)NH$_2$. In certain embodiments, R$^3$ is F. In certain embodiments, R$^3$ is —C(O)NH$_2$. In certain embodiments, R$^3$ is —CN.

In certain embodiments of any of the formulae herein, R$^3$ is hydrogen.

In certain embodiments of any of the formulae herein, L is a divalent C$_{1-6}$ aliphatic which is optionally substituted. In certain embodiments of any of the formulae herein, L is a divalent C$_{3-10}$ aryl which is optionally substituted. In certain embodiments of any of the formulae herein, L is a divalent 3-8 membered saturated or partially unsaturated carbocyclic ring which is optionally substituted. In certain embodiments of any of the formulae herein, L is a divalent 3-7 membered heterocylic ring having 1-4 heteroatoms independently selected from nitrogen, oxygen, or sulfur, which is optionally substituted. In certain embodiments of any of the formulae herein, L is a divalent 5-6 membered monocyclic heteroaryl ring having 1-4 heteroatoms independently selected from nitrogen, oxygen, or sulfur, which is optionally substituted.

In certain embodiments of any of the formulae herein, L is a divalent C$_{1-6}$ aliphatic-C$_{3-10}$ aryl, which is optionally substituted. In certain embodiments of any of the formulae herein, L is a divalent C$_{1-6}$ aliphatic-3-8 membered saturated or partially unsaturated carbocyclic ring, which is optionally substituted. In certain embodiments of any of the formulae herein, L is a divalent C$_{1-6}$ aliphatic-3-7 membered heterocylic ring having 1-4 heteroatoms independently selected from nitrogen, oxygen, or sulfur, which is optionally substituted. In certain embodiments of any of the formulae herein, L is a divalent C$_{1-6}$ aliphatic-5-6 membered monocyclic heteroaryl ring having 1-4 heteroatoms independently selected from nitrogen, oxygen, or sulfur which is optionally substituted.

In certain embodiments, L is a divalent C$_{1-6}$ aliphatic selected from methylene, ethylene, propylene, i-propylene, butylene, s-butylene, t-butylene, straight or branched pentylene, or straight or branched hexylene; each of which is optionally substituted.

In certain embodiments, L is a divalent phenyl, naphthyl, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; 1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, or xanthenyl; each of which is optionally substituted.

In certain embodiments, L is

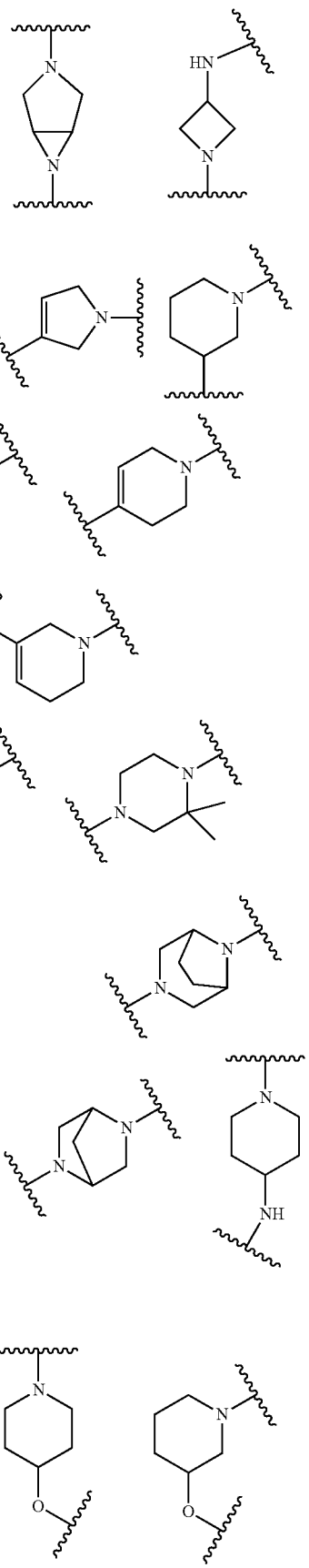

-continued
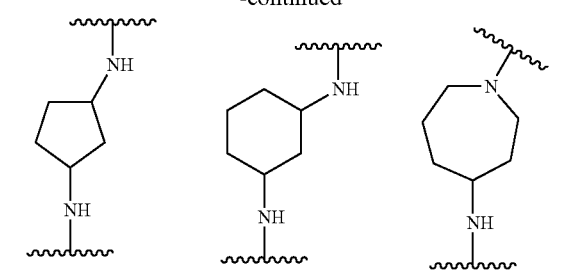
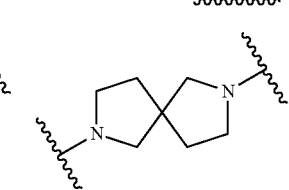
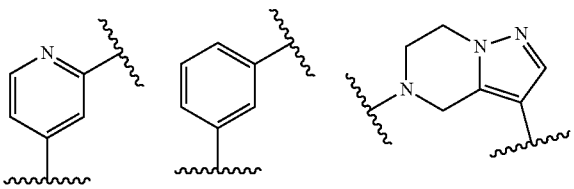
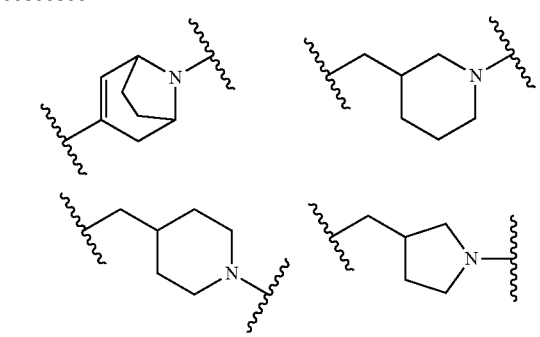
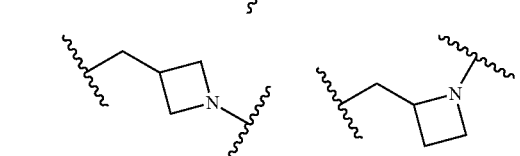
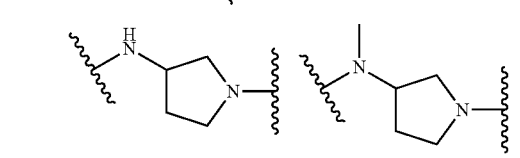
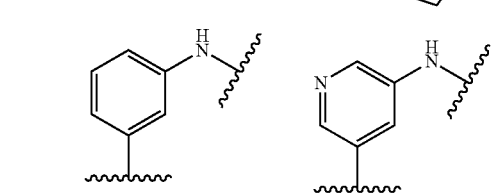
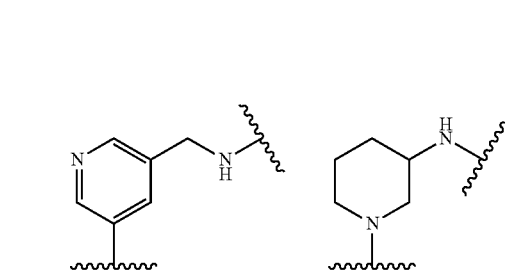
-continued
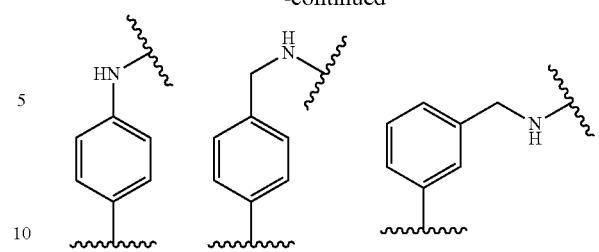
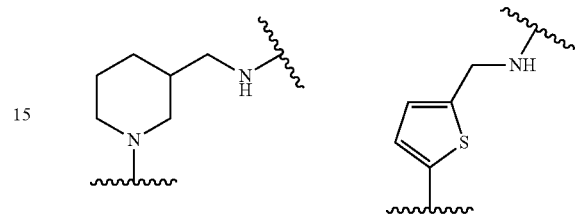
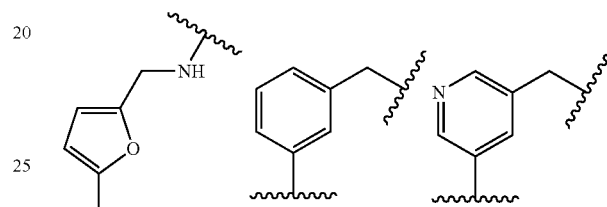
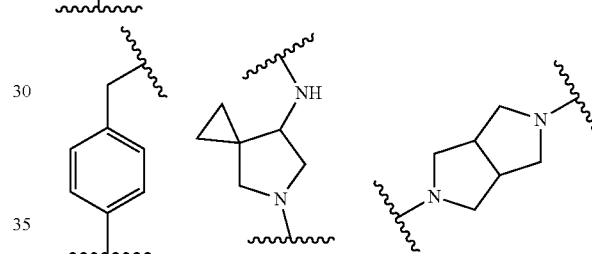
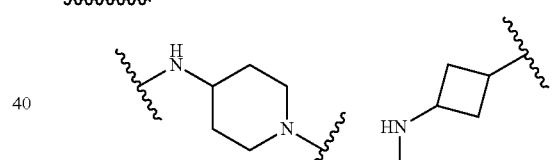
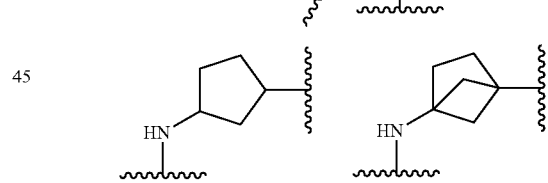
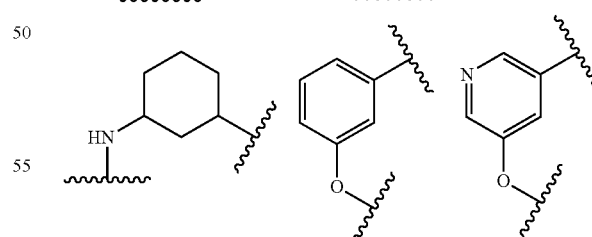
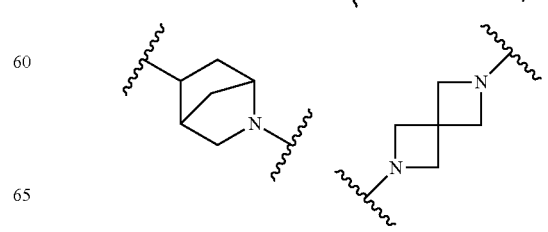

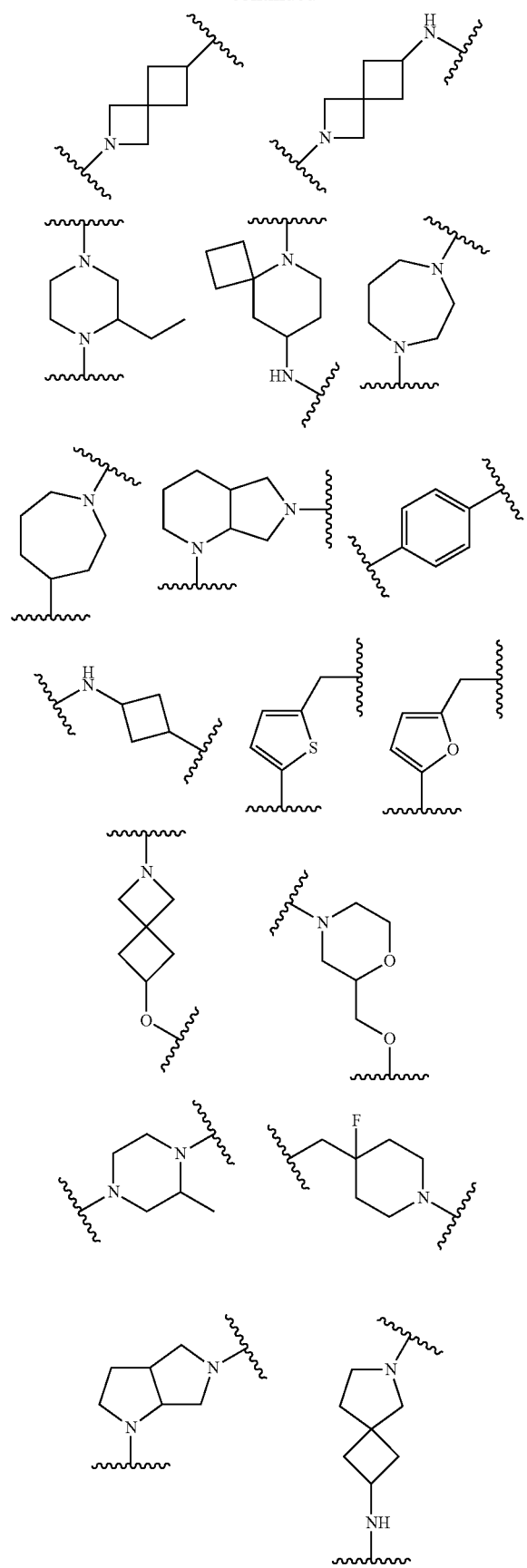
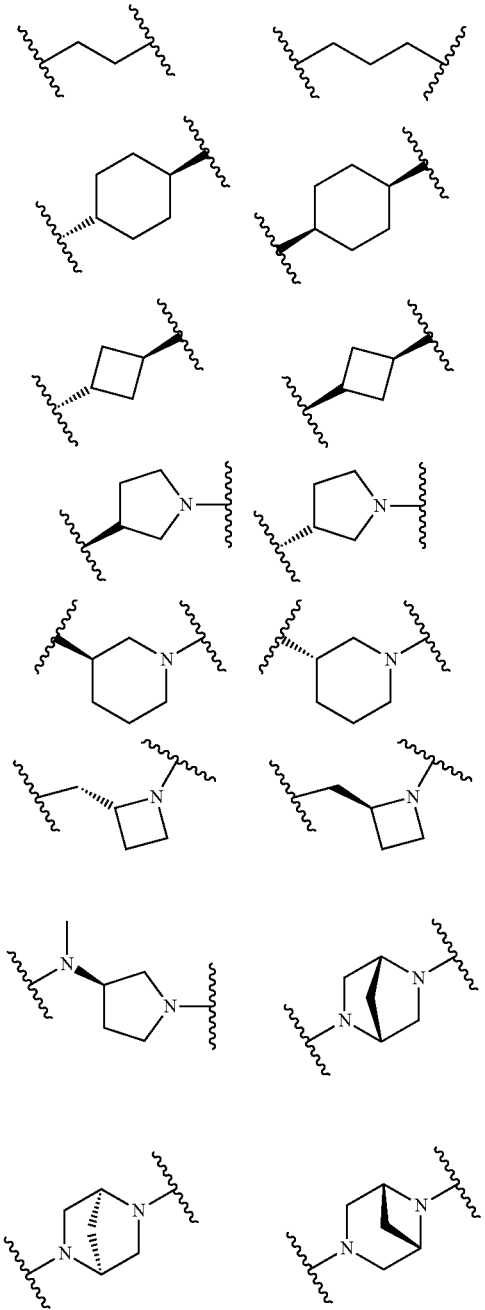
In certain embodiments, L

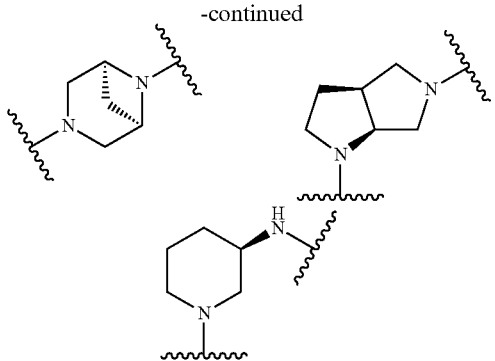

For each L described above, the invention contemplates substitution in either direction (e.g., in formula I,

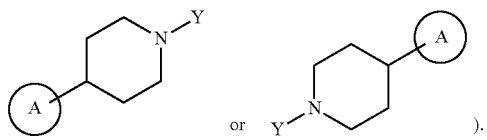

indicates either

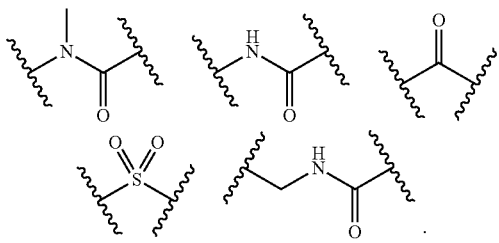

In certain embodiments of any of the formulae herein, Y is —NRC(O), —NRC(O)N(R), —NRSO$_2$, or N(R).

In certain embodiments of any of the formulae herein, Y is O, S, SO$_2$, SO, C(O), CO$_2$, or C(O)N(R).

In certain embodiments of any of the formulae herein, Y is absent.

In certain embodiments of any of the formulae herein, Y is

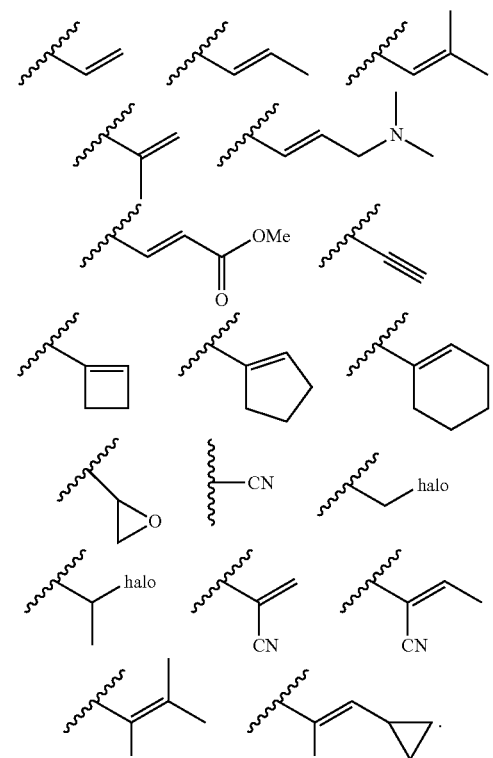

In certain embodiments of any of the formulae herein, R$^1$ is an optionally substituted C$_{1-6}$ aliphatic. In certain embodiments, R$^1$ is an optionally substituted C$_{3-10}$ aryl. In certain embodiments, R$^1$ is an optionally substituted 3-8 membered saturated or partially unsaturated carbocyclic ring. In certain embodiments, R$^1$ is an optionally substituted 3-7 membered heterocylic ring having 1-4 heteroatoms independently selected from nitrogen, oxygen, or sulfur. In certain embodiments, R$^1$ is an optionally substituted 5-6 membered monocyclic heteroaryl ring having 1-4 heteroatoms independently selected from nitrogen, oxygen, or sulfur.

In certain embodiments of any of the formulae herein, R$^1$ is C$_{1-6}$ aliphatic. In certain embodiments, R$^1$ is methyl, ethyl, propyl, i-propyl, butyl, s-butyl, t-butyl, straight or branched pentyl, or straight or branched hexyl; each of which is optionally substituted.

In certain embodiments of any of the formulae herein, R$^1$ is C$_{2-6}$ alkenyl, which is optionally substituted. In certain embodiments, R$^1$ is C$_{2-6}$ alkynyl, which is optionally substituted.

In certain embodiments of any of the formulae herein, R$^1$ is

In certain embodiments of any of the formulae herein, X is O, C(O), CO$_2$, C(O)N(R), —NRC(O), —NRC(O)N(R), —NRSO$_2$, or N(R). In certain embodiments, X is O, C(O)N(R), —NRC(O), or N(R). In certain embodiments, X is O, C(O)NH, —NHC(O), NH, or N(Me). In certain embodiments, X is absent.

In certain embodiments of any of the formulae herein, R$^4$ is hydrogen.

In certain embodiments of any of the formulae herein, R$^4$ is C$_{1-6}$ aliphatic, C$_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted.

In certain embodiments, R$^4$ is an optionally substituted C$_{1-6}$ aliphatic. In certain embodiments, R$^4$ is an optionally substituted C$_{3-10}$ aryl. In certain embodiments, R$^4$ is an optionally substituted 3-8 membered saturated or partially unsaturated carbocyclic ring. In certain embodiments, R$^4$ is an optionally substituted 3-7 membered heterocylic ring having 1-4 heteroatoms independently selected from nitrogen, oxygen, or sulfur. In certain embodiments, $R^4$ is an optionally substituted 5-6 membered monocyclic heteroaryl ring having 1-4 heteroatoms independently selected from nitrogen, oxygen, or sulfur.

In certain embodiments, $R^4$ is methyl, ethyl, propyl, i-propyl, butyl, s-butyl, t-butyl, straight or branched pentyl, straight or branched hexyl, or straight or branched heptyl. In certain embodiments, $R^4$ is methyl.

In certain embodiments, $R^4$ is phenyl, naphthyl, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H, 6H-1,5,2-dithiazinyl, dihydrofuro [2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; 1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, or xanthenyl; each of which is optionally substituted.

In certain embodiments, $R^4$ is phenyl, furanyl, furazanyl, imidazolidinyl, imidazolinyl, imidazolyl, 1H-indazolyl, indolenyl, isoxazolyl, oxadiazolyl, 1,2,3-oxadiazolyl, 1,2,4-oxadiazolyl; 1,2,5oxadiazolyl, 1,3,4-oxadiazolyl, oxazolidinyl, oxazolyl, oxazolidinyl, pyrimidinyl, piperazinyl, piperidinyl, purinyl, pyranyl, pyrazinyl, pyrazolidinyl, pyrazolinyl, pyrazolyl, pyridazinyl, pyridinyl, pyridyl, pyrimidinyl, pyrrolidinyl, pyrrolinyl, 2H-pyrrolyl, pyrrolyl, tetrahydrofuranyl, thiazolyl, thienyl, thiophenyl, oxetanyl, or azetidinyl, each of which is optionally substituted.

In certain embodiments, $R^4$ is phenyl, pyridinyl, piperidinyl, or pyrazolyl, each of which is optionally substituted.

In certain embodiments, $R^4$ is hydrogen, methyl,

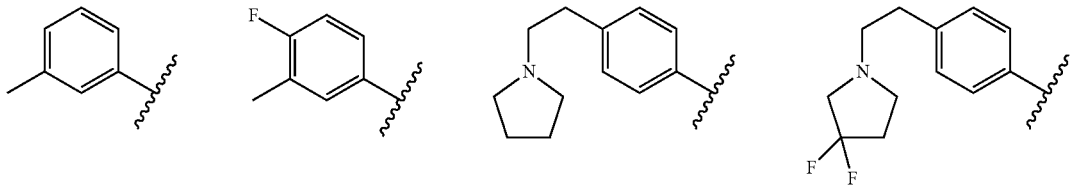

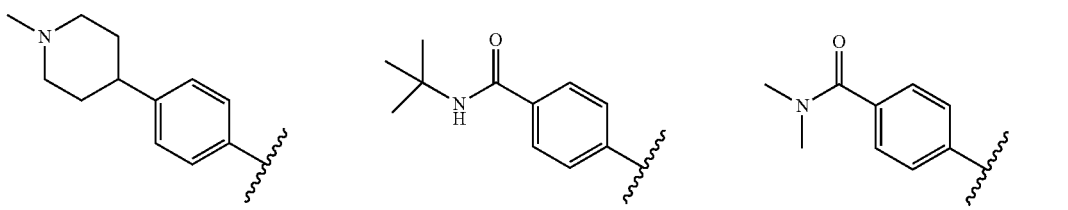

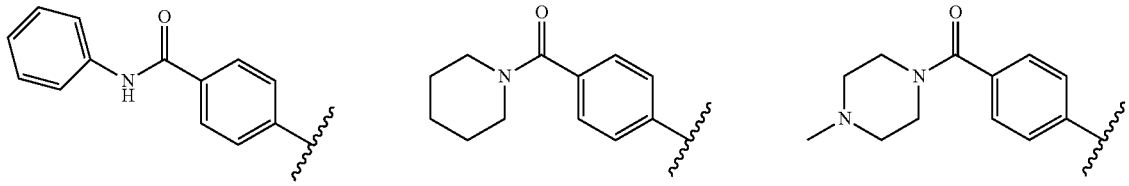

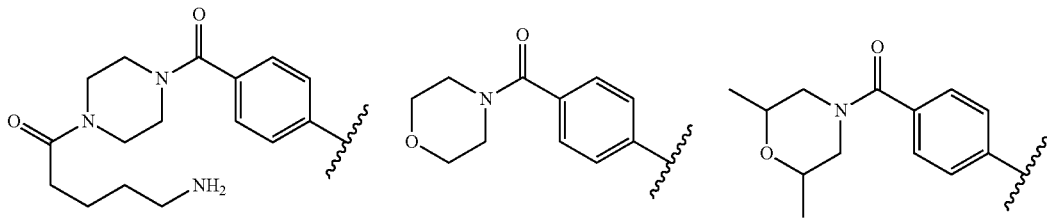

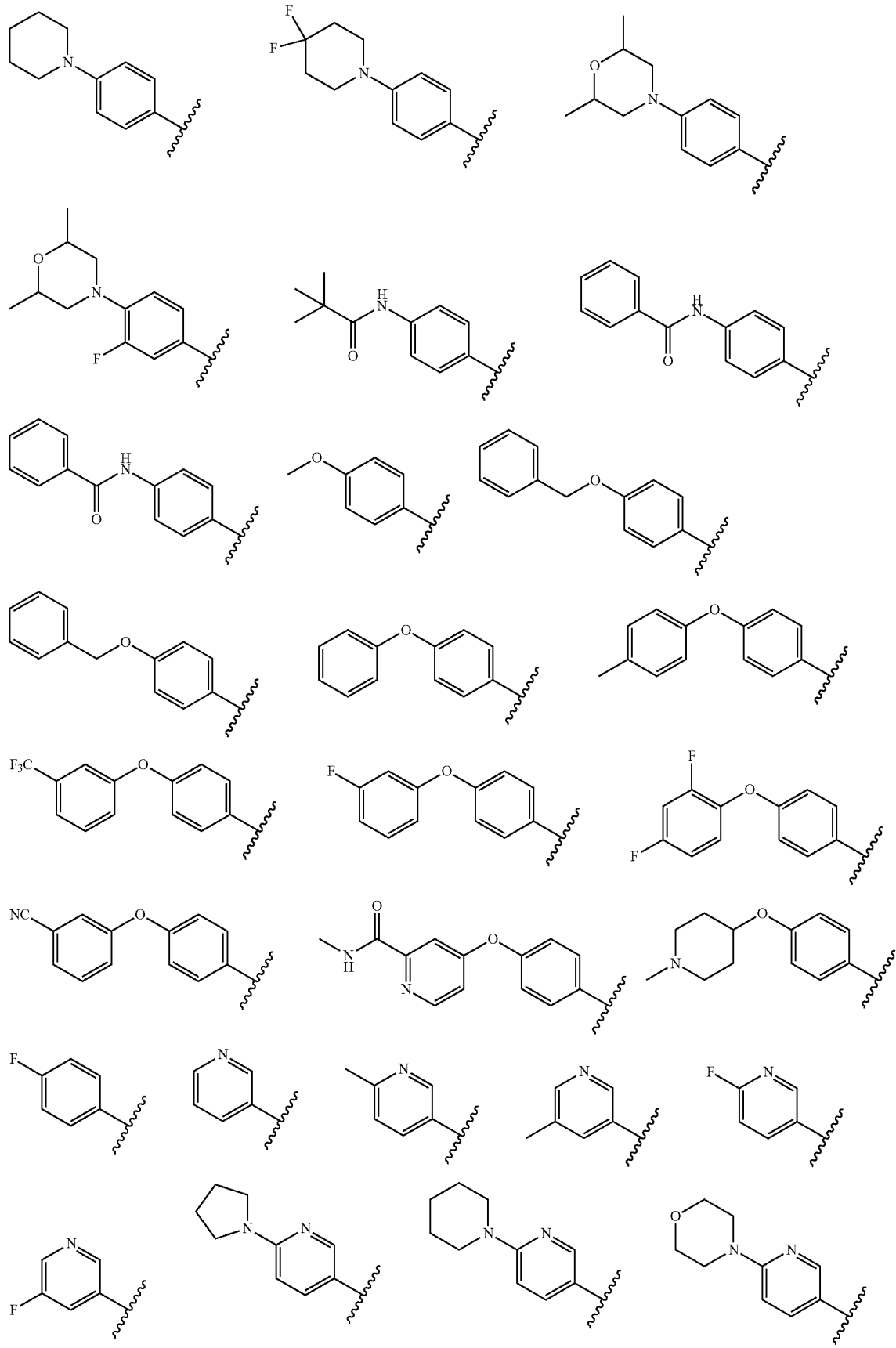

-continued
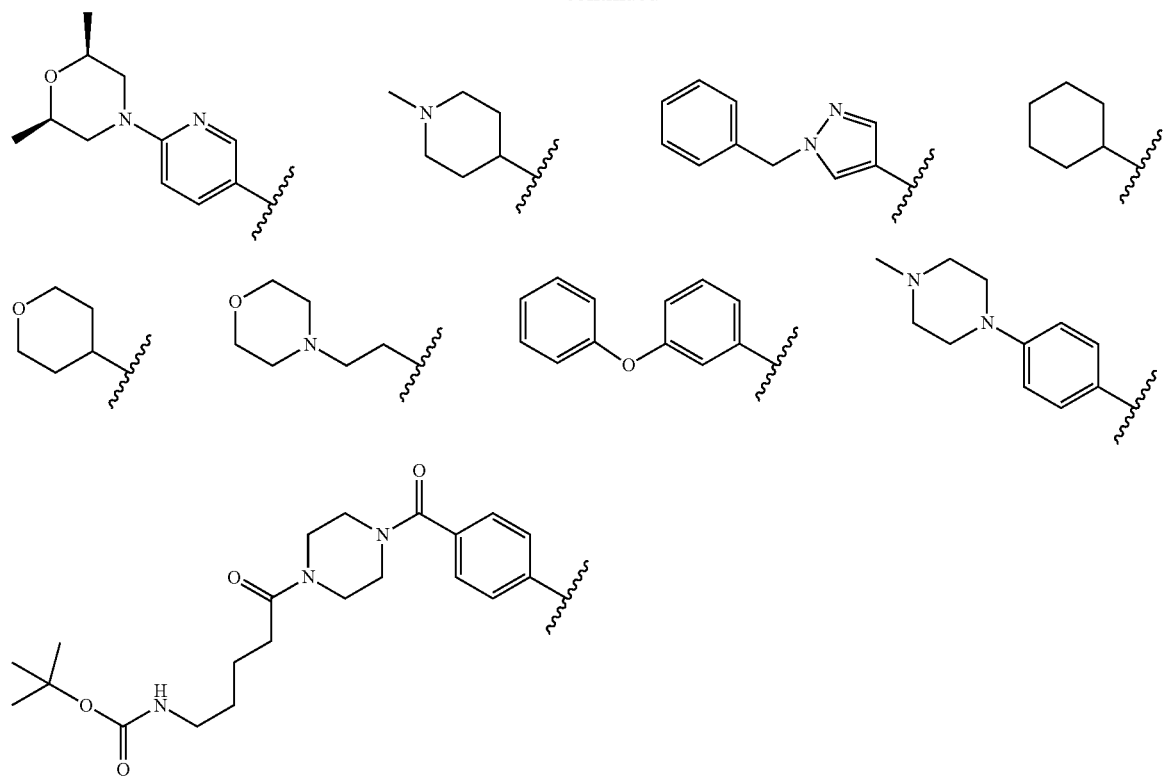
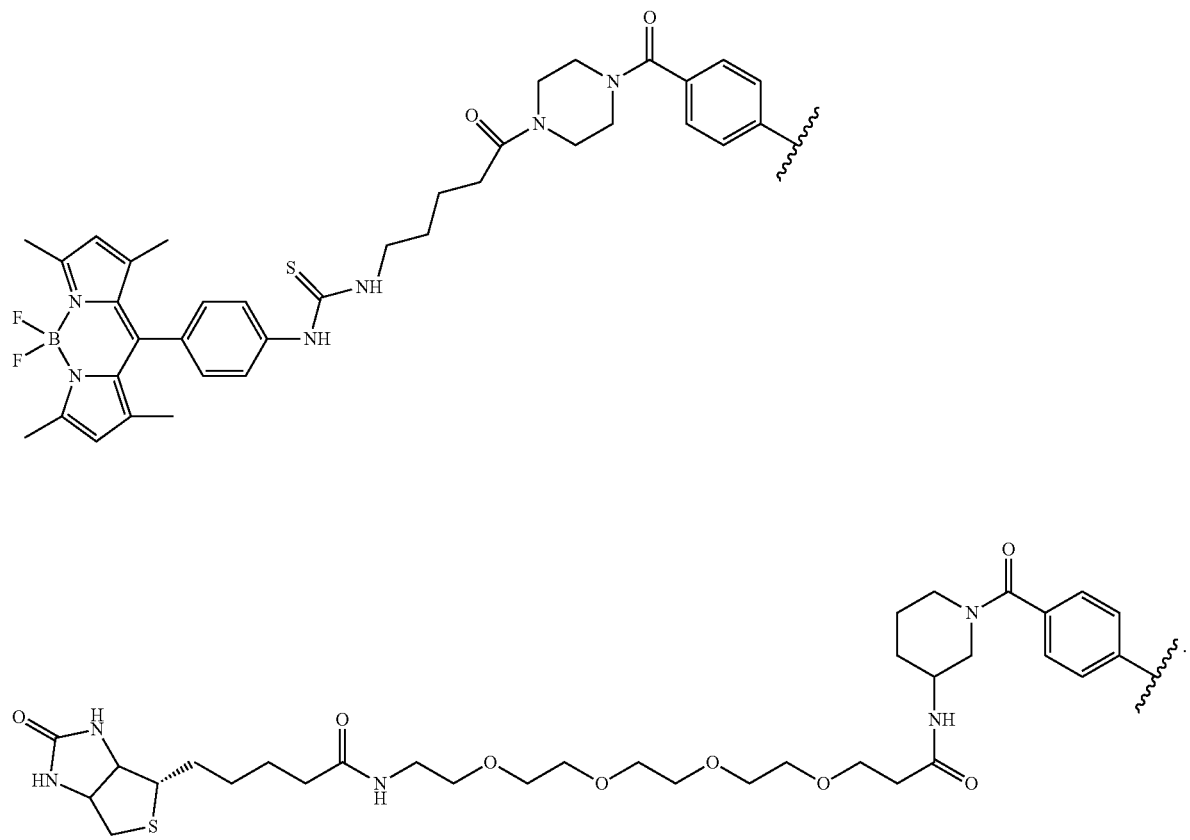

In certain embodiments of any of the formulae herein, X—R⁴ is absent.

In certain embodiments, each of $R^1$, $R^2$, $R^3$, $R^4$, X, Y, and L is as defined above and described in embodiments, classes and subclasses above and herein, singly or in combination.

In certain embodiments, the present invention provides a compound of formula I-a,

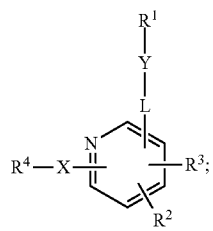

I-a or a pharmaceutically acceptable salt thereof, wherein each of $R^1$, $R^2$, $R^3$, $R^4$, X, L and Y is as defined above and described in embodiments, classes and subclasses above and herein, singly or in combination.

In certain embodiments, the present invention provides a compound of formula I-a1,

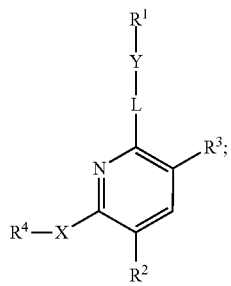

I-a1 or a pharmaceutically acceptable salt thereof, wherein each of $R^1$, $R^2$, $R^3$, $R^4$, X, L and Y is as defined above and described in embodiments, classes and subclasses above and herein, singly or in combination.

In certain embodiments, the present invention provides a compound of formula I-a2,

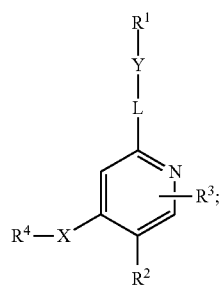

I-a2 or a pharmaceutically acceptable salt thereof, wherein each of $R^1$, $R^2$, $R^3$, $R^4$, X, L and Y is as defined above and described in embodiments, classes and subclasses above and herein, singly or in combination.

In certain embodiments, the present invention provides a compound of formula I-a3,

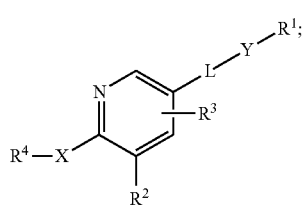

I-a3 or a pharmaceutically acceptable salt thereof, wherein each of $R^1$, $R^2$, $R^3$, $R^4$, X, L and Y is as defined above and described in embodiments, classes and subclasses above and herein, singly or in combination.

In certain embodiments, the present invention provides a compound of formula I-a4,

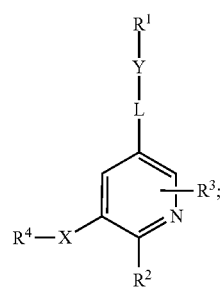

I-a4 or a pharmaceutically acceptable salt thereof, wherein each of $R^1$, $R^2$, $R^3$, $R^4$, X, L and Y is as defined above and described in embodiments, classes and subclasses above and herein, singly or in combination.

In certain embodiments, the present invention provides a compound of formula I-a5,

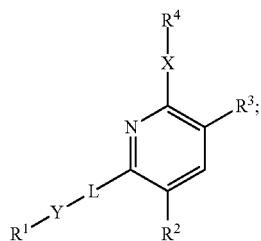

I-a5 or a pharmaceutically acceptable salt thereof, wherein each of $R^1$, $R^2$, $R^3$, $R^4$, X, L and Y is as defined above and described in embodiments, classes and subclasses above and herein, singly or in combination.

In certain embodiments, the present invention provides a compound of formula I-a6,

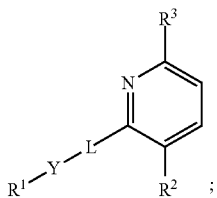

I-a6 or a pharmaceutically acceptable salt thereof, wherein each of $R^1$, $R^2$, $R^3$, L and Y is as defined above and described in embodiments, classes and subclasses above and herein, singly or in combination.

In certain embodiments, the present invention provides a compound of formula I-a7,

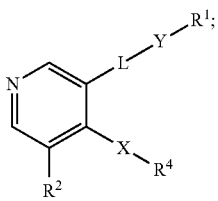

I-a7 or a pharmaceutically acceptable salt thereof, wherein each of $R^1$, $R^2$, $R^4$, X, L and Y is as defined above and described in embodiments, classes and subclasses above and herein, singly or in combination.

In certain embodiments, the present invention provides a compound of formula I-a8,

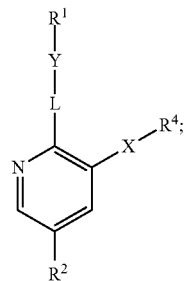

I-a8 or a pharmaceutically acceptable salt thereof, wherein each of $R^1$, $R^2$, $R^4$, X, L and Y is as defined above and described in embodiments, classes and subclasses above and herein, singly or in combination.

In certain embodiments, the present invention provides a compound of formula I-b,

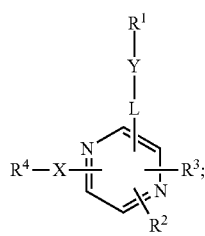

I-b or a pharmaceutically acceptable salt thereof, wherein each of $R^1$, $R^2$, $R^3$, $R^4$, X, L and Y is as defined above and described in embodiments, classes and subclasses above and herein, singly or in combination.

In certain embodiments, the present invention provides a compound of formula I-b1,

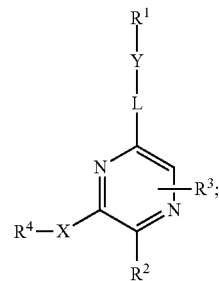

I-b1 or a pharmaceutically acceptable salt thereof, wherein each of $R^1$, $R^2$, $R^3$, $R^4$, X, L and Y is as defined above and described in embodiments, classes and subclasses above and herein, singly or in combination.

In certain embodiments, the present invention provides a compound of formula I-b2,

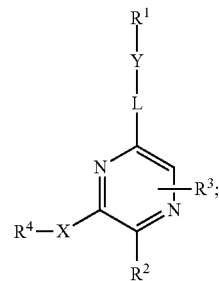

I-b2 or a pharmaceutically acceptable salt thereof, wherein each of $R^1$, $R^2$, $R^3$, $R^4$, X, L and Y is as defined above and described in embodiments, classes and subclasses above and herein, singly or in combination.

In certain embodiments, the compound is of formula I-c:

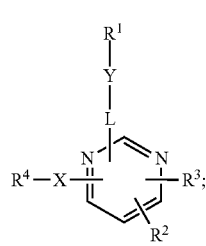

I-c or a pharmaceutically acceptable salt thereof, wherein each of $R^1$, $R^2$, $R^3$, $R^4$, X, L and Y is as defined above and described in embodiments, classes and subclasses above and herein, singly or in combination.

In certain embodiments, the compound is of formula I-c1:

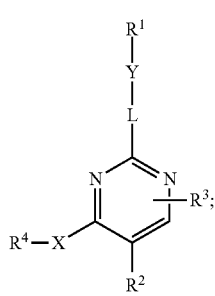

I-c1 or a pharmaceutically acceptable salt thereof, wherein each of $R^1$, $R^2$, $R^3$, $R^4$, X, L and Y is as defined above and described in embodiments, classes and subclasses above and herein, singly or in combination.

In certain embodiments, the compound is of formula I-c2:

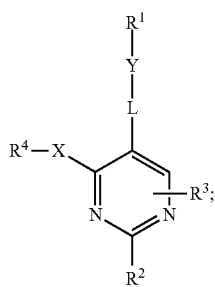

I-c2 or a pharmaceutically acceptable salt thereof, wherein each of $R^1$, $R^2$, $R^3$, $R^4$, X, L and Y is as defined above and described in embodiments, classes and subclasses above and herein, singly or in combination.

In certain embodiments, the compound is of formula I-c3:

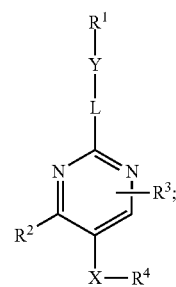

I-c3 or a pharmaceutically acceptable salt thereof, wherein each of $R^1$, $R^2$, $R^3$, $R^4$, X, L and Y is as defined above and described in embodiments, classes and subclasses above and herein, singly or in combination.

In certain embodiments, the compound is of formula I-c4:

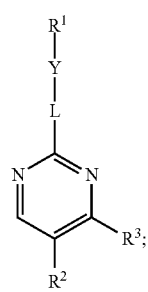

I-c4 or a pharmaceutically acceptable salt thereof, wherein each of $R^1$, $R^2$, $R^3$, L and Y is as defined above and described in embodiments, classes and subclasses above and herein, singly or in combination.

In certain embodiments, the compound is of formula I-c5:

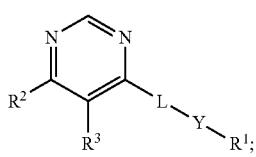

I-c5 or a pharmaceutically acceptable salt thereof, wherein each of $R^1$, $R^2$, $R^3$, L and Y is as defined above and described in embodiments, classes and subclasses above and herein, singly or in combination.

In certain embodiments, the compound is of formula I-d:

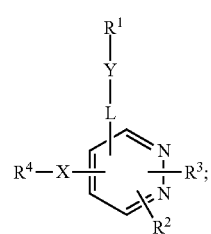

I-d or a pharmaceutically acceptable salt thereof, wherein each of $R^1$, $R^2$, $R^3$, $R^4$, X, L and Y is as defined above and described in embodiments, classes and subclasses above and herein, singly or in combination.

In certain embodiments, the compound is of formula I-d1:

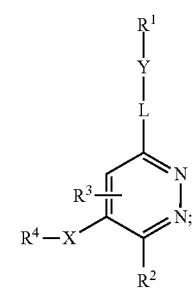

I-d1 or a pharmaceutically acceptable salt thereof, wherein each of $R^1$, $R^2$, $R^3$, $R^4$, X, L and Y is as defined above and described in embodiments, classes and subclasses above and herein, singly or in combination.

In certain embodiments, the invention provides a compound of formula I-a, wherein $R^2$ is —C(O)NH$_2$, and $R^3$ is absent.

In a further embodiment, L is a divalent $C_{1-6}$ aliphatic-3-8 membered saturated or partially unsaturated carbocyclic ring, which is optionally substituted, or a divalent $C_{1-6}$ aliphatic-3-7 membered heterocylic ring having 1-4 heteroatoms independently selected from nitrogen, oxygen, or sulfur, which is optionally substituted. In a further embodiment, L is

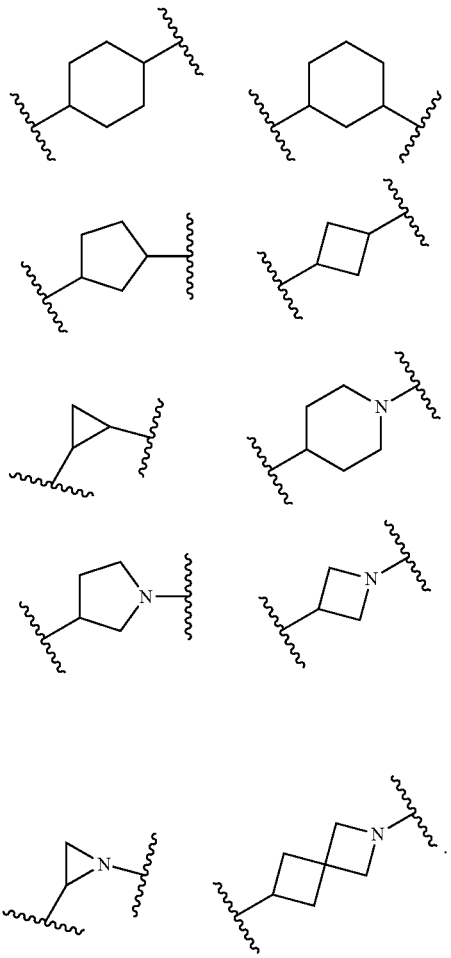

In a further embodiment, L is

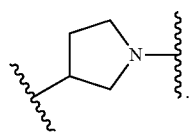

In a further embodiment, Y is —NRC(O), —NRC(O)N(R), —NRSO$_2$, or N(R). In a further embodiment, Y is

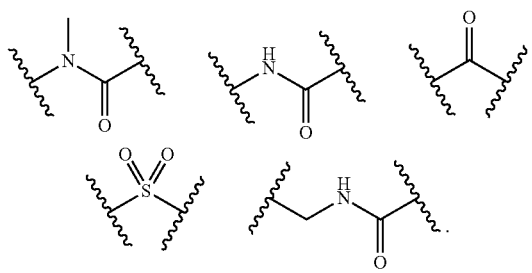

In a further embodiment, Y is

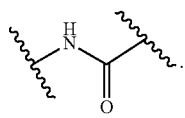 [SMILES: *NC(*)=O]

In a further embodiment, $R^1$ is

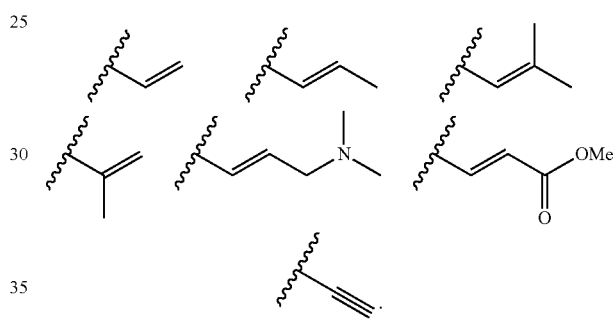

In a further embodiment, $R^1$ is

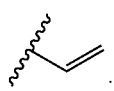

In a further embodiment, X is O and $R^4$ is an optionally substituted phenyl. In a further embodiment, $R^4$ is

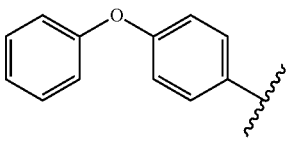

In a further embodiment, X is NH and $R^4$ is an optionally substituted phenyl. In a further embodiment, $R^4$ is

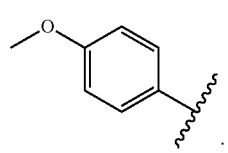

In a further embodiment, L is a divalent $C_{1-6}$ aliphatic-3-8 membered saturated or partially unsaturated carbocyclic ring, which is optionally substituted, or a divalent $C_{1-6}$ aliphatic-3-7 membered heterocylic ring having 1-4 heteroatoms independently selected from nitrogen, oxygen, or sulfur, which is optionally substituted. In a further embodiment, L is

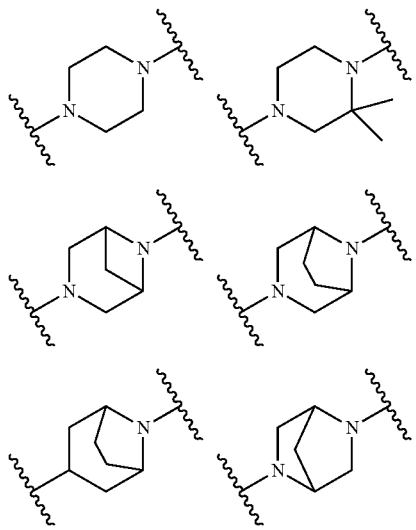

In a further embodiment, L is

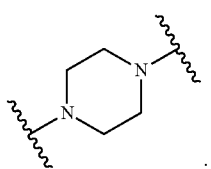 [SMILES: *N1CCN(*)CC1]

In a further embodiment, Y is —NRC(O), —NRC(O)N(R), —NRSO$_2$, or N(R). In a further embodiment, Y is

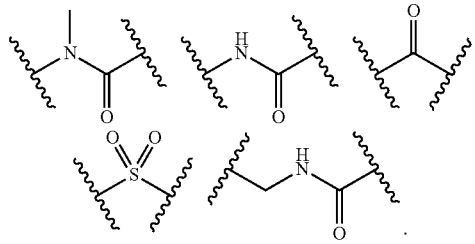

In a further embodiment, Y is

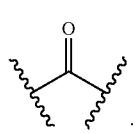

In a further embodiment, R$^1$ is

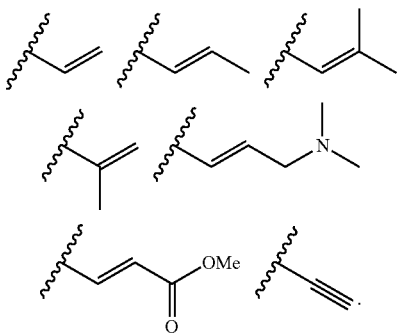

In a further embodiment, R$^1$ is

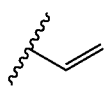

In a further embodiment, X is O and R$^4$ is an optionally substituted phenyl. In a further embodiment, R$^4$ is

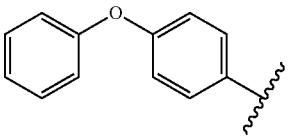

In a further embodiment, L is a divalent $C_{1-6}$ aliphatic-3-8 membered saturated or partially unsaturated carbocyclic ring, which is optionally substituted, or a divalent $C_{1-6}$ aliphatic-3-7 membered heterocylic ring having 1-4 heteroatoms independently selected from nitrogen, oxygen, or sulfur, which is optionally substituted. In a further embodiment, L is

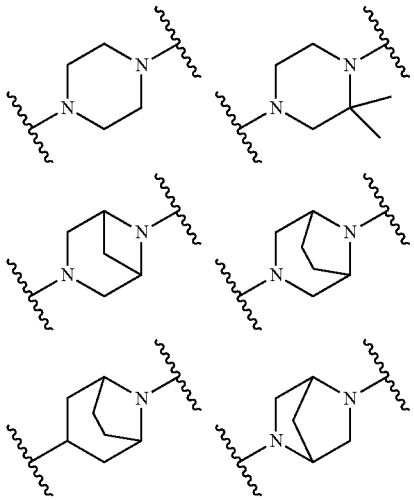

In a further embodiment, L is

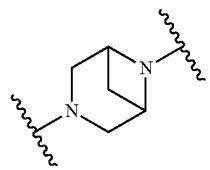

In a further embodiment, Y is —NRC(O), —NRC(O)N(R), —NRSO$_2$, or N(R). In a further embodiment, Y is

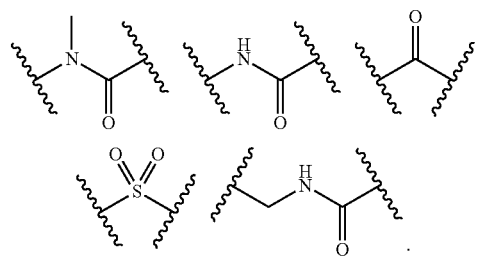

In a further embodiment, Y is

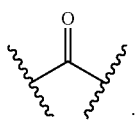 [SMILES: *C(*)=O]

In a further embodiment, R$^1$ is

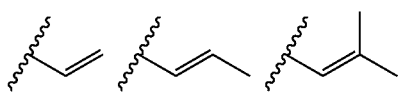

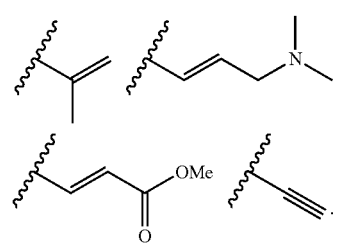

In a further embodiment, R$^1$ is

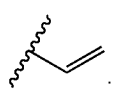

In a further embodiment, X is O and R$^4$ is an optionally substituted phenyl. In a further embodiment, R$^4$ is

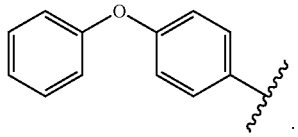 [SMILES: *c1ccc(Oc2ccccc2)cc1]

In certain embodiments, the invention provides a compound of formula I-c, wherein R$^2$ is —C(O)NH$_2$, and R$^3$ is absent.

In a further embodiment, L is a divalent C$_{1-6}$ aliphatic-3-8 membered saturated or partially unsaturated carbocyclic ring, which is optionally substituted, or a divalent C$_{1-6}$ aliphatic-3-7 membered heterocylic ring having 1-4 heteroatoms independently selected from nitrogen, oxygen, or sulfur, which is optionally substituted. In a further embodiment, L is

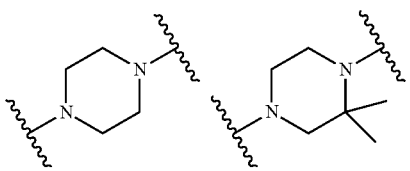

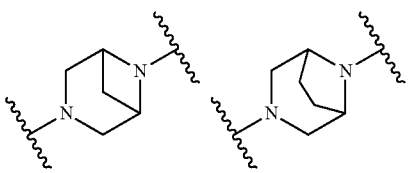

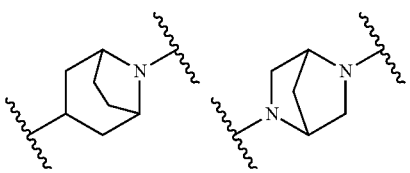

In a further embodiment, L

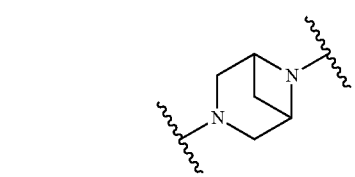

In a further embodiment, Y is —NRC(O), —NRC(O)N(R), —NRSO$_2$, or N(R). In a further embodiment, Y is

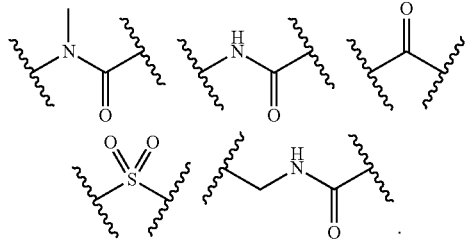

In a further embodiment, Y is

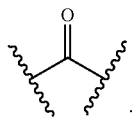 [SMILES: *C(*)=O]

In a further embodiment, R$^1$ is

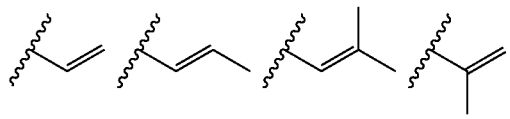

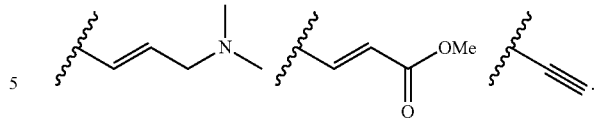

In a further embodiment, R$^1$ is

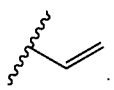

In a further embodiment, X is O and R$^4$ is an optionally substituted phenyl. In a further embodiment, R$^4$ is

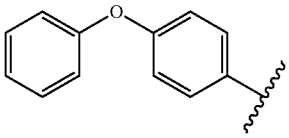

In certain embodiments, the invention provides a compound selected from Table 1:

TABLE 1

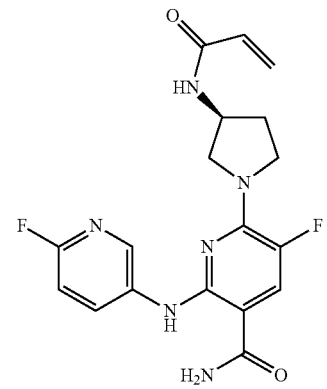 [SMILES: C=CC(=O)N[C@H]1CCN(c2nc(Nc3ccc(F)nc3)c(C(N)=O)cc2F)C1]

1

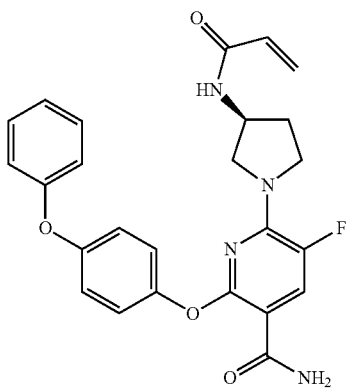 [SMILES: C=CC(=O)N[C@H]1CCN(c2nc(Oc3ccc(Oc4ccccc4)cc3)c(C(N)=O)cc2F)C1]

2

TABLE 1-continued
| | |
|---|---|
| 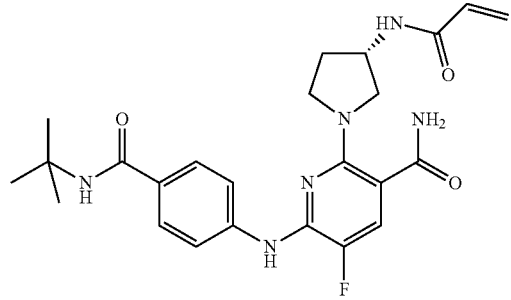 [SMILES: C=CC(=O)N[C@H]1CCN(c2nc(Nc3ccc(C(=O)NC(C)(C)C)cc3)c(F)cc2C(N)=O)C1] | 3 |
| 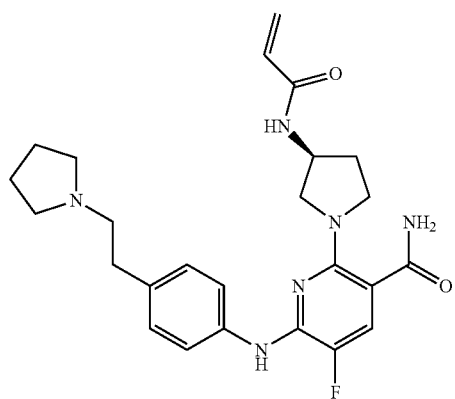 [SMILES: C=CC(=O)N[C@H]1CCN(c2nc(Nc3ccc(CCN4CCCC4)cc3)c(F)cc2C(N)=O)C1] | 4 |
| 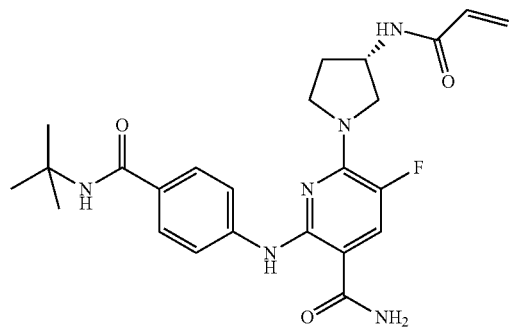 [SMILES: C=CC(=O)N[C@H]1CCN(c2nc(Nc3ccc(C(=O)NC(C)(C)C)cc3)c(C(N)=O)cc2F)C1] | 5 |
| 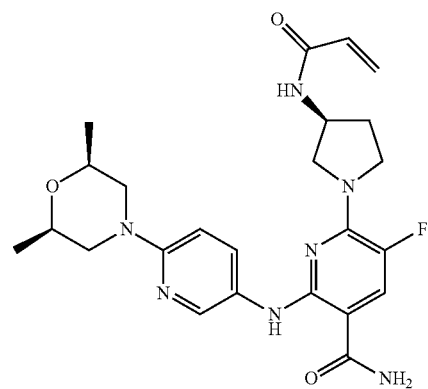 [SMILES: C=CC(=O)N[C@H]1CCN(c2nc(Nc3ccc(N4C[C@@H](C)O[C@@H](C)C4)nc3)c(C(N)=O)cc2F)C1] | 6 |

TABLE 1-continued
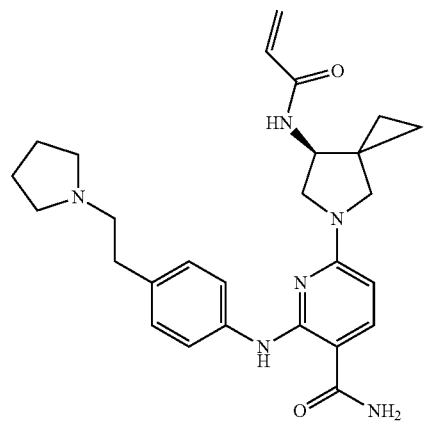 [SMILES: C=CC(=O)N[C@@H]1CN(c2ccc(C(N)=O)c(Nc3ccc(CCN4CCCC4)cc3)n2)CC12CC2]
7
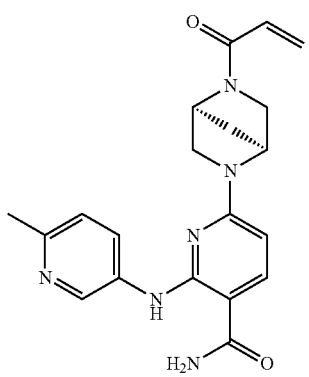 [SMILES: C=CC(=O)N1C[C@@H]2C[C@H]1CN2c1ccc(C(N)=O)c(Nc2ccc(C)nc2)n1]
8
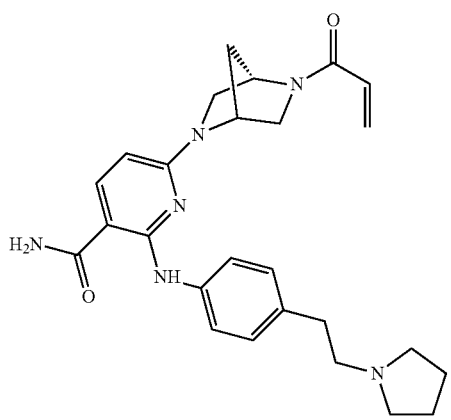 [SMILES: C=CC(=O)N1CC2C[C@H]1CN2c1ccc(C(N)=O)c(Nc2ccc(CCN3CCCC3)cc2)n1]
9
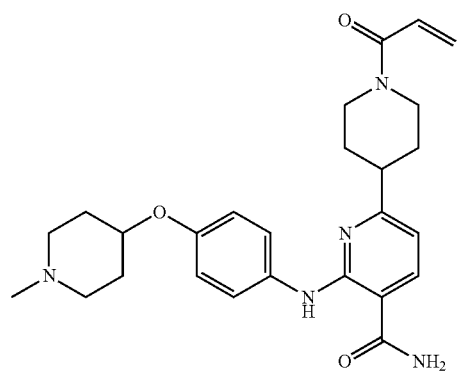 [SMILES: C=CC(=O)N1CCC(c2ccc(C(N)=O)c(Nc3ccc(OC4CCN(C)CC4)cc3)n2)CC1]
10

TABLE 1-continued
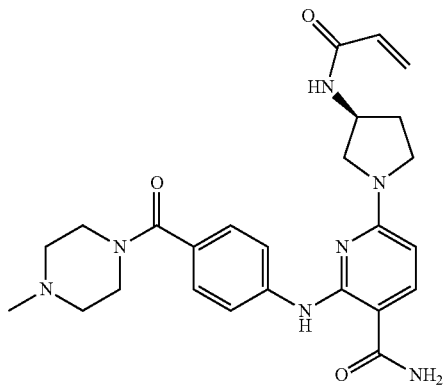 [SMILES: C=CC(=O)N[C@H]1CCN(c2ccc(C(N)=O)c(Nc3ccc(C(=O)N4CCN(C)CC4)cc3)n2)C1]
11
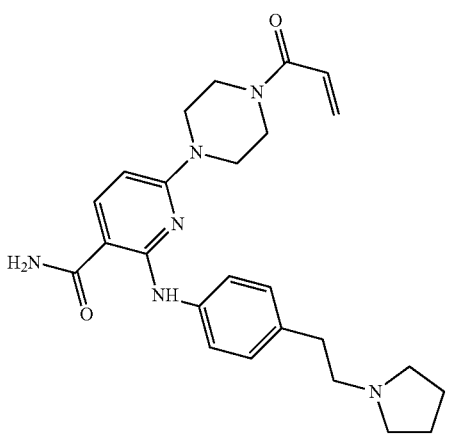 [SMILES: C=CC(=O)N1CCN(c2ccc(C(N)=O)c(Nc3ccc(CCN4CCCC4)cc3)n2)CC1]
12
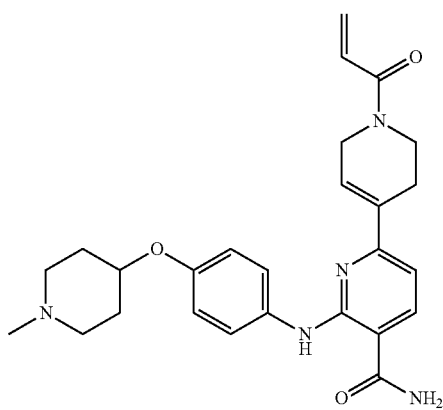 [SMILES: C=CC(=O)N1CC=C(c2ccc(C(N)=O)c(Nc3ccc(OC4CCN(C)CC4)cc3)n2)CC1]
13
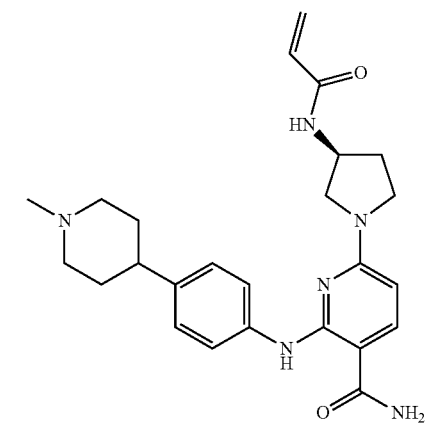 [SMILES: C=CC(=O)N[C@H]1CCN(c2ccc(C(N)=O)c(Nc3ccc(C4CCN(C)CC4)cc3)n2)C1]
14

TABLE 1-continued
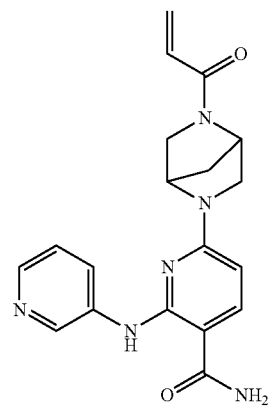 [SMILES: C=CC(=O)N1CC2CC1CN2c1ccc(C(N)=O)c(Nc2cccnc2)n1]
15
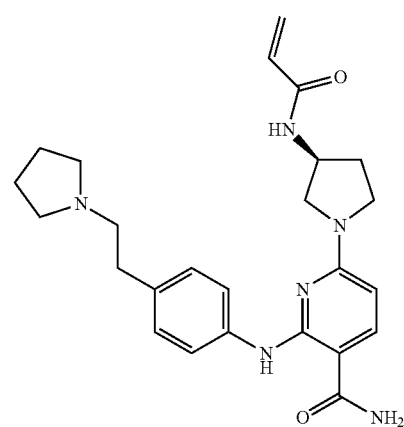 [SMILES: C=CC(=O)N[C@H]1CCN(c2ccc(C(N)=O)c(Nc3ccc(CCN4CCCC4)cc3)n2)C1]
16
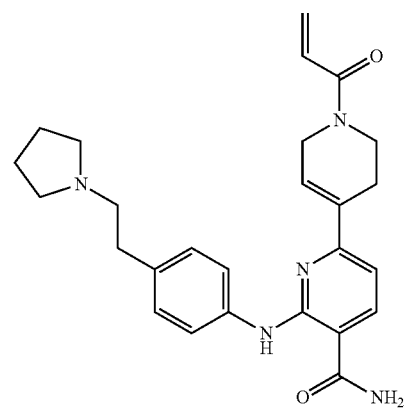
17

TABLE 1-continued
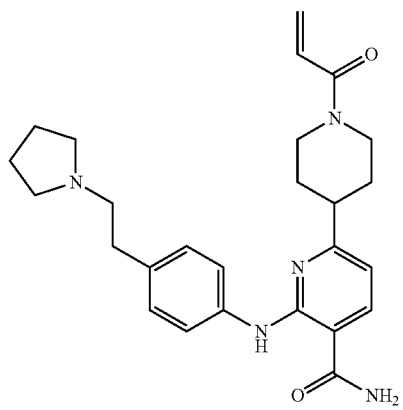
18
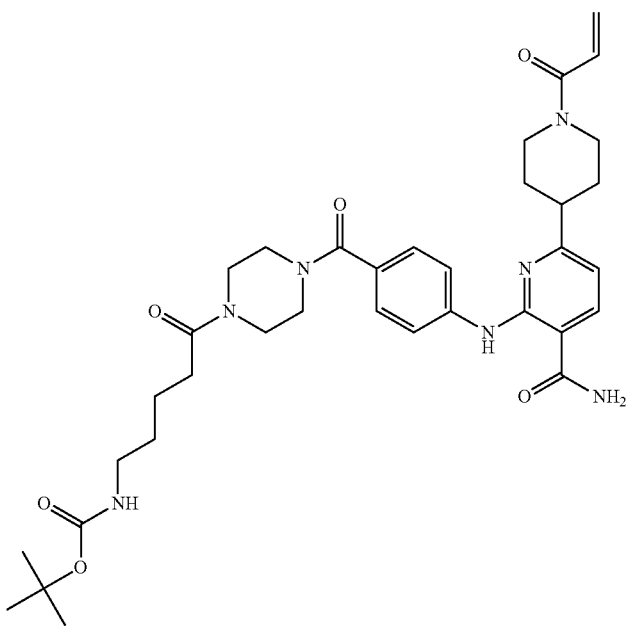 [SMILES: C=CC(=O)N1CCC(c2ccc(C(N)=O)c(Nc3ccc(C(=O)N4CCN(C(=O)CCCCNC(=O)OC(C)(C)C)CC4)cc3)n2)CC1]
19
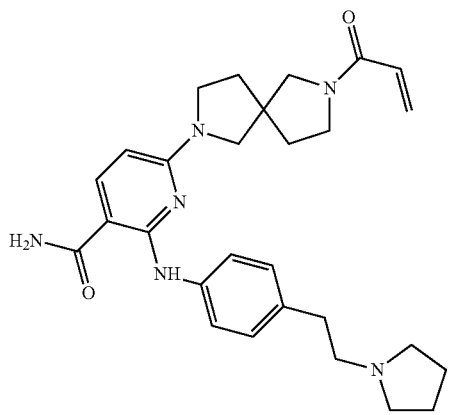 [SMILES: C=CC(=O)N1CCC2(CCN(c3ccc(C(N)=O)c(Nc4ccc(CCN5CCCC5)cc4)n3)C2)C1]
20

TABLE 1-continued
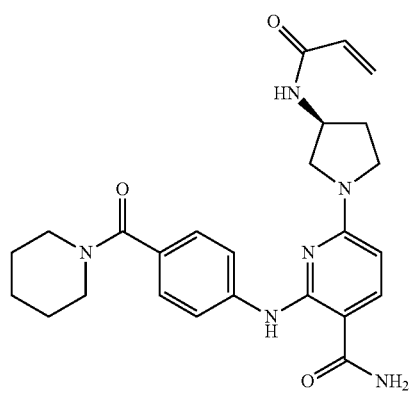 [SMILES: C=CC(=O)N[C@H]1CCN(c2ccc(C(N)=O)c(Nc3ccc(C(=O)N4CCCCC4)cc3)n2)C1]
21
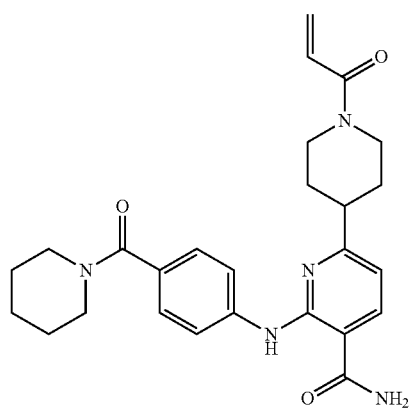 [SMILES: C=CC(=O)N1CCC(c2ccc(C(N)=O)c(Nc3ccc(C(=O)N4CCCCC4)cc3)n2)CC1]
22
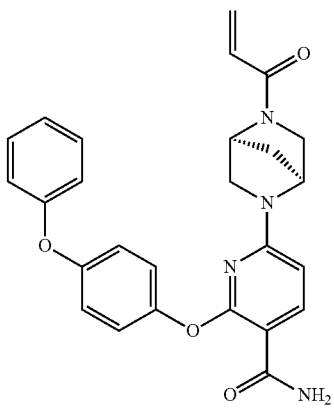 [SMILES: C=CC(=O)N1C[C@@H]2C[C@H]1CN2c1ccc(C(N)=O)c(Oc2ccc(Oc3ccccc3)cc2)n1]
23
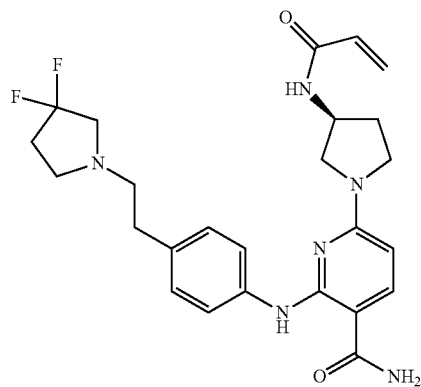 [SMILES: C=CC(=O)N[C@H]1CCN(c2ccc(C(N)=O)c(Nc3ccc(CCN4CCC(F)(F)C4)cc3)n2)C1]
24

TABLE 1-continued
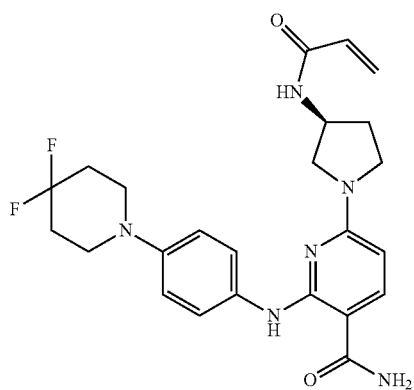 [SMILES: C=CC(=O)N[C@H]1CCN(c2ccc(C(N)=O)c(Nc3ccc(N4CCC(F)(F)CC4)cc3)n2)C1]
25
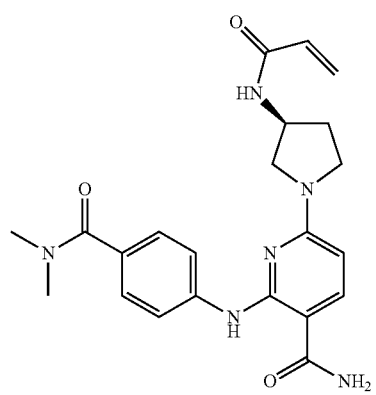 [SMILES: C=CC(=O)N[C@H]1CCN(c2ccc(C(N)=O)c(Nc3ccc(C(=O)N(C)C)cc3)n2)C1]
26
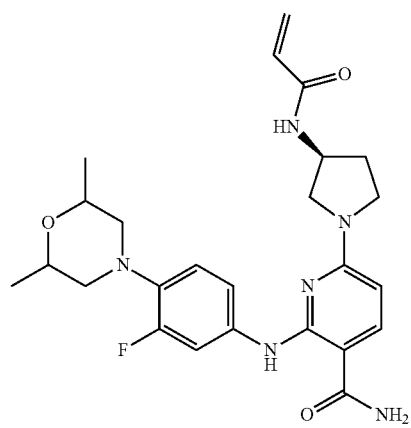 [SMILES: C=CC(=O)N[C@H]1CCN(c2ccc(C(N)=O)c(Nc3ccc(N4CC(C)OC(C)C4)c(F)c3)n2)C1]
27
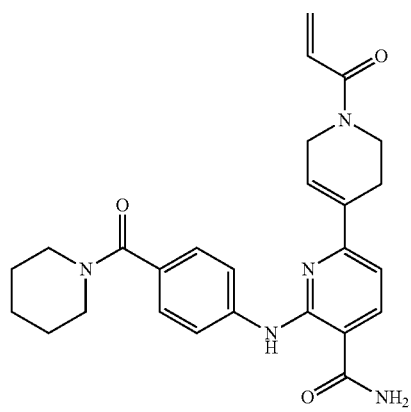 [SMILES: C=CC(=O)N1CC=C(c2ccc(C(N)=O)c(Nc3ccc(C(=O)N4CCCCC4)cc3)n2)CC1]
28

TABLE 1-continued
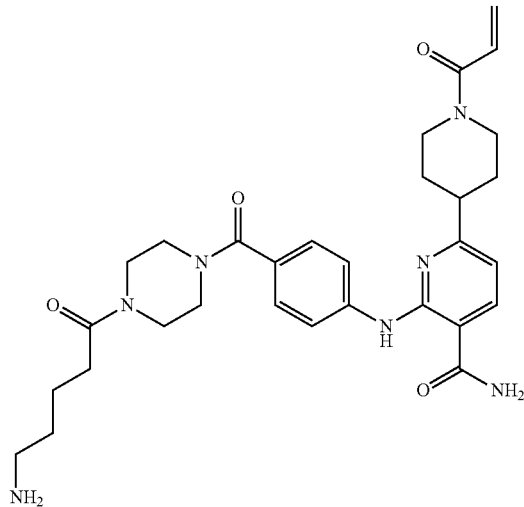 [SMILES: C=CC(=O)N1CCC(c2ccc(C(N)=O)c(Nc3ccc(C(=O)N4CCN(C(=O)CCCCN)CC4)cc3)n2)CC1]
29
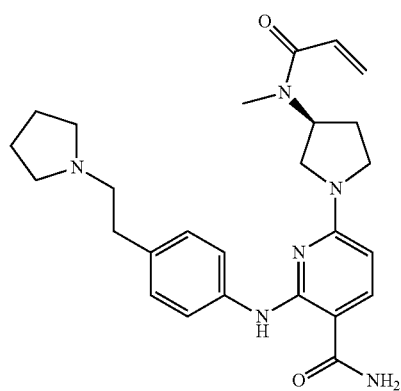 [SMILES: C=CC(=O)N(C)[C@H]1CCN(c2ccc(C(N)=O)c(Nc3ccc(CCN4CCCC4)cc3)n2)C1]
30
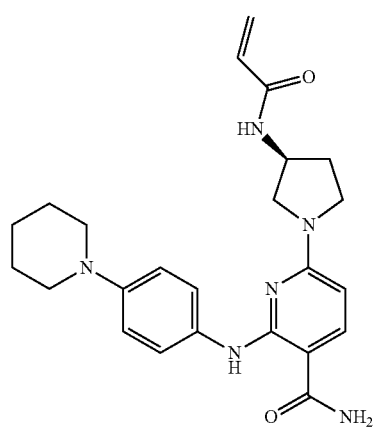 [SMILES: C=CC(=O)N[C@H]1CCN(c2ccc(C(N)=O)c(Nc3ccc(N4CCCCC4)cc3)n2)C1]
31

TABLE 1-continued
| | |
|---|---|
| 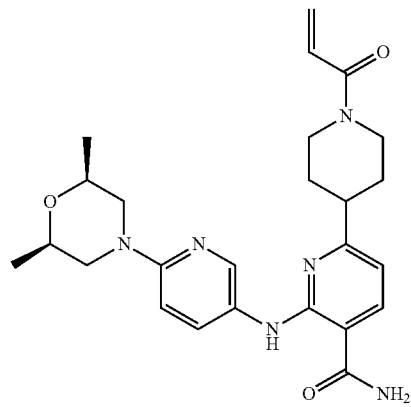 [SMILES: C=CC(=O)N1CCC(c2ccc(C(N)=O)c(Nc3ccc(N4C[C@@H](C)O[C@@H](C)C4)nc3)n2)CC1] | 32 |
| 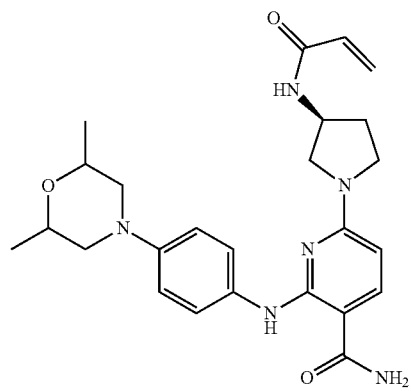 [SMILES: C=CC(=O)N[C@H]1CCN(c2ccc(C(N)=O)c(Nc3ccc(N4CC(C)OC(C)C4)cc3)n2)C1] | 33 |
| 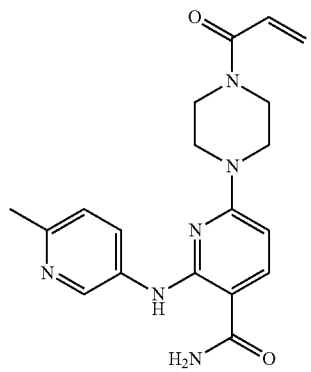 [SMILES: C=CC(=O)N1CCN(c2ccc(C(N)=O)c(Nc3ccc(C)nc3)n2)CC1] | 34 |
| 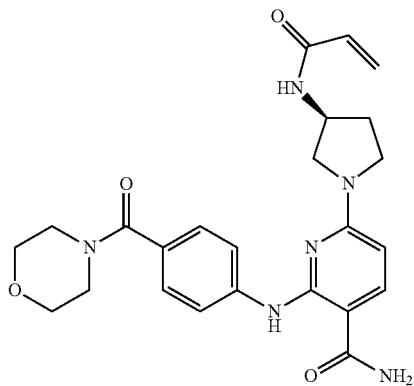 [SMILES: C=CC(=O)N[C@H]1CCN(c2ccc(C(N)=O)c(Nc3ccc(C(=O)N4CCOCC4)cc3)n2)C1] | 35 |

TABLE 1-continued
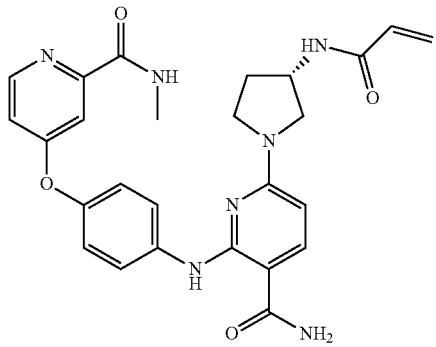 [SMILES: C=CC(=O)N[C@H]1CCN(c2ccc(C(N)=O)c(Nc3ccc(Oc4ccnc(C(=O)NC)c4)cc3)n2)C1]
36
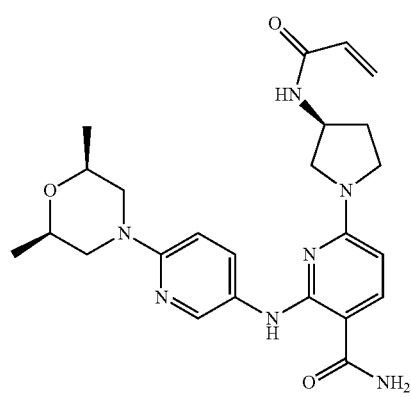 [SMILES: C=CC(=O)N[C@H]1CCN(c2ccc(C(N)=O)c(Nc3ccc(N4C[C@@H](C)O[C@@H](C)C4)nc3)n2)C1]
37
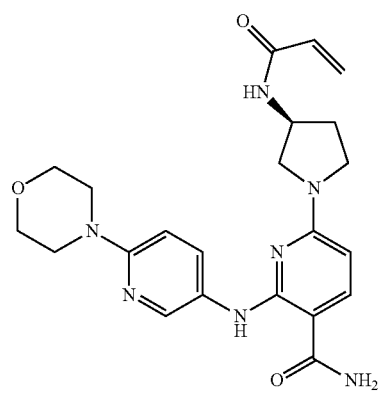 [SMILES: C=CC(=O)N[C@H]1CCN(c2ccc(C(N)=O)c(Nc3ccc(N4CCOCC4)nc3)n2)C1]
38
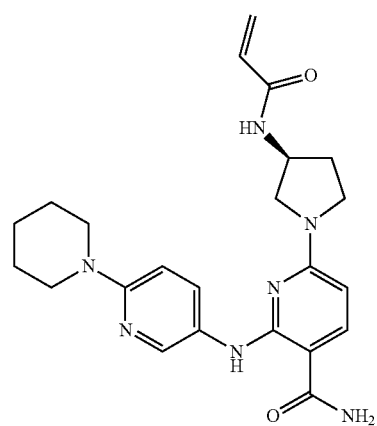 [SMILES: C=CC(=O)N[C@H]1CCN(c2ccc(C(N)=O)c(Nc3ccc(N4CCCCC4)nc3)n2)C1]
39

TABLE 1-continued
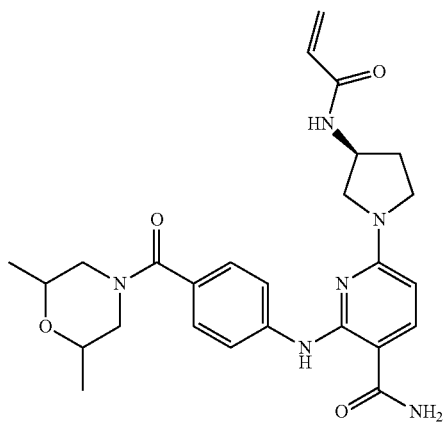 [SMILES: C=CC(=O)N[C@H]1CCN(c2ccc(C(N)=O)c(Nc3ccc(C(=O)N4CC(C)OC(C)C4)cc3)n2)C1]
40
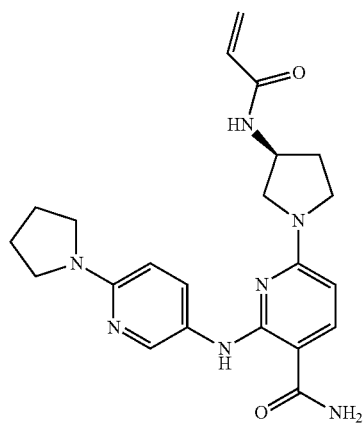 [SMILES: C=CC(=O)N[C@H]1CCN(c2ccc(C(N)=O)c(Nc3ccc(N4CCCC4)nc3)n2)C1]
41
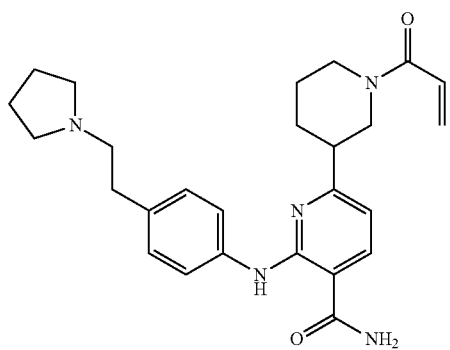 [SMILES: C=CC(=O)N1CCCC(c2ccc(C(N)=O)c(Nc3ccc(CCN4CCCC4)cc3)n2)C1]
42
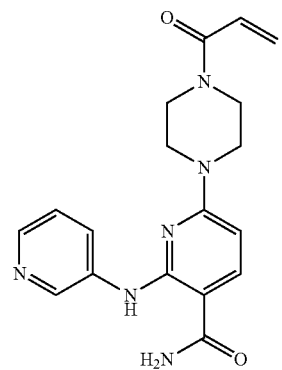 [SMILES: C=CC(=O)N1CCN(c2ccc(C(N)=O)c(Nc3cccnc3)n2)CC1]
43

TABLE 1-continued
| | |
|---|---|
| 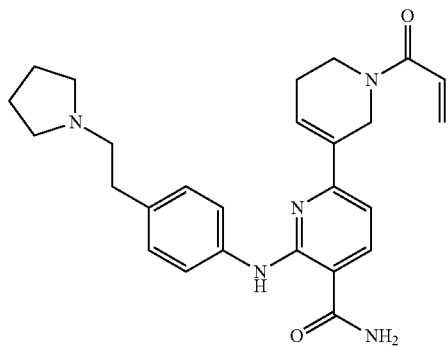 [SMILES: C=CC(=O)N1CCC=C(c2ccc(C(N)=O)c(Nc3ccc(CCN4CCCC4)cc3)n2)C1] | 44 |
| 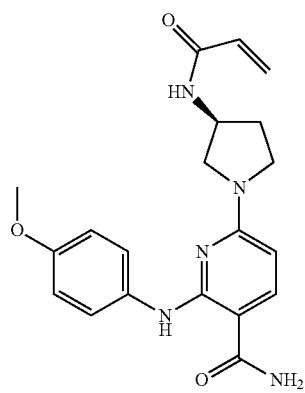 [SMILES: C=CC(=O)N[C@H]1CCN(c2ccc(C(N)=O)c(Nc3ccc(OC)cc3)n2)C1] | 45 |
| 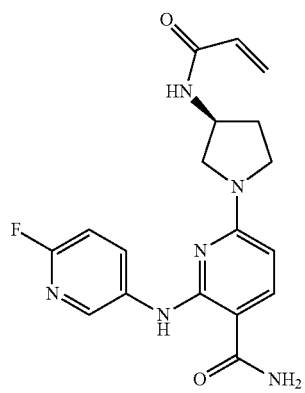 [SMILES: C=CC(=O)N[C@H]1CCN(c2ccc(C(N)=O)c(Nc3ccc(F)nc3)n2)C1] | 46 |
| 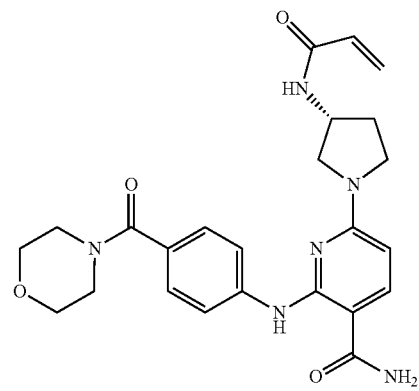 [SMILES: C=CC(=O)N[C@@H]1CCN(c2ccc(C(N)=O)c(Nc3ccc(C(=O)N4CCOCC4)cc3)n2)C1] | 47 |

TABLE 1-continued
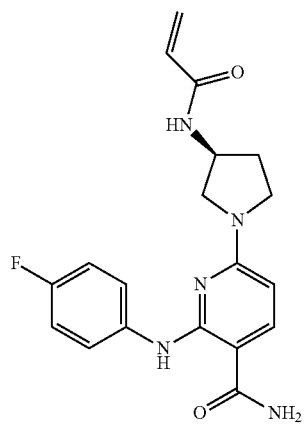 [SMILES: C=CC(=O)N[C@H]1CCN(c2ccc(C(N)=O)c(Nc3ccc(F)cc3)n2)C1]
48
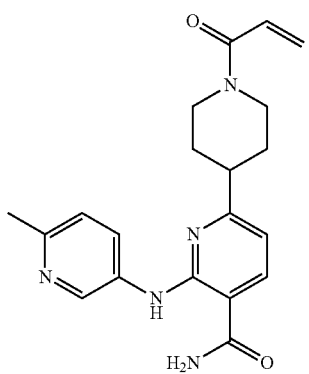 [SMILES: C=CC(=O)N1CCC(c2ccc(C(N)=O)c(Nc3ccc(C)nc3)n2)CC1]
49
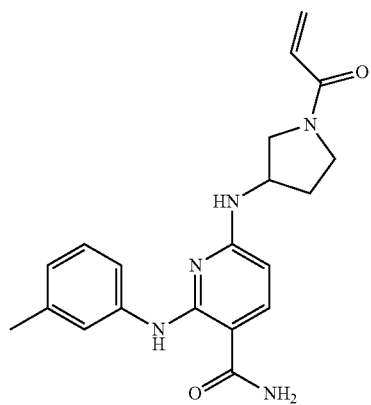 [SMILES: C=CC(=O)N1CCC(Nc2ccc(C(N)=O)c(Nc3cccc(C)c3)n2)C1]
50
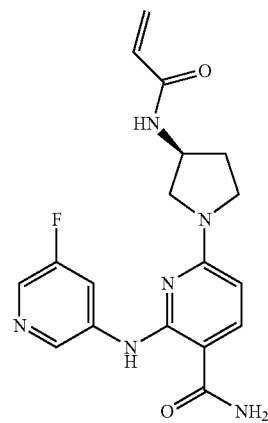 [SMILES: C=CC(=O)N[C@H]1CCN(c2ccc(C(N)=O)c(Nc3cncc(F)c3)n2)C1]
51

TABLE 1-continued
| | |
|---|---|
| 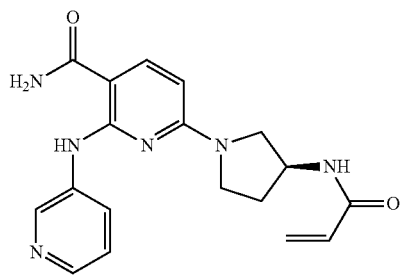 [SMILES: C=CC(=O)N[C@H]1CCN(c2ccc(C(N)=O)c(Nc3cccnc3)n2)C1] | 52 |
| 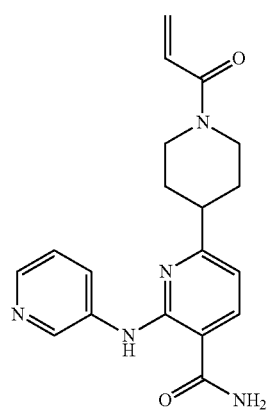 [SMILES: C=CC(=O)N1CCC(c2ccc(C(N)=O)c(Nc3cccnc3)n2)CC1] | 53 |
| 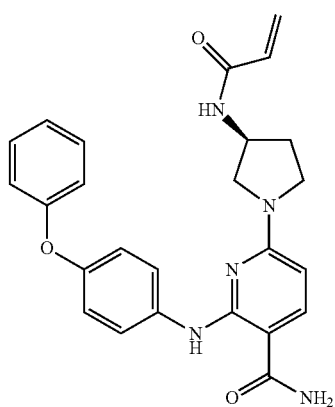 [SMILES: C=CC(=O)N[C@H]1CCN(c2ccc(C(N)=O)c(Nc3ccc(Oc4ccccc4)cc3)n2)C1] | 54 |
| 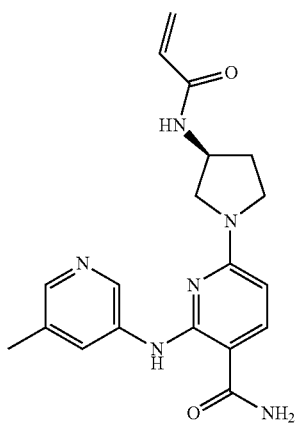 [SMILES: C=CC(=O)N[C@H]1CCN(c2ccc(C(N)=O)c(Nc3cncc(C)c3)n2)C1] | 55 |

TABLE 1-continued
| | |
|---|---|
| 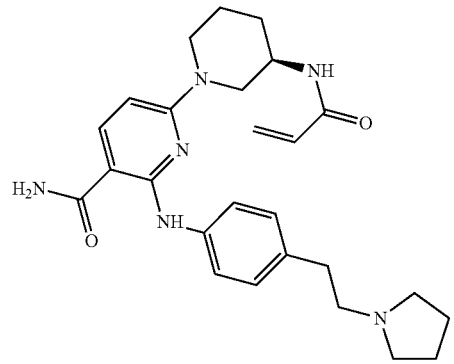 [SMILES: C=CC(=O)N[C@@H]1CCCN(c2ccc(C(N)=O)c(Nc3ccc(CCN4CCCC4)cc3)n2)C1] | 56 |
| 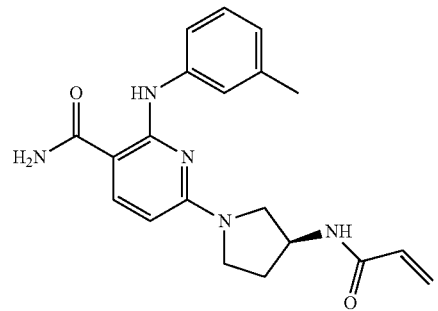 [SMILES: C=CC(=O)N[C@H]1CCN(c2ccc(C(N)=O)c(Nc3cccc(C)c3)n2)C1] | 57 |
| 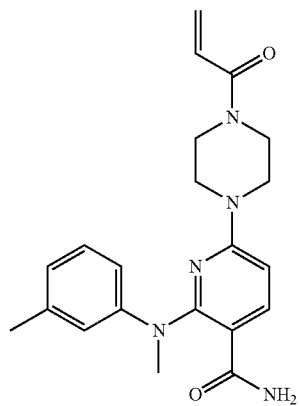 [SMILES: C=CC(=O)N1CCN(c2ccc(C(N)=O)c(N(C)c3cccc(C)c3)n2)CC1] | 58 |
| 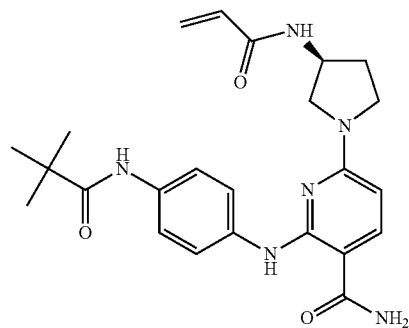 [SMILES: C=CC(=O)N[C@H]1CCN(c2ccc(C(N)=O)c(Nc3ccc(NC(=O)C(C)(C)C)cc3)n2)C1] | 59 |

TABLE 1-continued
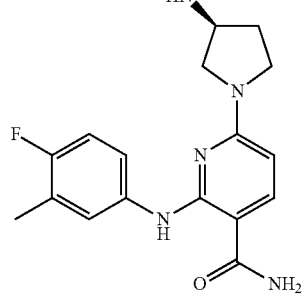
60
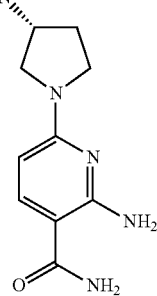
61
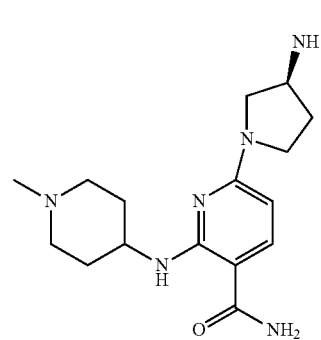
62

TABLE 1-continued
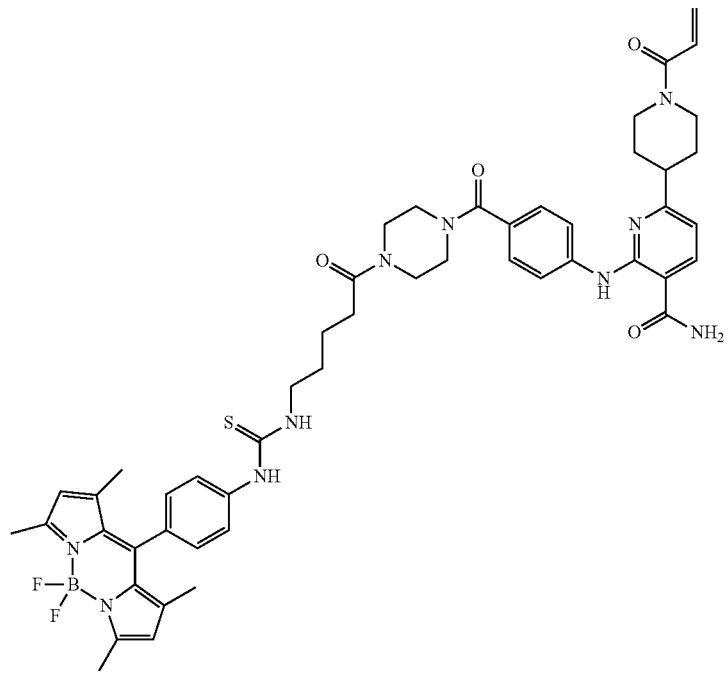
63
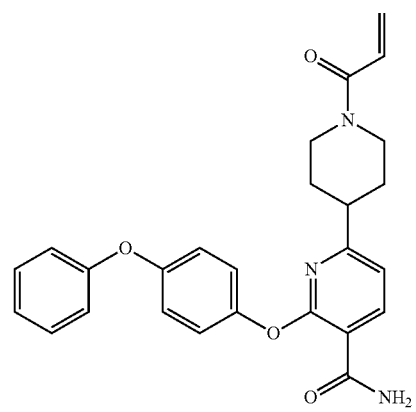 [SMILES: C=CC(=O)N1CCC(c2ccc(C(N)=O)c(Oc3ccc(Oc4ccccc4)cc3)n2)CC1]
64
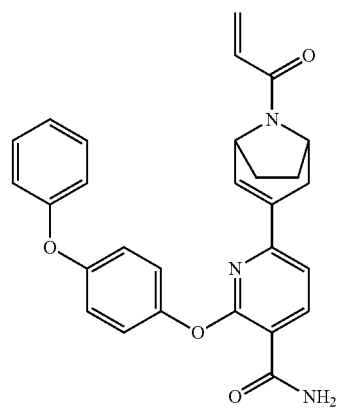 [SMILES: C=CC(=O)N1C2C=C(c3ccc(C(N)=O)c(Oc4ccc(Oc5ccccc5)cc4)n3)CC1CC2]
65

TABLE 1-continued
| | |
|---|---|
| 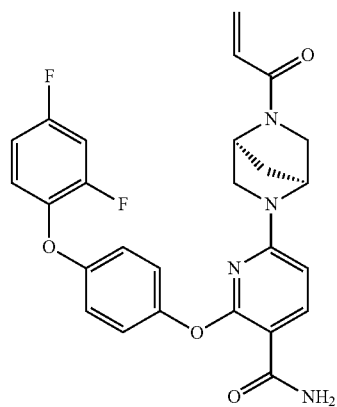 [SMILES: C=CC(=O)N1C[C@@H]2C[C@H]1CN2c1ccc(C(N)=O)c(Oc2ccc(Oc3ccc(F)cc3F)cc2)n1] | 66 |
| 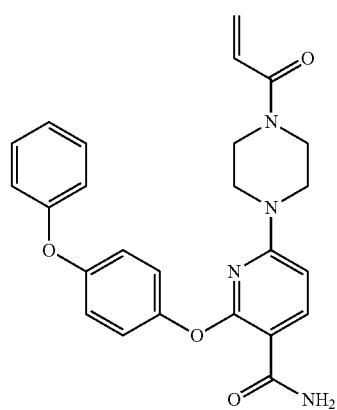 [SMILES: C=CC(=O)N1CCN(c2ccc(C(N)=O)c(Oc3ccc(Oc4ccccc4)cc3)n2)CC1] | 67 |
| 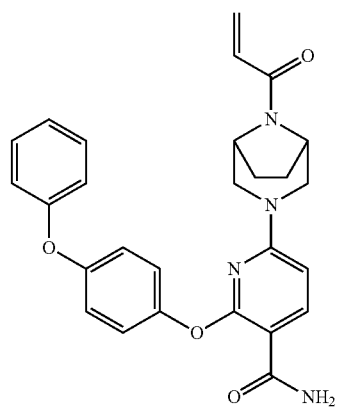 [SMILES: C=CC(=O)N1C2CCC1CN(c1ccc(C(N)=O)c(Oc3ccc(Oc4ccccc4)cc3)n1)C2] | 68 |
| 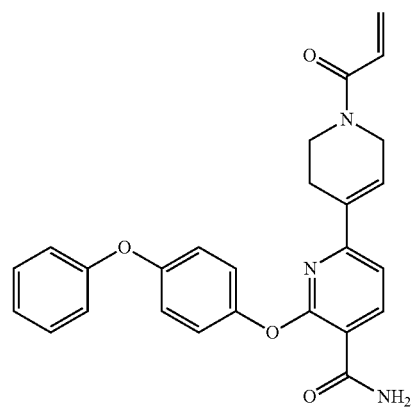 [SMILES: C=CC(=O)N1CC=C(c2ccc(C(N)=O)c(Oc3ccc(Oc4ccccc4)cc3)n2)CC1] | 69 |

TABLE 1-continued
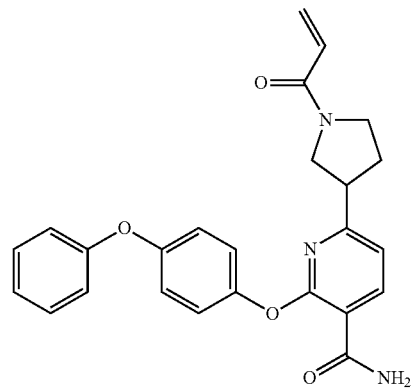 [SMILES: C=CC(=O)N1CCC(c2ccc(C(N)=O)c(Oc3ccc(Oc4ccccc4)cc3)n2)C1]
70
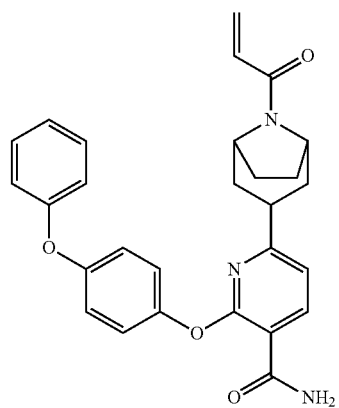 [SMILES: C=CC(=O)N1C2CCC1CC(c1ccc(C(N)=O)c(Oc3ccc(Oc4ccccc4)cc3)n1)C2]
71
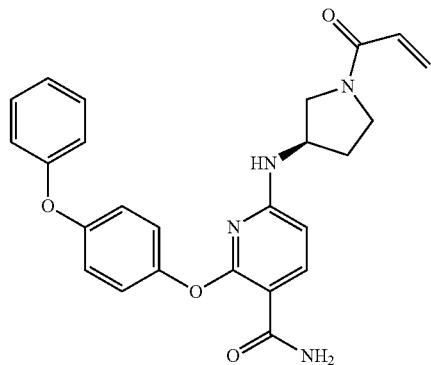 [SMILES: C=CC(=O)N1CC[C@@H](Nc2ccc(C(N)=O)c(Oc3ccc(Oc4ccccc4)cc3)n2)C1]
72
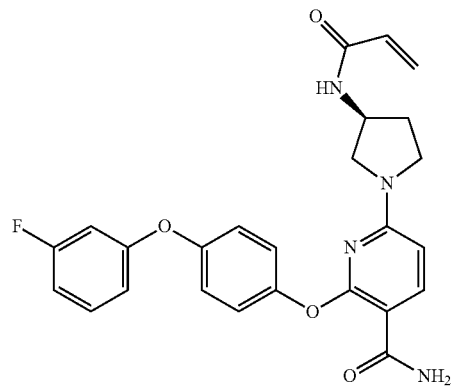 [SMILES: C=CC(=O)N[C@H]1CCN(c2ccc(C(N)=O)c(Oc3ccc(Oc4cccc(F)c4)cc3)n2)C1]
73

TABLE 1-continued
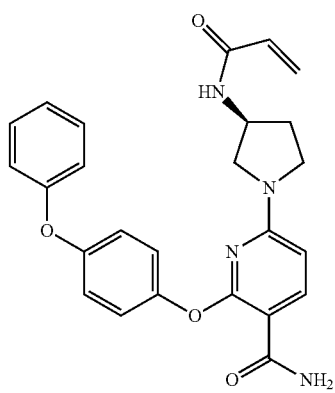 [SMILES: C=CC(=O)N[C@H]1CCN(c2ccc(C(N)=O)c(Oc3ccc(Oc4ccccc4)cc3)n2)C1]
74
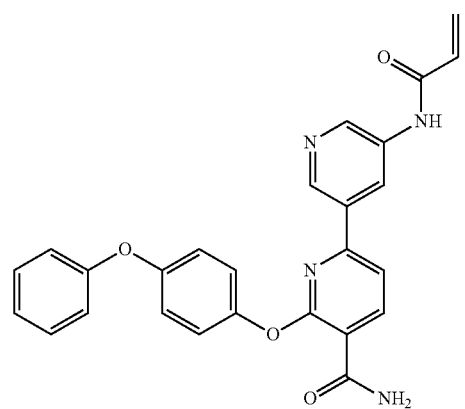 [SMILES: C=CC(=O)Nc1cncc(-c2ccc(C(N)=O)c(Oc3ccc(Oc4ccccc4)cc3)n2)c1]
75
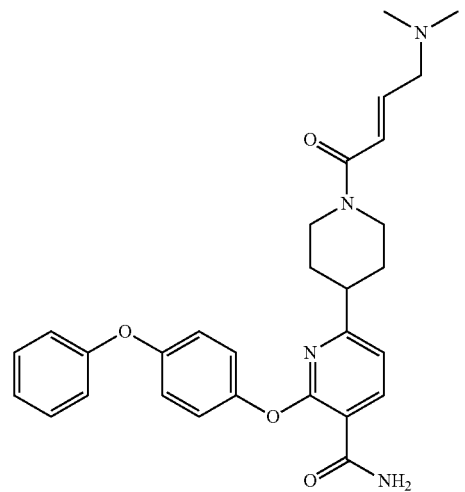 [SMILES: CN(C)C/C=C/C(=O)N1CCC(c2ccc(C(N)=O)c(Oc3ccc(Oc4ccccc4)cc3)n2)CC1]
76

TABLE 1-continued
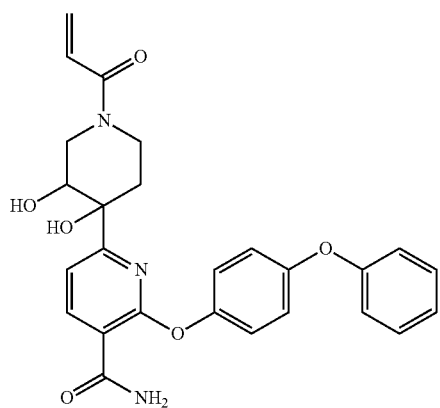 [SMILES: C=CC(=O)N1CCC(O)(c2ccc(C(N)=O)c(Oc3ccc(Oc4ccccc4)cc3)n2)C(O)C1]
77
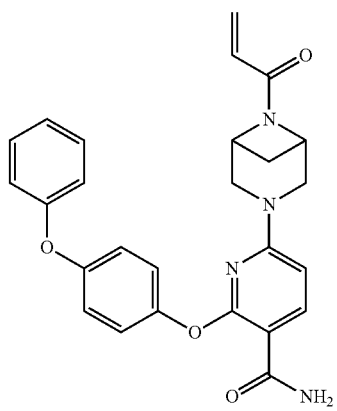 [SMILES: C=CC(=O)N1C2CC1CN(c1ccc(C(N)=O)c(Oc3ccc(Oc4ccccc4)cc3)n1)C2]
78
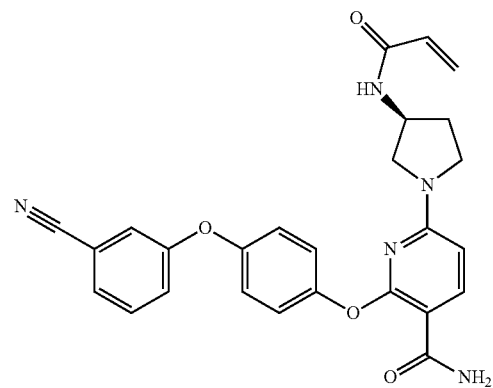 [SMILES: C=CC(=O)N[C@H]1CCN(c2ccc(C(N)=O)c(Oc3ccc(Oc4cccc(C#N)c4)cc3)n2)C1]
79
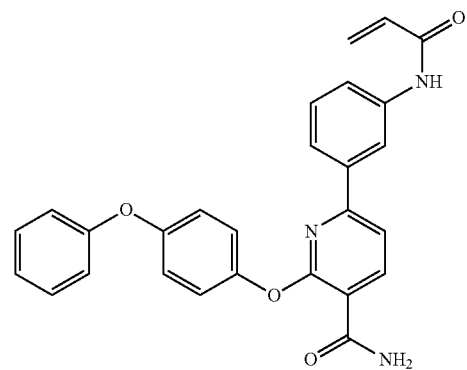 [SMILES: C=CC(=O)Nc1cccc(-c2ccc(C(N)=O)c(Oc3ccc(Oc4ccccc4)cc3)n2)c1]
80

TABLE 1-continued
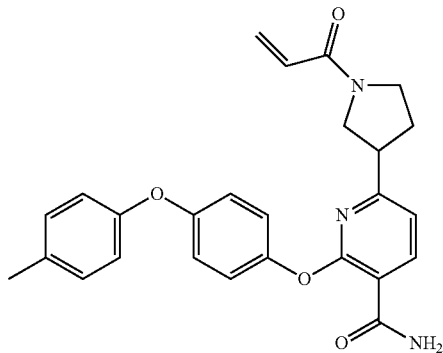
81
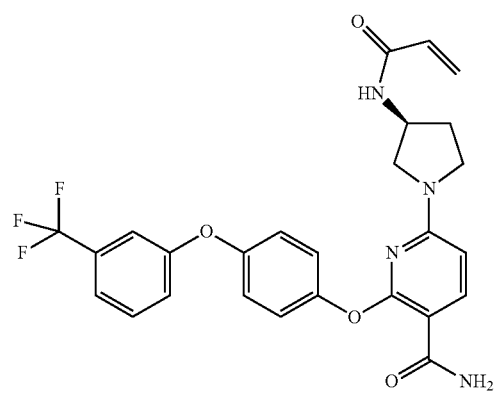 [SMILES: C=CC(=O)N[C@H]1CCN(c2ccc(C(N)=O)c(Oc3ccc(Oc4cccc(C(F)(F)F)c4)cc3)n2)C1]
82
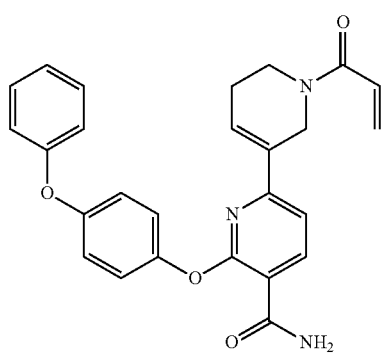 [SMILES: C=CC(=O)N1CCC=C(c2ccc(C(N)=O)c(Oc3ccc(Oc4ccccc4)cc3)n2)C1]
83
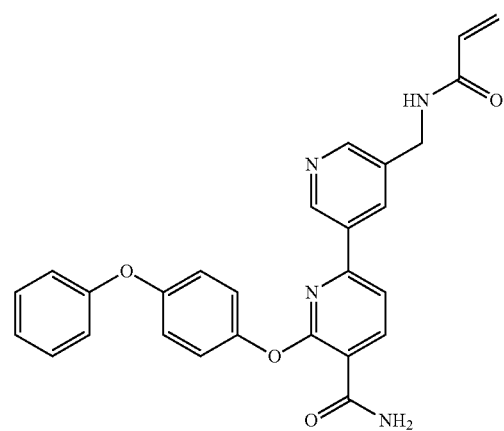
84

TABLE 1-continued
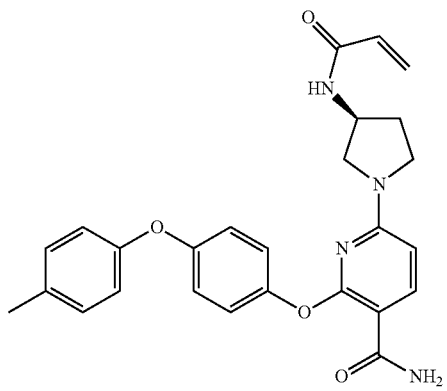 [SMILES: C=CC(=O)N[C@H]1CCN(c2ccc(C(N)=O)c(Oc3ccc(Oc4ccc(C)cc4)cc3)n2)C1]
85
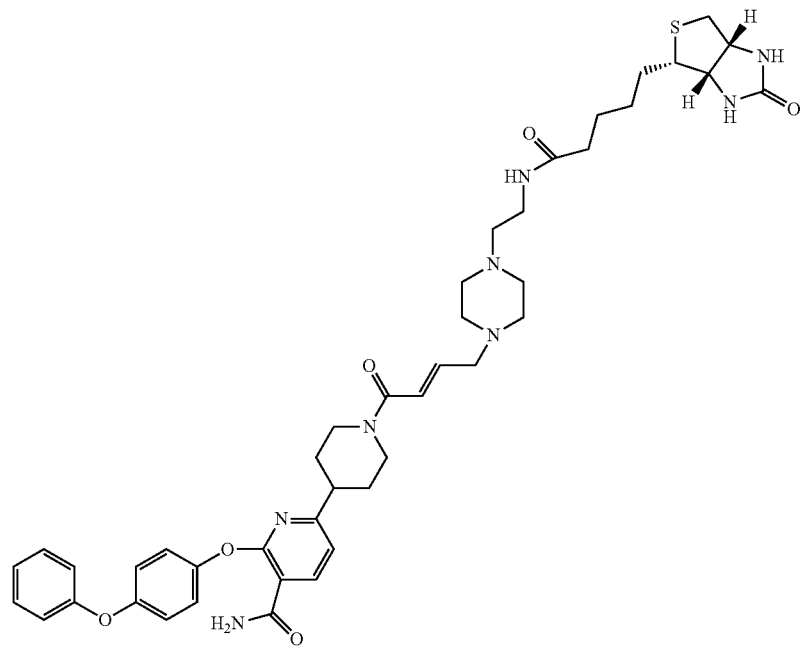 [SMILES: NC(=O)c1ccc(C2CCN(C(=O)/C=C/CN3CCN(CCNC(=O)CCCC[C@@H]4SC[C@@H]5NC(=O)N[C@@H]54)CC3)CC2)nc1Oc1ccc(Oc2ccccc2)cc1]
86
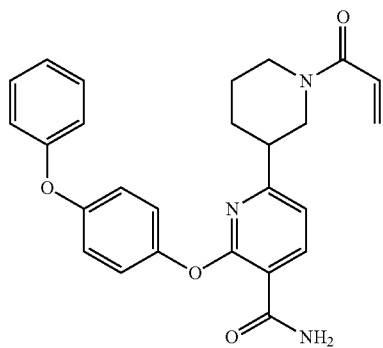 [SMILES: C=CC(=O)N1CCCC(c2ccc(C(N)=O)c(Oc3ccc(Oc4ccccc4)cc3)n2)C1]
87

TABLE 1-continued
| | |
|---|---|
| 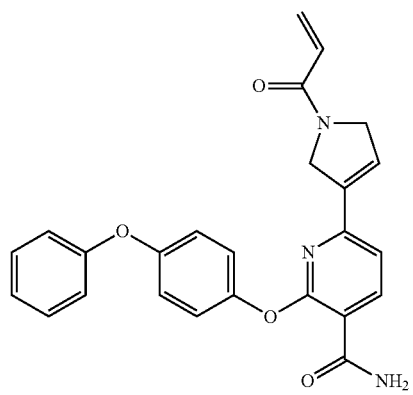 [SMILES: C=CC(=O)N1CC=C(c2ccc(C(N)=O)c(Oc3ccc(Oc4ccccc4)cc3)n2)C1] | 88 |
| 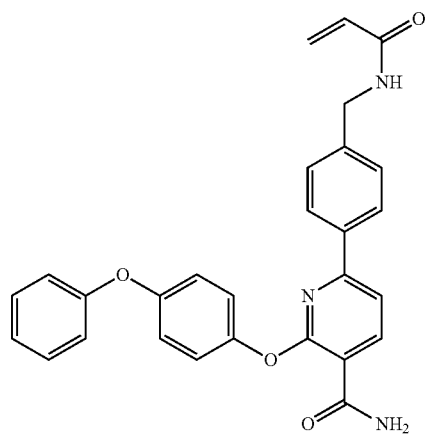 [SMILES: C=CC(=O)NCc1ccc(-c2ccc(C(N)=O)c(Oc3ccc(Oc4ccccc4)cc3)n2)cc1] | 89 |
| 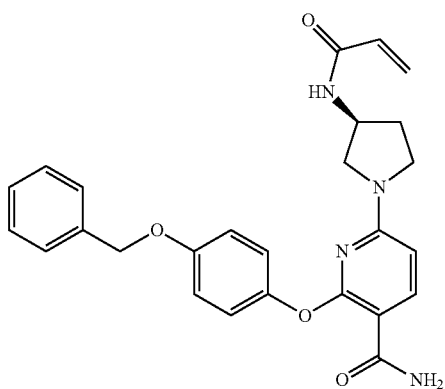 [SMILES: C=CC(=O)N[C@H]1CCN(c2ccc(C(N)=O)c(Oc3ccc(OCc4ccccc4)cc3)n2)C1] | 90 |
| 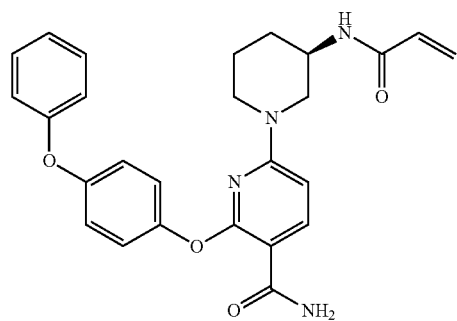 [SMILES: C=CC(=O)N[C@@H]1CCCN(c2ccc(C(N)=O)c(Oc3ccc(Oc4ccccc4)cc3)n2)C1] | 91 |

TABLE 1-continued
| | |
|---|---|
| 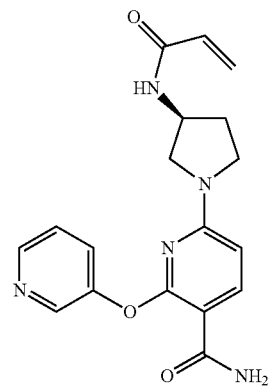 [SMILES: C=CC(=O)N[C@H]1CCN(c2ccc(C(N)=O)c(Oc3cccnc3)n2)C1] | 92 |
| 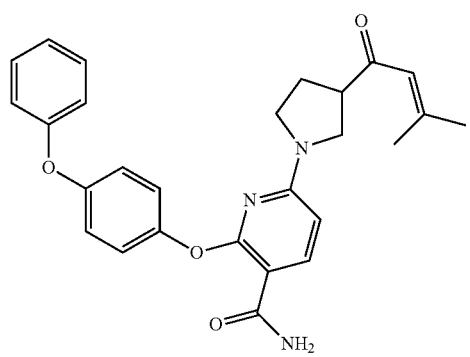 [SMILES: CC(C)=CC(=O)C1CCN(c2ccc(C(N)=O)c(Oc3ccc(Oc4ccccc4)cc3)n2)C1] | 93 |
| 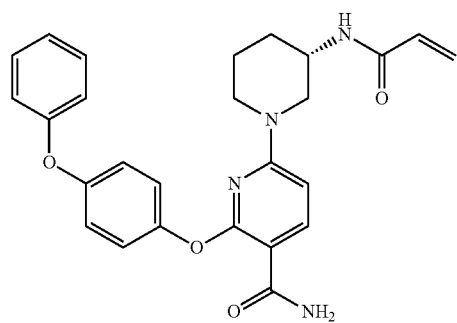 [SMILES: C=CC(=O)N[C@H]1CCCN(c2ccc(C(N)=O)c(Oc3ccc(Oc4ccccc4)cc3)n2)C1] | 94 |
| 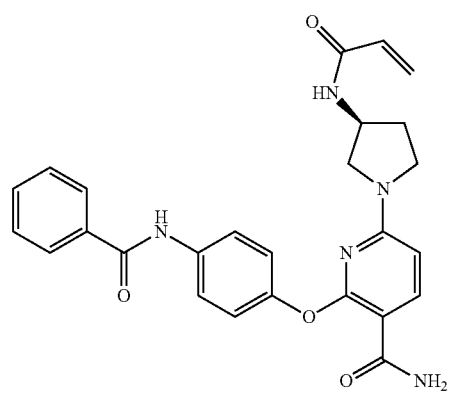 [SMILES: C=CC(=O)N[C@H]1CCN(c2ccc(C(N)=O)c(Oc3ccc(NC(=O)c4ccccc4)cc3)n2)C1] | 95 |

TABLE 1-continued
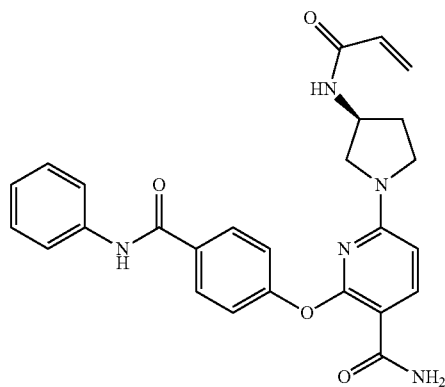 [SMILES: C=CC(=O)N[C@H]1CCN(c2ccc(C(N)=O)c(Oc3ccc(C(=O)Nc4ccccc4)cc3)n2)C1]
96
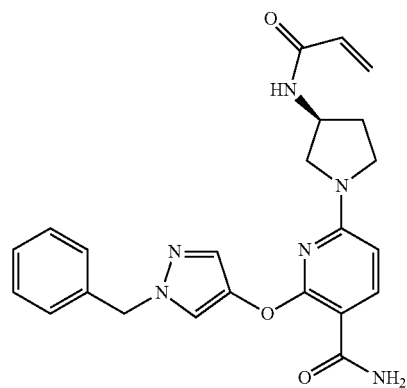 [SMILES: C=CC(=O)N[C@H]1CCN(c2ccc(C(N)=O)c(Oc3cnn(Cc4ccccc4)c3)n2)C1]
97
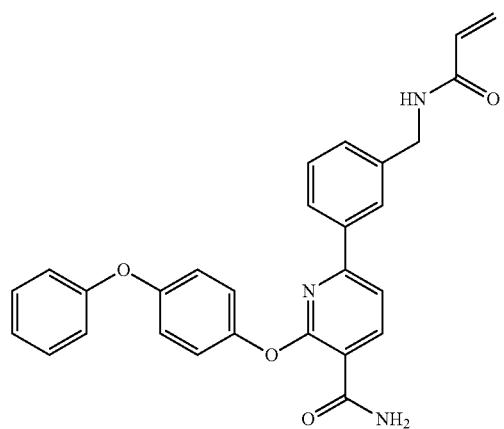 [SMILES: C=CC(=O)NCc1cccc(-c2ccc(C(N)=O)c(Oc3ccc(Oc4ccccc4)cc3)n2)c1]
98
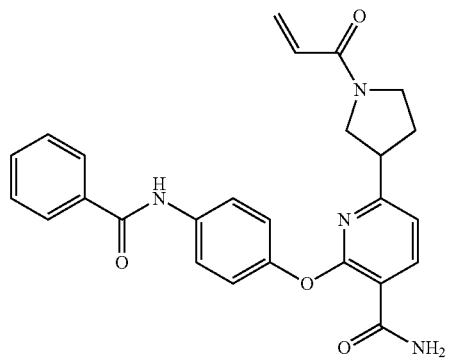 [SMILES: C=CC(=O)N1CCC(c2ccc(C(N)=O)c(Oc3ccc(NC(=O)c4ccccc4)cc3)n2)C1]
99

TABLE 1-continued
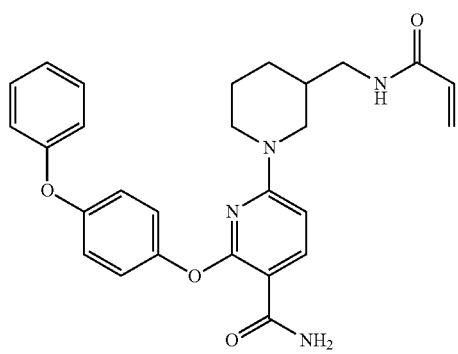 [SMILES: C=CC(=O)NCC1CCCN(c2ccc(C(N)=O)c(Oc3ccc(Oc4ccccc4)cc3)n2)C1]
100
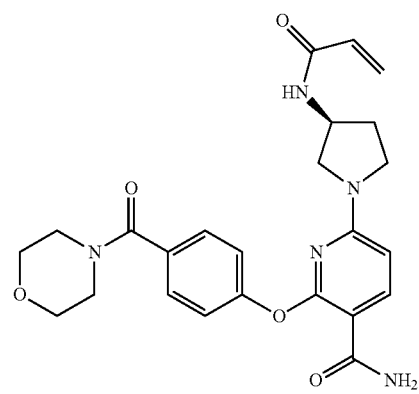 [SMILES: C=CC(=O)N[C@H]1CCN(c2ccc(C(N)=O)c(Oc3ccc(C(=O)N4CCOCC4)cc3)n2)C1]
101
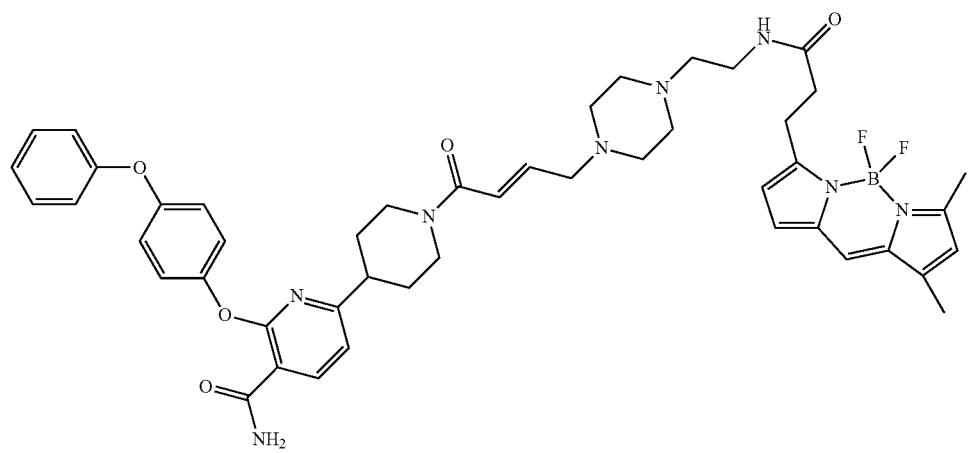
102
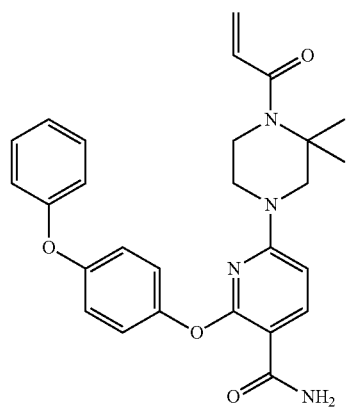 [SMILES: C=CC(=O)N1CCN(c2ccc(C(N)=O)c(Oc3ccc(Oc4ccccc4)cc3)n2)CC1(C)C]
103

TABLE 1-continued
| | |
|---|---|
| 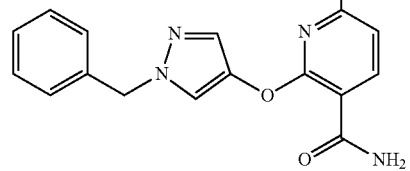 | 104 |
| 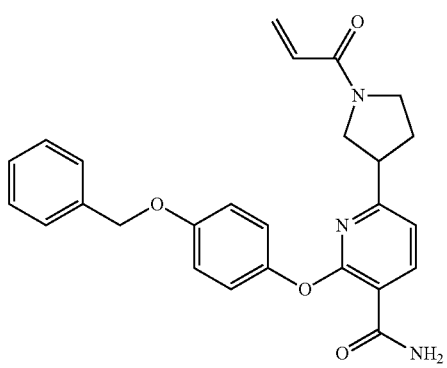 [SMILES: C=CC(=O)N1CCC(c2ccc(C(N)=O)c(Oc3ccc(OCc4ccccc4)cc3)n2)C1] | 105 |
| 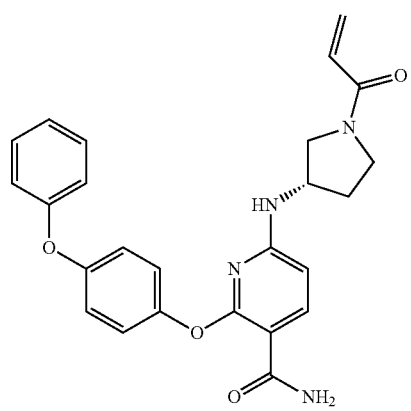 [SMILES: C=CC(=O)N1CC[C@H](Nc2ccc(C(N)=O)c(Oc3ccc(Oc4ccccc4)cc3)n2)C1] | 106 |
| 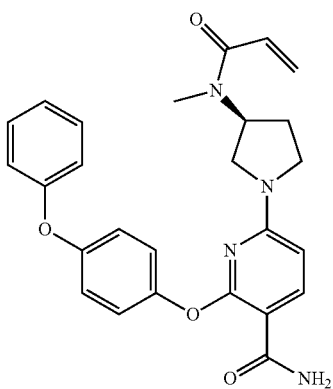 [SMILES: C=CC(=O)N(C)[C@H]1CCN(c2ccc(C(N)=O)c(Oc3ccc(Oc4ccccc4)cc3)n2)C1] | 107 |

TABLE 1-continued
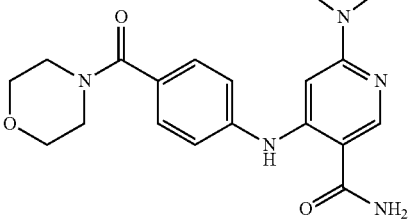
108
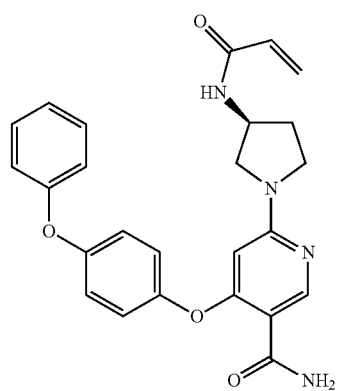 [SMILES: C=CC(=O)N[C@H]1CCN(c2cc(Oc3ccc(Oc4ccccc4)cc3)c(C(N)=O)cn2)C1]
109
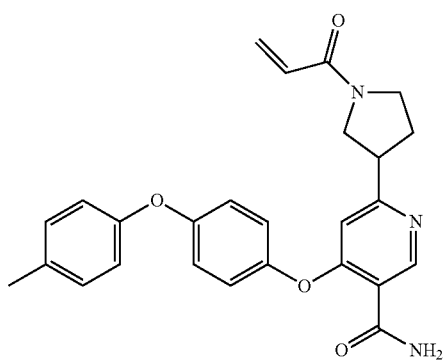
110
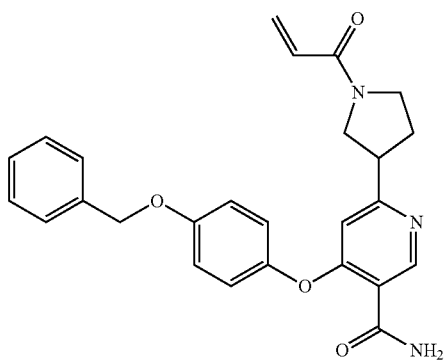 [SMILES: C=CC(=O)N1CCC(c2cc(Oc3ccc(OCc4ccccc4)cc3)c(C(N)=O)cn2)C1]
111

TABLE 1-continued
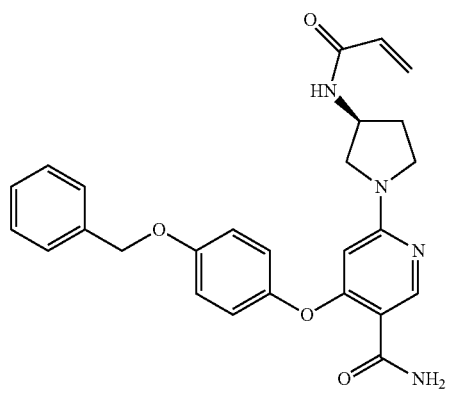 [SMILES: C=CC(=O)N[C@H]1CCN(c2cc(Oc3ccc(OCc4ccccc4)cc3)c(C(N)=O)cn2)C1]
112
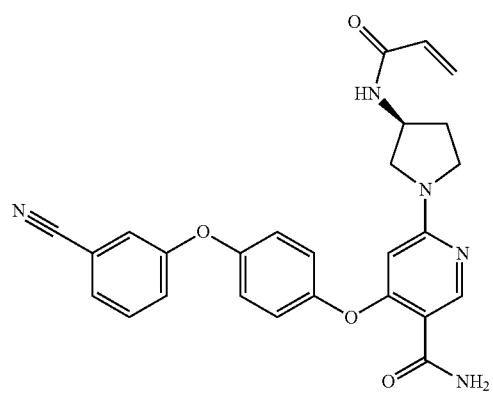 [SMILES: C=CC(=O)N[C@H]1CCN(c2cc(Oc3ccc(Oc4cccc(C#N)c4)cc3)c(C(N)=O)cn2)C1]
113
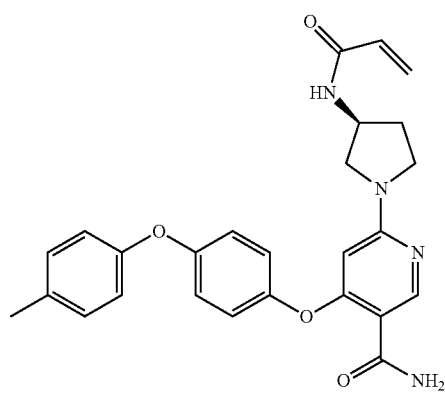 [SMILES: C=CC(=O)N[C@H]1CCN(c2cc(Oc3ccc(Oc4ccc(C)cc4)cc3)c(C(N)=O)cn2)C1]
114
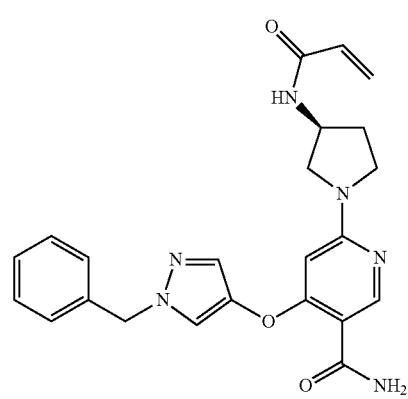
115

TABLE 1-continued
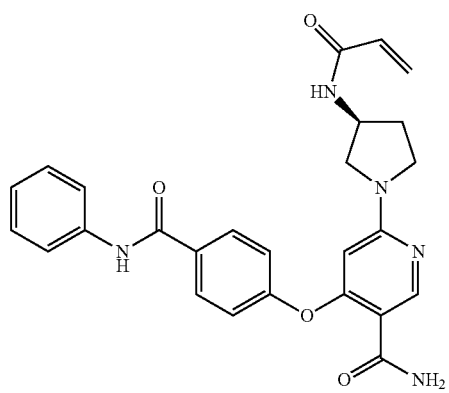 [SMILES: C=CC(=O)N[C@H]1CCN(c2cc(Oc3ccc(C(=O)Nc4ccccc4)cc3)c(C(N)=O)cn2)C1]
116
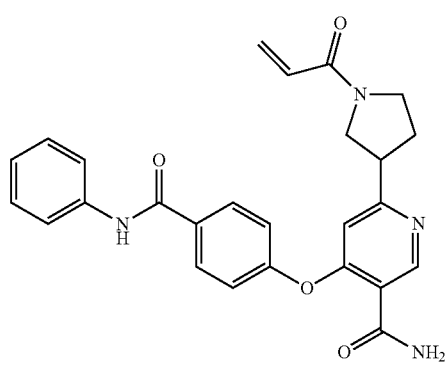 [SMILES: C=CC(=O)N1CCC(c2cc(Oc3ccc(C(=O)Nc4ccccc4)cc3)c(C(N)=O)cn2)C1]
117
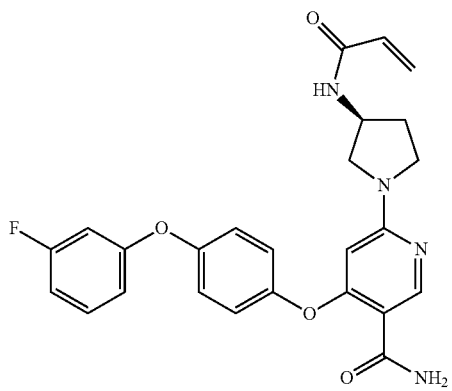
118
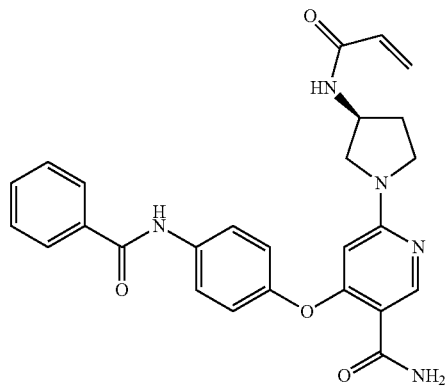 [SMILES: C=CC(=O)N[C@H]1CCN(c2cc(Oc3ccc(NC(=O)c4ccccc4)cc3)c(C(N)=O)cn2)C1]
119

TABLE 1-continued
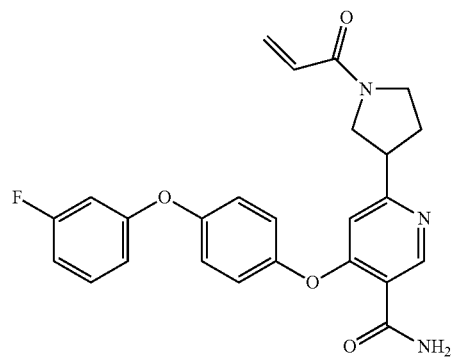 [SMILES: C=CC(=O)N1CCC(c2cc(Oc3ccc(Oc4cccc(F)c4)cc3)c(C(N)=O)cn2)C1]
120
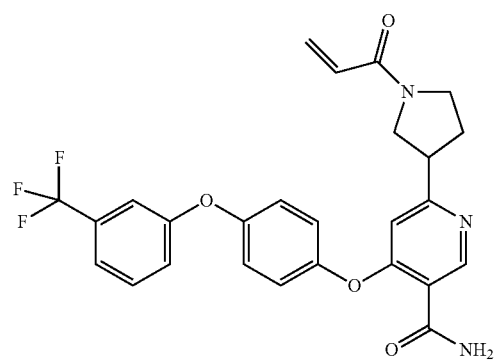 [SMILES: C=CC(=O)N1CCC(c2cc(Oc3ccc(Oc4cccc(C(F)(F)F)c4)cc3)c(C(N)=O)cn2)C1]
121
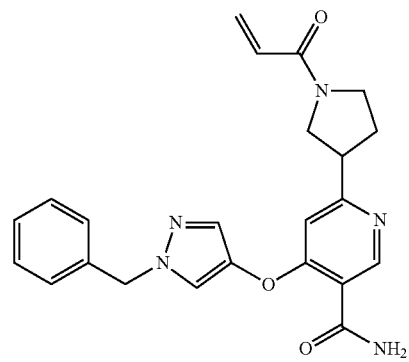 [SMILES: C=CC(=O)N1CCC(c2cc(Oc3cnn(Cc4ccccc4)c3)c(C(N)=O)cn2)C1]
122
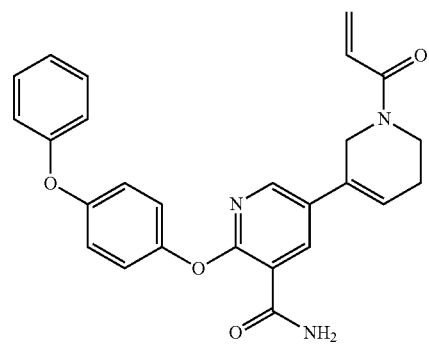 [SMILES: C=CC(=O)N1CCC=C(c2cnc(Oc3ccc(Oc4ccccc4)cc3)c(C(N)=O)c2)C1]
123

TABLE 1-continued
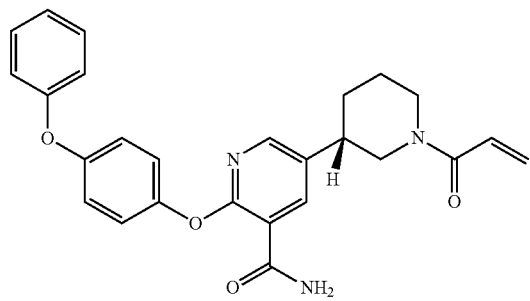 [SMILES: C=CC(=O)N1CCC[C@@H](c2cnc(Oc3ccc(Oc4ccccc4)cc3)c(C(N)=O)c2)C1] 124
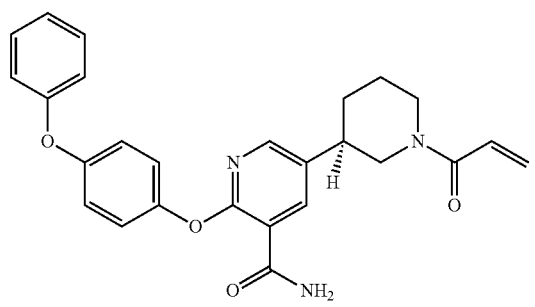 [SMILES: C=CC(=O)N1CCC[C@H](c2cnc(Oc3ccc(Oc4ccccc4)cc3)c(C(N)=O)c2)C1] 125
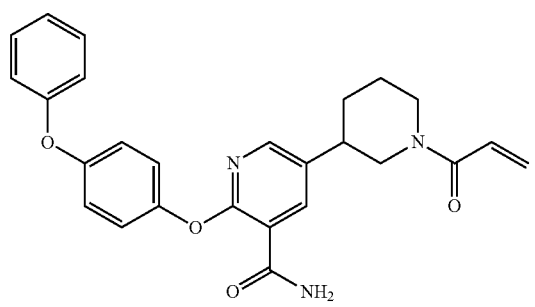 [SMILES: C=CC(=O)N1CCCC(c2cnc(Oc3ccc(Oc4ccccc4)cc3)c(C(N)=O)c2)C1] 126
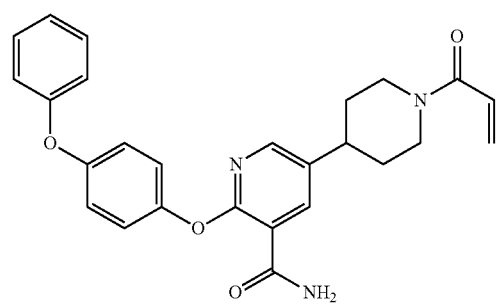 [SMILES: C=CC(=O)N1CCC(c2cnc(Oc3ccc(Oc4ccccc4)cc3)c(C(N)=O)c2)CC1] 127
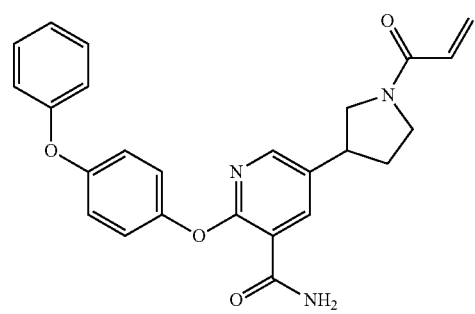 [SMILES: C=CC(=O)N1CCC(c2cnc(Oc3ccc(Oc4ccccc4)cc3)c(C(N)=O)c2)C1] 128

TABLE 1-continued
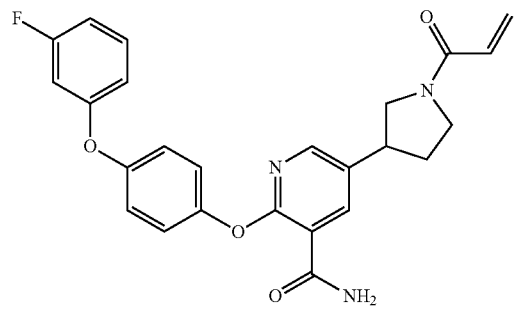
129
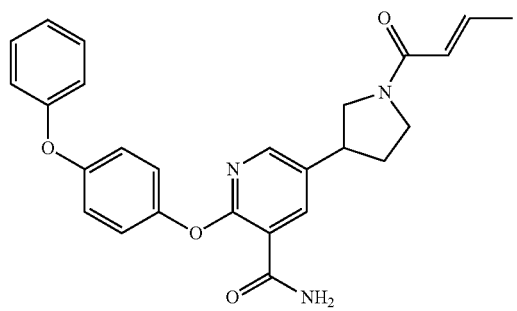 [SMILES: C/C=C/C(=O)N1CCC(c2cnc(Oc3ccc(Oc4ccccc4)cc3)c(C(N)=O)c2)C1]
130
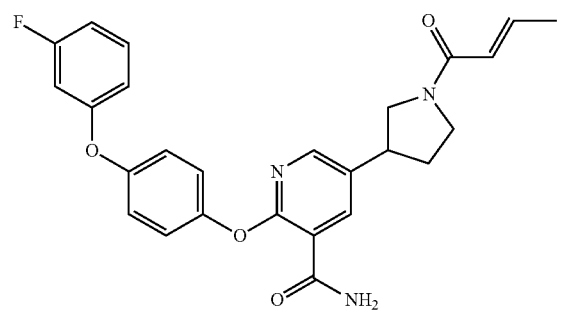 [SMILES: C/C=C/C(=O)N1CCC(c2cnc(Oc3ccc(Oc4cccc(F)c4)cc3)c(C(N)=O)c2)C1]
131
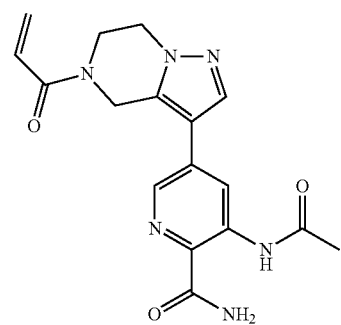 [SMILES: C=CC(=O)N1CCn2ncc(-c3cnc(C(N)=O)c(NC(C)=O)c3)c2C1]
132

TABLE 1-continued
| | |
|---|---|
| 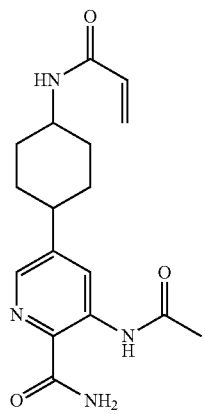 [SMILES: C=CC(=O)NC1CCC(c2cnc(C(N)=O)c(NC(C)=O)c2)CC1] | 133 |
| 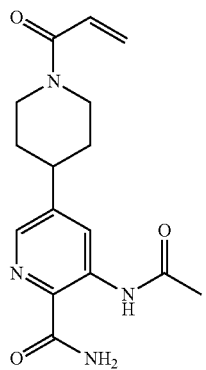 [SMILES: C=CC(=O)N1CCC(c2cnc(C(N)=O)c(NC(C)=O)c2)CC1] | 134 |
| 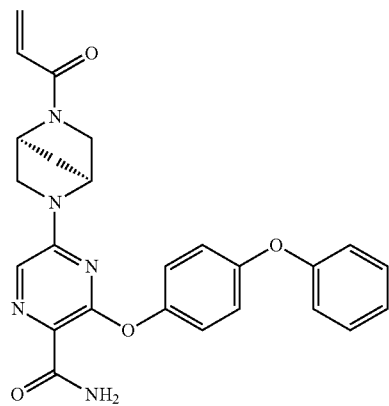 [SMILES: C=CC(=O)N1C[C@@H]2C[C@H]1CN2c1cnc(C(N)=O)c(Oc2ccc(Oc3ccccc3)cc2)n1] | 135 |
| 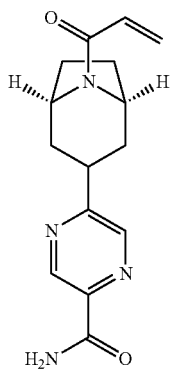 | 136 | ns
TABLE 1-continued
| | |
|---|---|
| 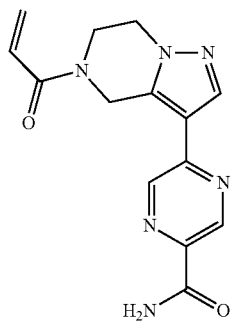 [SMILES: C=CC(=O)N1CCn2ncc(-c3cnc(C(N)=O)cn3)c2C1] | 137 |
| 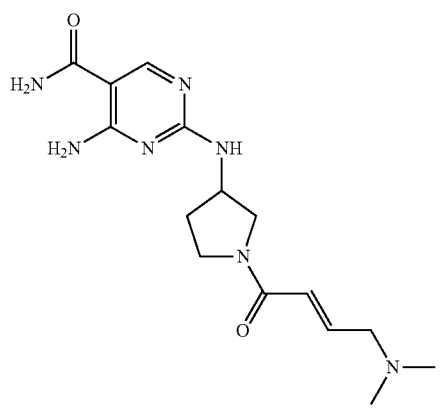 [SMILES: CN(C)C/C=C/C(=O)N1CCC(Nc2ncc(C(N)=O)c(N)n2)C1] | 138 |
| 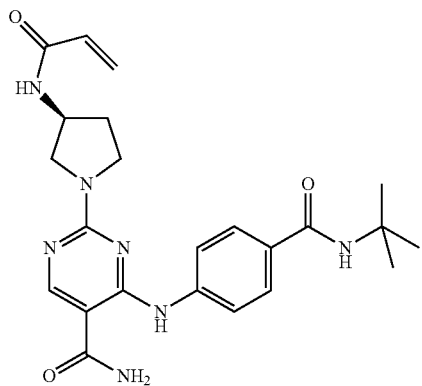 [SMILES: C=CC(=O)N[C@H]1CCN(c2ncc(C(N)=O)c(Nc3ccc(C(=O)NC(C)(C)C)cc3)n2)C1] | 139 |
| 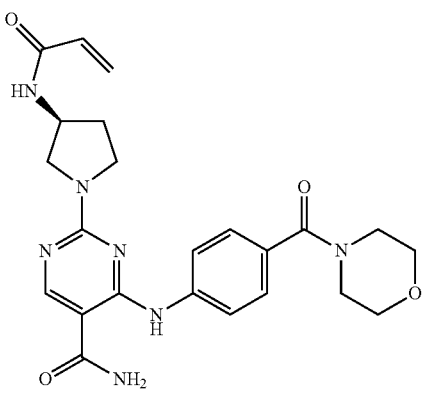 [SMILES: C=CC(=O)N[C@H]1CCN(c2ncc(C(N)=O)c(Nc3ccc(C(=O)N4CCOCC4)cc3)n2)C1] | 140 |

TABLE 1-continued
| | |
|---|---|
| 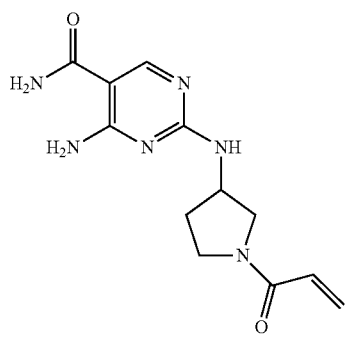 [SMILES: C=CC(=O)N1CCC(Nc2ncc(C(N)=O)c(N)n2)C1] | 141 |
| 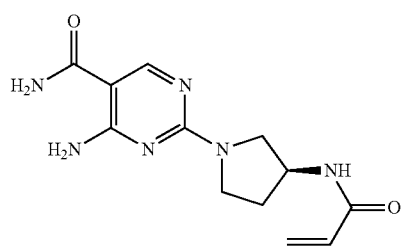 [SMILES: C=CC(=O)N[C@H]1CCN(c2ncc(C(N)=O)c(N)n2)C1] | 142 |
| 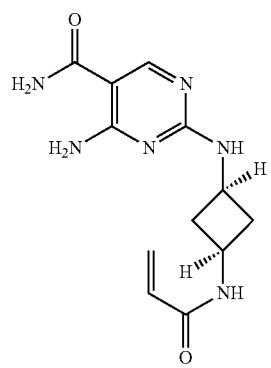 [SMILES: C=CC(=O)N[C@H]1C[C@@H](Nc2ncc(C(N)=O)c(N)n2)C1] | 143 |
| 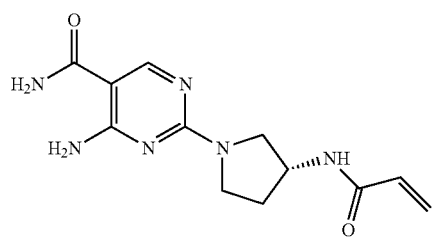 [SMILES: C=CC(=O)N[C@@H]1CCN(c2ncc(C(N)=O)c(N)n2)C1] | 144 |
| 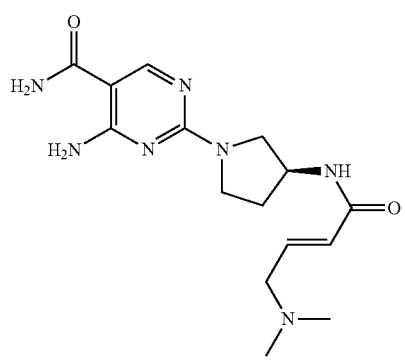 [SMILES: CN(C)C/C=C/C(=O)N[C@H]1CCN(c2ncc(C(N)=O)c(N)n2)C1] | 145 |

TABLE 1-continued
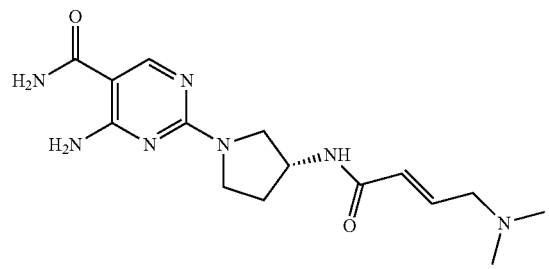 [SMILES: CN(C)C/C=C/C(=O)N[C@@H]1CCN(c2ncc(C(N)=O)c(N)n2)C1]
146
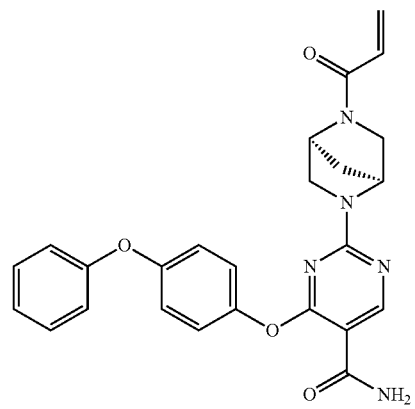 [SMILES: C=CC(=O)N1C[C@@H]2C[C@H]1CN2c1ncc(C(N)=O)c(Oc2ccc(Oc3ccccc3)cc2)n1]
147
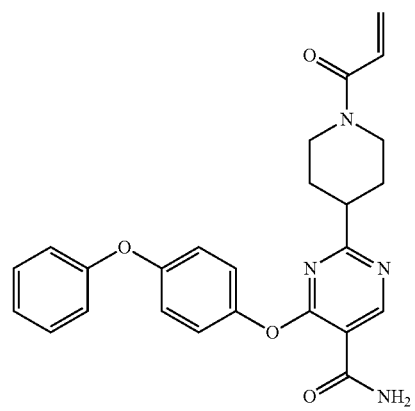 [SMILES: C=CC(=O)N1CCC(c2ncc(C(N)=O)c(Oc3ccc(Oc4ccccc4)cc3)n2)CC1]
148
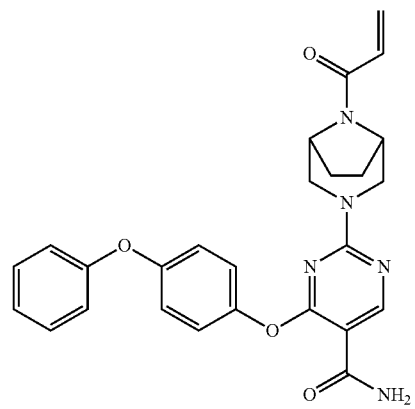 [SMILES: C=CC(=O)N1C2CCC1CN(c1ncc(C(N)=O)c(Oc3ccc(Oc4ccccc4)cc3)n1)C2]
149

TABLE 1-continued
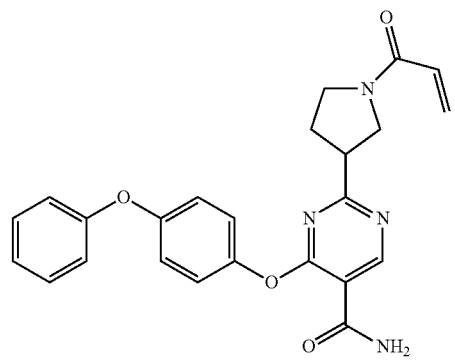 [SMILES: C=CC(=O)N1CCC(c2ncc(C(N)=O)c(Oc3ccc(Oc4ccccc4)cc3)n2)C1]
150
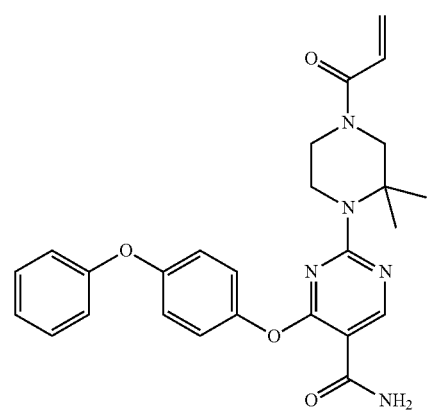 [SMILES: C=CC(=O)N1CCN(c2ncc(C(N)=O)c(Oc3ccc(Oc4ccccc4)cc3)n2)C(C)(C)C1]
151
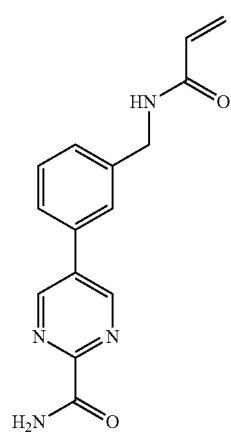
152
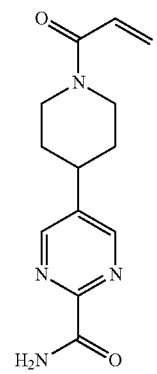 [SMILES: C=CC(=O)N1CCC(c2cnc(C(N)=O)nc2)CC1]
153

TABLE 1-continued
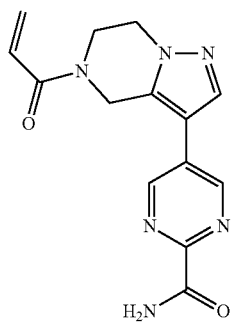 [SMILES: C=CC(=O)N1CCn2ncc(-c3cnc(C(N)=O)nc3)c2C1]
154
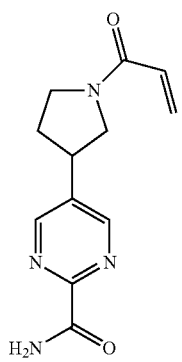
155
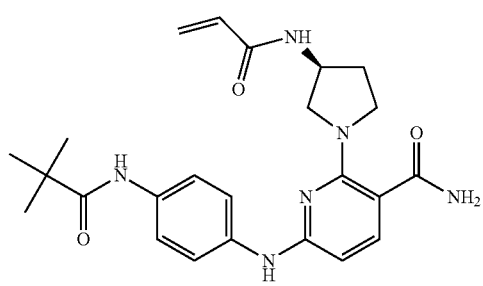 [SMILES: C=CC(=O)N[C@H]1CCN(c2nc(Nc3ccc(NC(=O)C(C)(C)C)cc3)ccc2C(N)=O)C1]
156
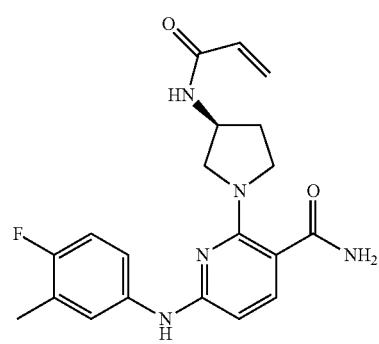 [SMILES: C=CC(=O)N[C@H]1CCN(c2nc(Nc3ccc(F)c(C)c3)ccc2C(N)=O)C1]
157

TABLE 1-continued
| | |
|---|---|
| 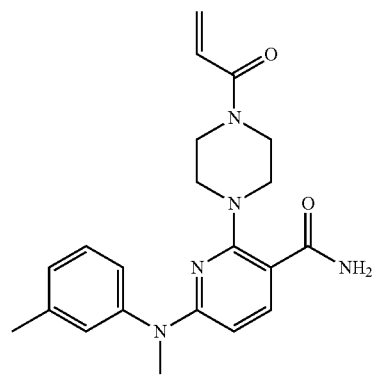 [SMILES: C=CC(=O)N1CCN(c2nc(N(C)c3cccc(C)c3)ccc2C(N)=O)CC1] | 158 |
| 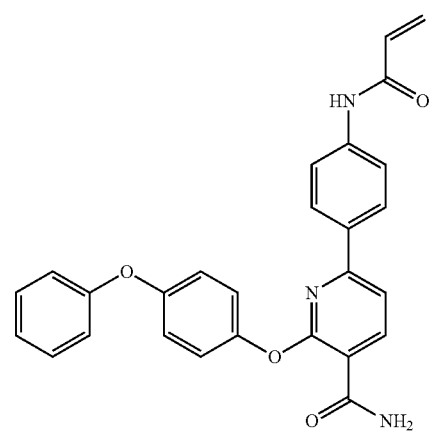 | 159 |
| 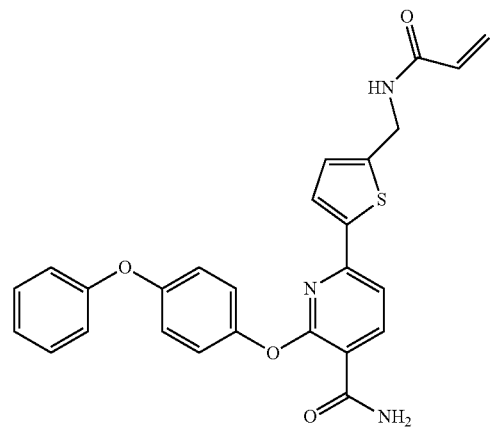 [SMILES: C=CC(=O)NCc1ccc(-c2ccc(C(N)=O)c(Oc3ccc(Oc4ccccc4)cc3)n2)o1] | 160 |

TABLE 1-continued
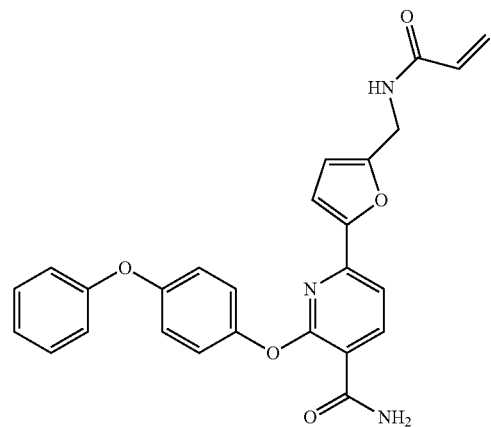
161
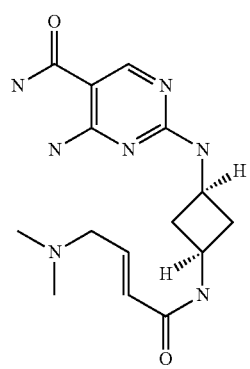 [SMILES: CN(C)C/C=C/C(=O)N[C@H]1C[C@@H](Nc2ncc(C(N)=O)c(N)n2)C1]
162
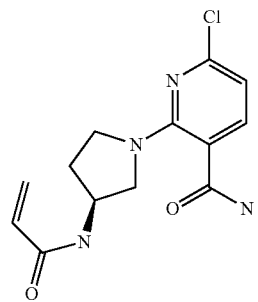 [SMILES: C=CC(=O)N[C@H]1CCN(c2nc(Cl)ccc2C(N)=O)C1]
163
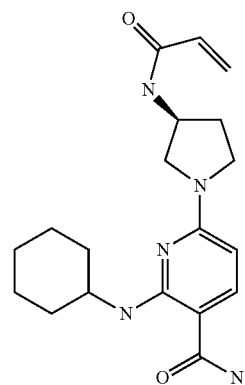 [SMILES: C=CC(=O)N[C@H]1CCN(c2ccc(C(N)=O)c(NC3CCCCC3)n2)C1]
164

TABLE 1-continued
| | |
|---|---|
| 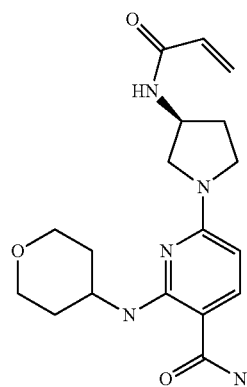 [SMILES: C=CC(=O)N[C@H]1CCN(c2ccc(C(N)=O)c(NC3CCOCC3)n2)C1] | 165 |
| 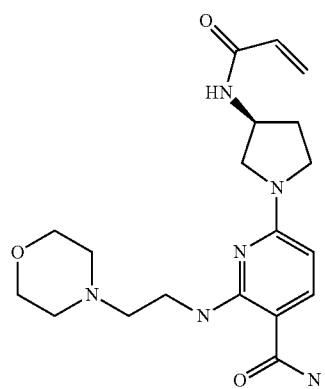 [SMILES: C=CC(=O)N[C@H]1CCN(c2ccc(C(N)=O)c(NCCN3CCOCC3)n2)C1] | 166 |
| 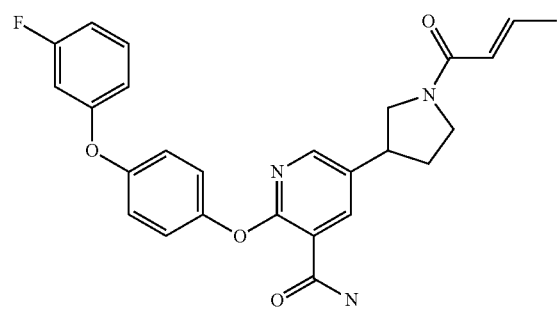 [SMILES: C/C=C/C(=O)N1CCC(c2cnc(Oc3ccc(Oc4cccc(F)c4)cc3)c(C(N)=O)c2)C1] | 167 |
| 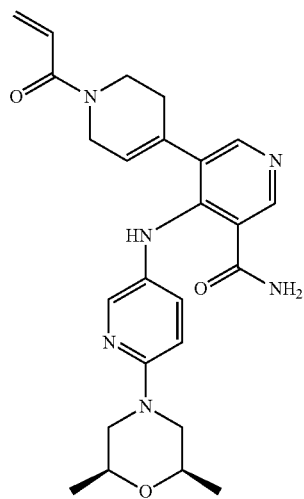 [SMILES: C=CC(=O)N1CC=C(c2cncc(C(N)=O)c2Nc2ccc(N3C[C@@H](C)O[C@@H](C)C3)nc2)CC1] | 168 |

TABLE 1-continued
| | |
|---|---|
| 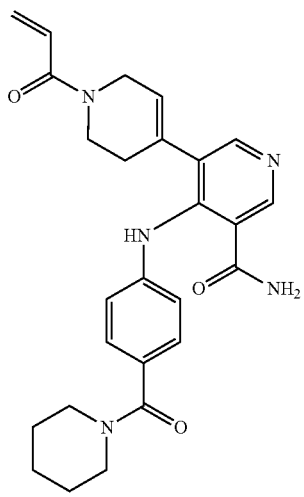 [SMILES: C=CC(=O)N1CC=C(c2cncc(C(N)=O)c2Nc2ccc(C(=O)N3CCCCC3)cc2)CC1] | 169 |
| 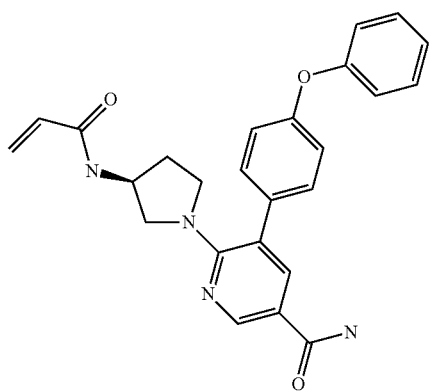 [SMILES: C=CC(=O)N[C@H]1CCN(c2ncc(C(N)=O)cc2-c2ccc(Oc3ccccc3)cc2)C1] | 170 |
| 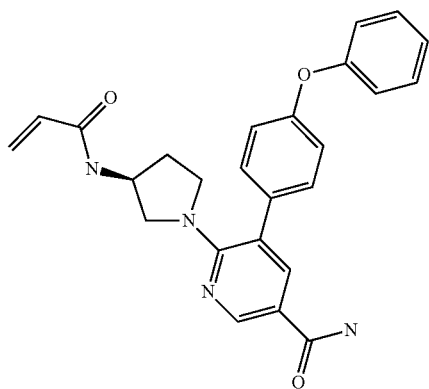 [SMILES: C=CC(=O)N[C@H]1CCN(c2ncc(C(N)=O)cc2-c2ccc(Oc3ccccc3)cc2)C1] | 171 |
| 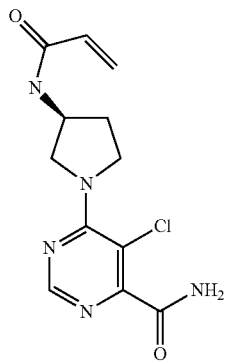 [SMILES: C=CC(=O)N[C@H]1CCN(c2ncnc(C(N)=O)c2Cl)C1] | 172 |

TABLE 1-continued
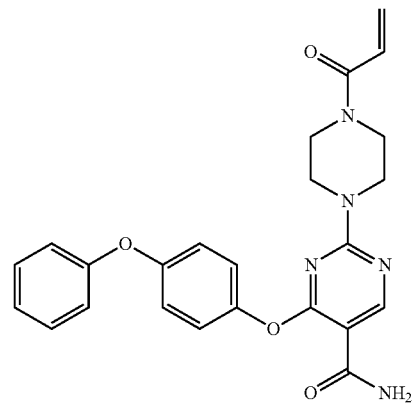
173
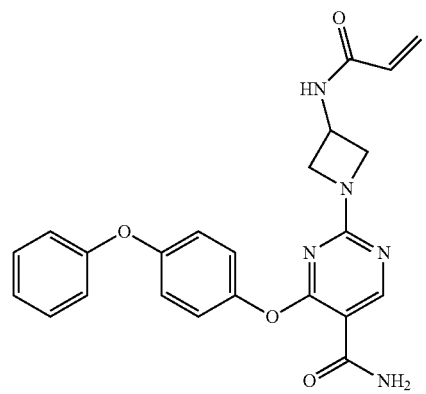 [SMILES: C=CC(=O)NC1CN(c2ncc(C(N)=O)c(Oc3ccc(Oc4ccccc4)cc3)n2)C1]
174
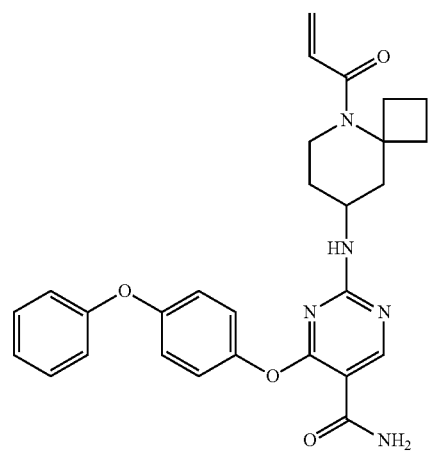 [SMILES: C=CC(=O)N1CCC(Nc2ncc(C(N)=O)c(Oc3ccc(Oc4ccccc4)cc3)n2)CC12CCC2]
175

TABLE 1-continued
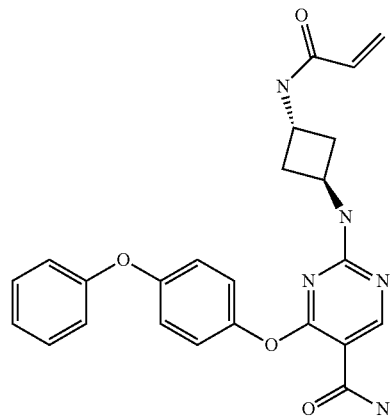 [SMILES: C=CC(=O)N[C@H]1C[C@H](Nc2ncc(C(N)=O)c(Oc3ccc(Oc4ccccc4)cc3)n2)C1]
176
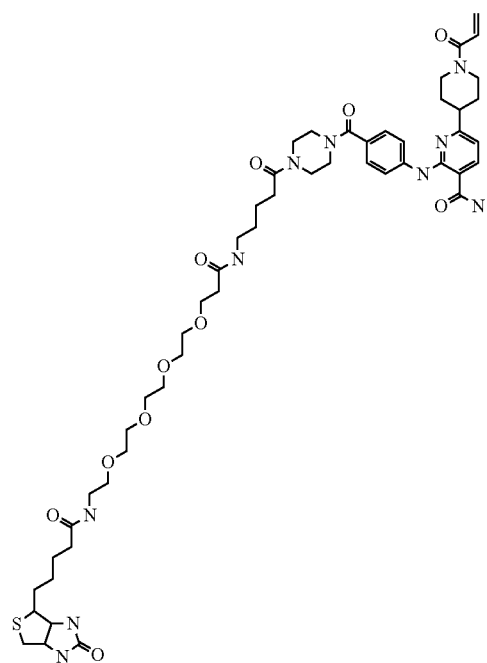 [SMILES: C=CC(=O)N1CCC(c2ccc(C(N)=O)c(Nc3ccc(C(=O)N4CCN(C(=O)CCCCNC(=O)CCOCCOCCOCCOCCNC(=O)CCCCC5SCC6NC(=O)NC65)CC4)cc3)n2)CC1]
177
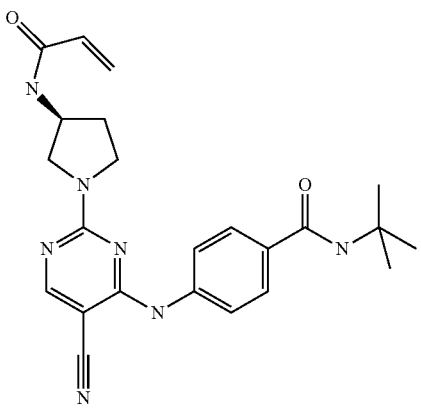 [SMILES: C=CC(=O)N[C@H]1CCN(c2ncc(C#N)c(Nc3ccc(C(=O)NC(C)(C)C)cc3)n2)C1]
178

TABLE 1-continued
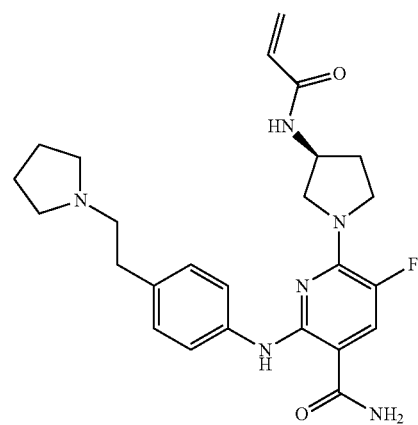 [SMILES: C=CC(=O)N[C@H]1CCN(c2nc(Nc3ccc(CCN4CCCC4)cc3)c(C(N)=O)cc2F)C1]
179
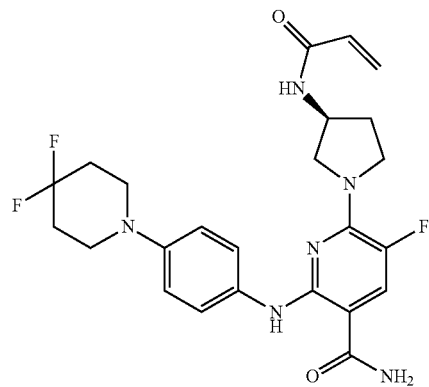 [SMILES: C=CC(=O)N[C@H]1CCN(c2nc(Nc3ccc(N4CCC(F)(F)CC4)cc3)c(C(N)=O)cc2F)C1]
180
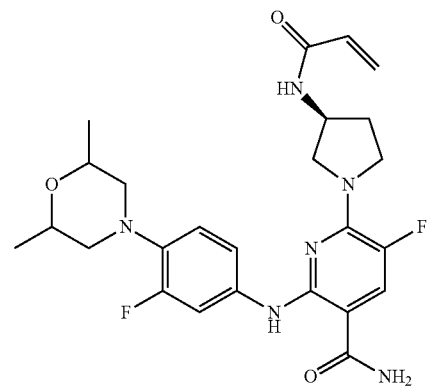 [SMILES: C=CC(=O)N[C@H]1CCN(c2nc(Nc3ccc(N4CC(C)OC(C)C4)c(F)c3)c(C(N)=O)cc2F)C1]
181

TABLE 1-continued
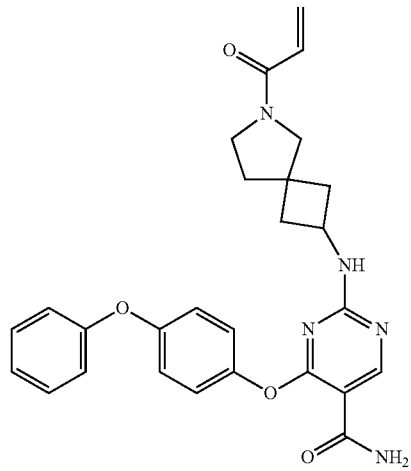 [SMILES: C=CC(=O)N1CCC2(CC(Nc3ncc(C(N)=O)c(Oc4ccc(Oc5ccccc5)cc4)n3)C2)C1]
182
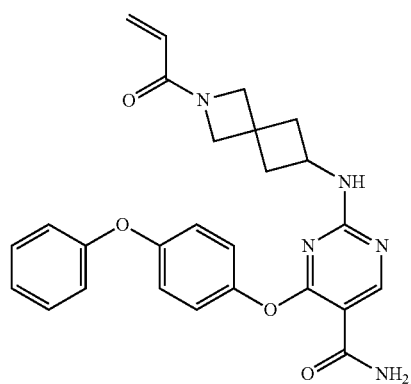 [SMILES: C=CC(=O)N1CC2(CC(Nc3ncc(C(N)=O)c(Oc4ccc(Oc5ccccc5)cc4)n3)C2)C1]
183
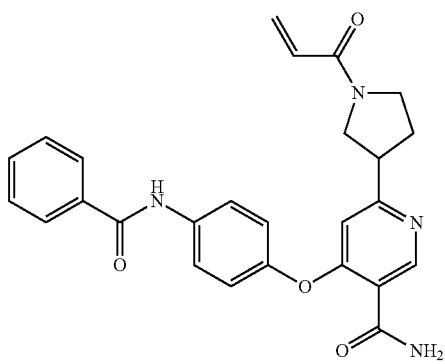 [SMILES: C=CC(=O)N1CCC(c2cc(Oc3ccc(NC(=O)c4ccccc4)cc3)c(C(N)=O)cn2)C1]
184
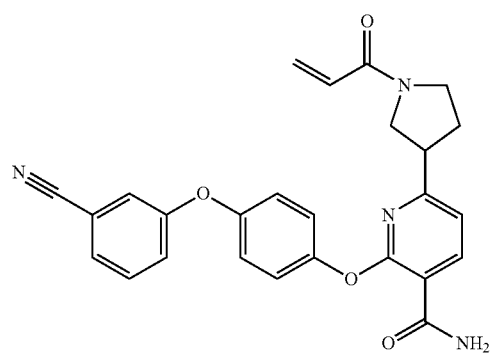 [SMILES: C=CC(=O)N1CCC(c2ccc(C(N)=O)c(Oc3ccc(Oc4cccc(C#N)c4)cc3)n2)C1]
185

TABLE 1-continued
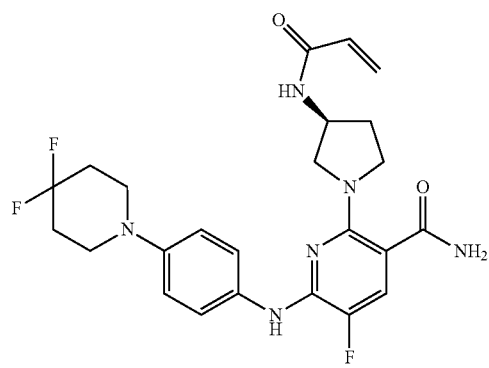 [SMILES: C=CC(=O)N[C@H]1CCN(c2nc(Nc3ccc(N4CCC(F)(F)CC4)cc3)c(F)cc2C(N)=O)C1]
186
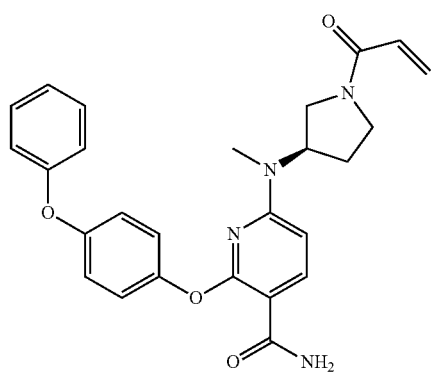 [SMILES: C=CC(=O)N1CC[C@@H](N(C)c2ccc(C(N)=O)c(Oc3ccc(Oc4ccccc4)cc3)n2)C1]
187
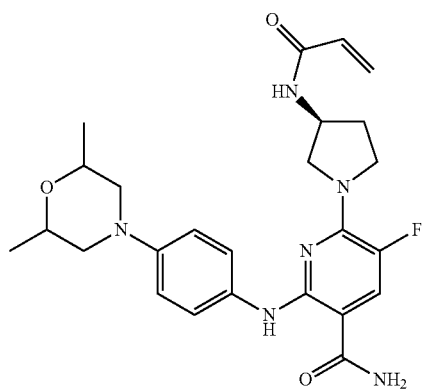 [SMILES: C=CC(=O)N[C@H]1CCN(c2nc(Nc3ccc(N4CC(C)OC(C)C4)cc3)c(C(N)=O)cc2F)C1]
188
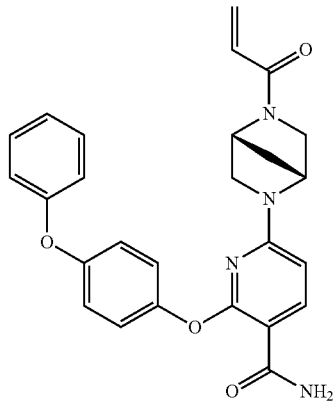 [SMILES: C=CC(=O)N1C[C@H]2C[C@@H]1CN2c1ccc(C(N)=O)c(Oc2ccc(Oc3ccccc3)cc2)n1]
189

TABLE 1-continued
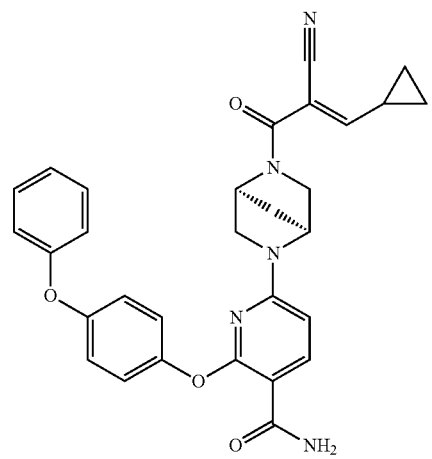 [SMILES: N#C/C(=C\C1CC1)C(=O)N1C[C@@H]2C[C@H]1CN2c1ccc(C(N)=O)c(Oc2ccc(Oc3ccccc3)cc2)n1]
190
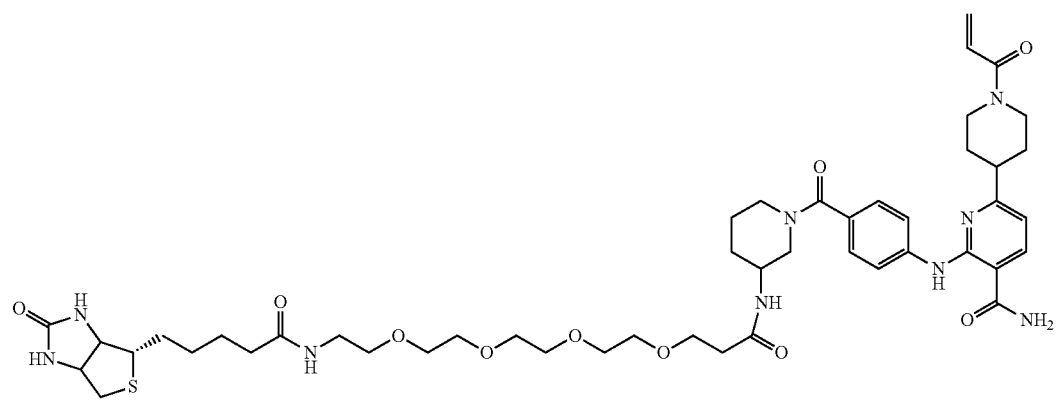 [SMILES: C=CC(=O)N1CCC(c2ccc(C(N)=O)c(Nc3ccc(C(=O)N4CCCC(NC(=O)CCOCCOCCOCCOCCNC(=O)CCCC[C@@H]5SCC6NC(=O)NC65)C4)cc3)n2)CC1]
191
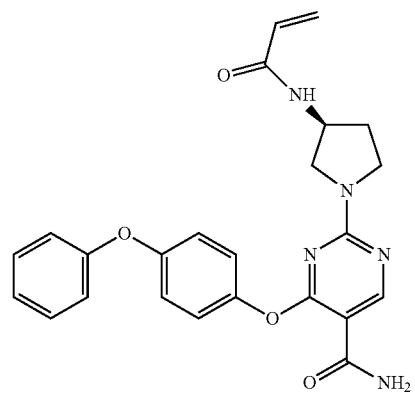 [SMILES: C=CC(=O)N[C@H]1CCN(c2ncc(C(N)=O)c(Oc3ccc(Oc4ccccc4)cc3)n2)C1]
192
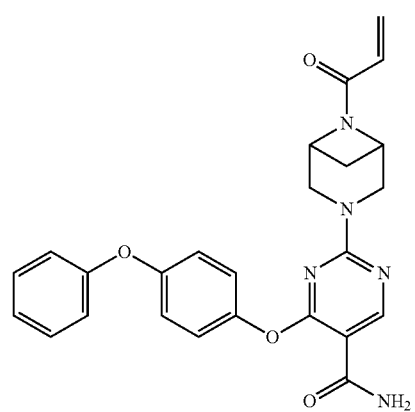 [SMILES: C=CC(=O)N1C2CC1CN(c1ncc(C(N)=O)c(Oc3ccc(Oc4ccccc4)cc3)n1)C2]
193

TABLE 1-continued
| | |
|---|---|
| 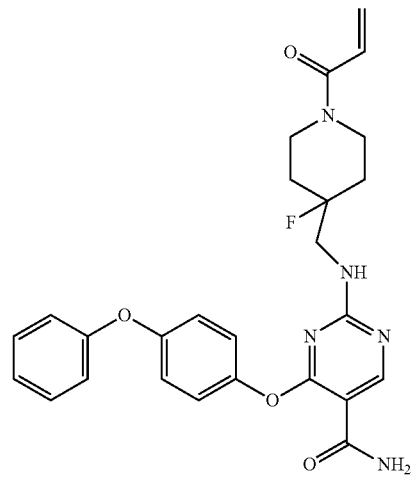 [SMILES: C=CC(=O)N1CCC(F)(CNc2ncc(C(N)=O)c(Oc3ccc(Oc4ccccc4)cc3)n2)CC1] | 194 |
| 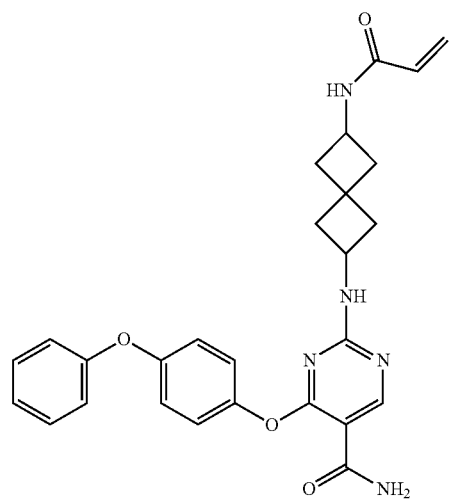 [SMILES: C=CC(=O)NC1CC2(C1)CC(Nc1ncc(C(N)=O)c(Oc3ccc(Oc4ccccc4)cc3)n1)C2] | 195 |
| 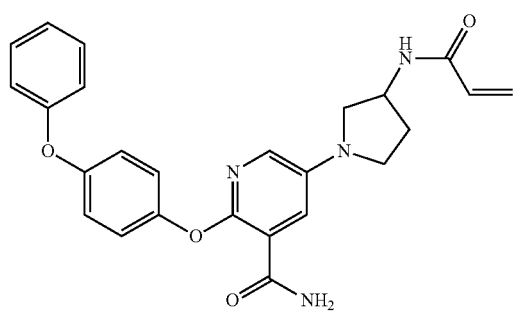 [SMILES: C=CC(=O)NC1CCN(c2cnc(Oc3ccc(Oc4ccccc4)cc3)c(C(N)=O)c2)C1] | 196 |
| 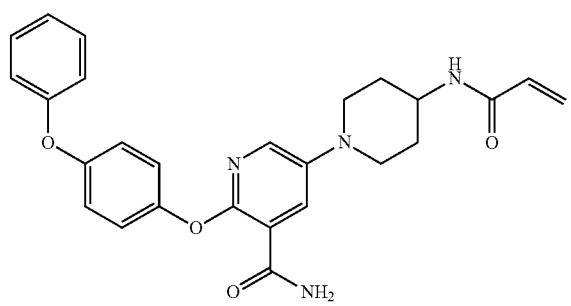 [SMILES: C=CC(=O)NC1CCN(c2cnc(Oc3ccc(Oc4ccccc4)cc3)c(C(N)=O)c2)CC1] | 197 |

TABLE 1-continued
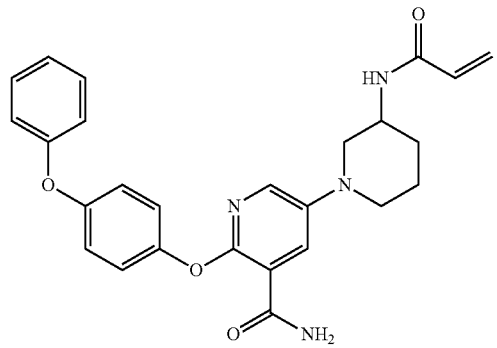 [SMILES: C=CC(=O)NC1CCCN(c2cnc(Oc3ccc(Oc4ccccc4)cc3)c(C(N)=O)c2)C1]
198
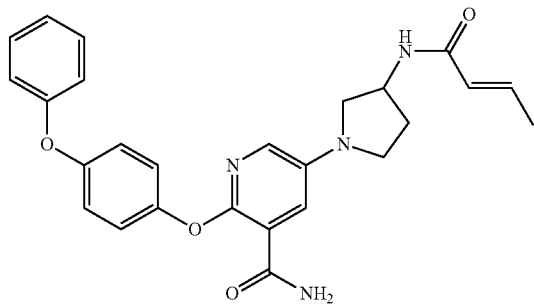 [SMILES: C/C=C/C(=O)NC1CCN(c2cnc(Oc3ccc(Oc4ccccc4)cc3)c(C(N)=O)c2)C1]
199
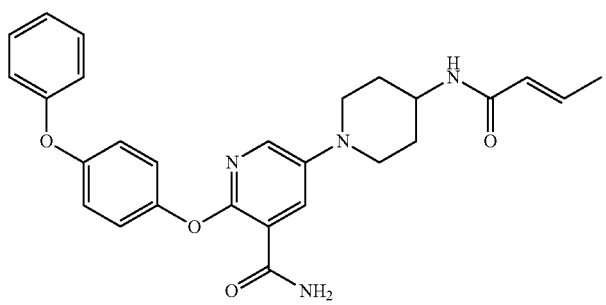 [SMILES: C/C=C/C(=O)NC1CCN(c2cnc(Oc3ccc(Oc4ccccc4)cc3)c(C(N)=O)c2)CC1]
200
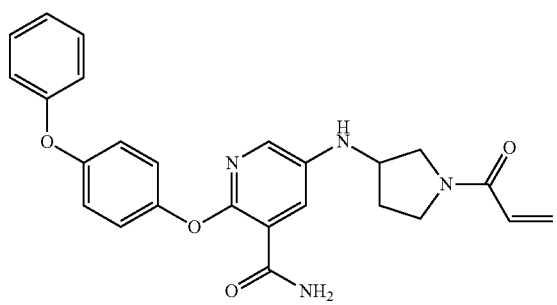 [SMILES: C=CC(=O)N1CCC(Nc2cnc(Oc3ccc(Oc4ccccc4)cc3)c(C(N)=O)c2)C1]
201
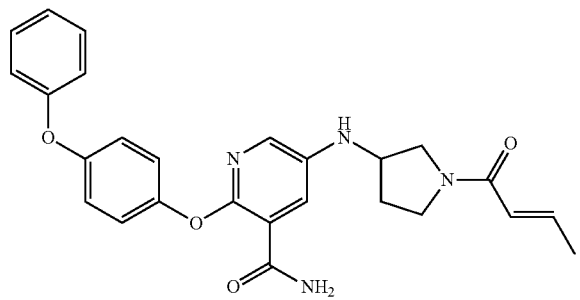 [SMILES: C/C=C/C(=O)N1CCC(Nc2cnc(Oc3ccc(Oc4ccccc4)cc3)c(C(N)=O)c2)C1]
202

TABLE 1-continued
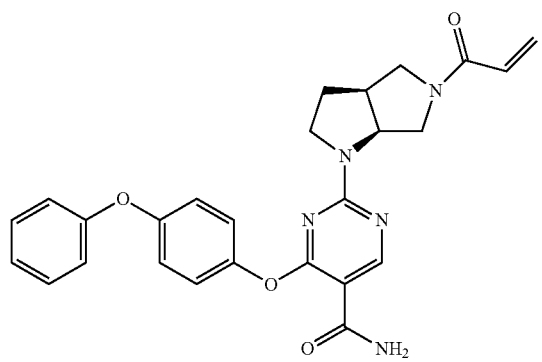 [SMILES: C=CC(=O)N1C[C@@H]2CCN(c3ncc(C(N)=O)c(Oc4ccc(Oc5ccccc5)cc4)n3)[C@@H]2C1]
203
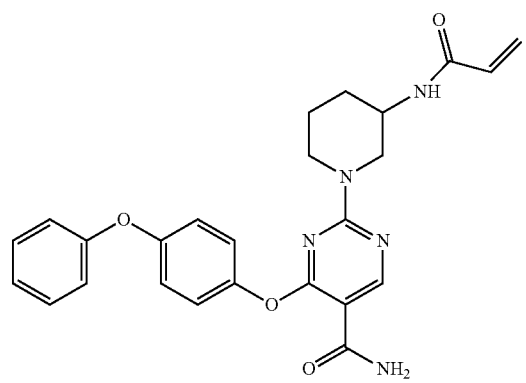 [SMILES: C=CC(=O)NC1CCCN(c2ncc(C(N)=O)c(Oc3ccc(Oc4ccccc4)cc3)n2)C1]
204
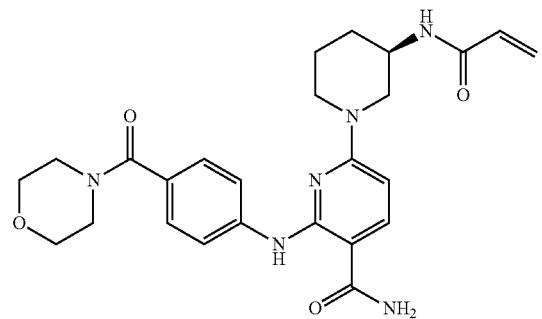 [SMILES: C=CC(=O)N[C@@H]1CCCN(c2ccc(C(N)=O)c(Nc3ccc(C(=O)N4CCOCC4)cc3)n2)C1]
205
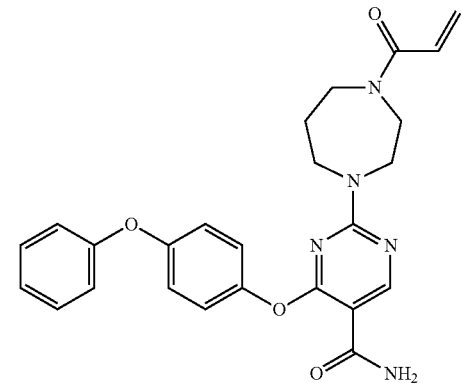 [SMILES: C=CC(=O)N1CCCN(c2ncc(C(N)=O)c(Oc3ccc(Oc4ccccc4)cc3)n2)CC1]
206

TABLE 1-continued
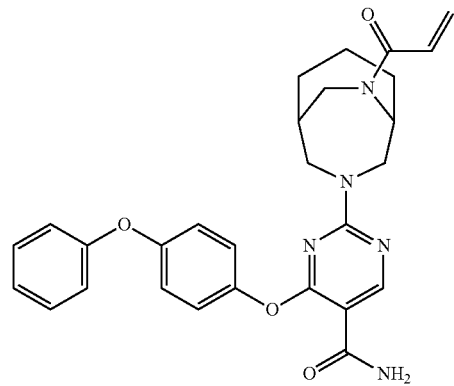 [SMILES: C=CC(=O)N1CC2CCCC1CN(c1ncc(C(N)=O)c(Oc3ccc(Oc4ccccc4)cc3)n1)C2]
208
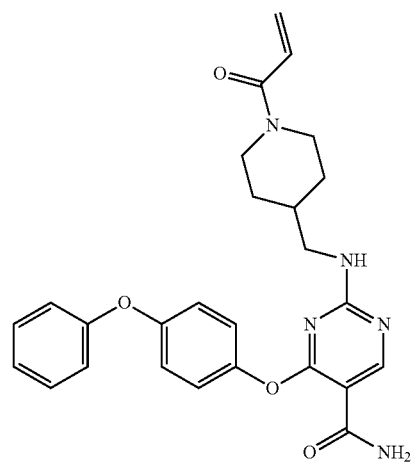 [SMILES: C=CC(=O)N1CCC(CNc2ncc(C(N)=O)c(Oc3ccc(Oc4ccccc4)cc3)n2)CC1]
209
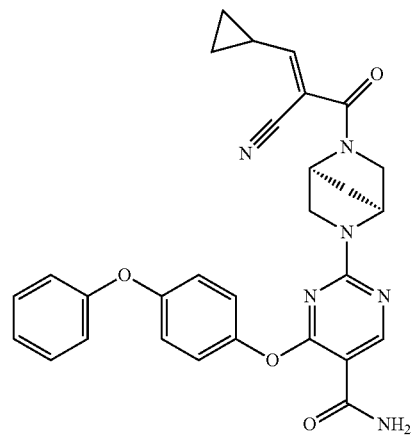 [SMILES: N#C/C(=C\C1CC1)C(=O)N1C[C@@H]2C[C@H]1CN2c1ncc(C(N)=O)c(Oc2ccc(Oc3ccccc3)cc2)n1]
210

TABLE 1-continued
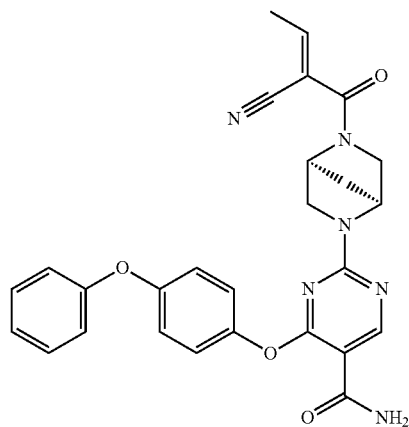 [SMILES: C/C=C(\C#N)C(=O)N1C[C@@H]2C[C@H]1CN2c1ncc(C(N)=O)c(Oc2ccc(Oc3ccccc3)cc2)n1] 211
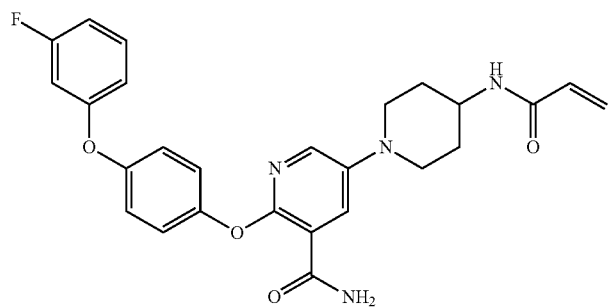 [SMILES: C=CC(=O)NC1CCN(c2cnc(Oc3ccc(Oc4cccc(F)c4)cc3)c(C(N)=O)c2)CC1] 212
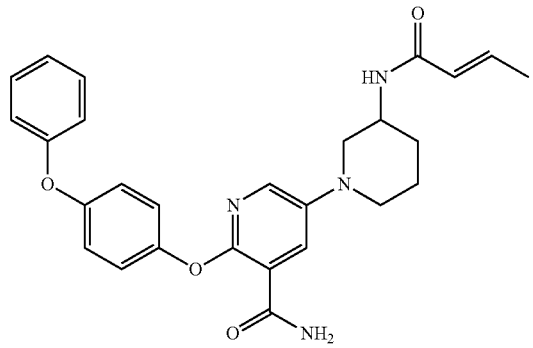 [SMILES: C/C=C/C(=O)NC1CCCN(c2cnc(Oc3ccc(Oc4ccccc4)cc3)c(C(N)=O)c2)C1] 213
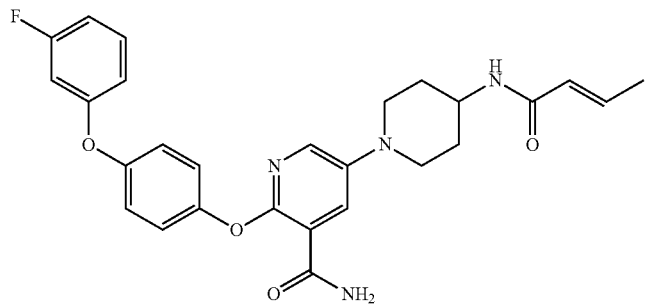 [SMILES: C/C=C/C(=O)NC1CCN(c2cnc(Oc3ccc(Oc4cccc(F)c4)cc3)c(C(N)=O)c2)CC1] 214

TABLE 1-continued
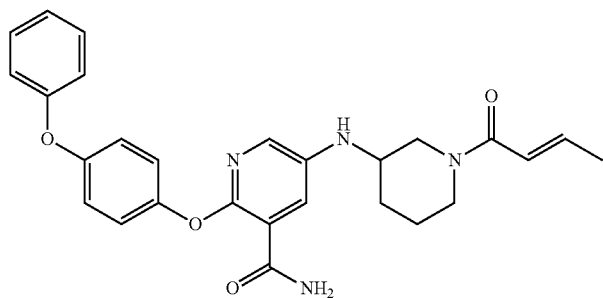 [SMILES: C/C=C/C(=O)N1CCCC(Nc2cnc(Oc3ccc(Oc4ccccc4)cc3)c(C(N)=O)c2)C1]
215
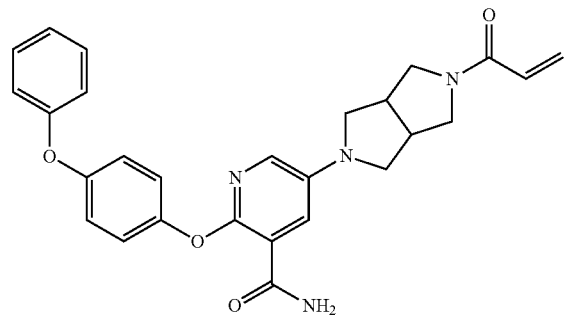 [SMILES: C=CC(=O)N1CC2CN(c3cnc(Oc4ccc(Oc5ccccc5)cc4)c(C(N)=O)c3)CC2C1]
216
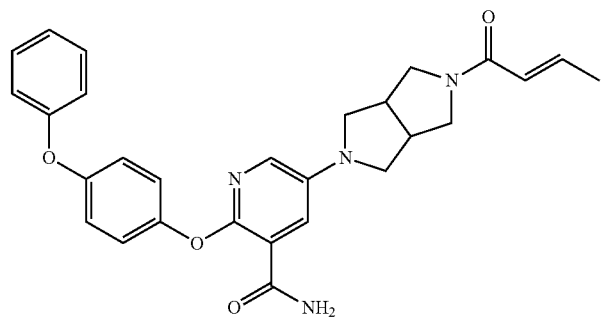 [SMILES: C/C=C/C(=O)N1CC2CN(c3cnc(Oc4ccc(Oc5ccccc5)cc4)c(C(N)=O)c3)CC2C1]
217
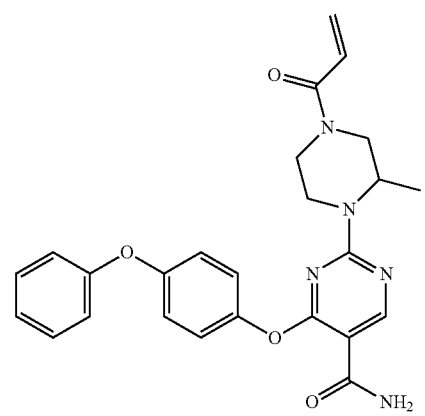 [SMILES: C=CC(=O)N1CCN(c2ncc(C(N)=O)c(Oc3ccc(Oc4ccccc4)cc3)n2)C(C)C1]
218

TABLE 1-continued
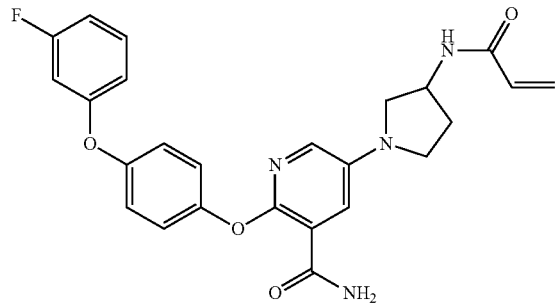 [SMILES: C=CC(=O)NC1CCN(c2cnc(Oc3ccc(Oc4cccc(F)c4)cc3)c(C(N)=O)c2)C1]
219
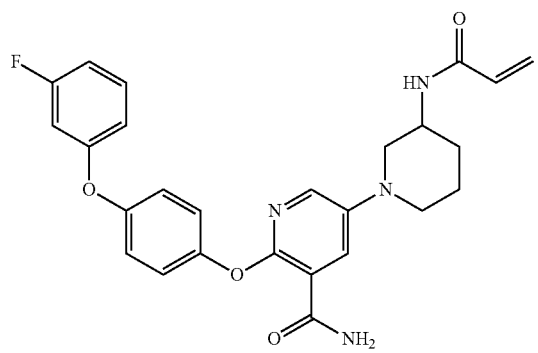 [SMILES: C=CC(=O)NC1CCCN(c2cnc(Oc3ccc(Oc4cccc(F)c4)cc3)c(C(N)=O)c2)C1]
220
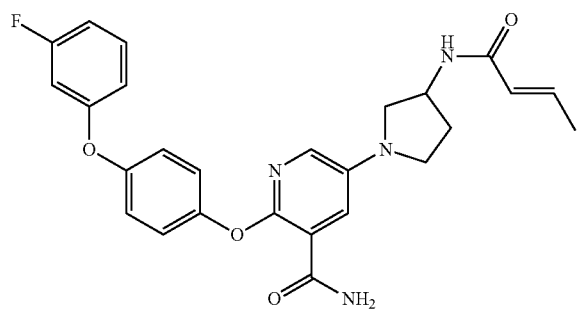 [SMILES: C/C=C/C(=O)NC1CCN(c2cnc(Oc3ccc(Oc4cccc(F)c4)cc3)c(C(N)=O)c2)C1]
221
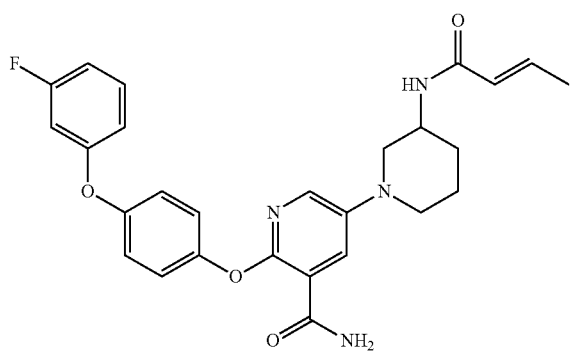 [SMILES: C/C=C/C(=O)NC1CCCN(c2cnc(Oc3ccc(Oc4cccc(F)c4)cc3)c(C(N)=O)c2)C1]
222
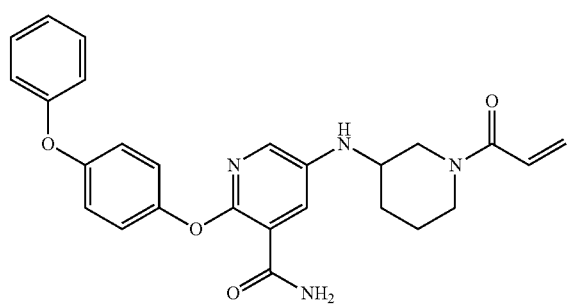 [SMILES: C=CC(=O)N1CCCC(Nc2cnc(Oc3ccc(Oc4ccccc4)cc3)c(C(N)=O)c2)C1]
223

TABLE 1-continued
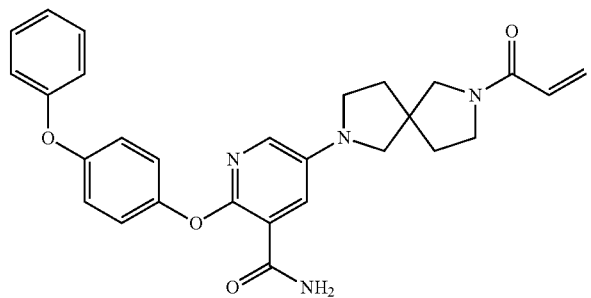 [SMILES: C=CC(=O)N1CCC2(CCN(c3cnc(Oc4ccc(Oc5ccccc5)cc4)c(C(N)=O)c3)C2)C1] 224
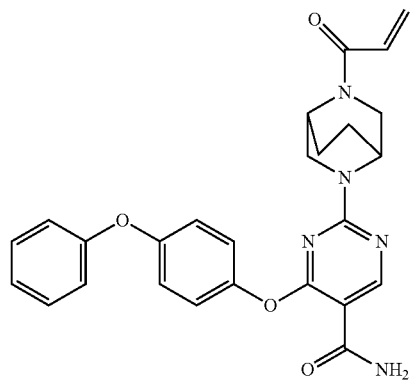 [SMILES: C=CC(=O)N1CC2CCC1CN2c1ncc(C(N)=O)c(Oc2ccc(Oc3ccccc3)cc2)n1] 225
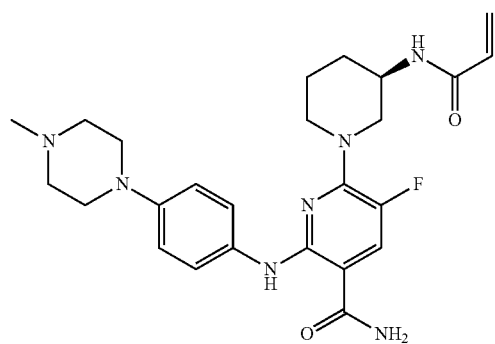 [SMILES: C=CC(=O)N[C@@H]1CCCN(c2nc(Nc3ccc(N4CCN(C)CC4)cc3)c(C(N)=O)cc2F)C1] 226
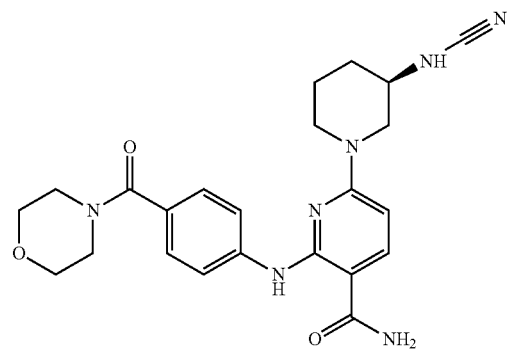 [SMILES: N#CN[C@@H]1CCCN(c2ccc(C(N)=O)c(Nc3ccc(C(=O)N4CCOCC4)cc3)n2)C1] 227

TABLE 1-continued
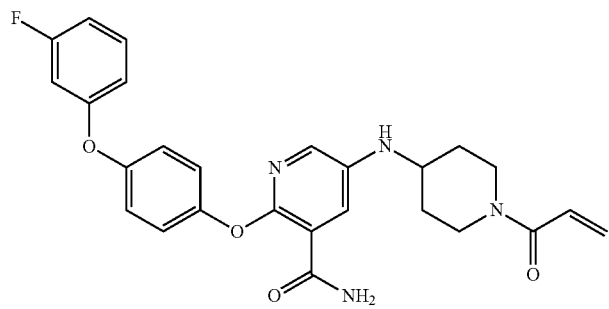 [SMILES: C=CC(=O)N1CCC(Nc2cnc(Oc3ccc(Oc4cccc(F)c4)cc3)c(C(N)=O)c2)CC1]
228
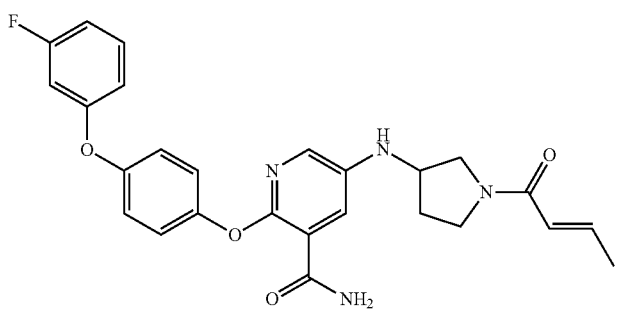 [SMILES: C/C=C/C(=O)N1CCC(Nc2cnc(Oc3ccc(Oc4cccc(F)c4)cc3)c(C(N)=O)c2)C1]
229
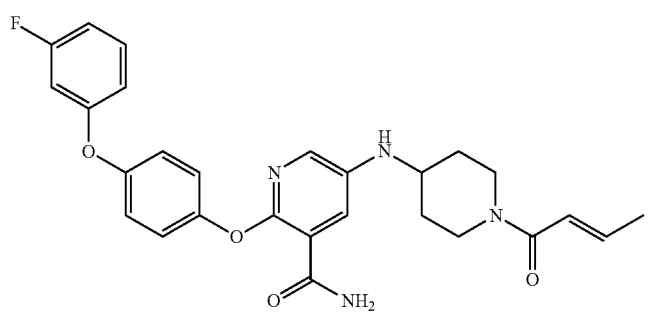 [SMILES: C/C=C/C(=O)N1CCC(Nc2cnc(Oc3ccc(Oc4cccc(F)c4)cc3)c(C(N)=O)c2)CC1]
230
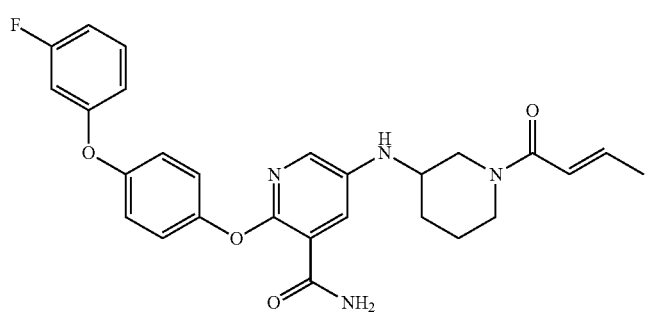 [SMILES: C/C=C/C(=O)N1CCCC(Nc2cnc(Oc3ccc(Oc4cccc(F)c4)cc3)c(C(N)=O)c2)C1]
231
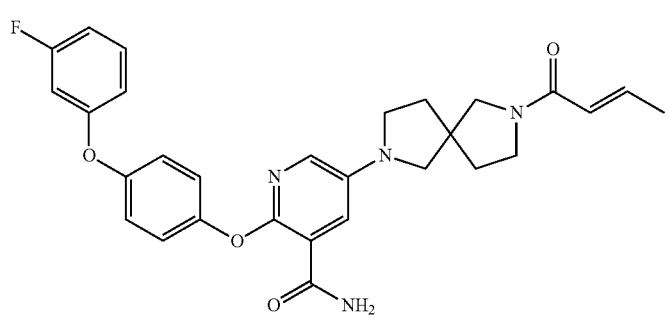 [SMILES: C/C=C/C(=O)N1CCC2(CCN(c3cnc(Oc4ccc(Oc5cccc(F)c5)cc4)c(C(N)=O)c3)C2)C1]
232

TABLE 1-continued
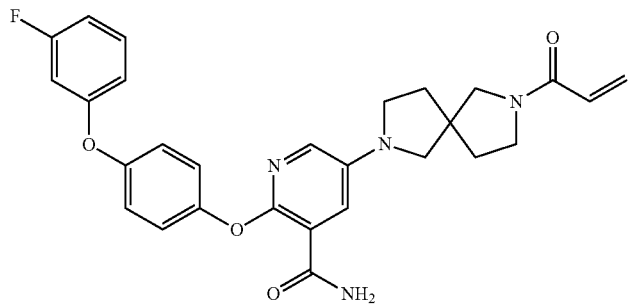 [SMILES: C=CC(=O)N1CCC2(CCN(c3cnc(Oc4ccc(Oc5cccc(F)c5)cc4)c(C(N)=O)c3)C2)C1]
233
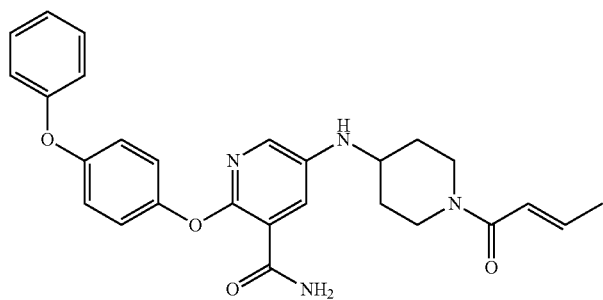 [SMILES: C/C=C/C(=O)N1CCC(Nc2cnc(Oc3ccc(Oc4ccccc4)cc3)c(C(N)=O)c2)CC1]
234
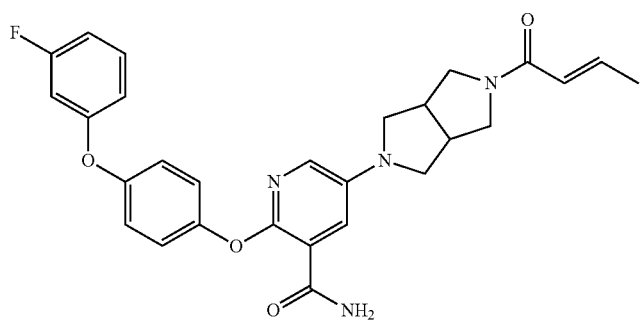 [SMILES: C/C=C/C(=O)N1CC2CN(c3cnc(Oc4ccc(Oc5cccc(F)c5)cc4)c(C(N)=O)c3)CC2C1]
235
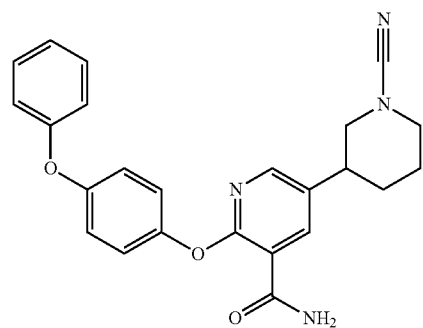
236

TABLE 1-continued
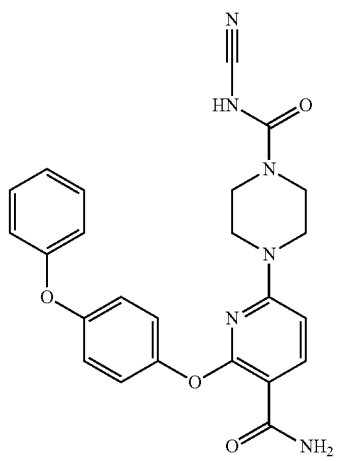 [SMILES: N#CNC(=O)N1CCN(c2ccc(C(N)=O)c(Oc3ccc(Oc4ccccc4)cc3)n2)CC1]
237
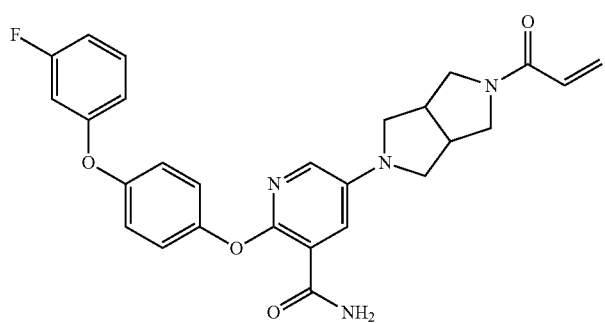 [SMILES: C=CC(=O)N1CC2CN(c3cnc(Oc4ccc(Oc5cccc(F)c5)cc4)c(C(N)=O)c3)CC2C1]
238
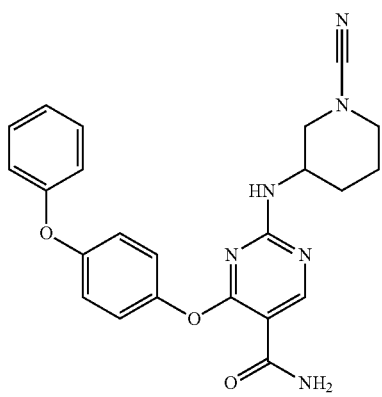 [SMILES: N#CN1CCCC(Nc2ncc(C(N)=O)c(Oc3ccc(Oc4ccccc4)cc3)n2)C1]
239
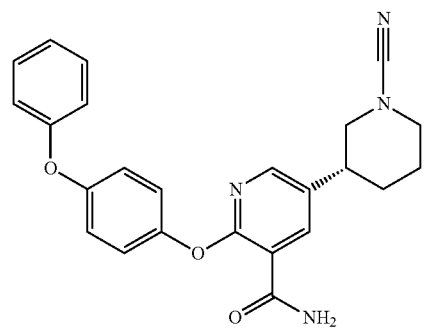 [SMILES: N#CN1CCC[C@H](c2cnc(Oc3ccc(Oc4ccccc4)cc3)c(C(N)=O)c2)C1]
240

TABLE 1-continued
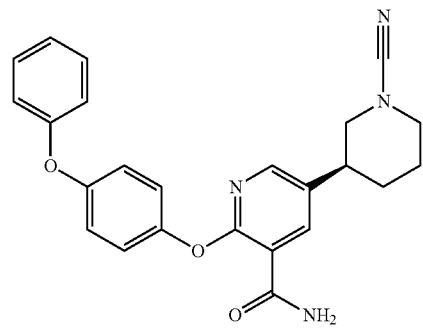 [SMILES: N#CN1CCC[C@@H](c2cnc(Oc3ccc(Oc4ccccc4)cc3)c(C(N)=O)c2)C1]
241
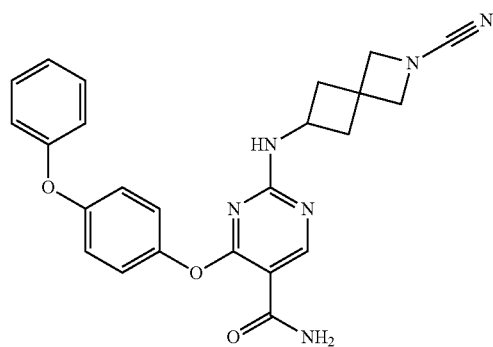 [SMILES: N#CN1CC2(CC(Nc3ncc(C(N)=O)c(Oc4ccc(Oc5ccccc5)cc4)n3)C2)C1]
242
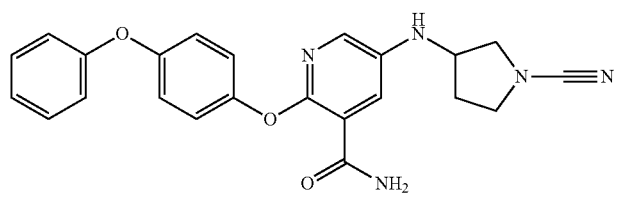 [SMILES: N#CN1CCC(Nc2cnc(Oc3ccc(Oc4ccccc4)cc3)c(C(N)=O)c2)C1]
243
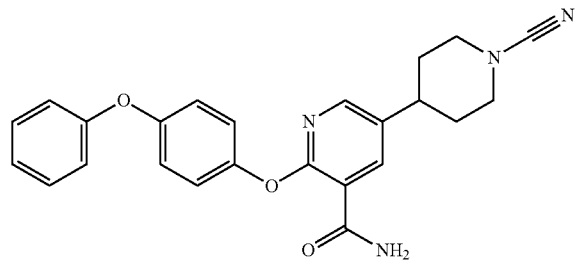 [SMILES: N#CN1CCC(c2cnc(Oc3ccc(Oc4ccccc4)cc3)c(C(N)=O)c2)CC1]
244
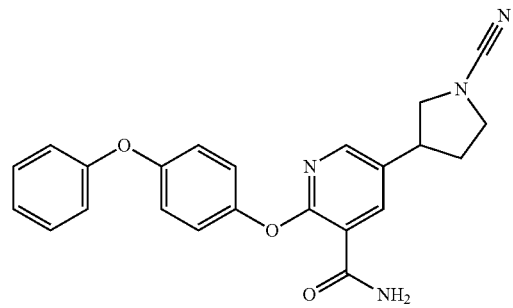 [SMILES: N#CN1CCC(c2cnc(Oc3ccc(Oc4ccccc4)cc3)c(C(N)=O)c2)C1]
245

TABLE 1-continued

| | |
|---|---|
| (structure) | 246 |
| (structure) | 247 |
| (structure) | 248 |
| (structure) | 249 |
| (structure) | 250 |
| (structure) | 251 |

TABLE 1-continued

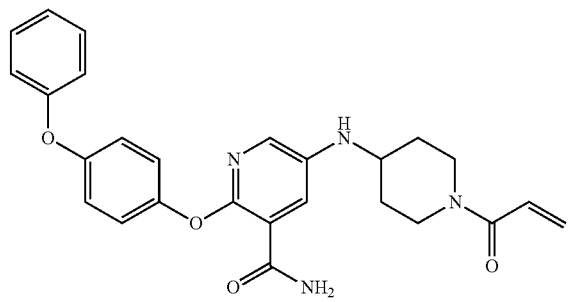 [SMILES: C=CC(=O)N1CCC(Nc2cnc(Oc3ccc(Oc4ccccc4)cc3)c(C(N)=O)c2)CC1]

252

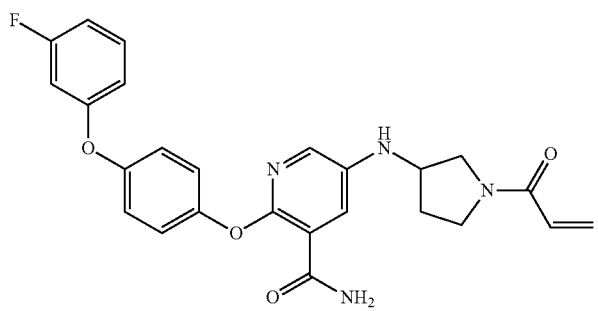 [SMILES: C=CC(=O)N1CCC(Nc2cnc(Oc3ccc(Oc4cccc(F)c4)cc3)c(C(N)=O)c2)C1]

253

As defined generally above, the group "L-Y—R$^1$" is a warhead group. Without wishing to be bound by any particular theory, it is believed that such warhead groups are particularly suitable for covalently binding to a key cysteine residue in the binding domain of certain protein kinases. Protein kinases having a cysteine residue in the binding domain are known to one of ordinary skill in the art and include BTK, or a mutant thereof. Thus, in some embodiments, L-R$^1$ is characterized in that the L-R$^1$ moiety is capable of covalently binding to a cysteine residue thereby irreversibly inhibiting the enzyme. In certain embodiments, the cysteine residue in the kinase domain in the ATP biding site. In certain embodiments, the cysteine residue is Cysteine-481.

In some embodiments, the present invention provides a compound selected from those depicted above, or a pharmaceutically acceptable salt thereof.

Various structural depictions may show a heteroatom without an attached group, radical, charge, or counterion. Those of ordinary skill in the art are aware that such depictions are meant to indicate that the heteroatom is attached to hydrogen (e.g.,

is understood to be

).

In certain embodiments, the compounds of the invention were synthesized in accordance with the schemes provided in the Examples below.

4. Uses, Formulation and Administration
Pharmaceutically Acceptable Compositions According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit BTK, or a mutant thereof, in a biological sample or in a patient. In certain embodiments, the amount of compound in compositions of this invention is such that is effective to measurably inhibit BTK, or a mutant thereof, in a biological sample or in a patient. In certain embodiments, a composition of this invention is formulated for administration to a patient in need of such composition.

The term "patient" or "subject", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that are used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

Compositions of the present invention are administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention include aqueous or oleaginous suspension. These suspensions are formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that are employed are water, Ringer's solution and isotonic sodium chloride solution. In addition, sterile, fixed oils are conventionally employed as a solvent or suspending medium.

For this purpose, any bland fixed oil employed includes synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms are also be used for the purposes of formulation.

Pharmaceutically acceptable compositions of this invention are orally administered in any orally acceptable dosage form. Exemplary oral dosage forms are capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents are optionally also added.

Alternatively, pharmaceutically acceptable compositions of this invention are administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention are also administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches are also used.

For topical applications, provided pharmaceutically acceptable compositions are formulated in a suitable ointment containing the active component suspended or dissolved in one or more carriers. Exemplary carriers for topical administration of compounds of this aremineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

Pharmaceutically acceptable compositions of this invention are optionally administered by nasal aerosol or inhalation. Such compositions are prepared according to techniques well-known in the art of pharmaceutical formulation and are prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that are optionally combined with the carrier materials to produce a composition in a single dosage form will vary depending upon the host treated, the particular mode of administration. Preferably, provided compositions should be formulated so that a dosage of between 0.01-100 mg/kg body weight/day of the compound can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

In certain embodiments, the invention provides a method for inhibiting BTK, or a mutant thereof, in a patient or in a biological sample comprising the step of administering to said patient or contacting said biological sample with a compound according to the invention.

In certain embodiments, the invention is directed to the use of compounds of the invention and/or physiologically acceptable salts thereof, for modulating or inhibiting a BTK enzyme. The term "modulation" denotes any change in BTK-mediated signal transduction, which is based on the action of the specific inventive compounds capable to interact with the BTK target in such a manner that makes recognition, binding and activating possible. The compounds are characterized by such a high affinity to BTK, which ensures a reliable binding of BTK. In certain embodiments, the substances are highly selective for BTK over most other kinases in order to guarantee an exclusive and directed recognition with the single BTK target. In the context of the present invention, the term "recognition"—without being limited thereto—relates to any type of interaction between the specific compounds and the target, particularly covalent or non-covalent binding or association, such as a covalent bond, hydrophobic/hydrophilic interactions, van der Waals forces, ion pairs, hydrogen bonds, ligand-receptor (enzyme-inhibitor) interactions, and the like. Such association may also encompass the presence of other molecules such as peptides, proteins or nucleotide sequences. The present protein/ligand (enzyme-inhibitor)-interaction is characterized by high affinity, high selectivity and minimal or even lacking cross-reactivity to other target molecules to exclude unhealthy and harmful impacts to the treated subject.

In certain embodiments, the present invention relates to a method for inhibiting a BTK enzyme, with at least one compound of formula (I) according to the invention and/or physiologically acceptable salts thereof, under conditions such that said BTK enzyme is inhibited. In certain embodiments, the system is a cellular system. In other embodiments, the system is an in-vitro translation which is based on the protein synthesis without living cells. The cellular system is defined to be any subject provided that the subject comprises cells. Hence, the cellular system can be selected from the group of single cells, cell cultures, tissues, organs and animals. In certain embodiments, the method for modulating a BTK enzyme is performed in-vitro. The prior teaching of the present specification concerning the compounds of formula (I), including any embodiments thereof, is valid and applicable without restrictions to the compounds according to formula (I) and their salts when used in the method for inhibiting BTK. The prior teaching of the present specification concerning the compounds of formula (I), including any embodiments thereof, is valid and applicable without restrictions to the compounds according to formula (I) and their salts when used in the method for inhibiting BTK.

Patients with mutations in BTK have a profound block in B cell development, resulting in the almost complete absence of mature B lymphocytes and plasma cells, severely reduced Ig levels and a profound inhibition of humoral response to recall antigens (reviewed in Vihinen et al Frontiers in Bioscience 5: d917-928). Mice deficient in BTK also have a reduced number of peripheral B cells and greatly decreased serum levels of IgM and IgG3. BTK deletion in mice has a profound effect on B cell proliferation induced by anti-IgM, and inhibits immune responses to thymus-independent type II antigens (Ellmeier et al, J Exp Med 192: 1611-1623 (2000)). BTK also plays a crucial role in mast cell activation through the high-affinity IgE receptor (Fc epsilon RI). BTK deficient murine mast cells have reduced degranulation and decreased production of proinflammatory cytokines following Fc epsilon RI cross-linking (Kawakami et al. Journal of Leukocyte Biology 65: 286-290).

Provided compounds are inhibitors of BTK and are therefore useful for treating one or more disorders associated with activity of BTK. Thus, in some embodiments, the present invention provides a method for treating a BTK-mediated disorder comprising the step of administering to a patient in need thereof a compound of the present invention, or pharmaceutically acceptable composition thereof.

As used herein, the term "BTK-mediated" disorders or conditions as used herein means any disease or other deleterious condition in which BTK, or a mutant thereof, is known to play a role. Accordingly, another embodiment of the present invention relates to treating or lessening the severity of one or more diseases in which BTK, or a mutant thereof, is known to play a role. Specifically, the present invention relates to a method of treating or lessening the severity of a disease or condition selected from a proliferative disorder or an autoimmune disorder, wherein said method comprises administering to a patient in need thereof a compound or composition according to the present invention.

In some embodiments, the present invention provides a method for treating or lessening the severity of one or more diseases and conditions associated with BTK. In some embodiments, the disease or condition is an autoimmune disease, e.g., inflammatory bowel disease, arthritis, systemic lupus erythematosus (SLE or lupus), lupus nephritis, vasculitis, idiopathic thrombocytopenic purpura (ITP), rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, autoimmune thyroiditis, Sjogren's syndrome, multiple sclerosis, systemic sclerosis, Lyme neuroborreliosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, autoimmune gastritis, pernicious anemia, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, membranous glomerulonephropathy, endometriosis, interstitial cystitis, pemphigus vulgaris, bullous pemphigoid, neuromyotonia, scleroderma, or vulvodynia. In certain embodiments, the disease or condition is systemic lupus erythematosus (SLE or lupus) or lupus nephritis.

In some embodiments, the disease or condition is a hyperproliferative disease or immunologically-mediated diseases including rejection of transplanted organs or tissues and Acquired Immunodeficiency Syndrome (AIDS, also known as HIV).

In some embodiments, the present invention provides a method for treating or lessening the severity of one or more diseases and conditions associated with BTK, wherein the disease or condition is selected from heteroimmune conditions or diseases, which include, but are not limited to graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis.

In some embodiments, the present invention provides a method for treating or lessening the severity of one or more diseases and conditions associated with BTK, wherein the disease or condition is selected from an inflammatory disease, e.g., asthma, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis.

In some embodiments, the present invention provides a method for treating or lessening the severity of one or more diseases and conditions associated with BTK, wherein the disease or condition is selected from a cancer. In one embodiment, the cancer is a B-cell proliferative disorder, e.g., diffuse large B cell lymphoma, follicular lymphoma, chronic lymphocytic lymphoma, chronic lymphocytic leukemia, acute lymphocytic leukemia, B-cell prolymphocytic leukemia, lymphoplasmacytic lymphoma/Waldenstrom macroglobulinemia, splenic marginal zone lymphoma, multiple myeloma (also known as plasma cell myeloma), non-Hodgkin's lymphoma, Hodgkin's lymphoma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis. In some embodiments, the cancer is breast cancer, prostate cancer, or cancer of the mast cells (e.g., mastocytoma, mast cell leukemia, mast cell sarcoma, systemic mastocytosis). In one embodiment, the cancer is bone cancer. In another embodiment, the cancer is of other primary origin and metastasizes to the bone. In certain embodiments, the cancer is colorectal cancer or pancreatic cancer.

In some embodiments, the present invention provides a method for treating or lessening the severity of one or more diseases or conditions associated with BTK including diseases of the bone and joints including, without limitation, rheumatoid arthritis, seronegative spondyloarthropathies (including ankylosing spondylitis, psoriatic arthritis and Reiter's disease), Behcet's disease, Sjogren's syndrome, systemic sclerosis, osteoporosis, bone cancer, and bone metastasis.

In some embodiments, the present invention provides a method for treating or lessening the severity of one or more diseases and conditions associated with BTK, wherein the disease or condition is selected from a thromboembolic disorder or cardiovascular disorder, e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, or deep venous thrombosis. In certain embodiments, the present invention provides an anti-thrombotic agent because Btk is also involved in the activation of platelets.

In some embodiments, the present invention provides a method for treating or lessening the severity of one or more diseases and conditions associated with BTK, including infectious and noninfectious inflammatory events and autoimmune and other inflammatory diseases. These autoimmune and inflammatory diseases, disorders, and syndromes include inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleraderma, mycosis fungoides, acute inflammatory responses (such as acute respiratory distress syndrome and ischemia/reperfusion injury), and Graves' disease. In certain embodiments, the diabetes is type I diabetes.

In some embodiments, the present invention provides a method for treating or lessening the severity of one or more diseases and conditions associated with BTK, selected from rheumatoid arthritis, multiple sclerosis, B-cell chronic lymphocytic leukemia, acute lymphocytic leukemia, hairy cell leukemia, non-Hodgkin's lymphoma, Hodgkin's lymphoma, multiple myeloma, bone cancer, bone metastasis, osteoporosis, diabetes (e.g. type I diabetes), irritable bowel syndrome, Crohn's disease, lupus and renal transplant.

It is another object of the invention to provide a method for treating diseases that are caused, mediated and/or propagated by BTK activity, wherein at least one compound of formula (I) according to the invention and/or physiologically acceptable salts thereof is administered to a mammal in need of such treatment. In certain embodiments, the invention provides a method for treating lupus, wherein at least one compound of formula (I) according to the invention and/or physiologically acceptable salts thereof is administered to a mammal in need of such treatment. In certain embodiments, the compound is administered in an effective amount as defined above. In certain embodiments, the treatment is an oral administration.

The method of the invention can be performed either in-vitro or in-vivo. The susceptibility of a particular cell to treatment with the compounds according to the invention can be particularly determined by in-vitro tests, whether in the course of research or clinical application. Typically, a culture of the cell is combined with a compound according to the invention at various concentrations for a period of time which is sufficient to allow the active agents to inhibit BTK activity, usually between about one hour and one week. In-vitro treatment can be carried out using cultivated cells from a biopsy sample or cell line.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

For identification of a signal transduction pathway and for detection of interactions between various signal transduction pathways, various scientists have developed suitable models or model systems, for example cell culture models and models of transgenic animals. For the determination of certain stages in the signal transduction cascade, interacting compounds can be utilized in order to modulate the signal. The compounds according to the invention can also be used as reagents for testing BTK-dependent signal transduction pathways in animals and/or cell culture models or in the clinical diseases mentioned in this application.

Moreover, the subsequent teaching of the present specification concerning the use of the compounds according to formula (I) and its derivatives for the production of a medicament for the prophylactic or therapeutic treatment and/or monitoring is considered as valid and applicable without restrictions to the use of the compound for the inhibition of BTK activity if expedient.

The invention also relates to the use of compounds according to formula (I) and/or physiologically acceptable salts thereof for the prophylactic or therapeutic treatment and/or monitoring of diseases that are caused, mediated and/or propagated by BTK activity. Furthermore, the invention relates to the use of compounds according to formula (I) and/or physiologically acceptable salts thereof for the production of a medicament for the prophylactic or therapeutic treatment and/or monitoring of diseases that are caused, mediated and/or propagated by BTK activity. In certain embodiments, the invention provides the use of a compound according to formula I or physiologically acceptable salts thereof, for the production of a medicament for the prophylactic or therapeutic treatment of a BTK-mediated disorder.

Compounds of formula (I) and/or a physiologically acceptable salt thereof can furthermore be employed as intermediate for the preparation of further medicament active ingredients. The medicament is preferably prepared in a non-chemical manner, e.g. by combining the active ingredient with at least one solid, fluid and/or semi-fluid carrier or excipient, and optionally in conjunction with a single or more other active substances in an appropriate dosage form.

Another object of the present invention are compounds of formula (I) according to the invention and/or physiologically acceptable salts thereof for use in the prophylactic or therapeutic treatment and/or monitoring of diseases that are caused, mediated and/or propagated by BTK activity. Another preferred object of the invention concerns compounds of formula (I) according to the invention and/or physiologically acceptable salts thereof for use in the prophylactic or therapeutic treatment and/or monitoring of lupus. The prior teaching of the present specification concerning the compounds of formula (I), including any preferred embodiment thereof, is valid and applicable without restrictions to the compounds according to formula (I) and their salts for use in the prophylactic or therapeutic treatment and/or monitoring of lupus.

The compounds of formula (I) according to the invention can be administered before or following an onset of disease once or several times acting as therapy. The aforementioned compounds and medical products of the inventive use are particularly used for the therapeutic treatment. A therapeutically relevant effect relieves to some extent one or more symptoms of a disorder, or returns to normality, either partially or completely, one or more physiological or biochemical parameters associated with or causative of a disease or pathological condition. Monitoring is considered as a kind of treatment provided that the compounds are administered in distinct intervals, e.g. in order to boost the response and eradicate the pathogens and/or symptoms of the disease completely. Either the identical compound or different compounds can be applied. The methods of the invention can also be used to reduce the likelihood of developing a disorder or even prevent the initiation of disorders associated with BTK activity in advance or to treat the arising and continuing symptoms.

In the meaning of the invention, prophylactic treatment is advisable if the subject possesses any preconditions for the aforementioned physiological or pathological conditions, such as a familial disposition, a genetic defect, or a previously incurred disease.

The invention furthermore relates to a medicament comprising at least one compound according to the invention and/or pharmaceutically usable derivatives, salts, solvates and stereoisomers thereof, including mixtures thereof in all ratios. In certain embodiments, the invention relates to a medicament comprising at least one compound according to the invention and/or physiologically acceptable salts thereof.

A "medicament" in the meaning of the invention is any agent in the field of medicine, which comprises one or more compounds of formula (I) or preparations thereof (e.g. a pharmaceutical composition or pharmaceutical formulation) and can be used in prophylaxis, therapy, follow-up or aftercare of patients who suffer from diseases, which are associated with BTK activity, in such a way that a pathogenic modification of their overall condition or of the condition of particular regions of the organism could establish at least temporarily.

In various embodiments, the active ingredient may be administered alone or in combination with other treatments. A synergistic effect may be achieved by using more than one compound in the pharmaceutical composition, i.e. the compound of formula (I) is combined with at least another agent as active ingredient, which is either another compound of formula (I) or a compound of different structural scaffold. The active ingredients can be used either simultaneously or sequentially.

Included herein are methods of treatment in which at least one chemical entity provided herein is administered in combination with an anti-inflammatory agent. Anti-inflammatory agents include but are not limited to NSAIDs, non-specific and COX-2 specific cyclooxygenase enzyme inhibitors, gold compounds, corticosteroids, methotrexate, tumor necrosis factor (TNF) antagonists, immunosuppressants and methotrexate.

Examples of NSAIDs include, but are not limited to, ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors such as celecoxib, valdecoxib, lumiracoxib dnd/or etoricoxib.

In some embodiments, the anti-inflammatory agent is a salicylate. Salicylates include by are not limited to acetylsalicylic acid or aspirin, sodium salicylate, and choline and magnesium salicylates.

The anti-inflammatory agent may also be a corticosteroid. For example, the corticosteroid may be cortisone, dexamethasone, methylprednisolone, prednisolone, prednisolone sodium phosphate, or prednisone.

In additional embodiments the anti-inflammatory agent is a gold compound such as gold sodium thiomalate or auranofin.

The invention also includes embodiments in which the anti-inflammatory agent is a metabolic inhibitor such as a dihydrofolate reductase inhibitor, such as methotrexate or a dihydroorotate dehydrogenase inhibitor, such as leflunomide.

Other embodiments of the invention pertain to combinations in which at least one anti-inflammatory compound is an anti-monoclonal antibody (such as eculizumab or pexelizumab), a TNF antagonist, such as entanercept, or infliximab, which is an anti-TNF alpha monoclonal antibody.

Still other embodiments of the invention pertain to combinations in which at least one active agent is an immunosuppressant compound such as an immunosuppressant compound chosen from methotrexate, leflunomide, cyclosporine, tacrolimus, azathioprine, and mycophenolate mofetil.

B-cells and B-cell precursors expressing BTK have been implicated in the pathology of B-cell malignancies, including, but not limited to, B-cell lymphoma, lymphoma (including Hodgkin's and non-Hodgkin's lymphoma), hairy cell lymphoma, multiple myeloma, chronic and acute myelogenous leukemia and chronic and acute lymphocytic leukemia.

BTK has been shown to be an inhibitor of the Fas/APO-1 (CD-95) death inducing signaling complex (DISC) in B-lineage lymphoid cells. The fate of leukemia/lymphoma cells may reside in the balance between the opposing proapoptotic effects of caspases activated by DISC and an upstream anti-apoptotic regulatory mechanism involving BTK and/or its substrates (Vassilev et al., J. Biol. Chem. 1998, 274, 1646-1656).

It has also been discovered that BTK inhibitors are useful as chemosensitizing agents, and, thus, are useful in combination with other chemotherapeutic drugs, in particular, drugs that induce apoptosis. Examples of other chemotherapeutic drugs that can be used in combination with chemosensitizing BTK inhibitors include topoisomerase I inhibitors (camptothecin or topotecan), topoisomerase II inhibitors (e.g. daunomycin and etoposide), alkylating agents (e.g. cyclophosphamide, melphalan and BCNU), tubulin directed agents (e.g. taxol and vinblastine), and biological agents (e.g. antibodies such as anti CD20 antibody, IDEC 8, immunotoxins, and cytokines).

The disclosed compounds of the formula I can be administered in combination with other known therapeutic agents, including anticancer agents. As used here, the term "anticancer agent" relates to any agent which is administered to a patient with cancer for the purposes of treating the cancer.

The anti-cancer treatment defined above may be applied as a monotherapy or may involve, in addition to the herein disclosed compounds of formula I, conventional surgery or radiotherapy or medicinal therapy. Such medicinal therapy, e.g. a chemotherapy or a targeted therapy, may include one or more, but preferably one, of the following anti-tumor agents:

Alkylating agents: such as altretamine, bendamustine, busulfan, carmustine, chlorambucil, chlormethine, cyclophosphamide, dacarbazine, ifosfamide, improsulfan, tosilate, lomustine, melphalan, mitobronitol, mitolactol, nimustine, ranimustine, temozolomide, thiotepa, treosulfan, mechloretamine, carboquone; apaziquone, fotemustine, glufosfamide, palifosfamide, pipobroman, trofosfamide, uramustine, TH-302[4], VAL-083[4];

Platinum Compounds: such as carboplatin, cisplatin, eptaplatin, miriplatine hydrate, oxaliplatin, lobaplatin, nedaplatin, picoplatin, satraplatin; lobaplatin, nedaplatin, picoplatin, satraplatin; DNA altering agents: such as amrubicin, bisantrene, decitabine, mitoxantrone, procarbazine, trabectedin, clofarabine; amsacrine, brostallicin, pixantrone, laromustine[1,3];

Topoisomerase Inhibitors: such as etoposide, irinotecan, razoxane, sobuzoxane, teniposide, topotecan; amonafide, belotecan, elliptinium acetate, voreloxin;

Microtubule modifiers: such as cabazitaxel, docetaxel, eribulin, ixabepilone, paclitaxel, vinblastine, vincristine, vinorelbine, vindesine, vinflunine; fosbretabulin, tesetaxel;

Antimetabolites: such as asparaginase[3], azacitidine, calcium levofolinate, capecitabine, cladribine, cytarabine, enocitabine, floxuridine, fludarabine, fluorouracil, gemcitabine, mercaptopurine, methotrexate, nelarabine, pemetrexed, pralatrexate, azathioprine, thioguanine, carmofur; doxifluridine, elacytarabine, raltitrexed, sapacitabine, tegafur[2,3], trimetrexate;

Anticancer antibiotics: such as bleomycin, dactinomycin, doxorubicin, epirubicin, idarubicin, levamisole, miltefosine, mitomycin C, romidepsin, streptozocin, valrubicin, zinostatin, zorubicin, daunorubicin, plicamycin; aclarubicin, peplomycin, pirarubicin;

Hormones/Antagonists: such as abarelix, abiraterone, bicalutamide, buserelin, calusterone, chlorotrianisene, degarelix, dexamethasone, estradiol, fluocortolone fluoxymesterone, flutamide, fulvestrant, goserelin, histrelin, leuprorelin, megestrol, mitotane, nafarelin, nandrolone, nilutamide, octreotide, prednisolone, raloxifene, tamoxifen, thyrotropin alfa, toremifene, trilostane, triptorelin, diethylstilbestrol; acolbifene, danazol, deslorelin, epitiostanol, orteronel, enzalutamide[1,3];

Aromatase inhibitors: such as aminoglutethimide, anastrozole, exemestane, fadrozole, letrozole, testolactone; formestane;

Small molecule kinase inhibitors: such as crizotinib, dasatinib, erlotinib, imatinib, lapatinib, nilotinib, pazopanib, regorafenib, ruxolitinib, sorafenib, sunitinib, vandetanib, vemurafenib, bosutinib, gefitinib, axitinib; afatinib, alisertib, dabrafenib, dacomitinib, dinaciclib, dovitinib, enzastaurin, nintedanib, lenvatinib, linifanib, linsitinib, masitinib, midostaurin, motesanib, neratinib, orantinib, perifosine, ponatinib, radotinib, rigosertib, tipifarnib, tivantinib, tivozanib, trametinib, pimasertib, brivanib alaninate, cediranib, apatinib[4], cabozantinib S-malate[1,3], ibrutinib[1,3], icotinib[4], buparlisib[2], cipatinib[4], cobimetinib[1,3], idelalisib[1,3], fedratinib[1], XL-647[4];

Photosensitizers: such as methoxsalen[3]; porfimer sodium, talaporfin, temoporfin;

Antibodies: such as alemtuzumab, besilesomab, brentuximab vedotin, cetuximab, denosumab, ipilimumab, ofatumumab, panitumumab, rituximab, tositumomab, trastuzumab, bevacizumab, pertuzumab[2,3]; catumaxomab, elotuzumab, epratuzumab, farletuzumab, mogamulizumab, necitumumab, nimotuzumab, obinutuzumab, ocaratuzumab, oregovomab, ramucirumab, rilotumumab, siltuximab, tocilizumab, zalutumumab, zanolimumab, matuzumab, dalotuzumab[1,2,3], onartuzumab[1,3], racotumomab[1], tabalumab[1,3], EMD-525797[4], nivolumab[1,3];

Cytokines: such as aldesleukin, interferon alfa[2], interferon alfa2a[3], interferon alfa2b[2,3]; celmoleukin, tasonermin, teceleukin, oprelvekin[1,3], recombinant interferon beta-1a[4];

Drug Conjugates: such as denileukin diftitox, ibritumomab tiuxetan, iobenguane I123, prednimustine, trastuzumab emtansine, estramustine, gemtuzumab, ozogamicin, aflibercept; cintredekin besudotox, edotreotide, inotuzumab ozogamicin, naptumomab estafenatox, oportuzumab monatox, technetium (99mTc) arcitumomab[1,3], vintafolide[1,3];

Vaccines: such as sipuleucel[3]; vitespen[3], emepepimut-S[3], oncoVAX[4], rindopepimut[3], troVax[4], MGN-1601[4], MGN-1703[4]; and Miscellaneous: alitretinoin, bexarotene, bortezomib, everolimus, ibandronic acid, imiquimod, lenalidomide, lentinan, metirosine, mifamurtide, pamidronic acid, pegaspargase, pentostatin, sipuleucel[3], sizofiran, tamibarotene, temsirolimus, thalidomide, tretinoin, vismodegib, zoledronic acid, vorinostat; celecoxib, cilengitide, entinostat, etanidazole, ganetespib, idronoxil, iniparib, ixazomib, lonidamine, nimorazole, panobinostat, peretinoin, plitidepsin, pomalidomide, procodazol, ridaforolimus, tasquinimod, telotristat, thymalfasin, tirapazamine, tosedostat, trabedersen, ubenimex, valspodar, gendicine[4], picibanil[4], reolysin[4], retaspimycin hydrochloride[1,3], trebananib[2,3], virulizin[4], carfilzomib[1,3], endostatin[4], immucothel[4], belinostat[3], MGN-1703[4].

([1] Prop. INN (Proposed International Nonproprietary Name); [2]Rec. INN (Recommended international Nonproprietary Names); [3] USAN (United States Adopted Name); [4] no INN).

In another aspect, the invention provides for a kit consisting of separate packs of an effective amount of a compound according to the invention and/or pharmaceutically acceptable salts, derivatives, solvates and stereoisomers thereof, including mixtures thereof in all ratios, and optionally, an effective amount of a further active ingredient. The kit comprises suitable containers, such as boxes, individual bottles, bags or ampoules. The kit may, for example, comprise separate ampoules, each containing an effective amount of a compound according to the invention and/or pharmaceutically acceptable salts, derivatives, solvates and stereoisomers thereof, including mixtures thereof in all ratios, and an effective amount of a further active ingredient in dissolved or lyophilized form.

As used herein, the terms "treatment," "treat," and "treating" refer to reversing, alleviating, delaying the onset of, or inhibiting the progress of a disease or disorder, or one or more symptoms thereof, as described herein. In some embodiments, treatment is administered after one or more symptoms have developed. In other embodiments, treatment is administered in the absence of symptoms. For example, treatment is administered to a susceptible individual prior to the onset of symptoms (e.g., in light of a history of symptoms and/or in light of genetic or other susceptibility factors). Treatment is also continued after symptoms have resolved, for example to prevent or delay their recurrence.

The compounds and compositions, according to the method of the present invention, are administered using any amount and any route of administration effective for treating or lessening the severity of a disorder provided above. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention are administered orally or parenterally at dosage levels of about 0.01 mg/kg to about 100 mg/kg and preferably from about 1 mg/kg to about 50 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms optionally contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions are formulated according to the known art using suitable dispersing or wetting agents and suspending agents. The sterile injectable preparation are also a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This is accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form also optionally comprises buffering agents.

Solid compositions of a similar type are also employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type are also employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms also comprise, as is normal practice, additional substances other than inert diluents, e.g., tableting lubricants and other tableting aids such a magnesium stearate and microcrystalline cellulose. In the case of capsules, tablets and pills, the dosage forms optionally also comprise buffering agents. They optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting BTK activity in a biological sample comprising the step of contacting said biological sample with a compound of this invention, or a composition comprising said compound.

According to another embodiment, the invention relates to a method of inhibiting BTK, or a mutant thereof, activity in a biological sample in a positive manner, comprising the step of contacting said biological sample with a compound of this invention, or a composition comprising said compound.

The compounds of the invention are useful in-vitro as unique tools for understanding the biological role of BTK, including the evaluation of the many factors thought to influence, and be influenced by, the production of BTK and the interaction of BTK. The present compounds are also useful in the development of other compounds that interact with BTK since the present compounds provide important structure-activity relationship (SAR) information that facilitate that development. Compounds of the present invention that bind to BTK can be used as reagents for detecting BTK in living cells, fixed cells, in biological fluids, in tissue homogenates, in purified, natural biological materials, etc. For example, by labeling such compounds, one can identify cells expressing BTK. In addition, based on their ability to bind BTK, compounds of the present invention can be used in in-situ staining, FACS (fluorescence-activated cell sorting), sodium dodecyl sulfate polyacrylamide gel electrophoresis (SDS-PAGE), ELISA (enzyme-linked immunoadsorptive assay), etc., enzyme purification, or in purifying cells expressing BTK inside permeabilized cells. The compounds of the invention can also be utilized as commercial research reagents for various medical research and diagnostic uses. Such uses can include but are not limited to: use as a calibration standard for quantifying the activities of candidate BTK inhibitors in a variety of functional assays; use as blocking reagents in random compound screening, i.e. in looking for new families of BTK ligands, the compounds can be used to block recovery of the presently claimed BTK compounds; use in the co-crystallization with BTK enzyme, i.e. the compounds of the present invention will allow formation of crystals of the compound bound to BTK, enabling the determination of enzyme/compound structure by x-ray crystallography; other research and diagnostic applications, wherein BTK is preferably activated or such activation is conveniently calibrated against a known quantity of an BTKinhibitor, etc.; use in assays as probes for determining the expression of BTK in cells; and developing assays for detecting compounds which bind to the same site as the BTK binding ligands.

The compounds of the invention can be applied either themselves and/or in combination with physical measurements for diagnostics of treatment effectiveness. Pharmaceutical compositions containing said compounds and the use of said compounds to treat BTK-mediated conditions is a promising, novel approach for a broad spectrum of therapies causing a direct and immediate improvement in the state of health, whether in human or animal. The orally bioavailable and active new chemical entities of the invention improve convenience for patients and compliance for physicians.

The compounds of formula (I), their salts, isomers, tautomers, enantiomeric forms, diastereomers, racemates, derivatives, prodrugs and/or metabolites are characterized by a high specificity and stability, low manufacturing costs and convenient handling. These features form the basis for a reproducible action, wherein the lack of cross-reactivity is included, and for a reliable and safe interaction with the target structure.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Modulation of BTK, or a mutant thereof, activity in a biological sample is useful for a variety of purposes that are known to one of skill in the art. Examples of such purposes include, but are not limited to, blood transfusion, organ transplantation, biological specimen storage, and biological assays.

5. Probe Compounds

In certain aspects, a compound of the present invention is tethered to a detectable moiety to form a probe compound. In one aspect, a probe compound of the invention comprises an irreversible protein kinase inhibitor of any formulae as described herein, a detectable moiety, and a tethering moiety that attaches the inhibitor to the detectable moiety.

In some embodiments, such probe compounds of the present invention comprise a provided compound of any formulae as described herein, tethered to a detectable moiety, $R^t$, by a bivalent tethering moiety, $-T^1-$. The tethering moiety is attached to a compound of the invention via $R^4$. One of ordinary skill in the art will appreciate that when a tethering moiety is attached to $R^4$, $R^4$ is a bivalent warhead group denoted as $R^{4'}$. In certain embodiments, a provided probe compound is selected from formula I-t:

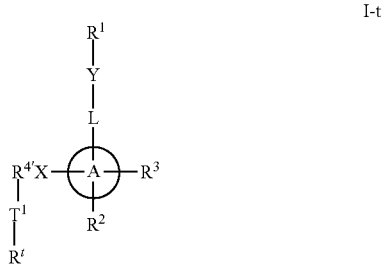

I-t wherein each of $R^1$, $R^2$, $R^3$, X, L, and Y, is as defined above, and described in classes and subclasses herein, $R^{4'}$ is a bivalent $R^4$; $T^1$ is a bivalent tethering moiety; and $R^t$ is a detectable moiety.

In some embodiments, such probe compounds of the present invention comprise a provided compound of any formulae as described herein, tethered to a detectable moiety, $R^t$, by a bivalent tethering moiety, $-T^1-$. The tethering moiety is attached to a compound of the invention via $R^1$. One of ordinary skill in the art will appreciate that when a tethering moiety is attached to $R^1$, $R^1$ is a bivalent warhead group denoted as $R^{1'}$. In certain embodiments, a provided probe compound is selected from formula I-s:

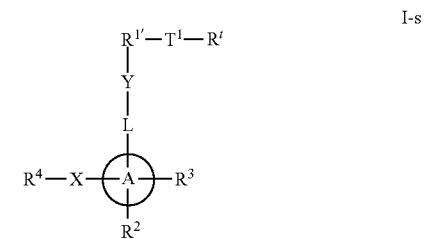

I-s wherein each of $R^2$, $R^3$, $R^4$, X, L, and Y, is as defined above, and described in classes and subclasses herein, $R^{1'}$ is a bivalent $R^1$; $T^1$ is a bivalent tethering moiety; and $R^t$ is a detectable moiety.

In some embodiments, $R^t$ is a detectable moiety selected from a primary label or a secondary label. In certain embodiments, $R^t$ is a detectable moiety selected from a fluorescent label (e.g., a fluorescent dye or a fluorophore), a mass-tag, a chemiluminescent group, a chromophore, an electron dense group, or an energy transfer agent. In some embodiments, $R^t$ is biotin, biotin sulfoxide, a radioisotope, or a fluorescent label.

As used herein, the term "detectable moiety" is used interchangeably with the term "label" and "reporter" and relates to any moiety capable of being detected, e.g., primary labels and secondary labels. A presence of a detectable moiety can be measured using methods for quantifying (in absolute, approximate or relative terms) the detectable moiety in a system under study. In some embodiments, such methods are well known to one of ordinary skill in the art and include any methods that quantify a reporter moiety (e.g., a label, a dye, a photocrosslinker, a cytotoxic compound, a drug, an affinity label, a photoaffinity label, a reactive compound, an antibody or antibody fragment, a biomaterial, a nanoparticle, a spin label, a fluorophore, a metal-containing moiety, a radioactive moiety, quantum dot(s), a novel functional group, a group that covalently or noncovalently interacts with other molecules, a photocaged moiety, an actinic radiation excitable moiety, a ligand, a photoisomerizable moiety, biotin, a biotin analog (e.g., biotin sulfoxide), a moiety incorporating a heavy atom, a chemically cleavable group, a photocleavable group, a redox-active agent, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, and any combination of the above).

Primary labels, such as radioisotopes (e.g., tritium, $^{32}P$, $^{33}P$, $^{35}S$, $^{14}C$, $^{123}I$, $^{124}I$, $^{125}I$, or $^{131}I$), mass-tags are stable isotopes (e.g., $^{13}C$, $^2H$, $^{17}O$, $^{18}O$, $^{15}N$, $^{19}F$, and $^{127}I$), positron emitting isotopes (e.g., $^{11}C$, $^{18}F$, $^{13}N$, $^{124}I$, and $^{15}O$), and fluorescent labels, which are signal generating reporter groups which can be detected without further modifications. Detectable moieties are analyzed by methods. Exemplary methods are fluorescence, positron emission tomography, SPECT medical imaging, chemiluminescence, electron-spin resonance, ultraviolet/visible absorbance spectroscopy, mass spectrometry, nuclear magnetic resonance, magnetic resonance, flow cytometry, autoradiography, scintillation counting, phosphoimaging, and electrochemical methods.

The term "secondary label" as used herein refers to moieties such as biotin and various protein antigens that require the presence of a second intermediate for production of a detectable signal. For biotin, the secondary intermediate includes streptavidin-enzyme or strepavidin-antibody conjugates. For antigen labels, secondary intermediates include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label", "fluorescent dye", and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 493/503, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxyfluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X, 5(6)-Carboxyfluorescein, 2,7-Dichlorofluorescein, N,N-Bis(2,4,6-trimethylphenyl)-3,4:9,10-perylenebis(dicarboximide), HPTS, Ethyl Eosin, DY-490XL MegaStokes, DY-485XL MegaStokes, Adirondack Green 520, ATTO 465, ATTO 488, ATTO 495, YOYO-1,5-FAM, BCECF, dichlorofluorescein, rhodamine 110, rhodamine 123, YO-PRO-1, SYTOX Green, Sodium Green, SYBR Green I, Alexa Fluor 500, FITC, Fluo-3, Fluo-4, fluoro-emerald, YoYo-1 ssDNA, YoYo-1 dsDNA, YoYo-1, SYTO RNASelect, Diversa Green-FP, Dragon Green, EvaGreen, Surf Green EX, Spectrum Green, NeuroTrace 500525, NBD-X, MitoTracker Green FM, LysoTracker Green DND-26, CBQCA, PA-GFP (post-activation), WEGFP (post-activation), FlASH-CCXXCC, Azami Green monomeric, Azami Green, green fluorescent protein (GFP), EGFP (Campbell Tsien 2003), EGFP (Patterson 2001), Kaede Green, 7-Benzylamino-4-Nitrobenz-2-Oxa-1,3-Diazole, Bexl, Doxorubicin, Lumio Green, and SuperGlo GFP.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-methoxytetrafluorobenzyl)oxy]phenyl]-3-methylglyceronyl]isonipecotic acid, 4'-[2,3,5,6-tetrafluoro-4-(pentafluorophenoxyl)]methyl acetophenone, and their derivatives. The synthesis and utility of these mass-tags is described in U.S. Pat. Nos. 4,650,750, 4,709,016, 5,360, 8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) are also used as mass-tags. Stable isotopes (e.g., $^{13}C$, $^{2}H$, $^{17}O$, $^{18}O$, and $^{15}N$) are also used as mass-tags.

The term "chemiluminescent group," as used herein, refers to a group which emits light as a result of a chemical reaction without the addition of heat. By way of example, luminol (5-amino-2,3-dihydro-1,4-phthalazinedione) reacts with oxidants like hydrogen peroxide ($H_2O_2$) in the presence of a base and a metal catalyst to produce an excited state product (3-aminophthalate, 3-APA).

The term "chromophore," as used herein, refers to a molecule which absorbs light of visible wavelengths, UV wavelengths or IR wavelengths.

The term "dye," as used herein, refers to a soluble, coloring substance which contains a chromophore.

The term "electron dense group," as used herein, refers to a group which scatters electrons when irradiated with an electron beam. Such groups include, but are not limited to, ammonium molybdate, bismuth subnitrate, cadmium iodide, carbohydrazide, ferric chloride hexahydrate, hexamethylene tetramine, indium trichloride anhydrous, lanthanum nitrate, lead acetate trihydrate, lead citrate trihydrate, lead nitrate, periodic acid, phosphomolybdic acid, phosphotungstic acid, potassium ferricyanide, potassium ferrocyanide, ruthenium red, silver nitrate, silver proteinate (Ag Assay: 8.0-8.5%) "Strong", silver tetraphenylporphin (S-TPPS), sodium chloroaurate, sodium tungstate, thallium nitrate, thiosemicarbazide (TSC), uranyl acetate, uranyl nitrate, and vanadyl sulfate.

The term "energy transfer agent," as used herein, refers to a molecule which either donates or accepts energy from another molecule. By way of example only, fluorescence resonance energy transfer (FRET) is a dipole-dipole coupling process by which the excited-state energy of a fluorescence donor molecule is non-radiatively transferred to an unexcited acceptor molecule which then fluorescently emits the donated energy at a longer wavelength.

The term "moiety incorporating a heavy atom," as used herein, refers to a group which incorporates an ion or atom which is usually heavier than carbon. In some embodiments, such ions or atoms include, but are not limited to, silicon, tungsten, gold, lead, and uranium.

The term "photoaffinity label," as used herein, refers to a label with a group, which, upon exposure to light, forms a covalent bond with a molecule for which the label has an affinity.

The term "photocaged moiety," as used herein, refers to a group which, upon illumination at certain wavelengths, covalently or non-covalently binds other ions or molecules.

The term "photoisomerizable moiety," as used herein, refers to a group wherein upon illumination with light changes from one isomeric form to another.

The term "radioactive moiety," as used herein, refers to a group whose nuclei spontaneously give off nuclear radiation, such as alpha, beta, or gamma particles; wherein, alpha particles are helium nuclei, beta particles are electrons, and gamma particles are high energy photons.

The term "spin label," as used herein, refers to molecules which contain an atom or a group of atoms exhibiting an unpaired electron spin (i.e. a stable paramagnetic group) that in some embodiments are detected by electron spin resonance spectroscopy and in other embodiments are attached to another molecule. Such spin-label molecules include, but are not limited to, nitryl radicals and nitroxides, and in some embodiments are single spin-labels or double spin-labels.

The term "quantum dots," as used herein, refers to colloidal semiconductor nanocrystals that in some embodiments are detected in the near-infrared and have extremely high quantum yields (i.e., very bright upon modest illumination).

One of ordinary skill in the art will recognize that a detectable moiety is attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties are directly attached to a provided compound or via a tethering moiety, such as a bivalent saturated or unsaturated hydrocarbon chain.

In some embodiments, detectable moieties are attached to a provided compound via click chemistry. In some embodiments, such moieties are attached via a 1,3-cycloaddition of an azide with an alkyne, optionally in the presence of a copper catalyst. Methods of using click chemistry are known in the art and include those described by Rostovtsev et al., Angew. Chem. Int. Ed. 2002, 41, 2596-99 and Sun et al., Bioconjugate Chem., 2006, 17, 52-57. In some embodiments, a click ready inhibitor moiety is provided and reacted with a click ready -T-$R^r$ moiety. As used herein, "click ready" refers to a moiety containing an azide or alkyne for use in a click chemistry reaction. In some embodiments, the click ready inhibitor moiety comprises an azide. In certain embodiments, the click ready -T-$R^r$ moiety comprises a strained cyclooctyne for use in a copper-free click chemistry reaction (for example, using methods described in Baskin et al., Proc. Natl. Acad. Sci. USA 2007, 104, 16793-16797).

In some embodiments, the detectable moiety, $R^r$, is selected from a label, a dye, a photocrosslinker, a cytotoxic compound, a drug, an affinity label, a photoaffinity label, a reactive compound, an antibody or antibody fragment, a biomaterial, a nanoparticle, a spin label, a fluorophore, a metal-containing moiety, a radioactive moiety, quantum dot(s), a novel functional group, a group that covalently or noncovalently interacts with other molecules, a photocaged moiety, an actinic radiation excitable moiety, a ligand, a photoisomerizable moiety, biotin, a biotin analog (e.g., biotin sulfoxide), a moiety incorporating a heavy atom, a chemically cleavable group, a photocleavable group, a redox-active agent, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, or a combination thereof.

In some embodiments, $R^r$ is biotin or an analog thereof. In certain embodiments, $R^r$ is biotin. In certain other embodiments, $R^r$ is biotin sulfoxide.

In another embodiment, $R^r$ is a fluorophore. In a further embodiment, the fluorophore is selected from Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 493/503, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X, 5(6)-Carboxyfluorescein, 2,7-Dichlorofluorescein, N,N-Bis(2,4,6-trimethylphenyl)-3,4:9,10-perylenebis(dicarboximide), HPTS, Ethyl Eosin, DY-490XL MegaStokes, DY-485XL MegaStokes, Adirondack Green 520, ATTO 465, ATTO 488, ATTO 495, YOYO-1,5-FAM, BCECF, dichlorofluorescein, rhodamine 110, rhodamine 123, YO-PRO-1, SYTOX Green, Sodium Green, SYBR Green I, Alexa Fluor 500, FITC, Fluo-3, Fluo-4, fluoro-emerald, YoYo-1 ssDNA, YoYo-1 dsDNA, YoYo-1, SYTO RNASelect, Diversa Green-FP, Dragon Green, EvaGreen, Surf Green EX, Spectrum Green, NeuroTrace 500525, NBD-X, MitoTracker Green FM, LysoTracker Green DND-26, CBQCA, PA-GFP (post-activation), WEGFP (post-activation), FLASH-CCXXCC, Azami Green monomeric, Azami Green, green fluorescent protein (GFP), EGFP (Campbell Tsien 2003), EGFP (Patterson 2001), Kaede Green, 7-Benzylamino-4-Nitrobenz-2-Oxa-1,3-Diazole, Bexl, Doxorubicin, Lumio Green, or SuperGlo GFP.

As described generally above, a provided probe compound comprises a tethering moiety, -$T^1$-, that attaches the irreversible inhibitor to the detectable moiety. As used herein, the term "tether" or "tethering moiety" refers to any bivalent chemical spacer. Exemplary tethers are a covalent bond, a polymer, a water soluble polymer, optionally substituted alkyl, optionally substituted heteroalkyl, optionally substituted heterocycloalkyl, optionally substituted cycloalkyl, optionally substituted heterocyclyl, optionally substituted heterocycloalkylalkyl, optionally substituted heterocycloalkylalkenyl, optionally substituted aryl, optionally substituted heteroaryl, optionally substituted heterocycloalkylalkenylalkyl, an optionally substituted amide moiety, an ether moiety, an ketone moiety, an ester moiety, an optionally substituted carbamate moiety, an optionally substituted hydrazone moiety, an optionally substituted hydrazine moiety, an optionally substituted oxime moiety, a disulfide moiety, an optionally substituted imine moiety, an optionally substituted sulfonamide moiety, a sulfone moiety, a sulfoxide moiety, a thioether moiety, or any combination thereof.

In some embodiments, the tethering moiety, -$T^1$-, is selected from a covalent bond, a polymer, a water soluble polymer, optionally substituted alkyl, optionally substituted heteroalkyl, optionally substituted heterocycloalkyl, optionally substituted cycloalkyl, optionally substituted heterocycloalkylalkyl, optionally substituted heterocycloalkylalkenyl, optionally substituted aryl, optionally substituted heteroaryl, and optionally substituted heterocycloalkylalkenylalkyl. In some embodiments, the tethering moiety is an optionally substituted heterocycle. In other embodiments, the heterocycle is selected from aziridine, oxirane, episulfide, azetidine, oxetane, pyrroline, tetrahydrofuran, tetrahydrothiophene, pyrrolidine, pyrazole, pyrrole, imidazole, triazole, tetrazole, oxazole, isoxazole, oxirene, thiazole, isothiazole, dithiolane, furan, thiophene, piperidine, tetrahydropyran, thiane, pyridine, pyran, thiapyrane, pyridazine, pyrimidine, pyrazine, piperazine, oxazine, thiazine, dithiane, and dioxane. In some embodiments, the heterocycle is piperazine. In further embodiments, the tethering moiety is optionally substituted with halogen, —CN, —OH, —$NO_2$, alkyl, S(O), and S(O)₂. In other embodiments, the water soluble polymer is a PEG group.

In other embodiments, the tethering moiety provides sufficient spatial separation between the detectable moiety and the protein kinase inhibitor moiety. In further embodiments, the tethering moiety is stable. In yet a further embodiment, the tethering moiety does not substantially affect the response of the detectable moiety. In other embodiments, the tethering moiety provides chemical stability to the probe compound. In further embodiments, the tethering moiety provides sufficient solubility to the probe compound.

In some embodiments, a tethering moiety, -T¹-, such as a water soluble polymer is coupled at one end to a provided irreversible inhibitor and to a detectable moiety, R', at the other end. In other embodiments, a water soluble polymer is coupled via a functional group or substituent of the provided irreversible inhibitor. In further embodiments, a water soluble polymer is coupled via a functional group or substituent of the reporter moiety.

In some embodiments, examples of hydrophilic polymers, for use in tethering moiety -T¹-, include, but are not limited to: polyalkyl ethers and alkoxy-capped analogs thereof (e.g., polyoxyethylene glycol, polyoxyethylene/propylene glycol, and methoxy or ethoxy-capped analogs thereof, polyoxyethylene glycol, the latter is also known as polyethylene glycol or PEG); polyvinylpyrrolidones; polyvinylalkyl ethers; polyoxazolines, polyalkyl oxazolines and polyhydroxyalkyl oxazolines; polyacrylamides, polyalkyl acrylamides, and polyhydroxyalkyl acrylamides (e.g., polyhydroxypropylmethacrylamide and derivatives thereof); polyhydroxyalkyl acrylates; polysialic acids and analogs thereof, hydrophilic peptide sequences; polysaccharides and their derivatives, including dextran and dextran derivatives, e.g., carboxymethyldextran, dextran sulfates, aminodextran; cellulose and its derivatives, e.g., carboxymethyl cellulose, hydroxyalkyl celluloses; chitin and its derivatives, e.g., chitosan, succinyl chitosan, carboxymethylchitin, carboxymethylchitosan; hyaluronic acid and its derivatives; starches; alginates; chondroitin sulfate; albumin; pullulan and carboxymethyl pullulan; polyaminoacids and derivatives thereof, e.g., polyglutamic acids, polylysines, polyaspartic acids, polyaspartamides; maleic anhydride copolymers such as: styrene maleic anhydride copolymer, divinylethyl ether maleic anhydride copolymer; polyvinyl alcohols; copolymers thereof, terpolymers thereof, mixtures thereof, and derivatives of the foregoing. In other embodiments, a water soluble polymer is any structural form. Exemplary forms are linear, forked or branched. In further embodiments, multifunctional polymer derivatives include, but are not limited to, linear polymers having two termini, each terminus being bonded to a functional group which is the same or different.

In some embodiments, a water polymer comprises a poly(ethylene glycol) moiety. In further embodiments, the molecular weight of the polymer is of a wide range. Exemlary ranges are between about 100 Da and about 100,000 Da or more. In yet further embodiments, the molecular weight of the polymer is between about 100 Da and about 100,000 Da, about 100,000 Da, about 95,000 Da, about 90,000 Da, about 85,000 Da, about 80,000 Da, about 75,000 Da, about 70,000 Da, about 65,000 Da, about 60,000 Da, about 55,000 Da, about 50,000 Da, about 45,000 Da, about 40,000 Da, about 35,000 Da, about 30,000 Da, about 25,000 Da, about 20,000 Da, about 15,000 Da, about 10,000 Da, about 9,000 Da, about 8,000 Da, about 7,000 Da, about 6,000 Da, about 5,000 Da, about 4,000 Da, about 3,000 Da, about 2,000 Da, about 1,000 Da, about 900 Da, about 800 Da, about 700 Da, about 600 Da, about 500 Da, about 400 Da, about 300 Da, about 200 Da, and about 100 Da. In some embodiments, the molecular weight of the polymer is between about 100 Da and 50,000 Da. In some embodiments, the molecular weight of the polymer is between about 100 Da and 40,000 Da. In some embodiments, the molecular weight of the polymer is between about 1,000 Da and 40,000 Da. In some embodiments, the molecular weight of the polymer is between about 5,000 Da and 40,000 Da. In some embodiments, the molecular weight of the polymer is between about 10,000 Da and 40,000 Da. In some embodiments, the poly(ethylene glycol) molecule is a branched polymer. In further embodiments, the molecular weight of the branched chain PEG is between about 1,000 Da and about 100,000 Da. Exemplary ranges are about 100,000 Da, about 95,000 Da, about 90,000 Da, about 85,000 Da, about 80,000 Da, about 75,000 Da, about 70,000 Da, about 65,000 Da, about 60,000 Da, about 55,000 Da, about 50,000 Da, about 45,000 Da, about 40,000 Da, about 35,000 Da, about 30,000 Da, about 25,000 Da, about 20,000 Da, about 15,000 Da, about 10,000 Da, about 9,000 Da, about 8,000 Da, about 7,000 Da, about 6,000 Da, about 5,000 Da, about 4,000 Da, about 3,000 Da, about 2,000 Da, and about 1,000 Da. In some embodiments, the molecular weight of a branched chain PEG is between about 1,000 Da and about 50,000 Da. In some embodiments, the molecular weight of a branched chain PEG is between about 1,000 Da and about 40,000 Da. In some embodiments, the molecular weight of a branched chain PEG is between about 5,000 Da and about 40,000 Da. In some embodiments, the molecular weight of a branched chain PEG is between about 5,000 Da and about 20,000 Da. The foregoing list for substantially water soluble backbones is by no means exhaustive and is merely illustrative, and in some embodiments, polymeric materials having the qualities described above are suitable for use in methods and compositions described herein.

In certain embodiments, the tethering moiety, -T¹-, has the following structure:

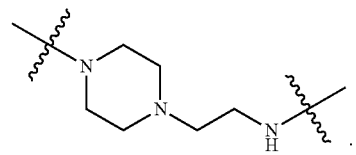 [SMILES: *NCCN1CCN(*)CC1]

In certain embodiments, the tethering moiety, -T¹-, has the following structure:

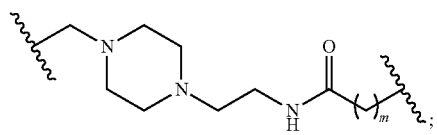

wherein m is 0, 1, 2, 3, 4, 5, 6, or 7.

In certain embodiments, —R' is quinine, phenylalanine, tyrosine, trptophan, NADH, FMN, EDANS, Lucifer Yellow, pyrene, 4-MU, AMC, DAPI, Hoechst33342, NBD, bimane, Cascade yellow, fluorescein, RH110, TMR, SRh101, naphthofluorescein, SNARF-1, propidium, BODIPY-FL, BODIPY-TR, Cy3, Cy5, Cy7, IRDye 700DX, or resorufin.

In some embodiments, -T$^1$-R$^t$ is of the following structure:

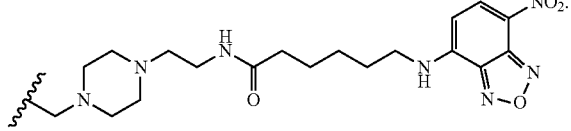

In some embodiments, -T$^1$-R$^t$ is of the following structure:

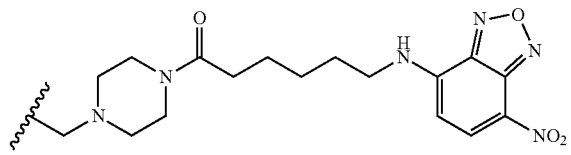 [SMILES: *CN1CCN(C(=O)CCCCCNc2ccc([N+](=O)[O-])c3nonc23)CC1]

In certain embodiments, -T$^1$-R$^t$ is of the following structure:

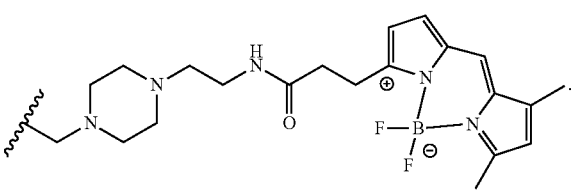

In certain embodiments, -T$^1$-R$^t$ is of the following structure:

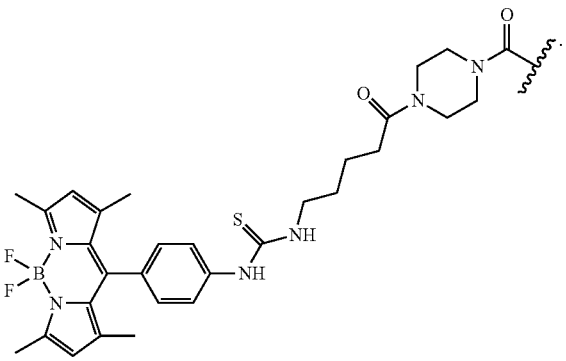

In certain embodiments, -T$^1$-R$^t$ is of the following structure:

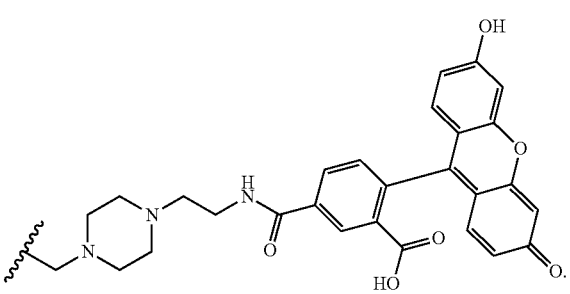 [SMILES: *CN1CCN(CCNC(=O)c2ccc(-c3c4ccc(=O)cc-4oc4cc(O)ccc34)c(C(=O)O)c2)CC1]

In certain embodiments, -T$^1$-R$^t$ is of the following structure:

In certain embodiments, -T$^1$-R$^t$ is of the following structure:

In certain embodiments, -T¹-Rʳ is of the following structure:

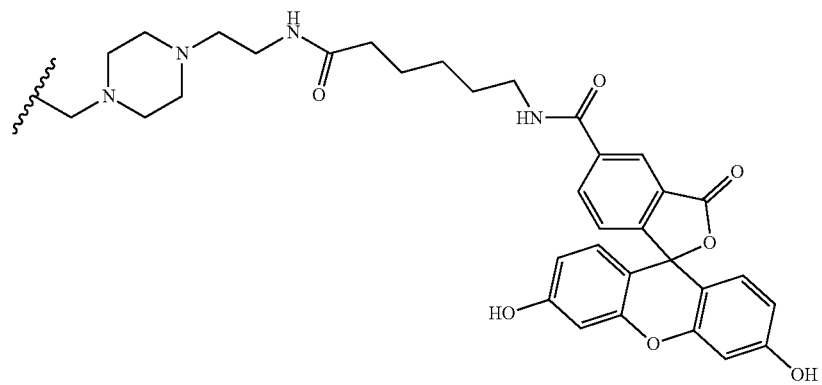 [SMILES: *CN1CCN(CCNC(=O)CCCCCNC(=O)c2ccc3c(c2)C(=O)OC32c3ccc(O)cc3Oc3cc(O)ccc32)CC1]

In certain embodiments, -T¹-Rʳ is of the following structure:

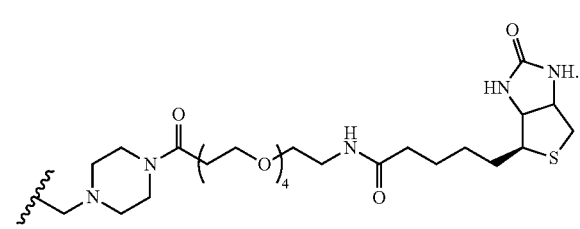

In certain embodiments, -T¹-Rʳ is of the following structure:

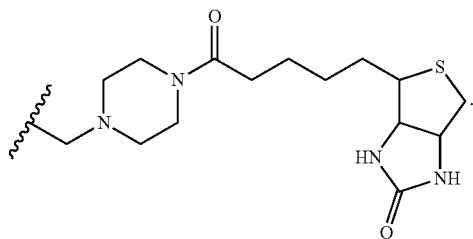 [SMILES: *CN1CCN(C(=O)CCCCC2SCC3NC(=O)NC32)CC1]

In certain embodiments, -T¹-Rʳ is of the following structure:

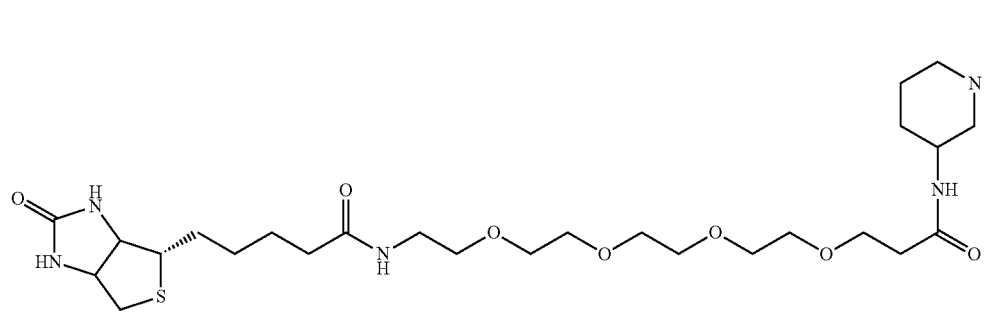

In some embodiments, a probe compound of formula I-t or formula I-s is derived from any compound described herein.

In certain embodiments, the probe compound is selected from compound 63, 86, 102, 177, or 191.

It will be appreciated that many -T¹-Rʳ reagents are commercially available.

In some embodiments, the present invention provides a method for determining occupancy of a protein kinase by a provided irreversible inhibitor (i.e., a compound of any of the formulae presented herein) in a patient, comprising providing one or more tissues, cell types, or a lysate thereof, obtained from a patient administered at least one dose of a compound of said irreversible inhibitor, contacting said tissue, cell type or lysate thereof with a probe compound (i.e., a compound of formula I-t or formula I-s) to covalent modify at least one protein kinase present in said lysate, and measuring the amount of said protein kinase covalently modified by the probe compound to determine occupancy of said protein kinase by said inhibitor as compared to occupancy of said protein kinase by said probe compound. In certain embodiments, the method further comprises the step of adjusting the dose of the compound of formulae presented herein to increase occupancy of the protein kinase. In certain other embodiments, the method further comprises the step of adjusting the dose of the compound of formulae presented herein to decrease occupancy of the protein kinase.

As used herein, the terms "occupancy" or "occupy" refer to the extent to which a protein kinase is modified by a provided covalent inhibitor compound. One of ordinary skill in the art would appreciate that it is desirable to administer the lowest dose possible to achieve the desired efficacious occupancy of the protein kinase.

In some embodiments, the protein kinase to be modified is BTK.

In some embodiments, the probe compound comprises the irreversible inhibitor for which occupancy is being determined.

In some embodiments, the present invention provides a method for assessing the efficacy of a provided irreversible inhibitor in a mammal, comprising administering a provided irreversible inhibitor to the mammal, administering a provided probe compound to tissues or cells isolated from the mammal, or a lysate thereof, measuring the activity of the detectable moiety of the probe compound, and comparing the activity of the detectable moiety to a standard.

In other embodiments, the present invention provides a method for assessing the pharmacodynamics of a provided irreversible inhibitor in a mammal, comprising administering a provided irreversible inhibitor to the mammal, administering a probe compound presented herein to one or more cell types, or a lysate thereof, isolated from the mammal, and measuring the activity of the detectable moiety of the probe compound at different time points following the administration of the inhibitor.

In yet other embodiments, the present invention provides a method for in vitro labeling of a protein kinase comprising contacting said protein kinase with a probe compound described herein. In one embodiment, the contacting step comprises incubating the protein kinase with a probe compound presented herein.

In certain embodiments, the present invention provides a method for in vitro labeling of a protein kinase comprising contacting one or more cells or tissues, or a lysate thereof, expressing the protein kinase with a probe compound described herein.

In certain other embodiments, the present invention provides a method for detecting a labeled protein kinase comprising separating proteins, the proteins comprising a protein kinase labeled by probe compound described herein, by electrophoresis and detecting the probe compound by fluorescence.

In some embodiments, the present invention provides a method for assessing the pharmacodynamics of a provided irreversible inhibitor in vitro, comprising incubating the provided irreversible inhibitor with the target protein kinase, adding the probe compound presented herein to the target protein kinase, and determining the amount of target modified by the probe compound.

In some embodiments, the probe is detected by sodium dodecyl sulfate polyacrylamide gel electrophoresis (SDS-PAGE). In other embodiments, the probe is detected by ELISA. In certain embodiments, the probe is detected by flow cytometry.

In other embodiments, the present invention provides a method for probing the kinome with irreversible inhibitors comprising incubating one or more cell types, or a lysate thereof, with a biotinylated probe compound to generate proteins modified with a biotin moiety, digesting the proteins, capturing with avidin or an analog thereof, and performing multi-dimensional LC-MS-MS to identify protein kinases modified by the probe compound and the adduction sites of said kinases.

In certain embodiments, the present invention provides a method for measuring protein synthesis in cells comprising incubating cells with an irreversible inhibitor of the target protein, forming lysates of the cells at specific time points, and incubating said cell lysates with an inventive probe compound to measure the appearance of free protein over an extended period of time.

In other embodiments, the present invention provides a method for determining a dosing schedule in a mammal for maximizing occupancy of a target protein kinase comprising assaying a one or more cell types, or a lysate thereof, isolated from the mammal, (derived from, e.g., splenocytes, peripheral B cells, whole blood, lymph nodes, intestinal tissue, or other tissues) from a mammal administered a provided irreversible inhibitor of any of the formulae presented herein, wherein the assaying step comprises contacting said one or more tissues, cell types, or a lysate thereof, with a provided probe compound and measuring the amount of protein kinase covalently modified by the probe compound.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

The symbols and conventions used in the following descriptions of processes, schemes, and examples are consistent with those used in the contemporary scientific literature, for example, the Journal of the American Chemical Society or the Journal of Biological Chemistry.

Unless otherwise indicated, all temperatures are expressed in ° C. (degrees Centigrade). All reactions were conducted at room temperature unless otherwise noted. All compounds of the present invention were synthesiszed by processes developed by the inventors.

For the examples using Schemes 1 to 17, the $^1$H-NMR spectra were recorded on a Bruker Avance III 400 MHz. Chemical shifts are expressed in parts per million (ppm, δ units). Coupling constants are in units of Hertz (Hz). Splitting patterns describe apparent multiplicities and are designated as s (singlet), d (doublet), t (triplet), q (quartet), m (multiplet), or br (broad).

Mass spectra were obtained on Agilent 1200 Series mass spectrometers from Agilent technologies, using either Atmospheric Chemical Ionization (APCI) or Electrospray Ionization (ESI). Column: XBridge C8, 3.5 µm, 4.6×50 mm; Solvent A: water+0.1% TFA; Solvent B: CAN; Flow: 2 ml/min; Gradient: 0 min: 5% B, 8 min: 100% B, 8.1 min: 100% B, 8.5 min: 5% B, 10 min 5% B.

HPLC data were obtained using Agilent 1100 series HPLC from Agilent technologies using XBridge column (C8, 3.5 µm, 4.6×50 mm). Solvent A: water+0.1% TFA; Solvent B: ACN; Flow: 2 ml/min; Gradient: 0 min: 5% B, 8 min: 100% B, 8.1 min: 100% B, 8.5 min: 5% B, 10 min 5% B.

The microwave reactions were conducted using Biotage Initiator Microwave Synthesizer using standard protocols that are known in the art.

Some abbreviations that may appear in this application are as follows:

| | |
|---|---|
| Aq. | Aqueous |
| BBFO | Broad band fluorine observation |

-continued

| | |
|---|---|
| BrettPhos | 2-(Dicyclohexylphosphino)3,6-dimethoxy-2',4',6'-triisopropyl-1,1'-biphenyl |
| δ | chemical shift |
| d | deuterium or doublet |
| dd | doublet of doublets |
| DCM | dichloromethane |
| DIPEA | diisopropylethylamine |
| DMF | dimethylformamide |
| DMSO | dimethylsulfoxide |
| dppf | 1,1'-bis(diphenylphosphino)ferrocene |
| eq. | equivalent |
| ES | electrospray |
| h | hour |
| $^1$H | proton |
| HPLC | high pressure liquid chromatography |
| IR | infrared |
| J | coupling constant |
| K | kelvin |
| LC | liquid chromatography |
| m | Multiplet or meta |
| M | molecular ion |
| Me | methyl |
| MHz | Megahertz |
| min | minute |
| mL | milliliter |
| MS | mass spectrometry |
| m/z | mass-to-charge ratio |
| N | Normality (equivalent per liter) |
| NMR | nuclear magnetic resonance |
| Pet | petroleum |
| RBF | Round Bottom Flask |
| RT | room temperature |
| RuPhos | 2-Dicyclohexylphosphino-2',6'-diisopropoxybiphenyl |
| s | singlet |
| TFA | Trifluoroacetic acid |
| THF | tetrahydrofuran |
| TLC | thin layer chromatography |
| UFLC | Ultra fast liquid chromatography |
| UV | ultraviolet |
| V | Volume |
| VT | Variable temperature |

Compound numbers utilized in the Examples below correspond to compound numbers set forth supra.

Example 1

Scheme 1

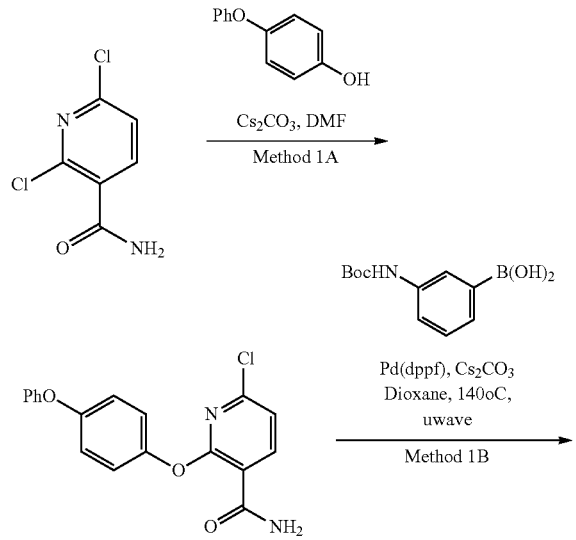

Methods Associated with Reaction Steps in Scheme 1:

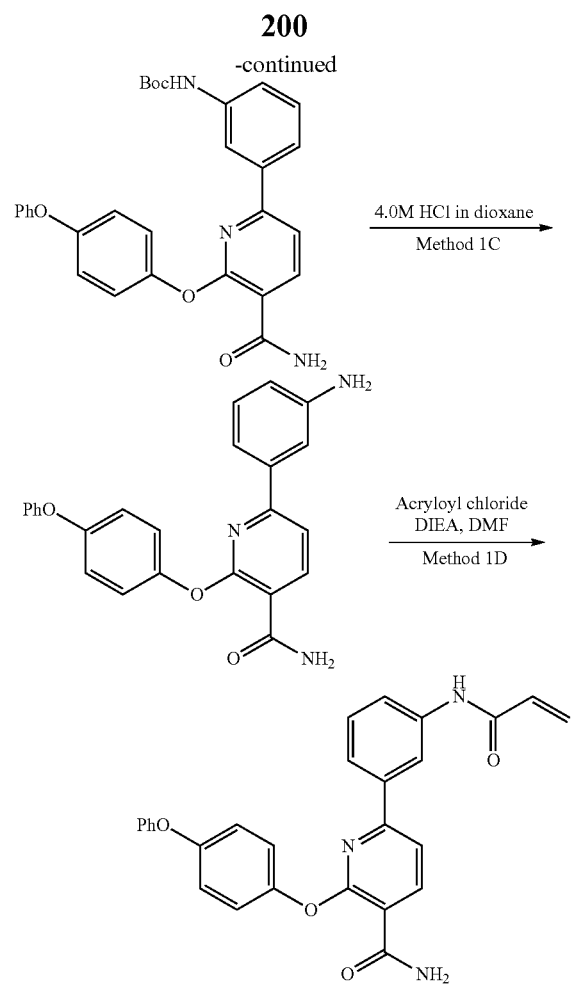

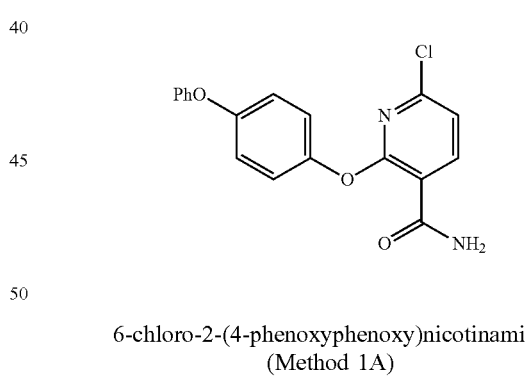

6-chloro-2-(4-phenoxyphenoxy)nicotinamide (Method 1A)

In a microwave vial containing 2,6-Dichloro-nicotinamide (940.00 mg; 4.92 mmol; 1.00 eq.) and 4-phenoxyphenol (962.16 mg; 5.17 mmol; 1.05 eq.) in DMF (25.00 ml; 259.39 mmol; 52.71 eq.) was added cesium carbonate (3.53 g; 10.83 mmol; 2.20 eq.).

After stirring at room temperature for 3 hr the reaction was added to 200 mL water and a solid precipitated. The solid was filtered and rinsed with water. The white solid was dissolved in 50 mL EA and washed with water (2×15 mL), sat NaHCO$_3$ (1×15 mL), and brine (1×15 mL); dried (Na2SO4); filtered; and concentrated to afford 6-chloro-2-(4-phenoxyphenoxy)nicotinamide (1.60 g, 83%) as an off-white solid. MS: m/z=341 [M+H]$^+$.

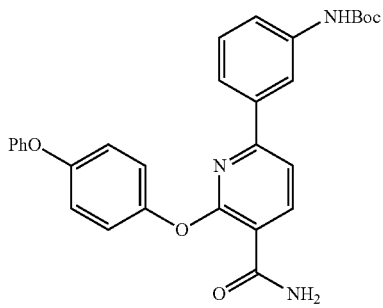 [SMILES: CC(C)(C)OC(=O)Nc1cccc(-c2ccc(C(N)=O)c(Oc3ccc(Oc4ccccc4)cc3)n2)c1]

tert-butyl (3-(5-carbamoyl-6-(4-phenoxyphenoxy)pyridin-2-yl)phenyl)carbamate (Method 1B)

Into a reaction vial with magnetic stir bar was added 6-Chloro-2-(4-phenoxy-phenoxy)-nicotinamide (175.00 mg; 0.51 mmol; 1.00 eq.), 3-Boc-aminophenylboronic acid (146.09 mg; 0.62 mmol; 1.20 eq.), and [1,1'-bis(diphenylphosphino)ferrocene]dichloropalladium(ii), complex with dichloromethane (1:1) (41.94 mg; 0.05 mmol; 0.10 eq.). The vessel was evacuated and back-filled with nitrogen. Added [1,4]Dioxane (3.00 ml) and cesium carbonate (770.34 μl; 1.54 mmol; 3.00 eq.) and then evacuated and back-filled with nitrogen again. Stirred at 150° C. in a microwave for 10 min. The reaction was concentrated, redissolved in ethyl acetate (3 mL), loaded on silica gel and purified via flash chromatography (Biotage): 25 g column using 25% ethyl acetate/hexanes isocratic for 1 min then ramped to 50% ethyl acetate/hexanes over 5 min at a flow rate of 25 mL/min. The product fractions were combined and concentrated to afford tert-butyl (3-(5-carbamoyl-6-(4-phenoxyphenoxy)pyridin-2-yl)phenyl)carbamate (187 mg, 73%) as a white solid.

MS: m/z=498 [M+H]$^+$.

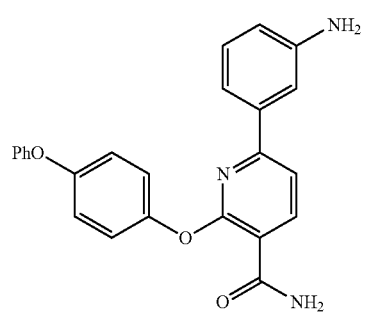 [SMILES: NC(=O)c1ccc(-c2cccc(N)c2)nc1Oc1ccc(Oc2ccccc2)cc1]

6-(3-aminophenyl)-2-(4-phenoxyphenoxy)nicotinamide (Method 1C)

In a 100 mL round bottom flask with magnetic stir bar {3-[5-Carbamoyl-6-(4-phenoxy-phenoxy)-pyridin-2-yl]-phenyl}-carbamic acid tert-butyl ester (182.00 mg; 0.37 mmol; 1.00 eq.) was suspended in MeOH (10 mL) and treated with 4.0M HCl/dioxane (10 mL). The reaction became homogeneous after 5 min. After 16 hr the reaction was concentrated, chased with toluene, and placed under high vacuum at 35° C. for 1 hr. Assumed 100% yield of 6-(3-aminophenyl)-2-(4-phenoxyphenoxy)nicotinamide (off-white solid). MS: m/z=398 [M+H]$^+$.

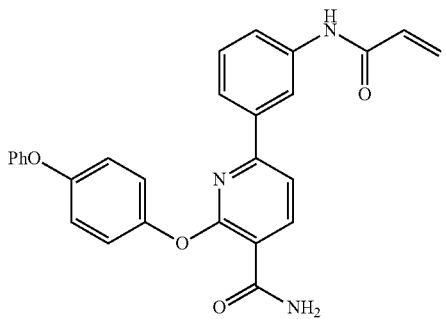 [SMILES: C=CC(=O)Nc1cccc(-c2ccc(C(N)=O)c(Oc3ccc(Oc4ccccc4)cc3)n2)c1]

6-(3-acrylamidophenyl)-2-(4-phenoxyphenoxy)nicotinamide (Method 1D) (80)

In a 100 mL round bottom flask with magnetic stir bar 6-(3-Amino-phenyl)-2-(4-phenoxy-phenoxy)-nicotinamide dihydrochloride (174.03 mg; 0.37 mmol; 1.00 eq.) was suspended in DCE (10 mL). The stirring suspension was then treated with DIPEA (257.79 μl; 1.48 mmol; 4.00 eq.) and the reaction became homogeneous. To the stirring solution was then added acryloyl chloride (31.56 μl; 0.39 mmol; 1.05 eq.). After 5 min the reaction was concentrated to a solid which was redissolved in DMSO (2 mL) and purified via prep HPLC: C-18 (10 um), 30×150 mm, 0.1% HCO$_2$H modified mobile phases (A=water, B=ACN), Method 25% ACN isocratic for 1 min then ramped to 75% ACN over 15 min at 60 mL/min. The product fractions were combined and lyophilized to afford 6-(3-acrylamidophenyl)-2-(4-phenoxyphenoxy)nicotinamide (35 mg, 19%) as a white solid. HPLC: 100% purity. MS m/z=452 [M+H]$^+$. $^1$H NMR (500 MHz, dmso-d$_6$) δ 10.24 (s, 1H), 8.37-8.15 (m, 1H), 7.80 (d, 1H), 7.70 (d, 1H), 7.65 (d, 1H), 7.54 (d, 1H), 7.38 (t, 1H), 7.33 (d, 1H), 7.13 (t, 1H), 7.05 (d, 1H), 6.43 (dd, 1H), 6.25 (d, 1H).

Example 2

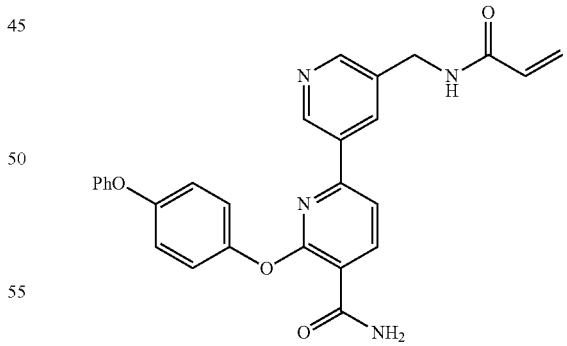

5'-(acrylamidomethyl)-6-(4-phenoxyphenoxy)-[2,3'-bipyridine]-5-carboxamide (84)

5'-(acrylamidomethyl)-6-(4-phenoxyphenoxy)-[2,3'-bipyridine]-5-carboxamide 61 mg (39%) was prepared from 2,6-Dichloro-nicotinamide, 4-phenoxyphenol, [5-(4,4,5,5-Tetramethyl-[1,3,2]dioxaborolan-2-yl)-pyridin-3-ylmethyl]-carbamic acid tert-butyl ester, and acryloyl chloride using methods 1A, 1B, 1C and 1D. HPLC: 100% purity. MS: m/z=467 [M+H]+. 1H NMR (400 MHz, DMSO-$d_6$) δ 8.92 (d, 1H), 8.66 (t, 1H), 8.54 (d, 1H), 8.32 (d, 1H), 8.12 (s, 1H), 7.85 (dd, 3H), 7.42 (t, 2H), 7.38-7.31 (m, 2H), 7.18-7.10 (m, 3H), 7.06 (d, 2H), 6.26 (dd, 1H), 6.13 (dd, 2.2 Hz, 1H), 5.62 (dd, 2.2 Hz, 1H), 4.41 (d, 2H).

Example 3

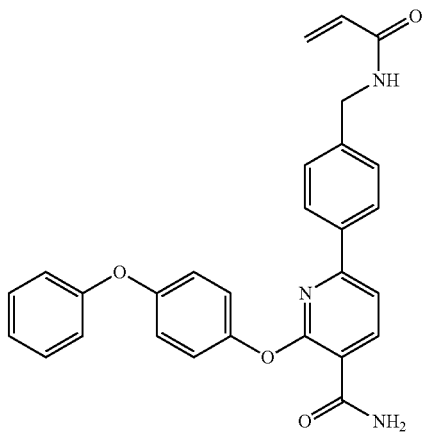 [SMILES: C=CC(=O)NCc1ccc(-c2ccc(C(N)=O)c(Oc3ccc(Oc4ccccc4)cc3)n2)cc1]

6-(4-(acrylamidomethyl)phenyl)-2-(4-phenoxyphenoxy)nicotinamide (89)

6-(4-(acrylamidomethyl)phenyl)-2-(4-phenoxyphenoxy)nicotinamide 96 mg (51%) was prepared from 2,6-Dichloro-nicotinamide, 4-phenoxyphenol, (4-(((tert-butoxycarbonyl)amino)methyl)-phenyl)boronic acid, and acryloyl chloride using methods 1A, 1B, 1C and 1D. HPLC: 99.7% purity. MS: m/z=466 [M+H]+. 1H NMR (400 MHz, DMSO) δ 8.63 (t, 1H), 8.28 (d, 1H), 7.81 (dd, 5H), 7.46-7.38 (m, 2H), 7.37-7.28 (m, 4H), 7.19-7.10 (m, 3H), 7.07-7.00 (m, 2H), 6.30 (dd, 1H), 6.15 (dd, 1H), 5.64 (dd, 1H), 4.39 (d, 2H).

Example 4

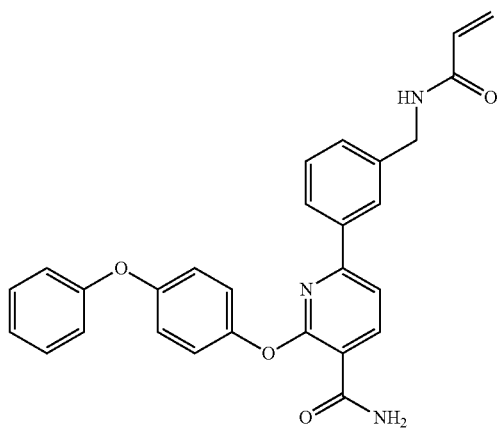 [SMILES: C=CC(=O)NCc1cccc(-c2ccc(C(N)=O)c(Oc3ccc(Oc4ccccc4)cc3)n2)c1]

6-(3-(acrylamidomethyl)phenyl)-2-(4-phenoxyphenoxy)nicotinamide (98)

6-(4-(acrylamidomethyl)phenyl)-2-(4-phenoxyphenoxy)nicotinamide 80 mg (43%) was prepared from 2,6-Dichloro-nicotinamide, 4-phenoxyphenol, (3-(((tert-butoxycarbonyl)amino)methyl)phenyl)-boronic acid, and acryloyl chloride using methods 1A, 1B, 1C and 1D. HPLC 100% purity. MS: m/z=466 [M+H]+. 1H NMR (400 MHz, DMSO-$d_6$) δ 8.61 (t, 1H), 8.30 (d, 1H), 7.91-7.68 (m, 5H), 7.45-7.37 (m, 3H), 7.37-7.29 (m, 3H), 7.18-7.10 (m, 3H), 7.05 (dd, Hz, 2H), 6.28 (dd, 1H), 6.13 (dd, 1H), 5.62 (dd, 1H), 4.38 (d, 2H).

Example 5

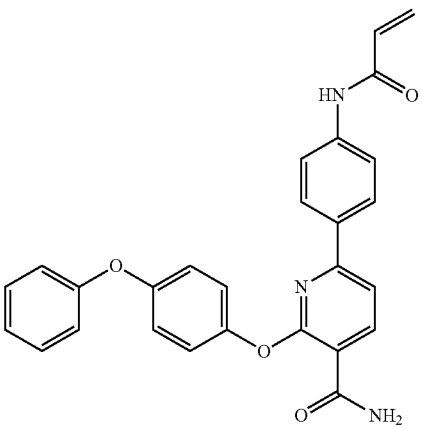 [SMILES: C=CC(=O)Nc1ccc(-c2ccc(C(N)=O)c(Oc3ccc(Oc4ccccc4)cc3)n2)cc1]

6-(4-acrylamidophenyl)-2-(4-phenoxyphenoxy)nicotinamide (159)

6-(4-acrylamidophenyl)-2-(4-phenoxyphenoxy)nicotinamide 65 mg (54%) was prepared from 2,6-Dichloro-nicotinamide, 4-phenoxyphenol, (4-((tert-butoxycarbonyl)amino)phenyl)boronic acid, and acryloyl chloride using methods 1A, 1B, 1C and 1D. HPLC 100% purity. MS: m/z=452 [M+H]+. 1H NMR (400 MHz, DMSO-$d_6$) δ 10.31 (s, 1H), 8.27 (d, 1H), 7.85 (d, 2H), 7.75 (dd, 5H), 7.49-7.40 (m, 2H), 7.37-7.30 (m, 2H), 7.20-7.12 (m, 3H), 7.05 (dd, 2H), 6.46 (dd, 1H), 6.29 (dd, 1H), 5.79 (dd, 1H).

Example 6

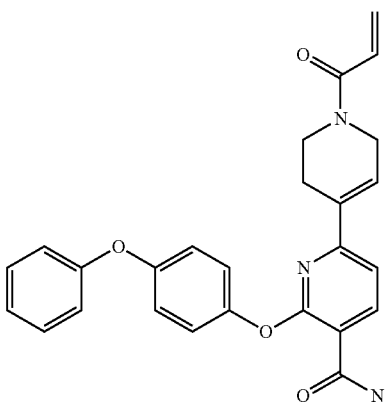 [SMILES: C=CC(=O)N1CC=C(c2ccc(C(N)=O)c(Oc3ccc(Oc4ccccc4)cc3)n2)CC1]

1'-acryloyl-6-(4-phenoxyphenoxy)-1',2',3',6'-tetrahydro-[2,4'-bipyridine]-5-carboxamide (69)

1'-acryloyl-6-(4-phenoxyphenoxy)-1',2',3',6'-tetrahydro-[2,4'-bipyridine]-5-carboxamide 38 mg (36%) was prepared from 2,6-Dichloro-nicotinamide, 4-phenoxyphenol, (1-(tert-butoxycarbonyl)-1,2,3,6-tetrahydropyridin-4-yl)boronic acid, and acryloyl chloride using methods 1A, 1B, 1C and 1D. HPLC 100% purity. MS: m/z=442 [M+H]⁺. ¹H NMR (400 MHz, DMSO-d₆) δ 8.21 (d, 1H), 7.75 (s, 2H), 7.38 (dd, 3H), 7.27 (d, 2H), 7.13 (dd, 3H), 7.01 (d, 2H), 6.94-6.69 (m, 1H), 6.59 (s, 1H), 6.12 (d, 1H), 5.69 (d, 1H), 4.23 (d, 2H), 3.68 (s, 2H), 2.38 (d, 2H).

Example 7

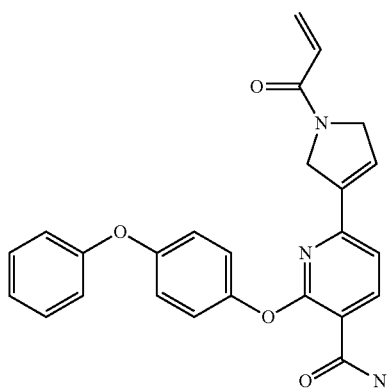 [SMILES: C=CC(=O)N1CC=C(c2ccc(C(N)=O)c(Oc3ccc(Oc4ccccc4)cc3)n2)C1]

6-(1-acryloyl-2,5-dihydro-1H-pyrrol-3-yl)-2-(4-phenoxyphenoxy)nicotinamide (88)

6-(1-acryloyl-2,5-dihydro-1H-pyrrol-3-yl)-2-(4-phenoxyphenoxy)nicotinamide 52 mg (62%) was prepared from 2,6-Dichloro-nicotinamide, 4-phenoxyphenol, tert-butyl 3-(4,4,5,5-tetramethyl-1,3,2-dioxaborolan-2-yl)-2,5-dihydro-1H-pyrrole-1-carboxylate, and acryloyl chloride using methods 1A, 1B, 1C and 1D. HPLC 100% purity. MS: m/z=428 [M+H]⁺. ¹H NMR (400 MHz, DMSO-d₆) δ 8.22 (dd, 1H), 7.79 (s, 2H), 7.52-7.36 (m, 3H), 7.33-7.23 (m, 2H), 7.21-6.96 (m, 5H), 6.55 (ddd, 2H), 6.20 (dt, 1H), 5.70 (ddd, 1H), 4.57 (s, 2H), 4.33 (s, 2H).

Example 8

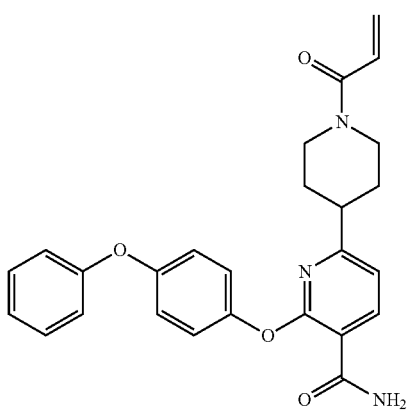

6-(1-acryloylpiperidin-4-yl)-2-(4-phenoxyphenoxy)nicotinamide (64)

6-(1-acryloylpiperidin-4-yl)-2-(4-phenoxyphenoxy)nicotinamide 34 (32%) was prepared from 2,6-Dichloro-nicotinamide, 4-phenoxyphenol, (1-(tert-butoxycarbonyl)-1,2,3,6-tetrahydropyridin-4-yl)boronic acid, and acryloyl chloride using methods 1A, 1B, 1C and 1D. The Boc protected penultimate product tetrahydropyridine was reduced to the Boc protected piperidine via standard hydrogenolysis (10% Pd—C, H₂ balloon). HPLC 100% purity. MS: m/z=444 [M+H]⁺. ¹H NMR (400 MHz, DMSO-d₆) δ 8.14 (d, 7.72 (s, 2H), 7.41 (t, 2H), 7.21 (d, 2H), 7.14 (t, 2H), 7.06 (d, 2H), 7.00 (d, 2H), 6.78 (dd, 1H), 6.07 (d, 1H), 5.64 (d, 1H), 4.36 (d, 1H), 4.02 (d, 1H), 3.13 (t, 1H), 2.86 (t, 1H), 2.76 (t, 1H), 1.78 (s, 2H), 1.49-1.29 (m, 2H).

Example 9

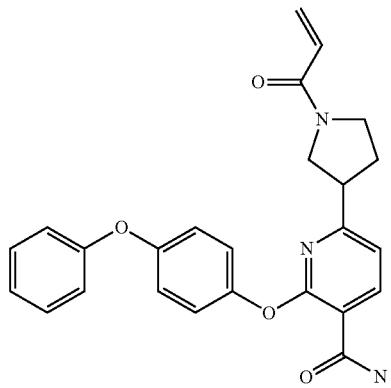 [SMILES: C=CC(=O)N1CCC(c2ccc(C(N)=O)c(Oc3ccc(Oc4ccccc4)cc3)n2)C1]

6-(1-acryloylpyrrolidin-3-yl)-2-(4-phenoxyphenoxy)nicotinamide (70)

6-(1-acryloylpyrrolidin-3-yl)-2-(4-phenoxyphenoxy)nicotinamide 52 mg (61%) was prepared from 2,6-Dichloro-nicotinamide, 4-phenoxyphenol, tert-butyl 3-(4,4,5,5-tetramethyl-1,3,2-dioxaborolan-2-yl)-2,5-dihydro-1H-pyrrole-1-carboxylate, and acryloyl chloride using methods 1A, 1B, 1C and 1D. The Boc protected penultimate product tetrahydropyridine was reduced to the Boc protected piperidine via standard hydrogenolysis (10% Pd—C, H₂ balloon). HPLC 100% purity. MS: m/z=430 [M+H]⁺. ¹H NMR (400 MHz, DMSO-d₆) δ 8.16 (dd, 1H), 7.74 (s, 2H), 7.40 (dd, 2H), 7.27-7.09 (m, 4H), 7.04 (t, 4H), 6.52-6.38 (m, 1H), 6.10 (d, 1H), 5.65-5.55 (m, 1H), 3.84 (t, 1H), 3.68 (dd, 1H), 3.60-3.48 (m, 2H), 3.48-3.37 (m, 1H), 2.16 (ddt, 1H), 2.02-1.75 (m, 1H).

Example 10

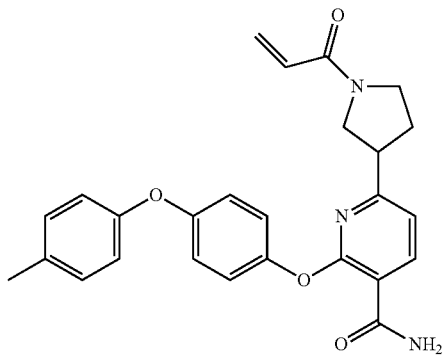

6-(1-acryloylpyrrolidin-3-yl)-2-(4-(p-tolyloxy)phenoxy)nicotinamide (81)

6-(1-Acryloyl-pyrrolidin-3-yl)-2-(4-p-tolyloxy-phenoxy)-nicotinamide (100.00 mg; 45.7%) was prepared from 2,6-Dichloro-nicotinamide, 4-(p-tolyloxy)phenol, tert-butyl 3-(4,4,5,5-tetramethyl-1,3,2-dioxaborolan-2-yl)-2,5-dihydro-1H-pyrrole-1-carboxylate, and acryloyl chloride using methods 1A, 1B, 1C and 1D. The Boc protected penultimate product tetrahydropyridine was reduced to the Boc protected piperidine via standard hydrogenolysis (10% Pd—C, H$_2$ balloon). HPLC 98.9% purity. MS: m/z=444.2 [M+H]$^+$. 1H NMR (400 MHz, DMSO-d6): 8.12 (dd, J=6.00, 7.62 Hz, 1H), 7.20-7.14 (m, 5H), 7.00-6.99 (m, 2H), 6.91 (d, J=8.44 Hz, 2H), 6.48-6.40 (m, 1H), 6.11-6.06 (m, 1H), 5.62-5.57 (m, 1H), 3.82-3.63 (m, 1H), 3.54-3.48 (m, 2H), 3.47-3.41 (m, 1H), 3.33-3.26 (m, 1H), 2.27 (s, 2H), 2.17-2.07 (m, 1H), 1.93-1.80 (m, 1H).

Example 11

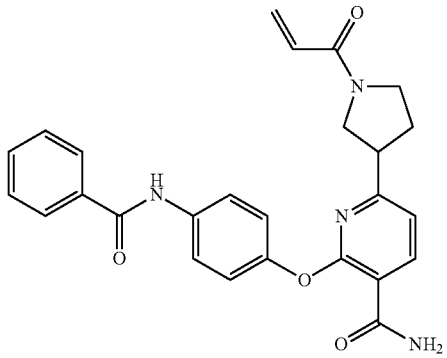 [SMILES: C=CC(=O)N1CCC(c2ccc(C(N)=O)c(Oc3ccc(NC(=O)c4ccccc4)cc3)n2)C1]

6-(1-acryloylpyrrolidin-3-yl)-2-(4-benzamidophenoxy)nicotinamide (99)

6-(1-Acryloyl-pyrrolidin-3-yl)-2-(4-benzoylamino-phenoxy)-nicotinamide (45.00 mg; 0.10 mmol; 28.5%) was prepared from 2,6-Dichloro-nicotinamide, N-(4-hydroxyphenyl)benzamide, tert-butyl 3-(4,4,5,5-tetramethyl-1,3,2-dioxaborolan-2-yl)-2,5-dihydro-1H-pyrrole-1-carboxylate, and acryloyl chloride using methods 1A, 1B, 1C and 1D. The Boc protected penultimate product tetrahydropyridine was reduced to the Boc protected piperidine via standard hydrogenolysis (10% Pd—C, H$_2$ balloon). HPLC 99.3% purity. MS: m/z=457.2 [M+H]$^+$. 400 MHz, DMSO-d6: 10.29 (s, 1H), 8.13 (t, J=7.48 Hz, 1H), 7.96 (dd, J=1.36, 6.84 Hz, 2H), 7.81-7.74 (m, 4H), 7.61-7.51 (m, 3H), 7.20-7.18 (m, 3H), 6.47-6.39 (m, 1H), 6.09-6.03 (m, 1H), 5.61-5.55 (m, 1H), 3.83-3.65 (m, 1H), 3.54-3.50 (m, 2H), 3.49-3.45 (m, 1H), 3.43-3.28 (m, 1H), 2.22-2.05 (m, 1H), 1.98-1.75 (m, 1H).

Example 12

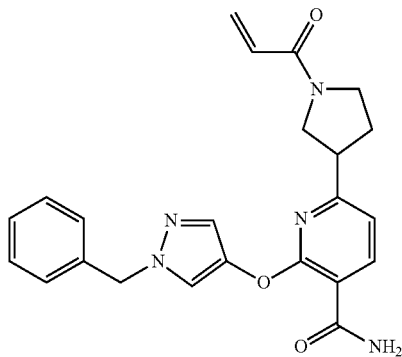 [SMILES: C=CC(=O)N1CCC(c2ccc(C(N)=O)c(Oc3cnn(Cc4ccccc4)c3)n2)C1]

tert-butyl 3-(4-((1-benzyl-1H-pyrazol-4-yl)oxy)-5-carbamoylpyridin-2-yl)pyrrolidine-1-carboxylate (104)

6-(1-Acryloyl-pyrrolidin-3-yl)-2-(1-benzyl-1H-pyrazol-4-yloxy)-nicotinamide (85.00 m; 37.4%) %) was prepared from 2,6-Dichloro-nicotinamide, 1-benzyl-1H-pyrazol-4-ol, tert-butyl 3-(4,4,5,5-tetramethyl-1,3,2-dioxaborolan-2-yl)-2,5-dihydro-1H-pyrrole-1-carboxylate, and acryloyl chloride using methods 1A, 1B, 1C and 1D. The Boc protected penultimate product tetrahydropyridine was reduced to the Boc protected piperidine via standard hydrogenolysis (10% Pd—C, H$_2$ balloon). HPLC-UV: 98.5% purity. LC/MS m/z=418 [M+H]$^{+1}$. 1H NMR (400 MHz, DMSO-d6): 8.64 (s, 1H), 8.01 (d, J=2.08 Hz, 1H), 7.71 (s, 2H), 7.54 (s, 1H), 7.38-7.24 (m, 4H), 6.81 (d, J=10.08 Hz, 1H), 6.61-6.52 (m, 1H), 6.15-6.09 (m, 1H), 6.10-6.08 (m, 1H), 5.67-5.61 (m, 1H), 5.35 (s, 2H), 3.93-3.91 (m, 1H), 3.78-3.71 (m, 1H), 3.63-3.48 (m, 2H), 3.46-3.32 (m, 1H), 2.22-1.90 (m, 2H).

Example 13

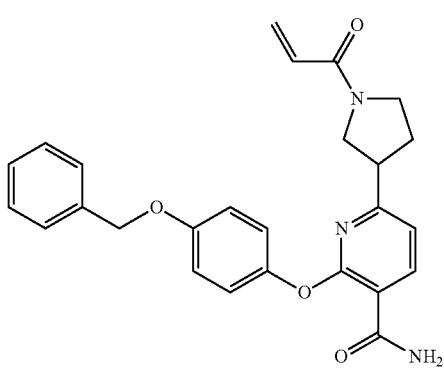 [SMILES: C=CC(=O)N1CCC(c2ccc(C(N)=O)c(Oc3ccc(OCc4ccccc4)cc3)n2)C1]

6-(1-acryloylpyrrolidin-3-yl)-2-(4-(benzyloxy)phenoxy)nicotinamide (105)

6-(1-Acryloyl-pyrrolidin-3-yl)-2-(4-benzyloxy-phenoxy)-nicotinamide (100.00 mg; 35.1%) was prepared from 2,6-Dichloro-nicotinamide, 1-benzyl-1H-pyrazol-4-ol, tert-butyl 3-(4,4,5,5-tetramethyl-1,3,2-dioxaborolan-2-yl)-2,5-dihydro-1H-pyrrole-1-carboxylate, and acryloyl chloride using methods 1A, 1B, 1C and 1D. The Boc protected penultimate product tetrahydropyridine was reduced to the Boc protected piperidine via standard hydrogenolysis (10% Pd—C, H$_2$ balloon). HPLC-UV: 98.5% purity. LC/MS m/z=444.2 [M+H]$^{+1}$. 1H NMR (400 MHz, DMSO-d6): 8.12-8.10 (m, 1H), 7.71 (s, 2H), 7.47-7.45 (m, 2H), 7.41-7.39 (m, 2H), 7.37-7.32 (m, 1H), 7.17-7.08 (m, 3H), 7.02-6.99 (m, 2H), 6.46-6.37 (m, 1H), 6.11-6.05 (m, 1H), 5.63-5.59 (m, 1H), 5.10 (s, 2H), 4.10-3.63 (m, 1H), 3.51-3.41 (m, 2H), 3.38-3.30 (m, 1H), 3.28-3.22 (m, 1H), 2.15-2.05 (m, 1H), 1.90-1.79 (m, 1H).

Example 14

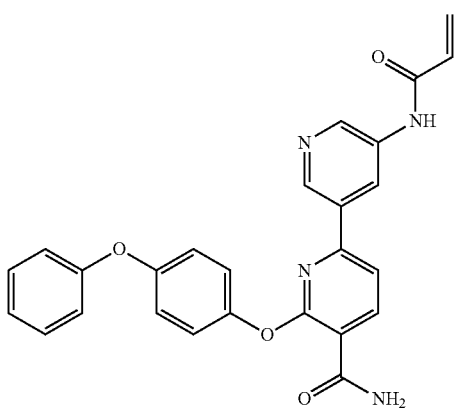 [SMILES: C=CC(=O)Nc1cncc(-c2ccc(C(N)=O)c(Oc3ccc(Oc4ccccc4)cc3)n2)c1]

5'-acrylamido-6-(4-phenoxyphenoxy)-[2,3'-bipyridine]-5-carboxamide (75)

5'-acrylamido-6-(4-phenoxyphenoxy)-[2,3*-bipyridine]-5-carboxamide 16 mg (9%) was prepared from 2,6-Dichloro-nicotinamide, 4-phenoxyphenol, (5-(((tert-butoxycarbonyl)amino)pyridin-3-yl)boronic acid, and acryloyl chloride using methods 1A, 1B, 1C and 1D HPLC 98% purity. MS: m/z=453 [M+H]$^+$. $^1$H NMR (400 MHz, DMSO-d$_6$) δ 10.48 (s, 1H), 8.77 (d, 2H), 8.63 (s, 1H), 8.32 (d, 1H), 7.83 (t, 3H), 7.46-7.30 (m, 4H), 7.19-7.01 (m, 5H), 6.45 (dd, 1H), 6.29 (d, 1H), 5.82 (d, 1H).

Example 15

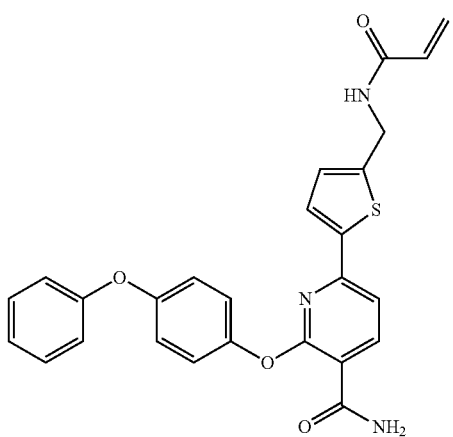

6-(5-(acrylamidomethyl)thiophen-2-yl)-2-(4-phenoxyphenoxy)nicotinamide (160)

6-(5-(acrylamidomethyl)thiophen-2-yl)-2-(4-phenoxyphenoxy)nicotinamide 102 mg (62%) was prepared from 2,6-Dichloro-nicotinamide, 4-phenoxyphenol, (5-(((tert-butoxycarbonyl)amino)methyl)thiophen-2-yl)boronic acid, and acryloyl chloride using methods 1A, 1B, 1C and 1D. HPLC 99% purity. MS: m/z=472 [M+H]$^+$. $^1$H NMR (400 MHz, DMSO-d$_6$) δ 8.69 (t, 1H), 8.22 (d, 1H), 7.75 (s, 2H), 7.63 (dd, 2H), 7.43 (t, 2H), 7.29 (d, 2H), 7.13 (dd, 3H), 7.05 (d, 2H), 7.00 (s, 1H), 6.24 (dd, 1H), 6.13 (d, 1H), 5.62 (d, 1H), 4.47 (d, 2H).

Example 16

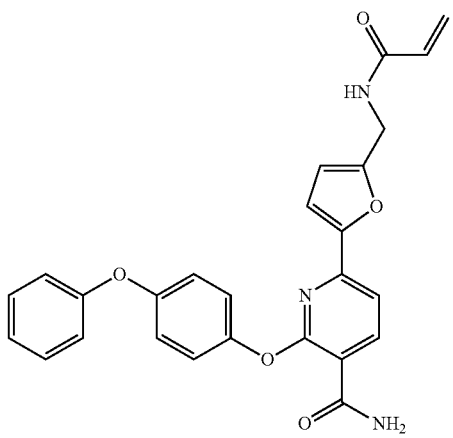 [SMILES: C=CC(=O)NCc1ccc(-c2ccc(C(N)=O)c(Oc3ccc(Oc4ccccc4)cc3)n2)o1]

6-(5-(acrylamidomethyl)furan-2-yl)-2-(4-phenoxyphenoxy)nicotinamide (161)

6-(5-(acrylamidomethyl)furan-2-yl)-2-(4-phenoxyphenoxy)nicotinamide 100 mg (69%) was prepared from 2,6-Dichloro-nicotinamide, 4-phenoxyphenol, (5-(((tert-butoxycarbonyl)amino)methyl)furan-2-yl)boronic acid, and acryloyl chloride using methods 1A, 1B, 1C and 1D. HPLC 99% purity. MS: m/z=456 [M+H]$^+$. $^1$H NMR (400 MHz, DMSO-d$_6$) δ 8.64 (t, 1H), 8.28 (d, 1H), 7.76 (s, 2H), 7.49-7.36 (m, 3H), 7.29 (t, 2H), 7.19-7.08 (m, 3H), 7.04 (d, 2H), 6.69 (d, 1H), 6.41 (d, 1H), 6.27 (dd, 1H), 6.14 (dd, 1H), 5.63 (dd, 1H), 4.42 (d, 2H).

Example 17

Scheme 2

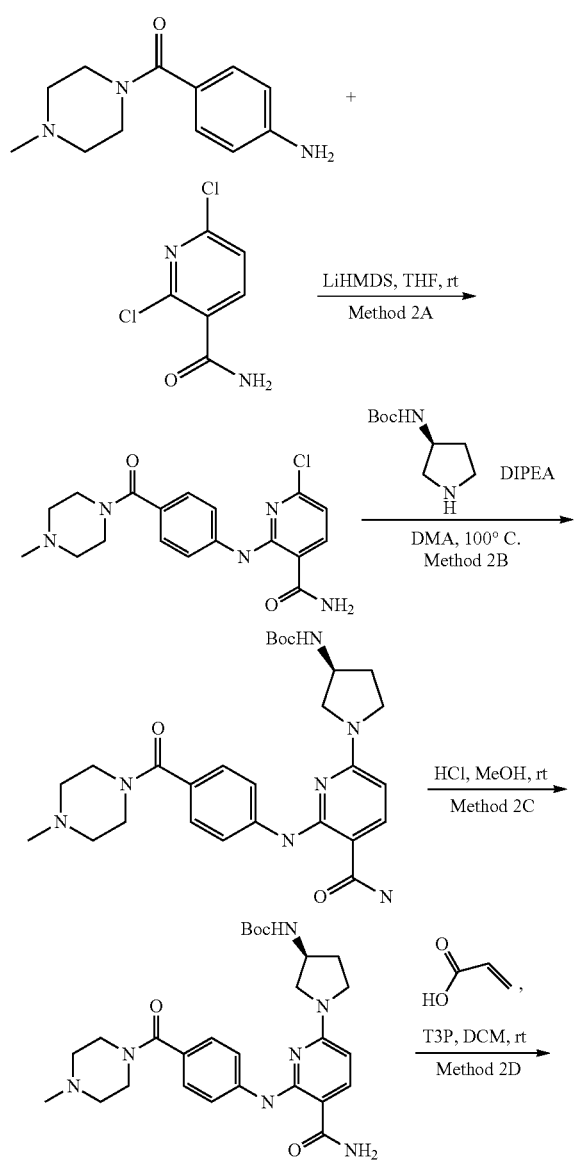

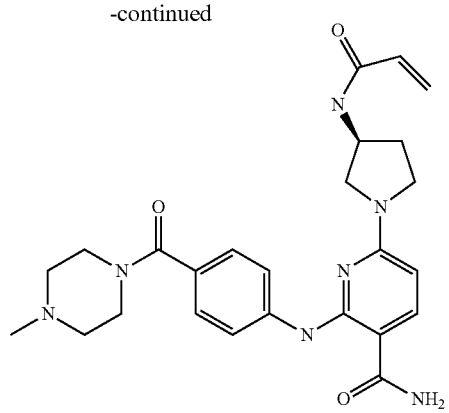

Methods Associated with Reaction Steps in Scheme 2:

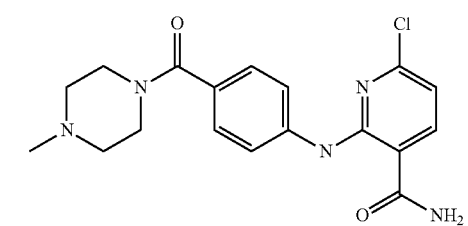 [SMILES: CN1CCN(C(=O)c2ccc(Nc3nc(Cl)ccc3C(N)=O)cc2)CC1]

6-chloro-2-((4-(4-methylpiperazine-1-carbonyl)phenyl)amino)nicotinamide (Method 2A)

In a microwaver vial containing 2,6-dichloro-nicotinamide (150.00 mg; 0.79 mmol; 1.00 eq.) and (4-aminophenyl)-(4-methyl-piperazin-1-yl)-methanone (206.64 mg; 0.94 mmol; 1.20 eq.) was added THF (10.00 ml; 123.43 mmol; 157.18 eq.) and sodium bis(trimethylsilyl)amide (2.30 ml; 2.36 mmol; 3.00 eq.) at −78° C. The reaction was stirred at rt for 1.5 h before it was quenched with 1 mL sat. NH$_4$Cl solution and extracted with EtOAc (5 mL×3). The combined organic layers were combined, concentrated and carried to the next step. MS: m/z=374 [M+H]+

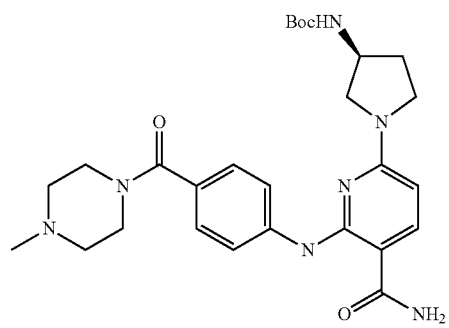 [SMILES: CN1CCN(C(=O)c2ccc(Nc3nc(N4CC[C@H](NC(=O)OC(C)(C)C)C4)ccc3C(N)=O)cc2)CC1]

(S)-tert-butyl (1-(5-carbamoyl-6-((4-(4-methylpiperazine-1-carbonyl)phenyl)amino)pyridin-2-yl)pyrrolidin-3-yl)carbamate (Method 2B)

In a microwave vial containing 6-Chloro-2-[4-(4-methylpiperazine-1-carbonyl)-phenylamino]-nicotinamide (136.00 mg; 0.36 mmol; 1.00 eq.) and (S)-Pyrrolidin-3-yl-carbamic acid tert-butyl ester (74.53 mg; 0.40 mmol; 1.10 eq.) in DMA (3.00 ml; 38.91 mmol; 106.95 eq.) was added DIPEA (0.18 ml; 1.09 mmol; 3.00 eq.). The reaction was stirred at 100° C. for 24 h before it was concentrated and carried to the next step. MS: m/z=524 [M+H]+

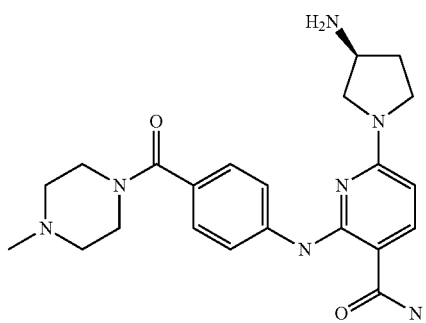 [SMILES: CN1CCN(C(=O)c2ccc(Nc3nc(N4CC[C@H](N)C4)ccc3C(N)=O)cc2)CC1]

(S)-6-(3-aminopyrrolidin-1-yl)-2-((4-(4-methylpiperazine-1-carbonyl)phenyl)amino)nicotinamide hydrochloride (Method 2C)

In a reaction vial containing ((S)-1-{5-Carbamoyl-6-[4-(4-methyl-piperazine-1-carbonyl)-phenylamino]-pyridin-2-yl}-pyrrolidin-3-yl)-carbamic acid tert-butyl ester (190.49 mg; 0.36 mmol; 1.00 eq.) in methanol (3.00 ml) was added hydrogen chloride (1.00 ml; 3.64 mmol; 10.00 eq.). The reaction was stirred at rt for 2 h before it was concentrated and carried to the next step. MS: m/z=424 [M+H]+

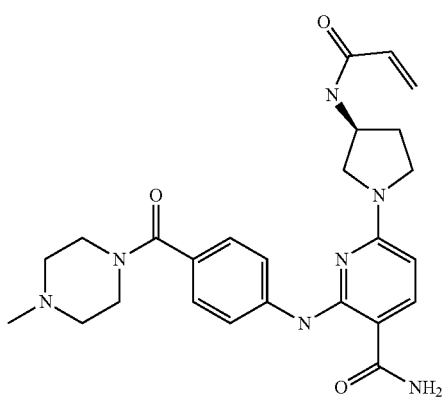 [SMILES: C=CC(=O)N[C@H]1CCN(c2ccc(C(N)=O)c(Nc3ccc(C(=O)N4CCN(C)CC4)cc3)n2)C1]

(S)-6-(3-acrylamidopyrrolidin-1-yl)-2-((4-(4-methylpiperazine-1 carbonyl)phenyl)amino)nicotinamide (Method 2D) (11)

To a 10 mL reaction vial containing the 6-((S)-3-aminopyrrolidin-1-yl)-2-[4-(4-methyl-piperazine-1-carbonyl)-phenylamino]-nicotinamide hydrochloride (165.59 mg; 0.36 mmol; 1.00 eq.) in 1,2-dichloroethane (4.00 ml; 50.53 mmol; 140.35 eq.) was added acrylic acid (30.22 µl; 0.43 mmol; 1.20 eq.) and ethyl-diisopropyl-amine (0.30 ml; 1.80 mmol; 5.00 eq.). The mixture was stirred for 5 min before 2,4,6-Tripropyl-[1,3,5,2,4,6]trioxatriphosphinane 2,4,6-trioxide (145.00 µl; 0.36 mmol; 1.00 eq.) was slowly added. The obtained mixture was stirred at rt for 1 h before it was concentrated and purified by acidic pre-HPLC. Fractions containing the desired product were combined and lyophilized overnight to afford the title product (TFA salt, 7.2 mg, 3.4% yield) as a white solid. HPLC: 93%, RT=2.18 min. MS: m/z=478 [M+H]+, RT=2.19 min. $^1$H-NMR (DMSO-D6) δ 12.0 (s, 1H), 8.49 (d, 1H), 7.99 (d, 1H), 7.82 (d, 2H), 7.44 (d, 2H), 7.34 (s, 1H), 7.12 (s, 1H), 7.00 (s, 1H), 6.25 (dd, 1H), 6.18 (d, 1H), 6.00 (d, 1H), 5.57 (d, 1H), 4.50 (s, 1H), 4.23 (s, 2H), 3.73 (s, 1H), 3.51 (s, 2H), 3.07 (s, 2H), 2.82 (s, 3H), 2.24 (m, 1H), 1.99 (m, 1H).

Example 18

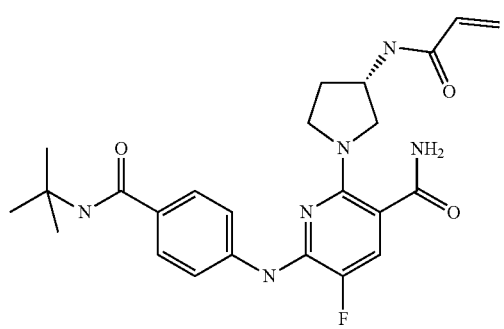 [SMILES: C=CC(=O)N[C@H]1CCN(c2nc(Nc3ccc(C(=O)NC(C)(C)C)cc3)c(F)cc2C(N)=O)C1]

(S)-2-(3-acrylamidopyrrolidin-1-yl)-6-((4-(tert-butylcarbamoyl)phenyl)amino)-5-fluoronicotinamide (3)

(S)-2-(3-acrylamidopyrrolidin-1-yl)-6-((4-(tert-butylcarbamoyl)phenyl)amino)-5-fluoronicotinamide 15.1 mg (24%) was prepared from 2,6-dichloro-5-fluoronicotinamide, 4-amino-N-(tert-butyl)benzamide, (S)-Pyrrolidin-3-yl-carbamic acid tert-butyl and acrylic acid with methods 2A, 2B, 2C and 2D. HPLC: 90.3%, RT=3.81 min. MS: m/z=469 [M+H]$^+$. $^1$H-NMR (DMSO-D6) δ 11.8 (s, 1H), 8.49 (d, 1H), 7.09 (d, 1H), 7.78 (m, 5H), 7.54 (s, 1H), 7.26 (s, 1H), 6.23 (m, 1H), 6.15 (d, 1H), 5.61 (d, 1H), 4.45 (s, 1H), 3.90 (s, 1H), 3.78 (s, 2H), 3.62 (m, 2H), 2.18 (s, 1H), 1.96 (s, 1H), 1.33 (s, 9H).

Example 19

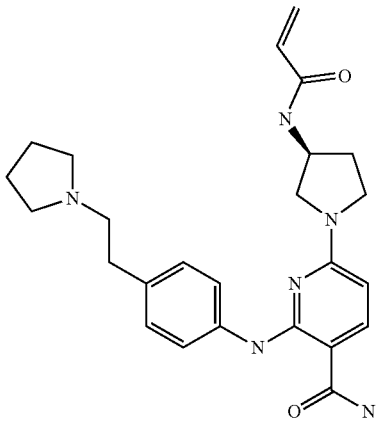 [SMILES: C=CC(=O)N[C@H]1CCN(c2ccc(C(N)=O)c(Nc3ccc(CCN4CCCC4)cc3)n2)C1]

6-((S)-3-Acryloylamino-pyrrolidin-1-yl)-2-[4-(2-pyrrolidin-1-yl-ethyl)-phenylamino]-nicotinamide (16)

6-((S)-3-Acryloylamino-pyrrolidin-1-yl)-2-[4-(2-pyrrolidin-1-yl)ethyl)-phenylamino]-nicotinamide 13.7 mg (42%) was prepared from 2,6-dichloro-nicotinamide, 4-(2-(pyrrolidin-1-yl)ethyl)aniline, (S)-Pyrrolidin-3-yl-carbamic acid tert-butyl ester and acrylic acid with methods 2A, 2B, 2C and 2D. HPLC: 99.9%, RT=2.40 min. MS: m/z=449 [M+H]+. $^1$H-NMR (DMSO-D6) δ 11.8 (s, 1H), 8.47 (d, 1H), 7.91 (d, 1H), 7.63 (d, 2H), 7.14 (d, 2H), 6.47 (dd, 1H), 6.25 (d, 1H), 5.81 (d, 1H), 5.64 (d, 1H), 4.50 (m, 1H), 3.62 (m, 3H), 2.54 (m, 2H), 2.70 (m, 2H), 2.25 (m, 1H), 1.93 (m, 1H), 1.61 (m, 4H).

Example 20

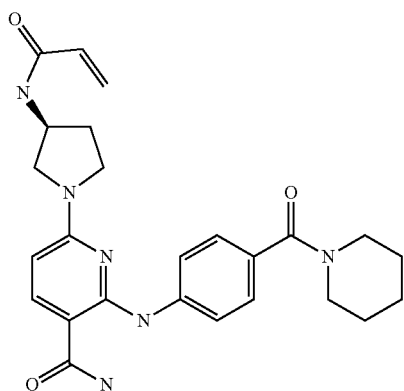 [SMILES: C=CC(=O)N[C@H]1CCN(c2ccc(C(N)=O)c(Nc3ccc(C(=O)N4CCCCC4)cc3)n2)C1]

6-((S)-3-Acryloylamino-pyrrolidin-1-yl)-2-[4-(piperidine-1-carbonyl)-phenylamino]-nicotinamide (21)

6-((S)-3-Acryloylamino-pyrrolidin-1-yl)-2-[4-(piperidine-1-carbonyl)-phenylamino]-nicotinamide 23.2 mg (43%) was prepared from 2,6-dichloro-nicotinamide, (4-aminophenyl)(piperidin-1-yl)methanone, (S)-Pyrrolidin-3-yl-carbamic acid tert-butyl ester and acrylic acid with methods 2A, 2B, 2C and 2D. HPLC: 98.6%, RT=3.81 min. MS: m/z=463 [M+H]+. $^1$H-NMR (DMSO-D6) δ 7.13 (m, 3H), 6.53 (d, 2H), 5.51 (d, 2H), 5.18 (d, 1H), 4.82 (m, 1H), 3.75 (m, 1H), 3.03 (m, 1H), 2.61-3.0 (m, 7H), 1.52 (m, 1H), 1.25 (m, 1H), 0.75 (m, 6H).

Example 21

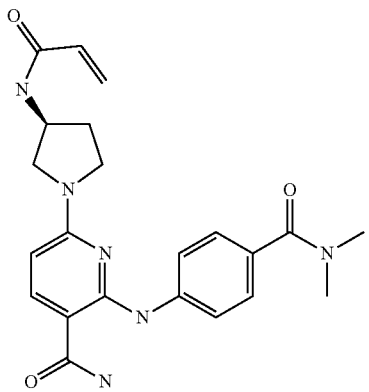 [SMILES: C=CC(=O)N[C@H]1CCN(c2ccc(C(N)=O)c(Nc3ccc(C(=O)N(C)C)cc3)n2)C1]

6-((S)-3-Acryloylamino-pyrrolidin-1-yl)-2-(4-dimethylcarbamoyl-phenylamino)-nicotinamide (26)

6-((S)-3-Acryloylamino-pyrrolidin-1-yl)-2-(4-dimethylcarbamoyl-phenylamino)-nicotinamide 19.0 mg (26%) was prepared from 2,6-dichloro-nicotinamide, 4-amino-N,N-dimethylbenzamide, (S)-pyrrolidin-3-yl-carbamic acid tert-butyl ester and acrylic acid with methods 2A, 2B, 2C and 2D. HPLC: 95.1%, RT=3.21 min. MS: m/z=423 [M+H]+. $^1$H-NMR (DMSO-D6) δ 11.8 (s, 1H), 8.47 (d, 1H), 7.96 (d, 1H), 7.77 (d, 2H), 7.38 (d, 2H), 6.25 (dd, 1H), 6.11 (d, 1H), 6.00 (d, 1H), 5.61 (d, 1H), 4.50 (m, 1H), 3.62 (m, 3H), 3.40 (m, 1H), 3.00 (s, 6H), 2.25 (m, 1H), 1.99 (m, 1H).

Example 22

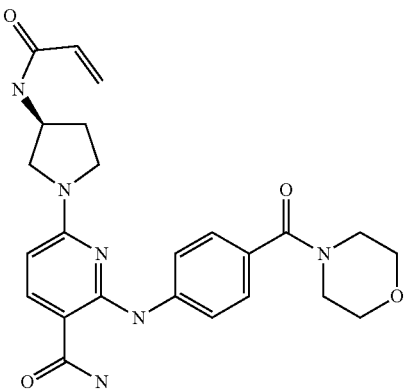 [SMILES: C=CC(=O)N[C@H]1CCN(c2ccc(C(N)=O)c(Nc3ccc(C(=O)N4CCOCC4)cc3)n2)C1]

6-((S)-3-Acryloylamino-pyrrolidin-1-yl)-2-[4-(morpholine-4-carbonyl)-phenylamino]-nicotinamide (35)

6-((S)-3-Acryloylamino-pyrrolidin-1-yl)-2-[4-(morpholine-4-carbonyl)-phenylamino]-nicotinamide 25.4 mg (32%) was prepared from 2,6-dichloro-nicotinamide, (4-aminophenyl)(morpholino)methanone, (S)-pyrrolidin-3-yl-carbamic acid tert-butyl ester and acrylic acid with methods 2A, 2B, 2C and 2D. HPLC: 99.5%, RT=2.77 min. MS: m/z=465 [M+H]+. $^1$H-NMR (DMSO-D6) δ 11.9 (s, 1H), 8.47 (d, 1H), 7.99 (d, 1H), 7.77 (d, 2H), 7.31 (d, 2H), 6.25 (dd, 1H), 6.11 (d, 1H), 6.00 (d, 1H), 5.58 (d, 1H), 4.50 (m, 1H), 3.50-3.75 (m, 11H), 2.25 (m, 1H), 1.99 (m, 1H).

Example 23

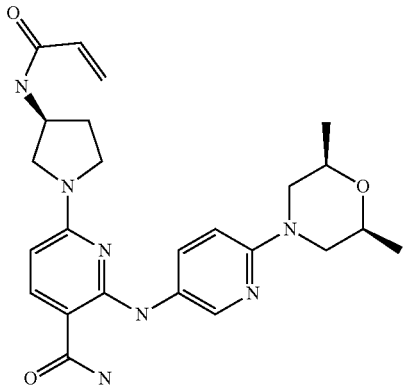 [SMILES: C=CC(=O)N[C@H]1CCN(c2ccc(C(N)=O)c(Nc3ccc(N4C[C@@H](C)O[C@@H](C)C4)nc3)n2)C1]

6-((S)-3-Acryloylamino-pyrrolidin-1-yl)-2-[6-(cis-2,6-dimethyl-morpholin-4-yl)-pyridin-3-ylamino]-nicotinamide (37)

6-((S)-3-Acryloylamino-pyrrolidin-1-yl)-2-[6-(cis-2,6-dimethyl-morpholin-4-yl)-pyridin-3-ylamino]-nicotinamide 35.1 mg (29%) was prepared from 2,6-dichloro-nicotinamide, 6-(cis-2,6-dimethylmorpholino)pyridin-3-amine, (S)-pyrrolidin-3-yl-carbamic acid tert-butyl ester and acrylic acid with methods 2A, 2B, 2C and 2D. HPLC: 97.9%, RT=3.49 min. MS: m/z=466 [M+H]+. 1H NMR (400 MHz, DMSO-d6) δ 11.41 (s, 1H), 8.56-8.21 (m, 2H), 8.05-7.70 (m, 2H), 6.82 (d, J=9.1 Hz, 1H), 6.39-6.02 (m, 2H), 5.86 (d, J=8.7 Hz, 1H), 5.60 (dd, J=9.9, 2.4 Hz, 1H), 4.46 (p, J=5.6 Hz, 1H), 4.02 (dd, J=12.7, 2.3 Hz, 2H), 3.86-3.46 (m, 3H), 2.39-2.14 (m, 3H), 1.93 (dq, J=12.1, 5.7 Hz, 1H), 1.16 (d, J=6.2 Hz, 6H).

Example 24

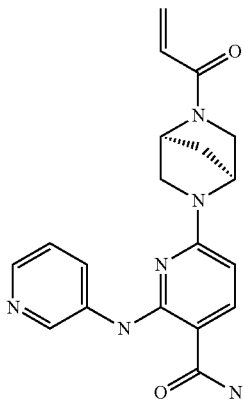 [SMILES: C=CC(=O)N1C[C@@H]2C[C@H]1CN2c1ccc(C(N)=O)c(Nc2cccnc2)n1]

6-((1S,4S)-5-acryloyl-2,5-diazabicyclo[2.2.1]heptan-2-yl)-2-(pyridin-3-ylamino)nicotinamide (15)

6-((1S,4S)-5-acryloyl-2,5-diazabicyclo[2.2.1]heptan-2-yl)-2-(pyridin-3-ylamino)nicotinamide 8.9 mg (33%) was prepared from 2,6-dichloro nicotinamide, pyridin-3-amine, (1S,4S)-tert-butyl 2,5-diazabicyclo[2.2.1]heptane-2-carboxylate and acrylic acid with methods 2A, 2B, 2C and 2D. HPLC: 99.9%, RT=2.0 min. MS: m/z=365 [M+H]+. 1H NMR (400 MHz, DMSO-d6) δ 11.80 (d, J=2.7 Hz, 1H), 8.78 (dd, J=7.1, 2.4 Hz, 1H), 8.27-8.11 (m, 2H), 7.97 (d, J=8.7 Hz, 1H), 7.81 (s, 2H), 7.43-6.93 (m, 2H), 6.80-6.43 (m, 1H), 6.14 (ddd, J=16.7, 4.3, 2.4 Hz, 2H), 5.67 (ddd, J=17.6, 10.2, 2.4 Hz, 2H), 4.98-4.53 (m, 2H), 3.84-3.43 (m, 3H), 2.01 (dq, J=29.2, 10.1 Hz, 2H). Some peaks overlap with H2O peak.

Example 25

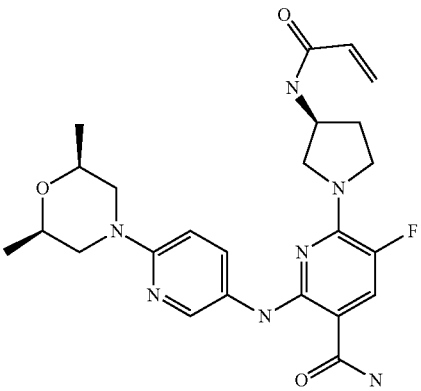 [SMILES: C=CC(=O)N[C@H]1CCN(c2nc(Nc3ccc(N4C[C@@H](C)O[C@@H](C)C4)nc3)c(C(N)=O)cc2F)C1]

6-((S)-3-Acryloylamino-pyrrolidin-1-yl)-2-[6-(cis-2,6-dimethyl-morpholin-4-yl)-pyridin-3-ylamino]-5-fluoro-nicotinamide (6)

6-((S)-3-Acryloylamino-pyrrolidin-1-yl)-2-[6-(cis-2,6-dimethyl-morpholin-4-yl)-pyridin-3-ylamino]-5-fluoro-nicotinamide 19.5 mg (42%) was prepared from 2,6-dichloro-5-fluoronicotinamide, 6-(cis-2,6-dimethylmorpholino)pyridin-3-amine, (S)-pyrrolidin-3-yl-carbamic acid tert-butyl ester and acrylic acid with methods 2A, 2B, 2C and 2D. HPLC: 95.8%, RT=2.39 min. MS: m/z=484 [M+H]+. 1H NMR (400 MHz, DMSO-d6) δ 8.61 (dd, J=44.0, 2.3 Hz, 2H), 8.31 (d, J=6.7 Hz, 1H), 7.99 (dd, J=9.1, 2.7 Hz, 1H), 7.43 (d, J=11.5 Hz, 2H), 6.83 (d, J=9.1 Hz, 1H), 6.22 (dd, J=17.1, 10.0 Hz, 1H), 6.09 (dd, J=17.1, 2.4 Hz, 1H), 5.58 (dd, J=10.0, 2.4 Hz, 1H), 4.31 (q, J=5.8 Hz, 1H), 4.13-3.98 (m, 2H), 3.73-3.47 (m, 3H), 3.12 (dd, J=11.1, 4.7 Hz, 1H), 2.32 (dd, J=12.6, 10.5 Hz, 2H), 2.19-2.01 (m, 1H), 1.91-1.73 (m, 1H), 1.35-1.23 (m, 1H), 1.17 (d, J=6.2 Hz, 6H).

Example 26

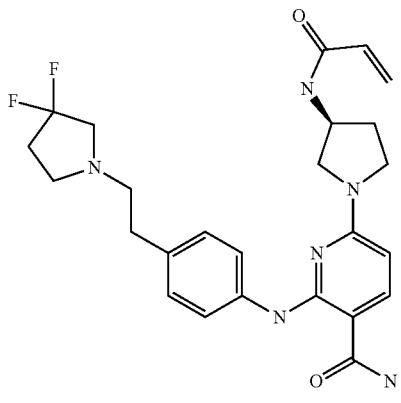 [SMILES: C=CC(=O)N[C@H]1CCN(c2ccc(C(N)=O)c(Nc3ccc(CCN4CCC(F)(F)C4)cc3)n2)C1]

6-((S)-3-Acryloylamino-pyrrolidin-1-yl)-2-{4-[2-(3,3-difluoro-pyrrolidin-1-yl)-ethyl]-phenylamino}-nicotinamide (24)

6-((S)-3-Acryloylamino-pyrrolidin-1-yl)-2-{4-[2-(3,3-difluoro-pyrrolidin-1-yl)-ethyl]-phenylamino}-nicotinamide 18.1 mg (26%) was prepared from 2,6-dichloro-nicotinamide, 4-(2-(3,3-difluoropyrrolidin-1-yl)ethyl)aniline, (S)-pyrrolidin-3-yl-carbamic acid tert-butyl ester and acrylic acid with methods 2A, 2B, 2C and 2D. HPLC: 98.7%, RT=2.48 min. MS: m/z=485 [M+H]+. $^1$H NMR (400 MHz, DMSO-d6) δ 11.67 (s, 1H), 8.41 (d, J=6.9 Hz, 1H), 7.92 (d, J=8.7 Hz, 1H), 7.64 (d, J=8.2 Hz, 2H), 7.14 (d, J=8.2 Hz, 2H), 6.35-6.04 (m, 2H), 5.89 (d, J=8.7 Hz, 1H), 5.61 (dd, J=10.0, 2.5 Hz, 1H), 4.48 (p, J=5.7 Hz, 1H), 3.89-3.48 (m, 3H), 2.50-2.93 (m, 6H), 2.37-2.11 (m, 3H), 1.95 (dq, J=12.4, 5.9 Hz, 1H), 1.27 (td, J=7.3, 4.8 Hz, 2H).

Example 27

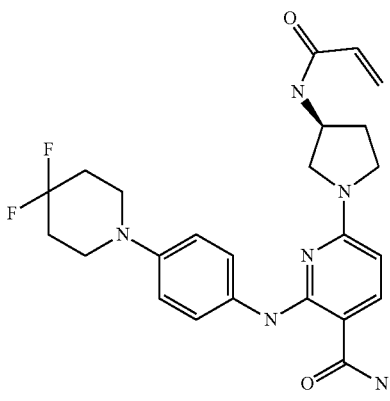 [SMILES: C=CC(=O)N[C@H]1CCN(c2ccc(C(N)=O)c(Nc3ccc(N4CCC(F)(F)CC4)cc3)n2)C1]

6-((S)-3-Acryloylamino-pyrrolidin-1-yl)-2-[4-(4,4-difluoro-piperidin-1-yl)-phenylamino]-nicotinamide (25)

6-((S)-3-Acryloylamino-pyrrolidin-1-yl)-2-[4-(4,4-difluoro-piperidin-1-yl)-phenylamino]-nicotinamide 15.7 mg (16%) was prepared from 2,6-dichloro-nicotinamide, 4-(4,4-difluoropiperidin-1-yl)aniline, (S)-pyrrolidin-3-yl-carbamic acid tert-butyl ester and acrylic acid with methods 2A, 2B, 2C and 2D. HPLC: 95.0%, RT=2.86 min. MS: m/z=471 [M+H]+. $^1$H NMR (400 MHz, DMSO-d6) δ 11.52 (s, 1H), 8.40 (d, J=7.0 Hz, 1H), 7.89 (d, J=8.7 Hz, 1H), 7.66-7.52 (m, 2H), 6.99-6.84 (m, 2H), 6.24 (dd, J=17.0, 10.0 Hz, 1H), 6.12 (dd, J=17.1, 2.5 Hz, 1H), 5.84 (d, J=8.7 Hz, 1H), 5.61 (dd, J=9.9, 2.5 Hz, 1H), 4.58-4.36 (m, 1H), 3.81-3.47 (m, 3H), 3.24 (t, J=5.7 Hz, 4H), 2.22 (dq, J=14.5, 7.9 Hz, 1H), 2.06 (tt, J=14.0, 5.7 Hz, 4H), 1.94 (dq, J=12.2, 5.5 Hz, 1H).

Example 28

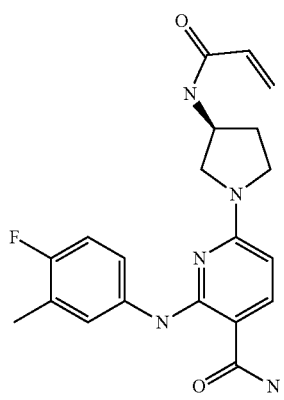 [SMILES: C=CC(=O)N[C@H]1CCN(c2ccc(C(N)=O)c(Nc3ccc(F)c(C)c3)n2)C1]

6-((S)-3-Acryloylamino-pyrrolidin-1-yl)-2-(4-fluoro-3-methyl-phenylamino)-nicotinamide (60)

6-((S)-3-Acryloylamino-pyrrolidin-1-yl)-2-(4-fluoro-3-methyl-phenylamino)-nicotinamide 5.9 mg (8.5%) was prepared from 2,6-dichloro-nicotinamide, 4-fluoro-3-methyl-aniline, (S)-pyrrolidin-3-yl-carbamic acid tert-butyl ester and acrylic acid with methods 2A, 2B, 2C and 2D. HPLC: 97.6%, RT=2.90 min. MS: m/z=384 [M+H]+. $^1$H NMR (400 MHz, DMSO-d6) δ 8.89 (s, 1H), 8.34 (d, J=6.6 Hz, 1H), 7.75 (dd, J=7.2, 2.6 Hz, 1H), 7.56-7.35 (m, 3H), 7.06-6.87 (m, 1H), 6.24 (dd, J=17.1, 10.0 Hz, 1H), 6.18-5.98 (m, 2H), 5.59 (dd, J=10.0, 2.4 Hz, 1H), 4.33 (h, J=6.2 Hz, 1H), 3.62 (dt, J=11.7, 6.2 Hz, 2H), 3.51 (dt, J=10.9, 7.0 Hz, 1H), 3.23 (dd, J=11.2, 5.0 Hz, 1H), 2.26-2.00 (m, 4H), 1.87 (dq, J=12.7, 6.7 Hz, 1H).

Example 29

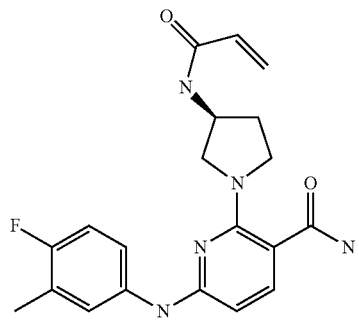 [SMILES: C=CC(=O)N[C@H]1CCN(c2nc(Nc3ccc(F)c(C)c3)ccc2C(N)=O)C1]

2-((S)-3-Acryloylamino-pyrrolidin-1-yl)-6-(4-fluoro-3-methyl-phenylamino)-nicotinamide (157)

2-((S)-3-Acryloylamino-pyrrolidin-1-yl)-6-(4-fluoro-3-methyl-phenylamino)-nicotinamide 5.7 mg (6.9%) was prepared from 2,6-dichloro-nicotinamide, 4-fluoro-3-methyl-aniline, (S)-pyrrolidin-3-yl-carbamic acid tert-butyl ester and acrylic acid with methods 2A, 2B, 2C and 2D. HPLC: 99.5%, RT=3.7 min. MS: m/z=384 [M+H]+. $^1$H NMR (400 MHz, DMSO-d6) δ 11.65 (s, 1H), 8.40 (d, J=6.8 Hz, 1H), 7.92 (d, J=8.7 Hz, 1H), 7.84-7.61 (m, 1H), 7.52 (s, 1H), 7.02 (t, J=9.2 Hz, 1H), 6.24 (dd, J=17.1, 10.0 Hz, 1H), 6.12 (dd, J=17.1, 2.4 Hz, 1H), 5.90 (d, J=8.7 Hz, 1H), 5.61 (dd, J=9.9, 2.5 Hz, 1H), 4.59-4.23 (m, 1H), 3.66 (d, J=56.3 Hz, 3H), 2.33-2.12 (m, 4H), 1.97 (q, J=5.7 Hz, 1H).

Example 30

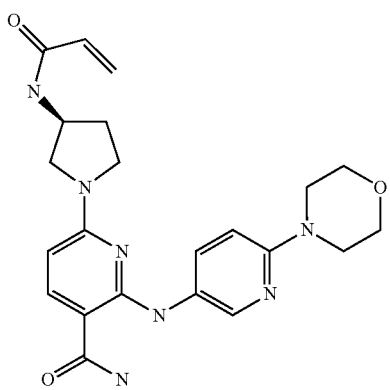 [SMILES: C=CC(=O)N[C@H]1CCN(c2ccc(C(N)=O)c(Nc3ccc(N4CCOCC4)nc3)n2)C1]

6-((S)-3-Acryloylamino-pyrrolidin-1-yl)-2-(6-morpholin-4-yl-pyridin-3-ylamino)-nicotinamide (38)

6-((S)-3-Acryloylamino-pyrrolidin-1-yl)-2-(6-morpholin-4-yl-pyridin-3-ylamino)-nicotinamide 22.9 mg (54%) was prepared from 2,6-dichloro-nicotinamide, 6-morpholinopyridin-3-amine, (S)-pyrrolidin-3-yl-carbamic acid tert-butyl ester and acrylic acid with methods 2A, 2B, 2C and 2D. HPLC: 99.9%, RT=2.89 min. MS: m/z=438 [M+H]+. $^1$H-NMR (DMSO-D6) δ 11.6 (s, 1H), 8.75 (d, 1H), 8.47 (d, 1H), 8.00 (d, 2H), 7.26 (s, 1H), 7.21 (m, 3H), 7.00 (s, 1H), 6.25 (dd, 1H), 6.14 (d, 1H), 5.91 d, 1H), 5.58 (d, 1H), 4.50 (s, 1H), 3.50-3.75 (m, 11H), 2.25 (m, 1H), 1.99 (m, 1H).

Example 31

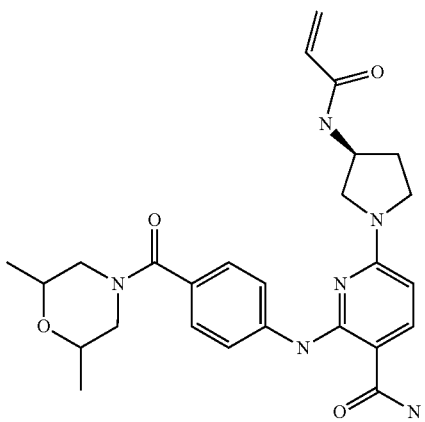 [SMILES: C=CC(=O)N[C@H]1CCN(c2ccc(C(N)=O)c(Nc3ccc(C(=O)N4CC(C)OC(C)C4)cc3)n2)C1]

6-((S)-3-Acryloylamino-pyrrolidin-1-yl)-2-[4-(2,6-dimethyl-morpholine-4-carbonyl)-phenylamino]-nicotinamide (40)

6-((S)-3-Acryloylamino-pyrrolidin-1-yl)-2-[4-(2,6-dimethyl-morpholine-4-carbonyl)-phenylamino]-nicotinamide 24.1 mg (48%) was prepared from 2,6-dichloro-nicotinamide, (4-aminophenyl)(2,6-dimethylmorpholino)methanone, (S)-pyrrolidin-3-yl-carbamic acid tert-butyl ester and acrylic acid with methods 2A, 2B, 2C and 2D. HPLC: 90.7%, RT=3.79 min (minor isomer), 3.93 min (major isomer). MS: m/z=493 [M+H]+. This product is a mixture of two diasteromers. major isomer $^1$H-NMR (DMSO-D6) δ 11.9 (s, 1H), 8.40 (d, 1H), 7.95 (d, 1H), 7.80 (d, 2H), 7.36 (d, 2H), 6.23 (dd, 1H), 6.14 (d, 1H), 5.99 (d, 1H), 5.58 (d, 1H), 4.50 (s, 1H), 3.50-3.75 (m, 3H), 3.13 (m, 1H), 2.25 (m, 1H), 1.99 (m, 1H), 1.26 (d, 6H), 1.09 (s, 4H). The minor isomer's protons overlaps with the ones of the major isomer, difficult to interpret.

Example 32

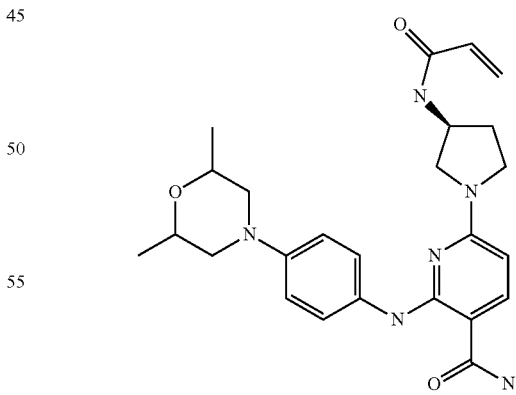

6-((S)-3-Acryloylamino-pyrrolidin-1-yl)-2-[4-(2,6-dimethyl-morpholin-4-yl)-phenylamino]-nicotinamide (33)

6-((S)-3-Acryloylamino-pyrrolidin-1-yl)-2-[4-(2,6-dimethyl-morpholin-4-yl)-phenylamino]-nicotinamide 20.9 mg (37%) was prepared from 2,6-dichloro-nicotinamide, (S)-pyrrolidin-3-yl-carbamic acid tert-butyl ester, 4-(2,6-dimethylmorpholino)aniline and acrylic acid with methods 2A, 2B, 2C and 2D. HPLC: 93.7%, RT=3.69 min. MS: m/z=465 [M+H]+. ¹H NMR (400 MHz, DMSO-d6) δ 11.49 (s, 1H), 8.40 (d, J=7.0 Hz, 1H), 7.89 (d, J=8.8 Hz, 1H), 7.63-7.50 (m, 2H), 6.96-6.77 (m, 2H), 6.34-5.94 (m, 2H), 5.84 (d, J=8.6 Hz, 1H), 5.61 (dd, J=9.9, 2.5 Hz, 1H), 4.48 (h, J=5.4 Hz, 1H), 3.80-3.44 (m, 6H), 2.20 (dt, J=11.8, 8.3 Hz, 3H), 2.04-1.81 (m, 1H), 1.15 (d, J=6.2 Hz, 6H).

Example 33

Example 34

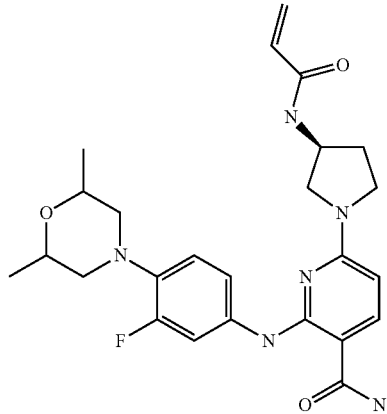

6-((S)-3-Acryloylamino-pyrrolidin-1-yl)-2-[4-(2,6-dimethyl-morpholin-4-yl)-3-fluoro-phenylamino]-nicotinamide (27)

6-((S)-3-Acryloylamino-pyrrolidin-1-yl)-2-[4-(2,6-dimethyl-morpholin-4-yl)-3-fluoro-phenylamino]-nicotinamide 19.4 mg (32%) was prepared from 2,6-dichloro-nicotinamide, (S)-pyrrolidin-3-yl-carbamic acid tert-butyl ester, 4-(2,6-dimethylmorpholino)-3-fluoroaniline and acrylic acid with methods 2A, 2B, 2C and 2D. HPLC: 94.8%, RT=3.39 min. MS: m/z=483 [M+H]+. ¹H NMR (400 MHz, DMSO-d6) δ 11.74 (s, 1H), 8.41 (d, J=6.9 Hz, 1H), 8.02-7.86 (m, 2H), 7.18 (dd, J=8.8, 2.3 Hz, 1H), 6.95 (t, J=9.3 Hz, 1H), 6.37-6.09 (m, 2H), 5.91 (d, J=8.7 Hz, 1H), 5.61 (dd, J=9.9, 2.5 Hz, 1H), 4.50 (dt, J=9.7, 4.9 Hz, 1H), 3.82-3.48 (m, 5H), 3.16 (d, J=11.1 Hz, 2H), 2.40-2.12 (m, 3H), 1.96 (dq, J=12.0, 5.7 Hz, 1H), 1.12 (d, J=6.2 Hz, 6H).

Example 35

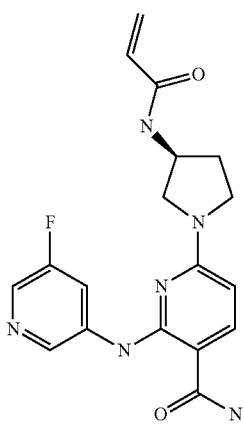 [SMILES: C=CC(=O)N[C@H]1CCN(c2ccc(C(N)=O)c(Nc3cncc(F)c3)n2)C1]

6-((S)-3-Acryloylamino-pyrrolidin-1-yl)-2-(5-fluoro-pyridin-3-ylamino)-nicotinamide (51)

6-((S)-3-Acryloylamino-pyrrolidin-1-yl)-2-(5-fluoro-pyridin-3-ylamino)-nicotinamide 12.6 mg (22%) was prepared from 2,6-dichloro-nicotinamide, (S)-pyrrolidin-3-yl-carbamic acid tert-butyl ester, 5-fluoropyridin-3-amine and acrylic acid with methods 2A, 2B, 2C and 2D. HPLC: 93.7%, RT=3.69 min. MS: m/z=371 [M+H]+. ¹H NMR (400 MHz, DMSO-d6) δ 12.17 (s, 1H), 8.60-8.37 (m, 3H), 8.10 (d, J=2.4 Hz, 1H), 7.99 (d, J=8.8 Hz, 1H), 7.87 (s, 1H), 6.24 (dd, J=17.1, 9.9 Hz, 1H), 6.12 (dd, J=17.2, 2.5 Hz, 1H), 6.03 (d, J=8.7 Hz, 1H), 5.61 (dd, J=9.9, 2.4 Hz, 1H), 4.50 (q, J=5.5 Hz, 1H), 3.68 (m, 3H), 2.24 (dq, J=13.8, 8.0, 7.5 Hz, 1H), 1.98 (dq, J=12.1, 5.8 Hz, 1H).

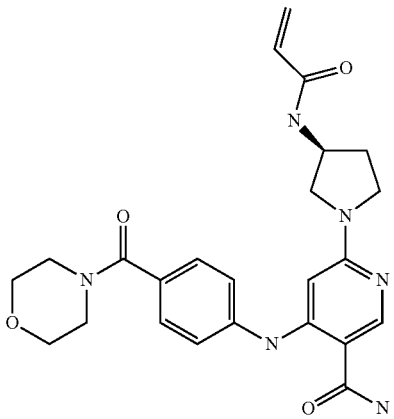 [SMILES: C=CC(=O)N[C@H]1CCN(c2cc(Nc3ccc(C(=O)N4CCOCC4)cc3)c(C(N)=O)cn2)C1]

6-((S)-3-Acryloylamino-pyrrolidin-1-yl)-4-[4-(morpholine-4-carbonyl)-phenylamino]-nicotinamide (108)

6-((S)-3-Acryloylamino-pyrrolidin-1-yl)-4-[4-(morpholine-4-carbonyl)-phenylamino]-nicotinamide 18.3 mg (24%) was prepared from 4,6-dichloronicotinamide, (4-aminophenyl)(morpholino)methanone, (S)-pyrrolidin-3-yl-carbamic acid tert-butyl ester and acrylic acid with methods 2A, 2B, 2C and 2D. HPLC: 98.7%, RT=2.43 min. MS: m/z=465 [M+H]+. ¹H-NMR (DMSO-D6) δ 7.54 (s, 1H), 6.75 (d, 2H), 6.19 (d, 2H), 5.44 (d, 1H), 5.29 (s, 1H), 4.74 (d, 1H), 3.75 (s, 1H), 2.66-3.0 (m, 8H), 1.52 (m, 1H), 1.26 (m, 1H), 0.83 (m, 2H), 0.52 (m, 2H), 0.25 (m, 1H).

Example 36

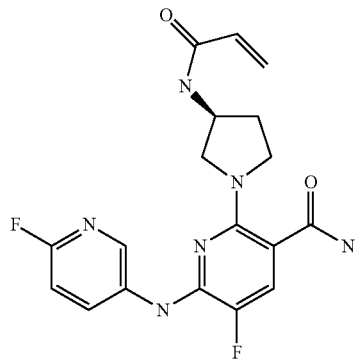 [SMILES: C=CC(=O)N[C@H]1CCN(c2nc(Nc3ccc(F)nc3)c(F)cc2C(N)=O)C1]

2-((S)-3-Acryloylamino-pyrrolidin-1-yl)-5-fluoro-6-(6-fluoro-pyridin-3-ylamino)-nicotinamide (1)

2-((S)-3-Acryloylamino-pyrrolidin-1-yl)-5-fluoro-6-(6-fluoro-pyridin-3-ylamino)-nicotinamide 11.4 mg (17%) was prepared from 2,6-dichloro-5-fluoronicotinamide, 6-fluoro-pyridin-3-amine, (S)-pyrrolidin-3-yl-carbamic acid tert-butyl ester and acrylic acid with methods 2A, 2B, 2C and 2D. HPLC: 96.5%, RT=3.27 min. MS: m/z=389 [M+H]+. ¹H-NMR (DMSO-D6) δ 11.61 (s, 1H), 8.50 (s, 1H), 8.37 (s, 1H), 8.25 (s, 1H), 8.00 (d, 1H), 7.74 (s, 1H), 7.00-7.43 (m, 2H), 6.25 (m, 1H), 6.14 (d, 1H), 5.58 (d, 1H), 4.40 (s, 1H), 3.89 (s, 1H), 3.75 (s, 2H), 3.53 (m, 1H), 2.14 (s, 1H), 1.96 (s, 1H).

Example 37

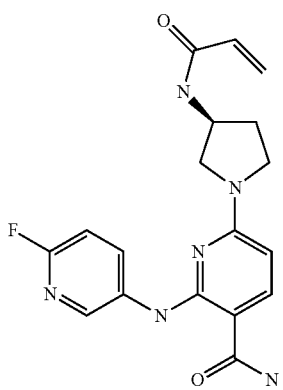 [SMILES: C=CC(=O)N[C@H]1CCN(c2ccc(C(N)=O)c(Nc3ccc(F)nc3)n2)C1]

6-((S)-3-Acryloylamino-pyrrolidin-1-yl)-2-(6-fluoro-pyridin-3-ylamino)-nicotinamide (46)

6-((S)-3-Acryloylamino-pyrrolidin-1-yl)-2-(6-fluoro-pyridin-3-ylamino)-nicotinamide 12.8 mg (41%) was prepared from 2,6-dichloro nicotinamide, 6-fluoropyridin-3-amine, (S)-pyrrolidin-3-yl-carbamic acid tert-butyl ester and acrylic acid with methods 2A, 2B, 2C and 2D. HPLC: 94.7%, RT=3.80 min. MS: m/z=371 [M+H]+. ¹H-NMR (DMSO-D6) δ 11.78 (s, 1H), 8.55 (s, 1H), 8.42 (d, 1H), 8.27 (s, 1H), 7.98 (d, 1H), 7.13 (s, 1H), 6.25 (m, 1H), 6.19 (d, 1H), 5.98 (d, 1H), 5.61 (d, 1H), 4.50 (s, 1H), 2.25 (s, 1H), 1.96 (s, 1H). Some peaks were buried under water peak.

Example 38

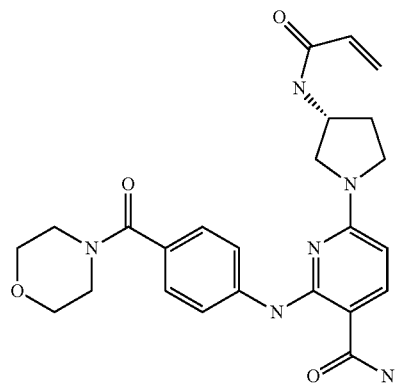 [SMILES: C=CC(=O)N[C@@H]1CCN(c2ccc(C(N)=O)c(Nc3ccc(C(=O)N4CCOCC4)cc3)n2)C1]

6-((R)-3-Acryloylamino-pyrrolidin-1-yl)-2-[4-(morpholine-4-carbonyl)-phenylamino]-nicotinamide (47)

6-((R)-3-Acryloylamino-pyrrolidin-1-yl)-2-[4-(morpholine-4-carbonyl)-phenylamino]-nicotinamide 33.5 mg (49%) was prepared from 2,6-dichloro-nicotinamide, (4-aminophenyl)(morpholino)methanone, (R)-Pyrrolidin-3-yl-carbamic acid tert-butyl ester and acrylic acid with methods 2A, 2B, 2C and 2D. HPLC: 96.8%, RT=2.77 min. MS: m/z=465 [M+H]+. ¹H-NMR (DMSO-D6) δ 11.9 (s, 1H), 8.47 (d, 1H), 7.99 (d, 1H), 7.77 (d, 2H), 7.31 (d, 2H), 6.25 (dd, 1H), 6.11 (d, 1H), 6.00 (d, 1H), 5.58 (d, 1H), 4.50 (m, 1H), 3.50-3.75 (m, 11H), 2.25 (m, 1H), 1.99 (m, 1H).

Example 39

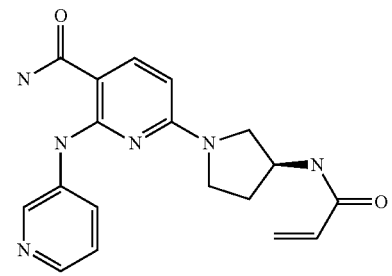 [SMILES: C=CC(=O)N[C@H]1CCN(c2ccc(C(N)=O)c(Nc3cccnc3)n2)C1]

6-((S)-3-Acryloylamino-pyrrolidin-1-yl)-2-(pyridin-3-ylamino)-nicotinamide (52)

6-((S)-3-Acryloylamino-pyrrolidin-1-yl)-2-(pyridin-3-ylamino)-nicotinamide 19.6 mg (17%) was prepared from 2,6-dichloro nicotinamide, pyridin-3-amine, (S)-pyrrolidin- 3-yl-carbamic acid tert-butyl ester and acrylic acid with methods 2A, 2B, 2C and 2D. HPLC: 99.5%, RT=2.13 min. MS: m/z=353 [M+H]+. ¹H-NMR (DMSO-D6) δ 11.81 (s, 1H), 8.90 (d, 1H), 8.42 (d, 1H), 8.27 (d, 1H), 8.14 A (d, 1H), 7.98 (d, 1H), 7.37 (d, 1H), 6.25 (dd, 1H), 6.19 (d, 1H), 6.00 (d, 1H), 5.55 (d, 1H), 4.50 (s, 1H), 3.75 (m 3H), 2.25 (s, 1H), 1.96 (s, 1H).

Example 40

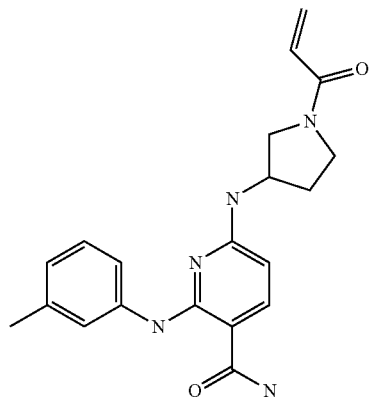 [SMILES: C=CC(=O)N1CCC(Nc2ccc(C(N)=O)c(Nc3cccc(C)c3)n2)C1]

6-(1-Acryloyl-pyrrolidin-3-ylamino)-2-m-toly-lamino-nicotinamide (50)

6-(1-Acryloyl-pyrrolidin-3-ylamino)-2-m-tolylamino-nicotinamide 15.5 mg (27%) was prepared from 2,6-dichloro nicotinamide, m-toluidine, tert-butyl 3-aminopyrrolidine-1-carboxylate and acrylic acid with methods 2A, 2B, 2C and 2D. HPLC: 90.0%, RT=3.53 min. MS: m/z=364 [M+H]+. ¹H NMR (400 MHz, DMSO-d6) δ 11.69 (d, J=7.9 Hz, 1H), 7.81 (d, J=8.7 Hz, 1H), 7.64 (s, 1H), 7.50-7.34 (m, 2H), 7.32-7.09 (m, 3H), 7.02 (s, 1H), 6.73 (d, J=7.5 Hz, 1H), 6.57 (ddd, J=49.5, 16.8, 10.2 Hz, 1H), 6.14 (ddd, J=16.8, 8.2, 2.3 Hz, 1H), 5.91 (dd, J=8.7, 2.1 Hz, 1H), 5.66 (ddd, J=20.7, 10.2, 2.3 Hz, 1H), 4.63-4.37 (m, 1H), 3.50 (m, 3H), 2.39-2.11 (m, 4H), 2.11-1.82 (m, 2H).

Example 41

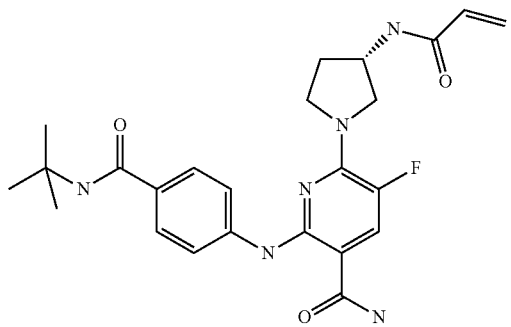 [SMILES: C=CC(=O)N[C@H]1CCN(c2nc(Nc3ccc(C(=O)NC(C)(C)C)cc3)c(C(N)=O)cc2F)C1]

6-((S)-3-Acryloylamino-pyrrolidin-1-yl)-2-(4-tert-butylcarbamoyl-phenylamino)-5-fluoro-nicotinamide (5)

6-((S)-3-Acryloylamino-pyrrolidin-1-yl)-2-(4-tert-butylcarbamoyl-phenylamino)-5-fluoro-nicotinamide 23.6 mg (45%) was prepared from 2,6-dichloro-5-fluoronicotinamide, 4-amino-N-(tert-butyl)benzamide, (S)-pyrrolidin-3-yl-carbamic acid tert-butyl ester and acrylic acid with methods 2A, 2B, 2C and 2D. HPLC: 93.1%, RT=4.10 min. MS: m/z=469 [M+H]+. ¹H-NMR (DMSO-D6) δ 9.01 (m, 1H), 8.37 (m, 1H), 7.80 (m, 2H), 7.75 (m, 2H), 7.53 (m, 3H), 7.21 (m, 1H), 6.25 (m, 1H), 6.13 (d, 1H), 5.58 (d, 1H), 4.29 (s, 1H), 3.61 (m, 2H), 3.48 (m, 1H), 3.25 (m, 1H), 2.13 (m, 1H), 1.81 (m, 1H), 1.32 (s, 9H).

Example 42

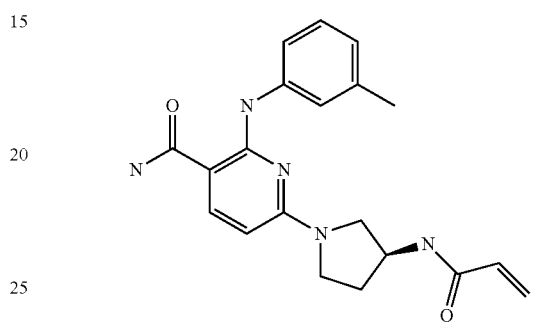

6-((S)-3-Acryloylamino-pyrrolidin-1-yl)-2-m-toly-lamino-nicotinamide (57)

6-((S)-3-Acryloylamino-pyrrolidin-1-yl)-2-m-tolylamino-nicotinamide 17.7 mg (42%) was prepared from 2,6-dichloro nicotinamide, m-toluidine, (S)-pyrrolidin-3-yl-carbamic acid tert-butyl ester and acrylic acid with methods 2A, 2B, 2C and 2D. HPLC: 90.0%, RT=3.51 min. MS: m/z=366 [M+H]+. ¹H-NMR (DMSO-D6) δ 11.73 (s, 1H), 8.44 (d, 1H), 7.0 (d, 1H), 7.61 (s, 1H), 7.50 (m, 1H), 7.23 (d, 1H), 6.24 (dd, 1H), 6.14 (d, 1H), 5.82 (m, 1H), 5.59 (m, 1H), 4.50 (s, 1H), 3.75 (m, 3H), 2.25 (m, 1H), 2.00 (m, 1H).

Example 43

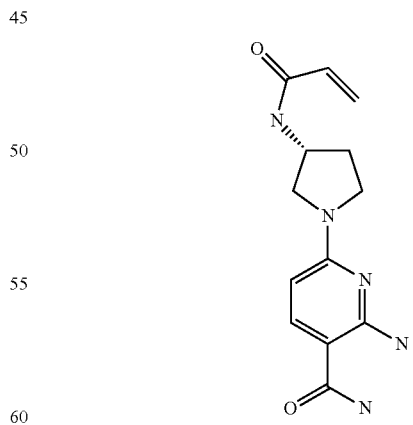

6-((R)-3-Acryloylamino-pyrrolidin-1-yl)-2-amino-nicotinamide (61)

6-((R)-3-Acryloylamino-pyrrolidin-1-yl)-2-amino-nicotinamide 35.4 mg (56%) was prepared from 2-amino-6- chloronicotinamide, (R)-pyrrolidin-3-yl-carbamic acid tert-butyl ester and acrylic acid with methods 2A, 2B, 2C and 2D. HPLC: 91.6%, RT=1.73 min. MS: m/z=276 [M+H]+. ¹H-NMR (DMSO-D6) δ 6.92 (d, 1H), 5.46 (d, 2H), 5.01 (d, 1H), 4.82 (m, 1H), 3.75 (m, 1H), 2.94 (m, 1H), 2.74 (m, 2H), 2.62 (m, 1H), 1.50 (m, 1H), 1.25 (m, 1H).

Example 44

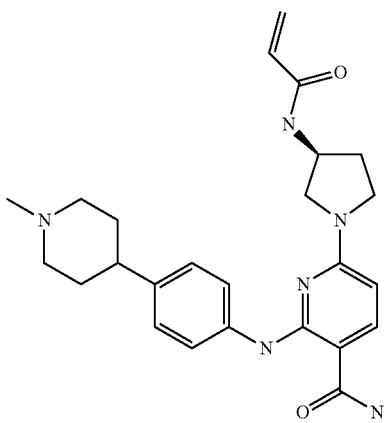 [SMILES: C=CC(=O)N[C@H]1CCN(c2ccc(C(N)=O)c(Nc3ccc(C4CCN(C)CC4)cc3)n2)C1]

6-((S)-3-Acryloylamino-pyrrolidin-1-yl)-2-[4-(1-methyl-piperidin-4-yl)-phenylamino]-nicotinamide (14)

6-((S)-3-Acryloylamino-pyrrolidin-1-yl)-2-[4-(1-methyl-piperidin-4-yl)-phenylamino]-nicotinamide 42.1 mg (38%) was prepared from 2,6-dichloro nicotinamide, 4-(1-methyl-piperidin-4-yl)aniline, (R)-pyrrolidin-3-yl-carbamic acid tert-butyl ester and acrylic acid with methods 2A, 2B, 2C and 2D. HPLC: 90.7%, RT=2.32 min. MS: m/z=449 [M+H]+. ¹H NMR (400 MHz, DMSO-d6) δ 11.67 (s, 1H), 8.41 (d, J=6.8 Hz, 1H), 7.91 (d, J=8.6 Hz, 1H), 7.63 (t, J=9.2 Hz, 3H), 7.14 (d, J=8.2 Hz, 3H), 6.30-6.06 (m, 3H), 5.88 (d, J=8.6 Hz, 1H), 5.61 (dd, J=10.1, 2.2 Hz, 1H), 4.47 (p, J=6.6, 6.1 Hz, 1H), 3.66 (dd, J=51.8, 12.0 Hz, 4H), 2.89 (d, J=9.6 Hz, 3H), 2.46-2.32 (m, 1H), 2.23 (s, 4H), 1.99 (dt, J=22.4, 13.7 Hz, 3H), 1.67 (dtd, J=37.1, 13.4, 12.7, 3.6 Hz, 5H).

Example 45

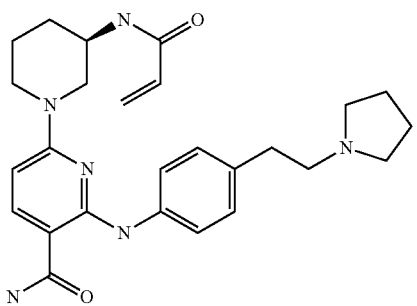 [SMILES: C=CC(=O)N[C@@H]1CCCN(c2ccc(C(N)=O)c(Nc3ccc(CCN4CCCC4)cc3)n2)C1]

(R)-3-Acryloylamino-6'-[4-(2-pyrrolidin-1-yl-ethyl)-phenylamino]-3,4,5,6-tetrahydro-2H-[1,2']bipyridinyl-5'-carboxylic acid amide (56)

(R)-3-Acryloylamino-6'-[4-(2-pyrrolidin-1-yl-ethyl)-phenylamino]-3,4,5,6-tetrahydro-2H-[1,2']bipyridinyl-5'-carboxylic acid amide 27.3 mg (44%) was prepared from 2,6-dichloro nicotinamide, 4-(2-(pyrrolidin-1-yl)ethyl)aniline, (R)-tert-butyl piperidin-3-ylcarbamate and acrylic acid with methods 2A, 2B, 2C and 2D. HPLC: 99.9%, RT=2.63 min. MS: m/z=462 [M+H]+. 1H NMR (400 MHz, DMSO-d6) δ 11.48 (s, 1H), 8.14 (d, 1H), 7.88 (d, 1H), 7.50 (d, 2H), 7.10 (d, 2H), 6.25 (m, 3H), 5.11 (d, 1H), 4.25 (m, 1H), 4.02 (m, 1H), 3.75 (m, 1H), 3.09 (m, 1H), 2.81 (m, 1H), 2.67 (s, 4H), 1.82 (m, 1H), 1.75 (m, 5H), 1.51 (m, 2H).

Example 46

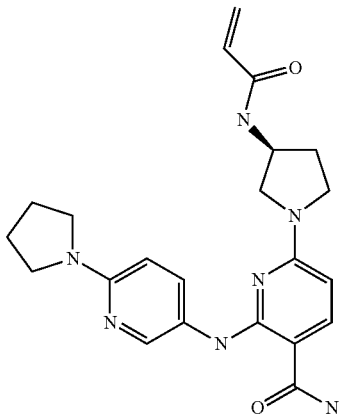 [SMILES: C=CC(=O)N[C@H]1CCN(c2ccc(C(N)=O)c(Nc3ccc(N4CCCC4)nc3)n2)C1]

6-((S)-3-Acryloylamino-pyrrolidin-1-yl)-2-(6-pyrrolidin-1-yl-pyridin-3-ylamino)-nicotinamide (41)

6-((S)-3-Acryloylamino-pyrrolidin-1-yl)-2-(6-pyrrolidin-1-yl-pyridin-3-ylamino)-nicotinamide 18.4 mg (22%) was prepared from 2,6-dichloro nicotinamide, 6-(pyrrolidin-1-yl)pyridin-3-amine, (R)-pyrrolidin-3-yl-carbamic acid tert-butyl ester and acrylic acid with methods 2A, 2B, 2C and 2D. HPLC: 99.9%, RT=2.62 min. MS: m/z=422 [M+H]+. 1H NMR (400 MHz, DMSO-d6) δ 11.24 (s, 1H), 8.50-8.26 (m, 2H), 7.87 (dd, J=13.0, 8.8 Hz, 2H), 6.43 (d, J=9.0 Hz, 1H), 6.23 (dd, J=17.3, 10.2 Hz, 1H), 6.17-6.03 (m, 1H), 5.82 (d, J=8.7 Hz, 1H), 5.69-5.50 (m, 1H), 4.53-4.36 (m, 1H), 3.74-3.62 (m, 1H), 3.53 (s, 3H), 2.21 (dt, J=13.1, 7.2 Hz, 1H), 2.03-1.83 (m, 5H).

Example 47

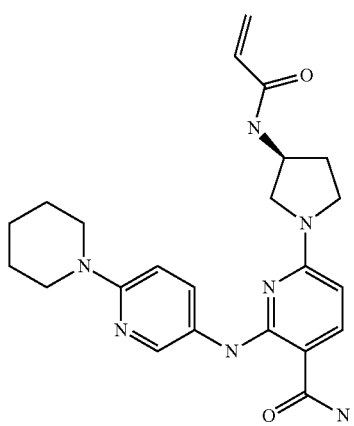 [SMILES: C=CC(=O)N[C@H]1CCN(c2ccc(C(N)=O)c(Nc3ccc(N4CCCCC4)nc3)n2)C1]

(S)-6-(3-acrylamidopyrrolidin-1-yl)-2-((6-(piperidin-1-yl)pyridin-3-yl)amino)nicotinamide (39)

(S)-6-(3-acrylamidopyrrolidin-1-yl)-2-((6-(piperidin-1-yl)pyridin-3-yl)amino)nicotinamide 41.6 mg (43%) was prepared from 2,6-dichloro nicotinamide, 6-(piperidi-1-yl)pyridin-3-amine, (R)-pyrrolidin-3-yl-carbamic acid tert-butyl ester and acrylic acid with methods 2A, 2B, 2C and 2D. HPLC: 98.2%, RT=2.86 min. MS: m/z=436 [M+H]+. $^1$H NMR (400 MHz, DMSO-d6) δ 8.06-7.82 (m, 1H), 7.17-6.96 (m, 2H), 6.22 (d, J=9.4 Hz, 1H), 5.54-5.43 (m, 2H), 5.11 (d, J=8.8 Hz, 1H), 4.88 (dd, J=7.2, 4.9 Hz, 1H), 3.78 (p, J=5.5 Hz, 1H), 3.03 (dd, J=11.3, 6.3 Hz, 1H), 2.98-2.76 (m, 2H), 2.76-2.59 (m, 5H), 1.55 (dq, J=13.9, 7.2 Hz, 1H), 1.28 (dq, J=12.4, 5.9 Hz, 1H), 0.91 (s, 6H).

Example 48

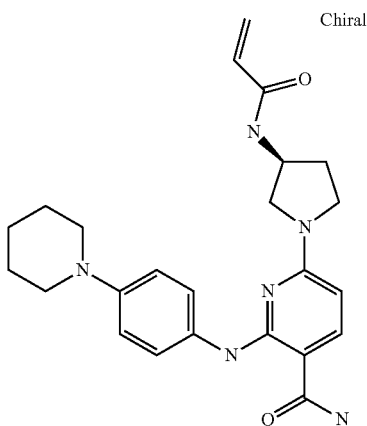 [SMILES: C=CC(=O)N[C@H]1CCN(c2ccc(C(N)=O)c(Nc3ccc(N4CCCCC4)cc3)n2)C1]

6-((S)-3-Acryloylamino-pyrrolidin-1-yl)-2-(4-piperidin-1-yl-phenylamino)-nicotinamide (31)

6-((S)-3-Acryloylamino-pyrrolidin-1-yl)-2-(4-piperidin-1-yl-phenylamino)-nicotinamide 27.4 mg (46%) was prepared from 2,6-dichloro nicotinamide, 4-(piperidin-1-yl)aniline, (R)-pyrrolidin-3-yl-carbamic acid tert-butyl ester and acrylic acid with methods 2A, 2B, 2C and 2D. HPLC: 93.4%, RT=2.51 min. MS: m/z=435 [M+H]+. $^1$H NMR (400 MHz, DMSO-d6) δ 11.47 (s, 1H), 8.42 (d, J=6.9 Hz, 1H), 7.88 (d, J=8.7 Hz, 1H), 7.56 (d, J=8.4 Hz, 2H), 6.87 (d, J=8.5 Hz, 2H), 6.38-6.05 (m, 2H), 5.83 (d, J=8.6 Hz, 1H), 5.61 (dt, J=10.0, 1.7 Hz, 1H), 4.46 (p, J=5.7 Hz, 1H), 3.80-3.46 (m, 3H), 3.03 (t, J=5.4 Hz, 4H), 2.21 (dq, J=13.9, 7.4 Hz, 1H), 1.93 (dq, J=11.7, 5.7, 5.2 Hz, 1H), 1.63 (p, J=5.6 Hz, 4H), 1.51 (p, J=5.8 Hz, 2H).

Example 49

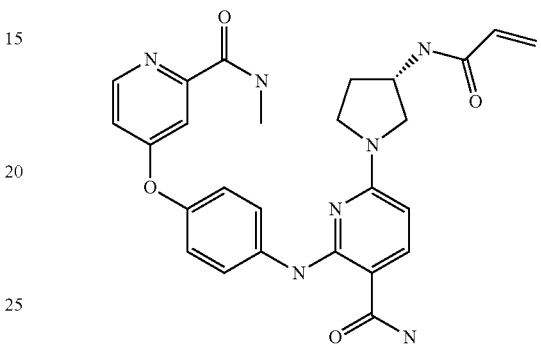

6-((S)-3-Acryloylamino-pyrrolidin-1-yl)-2-[4-(2-methylcarbamoyl-pyridin-4-yloxy)-phenylamino]-nicotinamide (36)

6-((S)-3-Acryloylamino-pyrrolidin-1-yl)-2-[4-(2-methylcarbamoyl-pyridin-4-yloxy)-phenylamino]-nicotinamide 33.7 mg (41%) was prepared from 2,6-dichloro nicotinamide, 4-(4-aminophenoxy)-N-methylpicolinamide, (R)-pyrrolidin-3-yl-carbamic acid tert-butyl ester and acrylic acid with methods 2A, 2B, 2C and 2D. HPLC: 97.2%, RT=3.03 min. MS: m/z=502 [M+H]+. $^1$H NMR (400 MHz, DMSO-d6) δ 11.89 (s, 1H), 8.75 (q, J=4.8 Hz, 1H), 8.51 (d, J=5.6 Hz, 1H), 8.40 (d, J=6.8 Hz, 1H), 7.95 (d, J=8.7 Hz, 1H), 7.86 (d, J=8.6 Hz, 2H), 7.41 (d, J=2.6 Hz, 1H), 7.15 (d, J=8.2 Hz, 3H), 6.23 (dd, J=17.1, 9.9 Hz, 1H), 6.21-6.04 (m, 1H), 5.94 (d, J=8.7 Hz, 1H), 5.69-5.53 (m, 1H), 4.48 (q, J=5.4 Hz, 1H), 3.67 (m, 3H), 2.80 (d, J=4.8 Hz, 3H), 2.22 (dq, J=15.0, 8.1, 7.6 Hz, 1H), 1.94 (dq, J=10.0, 4.7, 4.1 Hz, 1H).

Example 50

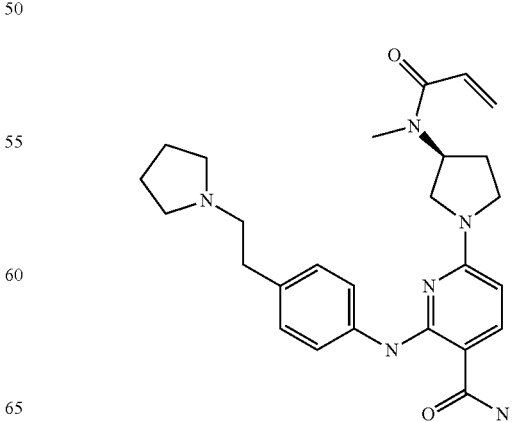

233

6-[(S)-3-(Acryloyl-methyl-amino)-pyrrolidin-1-yl]-2-[4-(2-pyrrolidin-1-yl-ethyl)-phenylamino]-nicotinamide (30)

6-[(S)-3-(Acryloyl-methyl-amino)-pyrrolidin-1-yl]-2-[4-(2-pyrrolidin-1-yl-ethyl)-phenylamino]-nicotinamide 9.1 mg (21%) was prepared from 2,6-dichloro nicotinamide, 4-(4-aminophenoxy)-N-methylpicolinamide, (S)-tert-butyl methyl(pyrrolidin-3-yl)carbamate and acrylic acid with methods 2A, 2B, 2C and 2D. HPLC: 99.6%, RT=2.60 min. MS: m/z=463 [M+H]+. $^1$H NMR (400 MHz, DMSO-d6) δ 11.75 (s, 1H), 7.91 (d, 1H), 7.72 (d, 2H), 7.20 (d, 2H), 6.14 (dd, 1H), 5.81 (d, 1H), 5.75 (d, 1H), 3.75 (m, 3H), 2.70-3.0 (m, 5H), 2.25 (m, 2H), 1.87 (m, 4H).

Example 51

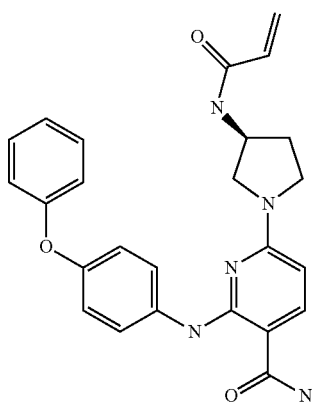 [SMILES: C=CC(=O)N[C@H]1CCN(c2ccc(C(N)=O)c(Nc3ccc(Oc4ccccc4)cc3)n2)C1]

6-((S)-3-Acryloylamino-pyrrolidin-1-yl)-2-(4-phenoxy-phenylamino)-nicotinamide (54)

6-((S)-3-Acryloylamino-pyrrolidin-1-yl)-2-(4-phenoxy-phenylamino)-nicotinamide 44.5 mg (54%) was prepared from 2,6-dichloro nicotinamide, 4-phenoxyaniline, (R)-pyrrolidin-3-yl-carbamic acid tert-butyl ester and acrylic acid with methods 2A, 2B, 2C and 2D. HPLC: 99.9%, RT=4.27 min. MS: m/z=444 [M+H]+. $^1$H NMR (400 MHz, DMSO-d6) δ 11.73 (s, 1H), 8.39 (d, J=6.9 Hz, 1H), 7.93 (d, J=8.7 Hz, 1H), 7.75 (d, J=8.5 Hz, 2H), 7.37 (t, J=7.7 Hz, 2H), 7.09 (t, J=7.4 Hz, 1H), 6.98 (dd, J=8.5, 3.9 Hz, 4H), 6.23 (dd, J=17.2, 9.8 Hz, 1H), 6.17-6.05 (m, 1H), 5.90 (d, J=8.7 Hz, 1H), 5.68-5.53 (m, 1H), 4.55-4.39 (m, 1H), 3.64 (d, J=50.0 Hz, 3H), 3.38 (s, 1H), 2.21 (dq, J=14.1, 7.4 Hz, 1H), 2.04-1.85 (m, 1H).

234

Example 52

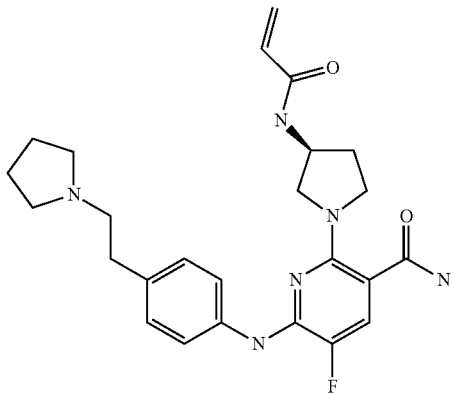 [SMILES: C=CC(=O)N[C@H]1CCN(c2nc(Nc3ccc(CCN4CCCC4)cc3)c(F)cc2C(N)=O)C1]

2-((S)-3-Acryloylamino-pyrrolidin-1-yl)-5-fluoro-6-[4-(2-pyrrolidin-1-yl-ethyl)-phenylamino]-nicotinamide (4)

2-((S)-3-Acryloylamino-pyrrolidin-1-yl)-5-fluoro-6-[4-(2-pyrrolidin-1-yl-ethyl)-phenylamino]-nicotinamide 14.4 mg (39%) were prepared from 2,6-dichloro-5-fluoronicotinamide, 4-(2-(pyrrolidin-1-yl)ethyl)aniline, (S)-Pyrrolidin-3-yl-carbamic acid tert-butyl ester and acrylic acid with methods 2A, 2B, 2C and 2D. HPLC: 99.9%, RT=2.28 min. MS: m/z=467 [M+H]+. $^1$H NMR (400 MHz, DMSO-d6) δ 8.74 (s, 1H), 8.34 (d, J=6.7 Hz, 1H), 7.77 (d, J=8.1 Hz, 2H), 7.66-7.36 (m, 2H), 7.25-7.00 (m, 3H), 6.32-6.00 (m, 2H), 5.59 (dt, J=10.1, 1.5 Hz, 1H), 4.33 (h, J=6.1 Hz, 1H), 3.58 (ddd, J=14.1, 11.1, 6.8 Hz, 2H), 3.44 (dt, J=11.7, 6.9 Hz, 1H), 3.18 (dd, J=11.2, 4.8 Hz, 1H), 3.09-2.67 (m, 8H), 2.12 (dq, J=13.2, 6.9 Hz, 1H), 1.94-1.69 (m, 5H).

Example 53

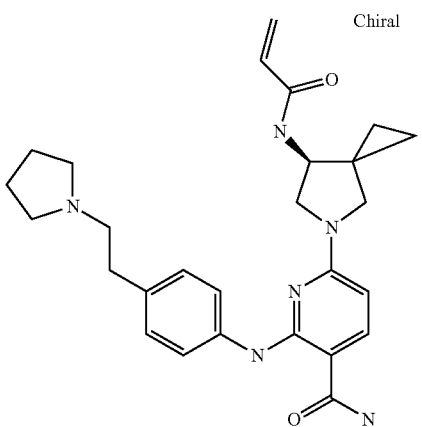 [SMILES: C=CC(=O)N[C@@H]1CN(c2ccc(C(N)=O)c(Nc3ccc(CCN4CCCC4)cc3)n2)CC12CC2]

6-((S)-7-Acryloylamino-5-aza-spiro[2.4]hept-5-yl)-2-[4-(2-pyrrolidin-1-yl-ethyl)-phenylamino]-nicotinamide (7)

6-((S)-7-Acryloylamino-5-aza-spiro[2.4]hept-5-yl)-2-[4-(2-pyrrolidin-1-yl-ethyl)-phenylamino]-nicotinamide 12.2 mg (29%) were prepared from 2,6-dichloro-nicotinamide, 4-(2-(pyrrolidin-1-yl)ethyl)aniline, (S)-tert-butyl 5-azaspiro[2.4]heptan-7-ylcarbamate and acrylic acid with methods 2A, 2B, 2C and 2D. HPLC: 99.9%, RT=2.89 min. MS: m/z=475 [M+H]+. $^1$H NMR (400 MHz, DMSO-d6) δ 11.66 (s, 1H), 8.44 (d, J=7.7 Hz, 1H), 7.92 (d, J=8.7 Hz, 1H), 7.61 (d, J=8.0 Hz, 2H), 7.12 (d, J=8.0 Hz, 2H), 6.28 (dd, J=17.1, 10.1 Hz, 1H), 6.11 (dt, J=17.0, 1.7 Hz, 1H), 5.86 (d, J=8.6 Hz, 1H), 5.60 (dt, J=10.1, 1.6 Hz, 1H), 4.13 (t, J=7.1 Hz, 1H), 3.81 (d, J=42.2 Hz, 2H), 3.57 (s, 1H), 2.73-2.57 (m, 4H), 1.68 (d, J=4.5 Hz, 4H), 0.96 (d, J=6.6 Hz, 1H), 0.87-0.55 (m, 4H).

Example 54

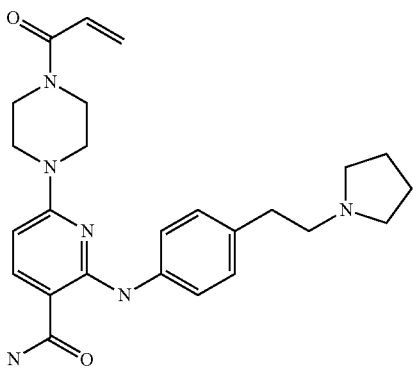 [SMILES: C=CC(=O)N1CCN(c2ccc(C(N)=O)c(Nc3ccc(CCN4CCCC4)cc3)n2)CC1]

6-(4-Acryloyl-piperazin-1-yl)-2-[4-(2-pyrrolidin-1-yl-ethyl)-phenylamino]-nicotinamide (12)

6-(4-Acryloyl-piperazin-1-yl)-2-[4-(2-pyrrolidin-1-yl-ethyl)-phenylamino]-nicotinamide 25.7 mg (28%) was prepared from 2,6-dichloro-nicotinamide, 4-(2-(pyrrolidin-1-yl)ethyl)aniline, tert-butyl piperazine-1-carboxylate and acrylic acid with methods 2A, 2B, 2C and 2D. HPLC: 99.9%, RT=2.89 min. MS: m/z=475 [M+H]+. $^1$H NMR (400 MHz, DMSO-d6) δ 11.52 (s, 1H), 7.97 (d, J=8.8 Hz, 1H), 7.50 (d, J=8.0 Hz, 2H), 7.16 (d, J=8.1 Hz, 2H), 6.96-6.75 (m, 1H), 6.32-6.02 (m, 2H), 5.82-5.52 (m, 1H), 3.68 (d, J=21.4 Hz, 8H), 2.69 (q, J=18.0, 13.2 Hz, 4H), 1.69 (d, J=5.3 Hz, 4H). Four protons overlap with solvent peaks.

Example 55

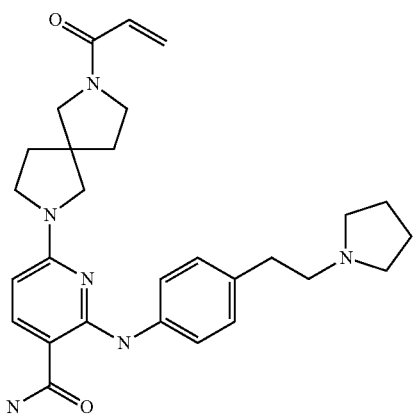 [SMILES: C=CC(=O)N1CCC2(CCN(c3ccc(C(N)=O)c(Nc4ccc(CCN5CCCC5)cc4)n3)C2)C1]

6-(7-Acryloyl-2,7-diaza-spiro[4.4]non-2-yl)-2-[4-(2-pyrrolidin-1-yl-ethyl)-phenylamino]-nicotinamide (20)

6-(7-Acryloyl-2,7-diaza-spiro[4.4]non-2-yl)-2-[4-(2-pyrrolidin-1-yl-ethyl)-phenylamino]-nicotinamide 28.1 mg (34%) was prepared from 2,6-dichloro-nicotinamide, 4-(2-(pyrrolidin-1-yl)ethyl)aniline, tert-butyl 2,7-diazaspiro[4.4]nonane-2-carboxylate and acrylic acid with methods 2A, 2B, 2C and 2D. HPLC: 99.5%, RT=3.69 min. MS: m/z=489 [M+H]+. $^1$H NMR (400 MHz, DMSO-d6) δ 11.64 (s, 1H), 7.91 (d, J=8.7 Hz, 1H), 7.62 (d, J=8.2 Hz, 2H), 7.11 (d, J=8.1 Hz, 2H), 6.60 (td, J=16.8, 10.2 Hz, 1H), 6.25-6.05 (m, 1H), 5.87 (d, J=8.7 Hz, 1H), 5.79-5.55 (m, 1H), 3.86-3.16 (m, 12H), 2.78-2.57 (m, 4H), 1.95 (dt, J=33.9, 6.9 Hz, 4H), 1.68 (q, J=3.3, 2.6 Hz, 4H).

Example 56

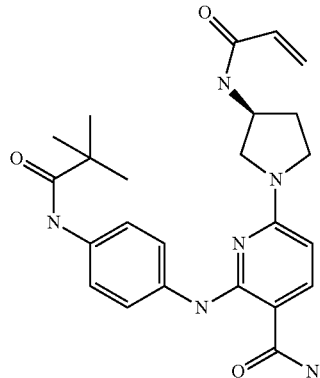 [SMILES: C=CC(=O)N[C@H]1CCN(c2ccc(C(N)=O)c(Nc3ccc(NC(=O)C(C)(C)C)cc3)n2)C1]

6-((S)-3-Acryloylamino-pyrrolidin-1-yl)-2-[4-(2,2-dimethyl-propionylamino)-phenylamino]-nicotinamide (59)

6-((S)-3-Acryloylamino-pyrrolidin-1-yl)-2-[4-(2,2-dimethyl-propionylamino)-phenylamino]-nicotinamide 29.3 mg (42%) was prepared from 2,6-dichloro nicotinamide, N-(4-aminophenyl)pivalamide, (R)-pyrrolidin-3-yl-carbamic acid tert-butyl ester and acrylic acid with methods 2A, 2B, 2C and 2D. HPLC: 90.0%, RT=2.91 min. MS: m/z=451 [M+H]+. $^1$H NMR (400 MHz, DMSO-d6) δ 9.14-8.99 (m, 1H), 8.96-8.79 (m, 1H), 8.36 (d, J=6.7 Hz, 1H), 7.76-7.59 (m, 2H), 7.59-7.34 (m, 4H), 6.97 (s, 1H), 6.36-6.18 (m, 1H), 6.18-5.97 (m, 2H), 5.60 (dd, J=9.9, 2.5 Hz, 1H), 4.33 (q, J=5.7, 5.0 Hz, 1H), 3.74-3.42 (m, 3H), 3.22 (dd, J=12.1, 4.8 Hz, 1H), 2.21-1.97 (m, 1H), 1.93-1.67 (m, 1H), 1.32-1.14 (m, 9H).

Example 57

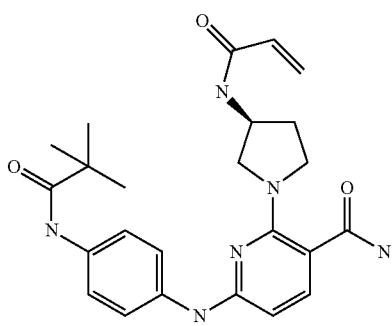 [SMILES: C=CC(=O)N[C@H]1CCN(c2nc(Nc3ccc(NC(=O)C(C)(C)C)cc3)ccc2C(N)=O)C1]

2-((S)-3-Acryloylamino-pyrrolidin-1-yl)-6-[4-(2,2-dimethyl-propionylamino)-phenylamino]-nicotinamide (156)

2-((S)-3-Acryloylamino-pyrrolidin-1-yl)-6-[4-(2,2-dimethyl-propionylamino)-phenylamino]-nicotinamide 5.7 mg (5%) was prepared from 2,6-dichloro nicotinamide, N-(4-aminophenyl)pivalamide, (R)-pyrrolidin-3-yl-carbamic acid tert-butyl ester and acrylic acid with methods 2A, 2B, 2C and 2D. HPLC: 96.5%, RT=3.5 min. MS: m/z=451 [M+H]+. $^1$H NMR (400 MHz, DMSO-d6) δ 11.85-11.34 (m, 1H), 9.32-8.86 (m, 1H), 8.47-8.20 (m, 1H), 8.13-7.90 (m, 1H), 7.84-7.34 (m, 5H), 6.24 (ddt, J=17.3, 9.9, 1.5 Hz, 1H), 6.18-6.00 (m, 1H), 3.89-3.45 (m, 3H), 6.00-5.82 (m, 1H), 5.71-5.46 (m, 1H), 4.70-4.35 (m, 1H), 2.23 (dq, J=14.5, 7.5 Hz, 1H), 1.95 (dd, J=12.1, 6.7 Hz, 1H), 1.32-1.14 (m, 9H).

Example 58

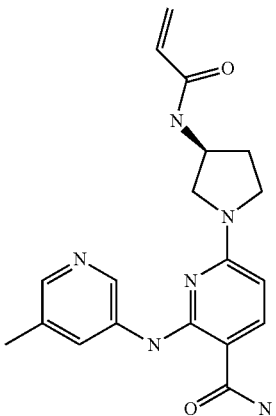 [SMILES: C=CC(=O)N[C@H]1CCN(c2ccc(C(N)=O)c(Nc3cncc(C)c3)n2)C1]

6-((S)-3-Acryloylamino-pyrrolidin-1-yl)-2-(5-methyl-pyridin-3-ylamino)-nicotinamide (55)

6-((S)-3-Acryloylamino-pyrrolidin-1-yl)-2-(5-methyl-pyridin-3-ylamino)-nicotinamide 18.7 mg (31%) was prepared from 2,6-dichloro nicotinamide, 5-methylpyridin-3-amine, (R)-pyrrolidin-3-yl-carbamic acid tert-butyl ester and acrylic acid with methods 2A, 2B, 2C and 2D. HPLC: 91.2%, RT=2.23 min. MS: m/z=367 [M+H]+. $^1$H NMR (400 MHz, DMSO-d6) δ 11.81 (s, 1H), 8.71 (d, J=2.3 Hz, 1H), 8.41 (d, J=6.8 Hz, 1H), 8.10 (s, 1H), 8.04-7.85 (m, 2H), 6.24 (dd, J=17.1, 10.0 Hz, 1H), 6.12 (dd, J=17.1, 2.5 Hz, 1H), 5.97 (d, J=8.8 Hz, 1H), 5.61 (dd, J=9.9, 2.5 Hz, 1H), 4.68-4.33 (m, 1H), 3.67 (d, J=59.7 Hz, 3H), 2.29 (s, 4H), 1.97 (dq, J=12.4, 5.9 Hz, 1H).

Example 59

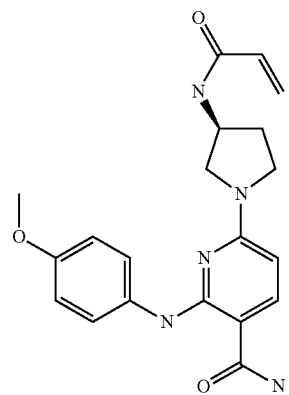 [SMILES: C=CC(=O)N[C@H]1CCN(c2ccc(C(N)=O)c(Nc3ccc(OC)cc3)n2)C1]

6-((S)-3-Acryloylamino-pyrrolidin-1-yl)-2-(4-methoxy-phenylamino)-nicotinamide (45)

6-((S)-3-Acryloylamino-pyrrolidin-1-yl)-2-(4-methoxy-phenylamino)-nicotinamide 12.9 mg (33%) was prepared from 2,6-dichloro nicotinamide, 4-methoxypyridin-3-amine, (R)-pyrrolidin-3-yl-carbamic acid tert-butyl ester and acrylic acid with methods 2A, 2B, 2C and 2D. HPLC: 97.2%, RT=2.80 min. MS: m/z=382 [M+H]+. $^1$H NMR (400 MHz, DMSO-d6) δ 11.52 (s, 1H), 8.39 (d, J=6.9 Hz, 1H), 7.90 (d, J=8.7 Hz, 1H), 7.62 (d, J=8.7 Hz, 2H), 6.98-6.75 (m, 2H), 6.24 (dd, J=17.1, 10.0 Hz, 1H), 6.12 (dd, J=17.1, 2.4 Hz, 1H), 5.85 (d, J=8.7 Hz, 1H), 5.60 (dd, J=10.0, 2.4 Hz, 1H), 4.59-4.34 (m, 2H), 3.57 (d, J=12.3 Hz, 2H), 2.21 (dq, J=13.9, 7.3 Hz, 1H), 1.93 (dq, J=12.1, 5.7 Hz, 1H).

Example 60

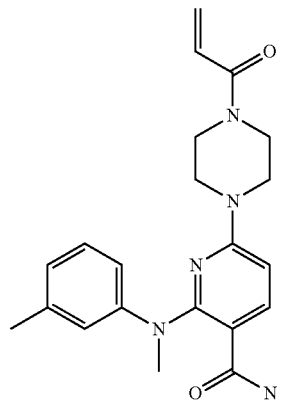 [SMILES: C=CC(=O)N1CCN(c2ccc(C(N)=O)c(N(C)c3cccc(C)c3)n2)CC1]

6-(4-Acryloyl-piperazin-1-yl)-2-(methyl-m-tolyl-amino)-nicotinamide (58)

6-(4-Acryloyl-piperazin-1-yl)-2-(methyl-m-tolyl-amino)-nicotinamide 25.1 mg (8.2%) was prepared from 2,6-dichloro nicotinamide, N,3-dimethylaniline, tert-butyl piperazine-1-carboxylate and acrylic acid with methods 2A, 2B, 2C and 2D. HPLC: 96.2%, RT=3.40 min. MS: m/z=380 [M+H]+. ¹H NMR (400 MHz, DMSO-d6) δ 7.81 (d, J=8.6 Hz, 1H), 7.33 (s, 1H), 7.06 (t, J=7.9 Hz, 1H), 7.00-6.77 (m, 2H), 6.75-6.53 (m, 4H), 6.15 (dd, J=16.7, 2.4 Hz, 1H), 5.71 (dd, J=10.4, 2.3 Hz, 1H), 3.67 (m, 8H), 2.21 (s, 3H).

Example 61

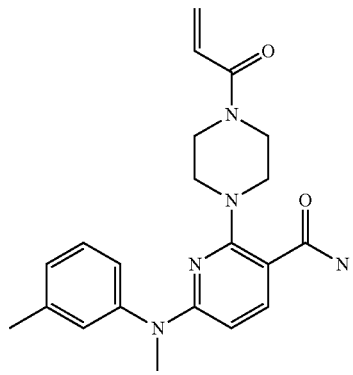 [SMILES: C=CC(=O)N1CCN(c2nc(N(C)c3cccc(C)c3)ccc2C(N)=O)CC1]

2-(4-Acryloyl-piperazin-1-yl)-6-(methyl-m-tolyl-amino)-nicotinamide (158)

2-(4-Acryloyl-piperazin-1-yl)-6-(methyl-m-tolyl-amino)-nicotinamide 8.8 mg (3.2%) was prepared from 2,6-dichloro nicotinamide, N,3-dimethylaniline, (R)-pyrrolidin-3-yl-carbamic acid tert-butyl ester and acrylic acid with methods 2A, 2B, 2C and 2D. HPLC: 99.9%, RT=3.82 min. MS: m/z=380 [M+H]+. ¹H NMR (400 MHz, DMSO-d6) δ 7.88-7.62 (m, 2H), 7.33 (t, J=7.7 Hz, 1H), 7.29-7.01 (m, 4H), 7.00-6.77 (m, 1H), 6.75-6.56 (m, 1H), 6.14 (dd, J=16.8, 2.3 Hz, 1H), 6.04 (d, J=8.5 Hz, 1H), 5.71 (dt, J=10.3, 2.7 Hz, 1H), 3.84-3.51 (m, 4H), 3.40 (s, 2H), 3.20 (s, 3H), 2.33 (s, 3H). Two protons overlap with solvent peaks.

Example 62

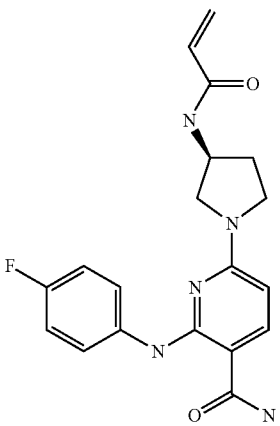 [SMILES: C=CC(=O)N[C@H]1CCN(c2ccc(C(N)=O)c(Nc3ccc(F)cc3)n2)C1]

6-((S)-3-Acryloylamino-pyrrolidin-1-yl)-2-(4-fluoro-phenylamino)-nicotinamide (48)

6-((S)-3-Acryloylamino-pyrrolidin-1-yl)-2-(4-fluoro-phenylamino)-nicotinamide 17.0 mg (17%) was prepared from 2,6-dichloro nicotinamide, 4-Fluoroaniline, tert-butyl piperazine-1-carboxylate and acrylic acid with methods 2A, 2B, 2C and 2D. HPLC: 96.1%, RT=3.46 min. MS: m/z=370 [M+H]+. ¹H NMR (400 MHz, DMSO-d6) δ 11.71 (s, 1H), 8.40 (d, J=6.9 Hz, 1H), 7.92 (d, J=8.7 Hz, 1H), 7.86-7.64 (m, 2H), 7.18-7.02 (m, 2H), 6.34-6.05 (m, 2H), 5.90 (d, J=8.7 Hz, 1H), 5.60 (dd, J=9.9, 2.5 Hz, 1H), 4.47 (h, J=5.4 Hz, 1H), 3.87-3.45 (m, 3H), 2.21 (dq, J=13.9, 7.5 Hz, 1H), 2.07-1.83 (m, 1H).

Example 63

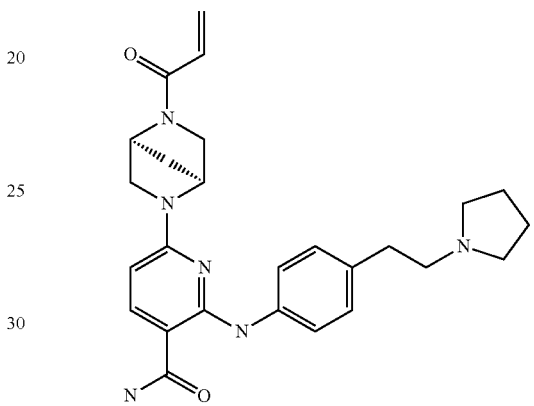

6-((1S,4S)-5-Acryloyl-2,5-diaza-bicyclo[2.2.1]hept-2-yl)-2-[4-(2-pyrrolidin-1-yl-ethyl)-phenylamino]-nicotinamide (9)

6-((1S,4S)-5-Acryloyl-2,5-diaza-bicyclo[2.2.1]hept-2-yl)-2-[4-(2-pyrrolidin-1-yl-ethyl)-phenylamino]-nicotinamide 15.9 mg (26%) was prepared from 2,6-dichloro nicotinamide, 4-(2-(pyrrolidin-1-yl)ethyl)aniline, (1S,4S)-tert-butyl 2,5-diazabicyclo[2.2.1]heptane-2-carboxylate and acrylic acid with methods 2A, 2B, 2C and 2D. HPLC: 99.9%, RT=2.89 min. MS: m/z=449 [M+H]+. ¹H NMR (400 MHz, DMSO-d6) δ 11.61 (s, 1H), 7.92 (d, J=8.7 Hz, 1H), 7.56 (d, J=8.0 Hz, 2H), 7.14 (d, J=8.1 Hz, 2H), 6.88-6.37 (m, 1H), 6.20-6.07 (m, 1H), 5.97 (s, 1H), 5.67 (dd, J=18.6, 10.3 Hz, 1H), 5.10-4.74 (m, 2H), 3.78-3.35 (m, 4H), 2.77-2.58 (m, 4H), 2.13-1.90 (m, 2H), 1.70 (d, J=5.1 Hz, 4H). Some peaks overlapped with the solvent peaks.

Example 64

Scheme 3

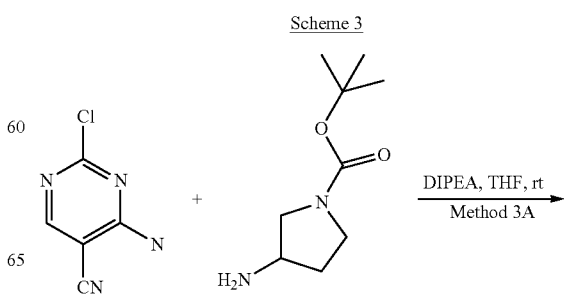

-continued

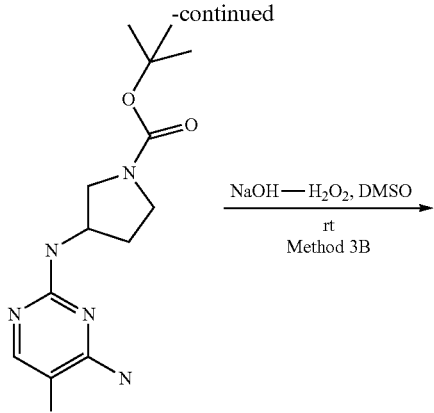

Method 3B: NaOH—H₂O₂, DMSO, rt

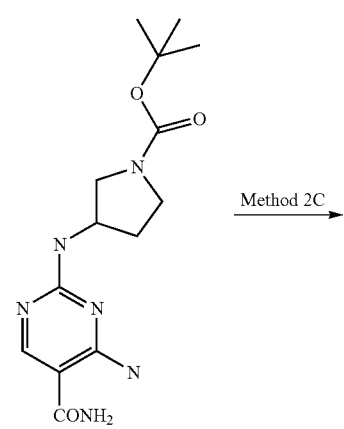

Method 2C

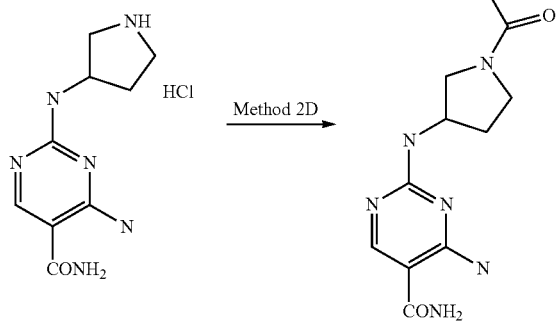

Method 2D

Methods Associated with Reaction Steps in Scheme 3:

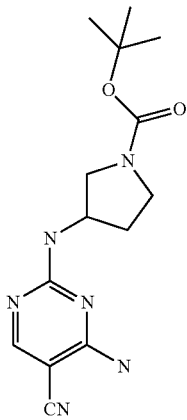 [SMILES: CC(C)(C)OC(=O)N1CCC(Nc2ncc(C#N)c(N)n2)C1]

tert-butyl 3-((4-amino-5-cyanopyrimidin-2-yl)amino)pyrrolidine-1-carboxylate (Method 3A)

In a microwave vial containing 4-amino-2-chloro-pyrimidine-5-carbonitrile (200.00 mg; 1.29 mmol; 1.00 eq.) and 3-amino-pyrrolidine-1-carboxylic acid tert-butyl ester (0.26 ml; 1.42 mmol; 1.10 eq.) in THF (6.0 mL) was added DIPEA (0.64 ml; 3.88 mmol; 3.00 eq.). The reaction was stirred at rt for 100 h before it was concentrated and carried to the next step. MS: m/z=305 [M+H]+.

Example 65

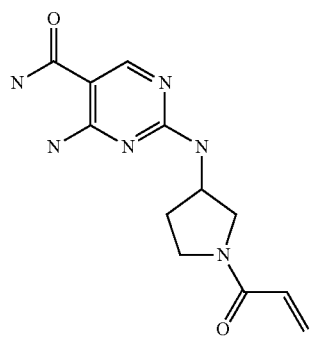 [SMILES: C=CC(=O)N1CCC(Nc2ncc(C(N)=O)c(N)n2)C1]

2-(1-Acryloyl-pyrrolidin-3-ylamino)-4-amino-pyrimidine-5-carboxylic acid amide (141)

2-(1-Acryloyl-pyrrolidin-3-ylamino)-4-amino-pyrimidine-5-carboxylic acid amide 22.1 mg (39%) was prepared from 2,4-dichloropyrimidine-5-carboxamide, tert-butyl 3-aminopyrrolidine-1-carboxylate and acrylic acid with methods 3A, 3B, 2C and 2D. HPLC: 98.0%, RT=1.22 min. MS: m/z=277 [M+H]+. ¹H-NMR (DMSO-D6) δ 8.42 (s, 1H), 6.55 (m, 1H), 6.13 (d, 1H), 5.37 (t, 1H), 4.41 (d, 1H), 3.78 (m, 1H), 3.61 (m, 1H), 2.13 (m, 1H), 1.84 (m, 1H).

Example 66

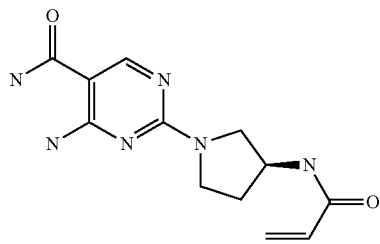 [SMILES: C=CC(=O)N[C@H]1CCN(c2ncc(C(N)=O)c(N)n2)C1]

2-((S)-3-Acryloylamino-pyrrolidin-1-yl)-4-amino-pyrimidine-5-carboxylic acid amide (142)

2-((S)-3-Acryloylamino-pyrrolidin-1-yl)-4-amino-pyrimidine-5-carboxylic acid amide 31.0 mg (44%) was prepared from 2,4-dichloropyrimidine-5-carboxamide, (S)-Pyrrolidin-3-yl-carbamic acid tert-butyl ester and acrylic acid with methods 3A, 3B, 2C and 2D. HPLC: 90.0%, RT=1.05 min. MS: m/z=277 [M+H]+. $^1$H-NMR (DMSO-D6) δ 8.42 (s, 1H), 8.31 (d, 1H), 6.25 (dd, 1H), 6.14 (d, 1H), 5.57 (d, 1H), 4.27 (s, 1H), 3.74 (s, 1H), 3.53 (s, 2H), 2.16 (m, 1H), 1.87 (m, 1H).

Example 67

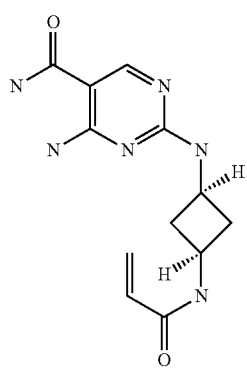 [SMILES: C=CC(=O)N[C@H]1C[C@@H](Nc2ncc(C(N)=O)c(N)n2)C1]

2-(3-Acryloylamino-cyclobutylamino)-4-amino-pyrimidine-5-carboxylic acid amide (143)

2-(3-Acryloylamino-cyclobutylamino)-4-amino-pyrimidine-5-carboxylic acid amide 19.1 mg (33%) was prepared from 2,4-dichloropyrimidine-5-carboxamide, cis-1,3-tert-butyl-3-aminocyclobutyl)carbamate and acrylic acid with methods 3A, 3B, 2C and 2D. HPLC: 90.0%, RT=1.30 min. MS: m/z=277 [M+H]+. $^1$H-NMR (MeOH-D4) δ 8.42 (s, 1H), 8.36 (d, 1H), 6.25 (dd, 1H), 6.09 (d, 1H), 5.57 (d, 1H), 4.01 (m, 1H), 3.98 (m, 1H), 2.56 (m, 1H), 1.87 (m, 1H).

Example 68

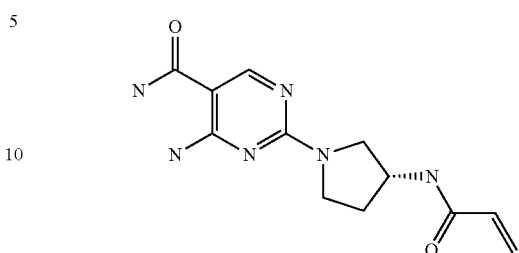

2-((R)-3-Acryloylamino-pyrrolidin-1-yl)-4-amino-pyrimidine-5-carboxylic acid amide (144)

2-((R)-3-Acryloylamino-pyrrolidin-1-yl)-4-amino-pyrimidine-5-carboxylic acid amide 13.7 mg (41%) was prepared from 2,4-dichloropyrimidine-5-carboxamide, (R)-pyrrolidin-3-yl-carbamic acid tert-butyl ester and acrylic acid with methods 3A, 3B, 2C and 2D. HPLC: 95.0%, RT=1.07 min. MS: m/z=277 [M+H]+. $^1$H-NMR (DMSO-D6) δ 8.42 (s, 1H), 8.31 (d, 1H), 6.25 (dd, 1H), 6.14 (d, 1H), 5.57 (d, 1H), 4.27 (s, 1H), 3.74 (s, 1H), 3.53 (s, 2H), 2.16 (m, 1H), 1.87 (m, 1H).

Example 69

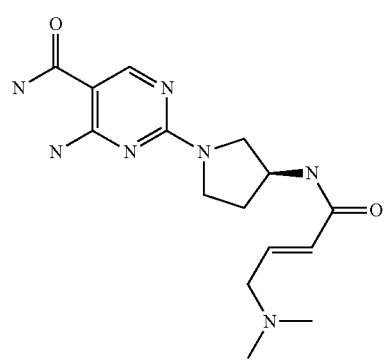 [SMILES: CN(C)C/C=C/C(=O)N[C@H]1CCN(c2ncc(C(N)=O)c(N)n2)C1]

4-Amino-2-[(S)-3-((E)-4-dimethylamino-but-2-enoylamino)-pyrrolidin-1-yl]-pyrimidine-5-carboxylic acid amide (145)

4-Amino-2-[(S)-3-((E)-4-dimethylamino-but-2-enoylamino)-pyrrolidin-1-yl]-pyrimidine-5-carboxylic acid amide 18.5 mg (10%) was prepared from 2,6-dichloro nicotinamide, (R)-pyrrolidin-3-yl-carbamic acid tert-butyl ester and (E)-4-dimethylamino-but-2-enoic acid hydrochloride with methods 3A, 3B, 2C and 2D. HPLC: 99.9%, RT=0.68 min. MS: m/z=334 [M+H]+. $^1$H-NMR (DMSO-D6) δ 8.42 (s, 1H), 8.25 (d, 1H), 6.67 (dd, 1H), 6.04 (d, 1H), 4.65 (s, 1H), 3.53 (m, 3H), 2.15 (m, 7H), 1.84 (m, 1H).

Example 70

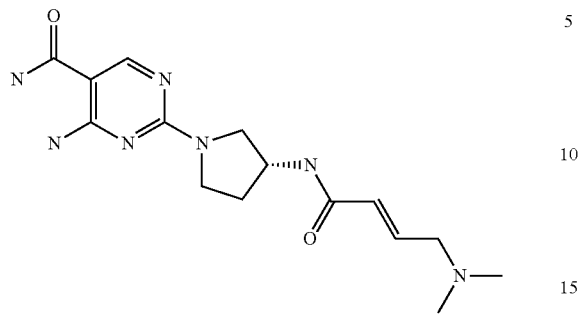

4-Amino-2-[(R)-3-((E)-4-dimethylamino-but-2-enoylamino)-pyrrolidin-1-yl]-pyrimidine-5-carboxylic acid amide (146)

4-Amino-2-[(R)-3-((E)-4-dimethylamino-but-2-enoylamino)-pyrrolidin-1-yl]-pyrimidine-5-carboxylic acid amide 18.8 mg (21%) was prepared from 2,6-dichloro nicotinamide, (S)-pyrrolidin-3-yl-carbamic acid tert-butyl ester and (E)-4-dimethylamino-but-2-enoic acid hydrochloride with methods 3A, 3B, 2C and 2D. HPLC: 96.3%, RT=0.68 min. MS: m/z=334 [M+H]+. $^1$H-NMR (DMSO-D6) δ 8.42 (s, 1H), 8.25 (d, 1H), 6.67 (dd, 1H), 6.04 (d, 1H), 4.65 (s, 1H), 3.53 (m, 3H), 2.15 (m, 7H), 1.84 (m, 1H).

Example 71

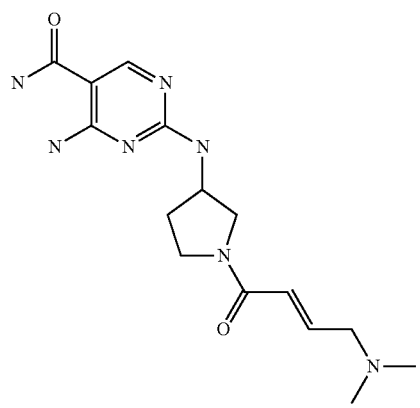 [SMILES: CN(C)C/C=C/C(=O)N1CCC(Nc2ncc(C(N)=O)c(N)n2)C1]

4-Amino-2-[1-((E)-4-dimethylamino-but-2-enoyl)-pyrrolidin-3-ylamino]-pyrimidine-5-carboxylic acid amide (138)

4-Amino-2-[1-((E)-4-dimethylamino-but-2-enoyl)-pyrrolidin-3-ylamino]-pyrimidine-5-carboxylic acid amide 15.2 mg (32%) was prepared from 2,6-dichloro nicotinamide, tert-butyl 3-aminopyrrolidine-1-carboxylate and (E)-4-dimethylamino-but-2-enoic acid hydrochloride with methods 3A, 3B, 2C and 2D. HPLC: 90.0%, RT=0.78 min. MS: m/z=334 [M+H]+.

Example 72

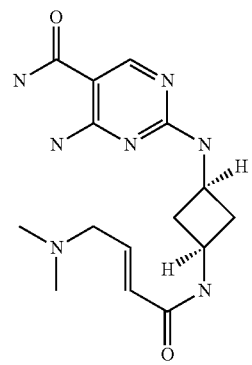 [SMILES: CN(C)C/C=C/C(=O)N[C@H]1C[C@@H](Nc2ncc(C(N)=O)c(N)n2)C1]

4-Amino-2-[3-(4-dimethylamino-but-2-enoylamino)-cyclobutylamino]-pyrimidine-5-carboxylic acid amide (162)

4-Amino-2-[1-((E)-4-dimethylamino-but-2-enoyl)-pyrrolidin-3-ylamino]-pyrimidine-5-carboxylic acid amide 11.9 mg (38%) was prepared from 2,6-dichloro nicotinamide, cis-1,3-tert-butyl-3-aminocyclobutyl) carbamate and (E)-4-dimethylamino-but-2-enoic acid hydrochloride with methods 3A, 3B, 2C and 2D. HPLC: 99.9%, RT=1.07 min. MS: m/z=334 [M+H]+.

Example 73

Scheme 4

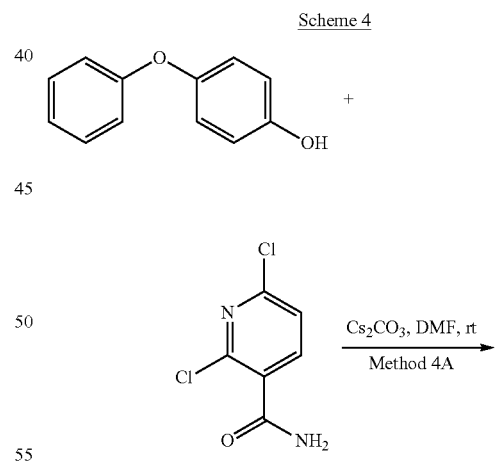

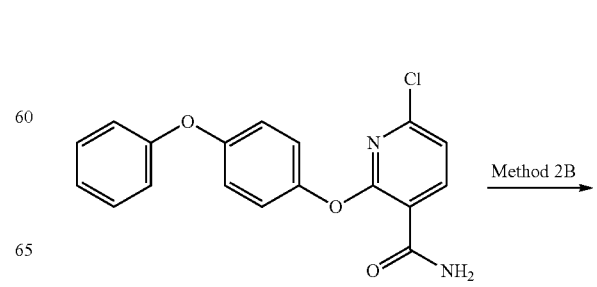

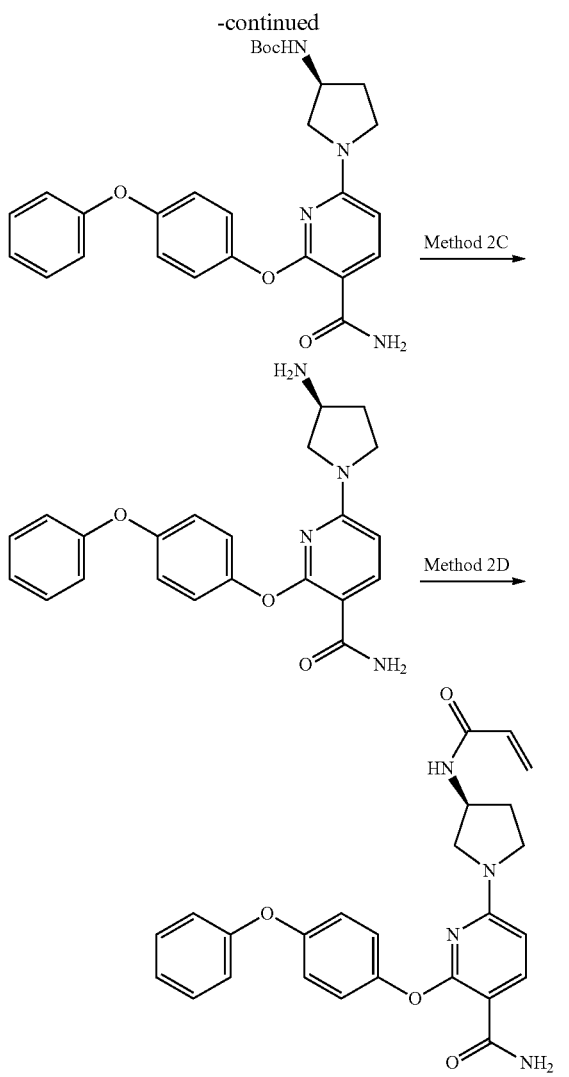

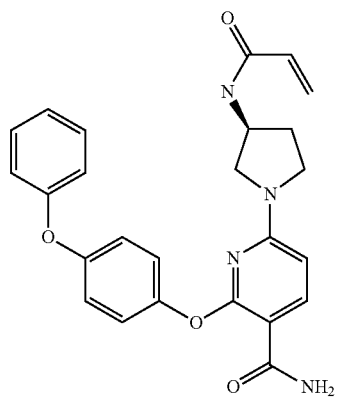 [SMILES: C=CC(=O)N[C@H]1CCN(c2ccc(C(N)=O)c(Oc3ccc(Oc4ccccc4)cc3)n2)C1]

6-((S)-3-Acryloylamino-pyrrolidin-1-yl)-2-(4-phenoxy-phenoxy)-nicotinamide (74)

6-((S)-3-Acryloylamino-pyrrolidin-1-yl)-2-(4-phenoxy-phenoxy)-nicotinamide 33.5 mg (54%) was prepared from 2,6-dichloro nicotinamide, 4-phenoxyphenol, (S)-pyrrolidin-3-yl-carbamic acid tert-butyl ester and acrylic acid with methods 4A, 2B, 2C and 2D. HPLC: 99.0%, RT=4.31 min. MS: m/z=445 [M+H]+. $^1$H-NMR (DMSO-D6) δ 8.31 (d, 1H), 8.07 (d, 1H), 7.34 (m, 4H), 7.25 (d, 2H), 7.15 (m, 3H), 7.00 (m, 2H), 6.20 (m, 2H), 6.13 (d, 1H), 5.61 (d, 1H), 4.35 (s, 1H), 3.50 (s, 1H), 3.08 (m, 1H), 2.14 (m, 1H), 1.80 (m, 1H).

Example 74

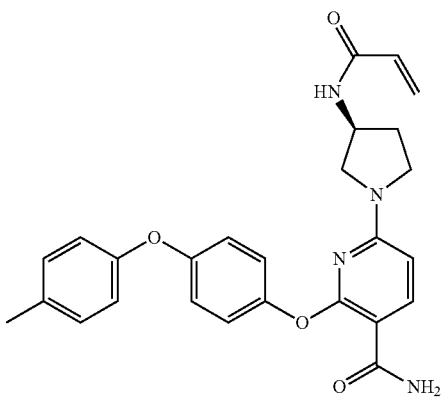 [SMILES: C=CC(=O)N[C@H]1CCN(c2ccc(C(N)=O)c(Oc3ccc(Oc4ccc(C)cc4)cc3)n2)C1]

(S)-6-(3-acrylamidopyrrolidin-1-yl)-2-(4-(p-tolyloxy)phenoxy)nicotinamide (85)

6-((S)-3-acryloylamino-pyrrolidin-1-yl)-2-(4-p-tolyloxy-phenoxy)-nicotinamide (40 mg, 50.7%) was prepared from 2,6-dichloro nicotinamide, 4-(p-tolyloxy)phenolff, (S)-pyrrolidin-3-yl-carbamic acid tert-butyl ester and acrylic acid with methods 4A, 2B, 2C and 2D excepting that purification of the final step was accomplished with 5% MeOH/CCl$_4$. HPLC-UV: 99.4% purity. LC/MS m/z=459.0 [M+H]+. $^1$H NMR (400 MHz, DMSO-d$_6$): δ 8.31 (d, J=6.96 Hz, 1H), 8.06 (d, J=8.52 Hz, 1H), 7.33-7.32 (m, 2H), 7.21-7.18 (m, 4H), 7.03-6.99 (m, 2H), 6.88-6.86 (m, 2H), 6.24-6.06 (m, Methods Associated with Reaction Steps in Scheme 4:

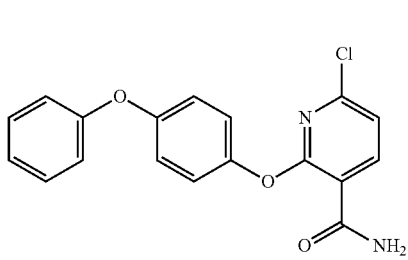

6-Chloro-2-(4-phenoxy-phenoxy)-nicotinamide (Method 4A)

In a microwave vial containing 2,6-Dichloro-nicotinamide (75.00 mg; 0.39 mmol; 1.00 eq.) and 4-Phenoxyphenol (76.77 mg; 0.41 mmol; 1.05 eq.) in DMF (4.00 ml; 51.88 mmol; 132.13 eq.) was added cesium carbonate (281.45 mg; 0.86 mmol; 2.20 eq.). The reaction was stirred at rt for 2 h before it was concentrated and carried to the next step. MS: m/z=341 [M+H]+.

3H), 5.60-5.57 (m, 1H), 4.37 (s, 1H), 3.46 (s, 1H), 3.31 (m, 2H), 3.05 (s, 1H), 2.27 (s, 3H), 2.07 (s, 1H), 1.81 (s, 1H).

Example 75

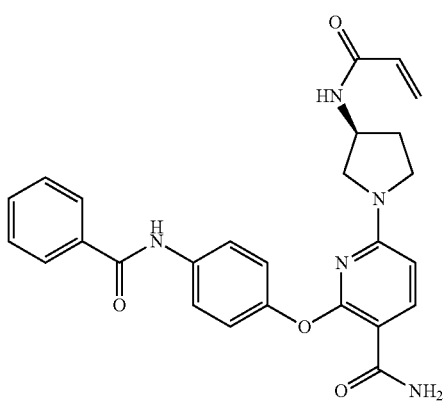 [SMILES: C=CC(=O)N[C@H]1CCN(c2ccc(C(N)=O)c(Oc3ccc(NC(=O)c4ccccc4)cc3)n2)C1]

(S)-6-(3-acrylamidopyrrolidin-1-yl)-2-(4-benzamidophenoxy)nicotinamide (95)

6-((S)-3-acryloylamino-pyrrolidin-1-yl)-2-(4-benzoylamino-phenoxy)-nicotinamide (35 mg, 44.9%) was prepared from 2,6-dichloro nicotinamide, 4-benzoylamino-phenol, (S)-pyrrolidin-3-yl-carbamic acid tert-butyl ester and acrylic acid with methods 4A, 2B, 2C and 2D excepting that purification of the final step was accomplished with 5% MeOH/CCl$_4$. HPLC-UV: HPLC-UV: 96.7% purity. LC/MS m/z=472.0 [M+H]+. $^1$H NMR (400 MHz, DMSO-d$_6$): δ 8.30 (d, J=6.92 Hz, 1H), 8.08 (d, J=8.52 Hz, 1H), 7.97-7.95 (m, 2H), 7.80 (d, J=8.96 Hz, 2H), 7.61-7.51 (m, 3H), 7.32 (d, J=7.60 Hz, 2H), 7.21-7.18 (m, 2H), 6.25-6.04 (m, 3H), 5.58-5.55 (m, 1H), 4.36 (s, 1H), 3.46 (s, 1H), 3.30 (s, 1H), 3.11 (d, J=8.08 Hz, 2H), 2.08 (s, 1H), 1.82 (s, 1H).

Example 76

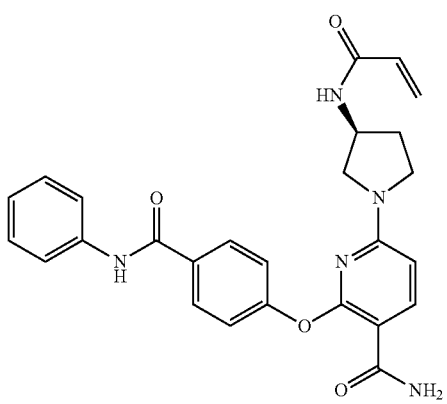 [SMILES: C=CC(=O)N[C@H]1CCN(c2ccc(C(N)=O)c(Oc3ccc(C(=O)Nc4ccccc4)cc3)n2)C1]

(S)-6-(3-acrylamidopyrrolidin-1-yl)-2-(4-(phenylcarbamoyl)phenoxy)nicotinamide (96)

6-((S)-3-acryloylamino-pyrrolidin-1-yl)-2-(4-phenylcarbamoyl-phenoxy)-nicotinamide (63.25 mg, 70.7%) was prepared from 2,6-dichloro nicotinamide, 4-hydroxy-N-phenyl-benzamide, (S)-pyrrolidin-3-yl-carbamic acid tert-butyl ester and acrylic acid with methods 4A, 2B, 2C and 2D excepting that purification of the final step was accomplished with 5% MeOH/CCl$_4$. HPLC-UV: 98.8% purity. LC/MS m/z=472.2 [M+H]+. $^1$H NMR (400 MHz, DMSO-d$_6$): δ 10.24 (s, 1H), 8.32 (d, J=6.88 Hz, 1H), 8.08 (d, J=8.56 Hz, 1H), 8.02 (d, J=8.68 Hz, 2H), 7.77 (d, J=7.72 Hz, 2H), 7.38-7.33 (m, 6H), 7.11-7.08 (m, 1H), 6.30 (d, J=8.56 Hz, 1H), 6.20-6.13 (m, 1H), 6.09-6.04 (m, 1H), 5.58-5.55 (m, 1H), 4.35 (s, 1H), 3.47 (s, 1H), 3.32-3.29 (m, 2H), 3.11 (d, J=7.80 Hz, 1H), 2.10-2.09 (m, 1H), 1.82 (s, 1H).

Example 77

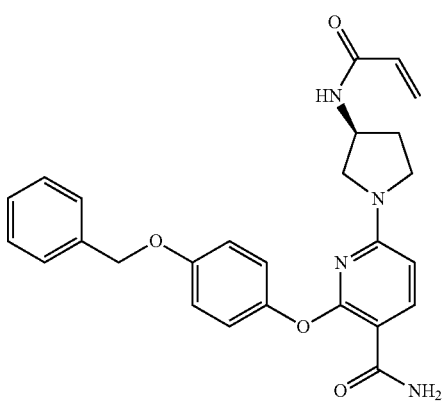 [SMILES: C=CC(=O)N[C@H]1CCN(c2ccc(C(N)=O)c(Oc3ccc(OCc4ccccc4)cc3)n2)C1]

(S)-6-(3-acrylamidopyrrolidin-1-yl)-2-(4-(benzyloxy)phenoxy)nicotinamide (90)

6-((S)-3-acryloylamino-pyrrolidin-1-yl)-2-(4-benzyloxy-phenoxy)-nicotinamide (53 mg, 61.3%) was prepared from 2,6-dichloro nicotinamide, 4-benzyloxy phenol, (S)-pyrrolidin-3-yl-carbamic acid tert-butyl ester and acrylic acid with methods 4A, 2B, 2C and 2D. HPLC-UV: 97% purity. LC/MS m/z=459.0 [M+H]+. $^1$H NMR (400 MHz, DMSO-d$_6$): δ 8.31 (d, J=6.84 Hz, 1H), 8.06 (d, J=8.52 Hz, 1H), 7.45-7.39 (m, 2H), 7.39-7.37 (m, 2H), 7.36-7.29 (m, 3H), 7.13-7.10 (m, 2H), 7.03-6.99 (m, 2H), 6.22-6.05 (m, 3H), 5.59-5.56 (m, 1H), 5.10 (s, 2H), 4.35 (s, 1H), 3.46 (s, 1H), 3.32 (m, 2H), 3.05 (s, 1H), 2.07 (s, 1H), 1.81 (s, 1H).

Example 78

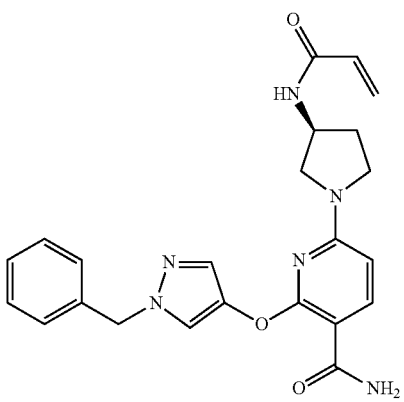 [SMILES: C=CC(=O)N[C@H]1CCN(c2ccc(C(N)=O)c(Oc3cnn(Cc4ccccc4)c3)n2)C1]

(S)-6-(3-acrylamidopyrrolidin-1-yl)-24(1-benzyl-1H-pyrazol-4-yl)oxy)nicotinamide (97)

6-((S)-3-amino-pyrrolidin-1-yl)-2-(1-benzyl-1H-pyrazol-4-yloxy)-nicotinamide was prepared from 2,6-dichloro nicotinamide, 1-benzyl-1H-pyrazol-4-ol, (S)-pyrrolidin-3-yl-carbamic acid tert-butyl ester and acrylic acid with methods 4A, 2B, 2C and 2D. HPLC-UV: 97% purity. LC/MS m/z=433 [M+H]⁺. ¹H NMR (DMSO-d₆, 400 MHz): δ 8.36-8.34 (d, J=6.84 Hz, 1H), 8.05-8.03 (d, J=8.48 Hz, 1H), 7.96 (s, 1H), 7.57 (s, 1H), 7.32-7.22 (m, 7H), 6.24-6.20 (m, 3H), 5.61-5.59 (d, J=9.7 Hz), 5.29 (s, 2H), 4.42-4.41 (m, 1H), 3.56-3.52 (m, 1H), 3.37-3.32 (m, 2H), 3.20-3.16 (m, 1H), 2.13-2.12 (m, 1H), 1.98-1.79 (m, 1H).

Example 79

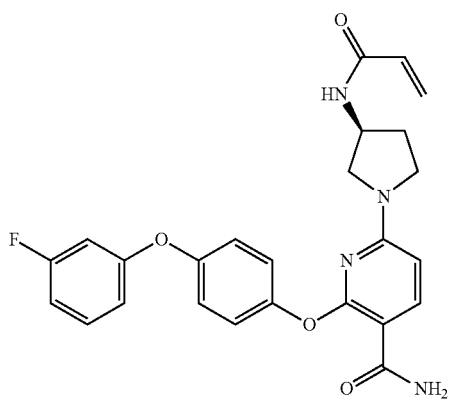 [SMILES: C=CC(=O)N[C@H]1CCN(c2ccc(C(N)=O)c(Oc3ccc(Oc4cccc(F)c4)cc3)n2)C1]

(S)-6-(3-acrylamidopyrrolidin-1-yl)-2-(4-(3-fluorophenoxy)phenoxy)nicotinamide (73)

6-((S)-3-Acryloylamino-pyrrolidin-1-yl)-2-[4-(3-fluorophenoxy)-phenoxy]-nicotinamide (100.00 mg; 23.2%) was prepared from 2,6-dichloro nicotinamide, 1-benzyl-1H-pyrazol-4-ol, (S)-pyrrolidin-3-yl-carbamic acid tert-butyl ester and acrylic acid with methods 4A, 2B, 2C and 2D. HPLC-UV: 96.7% purity. LC/MS m/z=463.0 [M+H]⁺. 400 MHz, DMSO-d6: 8.33 (d, J=6.64 Hz, 1H), 8.06 (d, J=8.52 Hz, 1H), 7.43-7.34 (m, 3H), 7.26-7.23 (m, 2H), 7.15-7.11 (m, 2H), 6.96-6.91 (m, 1H), 6.82-6.76 (m, 2H), 6.25-6.05 (m, 3H), 5.57 (dd, J=2.48, 9.84 Hz, 1H),4.35 (s, 1H), 3.46 (m, 1H), 3.33 (m, 2H), 3.05 (m, 1H), 2.07 (m, 1H), 1.80 (m, 1H).

Example 80

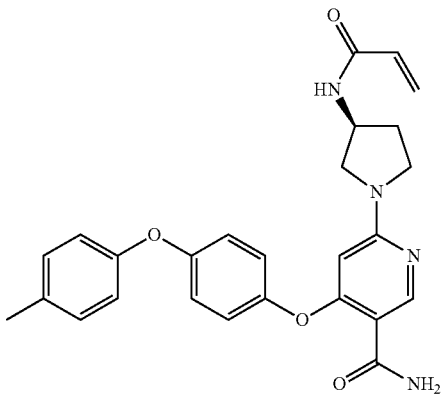 [SMILES: C=CC(=O)N[C@H]1CCN(c2cc(Oc3ccc(Oc4ccc(C)cc4)cc3)c(C(N)=O)cn2)C1]

(S)-6-(3-acrylamidopyrrolidin-1-yl)-4-(4-(p-tolyloxy)phenoxy)nicotinamide (114)

6-((S)-3-acryloylamino-pyrrolidin-1-yl)-4-(4-p-tolyloxy-phenoxy)-nicotinamide (100 mg, 44.1%) was prepared from 4,6-dichloro nicotinamide (this isomer reacts in a similar manner to the 2,6-isomer), 4-(p-tolyloxy)phenol, (S)-pyrrolidin-3-yl-carbamic acid tert-butyl ester, and acrylic acid with methods 4A, 2B, 2C and 2D. HPLC-UV: 96.7% purity. LC/MS m/z=459.0 [M+H]+. ¹H NMR (400 MHz, DMSO-d₆): δ 8.54 (s, 1H), 8.33 (d, J=6.4 Hz, 1H), 7.36 (m, 1H), 7.27 (m, 1H), 7.23-7.20 (m, 4H), 7.06 (d, J=8.8 Hz, 2H), 6.94 (d, J=8.2 Hz, 2H), 6.22-6.06 (m, 2H), 5.60-5.57 (m, 1H), 5.46 (s, 1H), 3.51 (m, 1H), 3.37-0.00 (m, 1H), 3.32 (m, 1H), 3.17 (m, 1H), 2.29 (s, 3H), 2.15-2.11 (m, 1H), 1.87-1.85 (m, 1H).

Example 81

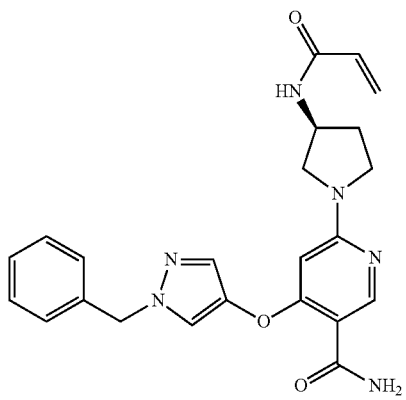 [SMILES: C=CC(=O)N[C@H]1CCN(c2cc(Oc3cnn(Cc4ccccc4)c3)c(C(N)=O)cn2)C1]

(S)-6-(3-acrylamidopyrrolidin-1-yl)-44(1-benzyl-1H-pyrazol-4-yl)oxy)nicotinamide (115)

The title compound was prepared in a manner similar to that as described in scheme 4 excepting that purification was accomplished by column chromatography using (5%, CHCl₃/MeOH) to afford 6-((S)-3-Acryloylamino-pyrrolidin-1-yl)-4-(1-benzyl-1H-pyrazol-4-yloxy)-nicotinamide (0.10 g; 0.22 mmol; 86.2%.) was prepared from 4,6-dichloro nicotinamide (this isomer reacts in a similar manner to the 2,6-isomer), 1-Benzyl-1H-pyrazol-4-ol, (S)-pyrrolidin-3-yl-carbamic acid tert-butyl ester, and acrylic acid with methods 4A, 2B, 2C and 2D. HPLC-UV: 96.2% purity. LC/MS m/z=433.0 [M+H]$^+$. 1HNMR (400 MHz): 8.50 (s, 1H), 8.35 (d, J=8.00 Hz, 1H), 8.03 (s, 1H), 7.54 (s, 1H), 7.35-7.28 (m, 3H), 7.26-7.20 (m, 4H), 6.24-6.60 (m, 2H), 5.61 (t, J=12.00 Hz, 2H), 5.39 (s, 2H), 4.40-4.39 (m, 1H), 3.49-3.42 (m, 1H), 3.37-3.35 (m, 1H), 3.13-3.12 (m, 1H), 2.17-2.12 (m, 1H), 1.89-1.85 (m, 1H).

Example 82

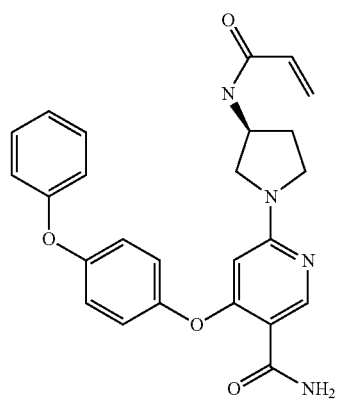 [SMILES: C=CC(=O)N[C@H]1CCN(c2cc(Oc3ccc(Oc4ccccc4)cc3)c(C(N)=O)cn2)C1]

6-((S)-3-Acryloylamino-pyrrolidin-1-yl)-4-(4-phenoxy-phenoxy)-nicotinamide (109)

6-((S)-3-Acryloylamino-pyrrolidin-1-yl)-4-(4-phenoxy-phenoxy)-nicotinamide 16.9 mg (38%) was prepared from 4,6-dichloro nicotinamide (this isomer reacts in a manner similar to the 2,4 isomer), 4-phenoxyphenol, (S)-Pyrrolidin-3-yl-carbamic acid tert-butyl ester and acrylic acid with methods 4A, 2B, 2C and 2D. HPLC: 99.6%, RT=3.76 min. MS: m/z=445 [M+H]+. $^1$H-NMR (DMSO-D6) δ 8.47 (s, 1H), 8.35 (d, 1H), 7.50 (d, 2H), 7.44 (m, 2H), 7.28 (m, 2H), 7.14 (m, 3H), 7.07 (m, 2H), 6.20 (m, 2H), 5.64 (m, 2H), 4.44 (m, 1H), 3.59 (s, 1H), 3.48 (s, 2H), 3.25 (s, 1H), 2.24 (m, 1H), 1.91 (m, 1H).

Example 83

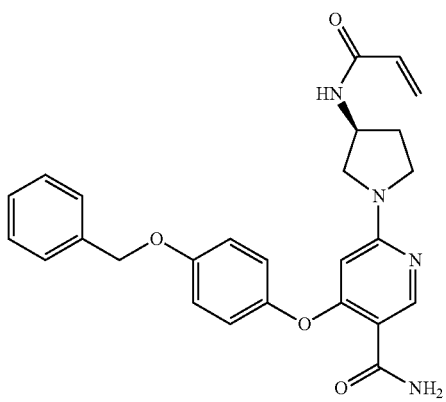 [SMILES: C=CC(=O)N[C@H]1CCN(c2cc(Oc3ccc(OCc4ccccc4)cc3)c(C(N)=O)cn2)C1]

(S)-6-(3-acrylamidopyrrolidin-1-yl)-4-(4-(benzyloxy)phenoxy)nicotinamide (112)

6-((S)-3-Acryloylamino-pyrrolidin-1-yl)-4-(4-benzyloxy-phenoxy)-nicotinamide (50.00 mg; 0.10 mmol; 22.1%) was prepared from 4,6-dichloro nicotinamide (this isomer reacts in a manner similar to the 2,4 isomer), 4-benzyloxy-phenol, (S)-Pyrrolidin-3-yl-carbamic acid tert-butyl ester and acrylic acid with methods 4A, 2B, 2C and 2D. HPLC-UV: 99.2% purity. LC/MS m/z=459.0 [M+H]$^+$. 400 MHz, DMSO-d6: 8.53 (s, 1H), 8.32 (d, J=6.7 Hz, 1H), 7.47-7.41 (m, 2H), 7.41-7.31 (m, 4H), 7.26 (s, 1H), 7.19-7.15 (m, 2H), 7.12-7.09 (m, 2H), 6.21-6.14 (m, 1H), 6.10-6.06 (m, 1H), 5.57 (dd, J=2.5, 9.8 Hz, 1H), 5.36 (s, 1H), 5.12 (s, 2H), 4.36-4.32 (m, 1H), 3.32-0.00 (m, 1H), 2.14-2.07 (m, 1H), 1.87-1.81 (m, 1H).

Example 84

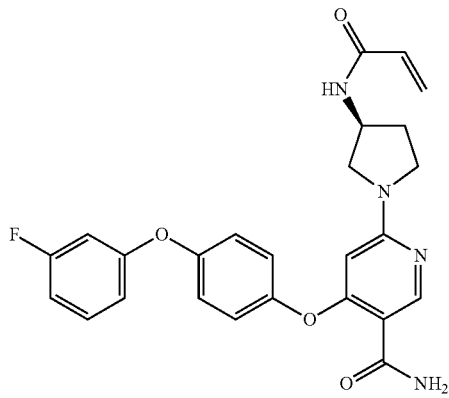 [SMILES: C=CC(=O)N[C@H]1CCN(c2cc(Oc3ccc(Oc4cccc(F)c4)cc3)c(C(N)=O)cn2)C1]

(S)-6-(3-acrylamidopyrrolidin-1-yl)-4-(4-(3-fluorophenoxy)phenoxy)nicotinamide (118)

6-((S)-3-Acryloylamino-pyrrolidin-1-yl)-4-[4-(3-fluorophenoxy)-phenoxy]-nicotinamide (50.00 mg; 0.10 mmol; 35.7%) was prepared from 4,6-dichloro nicotinamide (this isomer reacts in a manner similar to the 2,4 isomer), 3-fluoro-phenoxy phenol, (S)-Pyrrolidin-3-yl-carbamic acid tert-butyl ester and acrylic acid with methods 4A, 2B, 2C and 2D. HPLC-UV: 97.4% purity. LC/MS m/z=463.3 [M+H]$^+$. 400 MHz, DMSO-d6: 8.54 (s, 1H), 8.34 (d, J=6.6 Hz, 1H), 7.46-7.42 (m, 1H), 7.37-7.25 (m, 3H), 7.20-7.16 (m, 2H), 7.00-6.95 (m, 1H), 6.91-6.83 (m, 2H), 6.22-6.13 (m, 2H), 5.58 (dd, J=12.3, Hz, 1H), 5.50 (s, 1H), 4.38-4.34 (m, 1H), 3.55 (m, 1H), 3.33 (m, 2H), 3.16 (m, 1H), 2.17-2.09 (m, 1H), 1.89-1.83 (m, 1H)

Example 85

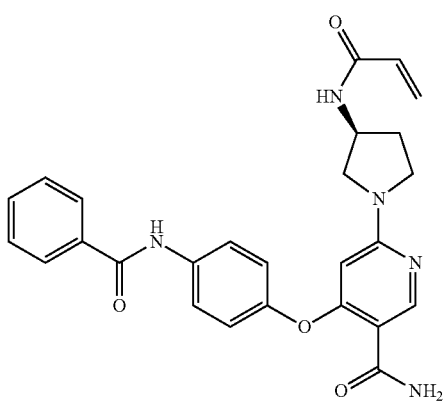 [SMILES: C=CC(=O)N[C@H]1CCN(c2cc(Oc3ccc(NC(=O)c4ccccc4)cc3)c(C(N)=O)cn2)C1]

(S)-6-(3-acrylamidopyrrolidin-1-yl)-4-(4-benzamidophenoxy)nicotinamide (119)

6-((S)-3-Acryloylamino-pyrrolidin-1-yl)-4-(4-benzoylamino-phenoxy)-nicotinamide (70.00 mg; 0.14 mmol; 41.8%; Purified Product) was prepared from 4,6-dichloro nicotinamide (this isomer reacts in a manner similar to the 2,4 isomer), 4-benzoylamino-phenol, (S)-Pyrrolidin-3-yl-carbamic acid tert-butyl ester and acrylic acid with methods 4A, 2B, 2C and 2D. HPLC-UV: 99.2% purity. LC/MS m/z=472.2 [M+H]$^+$. 400 MHz, DMSO-d6: 8.55 (s, 1H), 8.31 (d, J=6.5 Hz, 1H), 7.96-7.94 (m, 2H), 7.89-7.86 (m, 2H), 7.62-7.58 (m, 1H), 7.55-7.51 (m, 2H), 7.24-7.21 (m, 2H), 6.21-6.14 (m, 1H), 6.09-6.04 (m, 2H), 5.57 (dd, J=2.4, 9.8 Hz, 1H), 5.47 (s, 1H), 4.36-4.32 (m, 1H), 3.50 (m, 1H), 3.31 (m, 2H), 3.17-3.15 (m, 1H), 2.16-2.08 (m, 1H), 1.88-1.80 (m, 1H).

Example 86

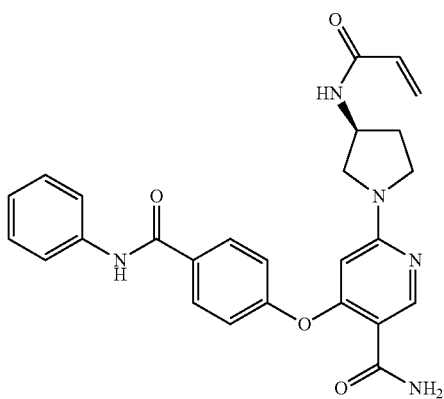 [SMILES: C=CC(=O)N[C@H]1CCN(c2cc(Oc3ccc(C(=O)Nc4ccccc4)cc3)c(C(N)=O)cn2)C1]

(S)-6-(3-acrylamidopyrrolidin-1-yl)-4-(4-(phenylcarbamoyl)phenoxy)nicotinamide (116)

6-((S)-3-Acryloylamino-pyrrolidin-1-yl)-4-(4-phenylcarbamoyl-phenoxy)-nicotinamide (50.00 mg; 29.4%)) was prepared from 4,6-dichloro nicotinamide (this isomer reacts in a manner similar to the 2,4 isomer), 4-hydroxy-N-phenylbenzamide, (S)-Pyrrolidin-3-yl-carbamic acid tert-butyl ester and acrylic acid with methods 4A, 2B, 2C and 2D. HPLC-UV: 98.2% purity. LC/MS m/z=472.2 [M+H]$^+$. 1H NMR (400 MHz, DMSO-d6): 10.26 (s, 1H), 8.55 (s, 1H), 8.34 (m, 1H), 8.12 (m, 2H), 7.78-7.75 (m, 2H), 7.37-7.29 (m, 6H), 7.10 (m, 1H), 6.17-6.15 (m, 1H), 6.10-6.09 (m, 1H), 5.68 (s, 1H), 5.57 (dd, J=2.44, 9.88 Hz, 1H), 4.10-4.00 (m, 1H), 3.60-3.50 (m, 1H), 3.30-3.10 (m, 1H), 2.20-2.10 (m, 1H), 1.90-1.75 (m, 1H).

Example 87

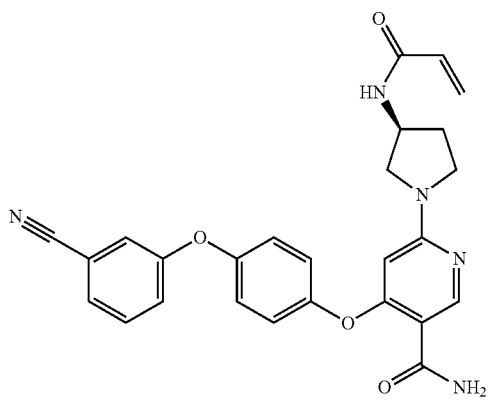 [SMILES: C=CC(=O)N[C@H]1CCN(c2cc(Oc3ccc(Oc4cccc(C#N)c4)cc3)c(C(N)=O)cn2)C1]

(S)-6-(3-acrylamidopyrrolidin-1-yl)-4-(4-(3-cyanophenoxy)phenoxy)nicotinamide (113)

6-((S)-3-Acryloylamino-pyrrolidin-1-yl)-4-[4-(3-cyanophenoxy)-phenoxy]-nicotinamide (100.00 mg; 0.21 mmol; 19.0%) was prepared from 4,6-dichloro nicotinamide (this isomer reacts in a manner similar to the 2,4 isomer), 3-cyano-phenoxy phenol, (S)-Pyrrolidin-3-yl-carbamic acid tert-butyl ester and acrylic acid with methods 4A, 2B, 2C and 2D. HPLC-UV: 98.7% purity. LC/MS m/z=470.1 [M+H]$^+$. 400 MHz, DMSO-d6: 8.54 (s, 1H), 8.34 (d, J=6.68 Hz, 1H), 7.62-7.59 (m, 2H), 7.52-7.52 (m, 1H), 7.38-7.35 (m, 2H), 7.30-7.22 (m, 3H), 7.21-7.19 (m, 2H), 6.22-6.05 (m, 2H), 5.58 (dd, J=2.48, 9.86 Hz, 1H), 5.51 (s, 1H), 4.38-4.34 (m, 1H), 3.50 (m, 1H), 3.33-3.27 (m, 2H), 3.16 (m, 1H), 2.15-2.11 (m, 1H), 1.88-1.83 (m, 1H).

Example 88

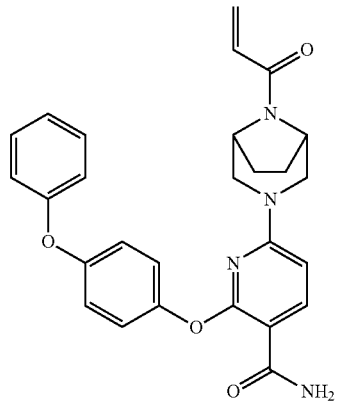

6-(8-Acryloyl-3,8-diaza-bicyclo[3.2.1]oct-3-yl)-2-(4-phenoxy-phenoxy)-nicotinamide (68)

6-(8-Acryloyl-3,8-diaza-bicyclo[3.2.1]oct-3-yl)-2-(4-phenoxy-phenoxy)-nicotinamide 32.7 mg (43%) was prepared from 2,6-dichloro nicotinamide, 4-phenoxyphenol, tert-butyl 3,8-diazabicyclo[3.2.1]octane-8-carboxylate and acrylic acid with methods 4A, 2B, 2C and 2D. HPLC: 98.5%, RT=4.69 min. MS: m/z=471 [M+H]+. $^1$H NMR (400 MHz, DMSO-d6) δ 8.08 (dd, J=8.6, 1.3 Hz, 1H), 7.41 (td, J=8.3, 4.2 Hz, 4H), 7.28-7.21 (m, 2H), 7.18-7.06 (m, 3H), 6.99 (d, J=7.9 Hz, 2H), 6.75 (dd, J=16.7, 10.3 Hz, 1H), 6.52 (d, J=8.7 Hz, 1H), 6.18 (dt, J=16.8, 1.8 Hz, 1H), 5.70 (dt, J=10.3, 1.7 Hz, 1H), 4.58 (t, J=4.7 Hz, 2H), 3.81 (dd, J=22.5, 12.5 Hz, 2H), 2.84 (dd, J=21.5, 12.4 Hz, 2H), 1.81 (ddd, J=55.0, 14.2, 8.1 Hz, 2H), 1.67-1.42 (m, 2H).

Example 89

6-[(S)-3-(Acryloyl-methyl-amino)-pyrrolidin-1-yl]-2-(4-phenoxy-phenoxy)-nicotinamide (107)

6-[(S)-3-(Acryloyl-methyl-amino)-pyrrolidin-1-yl]-2-(4-phenoxy-phenoxy)-nicotinamide 11.8 mg (34%) was prepared from 2,6-dichloro nicotinamide, 4-phenoxyphenol, (S)-tert-butyl methyl(pyrrolidin-3-yl)carbamate and acrylic acid with methods 4A, 2B, 2C and 2D. HPLC: 93.4%, RT=4.64 min. MS: m/z=459 [M+H]+. $^1$H NMR (400 MHz, DMSO-d6) δ 8.18-7.99 (m, 1H), 7.37 (t, J=7.6 Hz, 4H), 7.31-7.19 (m, 2H), 7.18-7.02 (m, 3H), 3.28-3.02 (m, 2H), 6.96 (d, J=8.0 Hz, 1H), 6.77 (t, J=28.5 Hz, 1H), 6.32-6.21 (m, 1H), 6.10 (t, J=14.4 Hz, 1H), 5.70 (d, J=11.6 Hz, 1H), 4.95 (d, J=134.1 Hz, 1H), 3.55-3.37 (m, 2H), 3.28-3.02 (m, 2H), 2.84 (d, J=51.4 Hz, 3H), 2.05 (s, 2H).

Example 90

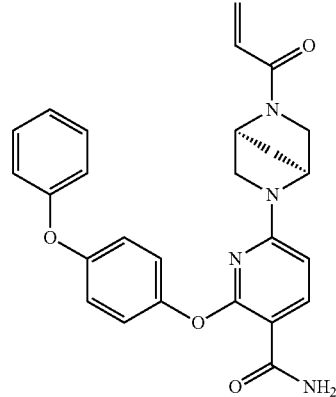 [SMILES: C=CC(=O)N1C[C@@H]2C[C@H]1CN2c1ccc(C(N)=O)c(Oc2ccc(Oc3ccccc3)cc2)n1]

6-((1S,4S)-5-acryloyl-2,5-diazabicyclo[2.2.1]heptan-2-yl)-2-(4-phenoxyphenoxy)nicotinamide (23)

6-((1S,4S)-5-acryloyl-2,5-diazabicyclo[2.2.1]heptan-2-yl)-2-(4-phenoxyphenoxy)nicotinamide 49.5 mg (51%) was prepared from 2,6-dichloro nicotinamide, 4-phenoxyphenol, (1S,4S)-tert-butyl 2,5-diazabicyclo[2.2.1]heptane-2-carboxylate and acrylic acid with methods 4A, 2B, 2C and 2D. HPLC: 97.4%, RT=4.48 min. MS: m/z=457 [M+H]+. $^1$H NMR (400 MHz, DMSO-d6) δ 8.16-7.95 (m, 1H), 7.50-7.31 (m, 4H), 7.32-7.18 (m, 2H), 7.18-7.04 (m, 3H), 6.99 (d, J=8.0 Hz, 2H), 6.81-6.18 (m, 2H), 6.12 (d, J=16.7 Hz, 1H), 5.65 (dd, J=9.9, 7.4 Hz, 1H), 5.00-4.71 (m, 1H), 4.53 (d, J=28.5 Hz, 1H), 3.40 (d, J=9.3 Hz, 1H), 3.10 (d, J=10.0 Hz, 1H), 1.90 (d, J=32.0 Hz, 2H). Some peaks overlaps with solvent peak.

Example 91

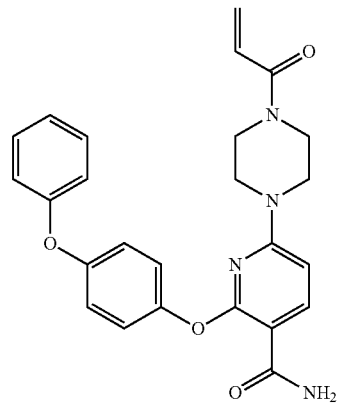

6-(4-acryloylpiperazin-1-yl)-2-(4-phenoxyphenoxy) nicotinamide (67)

6-(4-acryloylpiperazin-1-yl)-2-(4-phenoxyphenoxy)nicotinamide 38.1 mg (50%) was prepared from 2,6-dichloro nicotinamide, 4-phenoxyphenol, tert-butyl piperazine-1-carboxylate and acrylic acid with methods 4A, 2B, 2C and 2D.

HPLC: 95.8%, RT=4.54 min. MS: m/z=445 [M+H]+. ¹H NMR (400 MHz, DMSO-d6) δ 8.23-7.91 (m, 1H), 7.41 (dd, J=14.1, 6.3 Hz, 4H), 7.30-7.19 (m, 2H), 7.19-7.05 (m, 3H), 6.99 (d, J=7.9 Hz, 2H), 6.81 (dd, J=16.6, 10.3 Hz, 1H), 6.60 (d, J=8.6 Hz, 1H), 6.12 (dt, J=16.7, 1.8 Hz, 1H), 5.69 (dt, J=10.4, 1.7 Hz, 1H), 3.70-3.48 (m, 4H), 3.41 (d, J=13.8 Hz, 4H).

2,6-dichloro nicotinamide, 4-phenoxyphenol, (S)-tert-butyl 3-aminopyrrolidine-1-carboxylate and acrylic acid with methods 4A, 2B, 2C and 2D. HPLC: 90.7%, RT=4.85 min. MS: m/z=445 [M+H]+. ¹H-NMR (DMSO-D6) δ 8.00 (d, 1H), 7.50 (d, 1H), 7.44 (m, 4H), 7.28 (m, 2H), 7.16 (m, 3H), 7.00 (m, 2H), 6.57 (ddd, 1H), 6.25 (m, 1H), 6.14 (dd, 1H), 5.59 (m, 1H), 3.89 (s, 1H), 3.51 (m, 2H), 3.81 (m, 1H), 3.22 (m, 1H), 1.96 (m, 1H), 1.75 (m, 1H).

Example 92

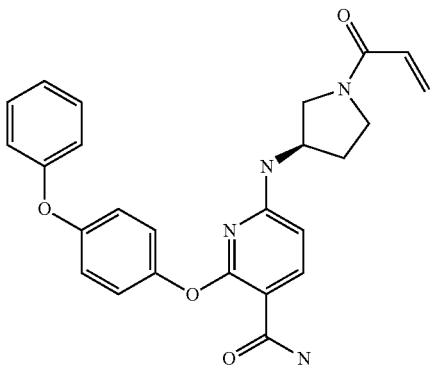 [SMILES: C=CC(=O)N1CC[C@@H](Nc2ccc(C(N)=O)c(Oc3ccc(Oc4ccccc4)cc3)n2)C1]

6-((R)-1-Acryloyl-pyrrolidin-3-ylamino)-2-(4-phenoxy-phenoxy)-nicotinamide (72)

6-((R)-1-Acryloyl-pyrrolidin-3-ylamino)-2-(4-phenoxyphenoxy)-nicotinamide 22.8 mg (7.9%) was prepared from 2,6-dichloro nicotinamide, 4-phenoxyphenol, (R)-tert-butyl 3-aminopyrrolidine-1-carboxylate and acrylic acid with methods 4A, 2B, 2C and 2D. HPLC: 97.4%, RT=4.85 min. MS: m/z=445 [M+H]+. ¹H-NMR (DMSO-D6) δ 8.00 (d, 1H), 7.41 (m, 1H), 7.25 (m, 2H), 7.14 (m, 3H), 7.00 (m, 2H), 6.37-6.54 (ddd, 1H), 6.28 (m, 1H), 6.14 (dd, 1H), 5.62 (m, 1H), 3.86 (s, 1H), 3.50 (m, 2H), 3.31 (m, 1H), 3.25 (m, 1H), 2.00 (m, 1H), 1.75 (m, 1H).

Example 93

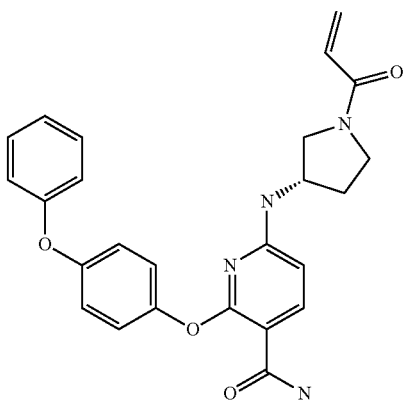 [SMILES: C=CC(=O)N1CC[C@H](Nc2ccc(C(N)=O)c(Oc3ccc(Oc4ccccc4)cc3)n2)C1]

6-((S)-1-Acryloyl-pyrrolidin-3-ylamino)-2-(4-phenoxy-phenoxy)-nicotinamide (106)

6-((S)-1-Acryloyl-pyrrolidin-3-ylamino)-2-(4-phenoxyphenoxy)-nicotinamide 6.9 mg (30%) was prepared from

Example 94

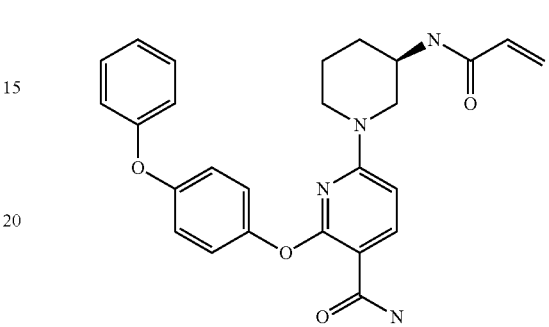

(R)-3-Acryloylamino-6'-(4-phenoxy-phenoxy)-3,4,5,6-tetrahydro-2H-[1,2']bipyridinyl-5'-carboxylic acid amide (91)

(R)-3-Acryloylamino-6'-(4-phenoxy-phenoxy)-3,4,5,6-tetrahydro-2H-[1,2']bipyridinyl-5'-carboxylic acid amide 14.7 mg (33%) was prepared from 2,6-dichloro nicotinamide, 4-phenoxyphenol, (R)-tert-butyl piperidin-3-ylcarbamate and acrylic acid with methods 4A, 2B, 2C and 2D. HPLC: 94.0%, RT=4.90 min. MS: m/z=459 [M+H]+. ¹H-NMR (DMSO-D6) δ 8.04 (dd, 2H), 7.41 (m, 4H), 7.25 (d, 2H), 7.14 (m, 1H), 7.00 (m, 4H), 6.73 (ddd, 1H), 6.54 (d, 1H), 6.34 (dd, 1H), 6.08 (d, 1H), 5.53 (d, 1H), 3.92 (d, 1H), 3.74 (d, 1H), 3.43 (m, 1H), 3.00 (t, 1H), 2.78 (dd, 1H), 1.78 (m, 1H), 1.60 (m, 1H), 1.46 (m, 2H).

Example 95

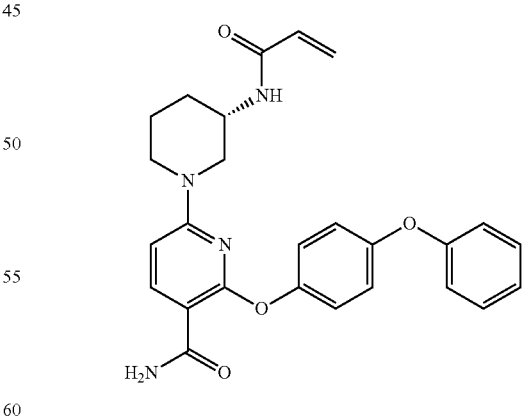

(S)-3-Acryloylamino-6'44-phenoxy-phenoxy)-3,4,5,6-tetrahydro-2H-[1,2']bipyridinyl-5'-carboxylic acid amide (94)

(S)-3-Acryloylamino-6'-(4-phenoxy-phenoxy)-3,4,5,6-tetrahydro-2H-[1,2']bipyridinyl-5'-carboxylic acid amide 18.0 mg (43%) was prepared from 2,6-dichloro nicotinamide, 4-phenoxyphenol, (S)-tert-butyl piperidin-3-ylcarbamate and acrylic acid with methods 4A, 2B, 2C and 2D. HPLC: 99.9%, RT=4.90 min. MS: m/z=459 [M+H]+. ¹H-NMR (DMSO-D6) δ 8.04 (dd, 2H), 7.41 (m, 4H), 7.25 (d, 2H), 7.14 (m, 1H), 7.00 (m, 4H), 6.73 (ddd, 1H), 6.54 (d, 1H), 6.34 (dd, 1H), 6.08 (d, 1H), 5.53 (d, 1H), 3.92 (d, 1H), 3.74 (d, 1H), 3.43 (m, 1H), 3.00 (t, 1H), 2.78 (dd, 1H), 1.78 (m, 1H), 1.60 (m, 1H), 1.46 (m, 2H).

Example 96

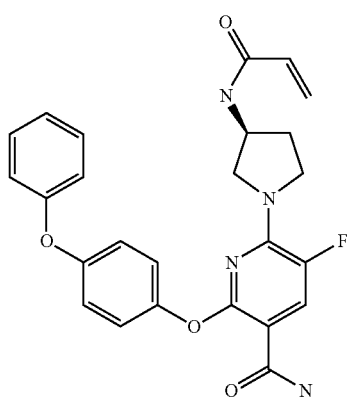 [SMILES: C=CC(=O)N[C@H]1CCN(c2nc(Oc3ccc(Oc4ccccc4)cc3)c(C(N)=O)cc2F)C1]

6-((S)-3-Acryloylamino-pyrrolidin-1-yl)-5-fluoro-2-(4-phenoxy-phenoxy)-nicotinamide (2)

6-((S)-3-Acryloylamino-pyrrolidin-1-yl)-5-fluoro-2-(4-phenoxy-phenoxy)-nicotinamide 24.9 mg (38%) was prepared from 2,6-dichloro-5-fluoronicotinamide, 4-phenoxyphenol, (S)-Pyrrolidin-3-yl-carbamic acid tert-butyl ester and acrylic acid with methods 4A, 2B, 2C and 2D. HPLC: 92.0%, RT=4.55 min. MS: m/z=463 [M+H]+. ¹H-NMR (DMSO-D6) δ 8.26 (d, 1H), 7.73 (s, 1H), 7.67 (d, 1H), 7.36 (m, 3H), 7.23 (d, 2H), 7.15 (m, 3H), 7.00 (d, 2H), 6.20 (dd, 1H), 6.12 (d, 1H), 5.59 (d, 1H), 4.25 (m, 1H), 3.40 (m, 1H), 3.29 (m, 1H), 3.21 (m, 1H), 3.03 (m, 1H), 2.02 (m, 1H), 1.75 (m, 1H).

Example 97

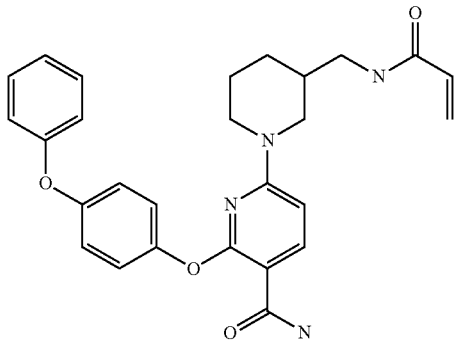 [SMILES: C=CC(=O)NCC1CCCN(c2ccc(C(N)=O)c(Oc3ccc(Oc4ccccc4)cc3)n2)C1]

3-(Acryloylamino-methyl)-6'-(4-phenoxy-phenoxy)-3,4,5,6-tetrahydro-2H-[1,2']bipyridinyl-5'-carboxylic acid amide (100)

3-(Acryloylamino-methyl)-6'-(4-phenoxy-phenoxy)-3,4,5,6-tetrahydro-2H-[1,2']bipyridinyl-5'-carboxylic acid amide 44.8 mg (58%) was prepared from 2,6-dichloro nicotinamide, 4-phenoxyphenol, tert-butyl (piperidin-3-ylmethyl)carbamate and acrylic acid with methods 4A, 2B, 2C and 2D. HPLC: 99.9%, RT=4.84 min. MS: m/z=473 [M+H]+. ¹H-NMR (DMSO-D6) δ 8.04 (d, 2H), 7.31 (m, 4H), 7.26 (d, 2H), 7.13 (m, 3H), 7.00 (d, 2H), 6.52 (d, 1H), 6.25 (dd, 1H), 6.07 (d, 1H), 5.55 (d, 1H), 3.81 (t, 2H), 3.00 (t, 2H), 2.75 (m, 1H), 2.62 (m, 1H), 1.75 (m, 1H), 1.58 (m, 2H), 1.25 (m, 2H).

Example 98

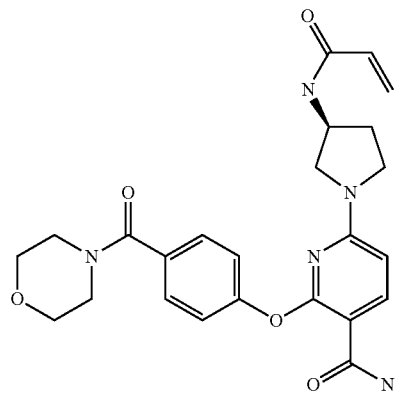 [SMILES: C=CC(=O)N[C@H]1CCN(c2ccc(C(N)=O)c(Oc3ccc(C(=O)N4CCOCC4)cc3)n2)C1]

6-((S)-3-Acryloylamino-pyrrolidin-1-yl)-2-[4-(morpholine-4-carbonyl)-phenoxy]-nicotinamide (101)

6-((S)-3-Acryloylamino-pyrrolidin-1-yl)-2-[4-(morpholine-4-carbonyl)-phenoxy]-nicotinamide 32.8 mg (44%) was prepared from 2,6-dichloro-5-fluoronicotinamide, (4-hydroxyphenyl)(morpholino)methanone, (S)-Pyrrolidin-3-yl-carbamic acid tert-butyl ester and acrylic acid with methods 4A, 2B, 2C and 2D. HPLC: 99.8%, RT=3.21 min. MS: m/z=466 [M+H]+. ¹H-NMR (DMSO-D6) δ 8.28 (d, 1H), 8.14 (d, 1H), 7.46 (d, 2H), 7.25 (m, 4H), 6.24 (d, 1H), 6.18 (dd, 1H), 6.07 (d, 1H), 5.56 (d, 1H), 4.38 (s, 1H), 3.46-3.54 (m, 10H), 3.03 (s, 1H), 2.14 (m, 1H), 1.77 (m, 1H).

Example 99

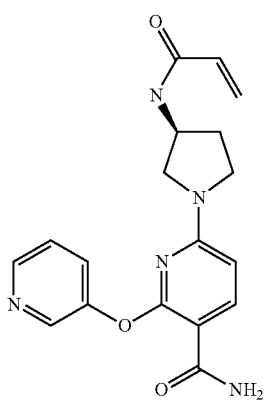 [SMILES: C=CC(=O)N[C@H]1CCN(c2ccc(C(N)=O)c(Oc3cccnc3)n2)C1]

6-((S)-3-Acryloylamino-pyrrolidin-1-yl)-2-(pyridin-3-yloxy)-nicotinamide (92)

6-((S)-3-Acryloylamino-pyrrolidin-1-yl)-2-(pyridin-3-yloxy)-nicotinamide 9.4 mg (31%) was prepared from 2,6-dichloro nicotinamide, pyridin-3-ol, (S)-Pyrrolidin-3-yl-carbamic acid tert-butyl ester and acrylic acid with method 4A, 2B, 2C and 2D. HPLC: 91.2%, RT=2.16 min. MS: m/z=354 [M+H]+. $^1$H NMR (400 MHz, DMSO-d6) δ 8.70-8.44 (m, 2H), 8.30 (d, J=6.9 Hz, 1H), 8.09 (d, J=8.5 Hz, 1H), 7.83 (ddd, J=8.4, 2.7, 1.3 Hz, 1H), 7.57 (dd, J=8.4, 4.7 Hz, 1H), 7.38 (s, 2H), 6.29 (d, J=8.6 Hz, 1H), 6.18 (dd, J=17.1, 9.8 Hz, 1H), 6.09 (dd, J=17.1, 2.6 Hz, 1H), 5.59 (dd, J=9.8, 2.6 Hz, 1H), 3.37 (d, J=62.7 Hz, 3H), 3.19-3.00 (m, 1H), 2.09 (d, J=7.3 Hz, 1H), 1.83 (dt, J=12.7, 7.1 Hz, 1H).

Example 100

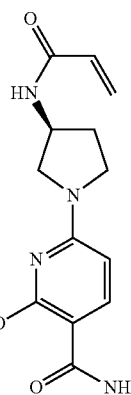

(S)-6-(3-acrylamidopyrrolidin-1-yl)-2-(4-(3-(trifluoromethyl)phenoxy)phenoxy)nicotinamide (82)

6-((S)-3-Acryloylamino-pyrrolidin-1-yl)-2-[4-(3-trifluoromethyl-phenoxy)-phenoxy]-nicotinamide (100.00 mg; 30.0%) was prepared from 2,6-dichloro nicotinamide, 3-trifluoromethyl-phenoxy-phenol, (S)-Pyrrolidin-3-yl-carbamic acid tert-butyl ester and acrylic acid with methods 4A, 2B, 2C and 2D. HPLC: 95.2%, RT=2.16 min. MS: m/z=513.2 [M+H]+. 400 MHz, DMSO-d6: 8.33 (d, J=6.56 Hz, 1H), 8.07 (d, J=8.52 Hz, 1H), 7.62 (t, J=8.00 Hz, 1H), 7.46 (d, J=7.76 Hz, 1H), 7.38-7.36 (m, 2H), 7.29-7.26 (m, 3H), 7.19-7.16 (m, 3H), 6.25-6.21 (m, 1H), 6.18-6.05 (m, 2H), 5.57 (dd, J=2.48, 9.82 Hz, 1H), 4.35 (bs, 1H), 3.48-0.00 (m, 1H), 3.33-3.27 (m, 2H), 3.08 (m, 1H), 2.08 (m, 1H), 1.82 (m, 1H).

Example 101

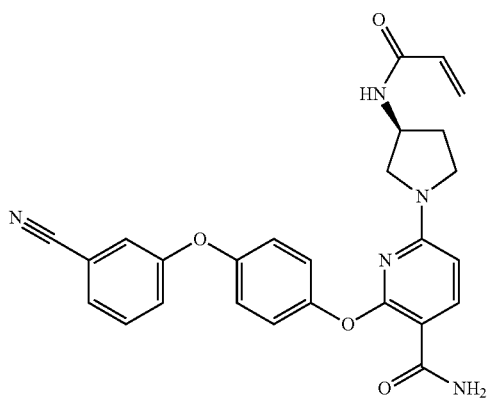

(S)-6-(3-acrylamidopyrrolidin-1-yl)-2-(4-(3-cyanophenoxy)phenoxy)nicotinamide (79)

6-((S)-3-Acryloylamino-pyrrolidin-1-yl)-2-[4-(3-cyanophenoxy)-phenoxy]-nicotinamide (50.00 mg; 0.10 mmol; 21.9%) was prepared from 2,6-dichloro nicotinamide, 3-cyanophenoxy-phenol, (S)-Pyrrolidin-3-yl-carbamic acid tert-butyl ester and acrylic acid with methods 4A, 2B, 2C and 2D. HPLC-UV: 95.5% purity. LC/MS m/z=470.2 [M+H]$^+$. 1H NMR (400 MHz, DMSO-d6): 8.33 (d, J=6.72 Hz, 1H), 8.07 (d, J=9.60 Hz, 1H), 7.61-7.56 (m, 2H), 7.38-7.34 (m, 2H), 7.28-7.25 (m, 3H), 7.17-7.13 (m, 3H), 6.25-6.21 (m, 1H), 6.18-6.05 (m, 2H), 5.57 (dd, J=2.52, 9.84 Hz, 1H), 4.35 (bs, 1H), 3.48 (m, 1H), 3.33-3.27 (m, 2H), 3.10 (m, 1H), 2.09 (m, 1H), 1.83 (m, 1H).

Example 102

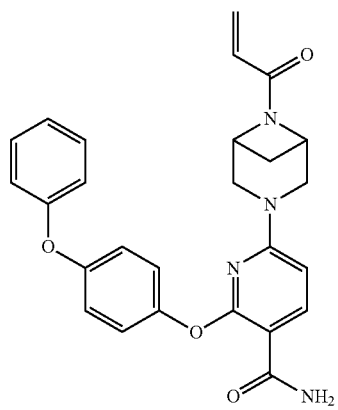 [SMILES: C=CC(=O)N1C2CC1CN(c1ccc(C(N)=O)c(Oc3ccc(Oc4ccccc4)cc3)n1)C2]

6-(6-Acryloyl-3,6-diaza-bicyclo[3.1.1]hept-3-yl)-2-(4-phenoxy-phenoxy)-nicotinamide formic acid (78)

6-(6-Acryloyl-3,6-diaza-bicyclo[3.1.1]hept-3-yl)-2-(4-phenoxy-phenoxy)-nicotinamide formic acid 25.1 mg (18%) was prepared from 2,6-dichloro nicotinamide, 4-phenoxy-phenol, tert-butyl 3,6-diazabicyclo[3.1.1]heptane-6-carboxylate and acrylic acid with method 4A, 2B, 2C and 2D HPLC: 99.9%, RT=4.34 min. MS: m/z=458 [M+H]+. $^1$H NMR (400 MHz, DMSO-d6) δ 8.12 (d, J=8.6 Hz, 1H), 7.41 (ddq, J=10.1, 5.6, 2.7 Hz, 4H), 7.32-7.21 (m, 2H), 7.20-7.04 (m, 3H), 7.04-6.92 (m, 2H), 6.53-6.26 (m, 2H), 6.08 (dd, J=16.9, 2.1 Hz, 1H), 5.65 (dd, J=10.2, 2.1 Hz, 1H), 4.76 (s, 1H), 4.50-4.21 (m, 1H), 2.65 (dt, J=8.6, 6.4 Hz, 1H), 1.54 (d, J=8.8 Hz, 1H). Some peaks overlap with H$_2$O peak.

Example 103

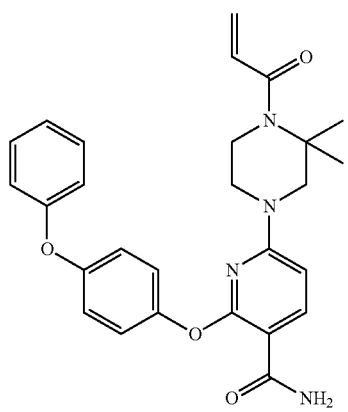 [SMILES: C=CC(=O)N1CCN(c2ccc(C(N)=O)c(Oc3ccc(Oc4ccccc4)cc3)n2)CC1(C)C]

6-(4-Acryloyl-3,3-dimethyl-piperazin-1-yl)-2-(4-phenoxy-phenoxy)-nicotinamide (103)

6-(4-Acryloyl-3,3-dimethyl-piperazin-1-yl)-2-(4-phenoxy-phenoxy)-nicotinamide 26.1 mg (47%) was prepared from 2,6-dichloro nicotinamide, 4-phenoxyphenol, tert-butyl 2,2-dimethylpiperazine-1-carboxylate and acrylic acid with method 4A, 2B, 2C and 2D. HPLC: 99.8%, RT=4.64 min. MS: m/z=473 [M+H]+. $^1$H NMR (400 MHz, DMSO-d6) δ 8.12 (d, J=8.6 Hz, 1H), 7.45-7.31 (m, 3H), 7.29-7.20 (m, 2H), 7.20-7.04 (m, 3H), 7.05-6.89 (m, 2H), 6.70 (dd, J=16.7, 10.5 Hz, 1H), 6.35 (d, J=8.5 Hz, 1H), 6.00 (dd, J=16.7, 2.3 Hz, 1H), 5.60 (dd, J=10.5, 2.3 Hz, 1H), 3.83 (t, J=5.6 Hz, 2H), 3.56 (s, 2H), 3.41 (t, J=5.5 Hz, 2H), 1.27 (s, 6H).

Example 104

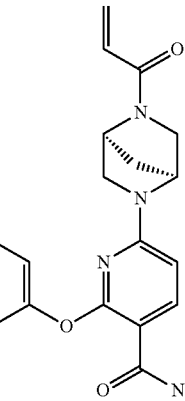

6-((1S,4S)-5-Acryloyl-2,5-diaza-bicyclo[2.2.1]hept-2-yl)-2-[4-(2,4-difluoro-phenoxy)-phenoxy]-nicotinamide (66)

6-((1S,4S)-5-Acryloyl-2,5-diaza-bicyclo[2.2.1]hept-2-yl)-2-[4-(2,4-difluoro-phenoxy)-phenoxy]-nicotinamide 31.8 mg (47%) was prepared from 2,6-dichloro nicotinamide, 4-(2,4-difluorophenoxy)phenol, (1S,4S)-tert-butyl 2,5-diazabicyclo[2.2.1]heptane-2-carboxylate and acrylic acid with method 4A, 2B, 2C and 2D. HPLC: 99.9%, RT=4.38 min. MS: m/z=493 [M+H]+. $^1$H NMR (400 MHz, DMSO-d6) δ 8.06 (d, J=8.4 Hz, 1H), 7.49 (ddd, J=11.5, 8.8, 3.0 Hz, 1H), 7.34 (d, J=8.9 Hz, 2H), 7.24 (ddd, J=14.5, 7.1, 4.1 Hz, 3H), 7.20-7.10 (m, 1H), 7.04 (d, J=8.6 Hz, 2H), 6.54 (m, 2H), 6.17-6.04 (m, 1H), 5.65 (ddd, J=9.7, 6.5, 2.1 Hz, 1H), 4.86 (d, J=47.0 Hz, 1H), 4.52 (d, J=29.7 Hz, 1H), 3.10 (d, J=10.0 Hz, 1H), 1.90 (d, J=30.6 Hz, 2H). Some peaks overlap with solvent peaks.

Example 105

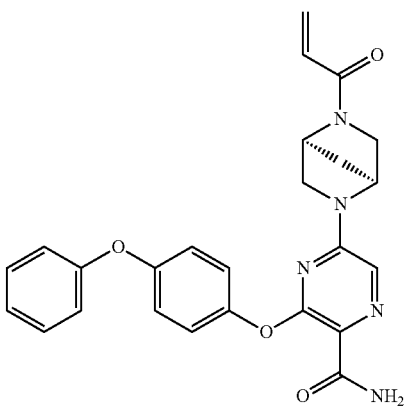 [SMILES: C=CC(=O)N1C[C@@H]2C[C@H]1CN2c1cnc(C(N)=O)c(Oc2ccc(Oc3ccccc3)cc2)n1]

5-((1S,4S)-5-Acryloyl-2,5-diaza-bicyclo[2.2.1]hept-2-yl)-3-(4-phenoxy-phenoxy)-pyrazine-2-carboxylic acid amide (135)

5-((1S,4S)-5-Acryloyl-2,5-diaza-bicyclo[2.2.1]hept-2-yl)-3-(4-phenoxy-phenoxy)-pyrazine-2-carboxylic acid amide 14.6 mg (25%) was prepared from 3,5-dichloropyrazine-2-carboxamide, (1S,4S)-tert-butyl 2,5-diazabicyclo[2.2.1]heptane-2-carboxylate, 4-phenoxyphenol and acrylic acid with method 4A, 2B, 2C and 2D. HPLC: 99.9%, RT=4.33 min. MS: m/z=457 [M+H]+. ¹H NMR (400 MHz, DMSO-d6) δ 7.85-7.70 (m, 1H), 7.64 (d, J=4.4 Hz, 1H), 7.51-7.34 (m, 3H), 7.34-7.24 (m, 2H), 7.22-7.07 (m, 3H), 7.03 (dt, J=7.6, 1.1 Hz, 2H), 6.53 (ddd, J=145.0, 16.7, 10.3 Hz, 1H), 6.11 (ddd, J=16.7, 5.4, 2.4 Hz, 1H), 5.80-5.58 (m, 1H), 4.83 (d, J=46.4 Hz, 1H), 4.50 (d, J=18.7 Hz, 1H), 3.80-3.64 (m, 1H), 3.53 (s, 1H), 2.83 (t, J=11.1 Hz, 1H), 1.89 (d, J=30.2 Hz, 2H).

Example 106

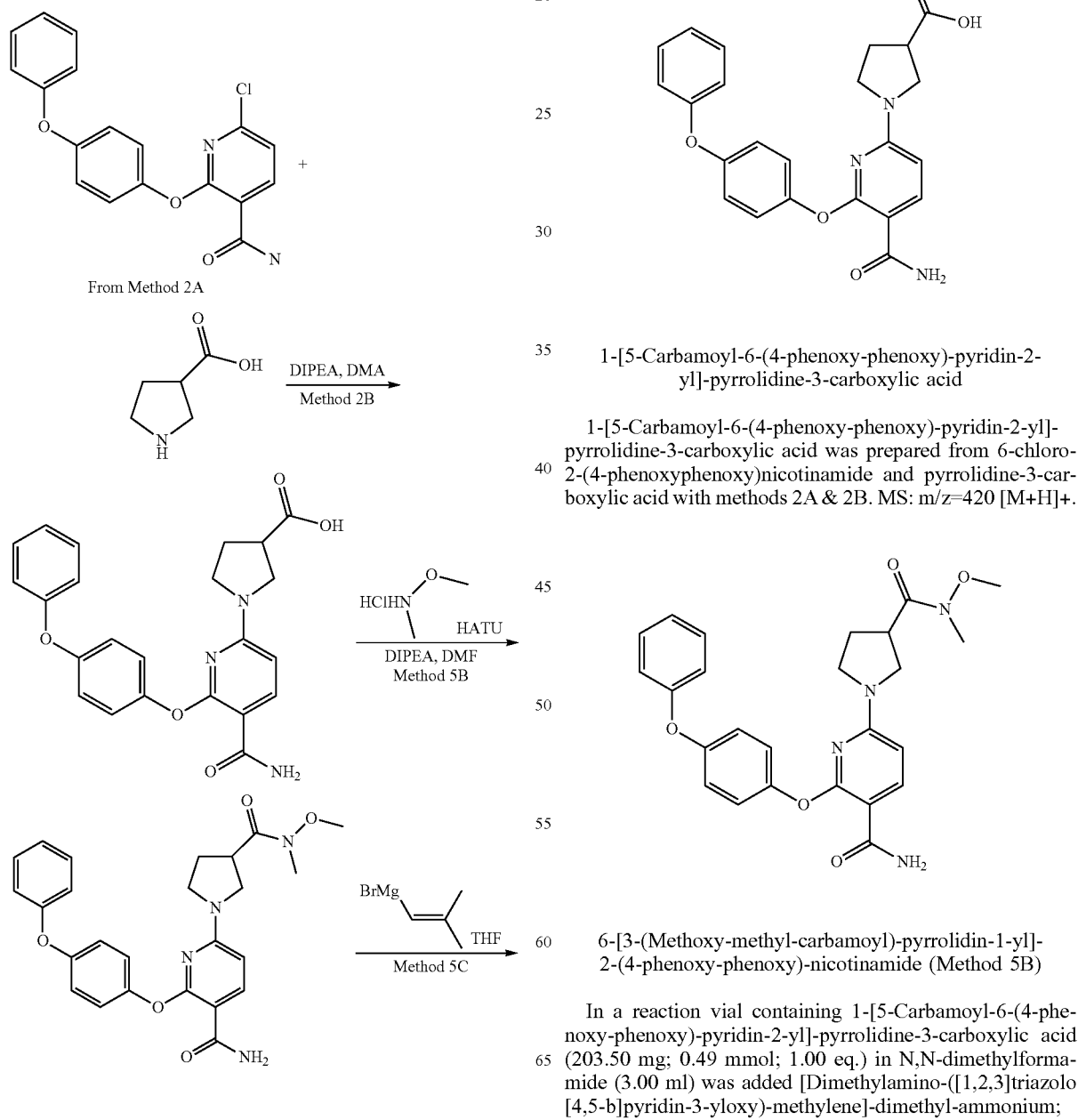

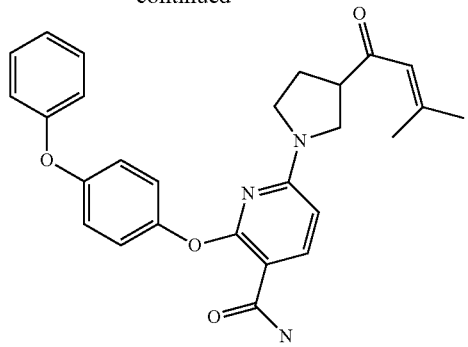

Methods Associated with Reaction Steps in Scheme 5:

1-[5-Carbamoyl-6-(4-phenoxy-phenoxy)-pyridin-2-yl]-pyrrolidine-3-carboxylic acid 1-[5-Carbamoyl-6-(4-phenoxy-phenoxy)-pyridin-2-yl]-pyrrolidine-3-carboxylic acid was prepared from 6-chloro-2-(4-phenoxyphenoxy)nicotinamide and pyrrolidine-3-carboxylic acid with methods 2A & 2B. MS: m/z=420 [M+H]+.

6-[3-(Methoxy-methyl-carbamoyl)-pyrrolidin-1-yl]-2-(4-phenoxy-phenoxy)-nicotinamide (Method 5B)

In a reaction vial containing 1-[5-Carbamoyl-6-(4-phenoxy-phenoxy)-pyridin-2-yl]-pyrrolidine-3-carboxylic acid (203.50 mg; 0.49 mmol; 1.00 eq.) in N,N-dimethylformamide (3.00 ml) was added [Dimethylamino-([1,2,3]triazolo[4,5-b]pyridin-3-yloxy)-methylene]-dimethyl-ammonium;

hexafluoro phosphate (387.41 mg; 1.02 mmol; 2.10 eq.) and Ethyl-diisopropyl-amine (0.30 ml; 1.70 mmol; 3.50 eq.) followed by O,N-Dimethyl-hydroxylamine hydrochloride (66.26 mg; 0.68 mmol; 1.40 eq.). The reaction was stirred at rt overnight before it was concentrated and carried to the next step without further purification. MS: m/z=463 [M+H]+.

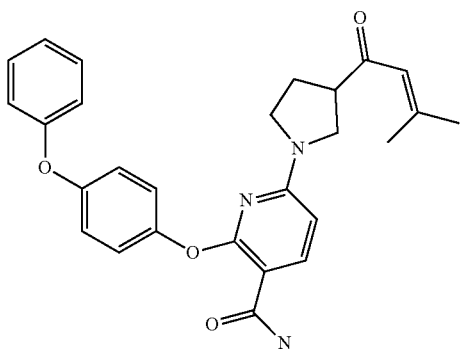 [SMILES: CC(C)=CC(=O)C1CCN(c2ccc(C(N)=O)c(Oc3ccc(Oc4ccccc4)cc3)n2)C1]

6-[3-(3-Methyl-but-2-enoyl)-pyrrolidin-1-yl]-2-(4-phenoxy-phenoxy)-nicotinamide (93) (Method 5C)

To the 100 mL RBF containing 6-[3-(Methoxy-methyl-carbamoyl)-pyrrolidin-1-yl]-2-(4-phenoxy-phenoxy)-nicotinamide (224.40 mg; 0.49 mmol; 1.00 eq.) in tetrahydrofuran (7.00 ml; 86.31 mmol; 177.89 eq.) was added 2-methylprop-1-en-1-yl)magnesium bromide 0.5M in THF (14.00 ml; 6.79 mmol; 14.00 eq.) drop wisely. The reaction was stirred at rt for 15 min before it was concentrated and purified with basic pre-HPLC (CH3CN/H2O). The collected the fractions of the desired product was lyophilized to afford the title product (parent, 5.9 mg, 2.6%) as a white solid. HPLC: 100%, RT=5.21 min. MS: m/z=458 [M+H]+, RT=4.51 min. $^1$H NMR (400 MHz, DMSO-d6) δ 8.08 (dd, J=8.5, 1.0 Hz, 1H), 7.45-7.28 (m, 4H), 7.28-7.20 (m, 2H), 7.15-7.03 (m, 3H), 7.03-6.94 (m, 2H), 6.24 (d, J=8.4 Hz, 2H), 2.17 (dq, J=13.0, 6.5 Hz, 1H), 2.08 (d, J=1.2 Hz, 3H), 2.04-1.83 (m, 4H), 1.65 (s, 1H). Some protons were overlapped with solvent peaks.

Example 107

Scheme 6

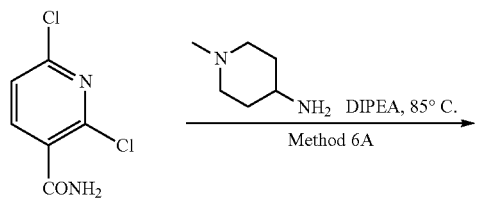

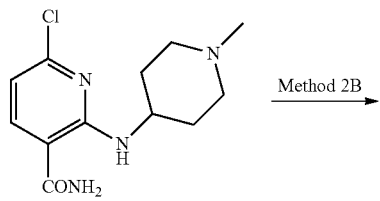

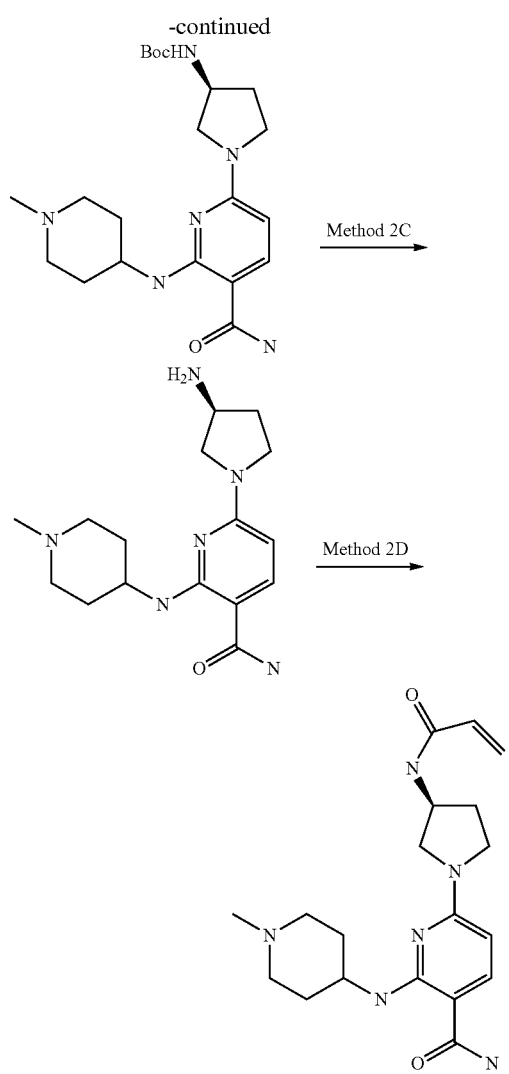

Methods Associated with Reaction Steps in Scheme 6:

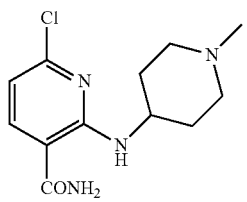 [SMILES: CN1CCC(Nc2nc(Cl)ccc2C(N)=O)CC1]

6-Chloro-2-(1-methyl-piperidin-4-ylamino)-nicotinamide (Method 6A)

In a microwave vial containing 2,6-Dichloro-nicotinamide (200.00 mg; 1.05 mmol; 1.00 eq.) and 1-methyl-piperidin-4-ylamine (179.34 μl; 1.26 mmol; 1.20 eq.) in N,N-dimethyl-acetamide (2.00 ml; 21.76 mmol; 20.79 eq.) was added DIPEA (0.35 ml; 2.09 mmol; 2.00 eq.). The reaction was stirred at 85° C. for 3 h before it was concentrated and carried to the next step. MS: m/z=269 [M+H]+.

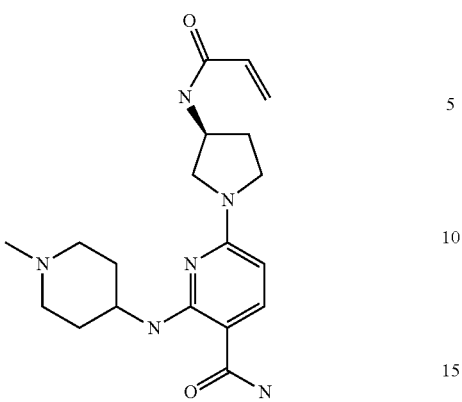

6-((S)-3-Acryloylamino-pyrrolidin-1-yl)-2-(1-methyl-piperidin-4-ylamino)-nicotinamide (62)

6-((S)-3-Acryloylamino-pyrrolidin-1-yl)-2-(1-methyl-piperidin-4-ylamino)-nicotinamide 17.9 mg (34%) was prepared from 2,6-dichloro nicotinamide, 1-methylpiperidin-4-amine, (R)-tert-butyl piperidin-3-ylcarbamate and acrylic acid with methods 6A, 2B, 2C and 2D. HPLC: 99.6%, RT=2.29 min. MS: m/z=373 [M+H]+. $^1$H-NMR (DMSO-D6) δ 8.43 (d, 1H), 7.78 (s, 1H), 6.25 (dd, 1H), 6.16 (d, 1H), 5.39 (d, 1H), 4.47 (m, 1H), 4.01 (m, 1H), 3.14 (m, 2H), 2.75 (m, 3H), 2.15 (m, 3H), 2.03 (s, 1H), 1.94 (m, 1H), 1.61 (m, 2H), 1.25 (m, 1H). Several peaks were overlapped with H$_2$O peak.

Example 108

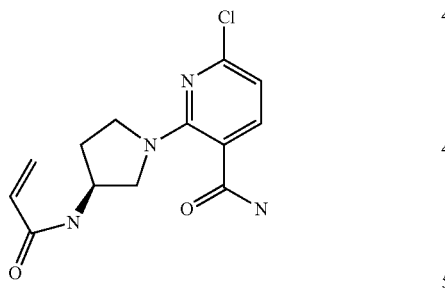

2-((S)-3-Acryloylamino-pyrrolidin-1-yl)-6-chloro-nicotinamide (163)

2-((S)-3-Acryloylamino-pyrrolidin-1-yl)-6-chloro-nicotinamide 5.4 mg (3.8%) was prepared from 2,6-dichloro nicotinamide, (R)-tert-butyl piperidin-3-ylcarbamate and acrylic acid with methods 2B, 2C and 2D. HPLC: 89.9%, RT=2.26 min. MS: m/z=294 [M+H]+. $^1$H NMR (400 MHz, DMSO-d6) δ 8.35 (d, J=6.7 Hz, 1H), 7.85 (s, 1H), 7.55 (d, J=7.7 Hz, 1H), 7.43 (s, 1H), 6.65 (d, J=7.7 Hz, 1H), 6.23 (dd, J=17.1, 10.0 Hz, 1H), 6.11 (dd, J=17.1, 2.4 Hz, 1H), 5.60 (dd, J=10.0, 2.4 Hz, 1H), 4.34 (h, J=6.3 Hz, 1H), 3.27-3.05 (m, 2H), 2.26-2.00 (m, 1H), 1.87 (dq, J=13.0, 6.3 Hz, 1H). Two protons overlap with solvent peak.

Example 109

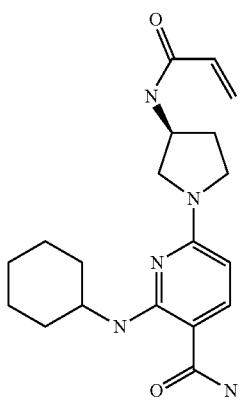 [SMILES: C=CC(=O)N[C@H]1CCN(c2ccc(C(N)=O)c(NC3CCCCC3)n2)C1]

6-((S)-3-Acryloylamino-pyrrolidin-1-yl)-2-cyclohexylamino-nicotinamide (164)

6-((S)-3-Acryloylamino-pyrrolidin-1-yl)-2-cyclohexylamino-nicotinamide 16.6 mg (47%) was prepared from 2,6-dichloro nicotinamide, cyclohexanamine, (R)-tert-butyl piperidin-3-ylcarbamate and acrylic acid with methods 6A, 2B, 2C and 2D. HPLC: 97.6%, RT=2.87 min. MS: m/z=358 [M+H]+. $^1$H-NMR (DMSO-D6) δ 8.92 (d, 1H), 8.39 (d, 1H), 7.75 (d, 1H), 6.23 (dd, 1H), 6.14 (d, 1H), 5.11 (d, 2H), 4.42 (m, 1H), 3.78 (m, 1H), 3.62 (m, 1H), 3.50 (m, 2H), 2.21 (m, 1H), 1.91 (m, 2H), 1.60 (m, 2H), 1.55 (m, 1H), 1.25 (m, 5H).

Example 110

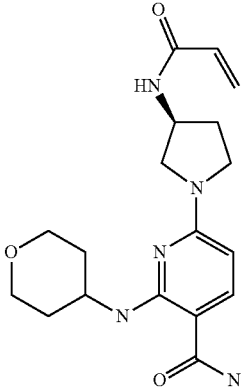 [SMILES: C=CC(=O)N[C@H]1CCN(c2ccc(C(N)=O)c(NC3CCOCC3)n2)C1]

6-((S)-3-Acryloylamino-pyrrolidin-1-yl)-2-(tetrahydro-pyran-4-ylamino)-nicotinamide (165)

6-((S)-3-Acryloylamino-pyrrolidin-1-yl)-2-(tetrahydro-pyran-4-ylamino)-nicotinamide 11.4 mg (9.4%) was prepared from 2,6-dichloro nicotinamide, tetrahydro-2H-pyran-4-amine, (R)-tert-butyl piperidin-3-ylcarbamate and acrylic acid with methods 6A, 2B, 2C and 2D. HPLC: 99.6%, RT=2.67 min. MS: m/z=340 [M+H]+. $^1$H NMR (400 MHz, DMSO-d6) δ 8.37 (d, J=6.9 Hz, 1H), 7.76 (d, J=8.6 Hz, 1H), 6.24 (dd, J=17.1, 10.0 Hz, 1H), 6.11 (dd, J=17.1, 2.4 Hz, 1H), 5.72-5.46 (m, 2H), 4.43 (h, J=5.7 Hz, 1H), 4.13-4.00 (m, 1H), 3.84 (dt, J=11.5, 3.9 Hz, 2H), 3.29 (d, J=11.2 Hz, 1H), 2.17 (dq, J=13.9, 7.4 Hz, 1H), 2.03-1.82 (m, 3H), 1.41 (dtt, J=13.9, 10.2, 3.8 Hz, 2H), 1.35-1.17 (m, 1H).

Example 111

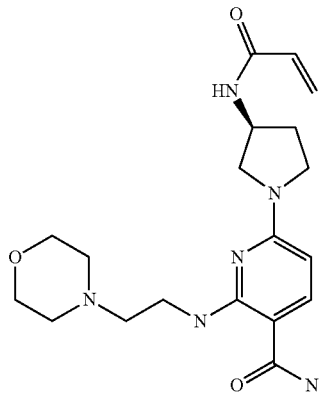 [SMILES: C=CC(=O)N[C@H]1CCN(c2ccc(C(N)=O)c(NCCN3CCOCC3)n2)C1]

6-((S)-3-Acryloylamino-pyrrolidin-1-yl)-2-(2-morpholin-4-yl-ethylamino)-nicotinamide (166)

6-((S)-3-Acryloylamino-pyrrolidin-1-yl)-2-(2-morpholin-4-yl-ethylamino)-nicotinamide 15.3 mg (26%) was prepared from 2,6-dichloro nicotinamide, 2-morpholinoethanamine, (R)-tert-butyl piperidin-3-ylcarbamate and acrylic acid with methods 6A, 2B, 2C and 2D. HPLC: 99.9%, RT=2.38 min. MS: m/z=389 [M+H]+. $^1$H-NMR (DMSO-D6) δ 9.00 (m, 1H), 8.41 (d, 1H), 7.74 d, 1H), 7.10 (m, 1H), 6.25 (dd, 1H), 6.10 (d, 1H), 5.61 (m, 2H), 4.42 (m, 1H), 3.50-3.75 (m, 10H), 2.20 (m, 1H), 1.92 (m, 1H). Some peaks were overlapped with DMSO peak.

Example 112

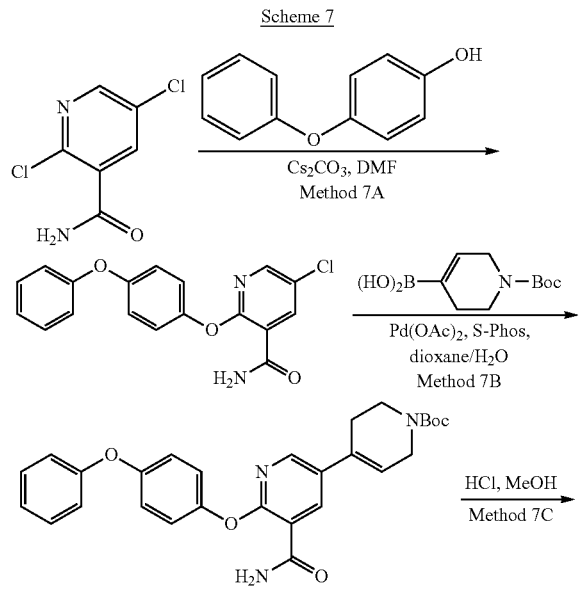

Scheme 7

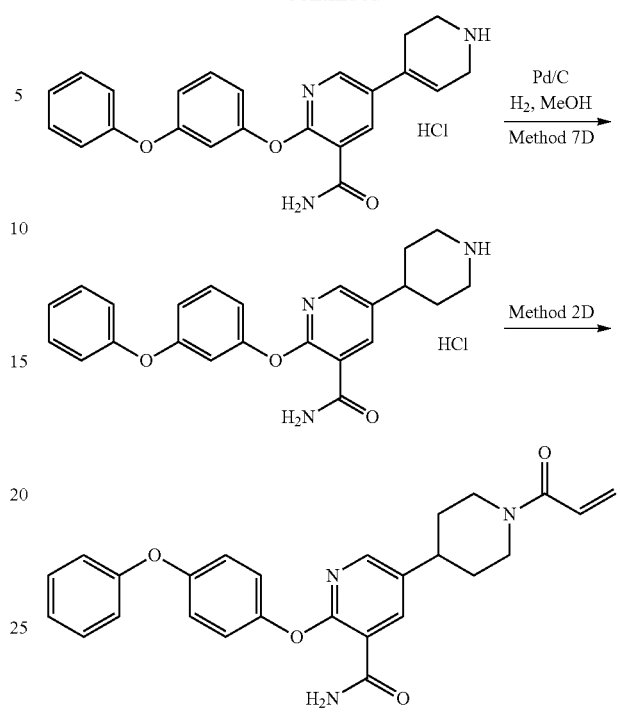

Methods Associated with Reaction Steps in Scheme 7:

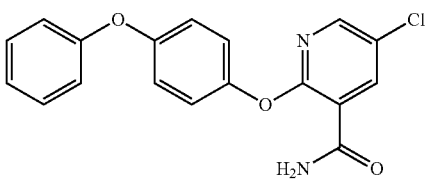 [SMILES: NC(=O)c1cc(Cl)cnc1Oc1ccc(Oc2ccccc2)cc1]

5-Chloro-2-(4-phenoxy-phenoxy)-nicotinamide (Method 7A)

In a microwave vial containing 5-Bromo-2-chloro-nicotinamide (250.00 mg; 1.06 mmol; 1.00 eq.) and 4-Phenoxyphenol (207.59 mg; 1.11 mmol; 1.05 eq.) in DMF (8.00 ml; 103.76 mmol; 97.72 eq.) was added cesium carbonate (761.07 mg; 2.34 mmol; 2.20 eq.). The reaction was stirred at rt for 16 h before it was filtered, concentrated and carried to the next step. MS: m/z=341 [M+H]+.

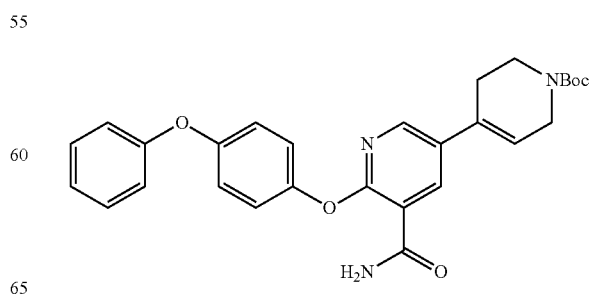

5-Carbamoyl-6-(4-phenoxy-phenoxy)-3',6'-dihydro-2'H-[3,4']bipyridinyl-1'-carboxylic acid tert-butyl ester (Method 7B)

In a microwave vial containing 5-Chloro-2-(4-phenoxy-phenoxy)-nicotinamide (100.00 mg; 0.29 mmol; 1.00 eq.), palladium(ii) acetate (6.59 mg; 0.03 mmol; 0.10 eq.), 2-dicyclohexylphosphino-2',6'-dimethoxybiphenyl (24.10 mg; 0.06 mmol; 0.20 eq.), N-Boc-1,2,3,6-tetrahydropyridine-4-boronic acid pinacol ester (108.89 mg; 0.35 mmol; 1.20 eq.) and cesium carbonate (210.36 mg; 0.65 mmol; 2.20 eq.) was added dioxane (4.00 ml; 70.42 mmol; 239.95 eq.) and water (0.40 ml; 33.31 mmol; 113.49 eq.). The reaction was stirred for 2 h at 120° C. before it was filtered, concentrated and carried to the next step. MS: m/z=488 [M+H]+.

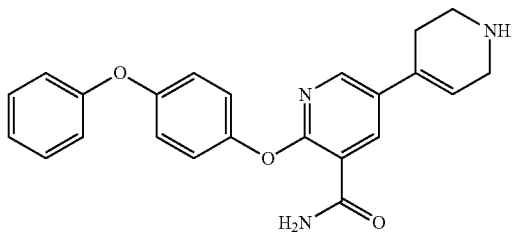 [SMILES: NC(=O)c1cc(C2=CCNCC2)cnc1Oc1ccc(Oc2ccccc2)cc1]

6-(4-phenoxyphenoxy)-1',2',3',6'-tetrahydro-[3,4'-bipyridine]-5-carboxamide (Method 7C)

In a 10 mL microwave vial containing 5-Carbamoyl-6-(4-phenoxy-phenoxy)-3',6'-dihydro-2'H-[3,4']bipyridinyl-1'-carboxylic acid tert-butyl ester (141.39 mg; 0.29 mmol; 1.00 eq.) in methanol (5.00 ml; 123.43 mmol; 425.63 eq.) was added hydrogen chloride (1.00 ml; 2.90 mmol; 10.00 eq.). The mixture was stirred at rt for 2 h before it was concentrated and dried. MS: m/z=388 [M+H]+.

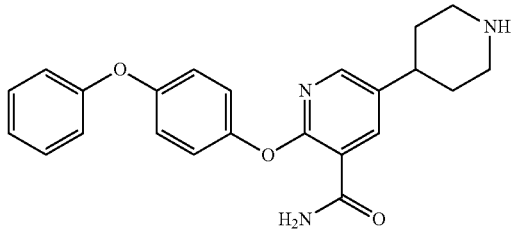 [SMILES: NC(=O)c1cc(C2CCNCC2)cnc1Oc1ccc(Oc2ccccc2)cc1]

2-(3-phenoxyphenoxy)-5-(piperidin-4-yl)nicotinamide (Method 7D)

To a round-bottom flask containing the residue from the last step was added methanol (10 mL). The solution was hydrogenated via an H-cube (50° C., Full $H_2$, 1.6 ml/min). The obtained product was concentrated and carried to the next step. MS: m/z=390 [M+H]+. MS: m/z=390[M+H]+.

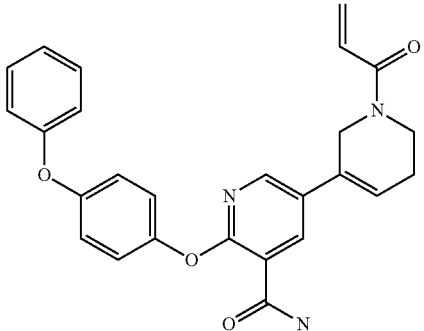 [SMILES: C=CC(=O)N1CCC=C(c2cnc(Oc3ccc(Oc4ccccc4)cc3)c(C(N)=O)c2)C1]

1'-Acryloyl-6-(4-phenoxy-phenoxy)-1',2',5',6'-tetrahydro-[3,3']bipyridinyl-5-carboxylic acid amide (123)

1'-Acryloyl-6-(4-phenoxy-phenoxy)-1',2',5',6'-tetrahydro-[3,3']bipyridinyl-5-carboxylic acid amide 33.7 mg (49%) was prepared from 5-Bromo-2-chloro-nicotinamide, 4-Phenoxy-phenol, 5-(4,4,5,5-Tetramethyl-[1,3,2]dioxaborolan-2-yl)-3,4-dihydro-2H-pyridine-1-carboxylic acid tert-butyl ester and acrylic acid with methods 7A, 7B, 7C, 7D and 2D. HPLC: 97.3%, RT=4.56 min. MS: m/z=442 [M+H]+. $^1$H NMR (400 MHz, DMSO-d6) δ 8.33 (d, J=13.4 Hz, 1H), 8.20 (d, J=23.7 Hz, 1H), 7.84 (d, J=15.8 Hz, 2H), 7.42 (t, J=7.6 Hz, 2H), 7.23 (d, J=8.2 Hz, 2H), 7.16 (t, J=7.4 Hz, 1H), 7.06 (dd, J=11.4, 8.3 Hz, 4H), 6.39 (d, J=14.3 Hz, 1H), 6.25-6.05 (m, 1H), 5.72 (t, J=9.2 Hz, 1H), 4.58-4.28 (m, 2H), 3.69 (dt, J=17.4, 5.8 Hz, 2H), 2.31 (d, J=22.0 Hz, 2H).

Example 113

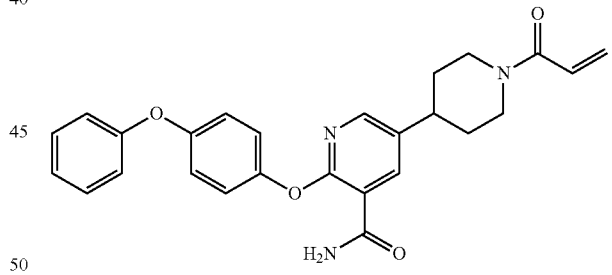

1'-Acryloyl-6-(4-phenoxy-phenoxy)-1',2',3',4',5',6'-hexahydro-[3,4']bipyridinyl-5-carboxylic acid amide (127)

1'-Acryloyl-6-(4-phenoxy-phenoxy)-1',2',3',4',5',6'-hexahydro-[3,4']bipyridinyl-5-carboxylic acid amide 11.6 mg (15%) was prepared from 5-Bromo-2-chloro-nicotinamide, 4-Phenoxy-phenol, N-Boc-1,2,3,6-tetrahydropyridine-4-boronic acid pinacol ester and acrylic acid with methods 7A, 7B, 7C, 7D and 2D. HPLC: 97.0%, RT=4.34 min. MS: m/z=444 [M+H]+. $^1$H-NMR (DMSO-D6) δ 8.14 (s, 1H), 8.03 (s, 1H), 7.74 (d, 2H), 7.43 (m, 2H), 7.0-7.24 (m, 7H), 6.81 (dd, 1H), 6.14 (d, 1H), 5.70 (d, 1H), 4.59 (d, 1H), 4.20 (d, 1H), 3.17 (m, 1H), 2.81 (m, 1H), 2.70 (m, 1H), 1.75 (m, 2H), 1.50 (m, 2H).

Example 114

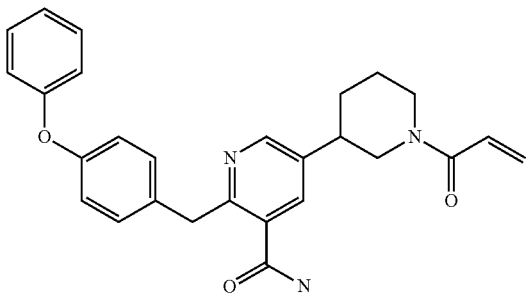 [SMILES: C=CC(=O)N1CCCC(c2cnc(Cc3ccc(Oc4ccccc4)cc3)c(C(N)=O)c2)C1]

1'-Acryloyl-6-(4-phenoxy-phenoxy)-1',2',3',4',5',6'-hexahydro-[3,3']bipyridinyl-5-carboxylic acid amide (126)

1'-Acryloyl-6-(4-phenoxy-phenoxy)-1',2',3',4',5',6'-hexahydro-[3,4']bipyridinyl-5-carboxylic acid amide 16.8 mg (28%) was prepared from 5-Bromo-2-chloro-nicotinamide, 4-Phenoxy-phenol, 5-(4,4,5,5-Tetramethyl-[1,3,2]dioxaborolan-2-yl)-3,4-dihydro-2H-pyridine-1-carboxylic acid tert-butyl ester and acrylic acid with methods 7A, 7B, 7C, 7D and 2D. HPLC: 94.8%, RT=4.34 min. MS: m/z=444 [M+H]+. $^1$H-NMR (DMSO-D6) δ 8.25 (m, 2H), 7.74 (d, 2H), 7.42 (m, 2H), 7.0-7.24 (m, 7H), 6.82 (dd, 1H), 6.14 (m, 1H), 5.62 (d, 1H), 4.48 (m, 1H), 4.08 (m, 1H), 3.17 (m, 1H), 2.75 (m, 1H), 1.83 (m, 1H), 1.75 (m, 2H), 1.50 (m, 2H).

Example 115

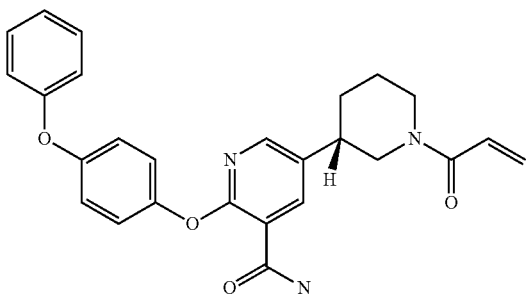 [SMILES: C=CC(=O)N1CCC[C@@H](c2cnc(Oc3ccc(Oc4ccccc4)cc3)c(C(N)=O)c2)C1]

(S)-5-(1-acryloylpiperidin-3-yl)-2-(4-phenoxyphenoxy)nicotinamide (125)

The title compound was isolated from mixture of 1'-Acryloyl-6-(4-phenoxy-phenoxy)-1',2',3',4',5',6'-hexahydro-[3,4']bipyridinyl-5-carboxylic acid amide via Supercritical Fluid Chromatography (SFC) using a ChiralPak AS-H column (20×250 mm) and 28% Ethanol+0.5% DMEA in CO$_2$ as the mobile phase.

Example 116

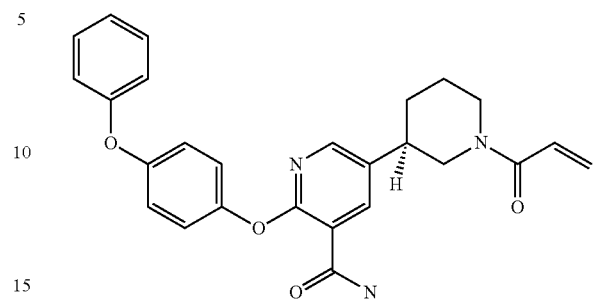

(R)-5-(1-acryloylpiperidin-3-yl)-2-(4-phenoxyphenoxy)nicotinamide (124)

The title compound was isolated from mixture of 1'-Acryloyl-6-(4-phenoxy-phenoxy)-1',2',3',4',5',6'-hexahydro-[3,4']bipyridinyl-5-carboxylic acid amide via Supercritical Fluid Chromatography (SFC) using a ChiralPak AS-H column (20×250 mm) and 28% Ethanol+0.5% DMEA in CO$_2$ as the mobile phase.

Example 117

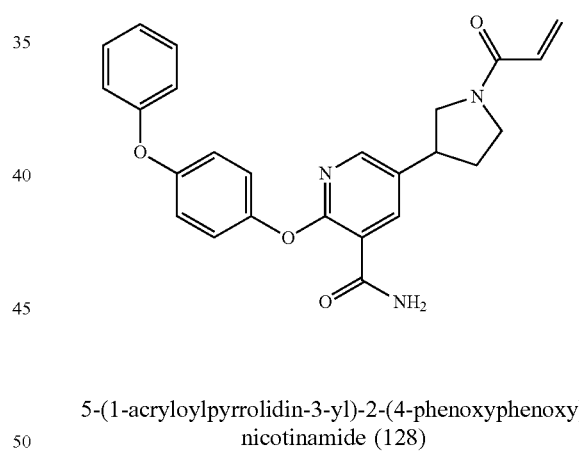

5-(1-acryloylpyrrolidin-3-yl)-2-(4-phenoxyphenoxy)nicotinamide (128)

5-(1-Acryloyl-pyrrolidin-3-yl)-2-(4-phenoxy-phenoxy)-nicotinamide (0.10 g; 0.23 mmol; 46.0%; white solid) was prepared from 5-Bromo-2-chloro-nicotinamide, 4-Phenoxy-phenol, tert-butyl 4-(4,4,5,5-tetramethyl-1,3,2-dioxaborolan-2-yl)-2,3-dihydro-1H-pyrrole-1-carboxylate, and acrylic acid with methods 7A, 7B, 7C, 7D and 2D. HPLC: 96.6%, RT=4.34 min. MS: m/z=430.2 [M+H]+. 1HNMR (400 MHz, DMSO-d6) ? 8.15-8.14 (t, J=3.1 Hz, 1H), 8.10-8.07 (dd, J=2.5, 10.6 Hz, 1H), 7.80-7.78 (d, J=8.7 Hz, 2H), 7.42-7.38 (m, 2H), 7.20-7.18 (m, 2H), 7.15-7.11 (m, 1H), 7.06-7.01 (m, 4H), 6.60-6.56 (m, 1H), 6.17-6.12 (m, 1H), 5.69-5.64 (m, 1H), 3.93-3.88 (m, 1H), 3.65-3.64 (t, J=3.6 Hz, 0.5H), 3.62-3.57 (m, 1H), 3.50-3.47 (m, 1H), 3.39-3.32 (m, 1H), 3.27-3.24 (m, 0.5H), 2.33-2.22 (m, 1H), 2.08-1.95 (m, 1H).

Example 118

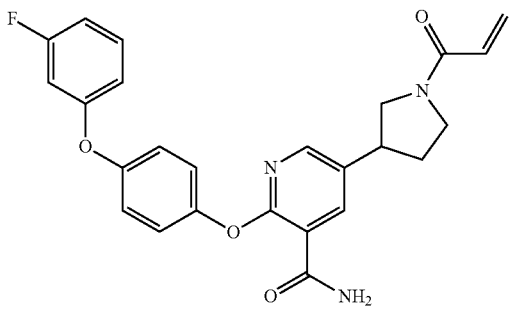 [SMILES: C=CC(=O)N1CCC(c2cnc(Oc3ccc(Oc4cccc(F)c4)cc3)c(C(N)=O)c2)C1]

5-(1-acryloylpyrrolidin-3-yl)-2-(4-(3-fluorophenoxy)phenoxy)nicotinamide (129)

5-(1-Acryloyl-pyrrolidin-3-yl)-2-[4-(3-fluoro-phenoxy)-phenoxy]-nicotinamide (100.00 mg; 42.1%) was prepared from 5-Bromo-2-chloro-nicotinamide, 4-Phenoxy-phenol, tert-butyl 4-(4,4,5,5-tetramethyl-1,3,2-dioxaborolan-2-yl)-2,3-dihydro-1H-pyrrole-1-carboxylate, and acrylic acid with methods 7A, 7B, 7C, 7D and 2D. HPLC: 95.6%. MS: m/z=448.2 [M+H]+. 1HNMR (400 MHz, DMSO-d6): ? 8.16-8.15 (t, J=3.1 Hz, 1H), 8.11-8.07 (d, J=2.4 Hz, 1H), 7.81-7.79 (d, J=10.3 Hz, 2H), 7.42-7.39 (t, J=7.0 Hz, 1H), 7.23-7.21 (t, J=8.1 Hz, 2H), 7.13-7.11 (t, J=6.9 Hz, 2H), 6.98-6.95 (t, J=6.1 Hz, 1H), 6.89-6.82 (m, 2H), 6.61-6.57 (m, 1H), 6.17-6.12 (m, 1H), 5.70-5.64 (m, 1H), 3.94-3.89 (m, 1H), 3.82-3.42 (m, 4H), 2.32-2.21 (m, 1H), 2.08-1.96 (m, 1H).

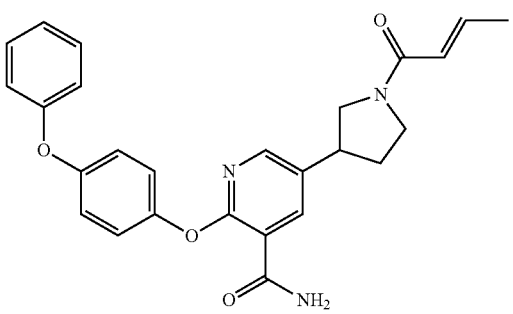 [SMILES: C/C=C/C(=O)N1CCC(c2cnc(Oc3ccc(Oc4ccccc4)cc3)c(C(N)=O)c2)C1]

(E)-5-(1-(but-2-enoyl)pyrrolidin-3-yl)-2-(4-phenoxyphenoxy)nicotinamide (130)

To a stirred solution of 2-(4-Phenoxy-phenoxy)-5-pyrrolidin-3-yl-nicotinamide (200.00 mg; 0.46 mmol; 1.00 eq.) (synthesized according to methods 7A, 7B, 7C, and 7D) in DCM (4.00 ml; 20.00 V) was added (E)-But-2-enoyl chloride (57.72 mg; 0.55 mmol; 1.20 eq.) dropwise at then stirred for 15 min at −10° C. N,N-diisopropylethylamine (0.24 ml; 1.37 mmol; 3.00 eq.) was then added dropwise. The mixture was then stirred at for 30 min at −10° C. The reaction was quenched with water (50 mL) and extracted with DCM (3×30 mL). The combined organic layer was washed with brine (1×20 mL), dried over sodium sulphate, and then concentrated to dryness. Crude reaction was then purified by column chromatography over silica using DCM:MeOH (9.5:0.5) as an eluent to afford 5-[1-((E)-But-2-enoyl)-pyrrolidin-3-yl]-2-(4-phenoxy-phenoxy)-nicotinamide (100.00 mg; 46.6%). HPLC-UV: 95% purity. LC/MS m/z=444 [M+H]+. 1HNMR (400 MHz, DMSO-d6) 8.15-8.13 (dd, J=5.6, 2.5 Hz, 1H), 8.10-8.06 (dd, J=12.1, 2.5 Hz, 1H), 7.80-7.77 (t, J=7.6 Hz, 2H), 7.42-7.37 (m, 2H), 7.20-7.12 (m, 3H), 7.07-7.01 (m, 4H), 6.72-6.65 (m, 1H), 6.31-6.27 (m, 1H), 4.02-3.86 (m, 1H), 3.63-3.44 (m, 3H), 3.27-3.22 (m, 1H), 2.32-2.21 (m, 1H), 1.97-1.93 (m, 1H), 1.85-1.81 (m, 3H).

Example 120

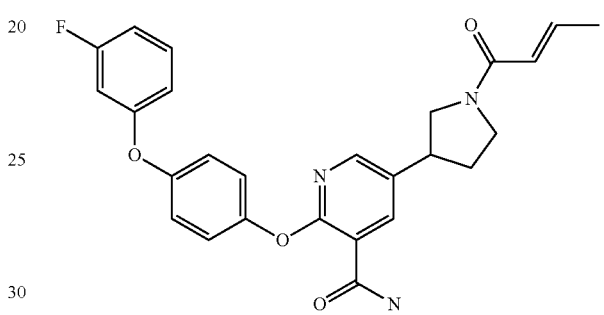

5-[1-((E)-But-2-enoyl)-pyrrolidin-3-yl]-2-[4-(3-fluoro-phenoxy)-phenoxy]-nicotinamide (167)

To a stirred solution of 2-[4-(3-Fluoro-phenoxy)-phenoxy]-5-pyrrolidin-3-yl-nicotinamide (200.00 mg; 0.51 mmol; 1.00 eq.) (synthesized according to methods with method F, G, HA, HB) in dry DCM (4.00 ml; 20.00 V) was added (E)-But-2-enoyl chloride (63.77 mg; 0.61 mmol; 1.20 eq.) dropwise at then stirred for 15 min at −10° C. N,N-diisopropylethylamine (0.27 ml; 1.53 mmol; 3.00 eq.) was then added dropwise. The mixture was then stirred at for 30 min at −10° C. After completion of the reaction by TLC, the reaction mixture was quenched with water (50 mL) and extracted with DCM (3×30 mL). The combined organic layer was washed with brine (1×20 mL), dried over sodium sulphate and concentrated under vaccum. The crude was purified by column chromatograpy using DCM:MeOH (9.5:0.5) as an eluent to afford 5-[1-((E)-But-2-enoyl)-pyrrolidin-3-yl]-2-[4-(3-fluoro-phenoxy)-phenoxy]-nicotinamide (50.00 mg; 20.6%) HPLC-UV: 95% purity. LC/MS m/z=444 [M+H]+. 1H NMR (400 MHz, DMSO-d6) 8.16-8.13 (dd, J=8.0, 2.5 Hz, 1H), 8.10-8.06 (dd, J=12.0, 2.4 Hz, 1H), 7.82-7.78 (m, 2H), 7.43-7.41 (m, 1H), 7.23-7.21 (d, J=8.9 Hz, 2H), 7.13-7.10 (dd, J=8.9, 1.1 Hz, 2H), 6.97-6.96 (d, J=2.2 Hz, 1H), 6.89-6.82 (m, 2H), 6.69-6.63 (m, 1H), 6.31-6.27 (m, 1H), 4.03-3.87 (m, 1H), 3.74-3.55 (m, 3H), 3.48-3.33 (m, 1H), 2.32-2.20 (m, 1H), 2.07-1.93 (m, 1H), 1.85-1.80 (m, 3H).

281

Example 121

Scheme 8

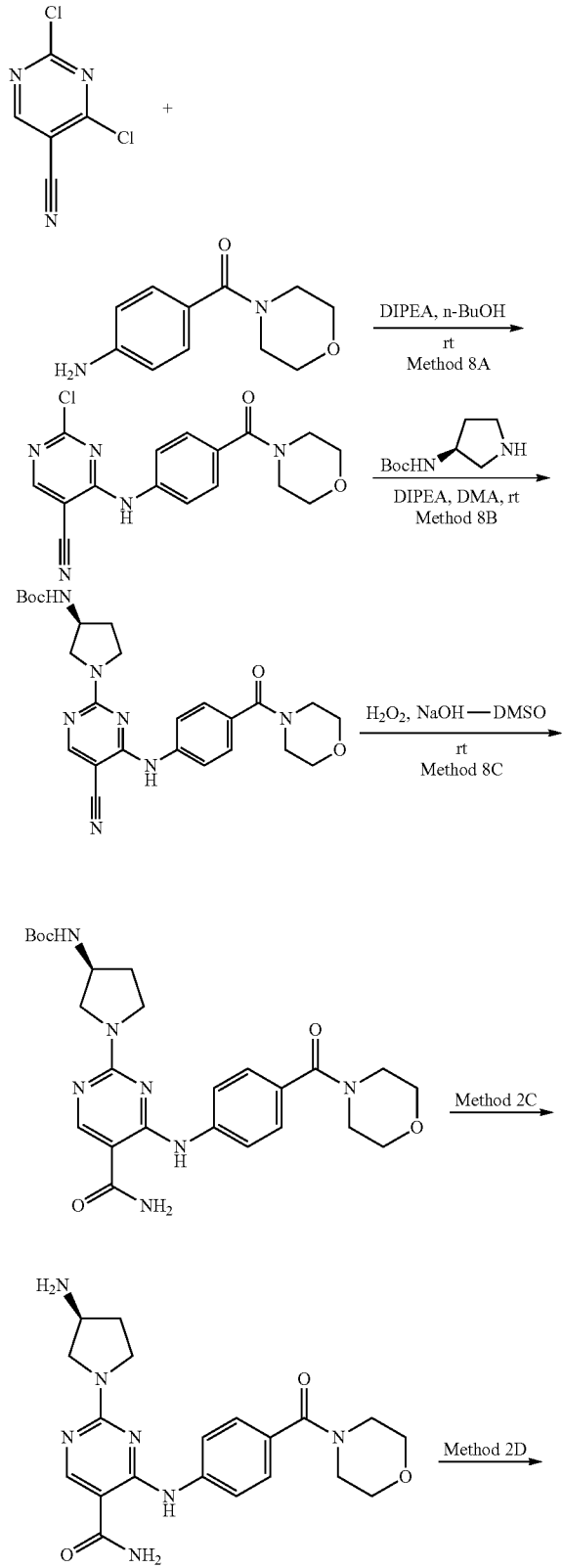

Methods Associated with Reaction Steps in Scheme 8:

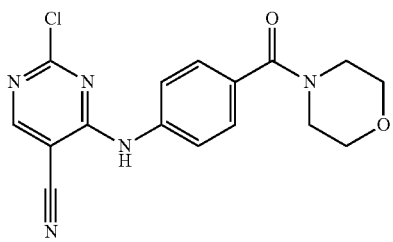 [SMILES: N#Cc1cnc(Cl)nc1Nc1ccc(C(=O)N2CCOCC2)cc1]

2-Chloro-4-[4-(morphine-4-carbonyl)-phenylamino]-pyrimidine-5-carbonitrile (Method 8A)

In a microwave vial containing 2,4-dichloro-pyrimidine-5-carbonitrile (250.00 mg; 1.44 mmol; 1.00 eq.) in butan-1-ol (10.00 ml; 110.09 mmol; 76.62 eq.) at 0° C. was added DIPEA (0.71 ml; 4.31 mmol; 3.00 eq.) and (4-Amino-phenyl)-morpholin-4-yl-methanone (296.35 mg; 1.44 mmol; 1.00 eq.). The mixture was stirred at rt for 1 h before it was concentrated and carried to the next step. MS: m/z=344 [M+H]+.

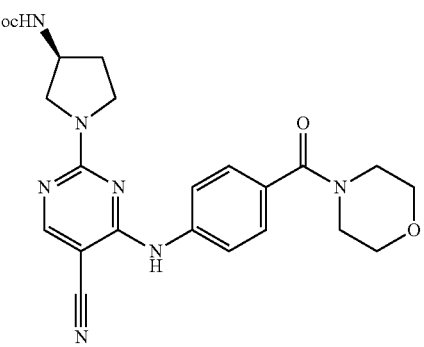

{(S)-1-[4-(4-tert-Butylcarbamoyl-phenylamino)-5-cyano-pyrimidin-2-yl]-pyrrolidin-3-yl}-carbamic acid tert-butyl ester (Method 8B)

In a microwave vial containing N-tert-butyl-4-(2-chloro-5-cyano-pyrimidin-4-ylamino)-benzamide (379.25 mg; 1.15 mmol; 1.00 eq.) and (S)-pyrrolidin-3-yl-carbamic acid tert-butyl ester (214.19 mg; 1.15 mmol; 1.00 eq.) in N,N-dimethyl-acetamide (4.00 ml) was added DIPEA (0.57 ml; 3.45 mmol; 3.00 eq.). The mixture was stirred at rt for 0.5 h before it was concentrated, dried and carried to the next step. MS: m/z=510 [M+H]+.

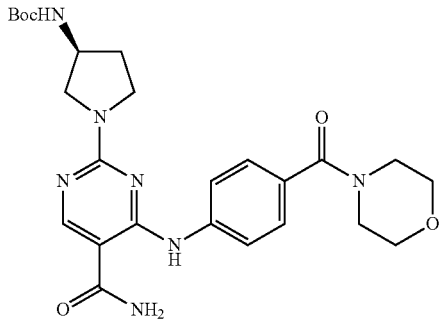 [SMILES: CC(C)(C)OC(=O)N[C@H]1CCN(c2ncc(C(N)=O)c(Nc3ccc(C(=O)N4CCOCC4)cc3)n2)C1]

{(S)-1-[4-(4-tert-Butylcarbamoyl-phenylamino)-5-carbamoyl-pyrimidin-2-yl]-pyrrolidin-3-yl}-carbamic acid tert-butyl ester (Method 8C)

In a 25 mL round bottom flask containing {(S)-1-[4-(4-tert-Butylcarbamoyl-phenylamino)-5-cyano-pyrimidin-2-yl]-pyrrolidin-3-yl}-carbamic acid tert-butyl ester (551.51 mg; 1.15 mmol; 1.00 eq.), 2.0M NaOH aq. (11.50 ml; 23.00 mmol; 20.00 eq.) and DMSO (5.70 ml) was slowly added $H_2O_2$ (2.24 ml; 23.00 mmol; 20.00 eq.). The reaction was stirred at rt for 16 h before it was filtered. The liquid was extracted with EtOAc (5 mL×3). The combined organic layers were combined, concentrated, dried and carried to the next step. MS: m/z=528 [M+H]+.

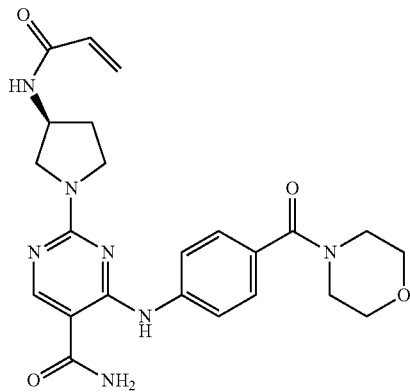 [SMILES: C=CC(=O)N[C@H]1CCN(c2ncc(C(N)=O)c(Nc3ccc(C(=O)N4CCOCC4)cc3)n2)C1]

2-((S)-3-Acryloylamino-pyrrolidin-1-yl)-4-[4-(morpholine-4-carbonyl)-phenylamino]-pyrimidine-5-carboxylic acid amide (140)

2-((S)-3-Acryloylamino-pyrrolidin-1-yl)-4-[4-(morpholine-4-carbonyl)-phenylamino]-pyrimidine-5-carboxylic acid amide 13.7 mg (49%) was prepared from 2,4-dichloropyrimidine-5-carbonitrile, (4-aminophenyl)(morpholino)methanone, (S)-pyrrolidin-3-yl-carbamic acid tert-butyl ester and acrylic acid with methods 8A, 8B, 8C, 2C and 2D. HPLC: 91.6%, RT=2.22 min. MS: m/z=466 [M+H]+. $^1$H-NMR (DMSO-D6) δ 11.79 (s, 1H), 8.75 (s, 1H), 8.44 (m, 1H), 8.0 (m, 3H), 7.47 (m, 3H), 6.25 (dd, 1H), 6.14 (d, 1H), 5.59 (d, 1H), 4.50 (m, 1H), 3.51-3.75 (m, 12H), 2.24 (m, 1H), 2.00 (m, 1H).

Example 122

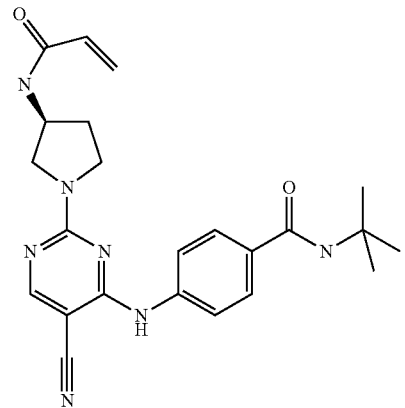 [SMILES: C=CC(=O)N[C@H]1CCN(c2ncc(C#N)c(Nc3ccc(C(=O)NC(C)(C)C)cc3)n2)C1]

4-[2-((S)-3-Acryloylamino-pyrrolidin-1-yl)-5-cyano-pyrimidin-4-ylamino]-N-tert-butyl-benzamide 4-[2-((S)-3-Acryloylamino-pyrrolidin-1-yl)-5-cyano-pyrimidin-4-ylamino]-N-tert-butyl-benzamide 7.9 mg (6.6%) was prepared from 2,4-dichloropyrimidine-5-carbonitrile, 4-amino-N-(tert-butyl) benzamide, (S)-pyrrolidin-3-yl-carbamic acid tert-butyl ester and acrylic acid with methods 8A, 8B, 8C, 2C and 2D. HPLC: 98.6%, RT=3.38 min. MS: m/z=434 [M+H]+. $^1$H-NMR (DMSO-D6) δ 10.02 (s, 1H), 8.46 (m, 2H), 7.79 (m, 4H), 7.57 (s, 1H), 6.15 (dd, 1H), 6.12 (d, 1H), 5.57 (d, 1H), 4.50 (s, 1H), 2.25 (m, 1H), 2.00 (m, 1H), 1.31 (s, 9H). Four protons overlapped with solvent peak.

Example 123

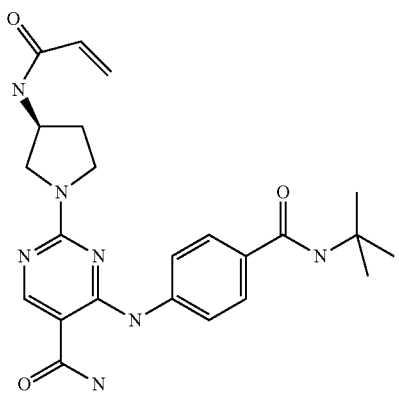 [SMILES: C=CC(=O)N[C@H]1CCN(c2ncc(C(N)=O)c(Nc3ccc(C(=O)NC(C)(C)C)cc3)n2)C1]

(S)-2-(3-acrylamidopyrrolidin-1-yl)-4-((4-(tert-butylcarbamoyl)phenyl)amino)pyrimidine-5-carboxamide (139)

(S)-2-(3-acrylamidopyrrolidin-1-yl)-4-((4-(tert-butylcarbamoyl)phenyl)amino)pyrimidine-5-carboxamide 23.7 mg (45%) was prepared from 2,4-dichloropyrimidine-5-carbonitrile, 4-amino-N-(tert-butyl) benzamide, (S)-pyrrolidin-3-yl-carbamic acid tert-butyl ester and acrylic acid with methods 8A, 8B, 8C, 2C and 2D. HPLC: 97.8%, RT=3.0 min. MS: m/z=452 [M+H]+. HPLC: 91.6%, RT=2.22 min. MS: m/z=466 [M+H]+. ¹H-NMR (DMSO-D6) δ 12.01 (d, 1H), 8.71 (d, 1H), 8.48 (d, 1H), 8.22 (bs, 1H), 7.50-7.75 (m, 5H), 6.15 (dd, 1H), 6.12 (d, 1H), 5.57 (d, 1H), 4.50 (s, 1H), 2.25 (m, 1H), 2.01 (m, 1H), 1.37 (s, 9H). Four protons overlapped with solvent peak.

Example 124

Scheme 9

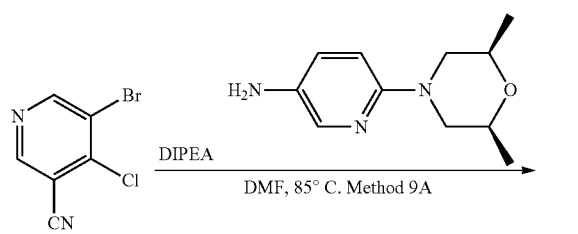

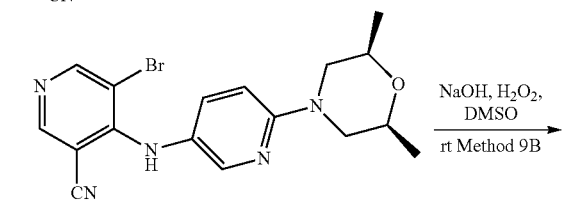

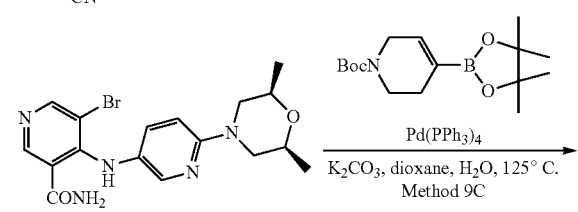

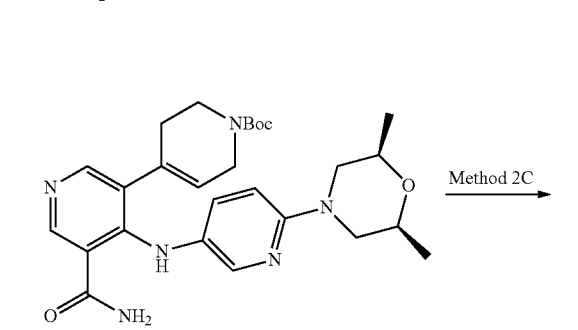

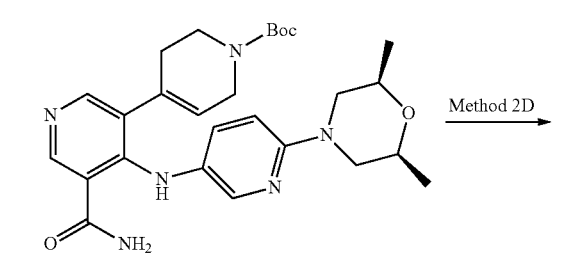

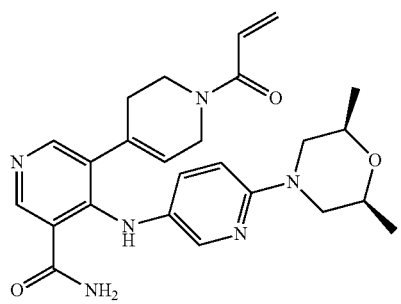

Methods Associated With Reaction Steps in Scheme 9

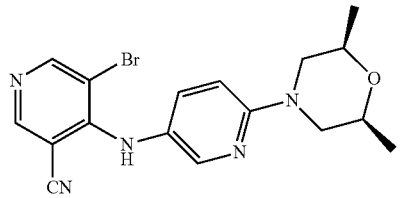 [SMILES: C[C@@H]1CN(c2ccc(Nc3c(Br)cncc3C#N)cn2)C[C@H](C)O1]

5-Bromo-4-[6-(cis-2,6-dimethyl-morpholin-4-yl)-pyridin-3-ylamino]-nicotinonitrile (Method 9A)

In a 5 mL microwave vial containing 5-Bromo-4-chloro-nicotinonitrile (50.00 mg; 0.23 mmol; 1.00 eq.) and 6-cis-2,6-Dimethyl-morpholin-4-yl)-pyridin-3-ylamine (52.43 mg; 0.25 mmol; 1.10 eq.) in DMF (1.00 ml; 38.91 mmol; 169.21 eq.) was added DIPEA (0.11 ml; 0.69 mmol; 3.00 eq.). The reaction was stirred at 85° C. for 16 h before it was concentrated and carried to the next step. MS: m/z=389 [M+H]+.

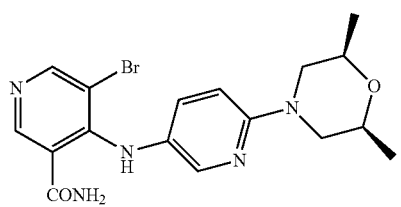 [SMILES: C[C@@H]1CN(c2ccc(Nc3c(Br)cncc3C(N)=O)cn2)C[C@H](C)O1]

5-Bromo-4-[6-(cis-2,6-dimethyl-morpholin-4-yl)-pyridin-3-ylamino]-nicotinamide (Method In a 25 mL round bottom flask containing 5-Bromo-4-[6-(cis-2,6-dimethyl-morpholin-4-yl)-pyridin-3-ylamino]-nicotinonitrile (89.30 mg; 0.23 mmol; 1.00 eq.), 2.0N NaOH aq (2.30 ml; 4.60 mmol; 20.00 eq.) and DMSO (0.50 ml) was slowly added H₂O₂ (0.67 ml; 6.90 mmol; 30.00 eq.). After 4 h, the reaction was completed. The reaction mixture was extracted with EtOAc (5 mL×3). The combined organic layers were concentrated and carried to the next step. MS: m/z=406 [M+H]+.

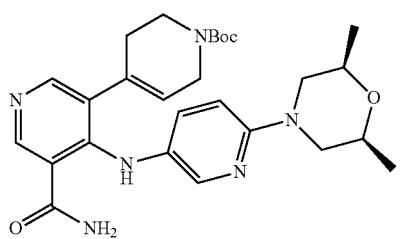 [SMILES: C[C@@H]1CN(c2ccc(Nc3c(C(N)=O)cncc3C3=CCN(C(=O)OC(C)(C)C)CC3)cn2)C[C@H](C)O1]

5-Carbamoyl-4-[6-(cis-2,6-dimethyl-morpholin-4-yl)-pyridin-3-ylamino]-3',6'-dihydro-2'H-[3,4']bipyridinyl-1'-carboxylic acid tert-butyl ester (Method C)

In a microwave vial containing 5-Bromo-4-[6-(cis-2,6-dimethyl-morpholin-4-yl)-pyridin-3-ylamino]-nicotinamide (93.44 mg; 0.23 mmol; 1.00 eq.), N-Boc-1,2,3,6-tetrahydropyridine-4-boronic acid pinacol ester and tetrakis(triphenylphosphine)palladium(0) was added dioxane (3.00 ml; 35.21 mmol; 153.08 eq.) and water (0.75 ml; 41.63 mmol; 181.01 eq.). The reaction was stirred for 1 h at 115° C. before it was concentrated and carried to the next step. MS: m/z=509 [M+H]+.

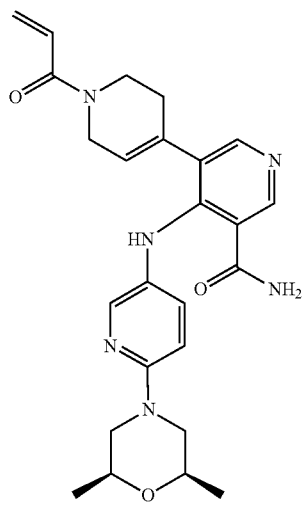 [SMILES: C=CC(=O)N1CC=C(c2cncc(C(N)=O)c2Nc2ccc(N3C[C@@H](C)O[C@@H](C)C3)nc2)CC1]

1'-Acryloyl-4-[6-(cis-2,6-dimethyl-morpholin-4-yl)-pyridin-3-ylamino]-1',2',3',6'-tetrahydro-[3,4']bipyridinyl-5-carboxylic acid amide (168)

1'-Acryloyl-4-[6-(cis-2,6-dimethyl-morpholin-4-yl)-pyridin-3-ylamino]-1',2',3',6'-tetrahydro-[3,4']bipyridinyl-5-carboxylic acid amide 12.8 mg (49%) was prepared from 5-bromo-4-chloro-nicotinonitrile, 6-cis-2,6-dimethyl-morpholin-4-yl)-pyridin-3-ylamine, N-Boc-1,2,3,6-tetrahydropyridine-4-boronic acid pinacol ester and acrylic acid with methods 9A, 9B, 9C, 2C and 2D. HPLC: 86.5%, RT=1.80 min. MS: m/z=463 [M+H]+. $^1$H NMR (400 MHz, DMSO-d6) δ 10.13 (s, 1H), 8.67 (s, 1H), 8.25 (s, 1H), 8.00 (s, 1H), 7.84 (d, J=2.8 Hz, 1H), 7.67 (s, 1H), 7.21 (d, J=8.8 Hz, 1H), 6.87-6.62 (m, 2H), 6.16-6.00 (m, 1H), 5.75-5.55 (m, 2H), 4.05-3.94 (m, 2H), 3.63-3.53 (m, 2H), 3.50 (t, J=5.9 Hz, 1H), 3.06 (d, J=7.2 Hz, 2H), 2.41-2.21 (m, 2H), 1.97 (s, 2H), 1.65 (s, 1H), 1.13 (d, J=6.2 Hz, 6H).

Example 125

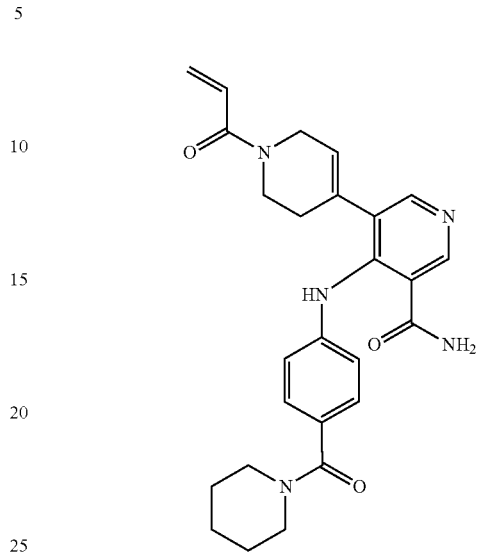

1'-Acryloyl-4-[4-(piperidine-1-carbonyl)-phenylamino]-1',2',3',6'-tetrahydro-[3,4']bipyridinyl-5-carboxylic acid amide (169)

1'-Acryloyl-4-[4-(piperidine-1-carbonyl)-phenylamino]-1',2',3',6'-tetrahydro-[3,4']bipyridinyl-5-carboxylic acid amide 15.3 mg (41%) was prepared from 5-Bromo-4-chloro-nicotinonitrile, (4-aminophenyl)(piperidin-1-yl)methanone, tert-butyl 4-(4,4,5,5-tetramethyl-1,3,2-dioxaborolan-2-yl)-5,6-dihydropyridine-1(2H)-carboxylate and acrylic acid with methods 9A, 9B, 9C, 2C and 2D. HPLC: 92.8%, RT=2.35 min. MS: m/z=460 [M+H]+. $^1$H NMR (400 MHz, DMSO-d6) δ 10.12 (d, J=5.3 Hz, 1H), 8.72 (s, 1H), 8.30 (s, 1H), 8.20 (s, 1H), 7.76 (s, 1H), 7.23 (d, J=8.2 Hz, 2H), 6.91 (d, J=8.1 Hz, 2H), 6.79-6.55 (m, 1H), 6.04 (t, J=15.0 Hz, 1H), 5.82-5.55 (m, 2H), 3.89 (d, J=34.6 Hz, 2H), 2.97 (d, J=6.5 Hz, 2H), 1.64-1.31 (m, 6H). The rest protons overlap with solvent peaks.

Example 126

Scheme 10

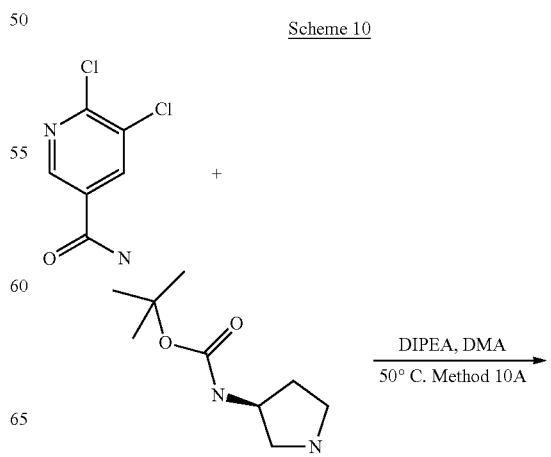

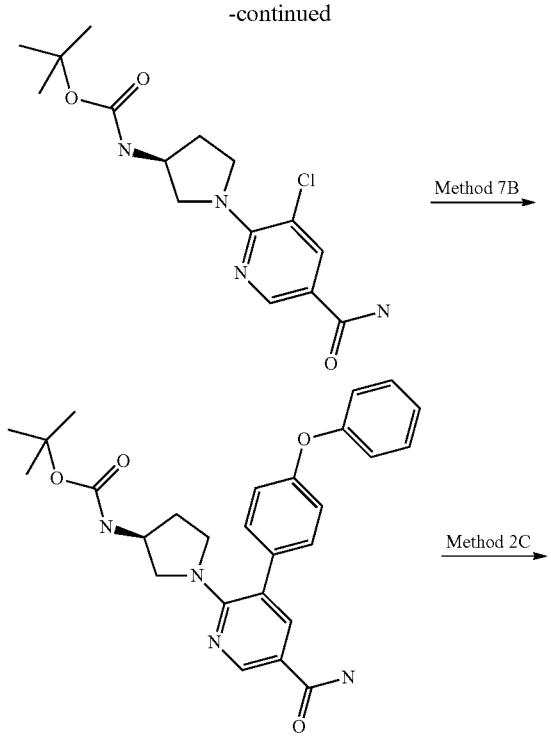

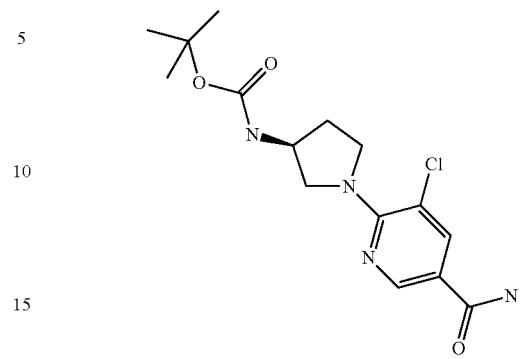

Methods Associated with Reaction Steps in Scheme 10:

[(S)-1-(5-Carbamoyl-3-chloro-pyridin-2-yl)-pyrrolidin-3-yl]-carbamic acid tert-butyl ester (Method 10A)

In a microwave vial containing 5,6-Dichloro-nicotinamide (250.00 mg; 1.31 mmol; 1.00 eq.) and (S)-pyrrolidin-3-yl-carbamic acid tert-butyl ester (292.52 mg; 1.57 mmol; 1.20 eq.) was added DMF (5.00 ml; 64.85 mmol; 49.55 eq.) and DIPEA (0.43 ml; 2.62 mmol; 2.00 eq.). The reaction was stirred at 50° C. for 2 h before it was concentrated and carried to the next step. MS: m/z=341 [M+H]+.

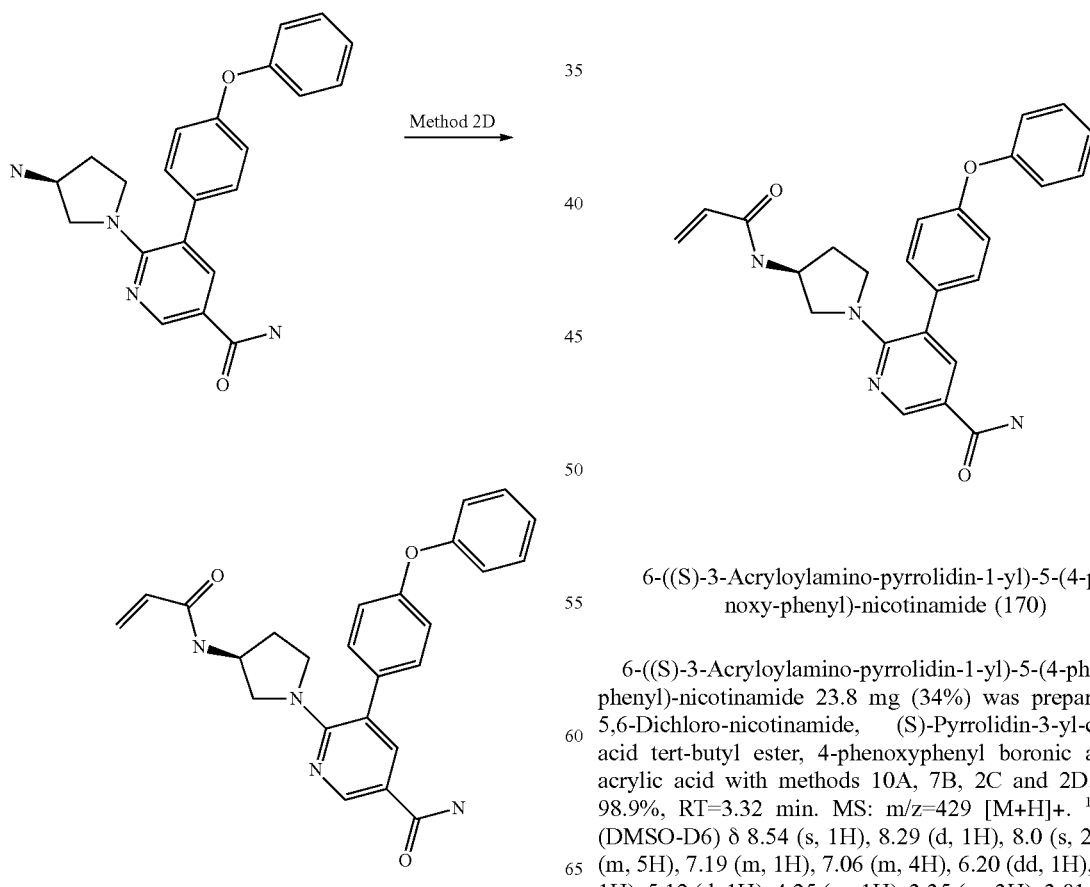

6-((S)-3-Acryloylamino-pyrrolidin-1-yl)-5-(4-phenoxy-phenyl)-nicotinamide (170)

6-((S)-3-Acryloylamino-pyrrolidin-1-yl)-5-(4-phenoxyphenyl)-nicotinamide 23.8 mg (34%) was prepared from 5,6-Dichloro-nicotinamide, (S)-Pyrrolidin-3-yl-carbamic acid tert-butyl ester, 4-phenoxyphenyl boronic acid and acrylic acid with methods 10A, 7B, 2C and 2D. HPLC: 98.9%, RT=3.32 min. MS: m/z=429 [M+H]+. $^1$H-NMR (DMSO-D6) δ 8.54 (s, 1H), 8.29 (d, 1H), 8.0 (s, 2H), 7.44 (m, 5H), 7.19 (m, 1H), 7.06 (m, 4H), 6.20 (dd, 1H), 6.06 (d, 1H), 5.12 (d, 1H), 4.25 (m, 1H), 3.35 (m, 3H), 3.01 (m, 1H), 2.01 (m, 1H), 1.79 (m, 1H).

Scheme 11

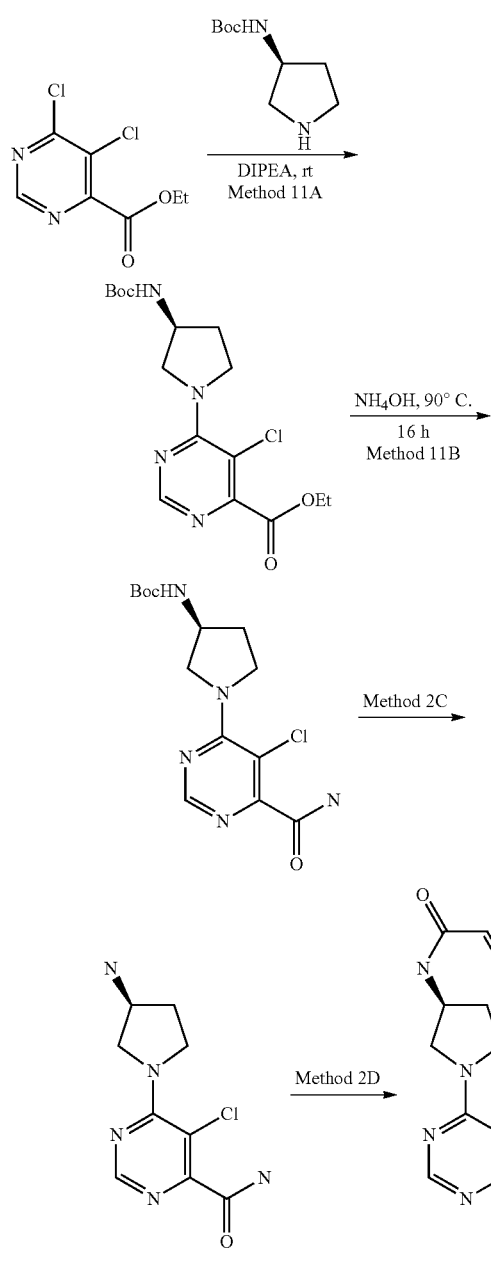

Methods Associated with Reaction Steps in Scheme 11:

6-((S)-3-tert-Butoxycarbonylamino-pyrrolidin-1-yl)-5-chloro-pyrimidine-4-carboxylic acid ethyl ester (Method 11A)

In a microwave vial containing 5,6-Dichloro-pyrimidine-4-carboxylic acid ethyl ester (25.00 mg; 0.11 mmol; 1.00 eq.) and (S)-pyrrolidin-3-yl-carbamic acid tert-butyl ester (23.17 mg; 0.12 mmol; 1.10 eq.) in N,N-dimethyl-acetamide (1.00 ml; 32.64 mmol; 288.63 eq.) was added DIPEA (0.06 ml; 0.34 mmol; 3.00 eq.). The mixture was stirred at rt for 30 min before it was concentrated and carried to the next step. MS: m/z=371 [M+H]+.

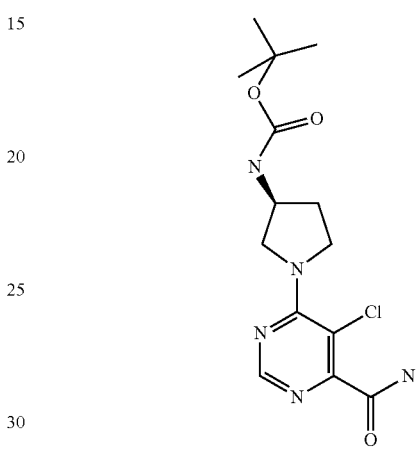

[(S)-1-(6-Carbamoyl-5-chloro-pyrimidin-4-yl)-pyrrolidin-3-yl]-carbamic acid tert-butyl ester (Method 11B)

In a microwave vial containing 6-((S)-3-tert-Butoxycarbonylamino-pyrrolidin-1-yl)-5-chloro-pyrimidine-4-carboxylic acid ethyl ester (41.94 mg; 1.00 eq.) was added ammonium hydroxide (1.50 ml). The mixture was stirred at 90° C. for 16 h before it was concentrated and carried to the next step. MS: m/z=342 [M+H]+.

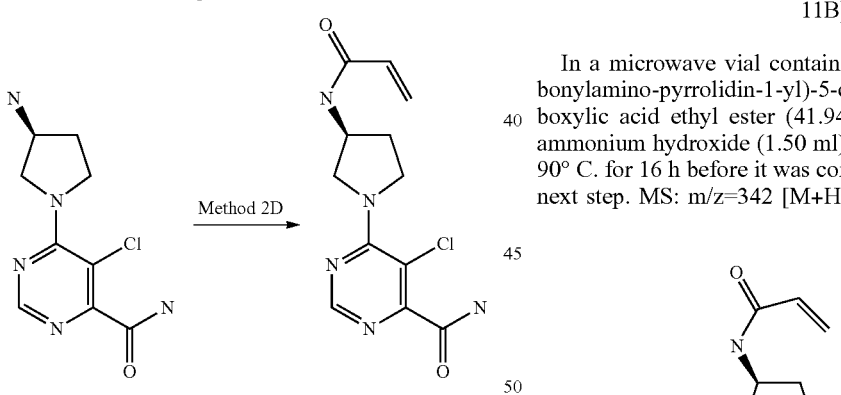

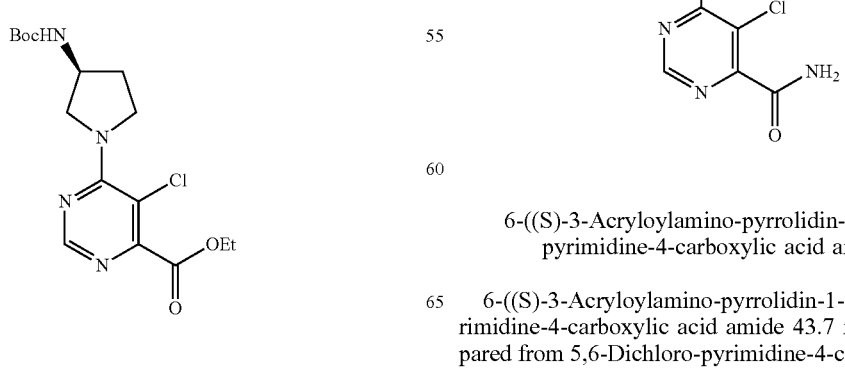

6-((S)-3-Acryloylamino-pyrrolidin-1-yl)-5-chloro-pyrimidine-4-carboxylic acid amide (172)

6-((S)-3-Acryloylamino-pyrrolidin-1-yl)-5-chloro-pyrimidine-4-carboxylic acid amide 43.7 mg (55%) was prepared from 5,6-Dichloro-pyrimidine-4-carboxylic acid ethyl ester, (S)-pyrrolidin-3-yl-carbamic acid tert-butyl ester, ammonium hydroxide, acrylic acid with methods 11A, 11B, 2C and 2D. HPLC: 99.0%, RT=1.87 min. MS: m/z=296 [M+H]+. ¹H-NMR (DMSO-D6) δ 8.41 (m, 2H), 7.91 (d, 1H), 7.45 (m, 1H), 6.25 (dd, 1H), 6.13 (d, 1H), 5.59 (d, 1H), 4.37 (m, 1H), 4.00 (m, 1H), 3.59 (m, 2H), 3.45 (m, 1H), 2.14 (m, 1H), 1.90 (m, 1H).

Example 127

Scheme 12

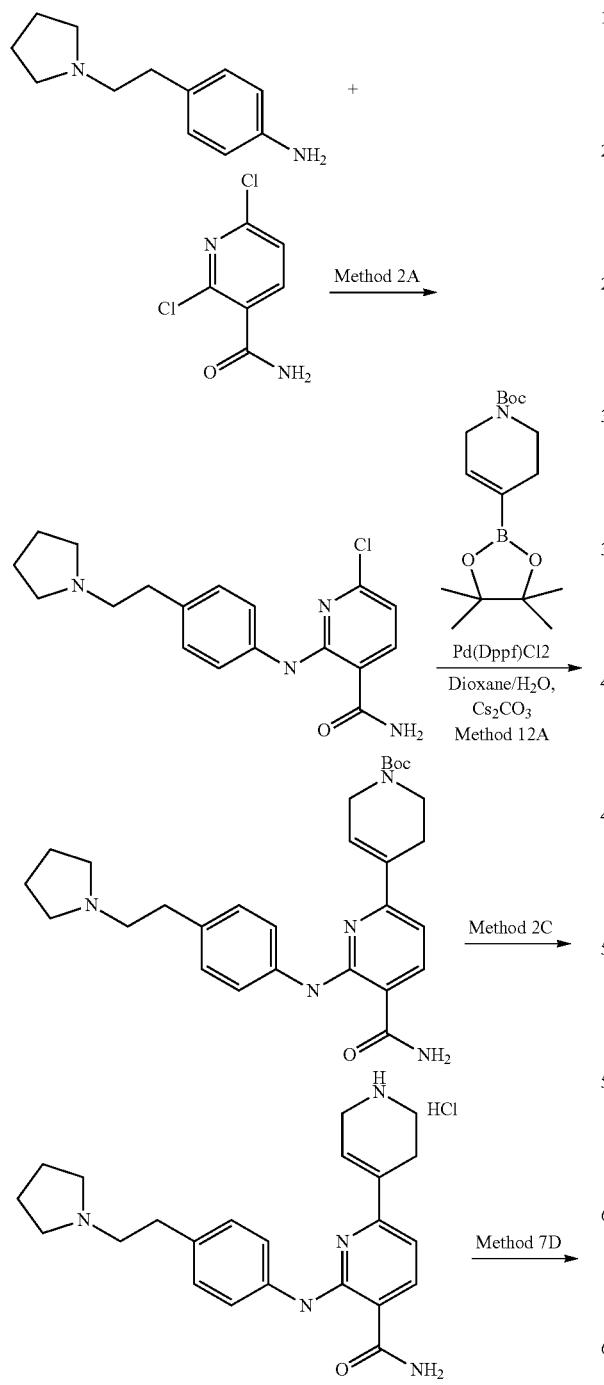

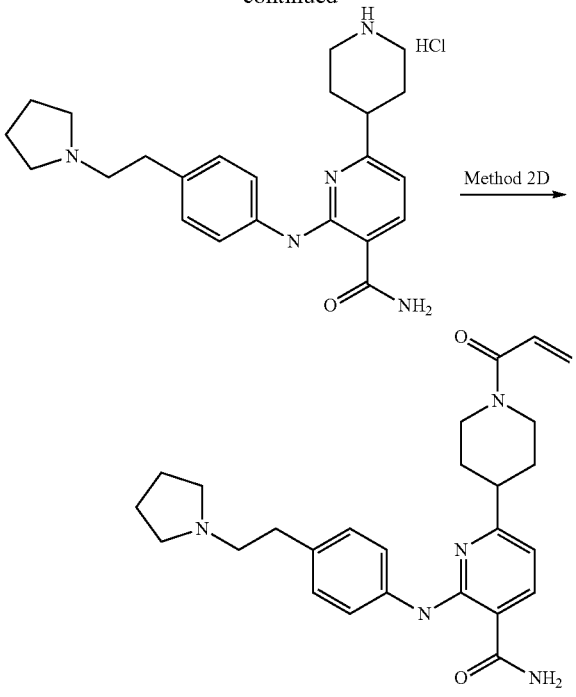

Methods Associated with Reaction Steps in Scheme 12:

tert-butyl 5-carbamoyl-6-((4-(2-(pyrrolidin-1-yl)ethyl)phenyl)amino)-5',6'-dihydro-[2,4'-bipyridine]-1'(2'H)-carboxylate Method (12A)

In a microwave vial containing 6-Chloro-2-[4-(2-pyrrolidin-1-yl-ethyl)-phenylamino]-nicotinamide (150.00 mg; 0.43 mmol; 1.00 eq.), n-boc-1,2,3,6-tetrahydropyridine-4-boronic acid pinacol ester (161.40 mg; 0.52 mmol; 1.20 eq.) and cesium carbonate (311.81 mg; 0.96 mmol; 2.20 eq.) was added dioxane (4.00 ml; 46.94 mmol; 107.92 eq.) and water (1.00 ml; 55.51 mmol; 127.61 eq.). The solution was purged with N₂ for 1 min before [1,1'-bis(diphenylphosphino)ferrocene]dichloropalladium(ii), complex with dichloromethane (35.52 mg; 0.04 mmol; 0.10 eq.) was added. The reaction mixture was stirred at 140° C. for 1 h before it was filtered, concentrated and purified with 11 g KPNH column. The collected desired fractions were combined and dried to afford the desired product. MS: m/z=492 [M+H]+.

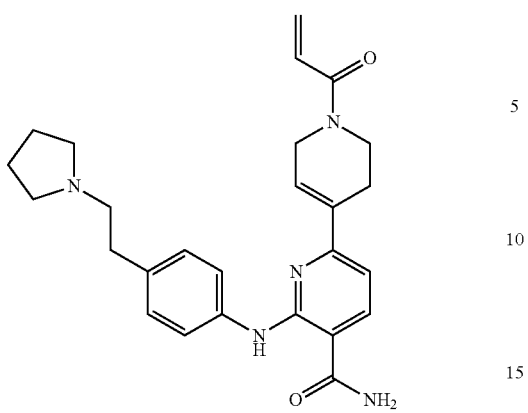

1'-Acryloyl-6-[4-(2-pyrrolidin-1-yl-ethyl)-phenylamino]-1',2',3',6'-tetrahydro-[2,4']bipyridinyl-5-carboxylic acid amide (17)

1'-Acryloyl-6-[4-(2-pyrrolidin-1-yl)-phenylamino]-1',2',3',6'-tetrahydro-[2,4']bipyridinyl-5-carboxylic acid amide 16.0 mg (34%) was prepared from 2,6-dichloro nicotinamide, tert-butyl 4-(4,4,5,5-tetramethyl-1,3,2-dioxaborolan-2-yl)-5,6-dihydropyridine-1(2H)-carboxylate, 4-(2-(pyrrolidin-1-yl)ethyl)anilineand acrylic acid with methods 2A, 12A, 2C, and 2D (hydrogenation step, Method 7D, is omitted). HPLC: 99.9%, RT=2.62 min. MS: m/z=446 [M+H]+. $^1$H NMR (400 MHz, DMSO-d6) δ 11.24 (s, 1H), 8.36-7.95 (m, 2H), 7.81-7.43 (m, 3H), 7.20 (d, J=8.0 Hz, 2H), 7.15-6.75 (m, 3H), 6.16 (d, J=16.7 Hz, 1H), 5.84-5.46 (m, 1H), 4.32 (d, J=41.2 Hz, 2H), 3.78 (dt, J=12.6, 5.6 Hz, 2H), 3.07-2.55 (m, 11H), 1.77 (s, 4H).

Example 128

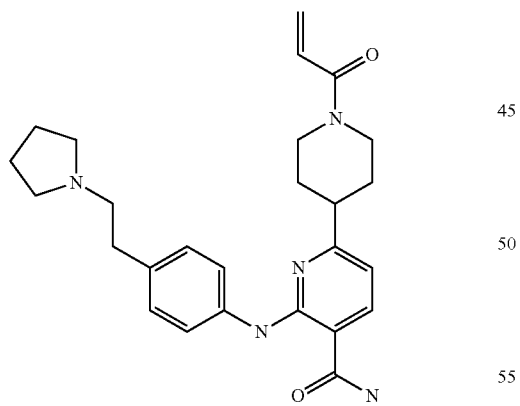

1'-Acryloyl-6-[4-(2-pyrrolidin-1-yl-ethyl)-phenylamino]-1',2',3',4',5',6'-hexahydro-[2,4']bipyridinyl-5-carboxylic acid amide (18)

1'-Acryloyl-6-[4-(2-pyrrolidin-1-yl)-phenylamino]-1',2',3',4',5',6'-hexahydro-[2,4']bipyridinyl-5-carboxylic acid amide 18.3 mg (48%) was prepared from 2,6-dichloro nicotinamide, tert-butyl 4-(4,4,5,5-tetramethyl-1,3,2-dioxaborolan-2-yl)-5,6-dihydropyridine-1(2H)-carboxylate, 4-(2-(pyrrolidin-1-yl)ethyl)anilineand acrylic acid with methods 2A, 12A, 2C, 7D and 2D. HPLC: 99.9%, RT=2.39 min. MS: m/z=448 [M+H]+. $^1$H NMR (400 MHz, DMSO-d6) δ 11.15 (s, 1H), 8.32-7.95 (m, 2H), 7.68-7.45 (m, 3H), 7.22-7.07 (m, 2H), 6.86 (dd, J=16.7, 10.5 Hz, 1H), 6.72 (d, J=8.0 Hz, 1H), 6.12 (dd, J=16.7, 2.5 Hz, 1H), 5.68 (dd, J=10.4, 2.5 Hz, 1H), 4.36 (dd, J=151.8, 13.1 Hz, 2H), 3.19 (t, J=13.0 Hz, 1H), 2.92 (tt, J=11.6, 3.6 Hz, 1H), 2.83-2.64 (m, 3H), 2.64-2.55 (m, 2H), 1.93 (d, J=12.7 Hz, 2H), 1.68 (p, J=3.0 Hz, 6H).

Example 129

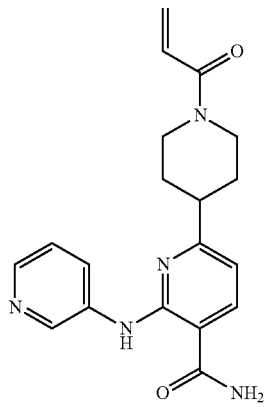 [SMILES: C=CC(=O)N1CCC(c2ccc(C(N)=O)c(Nc3cccnc3)n2)CC1]

1'-Acryloyl-6-(pyridin-3-ylamino)-1',2',3',4',5',6'-hexahydro-[2,4']bipyridinyl-5-carboxylic acid amide (53)

1'-Acryloyl-6-(pyridin-3-ylamino)-1',2',3',4',5',6'-hexahydro-[2,4']bipyridinyl-5-carboxylic acid amide 43.8 mg (49%) was prepared from 2,6-dichloro nicotinamide, pyridin-3-amine, 4-(4,4,5,5-tetramethyl-1,3,2-dioxaborolan-2-yl)-5,6-dihydropyridine-1(2H)-carboxylate, 4- and acrylic acid with methods 2A, 12A, 2C, 7D and 2D. HPLC: 92.3%, RT=4.50 min. MS: m/z=352 [M+H]+. $^1$H NMR (400 MHz, DMSO-d6) δ 11.31 (s, 1H), 8.87 (d, J=2.4 Hz, 1H), 8.40-7.97 (m, 4H), 7.66 (s, 1H), 7.46-7.27 (m, 1H), 6.86 (dd, J=16.6, 9.5 Hz, 2H), 6.12 (dd, J=16.7, 2.5 Hz, 1H), 5.68 (dd, J=10.5, 2.5 Hz, 1H), 4.57 (d, J=13.1 Hz, 1H), 4.19 (d, J=13.4 Hz, 1H), 3.19 (t, J=13.0 Hz, 1H), 2.96 (tt, J=11.7, 3.7 Hz, 1H), 2.77 (t, J=12.6 Hz, 1H), 1.95 (d, J=13.0 Hz, 2H), 1.69-1.45 (m, 2H).

Example 130

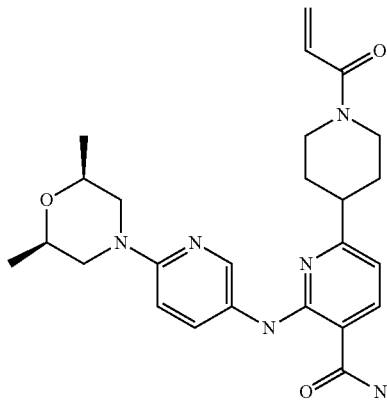 [SMILES: C=CC(=O)N1CCC(c2ccc(C(N)=O)c(Nc3ccc(N4C[C@@H](C)O[C@@H](C)C4)nc3)n2)CC1]

1'-Acryloyl-6-[6-((2R,6S)-2,6-dimethyl-morpholin-4-yl)-pyridin-3-ylamino]-1',2',3',4',5',6'-hexahydro-[2,4']bipyridinyl-5-carboxylic acid amide (32)

1'-Acryloyl-6-[6-((2R,6S)-2,6-dimethyl-morpholin-4-yl)-pyridin-3-ylamino]-1',2',3',4',5',6'-hexahydro-[2,4']bipyridinyl-5-carboxylic acid amide 13.8 mg (38%) was prepared from 2,6-dichloro nicotinamide, tert-butyl 4-(4,4,5,5-tetramethyl-1,3,2-dioxaborolan-2-yl)-5,6-dihydropyridine-1(2H)-carboxylate, 6-(cis-2,6-dimethylmorpholino)pyridin-3-amine and acrylic acid with methods 2A, 12A, 2C, 7D and 2D. HPLC: 97.7%, RT=2.77 min. MS: m/z=465 [M+H]+. $^1$H NMR (400 MHz, DMSO-d6) δ 10.95 (s, 1H), 8.52 (s, 1H), 8.29-8.00 (m, 2H), 8.05-7.82 (m, 1H), 7.56 (s, 1H), 7.35-7.01 (m, 2H), 6.98-6.79 (m, 2H), 6.72 (d, J=7.9 Hz, 1H), 6.11 (dd, J=16.7, 2.5 Hz, 1H), 5.68 (dd, J=10.4, 2.5 Hz, 1H), 4.36 (dd, J=155.5, 13.3 Hz, 2H), 4.05 (dd, J=12.9, 2.3 Hz, 2H), 3.64 (ddt, J=12.3, 8.6, 6.0 Hz, 2H), 3.29-3.08 (m, 1H), 2.89 (ddt, J=11.8, 8.1, 3.6 Hz, 1H), 2.85-2.66 (m, 1H), 2.40 (t, J=11.6 Hz, 2H), 2.02-1.83 (m, 2H), 1.70-1.44 (m,2), 1.17 (d, J=6.2 Hz, 6H).

Example 131

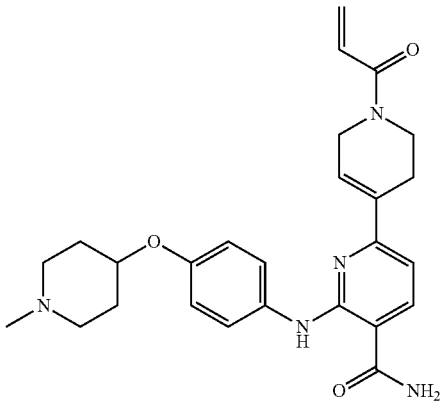 [SMILES: C=CC(=O)N1CC=C(c2ccc(C(N)=O)c(Nc3ccc(OC4CCN(C)CC4)cc3)n2)CC1]

1'-Acryloyl-6-[4-(1-methyl-piperidin-4-yloxy)-phenylamino]-1',2',3',6'-tetrahydro-[2,4']bipyridinyl-5-carboxylic acid amide (13)

1'-Acryloyl-6-[4-(1-methyl-piperidin-4-yloxy)-phenylamino]-1',2',3',6'-tetrahydro-[2,4']bipyridinyl-5-carboxylic acid amide 28 mg (62%) was prepared from 2,6-dichloro nicotinamide, tert-butyl 4-(4,4,5,5-tetramethyl-1,3,2-dioxaborolan-2-yl)-5,6-dihydropyridine-1(2H)-carboxylate, 4-((1-methylpiperidin-4-yl)oxy)aniline and acrylic acid with methods 2A, 12A, 2C, and 2D (hydrogenation step, Method 7D, is omitted). HPLC: 89.6%, RT=2.86 min. MS: m/z=462 [M+H]+. $^1$H NMR (400 MHz, DMSO-d6) δ 11.11 (s, 1H), 8.43-8.00 (m, 2H), 7.61 (d, J=8.2 Hz, 3H), 7.11-6.64 (m, 5H), 6.15 (d, J=16.7 Hz, 1H), 5.86-5.59 (m, 1H), 4.51 (s, 1H), 4.41-4.14 (m, 2H), 3.76 (dt, J=11.9, 5.6 Hz, 2H), 3.27-3.07 (m, 1H), 2.77-2.55 (m, 4H), 2.19-1.62 (m, 4H). Some peaks overlap with solvent peaks.

Example 132

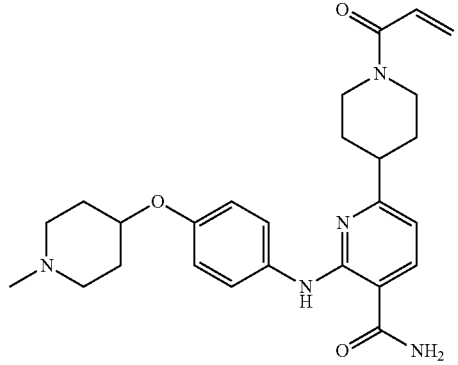 [SMILES: C=CC(=O)N1CCC(c2ccc(C(N)=O)c(Nc3ccc(OC4CCN(C)CC4)cc3)n2)CC1]

1'-Acryloyl-6-[4-(1-methyl-piperidin-4-yloxy)-phenylamino]-1',2',3',4',5',6'-hexahydro-[2,4']bipyridinyl-5-carboxylic acid amide (10)

1'-Acryloyl-6-[4-(1-methyl-piperidin-4-yloxy)-phenylamino]-1',2',3',4',5',6'-hexahydro-[2,4']bipyridinyl-5-carboxylic acid amide 32.1 mg (52%) was prepared from 2,6-dichloro nicotinamide, tert-butyl 4-(4,4,5,5-tetramethyl-1,3,2-dioxaborolan-2-yl)-5,6-dihydropyridine-1(2H)-carboxylate, 4-((1-methylpiperidin-4-yl)oxy)aniline and acrylic acid with methods 2A, 12A, 2C, 7D and 2D. HPLC: 99.9%, RT=2.18 min. MS: m/z=465 [M+H]+. $^1$H NMR (400 MHz, DMSO-d6) δ 11.02 (s, 1H), 8.25-7.92 (m, 2H), 7.75-7.38 (m, 3H), 7.03-6.76 (m, 3H), 6.69 (d, J=8.0 Hz, 1H), 6.11 (dd, J=16.7, 2.5 Hz, 1H), 5.68 (dd, J=10.5, 2.5 Hz, 1H), 4.54 (d, J=12.8 Hz, 1H), 4.40-4.06 (m, 2H), 3.18 (t, J=12.8 Hz, 1H), 2.89 (tt, J=11.7, 3.8 Hz, 1H), 2.76 (t, J=12.8 Hz, 1H), 2.62 (s, 2H), 1.98-1.80 (m, 4H), 1.62 (dtd, J=12.8, 8.8, 3.7 Hz, 4H).

Example 133

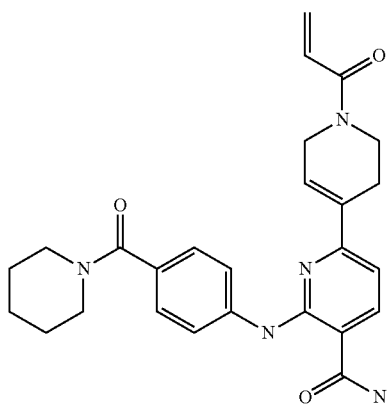 [SMILES: C=CC(=O)N1CC=C(c2ccc(C(N)=O)c(Nc3ccc(C(=O)N4CCCCC4)cc3)n2)CC1]

1'-Acryloyl-6-[4-(piperidine-1-carbonyl)-phenylamino]-1',2',3',6'-tetrahydro-[2,4']bipyridinyl-5-carboxylic acid amide (28)

1'-Acryloyl-6-[4-(piperidine-1-carbonyl)-phenylamino]-1',2',3',6'-tetrahydro-[2,4']bipyridinyl-5-carboxylic acid amide 35.1 mg (47%) was prepared from 2,6-dichloro nicotinamide, tert-butyl 4-(4,4,5,5-tetramethyl-1,3,2-dioxaborolan-2-yl)-5,6-dihydropyridine-1(2H)-carboxylate, (4-aminophenyl)(piperidin-1-yl)methanone and acrylic acid with methods 2A, 12A, 2C, and 2D (hydrogenation step, Method 7D, is omitted). HPLC: 99.9%, RT=3.84 min. MS: m/z=460 [M+H]+. $^1$H NMR (400 MHz, DMSO-d6) δ 11.48 (s, 1H), 8.39-8.05 (m, 2H), 7.90-7.61 (m, 3H), 7.50-7.36 (m, 1H), 7.10 (d, J=8.5 Hz, 1H), 7.03-6.68 (m, 2H), 6.15 (d, J=16.8 Hz, 1H), 5.86-5.57 (m, 1H), 4.33 (d, J=42.5 Hz, 2H), 3.78 (dt, J=12.2, 6.0 Hz, 2H), 3.66-3.39 (m, 4H), 2.64 (d, J=25.8 Hz, 2H), 1.78-1.23 (m, 6H).

Example 134

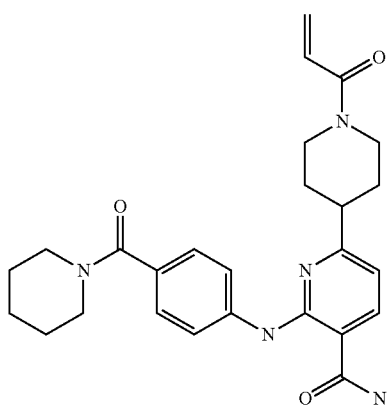 [SMILES: C=CC(=O)N1CCC(c2ccc(C(N)=O)c(Nc3ccc(C(=O)N4CCCCC4)cc3)n2)CC1]

1'-Acryloyl-6-[4-(piperidine-1-carbonyl)-phenylamino]-1',2',3',4',5',6'-hexahydro-[2,4']bipyridinyl-5-carboxylic acid amide (22)

1'-Acryloyl-6-[4-(piperidine-1-carbonyl)-phenylamino]-1',2',3',4',5',6'-hexahydro-[2,4']bipyridinyl-5-carboxylic acid amide 26.6 mg (38%) was prepared from 2,6-dichloro nicotinamide, tert-butyl 4-(4,4,5,5-tetramethyl-1,3,2-dioxaborolan-2-yl)-5,6-dihydropyridine-1(2H)-carboxylate, (4-aminophenyl)(piperidin-1-yl)methanone and acrylic acid with methods 2A, 12A, 2C, 7D and 2D. HPLC: 96.5%, RT=3.40 min. MS: m/z=460 [M+H]+. No NMR data due to only limited amount of the product obtained.

Example 135

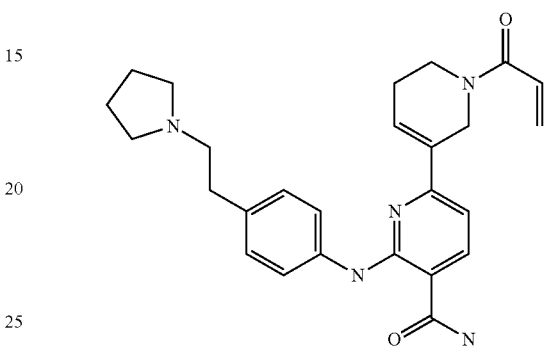

1'-Acryloyl-6-[4-(2-pyrrolidin-1-yl-ethyl)-phenylamino]-1',2',5',6'-tetrahydro-[2,3']bipyridinyl-5-carboxylic acid amide (44)

1'-Acryloyl-6-[4-(2-pyrrolidin-1-yl-ethyl)-phenylamino]-1',2',5',6'-tetrahydro-[2,3']bipyridinyl-5-carboxylic acid amide 25.7 mg (33%) was prepared from 2,6-dichloro nicotinamide, 4-(2-(pyrrolidin-1-yl)ethyl)aniline, tert-butyl 3-(4,4,5,5-tetramethyl-1,3,2-dioxaborolan-2-yl)-5,6-dihydropyridine-1(2H)-carboxylate, 4- and acrylic acid with methods 2A, 12A, 2C, and 2D (hydrogenation step, Method 7D, is omitted). HPLC: 99.9%, RT=2.77 min. MS: m/z=446 [M+H]+. $^1$H NMR (400 MHz, DMSO-d6) δ 11.30 (d, J=28.3 Hz, 1H), 8.50-8.00 (m, 2H), 7.67 (dd, J=22.5, 7.5 Hz, 3H), 7.25 (s, 1H), 7.24-7.09 (m, 2H), 7.03-6.77 (m, 2H), 6.16 (d, J=16.8 Hz, 1H), 5.76 (dd, J=19.9, 10.5 Hz, 1H), 4.75-4.33 (m, 2H), 3.71 (dt, J=18.3, 5.7 Hz, 2H), 2.93 (t, J=8.4 Hz, 2H), 2.39 (d, J=21.4 Hz, 2H), 1.91 (s, 4H).

Example 136

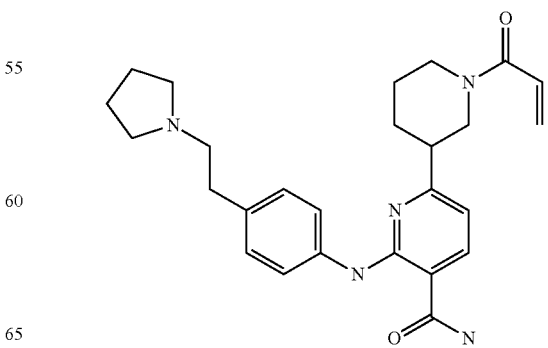

301

1'-Acryloyl-6-[4-(2-pyrrolidin-1-yl-ethyl)-phenylamino]-1',2',3',4',5',6'-hexahydro-[2,3']bipyridinyl-5-carboxylic acid amide (42)

1'-Acryloyl-6-[4-(2-pyrrolidin-1-yl-ethyl)-phenylamino]-1',2',3',4',5',6'-hexahydro-[2,3']bipyridinyl-5-carboxylic acid amide 21.4 mg (46%) was prepared from 2,6-dichloro nicotinamide, 4-(2-(pyrrolidin-1-yl)ethyl)aniline, tert-butyl 3-(4,4,5,5-tetramethyl-1,3,2-dioxaborolan-2-yl)-5,6-dihydropyridine-1(2H)-carboxylate, 4- and acrylic acid with methods 2A, 12A, 2C, 7D and 2D. HPLC: 90.5%, RT=2.98 min. MS: m/z=448[M+H]+. $^1$H NMR (400 MHz, DMSO-d6) δ 11.17 (d, J=8.0 Hz, 1H), 8.31-8.01 (m, 2H), 7.62 (t, J=5.9 Hz, 3H), 7.16 (d, J=8.1 Hz, 2H), 6.96-6.68 (m, 2H), 6.11 (dd, J=16.6, 9.3 Hz, 1H), 5.67 (dd, J=18.5, 10.5 Hz, 1H), 4.53 (dd, J=65.5, 12.7 Hz, 1H), 4.17 (dd, J=61.2, 13.6 Hz, 1H), 3.21-2.84 (m, 1H), 2.84-2.57 (m, 6H), 2.06 (d, J=14.0 Hz, 1H), 1.80 (d, J=11.4 Hz, 2H), 1.76-1.59 (m, 4H), 1.50 (d, J=14.0 Hz, 1H).

Example 137

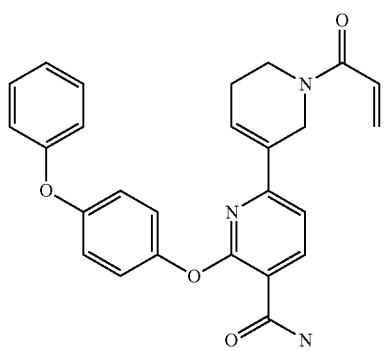 [SMILES: C=CC(=O)N1CCC=C(c2ccc(C(N)=O)c(Oc3ccc(Oc4ccccc4)cc3)n2)C1]

1'-Acryloyl-6-(4-phenoxy-phenoxy)-1',2',5',6'-tetrahydro-[2,3']bipyridinyl-5-carboxylic acid amide (83)

1'-Acryloyl-6-(4-phenoxy-phenoxy)-1',2',3',4',5',6'-hexahydro-[2,3']bipyridinyl-5-carboxylic acid amide 19.4 mg (37%) was prepared from 2,6-dichloro nicotinamide, 4-phenoxyphenol, tert-butyl 3-(4,4,5,5-tetramethyl-1,3,2-dioxaborolan-2-yl)-5,6-dihydropyridine-1(2H)-carboxylate, 4- and acrylic acid with methods 1A, 12A, 2C, and 2D (hydrogenation step, Method 7D, is omitted). HPLC: 99.9%, RT=4.45 min. MS: m/z=442[M+H]+. $^1$H NMR (400 MHz, DMSO-d6) δ 8.21 (d, J=7.9 Hz, 1H), 7.78 (d, J=9.1 Hz, 2H), 7.58-7.22 (m, 5H), 7.22-6.98 (m, 5H), 6.95-6.37 (m, 2H), 6.10 (dd, J=23.8, 16.8 Hz, 1H), 5.67 (dd, J=30.9, 10.5 Hz, 1H), 4.23 (d, J=11.8 Hz, 2H), 3.63 (dt, J=12.7, 5.8 Hz, 2H), 2.31 (d, J=20.8 Hz, 2H).

302

Example 138

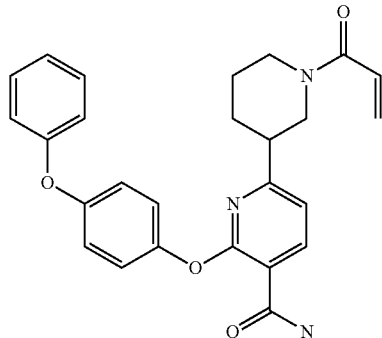 [SMILES: C=CC(=O)N1CCCC(c2ccc(C(N)=O)c(Oc3ccc(Oc4ccccc4)cc3)n2)C1]

1'-Acryloyl-6-(4-phenoxy-phenoxy)-1',2',3',4',5',6'-hexahydro-[2,3']bipyridinyl-5-carboxylic acid amide (87)

1'-Acryloyl-6-(4-phenoxy-phenoxy)-1',2',3',4',5',6'-hexahydro-[2,3']bipyridinyl-5-carboxylic acid amide 28.2 mg (47%) was prepared from 2,6-dichloro nicotinamide, 4-phenoxyphenol, tert-butyl 3-(4,4,5,5-tetramethyl-1,3,2-dioxaborolan-2-yl)-5,6-dihydropyridine-1(2H)-carboxylate, 4- and acrylic acid with methods 2A, 12A, 2C, 7D and 2D. HPLC: 98.7%, RT=4.49 min. MS: m/z=444 [M+H]+. $^1$H NMR (400 MHz, DMSO-d6) δ 8.15 (d, J=6.9 Hz, 1H), 7.74 (s, 2H), 7.50-7.35 (m, 2H), 7.35-7.20 (m, 2H), 7.13 (dd, J=26.2, 8.3 Hz, 3H), 7.01 (d, J=8.1 Hz, 2H), 6.71 (ddd, J=71.8, 16.6, 10.5 Hz, 1H), 6.05 (t, J=18.5 Hz, 1H), 5.61 (dd, J=36.8, 10.7 Hz, 1H), 4.35 (dd, J=53.4, 10.8 Hz, 1H), 4.00 (d, J=11.8 Hz, 1H), 3.00 (dt, J=33.1, 12.4 Hz, 1H), 2.65 (p, J=11.5 Hz, 2H), 1.93 (s, 1H), 1.70 (dt, J=12.8, 3.2 Hz, 1H), 1.57 (s, 1H), 1.40 (s, 1H).

Example 139

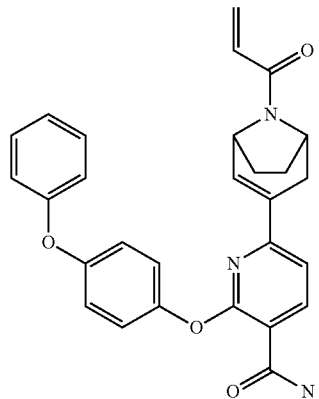 [SMILES: C=CC(=O)N1C2C=C(c3ccc(C(N)=O)c(Oc4ccc(Oc5ccccc5)cc4)n3)CC1CC2]

6-(8-Acryloyl-8-aza-bicyclo[3.2.1]oct-2-en-3-yl)-2-(4-phenoxy-phenoxy)-nicotinamide (65)

6-(8-Acryloyl-8-aza-bicyclo[3.2.1]oct-2-en-3-yl)-2-(4-phenoxy-phenoxy)-nicotinamide 28.5 mg (44%) was prepared from 2,6-dichloro nicotinamide, 4-phenoxyphenol, tert-butyl 3-(4,4,5,5-tetramethyl-1,3,2-dioxaborolan-2-yl)-8-azabicyclo[3.2.1]oct-3-ene-8-carboxylate, 4- and acrylic acid with methods 1A, 12A, 2C, and 2D (hydrogenation step, Method 7D, is omitted). HPLC: 94.2%, RT=4.50 min. MS: m/z=470 [M+H]+. $^1$H NMR (400 MHz, DMSO-d6) δ 8.17 (dd, J=7.9, 2.1 Hz, 2H), 7.75 (d, J=11.0 Hz, 3H), 7.43 (td, J=7.9, 3.2 Hz, 4H), 7.38-7.23 (m, 5H), 7.13 (t, J=7.3 Hz, 6H), 7.01 (d, J=8.1 Hz, 4H), 6.88 (t, J=7.6 Hz, 2H), 6.73 (ddd, J=21.4, 16.8, 10.3 Hz, 2H), 6.24-6.00 (m, 2H), 5.86-5.56 (m, 2H), 4.83 (dt, J=19.1, 5.4 Hz, 2H), 4.71 (q, J=7.6 Hz, 2H), 2.87-2.60 (m, 1H), 2.34 (d, J=17.5 Hz, 1H), 2.18 (d, J=17.5 Hz, 1H), 2.09-1.91 (m, 1H), 1.88 (d, J=9.7 Hz, 2H), 1.75-1.49 (m, 1H). One proton overlaps with solvent peak.

Example 140

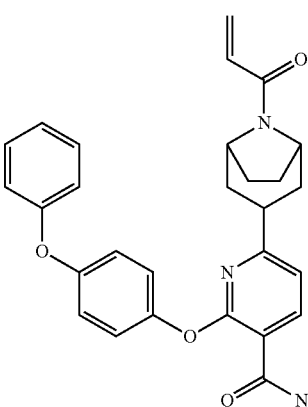 [SMILES: C=CC(=O)N1C2CCC1CC(c1ccc(C(N)=O)c(Oc3ccc(Oc4ccccc4)cc3)n1)C2]

6-(8-Acryloyl-8-aza-bicyclo[3.2.1]oct-3-yl)-2-(4-phenoxy-phenoxy)-nicotinamide (71)

6-(8-Acryloyl-8-aza-bicyclo[3.2.1]oct-3-yl)-2-(4-phenoxy-phenoxy)-nicotinamide 16.7 mg (35%) was prepared from 2,6-dichloro nicotinamide, 4-phenoxyphenol, tert-butyl 3-(4,4,5,5-tetramethyl-1,3,2-dioxaborolan-2-yl)-8-azabicyclo[3.2.1]oct-3-ene-8-carboxylate, 4- and acrylic acid with methods 1A, 12A, 2C, 7D and 2D. HPLC: 94.2%, RT=4.50 min. MS: m/z=470 [M+H]+. $^1$H NMR (400 MHz, DMSO-d6) δ 8.16 (d, J=7.8 Hz, 1H), 7.74 (s, 2H), 7.49-7.36 (m, 2H), 7.36-7.23 (m, 3H), 7.20-7.09 (m, 3H), 7.07-6.96 (m, 2H), 6.69 (dd, J=16.7, 10.4 Hz, 1H), 6.16 (dd, J=16.7, 2.5 Hz, 1H), 5.67 (dd, J=10.3, 2.5 Hz, 1H), 4.49-4.14 (m, 2H), 2.97 (tt, J=7.6, 3.8 Hz, 1H), 2.24-1.91 (m, 4H), 1.68 (dt, J=11.6, 7.3 Hz, 1H), 1.54 (ddt, J=13.0, 9.2, 4.1 Hz, 1H), 1.39-1.17 (m, 2H).

Example 141

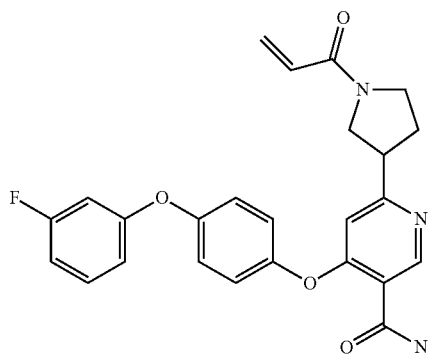 [SMILES: C=CC(=O)N1CCC(c2cc(Oc3ccc(Oc4cccc(F)c4)cc3)c(C(N)=O)cn2)C1]

1'-((E)-4-Dimethylamino-but-2-enoyl)-6-(4-phenoxy-phenoxy)-1',2',3',4',5',6'-hexahydro-[2,4']bipyridinyl-5-carboxylic acid amid (76)

1'-((E)-4-Dimethylamino-but-2-enoyl)-6-(4-phenoxy-phenoxy)-1',2',3',4',5',6'-hexahydro-[2,4']bipyridinyl-5-carboxylic acid amide was made in a manner similar to that described above using methods using methods 1A, 12A, 2C, 7D and 2D to give 6-(4-Phenoxy-phenoxy)-1',2',3',4',5',6'-hexahydro-[2,4']bipyridinyl-5-carboxylic acid amide and (E)-4-Dimethylamino-but-2-enoic acid 21 mg (29%). HPLC: 94%, RT=3.40 min. MS: m/z=501 [M+H]+, $^1$H NMR (400 MHz, DMSO) δ 8.20-8.07 (m, 1H), 7.80-7.69 (m, 2H), 7.46-7.37 (m, 2H), 7.26-6.94 (m, 5H), 6.61-6.52 (m, 2H), 4.34 (s, 1H), 3.99 (s, 1H), 3.31 (s, 3H), 3.18-2.97 (s, 7H), 2.95-2.92 (m, 2H), 2.91-2.58 (m, 3H), 1.83-1.68 (m, 2H), 1.47-1.29 (m, 2H).

Example 142

6-(1-Acryloyl-pyrrolidin-3-yl)-4-[4-(3-fluoro-phenoxy)-phenoxy]-nicotinamide (120)

6-(1-Acryloyl-pyrrolidin-3-yl)-4-[4-(3-fluoro-phenoxy)-phenoxy]-nicotinamide (50.00 mg; 0.11 mmol; 22.1%) was prepared from 4,6-dichloro nicotinamide (this isomer reacts in a manner similar to the 2,4 isomer), 4-(p-tolyloxy)phenol, (S)-Pyrrolidin-3-yl-carbamic acid tert-butyl ester and acrylic acid with methods 1A, 12A, 2C, 7D and 2D. HPLC-UV: 99.6% purity. LC/MS m/z=448.0 [M+H]$^+$. 1H NMR (400 MHz, DMSO-d6): 8.69 (s, 1H), 7.75-7.73 (m, 2H), 7.44-7.30 (m, 1H), 7.29-7.27 (m, 2H), 7.20-7.17 (m, 2H), 6.99-6.87 (m, 3H), 6.68 (d, J=12.92 Hz, 1H), 6.56-6.52 (m, 1H), 6.13-6.08 (m, 1H), 5.66-5.60 (m, 1H), 3.92-3.32 (m, 5H), 2.23-1.93 (m, 2H).

Example 143

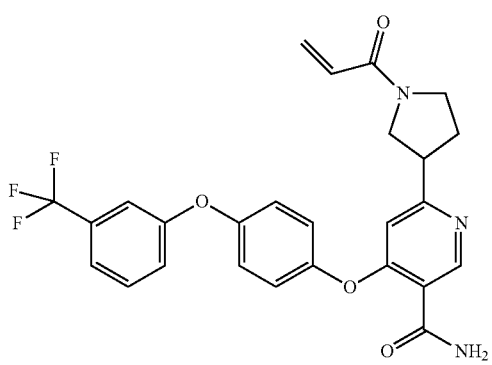 [SMILES: C=CC(=O)N1CCC(c2cc(Oc3ccc(Oc4cccc(C(F)(F)F)c4)cc3)c(C(N)=O)cn2)C1]

6-(1-acryloylpyrrolidin-3-yl)-4-(4-(3-(trifluoromethyl)phenoxy)phenoxy)nicotinamide (121)

6-(1-Acryloyl-pyrrolidin-3-yl)-4-[4-(3-trifluoromethyl-phenoxy)-phenoxy]-nicotinamide (50.00 mg; 22.3%) was prepared from 4,6-dichloro nicotinamide (this isomer reacts in a manner similar to the 2,4 isomer), 4-(3-trifluoromethylphenoxyoxy)phenol, (S)-Pyrrolidin-3-yl-carbamic acid tert-butyl ester and acrylic acid with methods 1A, 12A, 2C, 7D and 2D. HPLC-UV: 99.6% purity. LC/MS m/z=498.0 [M+H]$^+$. 1H NMR (400 MHz, DMSO-d6): 8.70 (d, J=1.44 Hz, 1H), 7.76-7.74 (m, 2H), 7.66-7.62 (m, 1H), 7.52-7.50 (m, 1H), 7.36-7.28 (m, 4H), 7.24-7.21 (m, 2H), 6.67 (d, J=12.52 Hz, 1H), 6.60-6.52 (m, 1H), 6.13-6.08 (m, 1H), 5.66-5.63 (m, 1H), 3.92-3.32 (m, 5H), 2.23-1.93 (m, 2H).

Example 144

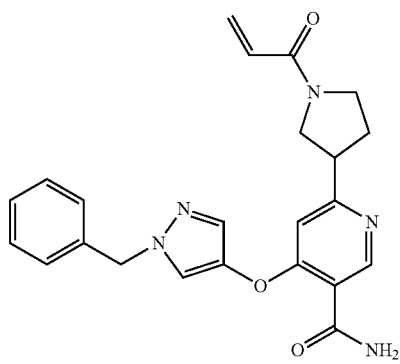 [SMILES: C=CC(=O)N1CCC(c2cc(Oc3cnn(Cc4ccccc4)c3)c(C(N)=O)cn2)C1]

6-(1-acryloylpyrrolidin-3-yl)-4-((1-benzyl-1H-pyrazol-4-yl)oxy)nicotinamide (122)

6-(1-Acryloyl-pyrrolidin-3-yl)-4-(1-benzyl-1H-pyrazol-4-yloxy)-nicotinamide (100.00 mg; 0.20; 43.5%) was prepared from 4,6-dichloro nicotinamide (this isomer reacts in a manner similar to the 2,4 isomer), 4-(3-trifluoromethylphenoxyoxy)phenol, (S)-Pyrrolidin-3-yl-carbamic acid tert-butyl ester and acrylic acid with methods 1A, 12A, 2C, 7D and 2D. HPLC-UV: 99.6% purity. LC/MS m/z=418.0 [M+H]$^+$. 1H NMR (400 MHz, DMSO-d6): 8.64 (s, 1H), 8.01 (d, J=2.08 Hz, 1H), 7.71 (s, 2H), 7.54 (s, 1H), 7.38-7.24 (m, 4H), 6.81 (d, J=10.08 Hz, 1H), 6.61-6.52 (m, 1H), 6.15-6.09 (m, 1H), 6.10-6.08 (m, 1H), 5.67-5.61 (m, 1H), 5.35 (s, 2H), 3.93-3.91 (m, 1H), 3.78-3.71 (m, 1H), 3.63-3.48 (m, 2H), 3.46-3.32 (m, 1H), 2.22-1.90 (m, 2H).

Example 145

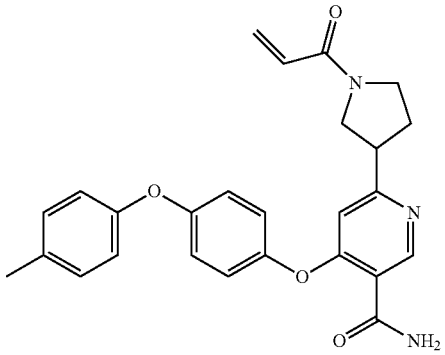 [SMILES: C=CC(=O)N1CCC(c2cc(Oc3ccc(Oc4ccc(C)cc4)cc3)c(C(N)=O)cn2)C1]

6-(1-acryloylpyrrolidin-3-yl)-4-(4-(p-tolyloxy)phenoxy)nicotinamide (110)

6-(1-Acryloyl-pyrrolidin-3-yl)-4-(4-p-tolyloxy-phenoxy)-nicotinamide (50.00 mg; 44.5%) was prepared from 4,6-dichloro nicotinamide (this isomer reacts in a manner similar to the 2,4 isomer), 4-(p-tolyloxy)phenol, (S)-Pyrrolidin-3-yl-carbamic acid tert-butyl ester and acrylic acid with methods 1A, 12A, 2C, 7D and 2D. HPLC-UV: 99.7% purity. LC/MS m/z=444.5 [M+H]$^+$. 1H NMR (400 MHz, DMSO-d6): 8.69 (s, 1H), 7.73-7.70 (m, 2H), 7.24-7.21 (m, 4H), 7.08-7.04 (m, 2H), 6.99-6.95 (m, 2H), 6.65-6.58 (m, 1H), 6.57-6.51 (m, 1H), 6.10-6.08 (m, 1H), 5.66-5.60 (m, 1H), 3.91-3.88 (m, 1H), 3.74-3.71 (m, 1H), 3.70-3.58 (m, 2H), 3.57-3.50 (m, 1H), 2.29 (s, 3H), 2.20-1.95 (m, 2H).

Example 146

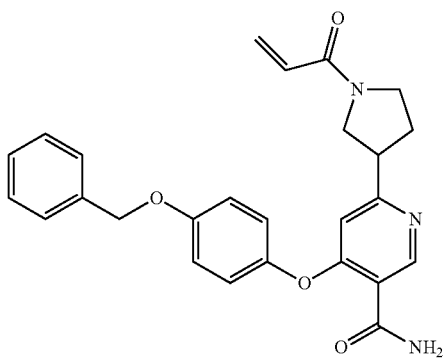 [SMILES: C=CC(=O)N1CCC(c2cc(Oc3ccc(OCc4ccccc4)cc3)c(C(N)=O)cn2)C1]

6-(1-acryloylpyrrolidin-3-yl)-4-(4-(benzyloxy)phenoxy)nicotinamide (111)

6-(1-Acryloyl-pyrrolidin-3-yl)-4-(4-benzyloxy-phenoxy)-nicotinamide (50.00 mg; 0.11 mmol; 29.6%; pale yellow solid; Purified Product) was prepared from 4,6-dichloro nicotinamide (this isomer reacts in a manner similar to the 2,4 isomer), 4-benzyloxy-phenol, (S)-Pyrrolidin-3-yl-carbamic acid tert-butyl ester and acrylic acid with methods 1A, 12A, 2C, 7D and 2D. HPLC-UV: 99.6% purity. LC/MS m/z=444.2 [M+H]$^+$. 1H NMR (400 MHz, DMSO-d6): 8.68 (s, 1H), 7.71 (s, 2H), 7.48-7.46 (m, 2H), 7.42-7.39 (m, 2H), 7.36-7.34 (m, 1H), 7.20-7.17 (m, 2H), 7.14-7.11 (m, 2H), 6.56-6.50 (m, 2H), 6.13-6.07 (m, 1H), 5.66-5.60 (m, 1H), 5.22 (s, 2H), 3.91-3.87 (m, 1H), 3.73-3.69 (m, 1H), 3.46-3.48 (m, 2H), 3.44-3.32 (m, 1H), 2.08-1.89 (m, 2H).

Example 147

Scheme 13

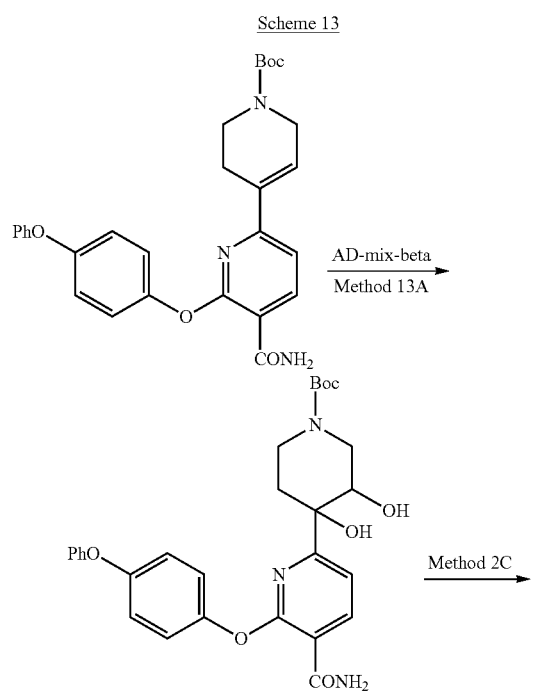

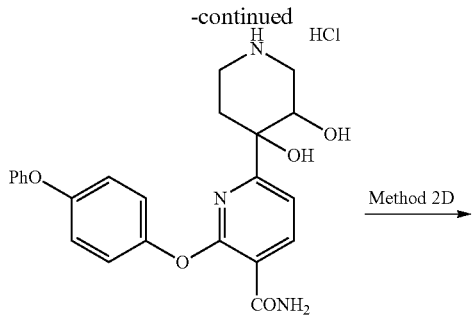

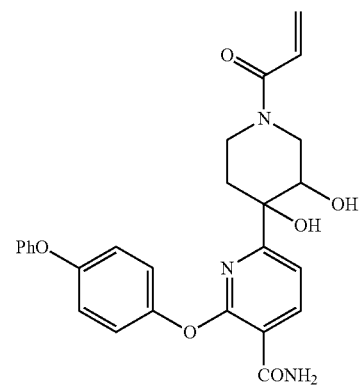

Methods Associated with Scheme 13:

tert-butyl 4-(5-carbamoyl-6-(4-phenoxyphenoxy)pyridin-2-yl)-3,4-dihydroxypiperidine-1-carboxylate (Method 13A)

The mixture of tert-butyl 5-carbamoyl-6-(4-phenoxyphenoxy)-5',6'-dihydro-[2,4'-bipyridine]-1'(2'H)-carboxylate (synthesized according to Methods 1A & 12A.) (1.8 g, 3.7 mmol, 1 eq), KOsO$_4$ (300 mg), methanesulfonamide (0.8 g), K$_3$Fe(CN)$_6$ and K$_2$CO$_3$ (1:1) (20 g) in t-BuOH (40 mL) and water (40 mL) was stirred at 50° C. for 48 h. Water (500 mL) was added and extracted by EA (100 mL*3). The organic layer was dried and concentrated to give the crude solid which was purified by re-crystallization in TBME. LC/MS m/z=522.2 [M+H]$^+$.

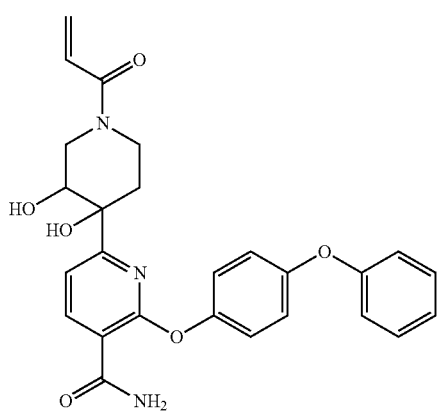

1'-Acryloyl-3',4'-dihydroxy-6-(4-phenoxy-phenoxy)-1',2',3',4',5',6'-hexahydro-[2,4']bipyridinyl-5-carboxylic acid amide (77)

1'-Acryloyl-3',4'-dihydroxy-6-(4-phenoxy-phenoxy)-1',2',3',4',5',6'-hexahydro-[2,4']bipyridinyl-5-carboxylic acid amide 53.9 mg (56%) was prepared with tert-butyl 4-(5-carbamoyl-6-(4-phenoxyphenoxy)pyridin-2-yl)-3,4-dihydroxypiperidine-1-carboxylate with method 2C and 2D. HPLC: 99.3%, RT=3.66 min. MS: m/z=476 [M+H]+. ¹H NMR (400 MHz, DMSO-d6) δ 8.19 (d, J=7.7 Hz, 1H), 7.73 (d, J=12.7 Hz, 2H), 7.55-7.34 (m, 3H), 7.29-7.08 (m, 3H), 7.08-6.94 (m, 4H), 6.74 (dd, J=16.7, 10.5 Hz, 1H), 6.05 (dt, J=17.0, 3.4 Hz, 1H), 5.63 (dd, J=10.4, 4.4 Hz, 1H), 5.19 (d, J=10.5 Hz, 1H), 4.82 (t, J=6.5 Hz, 1H), 4.41-4.01 (m, 1H), 3.77 (dd, J=21.0, 13.0 Hz, 1H), 3.56 (dq, J=10.7, 5.7, 5.1 Hz, 1H), 3.28-3.09 (m, 1H), 2.83 (dt, J=64.4, 12.0 Hz, 1H), 1.78-1.57 (m, 1H), 1.49 (d, J=13.9 Hz, 1H).

Scheme 14

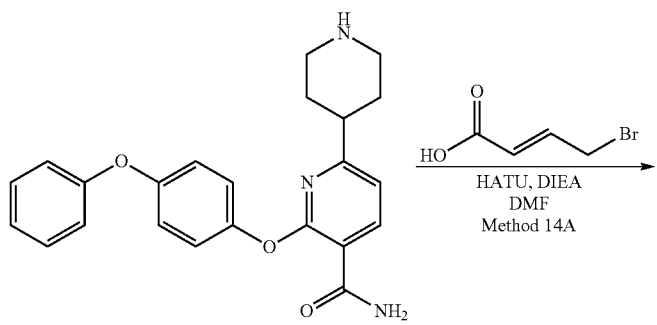

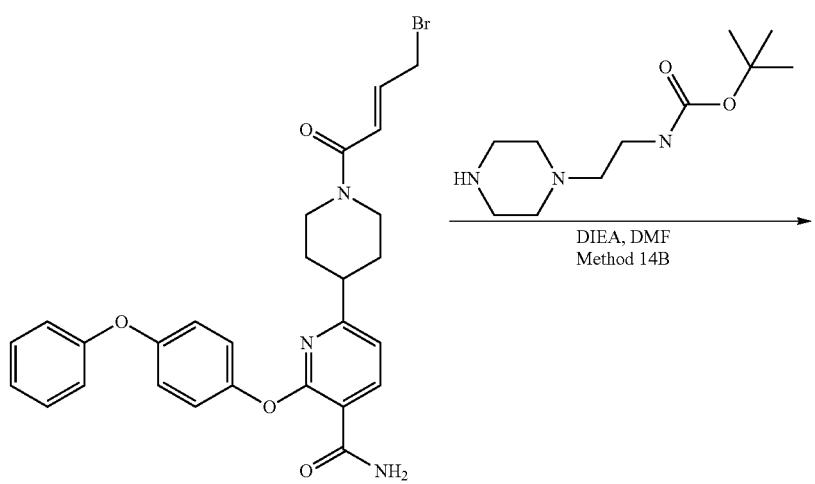

-continued
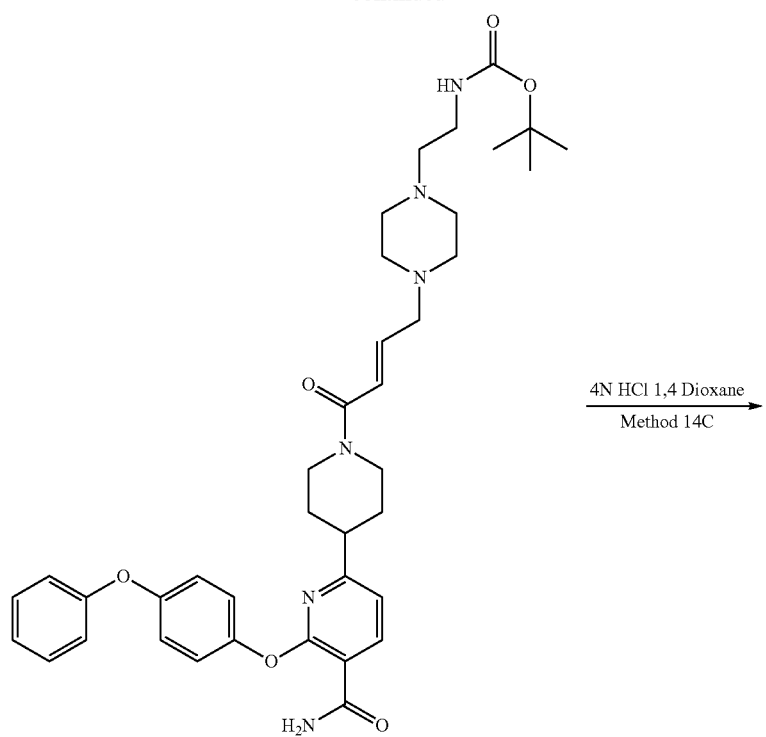
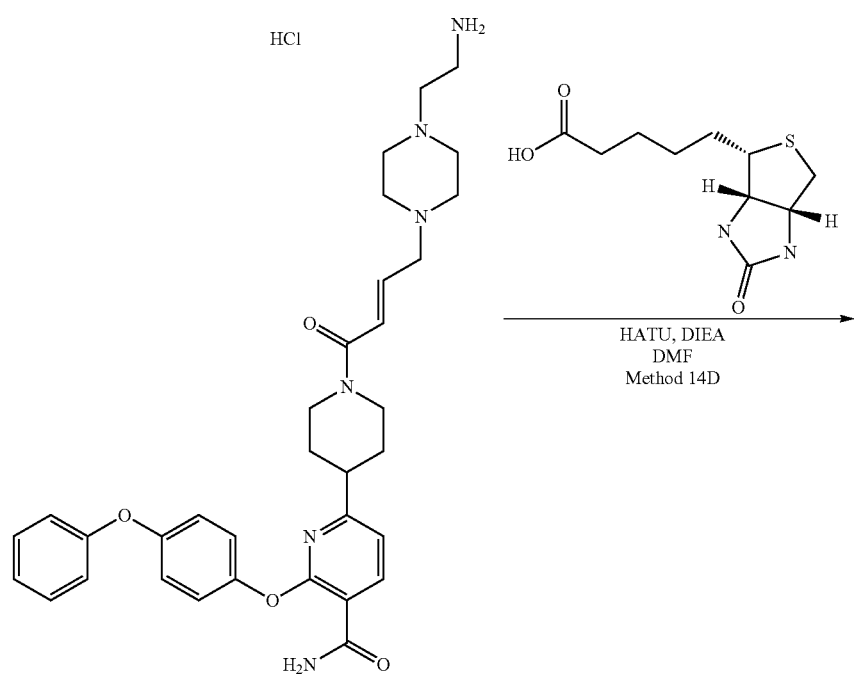

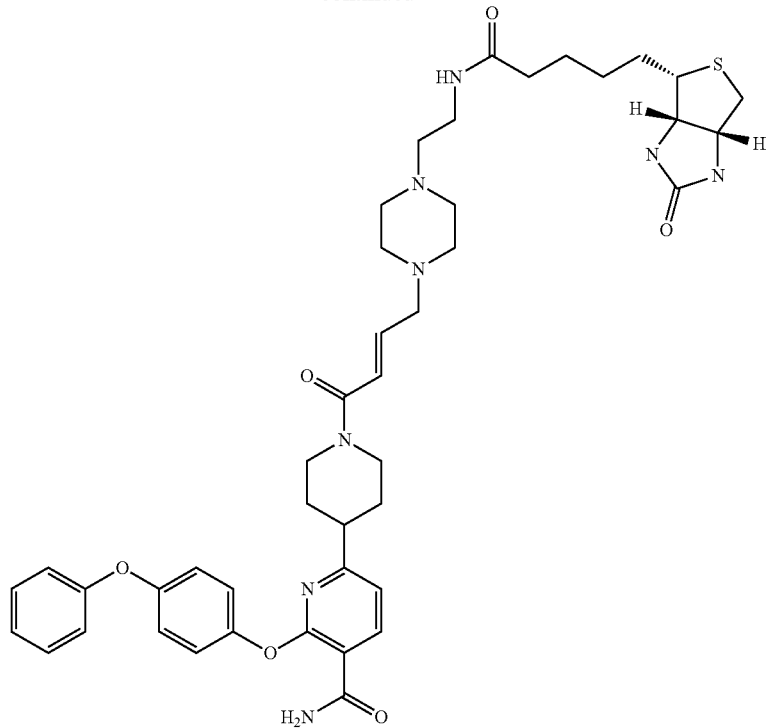
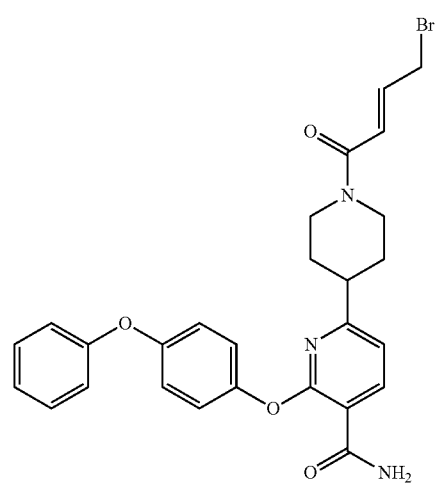

(E)-6-(1-(4-bromobut-2-enoyl)piperidin-4-yl)-2-(4-phenoxyphenoxy)nicotinamide (Method 14A)

6-(4-Phenoxy-phenoxy)-1',2',3',4',5',6'-hexahydro-[2,4']bipyridinyl-5-carboxylic acid amide (289.00 mg; 0.74 mmol; 1.00 eq.), o-(7-azabenzotriazol-1-yl)-n,n,n',n'-tetramethyluronium hexafluoro-phosphate (310.38 mg; 0.82 mmol; 1.10 eq.), (E)-4-Bromo-but-2-enoic acid (134.67 mg; 0.82 mmol; 1.10 eq.), and Triethylamine (0.31 ml; 2.23 mmol; 3.00 eq.) were all combined into DMF (5 ml). The reaction was stirred at RT overnight then all solvent was removed. The crude 6-(4-Phenoxy-phenoxy)-1'-[(E)-4-([1,2,3]triazolo[4,5-b]pyridin-3-yloxy)-but-2-enoyl]-1',2',3',4',5',6'-hexahydro-[2,4']bipyridinyl-5-carboxylic acid amide was carried into next reaction without any purification.

MS: m/z=537.3/592.1 [M+H]+.

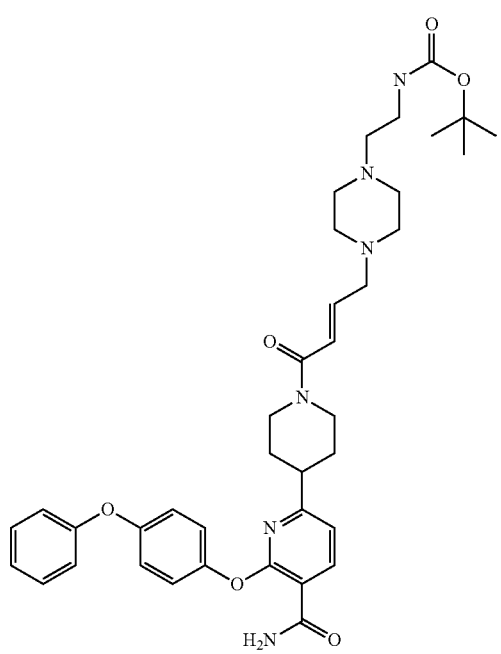 [SMILES: CC(C)(C)OC(=O)NCCN1CCN(C/C=C/C(=O)N2CCC(c3ccc(C(N)=O)c(Oc4ccc(Oc5ccccc5)cc4)n3)CC2)CC1]

(E)-tert-butyl (2-(4-(4-(4-(5-carbamoyl-6-(4-phenoxyphenoxy)pyridin-2-yl)piperidin-1-yl)-4-oxobut-2-en-1-yl)piperazin-1-yl)ethyl)carbamate (Method 14B)

Crude 6-(4-Phenoxy-phenoxy)-1'-[(E)-4-([1,2,3]triazolo[4,5-b]pyridin-3-yloxy)-but-2-enoyl]-1',2',3',4',5',6'-hexahydro-[2,4']bipyridinyl-5-carboxylic acid amide was combined with tert-butyl (2-(piperazin-1-yl)ethyl)carbamate (398.11 mg, 0.742 mmol, 1 eq) along with DIEA (0.366 ml, 2.23 mmol, into DMF (5 mL). The reaction was heated to 80° C. for 5 hr. Heating was then removed on the solvent was removed under reduced pressure. The reaction was then purified via flash column chromatography on silica using a gradient of 0-20% MeOH/DCM to give (E)-tert-butyl (2-(4-(4-(4-(5-carbamoyl-6-(4-phenoxyphenoxy)pyridin-2-yl)piperidin-1-yl)-4-oxobut-2-en-1-yl)piperazin-1-yl)ethyl)carbamate (33.2 mg, 22%) as a brown solid. MS: m/z=685.2 [M+H]+.

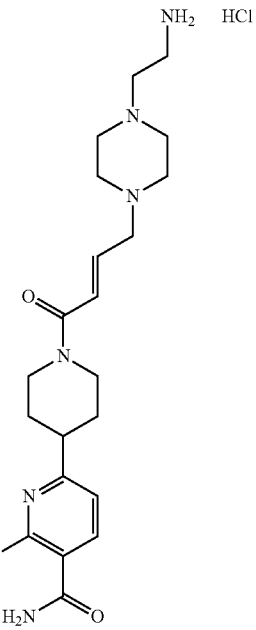

1'-{(E)-4-[4-(2-Amino-ethyl)-piperazin-1-yl]-but-2-enoyl}-6-(4-phenoxy-phenoxy)-1',2',3',4',5',6'-hexahydro-[2,4']bipyridinyl-5-carboxylic acid amide hydrochloride (Method 14C)

[2-(4-{(E)-4-[5-Carbamoyl-6-(4-phenoxy-phenoxy)-3',4',5',6'-tetrahydro-TH-[2,4']bipyridinyl-1'-yl]-4-oxo-but-2-enyl}-piperazin-1-yl)-ethyl]-carbamic acid tert-butyl ester (31.00 mg; 0.05 mmol; 1.00 eq.) was combined with 4 N 1,4 dioxane (5 ml) along with MeOH (1 ml). The reaction was stirred at RT for 1.5 hrs then dried under vacuum for 1 hr to give 1'-{(E)-4-[4-(2-Amino-ethyl)-piperazin-1-yl]-but-2-enoyl}-6-(4-phenoxy-phenoxy)-1',2',3',4',5',6'-hexahydro-[2,4']bipyridinyl-5-carboxylic acid amide hydrochloride which was used without purification. MS: m/z=585.1 [M+H]+.

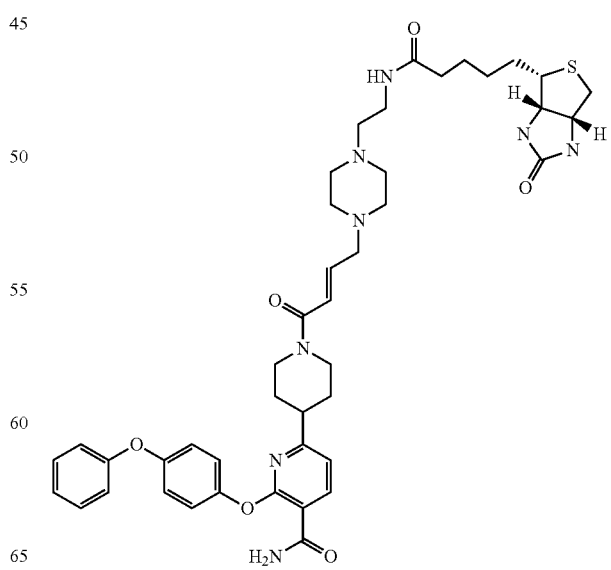

317

6-(1-((E)-4-(4-(2-(5-((3aS,4S,6aR)-2-oxohexahydro-1H-thieno[3,4-d]imidazol-4-yl)pentanamido)ethyl)piperazin-1-yl)but-2-enoyl)piperidin-4-yl)-2-(4-phenoxyphenoxy)nicotinamide (Method 14D) (86)

1'-{(E)-4-[4-(2-Amino-ethyl)-piperazin-1-yl]-but-2-enoyl}-6-(4-phenoxy-phenoxy)-1',2',3',4',5',6'-hexahydro-[2,4']bipyridinyl-5-carboxylic acid amide hydrochloride (11.00 mg; 0.02 mmol; 1.00 eq.) was combined with 5-((3aR,6S,6aS)-2-Oxo-hexahydro-thieno[3,4-d]imidazol-6-yl)-pentanoic acid (4.48 mg; 0.02 mmol; 1.15 eq.), 1-(3-dimethylaminopropyl)-3-ethylcarbodiimide (0.02 mmol; 1.50 eq.; 3.71 mg; 0.00 ml), and Triethylamin (0.01 ml; 0.08 mmol; 5.00 eq.) in DCM (23.40 mmol; 1468.27 eq.; 1987.50 mg; 1.50 ml). The reaction mixture was stirred at RT over 2 days. The reaction was then diluted with DCM (4 ml) and extreacted with H$_2$O (3×'s 4 ml). Organics were concentrated and crude reaction was purified via reverse phase chromatography using a gradient of 25-95% CH$_3$CN/H2O (0.1% Formic Acid) to give 1'-[4-(4-{2-[5-((3 aR,6S,6aS)-2-Oxo-hexahydro-thieno[3,4-d]imidazol-6-yl)-pentanoylamino]-ethyl}-piperazin-1-yl)-but-2-enoyl]-6-(4-phenoxy-phenoxy)-1',2',3',4',5',6'-hexahydro-[2,4']bipyridinyl-5-carboxylic acid amide (2.50 mg; 17%) as a white solid. HPLC: 90%, RT=3.11 min. MS: m/z=812 [M+H]+. $^1$H NMR (400 MHz, CDCl$_3$) δ 8.56 (d, J=7.8 Hz, 1H), 7.89 (s, 1H), 7.79-7.66 (m, 2H), 7.50-7.31 (m, 2H), 7.19-6.99 (m, 5H), 6.78 (dd, J=14.2, 7.2 Hz, 1H), 6.43 (d, J=15.4 Hz, 1H), 5.82-5.65 (m, 2H), 4.92-4.84 (s, 2H), 4.34-4.27 (m, 2H), 4.35 (s, 2H), 3.95 (s, 2H), 3.52 (d, J=3.8 Hz, 2H), 3.28-3.07 (m, 2H), 3.05-2.78 (m, 15H), 2.24 (dd, J=13.3, 7.0 Hz, 2H), 1.93-1.80 (m, 2H), 1.61-1.34 (m, 4H).

Example 149

Scheme 15

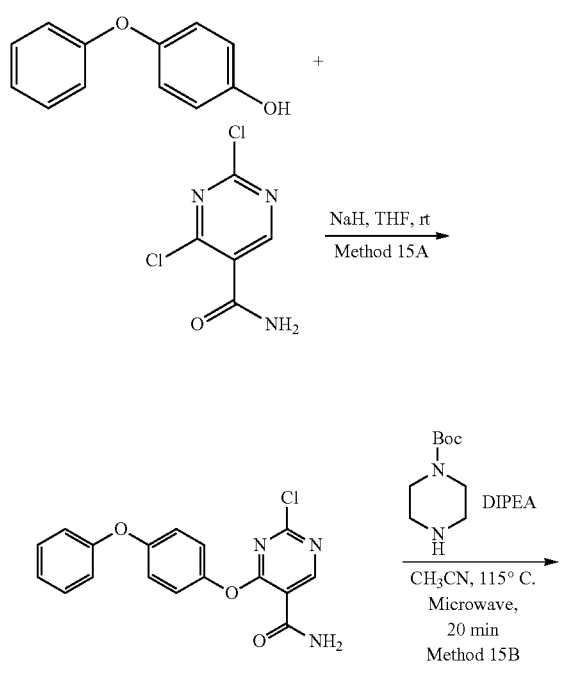

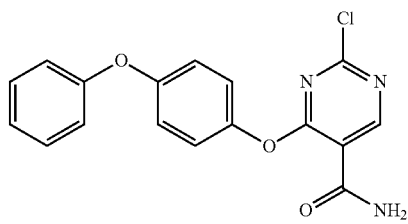 [SMILES: NC(=O)c1cnc(Cl)nc1Oc1ccc(Oc2ccccc2)cc1]

318

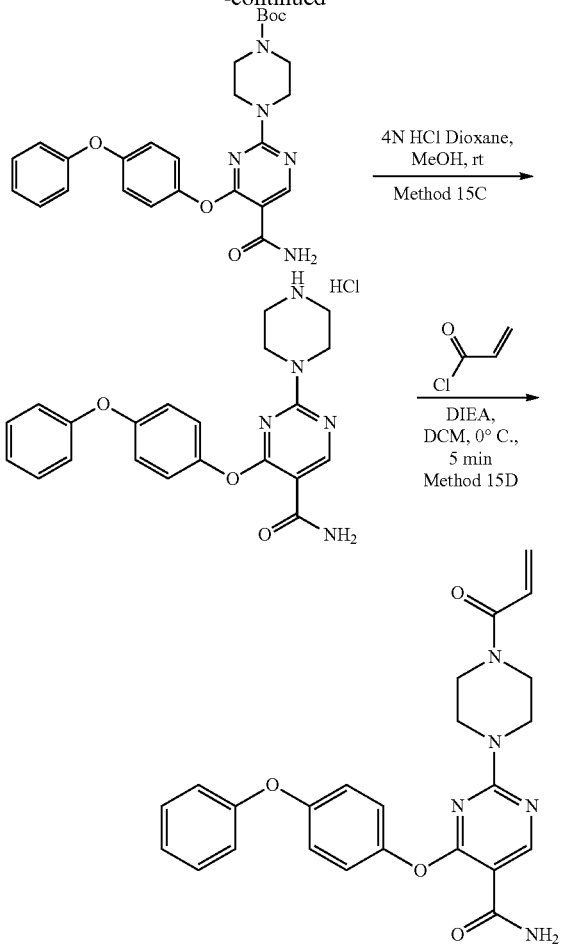

Methods Associated with Reaction Steps in Scheme 15

2-Chloro-4-(4-phenoxy-phenoxy)-pyrimidine-5-carboxylic acid amide (Method 15A)

2,4-Dichloro-pyrimidine-5-carboxylic acid amide (2000.00 mg; 10.42 mmol; 1.00 eq.) was dissolved into THF (200.00 ml; 2468.59 mmol; 236.99 eq.) and then cooled to 0° C. on an ice bath. 4-Phenoxy-phenol (1745.67 mg; 9.37 mmol; 0.90 eq.) was then added followed by sodium hydride, 60% in mineral oil (833.32 mg; 20.83 mmol; 2.00 eq.). Reaction was diluted with saturated sodium hydrogen carbonate then extracted three times with EtOAc. Organics were combined then concentrated to dryness. Purified on silica using a gradient of 0-50% EtOAC/Hexanes to give 2-Chloro-4-(4-phenoxy-phenoxy)-pyrimidine-5-carboxylic acid amide (2876.00 mg; 80%) as a white solid. MS: m/z=392.2[M+H]+.

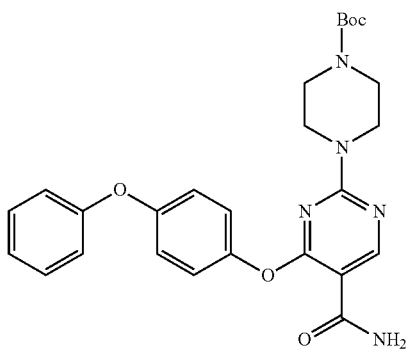 [SMILES: CC(C)(C)OC(=O)N1CCN(c2ncc(C(N)=O)c(Oc3ccc(Oc4ccccc4)cc3)n2)CC1]

4-[5-Carbamoyl-4-(4-phenoxy-phenoxy)-pyrimidin-2-yl]-piperazine-1-carboxylic acid tert-butyl ester (Method 15B)

2-Chloro-4-(4-phenoxy-phenoxy)-pyrimidine-5-carboxylic acid amide (0.41 mmol; 1.00 eq.; 141.00 mg) was combined with Piperazine-1-carboxylic acid tert-butyl ester (0.45 mmol; 1.10 eq.; 105.66 mg) and C8H19N (1.24 mmol; 3.00 eq.; 159.97 mg; 0.22 ml) into MeCN (76.58 mmol; 185.62 eq.; 3144.00 mg; 4.00 ml). The mixture was then heated in the microwave for 20 minutes are 115° C. The reaction was then purified directly on silica using a gradient of 25-100% EtOAC to give 4-[5-Carbamoyl-4-(4-phenoxy-phenoxy)-pyrimidin-2-yl]-piperazine-1-carboxylic acid tert-butyl ester 90 mg (44%). MS: m/z=492.3 [M+H]+.

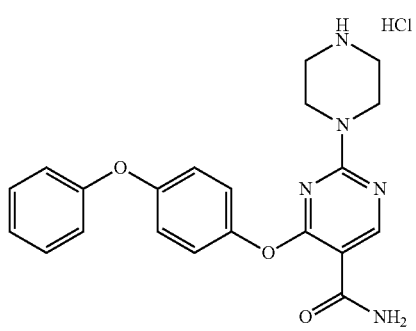 [SMILES: Cl ; NC(=O)c1cnc(N2CCNCC2)nc1Oc1ccc(Oc2ccccc2)cc1]

4-(4-Phenoxy-phenoxy)-2-piperazin-1-yl-pyrimidine-5-carboxylic acid amide hydrochloride (Method 15C)

4-[5-Carbamoyl-4-(4-phenoxy-phenoxy)-pyrimidin-2-yl]-piperazine-1-carboxylic acid tert-butyl ester (0.32 mmol; 1.00 eq.; 158.00 mg) was combined with HCl solution 4M in Dioxane (5.00 ml). The reaction was stirred at RT for 1 hr. All the solvent was then removed and the residue was dried to give 4-(4-Phenoxy-phenoxy)-2-piperazin-1-yl-pyrimidine-5-carboxylic acid amide hydrochloride 138.00 mg, which was used without purification. MS: m/z=392.1 [M+H]+

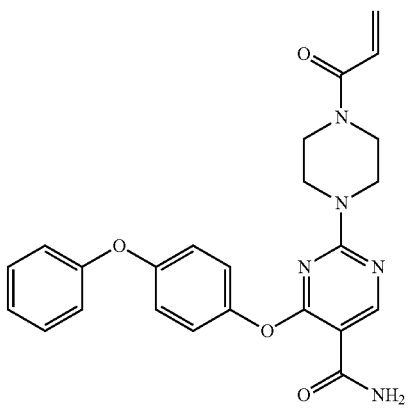 [SMILES: C=CC(=O)N1CCN(c2ncc(C(N)=O)c(Oc3ccc(Oc4ccccc4)cc3)n2)CC1]

2-(4-Acryloyl-piperazin-1-yl)-4-(4-phenoxy-phenoxy)-pyrimidine-5-carboxylic acid amide (173) (Method 15D)

4-(4-Phenoxy-phenoxy)-2-piperazin-1-yl-pyrimidine-5-carboxylic acid amide hydrochloride (0.32 mmol; 1.00 eq.; 137.00 mg) was suspended in DCM (78.00 mmol; 243.62 eq.; 6625.00 mg; 5.00 ml) and cooled to 0° C. on an ice bath. DIEA (0.96 mmol; 3.00 eq.; 124.06 mg; 0.16 ml) was then added followed by a solution of Acryloyl chloride (0.35 mmol; 1.10 eq.; 31.88 mg; 0.03 ml) in 1 mL DCM which was added dropwise over five minutes. 1 mL of MeOH was then added and all solvent was removed. The reaction was purified via reverse phase using a gradient of 30-80% $CH_3CN/H_2O$ (0.1% formic acid) over 15 minutes to give 2-(4-Acryloyl-piperazin-1-yl)-4-(4-phenoxy-phenoxy)-pyrimidine-5-carboxylic acid amide 16.00 mg (11%). HPLC: 98%, RT=4.01 min. MS: m/z=446.1 [M+H]+. $^1$H NMR (400 MHz, CDCl$_3$) δ 9.08 (s, 1H), 7.45-7.35 (m, 3H), 7.25-7.0 (m, 8H), 6.64-6.52 (m, 1H), 6.35 (dd, J=16.8, 1.8 Hz, 1H), 5.76 (dd, J=10.5, 1.8 Hz, 1H), 4.02-3.28 (m, 8H).

Example 150

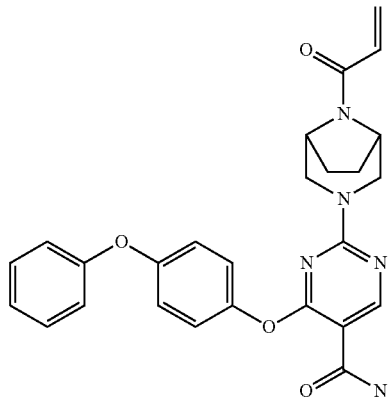 [SMILES: C=CC(=O)N1C2CCC1CN(c1ncc(C(N)=O)c(Oc3ccc(Oc4ccccc4)cc3)n1)C2]

2-(8-Acryloyl-3,8-diaza-bicyclo[3.2.1]oct-3-yl)-4-(4-phenoxy-phenoxy)-pyrimidine-5-carboxylic acid amide (149)

2-(8-Acryloyl-3,8-diaza-bicyclo[3.2.1]oct-3-yl)-4-(4-phenoxy-phenoxy)-pyrimidine-5-carboxylic acid amide was prepared from 2,4-dichloropyrimidine-5-carboxamide, 3,8-Diaza-bicyclo[3.2.1]octane-8-carboxylic acid tert-butyl ester, and acryloyl chloride with methods 15A, 15B, 15C and 15D. HPLC: 91.3%, RT=4.21 min. MS: m/z=472 [M+H]+ 3.71 min. $^1$H NMR (400 MHz, DMSO) δ 8.67 (s, 1H), 7.63-7.22 (m, 4H), 7.10 (ddd, J=35.5, 16.5, 8.7 Hz, 3H), 6.94-6.57 (m, 3H), 6.19 (dd, J=16.7, 2.1 Hz, 1H), 5.71 (d, J=10.5 Hz, 1H), 4.71-4.31 (m, 2H), 3.80 (d, J=59.4 Hz, 1H), 3.12-2.72 (m, 4H), 1.99-1.33 (m, 4H).

Example 151

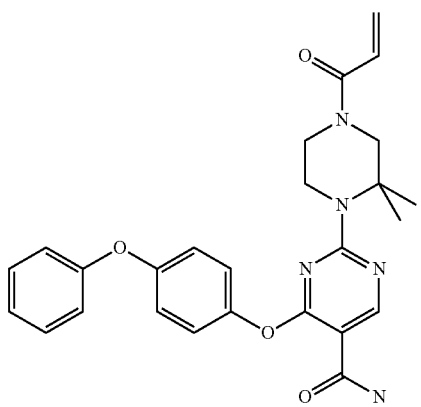 [SMILES: C=CC(=O)N1CCN(c2ncc(C(N)=O)c(Oc3ccc(Oc4ccccc4)cc3)n2)C(C)(C)C1]

6-((S)-3-Acryloylamino-pyrrolidin-1-yl)-2-[4-(2-pyrrolidin-1-yl-ethyl)-phenylamino]-nicotinamide (151)

6-((S)-3-Acryloylamino-pyrrolidin-1-yl)-2-[4-(2-pyrrolidin-1-yl-ethyl)-phenylamino]-nicotinamide was prepared from 2,4-dichloropyrimidine-5-carboxamide, 4-(2-(pyrrolidin-1-yl)ethyl)aniline, (S)-Pyrrolidin-3-yl-carbamic acid tert-butyl ester and acryloyl chloride with methods 15A, 15B, 15C and 15D. HPLC: 99.9%, RT=4.30 min. MS: m/z=475 [M+H]+. $^1$H NMR (400 MHz, DMSO) δ 8.75 (s, 1H), 7.57-7.22 (m, 3H), 7.29-6.90 (m, 7H), 6.70 (dd, J=16.9, 10.3 Hz, 1H), 5.99 (d, J=16.7 Hz, 1H), 5.59 (d, J=11.3 Hz, 1H), 3.97-3.57 (m, 4H), 3.55-3.45 9M, 2H), 1.40 (s, 3H), 1.26 (s, 3H).

Example 152

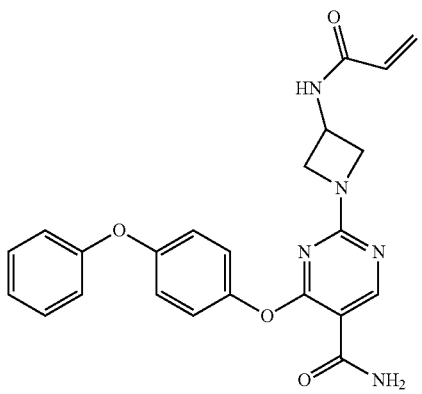 [SMILES: C=CC(=O)NC1CN(c2ncc(C(N)=O)c(Oc3ccc(Oc4ccccc4)cc3)n2)C1]

2-(3-Acryloylamino-azetidin-1-yl)-4-(4-phenoxy-phenoxy)-pyrimidine-5-carboxylic acid amide (174)

2-(3-Acryloylamino-azetidin-1-yl)-4-(4-phenoxy-phenoxy)-pyrimidine-5-carboxylic acid amide 22.6 mg (38%) was prepared from 2,4-dichloropyrimidine-5-carboxamide, 4-(2-(pyrrolidin-1-yl)ethyl)aniline, (S)-Pyrrolidin-3-yl-carbamic acid tert-butyl ester and acrylic acid with methods 15A, 15B, 15C and 15D. HPLC: 99.9%, RT=4.30 min. MS: m/z=475 [M+H]+. $^1$H NMR (400 MHz, DMSO) δ 8.71 (s, 1H), 7.56-7.22 (m, 3H), 7.25-6.88 (m, 7H), 6.71 (dd, J=16.9, 10.3 Hz, 1H), 6.0 (d, J=16.7 Hz, 1H), 5.60 (d, J=11.3 Hz, 1H), 4.44-4.33 (m, 1H) 3.87-3.57 (m, 4H).

Example 153

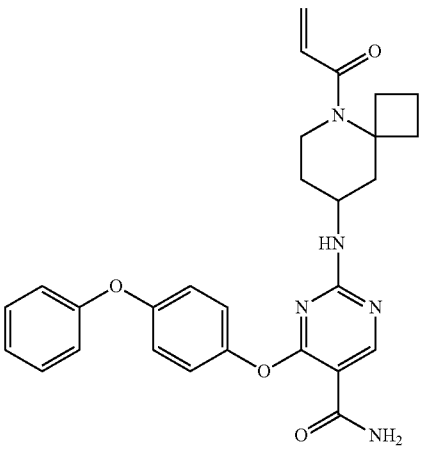 [SMILES: C=CC(=O)N1CCC(Nc2ncc(C(N)=O)c(Oc3ccc(Oc4ccccc4)cc3)n2)CC12CCC2]

2-(5-Acryloyl-5-aza-spiro[3.5]non-8-ylamino)-4-(4-phenoxy-phenoxy)-pyrimidine-5-carboxylic acid amide (175)

2-(5-Acryloyl-5-aza-spiro[3.5]non-8-ylamino)-4-(4-phenoxy-phenoxy)-pyrimidine-5-carboxylic acid amide 47.00 mg (29%) was prepared from 2,4-dichloropyrimidine-5-carboxamide, 4-(2-(pyrrolidin-1-yl)ethyl)aniline, (S)-Pyrrolidin-3-yl-carbamic acid tert-butyl ester and acrylic acid with methods 15A, 15B, 15C and 15D. HPLC: 99.9%, RT=4.88 min. MS: m/z=500.2 [M+H]+. $^1$H NMR (400 MHz, CDCl$_3$) δ 9.76 (s, 1H), 8.94 (s, 1H), 7.42 (t, J=7.9 Hz, 2H), 7.31-6.87 (m, 7H), 6.33 (ddd, J=18.6, 16.7, 6.1 Hz, 3H), 5.66 (dd, J=10.3, 1.8 Hz, 1H), 4.11-3.55 (m, 2H), 3.10-2.56 (m, 2H), 2.35-1.08 (m, 9H).

Example 154

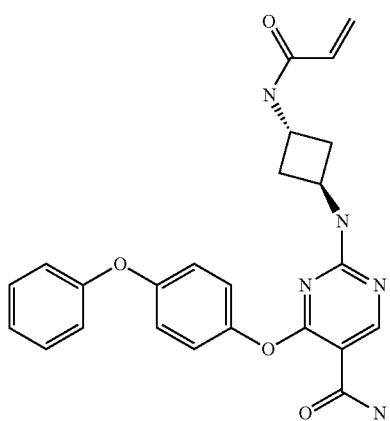 [SMILES: C=CC(=O)N[C@H]1C[C@H](Nc2ncc(C(N)=O)c(Oc3ccc(Oc4ccccc4)cc3)n2)C1]

2-(((1r,3r)-3-acrylamidocyclobutyl)amino)-4-(4-phenoxyphenoxy)pyrimidine-5-carboxamide (176)

2-(((1r,3r)-3-acrylamidocyclobutyl)amino)-4-(4-phenoxyphenoxy)pyrimidine-5-carboxamide 51 mg (56%) was prepared using methods 15A, 15B, 15C and 15D. HPLC: 98.9%, RT=3.52 min. MS: m/z=447.1 [M+H]+. $^1$H NMR (400 MHz, CDCl$_3$) δ 8.88 (s, 1H), 7.43-7.24 (m, 2H), 7.19-6.90 (m, 8H), 6.30-5.99 (m, 2H), 5.61 (d, J=10.3 Hz, 1H), 4.26-3.97 (m, 1H), 3.71-3.56 (m, 1H), 3.37 (m, 2H), 2.74 (m, 2H), 2.03-1.58 (m, 2H).

Example 155

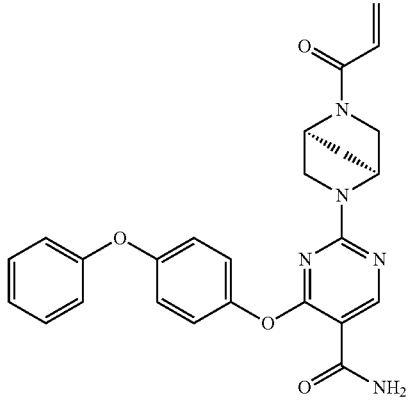 [SMILES: C=CC(=O)N1C[C@@H]2C[C@H]1CN2c1ncc(C(N)=O)c(Oc2ccc(Oc3ccccc3)cc2)n1]

2-((1S,4S)-5-acryloyl-2,5-diazabicyclo[2.2.1]heptan-2-yl)-4-(4-phenoxyphenoxy)pyrimidine-5-carboxamide (147)

2-((1S,4S)-5-acryloyl-2,5-diazabicyclo[2.2.1]heptan-2-yl)-4-(4-phenoxyphenoxy)pyrimidine-5-carboxamide 137 mg (52%) was prepared using methods 15A, 15B, 15C and 15D. HPLC: 99.9%, RT=3.52 min. MS: m/z=456.3 [M+H]+. $^1$H NMR (400 MHz, DMSO) δ 8.71 (s, 1H), 7.56-7.22 (m, 4H), 7.22-6.80 (m, 6H), 6.74 (dd, J=16.8, 10.4 Hz, 1H), 6.13 (dd, J=16.7, 2.3 Hz, 1H), 5.65 (d, J=9.7 Hz, 1H), 5.13-4.68 (m, 2H), 4.39-4.31 (m, 1H), 3.82-3.36 (m, 2H), 3.09-3.02 (m, 2H), 2.26-1.83 (m, 1H).

Example 156

Scheme 16

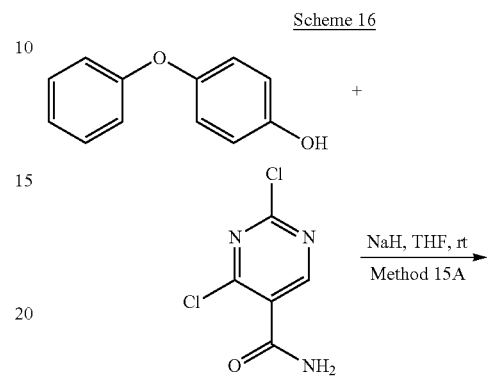

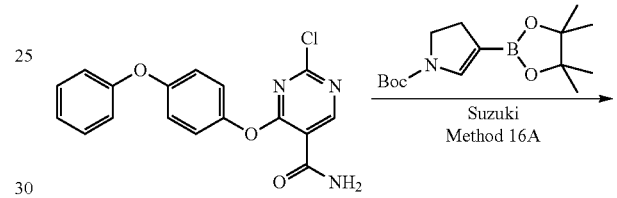

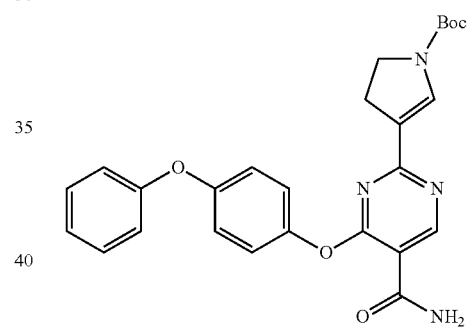

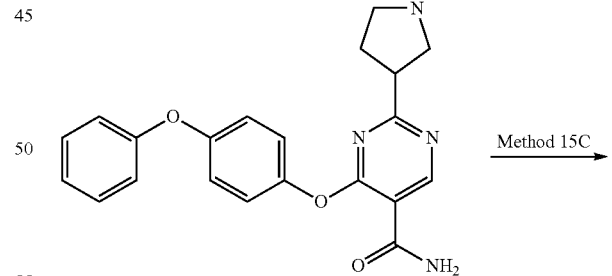

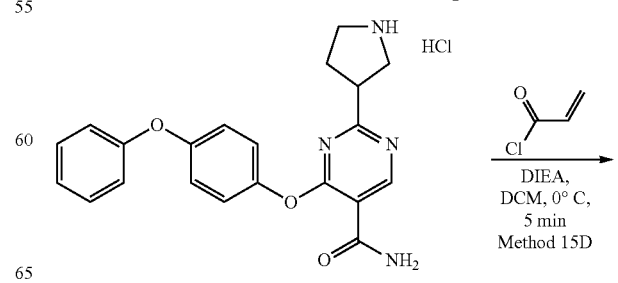

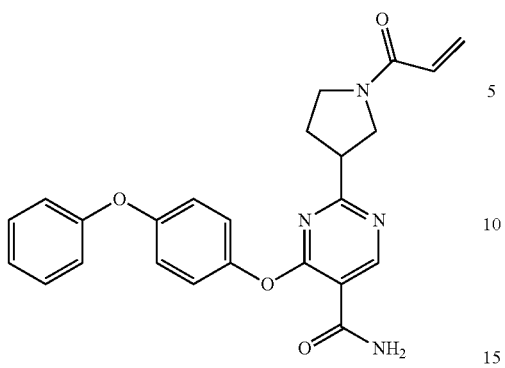

Methods Associated with Reaction Steps in Scheme 16:

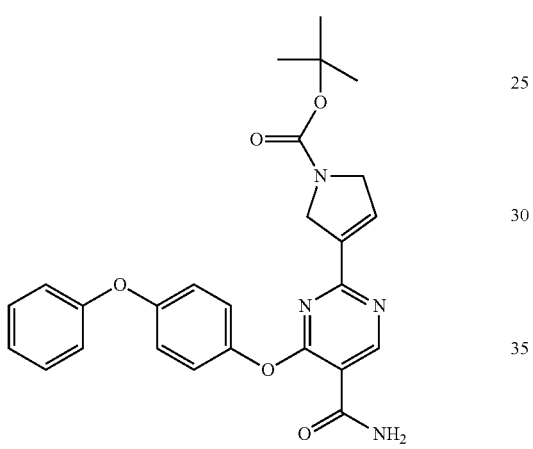

3-[5-Carbamoyl-4-(4-phenoxy-phenoxy)-pyrimidin-2-yl]-2,5-dihydro-pyrrole-1-carboxylic acid tert-butyl ester (Method 16A)

2-Chloro-4-(4-phenoxy-phenoxy)-pyrimidine-5-carboxylic acid amide (250.00 mg; 0.73 mmol; 1.00 eq.) (prepared from Method 15A), 3-(4,4,5,5-Tetramethyl-[1,3,2]dioxaborolan-2-yl)-2,5-dihydro-pyrrole-1-carboxylic acid tert-butyl ester (259.12 mg; 0.88 mmol; 1.20 eq.), and [1,1'-bis(diphenylphosphino)ferrocene]dichloropalladium(ii), complex with dichloromethane (1:1) (59.74 mg; 0.07 mmol; 0.10 eq.) were combined into a microwave vessel. The vessel was evacuated and back-filled with N2 (3×). Added [1,4]dioxane (3.00 ml; 34.05 mmol; 46.55 eq.) and then evacuated and back-filled with N2 (3×) again. Stirred at 140° C. in a microwave for 20 min. Reaction mixture purified directly via flash silica column chromatography using 10% EA/Hex isocratic for 1 min then ramped to 60% EA/Hex over 5 min to give 3-[5-Carbamoyl-4-(4-phenoxy-phenoxy)-pyrimidin-2-yl]-2,5-dihydro-pyrrole-1-carboxylic acid tert-butyl ester (336.00 mg; 0.71 mmol) as an white solid. MS: m/z=475 [M+H]+.

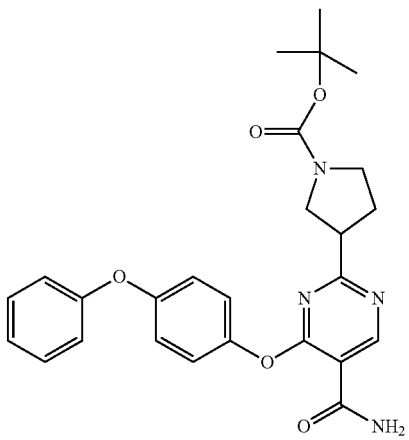 [SMILES: CC(C)(C)OC(=O)N1CCC(c2ncc(C(N)=O)c(Oc3ccc(Oc4ccccc4)cc3)n2)C1]

3-[5-Carbamoyl-4-(4-phenoxy-phenoxy)-pyrimidin-2-yl]-pyrrolidine-1-carboxylic acid tert-butyl ester 3-[5-Carbamoyl-4-(4-phenoxy-phenoxy)-pyrimidin-2-yl]-pyrrolidine-1-carboxylic acid tert-butyl ester 276.00 mg was prepared from 3-[5-Carbamoyl-4-(4-phenoxy-phenoxy)-pyrimidin-2-yl]-2,5-dihydro-pyrrole-1-carboxylic acid tert-butyl ester using Method 7D which was carried forward without purification. MS: m/z=477.2 [M+H]+.

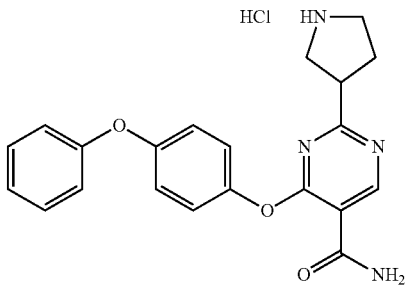 [SMILES: Cl ; NC(=O)c1cnc(C2CCNC2)nc1Oc1ccc(Oc2ccccc2)cc1]

4-(4-Phenoxy-phenoxy)-2-pyrrolidin-3-yl-pyrimidine-5-carboxylic acid amide hydrochloride 4-(4-Phenoxy-phenoxy)-2-pyrrolidin-3-yl-pyrimidine-5-carboxylic acid amide hydrochloride 58.00 mg was prepared from 3-[5-Carbamoyl-4-(4-phenoxy-phenoxy)-pyrimidin-2-yl]-pyrrolidine-1-carboxylic acid tert-butyl ester using Method 15 C. Material was used directly without additional purification. MS: m/z=377.1 [M+H]+.

327

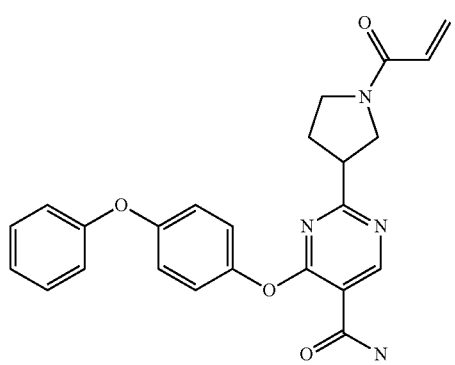 [SMILES: C=CC(=O)N1CCC(c2ncc(C(N)=O)c(Oc3ccc(Oc4ccccc4)cc3)n2)C1]

2-(1-Acryloyl-pyrrolidin-3-yl)-4-(4-phenoxy-phenoxy)-pyrimidine-5-carboxylic acid amide (150)

2-(1-Acryloyl-pyrrolidin-3-yl)-4-(4-phenoxy-phenoxy)-pyrimidine-5-carboxylic acid amide 18.00 mg (11%) was prepared from 4-(4-Phenoxy-phenoxy)-2-pyrrolidin-3-yl-pyrimidine-5-carboxylic acid amide hydrochloride using procedure 15D. HPLC: 100%, RT=3.79 min. MS: m/z=431 [M+H]+. $^1$H NMR (400 MHz, DMSO) δ 8.90 (d, J=3.8 Hz, 1H), 7.87 (d, J=20.6 Hz, 2H), 7.42 (d, J=7.5 Hz, 1H), 7.29 (d, J=8.8 Hz, 1H), 7.17 (t, J=7.3 Hz, 1H), 7.07 (t, J=8.7 Hz, 2H), 6.50-6.47 (m, 1H), 6.10 (d, J=16.9 Hz, 1H), 5.72-5.55 (m, 1H), 3.95-3.43 (m, 4H), 3.45-3.34 (m, 1H), 2.34-1.88 (d, 2H).

328

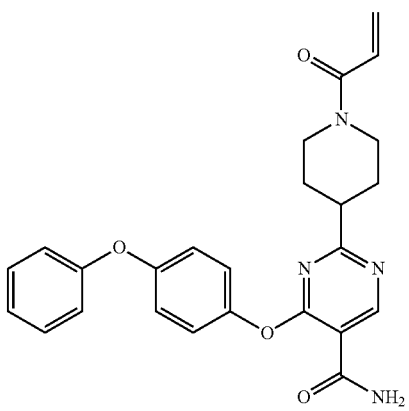

2-(1-Acryloyl-piperidin-4-yl)-4-(4-phenoxy-phenoxy)-pyrimidine-5-carboxylic acid amide (148)

2-(1-Acryloyl-piperidin-4-yl)-4-(4-phenoxy-phenoxy)-pyrimidine-5-carboxylic acid amide was prepared in a manner similar to that described above using -(4,4,5,5-Tetramethyl-[1,3,2]dioxaborolan-2-yl)-3,6-dihydro-2H-pyridine-1-carboxylic acid tert-butyl ester with methods 16A, 7D, 15C and 15D. HPLC: 95.1%, RT=3.21 min. MS: m/z=423 [M+H]+. $^1$H NMR (400 MHz, DMSO) δ 8.89 (s, 1H), 7.97-7.79 (m, 2H), 7.43 (t, J=7.6 Hz, 1H), 7.30 (d, J=8.8 Hz, 1H), 7.21-6.95 (m, 5H), 6.88-6.74 (m, 2H), 6.08 (d, J=14.8 Hz, 1H), 5.65 (d, J=12.4 Hz, 1H), 4.26 (s, 1H), 3.96 (s, 1H), 3.76-2.24 (m, 4H), 1.92-1.78 (m, 2H), 1.61-1.37 (m, 2H).

Example 158

Scheme 17

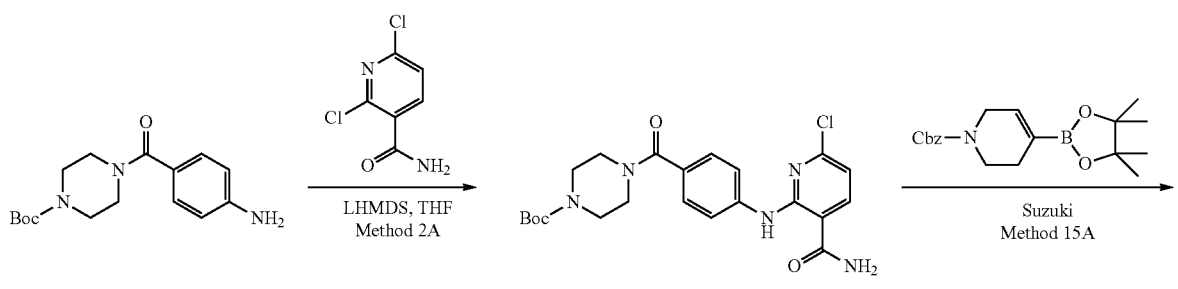

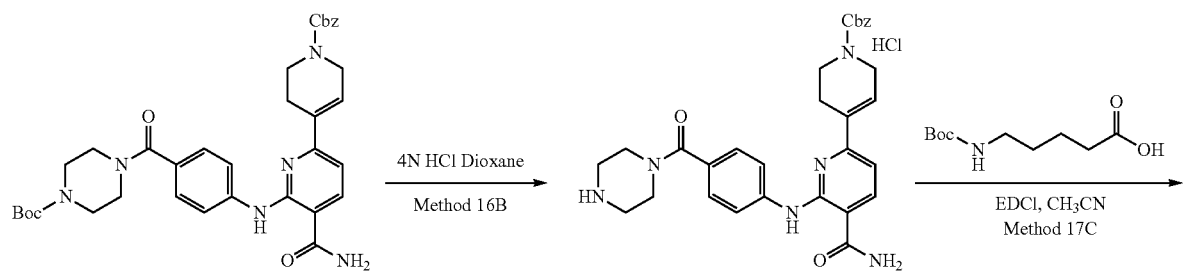

-continued
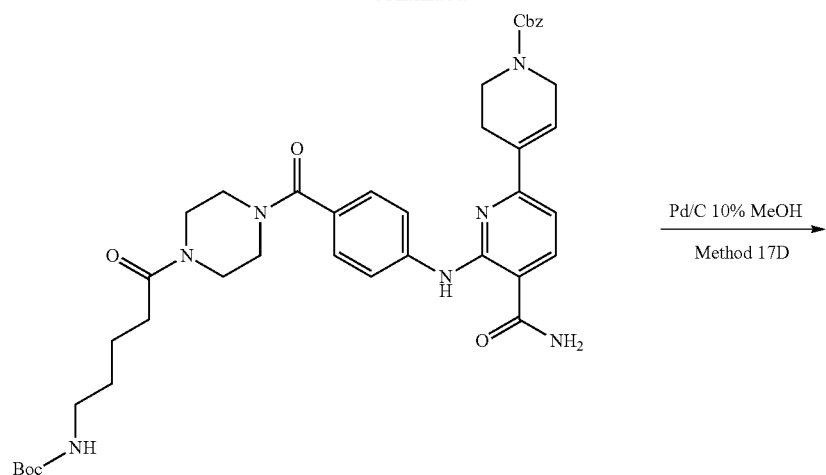
Pd/C 10% MeOH
Method 17D
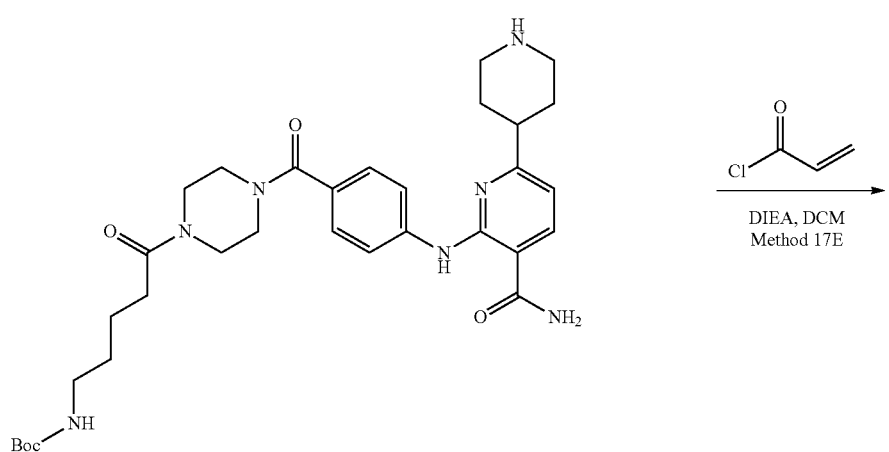
DIEA, DCM
Method 17E
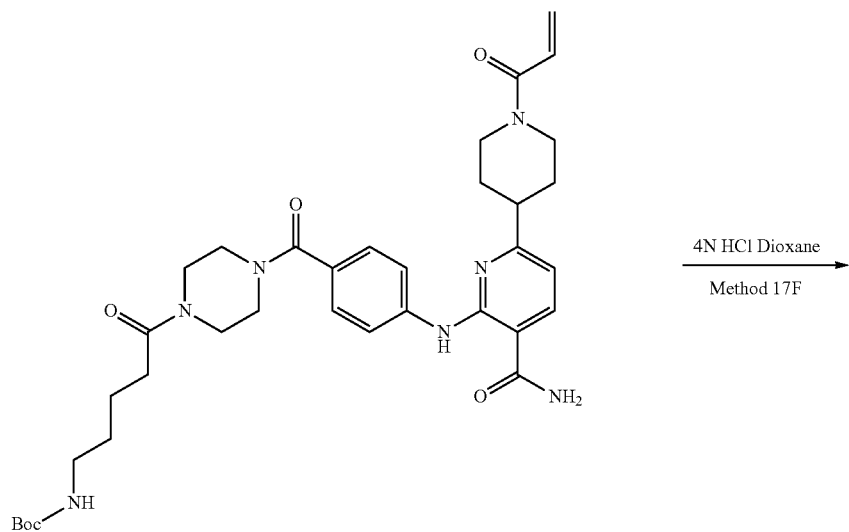
4N HCl Dioxane
Method 17F

331
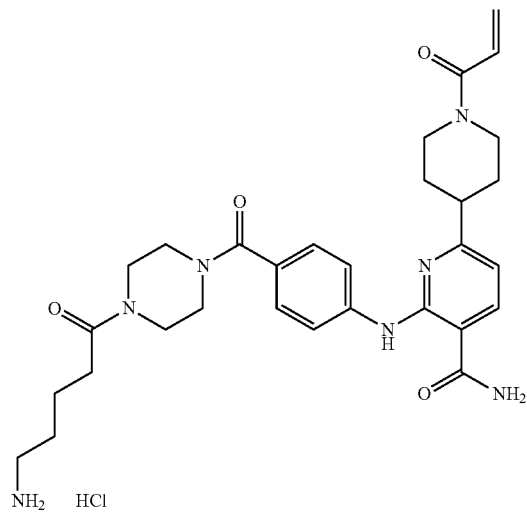
332
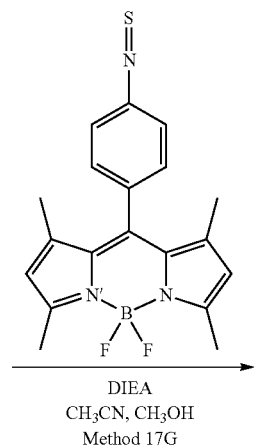
→ DIEA
CH₃CN, CH₃OH
Method 17G
-continued
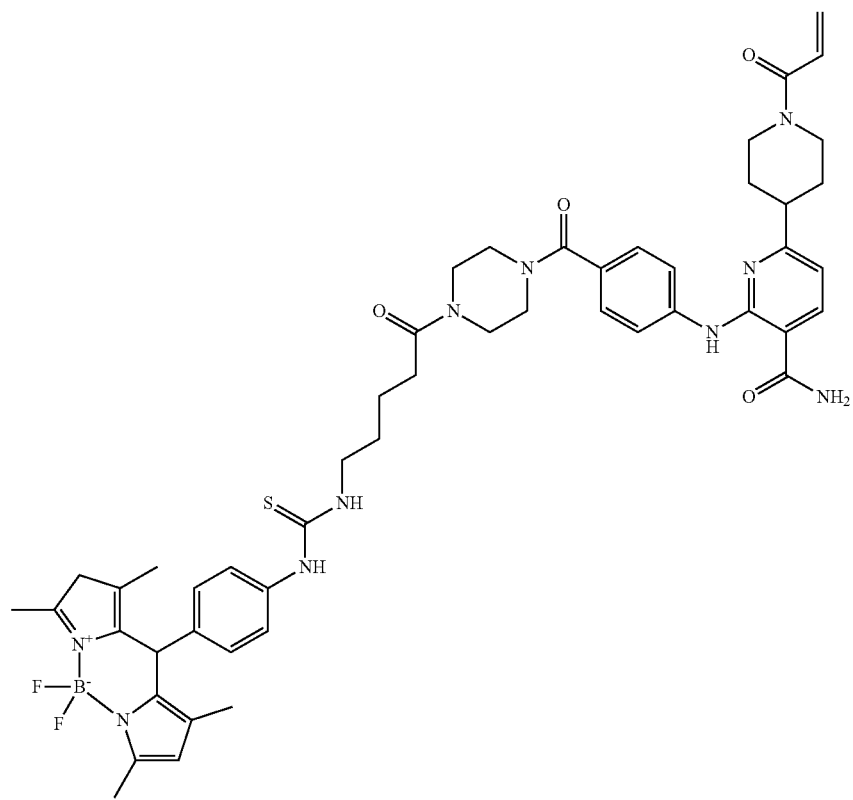 [SMILES: C=CC(=O)N1CCC(c2ccc(C(N)=O)c(Nc3ccc(C(=O)N4CCN(C(=O)CCCCNC(=S)Nc5ccc(C6C7=C(C)CC(C)=[N+]7[B-](F)(F)n7c(C)cc(C)c76)cc5)CC4)cc3)n2)CC1]

Methods Associated with Reaction Steps in Scheme 12:

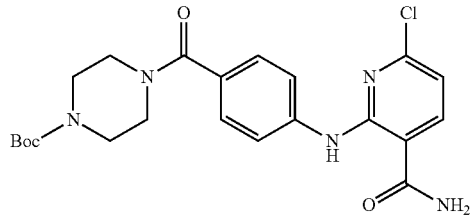 [SMILES: CC(C)(C)OC(=O)N1CCN(C(=O)c2ccc(Nc3nc(Cl)ccc3C(N)=O)cc2)CC1]

Carbamoyl-6-chloro-pyridin-2-ylamino)-benzoyl]-piperazine-1-carboxylic acid tert-butyl ester Carbamoyl-6-chloro-pyridin-2-ylamino)-benzoyl]-piperazine-1-carboxylic acid tert-butyl ester was prepared from 2,6-Dichloro-nicotinamide and 4-(4-Amino-benzoyl)-piperazine-1-carboxylic acid tert-butyl ester using Method 2A, excepting that the compound was purified on 25 g of 25 micron silica using a gradient of 10-65% ethyl acetate in hexanes. MS: m/z=460 [M+H]+.

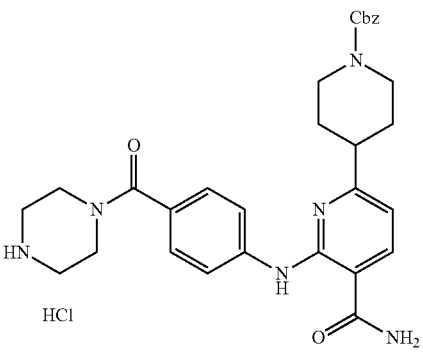

5-Carbamoyl-6-[4-(piperazine-1-carbonyl)-phenylamino]-3',6'-dihydro-2'H-[2,4']bipyridinyl-1'-carboxylic acid benzyl ester hydrochloride)

5-Carbamoyl-6-[4-(piperazine-1-carbonyl)-phenylamino]-3',6'-dihydro-2'H-[2,4']bipyridinyl-1'-carboxylic acid benzyl ester hydrochloride (892.00 mg; 1.55 mmol) was prepared from 6-[4-(4-tert-Butoxycarbonyl-piperazine-1-carbonyl)-phenylamino]-5-carbamoyl-3',6'-dihydro-2'W [2,4']bipyridinyl-1'-carboxylic acid benzyl ester using Method 16B which was used without additional purification. MS: m/z=541 [M+H]+.

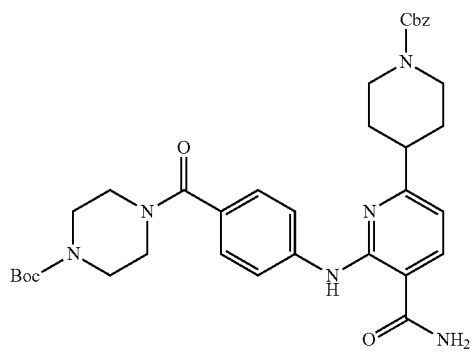 [SMILES: CC(C)(C)OC(=O)N1CCN(C(=O)c2ccc(Nc3nc(C4CCN(C(=O)OCc5ccccc5)CC4)ccc3C(N)=O)cc2)CC1]

6-[4-(4-tert-Butoxycarbonyl-piperazine-1-carbonyl)-phenylamino]-5-carbamoyl-3',6'-dihydro-2'H-[2,4'] bipyridinyl-1'-carboxylic acid benzyl ester 6-[4-(4-tert-Butoxycarbonyl-piperazine-1-carbonyl)-phenylamino]-5-carbamoyl-3',6'-dihydro-2'H-[2,4']bipyridinyl-1'-carboxylic acid benzyl ester 994.00 mg, 78% was prepared from Carbamoyl-6-chloro-pyridin-2-ylamino)-benzoyl]-piperazine-1-carboxylic acid tert-butyl ester using Method 16A, excepting that the reaction was directly purified via flash chromatography using silica and a gradient of 25-50% ethyl acetate in hexane. MS: m/z=641.3 [M+H]+.

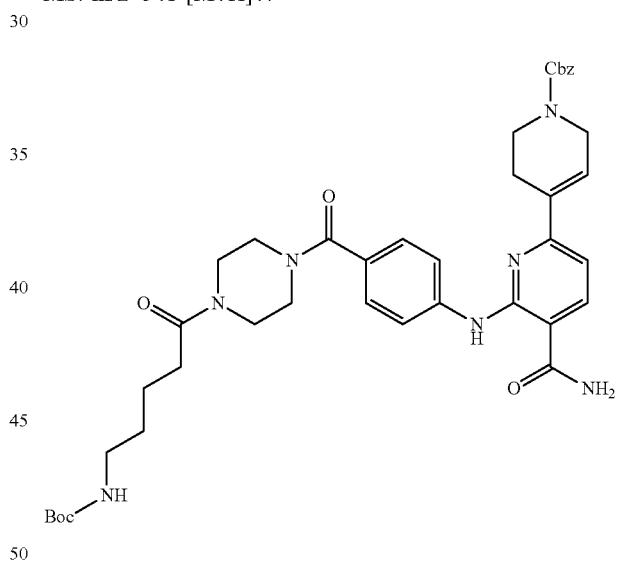

6-{4-[4-(5-tert-Butoxycarbonylamino-pentanoyl)-piperazine-1-carbonyl]-phenylamino}-5-carbamoyl-3',6'-dihydro-2'H-[2,4']bipyridinyl-1'-carboxylic acid benzyl ester (Method 17C)

5-Carbamoyl-6-[4-(piperazine-1-carbonyl)-phenylamino]-3',6'-dihydro-2'H-[2,4']bipyridinyl-1'-carboxylic acid benzyl ester hydrochloride (1.35 mmol; 1.00 eq.; 780.00 mg) was combined with 5-tert-Butoxycarbonylamino-pentanoic acid (1.62 mmol; 1.20 eq.; 352.39 mg) and 1(3-dimethylaminopropyl)3-ethylcarbodiimide*HCl (EDCI) (2.70 mmol; 2.00 eq.; 518.22 mg). Triethylamine (4.05 mmol; 3.00 eq.; 410.32 mg; 0.56 ml) was then added and the reaction was stirred at RT for two hours. Reaction was quenched with water and diluted with 250 mL dichloromethane. Organics were washed three times with sat.

sodium hydrogen carbonate then dried over sodium sulfate, filtered, then concentrated to dryness. Reaction was purified on 40 g of 25 micron silica using a gradient of 25-100% ethyl acetate in hexanes then 0-20% methanol in dichloromethane to give 6-{4-[4-(5-tert-Butoxycarbonylamino-pentanoyl)-piperazine-1-carbonyl]-phenylamino}-5-carbamoyl-3',6'-dihydro-2'H-[2,4']bipyridinyl-1'-carboxylic acid benzyl ester (761.00 mg; 1.03 mmol)). MS: m/z=741 [M+H]+.

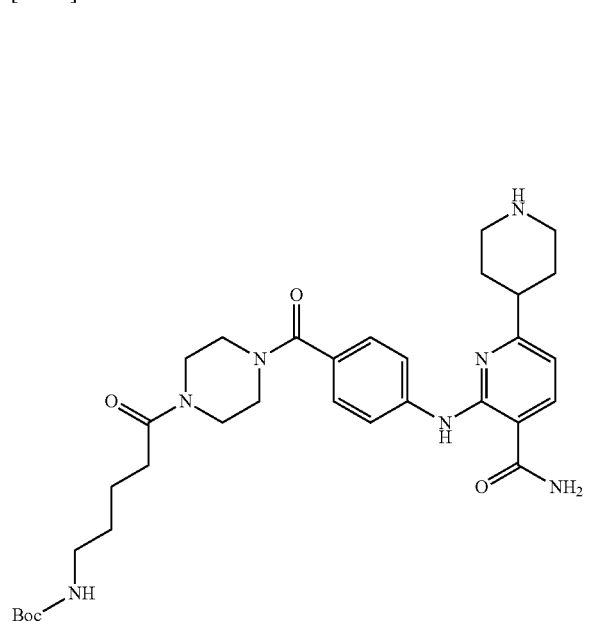

(5-{4-[4-(5-Carbamoyl-1',2',3',4',5',6'-hexahydro-[2,4']bipyridinyl-6-ylamino)-benzoyl]-piperazin-1-yl}-5-oxo-pentyl)-carbamic acid tert-butyl ester (225.00 mg; 0.37 mmol) (Method 17D)

6-{4-[4-(5-tert-Butoxycarbonylamino-pentanoyl)-piperazine-1-carbonyl]-phenylamino}-5-carbamoyl-3 bipyridinyl-1'-carboxylic acid benzyl ester (0.61 mmol; 1.00 eq.; 448.60 mg) was dissolved in methanol (15.00 ml) and then treated with about 100 mg of Pd/C (10% Degaussa Type). The flask was then evacuated then purged with nitrogen. The process was repeated then the flask was charged with hydrogen from a balloon and stirring was commenced. The reaction was hydrogenated for 1.5 hours at 1 atm pressure at RT. Continued hydrogenation for additional half hour (2 hours total reaction time) then reaction was evacuated, purged with nitrogen, and catalyst was removed by filtration through a plug of celite. All solvent was removed then dissolved in 10% MeOH/DCM (10 mL). Added 200 mg of Thiourea Metal Scavenger (Si-Thiourea, loading=1.17 mmol/g; Silicycle Cat# R69530B) and stirred for 2 hours. Silica scavenger was then removed via filtration (celite) and cake was washed with DCM. All solvent was then removed and residue was dried overnight to give (5-{4-[4-(5-Carbamoyl-1',2',3',4',5',6'-hexahydro-[2,4']bipyridinyl-6-ylamino)-benzoyl]-piperazin-1-yl}-5-oxo-pentyl)-carbamic acid tert-butyl ester (225.00 mg) which was used without additional purification. MS: m/z=608 [M+H]+.

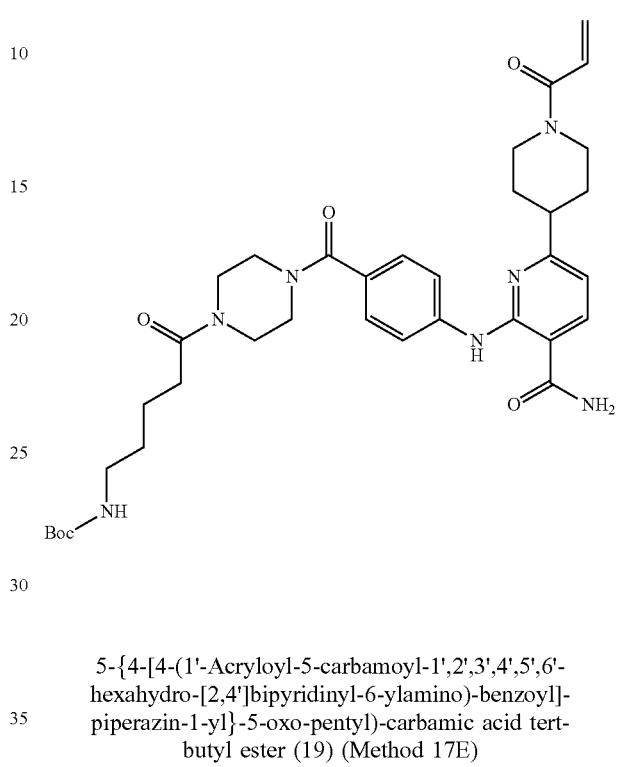

5-{4-[4-(1'-Acryloyl-5-carbamoyl-1',2',3',4',5',6'-hexahydro-[2,4']bipyridinyl-6-ylamino)-benzoyl]-piperazin-1-yl}-5-oxo-pentyl)-carbamic acid tert-butyl ester (19) (Method 17E)

(5-{4-[4-(5-Carbamoyl-1',2',3',4',5',6'-hexahydro-[2,4]bipyridinyl-6-ylamino)-benzoyl]-piperazin-1-yl}-5-oxo-pentyl)-carbamic acid tert-butyl ester (0.65 mmol; 1.00 eq.; 392.00 mg) was dissolved in DCM (5 mL) then treated with DIEA (2.26 mmol; 3.50 eq.; 291.56 mg; 0.39 ml). Reaction was then cooled to 0° C. on an ice bath. Acryloyl chloride (0.65 mmol; 1.01 eq.; 58.96 mg; 0.05 ml) (in 1 mL DCM) was then added dropwise. After 30 min reaction was quenched with 1 mL MeOH and concentrated to dryness. Reaction was then purified on 25 g of 25 micron silica using a gradient of 0-20% MeOH in DCM to give (5-{4-[4-(1'-Acryloyl-5-carbamoyl-1',2',3',4',5',6'-hexahydro-[2,4']bipyridinyl-6-ylamino)-benzoyl]-piperazin-1-yl}-5-oxo-pentyl)-carbamic acid tert-butyl ester (331.00 mg, 77%). HPLC: 90.9%, RT=2.40 min. MS: m/z=663 [M+H]+. $^1$H NMR (400 MHz, CDCl$_3$) δ 10.90 (s, 1H), 7.78 (d, J=8.3 Hz, 2H), 7.41 (d, J=8.6 Hz, 2H), 6.72-6.60 (m, 3H), 6.48 (dd, J=13.1, 6.5 Hz, 1H), 6.32 (dd, J=16.8, 1.9 Hz, 1H), 6.25-6.05 (m, 1H), 6.05-5.86 (m, 1H), 5.86-5.63 (m, 1H), 4.89-4.59 (m, 2H), 4.24-3.96 (m, 2H), 3.82-3.50 (m, 8H), 3.35-3.04 (m, 2H), 3.04-2.68 (m, 2H), 2.49-2.30 (m, 2H), 2.14-2.02 (m, 1H), 1.94-1.54 (m, 8H), 1.46 (s, 9H).

Example 159

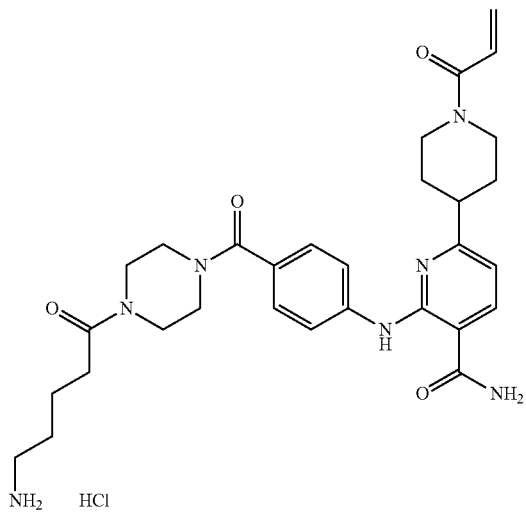 [SMILES: C=CC(=O)N1CCC(c2ccc(C(N)=O)c(Nc3ccc(C(=O)N4CCN(C(=O)CCCCN)CC4)cc3)n2)CC1 ; Cl]

1'-Acryloyl-6-{4-[4-(5-amino-pentanoyl)-piperazine-1-carbonyl]-phenylamino}-1',2',3',4',5',6'-hexahydro-[2,4']bipyridinyl-5-carboxylic acid amide hydrochloride (29) (Method 17F)

(5-{4-[4-(1'-Acryloyl-5-carbamoyl-1',2',3',4',5',6'-hexahydro-[2,4']bipyridinyl-6-ylamino)-benzoyl]-piperazin-1-yl}-5-oxo-pentyl)-carbamic acid tert-butyl ester (0.50 mmol; 1.00 eq.; 331.00 mg) was combined with HCl solution 4M in Dioxane (3 mL) and MeOH (1 mL) at RT under nitrogen. The mixture was stirred at RT for 1 hour. All solvent was then removed on the and the resulting residue was dried overnight to give 1'-Acryloyl-6-{4-[4-(5-amino-pentanoyl)-piperazine-1-carbonyl]-phenylamino}-1',2',3',4',5',6'-hexahydro-[2,4']bipyridinyl-5-carboxylic acid amide hydrochloride (306.00 mg) as a yellow solid which was used without purification. MS: m/z=562 [M+H]+. $^1$H NMR (400 MHz, MeOD) δ 8.42 (d, J=7.8 Hz, 1H), 7.70 (d, J=8.2 Hz, 2H), 7.58 (d, J=8.5 Hz, 2H), 7.01 (d, J=8.0 Hz, 1H), 6.82 (dd, J=16.8, 10.7 Hz, 1H), 6.23 (dd, J=16.8, 1.9 Hz, 1H), 5.73 (dt, J=96.5, 48.2 Hz, 1H), 4.8-4.61 (m, 2H), 4.45-4.12 (m, 2H), 3.88-3.45 (m, 8H), 3.26-3.07 (m, 2H), 3.04-2.72 (m, 3H), 2.61-2.46 (m, 2H), 2.15-1.95 (m, 1H), 1.47-1.29 (m, 8H).

Example 160

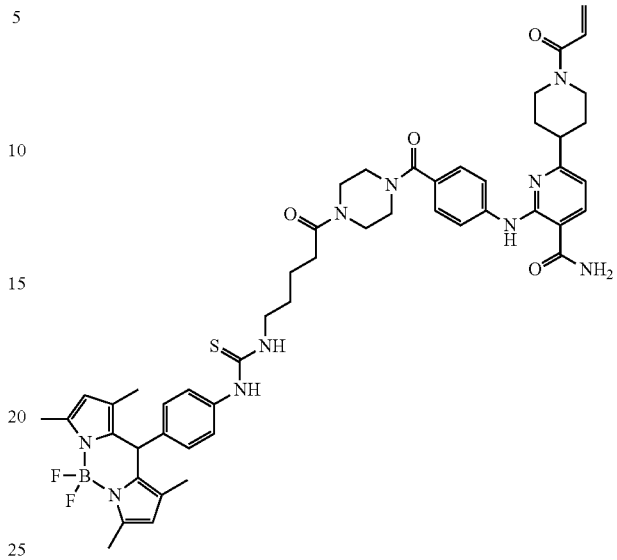

1'-Acryloyl-6-{4-[4-(5-{3-[4-(4,4-difluoro-1,3,5,7-tetramethyl-3a,4alambda4-diaza-4lambda4-bora-s-indacen-8-yl)-phenyl]-thioureido}-pentanoyl)-piperazine-1-carbonyl]-phenylamino}-1',2',3',4',5',6'-hexahydro-[2,4']bipyridinyl-5-carboxylic acid amide (63) (Method 17G)

1'-Acryloyl-6-{4-[4-(5-amino-pentanoyl)-piperazine-1-carbonyl]-phenylamino}-1',2',3',4',5',6'-hexahydro-[2,4']bipyridinyl-5-carboxylic acid amide hydrochloride (0.14 mmol; 1.00 eq.; 83.00 mg) was combined with 4,4-Difluoro-8-(4-isothiocyanato-phenyl)-1,3,5,7-tetramethyl-3a,4alambda4-diaza-4lambda4-bora-s-indacene (0.15 mmol; 1.10 eq.; 58.19 mg) and Hünig's base (0.42 mmol; 3.00 eq.; 53.77 mg; 0.07 ml) into a mixture of MeCN (38.29 mmol; 275.95 eq.; 1572.00 mg; 2.00 ml) and MeOH (12.34 mmol; 88.95 eq.; 395.50 mg; 0.50 ml). The mixture was stirred at RT for 1.5 hrs. All solvent was then removed and the material was purified on silica (15 micron) using a gradient of 0-20% MeOH in DCM to give 1'-Acryloyl-6-{4-[4-(5-{3-[4-(4,4-difluoro-1,3,5,7-tetramethyl-3a,4alambda4-diaza-4lambda4-bora-s-indacen-8-yl)-phenyl]-thioureido}-pentanoyl)-piperazine-1-carbonyl]-phenylamino}-1',2',3',4', 5',6'-hexahydro-[2,4']bipyridinyl-5-carboxylic acid amide (56.00 mg, 42%). HPLC: 99%, RT=6.46 min. MS: m/z=943 [M+H]+. $^1$H NMR (400 MHz, Chloroform-d) δ 10.91 (s, 1H), 7.98 (bs, 1H), 7.87-7.77 (m, 2H), 7.73 (d, J=7.9 Hz, 1H), 7.51-7.36 (m, 4H), 7.36-7.25 (m, 4H), 6.85 (s, 1H), 6.73-6.58 (m, 2H), 6.31 (dd, J=16.8, 2.0 Hz, 1H), 5.99 (s, 2H), 5.73 (dd, J=10.6, 2.0 Hz, 1H) 4.81-4.65 (m, 2H), 4.23-4.08 (m, 2H), 3.83-3.47 (m, 12H), 3.31-3.15 (m, 1H), 3.00-2.72 (m, 2H), 2.56 (s, 3H), 2.50-2.37 (m, 2H) 2.11-1.97 (m, 2H), 1.89-1.67 (m, 4H), 1.42 (s, 3H), 1.61 (s, 6H).

Example 161

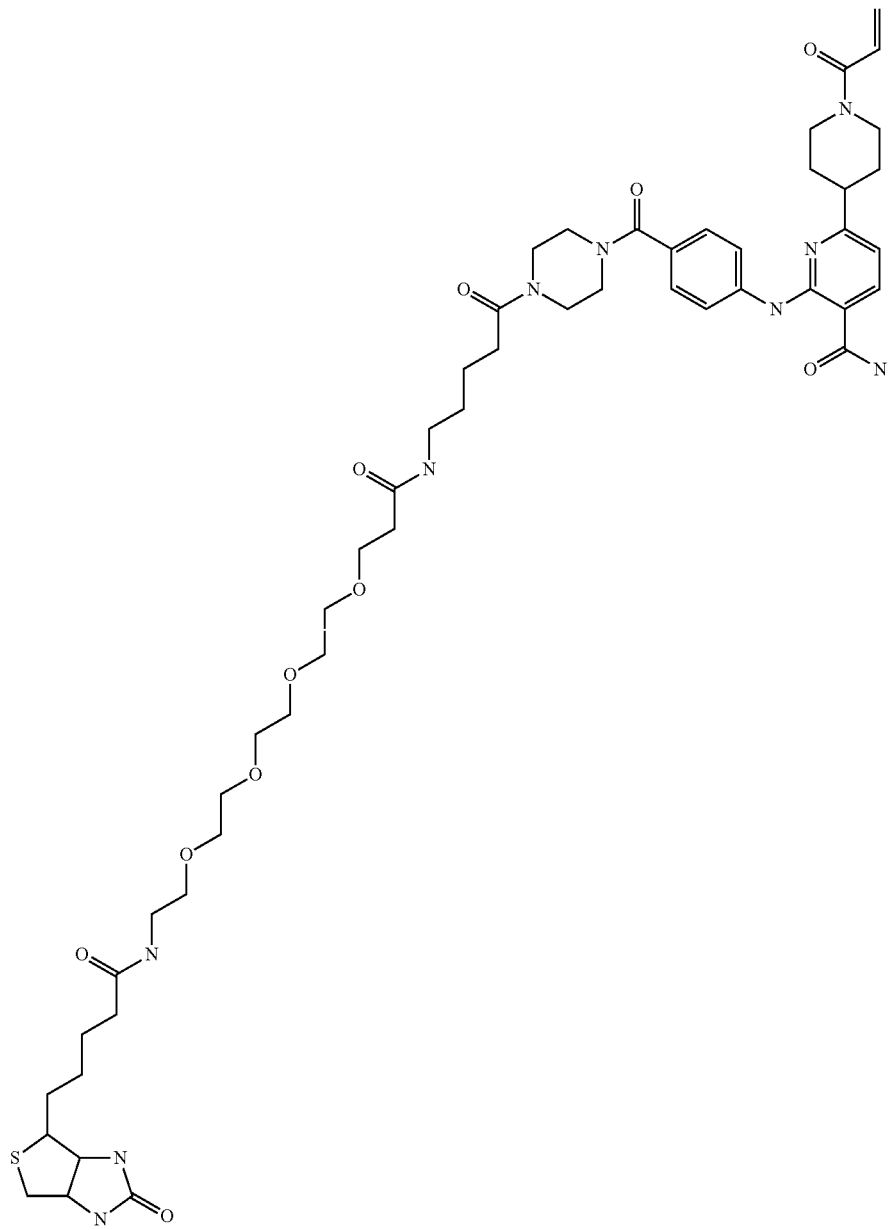 [SMILES: C=CC(=O)N1CCC(c2ccc(C(N)=O)c(Nc3ccc(C(=O)N4CCN(C(=O)CCCCNC(=O)CCOCCOCCOCCOCCNC(=O)CCCCC5SCC6NC(=O)NC65)CC4)cc3)n2)CC1]

6-(1-acryloylpiperidin-4-yl)-24(4-(4-(5,21-dioxo-1-(2-oxohexahydro-1H-thieno[3,4-d]imidazol-4-yl)-9,12,15,18-tetraoxa-6,22-diazaheptacosan-27-oyl)piperazine-1-carbonyl)phenyl)amino)nicotinamide (177)

1'-Acryloyl-6-{4-[4-(5-amino-pentanoyl)-piperazine-1-carbonyl]-phenylamino}-1',2',3',4',5',6'-hexahydro-[2,4']bipyridinyl-5-carboxylic acid amide hydrochloride (0.13 mmol; 1.00 eq.; 80.00 mg), described above, was combined with 3-{2-[2-(2-{2-[5-(2-Oxo-hexahydro-thieno[3,4-d]imidazol-4-yl)-pentanoylamino]-ethoxy}-ethoxy)-ethoxy]-ethoxy}-propionic acid 2,5-dioxo-pyrrolidin-1-yl ester (0.14 mmol; 1.01 eq.; 79.52 mg; 0.07 ml) and Hünig base (0.40 mmol; 3.00 eq.; 51.82 mg; 0.07 ml) into MeCN. The mixture was then heated to 60° C. for 1 hr. The reaction was then purified via column chromatography using a gradent of 0-15% MeOH/DCM to give 6-(1-acryloylpiperidin-4-yl)-2-((4-(4-(5,21-dioxo-1-(2-oxohexahydro-1H-thieno[3,4-d]imidazol-4-yl)-9,12,15,18-tetraoxa-6,22-diazaheptacosan-27-oyl)piperazine-1-carbonyl)phenyl)amino)nicotinamide (44.00 mg, 32%). HPLC: 99%, RT=6.46 min. MS: m/z=1035 [M+H]+. $^1$H NMR (400 MHz, MeOD) δ 8.06 (d, J=7.9 Hz, 1H), 7.88 (d, J=8.7 Hz, 2H), 7.44 (d, J=8.7 Hz, 2H), 6.94-6.71 (m, 2H), 6.24 (dd, J=16.8, 2.0 Hz, 2H), 5.78 (dd, J=10.6, 2.0 Hz, 1H), 5.48 (dt, J=34.5, 22.2 Hz, 2H), 4.50 (dd, J=12.9, 5.2 Hz, 1H), 4.43-4.25 (m, 2H), 3.80-3.51 (m, 15H), 3.39-3.34 (m, 4H), 3.22 (dd, J=23.8, 17.0 Hz, 3H), 3.06-2.84 (m, 3H), 2.47 (dt, J=12.3, 5.7 Hz, 3H), 2.37-2.01 (m, 4H), 1.86-1.53 (m, 7H), 1.54-1.27 (m, 4H).

Example 162

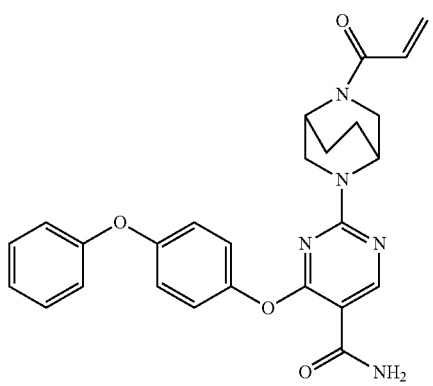 [SMILES: C=CC(=O)N1CC2CCC1CN2c1ncc(C(N)=O)c(Oc2ccc(Oc3ccccc3)cc2)n1]

2-(5-acryloyl-2,5-diazabicyclo[2.2.2]octan-2-yl)-4-(4-phenoxyphenoxy)pyrimidine-5-carboxamide (225)

2-(5-acryloyl-2,5-diazabicyclo[2.2.2]octan-2-yl)-4-(4-phenoxyphenoxy)pyrimidine-5-carboxamide was prepared from 2,4-dichloropyrimidine-5-carboxamide, tert-butyl 2,5-diazabicyclo[2.2.2]octane-2-carboxylate, and acryloyl chloride, with methods 15A, 15B, 15C and 15D. HPLC: 91.3%, RT=4.21 min. MS: m/z=472 [M+H]. $^1$H NMR (400 MHz, DMSO-d6) δ 8.74 (d, J=13.4 Hz, 1H), 7.63-7.25 (m, 6H), 7.25-6.35 (m, 5H), 6.66 (ddd, J=98.4, 16.7, 10.4 Hz, 1H), 6.14 (dd, J=19.3, 16.7 Hz, 1H), 5.68 (dd, J=21.0, 9.9 Hz, 1H), 4.99 (d, J=8.9 Hz, 1H), 4.81-4.12 (m, 4H) 3.71=3.68 (m, 1H), 1.93-1.86 (m, 4H).

Example 163

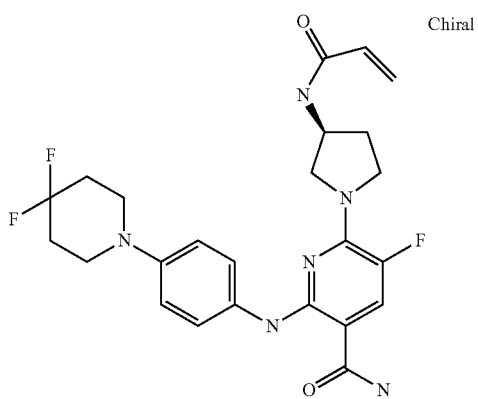 [SMILES: C=CC(=O)N[C@H]1CCN(c2nc(Nc3ccc(N4CCC(F)(F)CC4)cc3)c(C(N)=O)cc2F)C1]

6-((S)-3-Acryloylamino-pyrrolidin-1-yl)-2-[4-(4,4-difluoro-piperidin-1-yl)-phenylamino]-5-fluoro-nicotinamide (180)

6-((S)-3-Acryloylamino-pyrrolidin-1-yl)-2-[4-(4,4-difluoro-piperidin-1-yl)-phenylamino]-5-fluoro-nicotinamide was prepared from 2,6-dichloro-5-fluoronicotinamide, 4-(4,4-difluoropiperidin-1-yl)aniline, (S)-Pyrrolidin-3-yl-carbamic acid tert-butyl ester and acrylic acid with method 2A, 2B, 2C and 2D. HPLC: 96.0%, RT=3.04 min. MS: m/z=489 [M+H]+. $^1$H-NMR (DMSO-D6) δ 11.4 (s, 1H), 8.32 (m, 1H), 7.82 (d, 1H), 7.51 (d, 2H), 6.25 (m, 1H), 6.16 (d, 1H), 5.10 (d, 1H), 4.35 (m, 1H), 4.76 (m, 1H), 3.77 (m, 2H), 3.07 (m, 1H), 3.22 (m, 4H), 2.0 (m, 6H).

Example 164

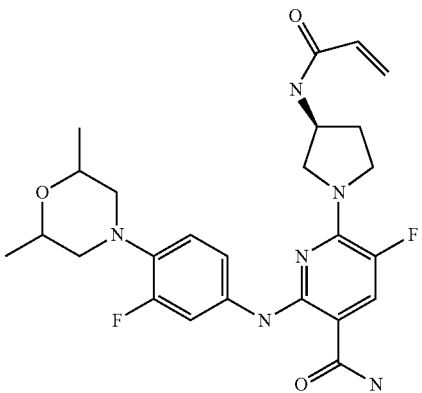 [SMILES: C=CC(=O)N[C@H]1CCN(c2nc(Nc3ccc(N4CC(C)OC(C)C4)c(F)c3)c(C(N)=O)cc2F)C1]

6-((S)-3-Acryloylamino-pyrrolidin-1-yl)-2-[4-(2,6-dimethyl-morpholin-4-yl)-3-fluoro-phenylamino]-5-fluoro-nicotinamide (181)

6-((S)-3-Acryloylamino-pyrrolidin-1-yl)-2-[4-(2,6-dimethyl-morpholin-4-yl)-3-fluoro-phenylamino]-5-fluoro-nicotinamide was prepared from 2,6-dichloro-5-fluoronicotinamide, 4-(2,6-dimethylmorpholino)-3-fluoroaniline, (S)-Pyrrolidin-3-yl-carbamic acid tert-butyl ester and acrylic acid with method 2A, 2B, 2C and 2D. HPLC: 96.3%, RT=3.65 min. MS: m/z=501 [M+H]+. $^1$H-NMR (DMSO-D6) δ 11.54 (s, 1H), 8.37 (d, 1H), 7.82 (d, 1H), 7.76 (d, 1H), 7.14 (m, 1H), 6.96 (m, 1H), 6.23 (m, 1H), 6.14 (d, 1H), 5.60 (d, 1H), 4.43 (m, 1H), 3.83 (m, 1H), 3.75 (m, 4H), 3.54 (m, 1H), 3.16 (d, 2H), 2.25 (m, 2H), 2.20 (m, 1H), 1.95 (m, 1H), 1.11 (d, 6H).

Example 165

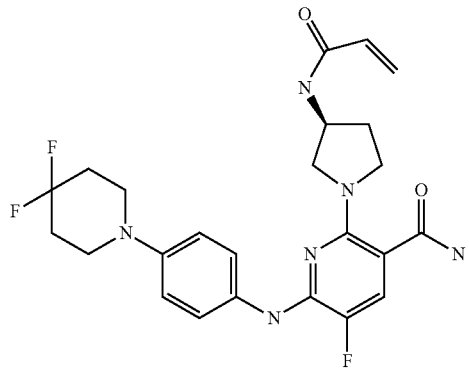 [SMILES: C=CC(=O)N[C@H]1CCN(c2nc(Nc3ccc(N4CCC(F)(F)CC4)cc3)c(F)cc2C(N)=O)C1]

2-((S)-3-Acryloylamino-pyrrolidin-1-yl)-6-[4-(4,4-difluoro-piperidin-1-yl)-phenylamino]-5-fluoro-nicotinamide formic acid (186)

2-((S)-3-Acryloylamino-pyrrolidin-1-yl)-6-[4-(4,4-difluoro-piperidin-1-yl)-phenylamino]-5-fluoro-nicotinamide formic acid was prepared from 2,6-dichloro-5-fluoronicotinamide, 4-(4,4-difluoropiperidin-1-yl)aniline, (S)-Pyrrolidin-3-yl-carbamic acid tert-butyl ester and acrylic acid with method 2A, 2B, 2C and 2D. HPLC: 92.0%, RT=2.66 min. MS: m/z=489 [M+H]+. $^1$H-NMR (DMSO-D6) δ 8.64 (s, 1H), 8.36 (d, 1H), 7.70 (d, 2H), 7.50 (m, 2H), 7.01 (m, 3H), 6.25 (m, 1H), 6.13 (m, 1H), 5.57 (m, 1H), 4.27 (m, 1H), 3.50 (m, 2H), 2.0 (m, 5H), 1.77 (m, 1H). Some peaks were overlapped with water peak.

Example 166

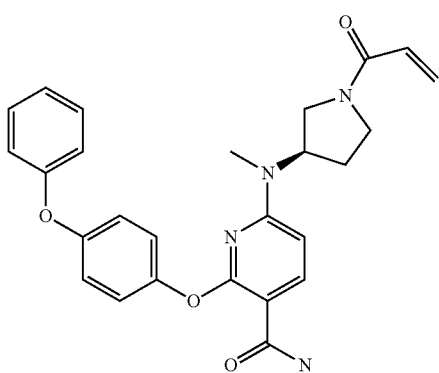 [SMILES: C=CC(=O)N1CC[C@@H](N(C)c2ccc(C(N)=O)c(Oc3ccc(Oc4ccccc4)cc3)n2)C1]

6-[((R)-1-Acryloyl-pyrrolidin-3-yl)-methyl-amino]-2-(4-phenoxy-phenoxy)-nicotinamide (187)

6-[((R)—1-Acryloyl-pyrrolidin-3-yl)-methyl-amino]-2-(4-phenoxy-phenoxy)-nicotinamide was prepared from 2,6-dichloro-nicotinamide, 4-phenoxyphenol, (R)-tert-butyl 3-(methylamino)pyrrolidine-1-carboxylate and acrylic acid with method 4A, 2B, 2C and 2D. HPLC: 99.6%, RT=4.24 min. MS: m/z=459 [M+H]+. $^1$H-NMR (DMSO-D6) δ 8.14 (d, 1H), 7.32 (m, 4H), 7.25 (d, 2H), 7.19 (m, 1H), 7.04 (m, 2H), 7.00 (m, 2H), 6.50 (m, 2H), 6.19 (d, 1H), 5.66 (t, 1H), 4.70 (m, 1H), 3.52 (m, 1H), 2.79 (d, 3H), 2.0 (m, 2H). Some peaks were overlapped with water peak.

Example 167

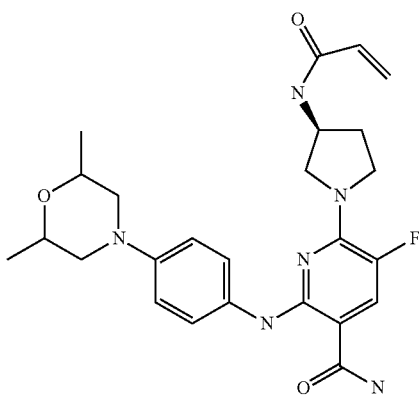 [SMILES: C=CC(=O)N[C@H]1CCN(c2nc(Nc3ccc(N4CC(C)OC(C)C4)cc3)c(C(N)=O)cc2F)C1]

6-((S)-3-Acryloylamino-pyrrolidin-1-yl)-2-[4-(2,6-dimethyl-morpholin-4-yl)-phenylamino]-5-fluoronicotinamide (188)

6-((S)-3-Acryloylamino-pyrrolidin-1-yl)-2-[4-(2,6-dimethyl-morpholin-4-yl)-phenylamino]-5-fluoro-nicotinamide was prepared from 2,6-dichloro-5-fluoronicotinamide, 4-(2,6-dimethylmorpholino)aniline, (S)-Pyrrolidin-3-yl-carbamic acid tert-butyl ester and acrylic acid with method 2A, 2B, 2C and 2D. HPLC: 95.3%, RT=2.90 min. MS: m/z=483 [M+H]+. $^1$H-NMR (DMSO-D6) δ 11.26 (s, 1H0, 8.41 (d, 1H), 7.85 (d, 1H), 7.50 (d, 2H), 6.83 (2H), 6.25 (m, 1H), 6.14 (d, 1H), 5.60 (d, 1H), 4.46 (m, 1H), 3.82 (m, 1H), 3.75 (m, 4H), 3.04 (m, 1H), 3.50 (m, 2H), 2.20 (m, 3H), 1.91 (m, 1H), 1.14 (m, 6H).

Example 168

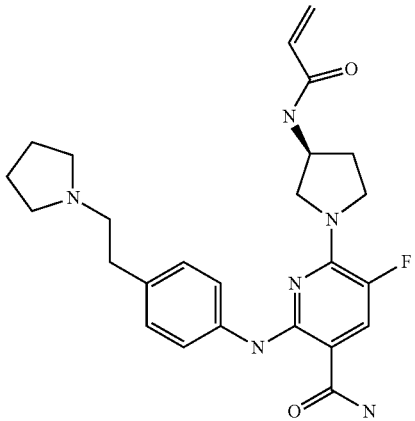 [SMILES: C=CC(=O)N[C@H]1CCN(c2nc(Nc3ccc(CCN4CCCC4)cc3)c(C(N)=O)cc2F)C1]

6-((S)-3-Acryloylamino-pyrrolidin-1-yl)-5-fluoro-2-[4-(2-pyrrolidin-1-yl-ethyl)-phenylamino]-nicotinamide (179)

6-((S)-3-Acryloylamino-pyrrolidin-1-yl)-5-fluoro-2-[4-(2-pyrrolidin-1-yl-ethyl)-phenylamino]-nicotinamide was prepared from 2,6-dichloro-5-fluoronicotinamide, 4-(2-(pyrrolidin-1-yl)ethyl)aniline, (S)-Pyrrolidin-3-yl-carbamic acid tert-butyl ester and acrylic acid with method 2A, 2B, 2C and 2D. HPLC: 95.4%, RT=2.70 min. MS: m/z=467 [M+H]+. $^1$H-NMR (DMSO-D6) δ 11.50 (s, 1H), 8.37 (m, 1H), 7.82 (d, 1H), 7.53 (d, 2H), 7.20 (d, 2H), 6.25 (m, 1H), 6.15 (d, 1H), 5.61 (d, 1H), 4.45 (m, 1H), 3.87 (m, 1H), 3.75 (m, 2H), 3.54 (m, 1H), 2.56 (m, 4H), 2.48 (m, 2H), 2.25 (m, 1H), 1.97 (m, 1H), 1.70 (m, 4H). Some peaks were overlapped with solvent peak.

Example 169

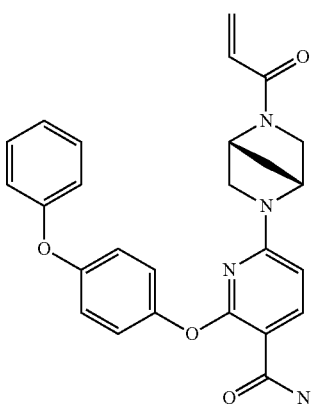 [SMILES: C=CC(=O)N1C[C@H]2C[C@@H]1CN2c1ccc(C(N)=O)c(Oc2ccc(Oc3ccccc3)cc2)n1]

6-((1R,4R)-5-Acryloyl-2,5-diaza-bicyclo[2.2.1]hept-2-yl)-2-(4-phenoxy-phenyl)-nicotinamide (189)

6-((1R,4R)-5-Acryloyl-2,5-diaza-bicyclo[2.2.1]hept-2-yl)-2-(4-phenoxy-phenoxy)-nicotinamide was prepared from 2,6-dichloro nicotinamide, 4-phenoxyphenol, (1S,4S)-tert-butyl 2,5-diazabicyclo[2.2.1]heptane-2-carboxylate and acrylic acid with methods 4A, 2B, 2C and 2D. HPLC: 100%, RT=4.16 min. MS: m/z=457 [M+H]+. $^1$H NMR (400 MHz, DMSO-d6) δ 8.16-7.95 (m, 1H), 7.50-7.31 (m, 4H), 7.32-7.18 (m, 2H), 7.18-7.04 (m, 3H), 6.99 (d, J=8.0 Hz, 2H), 6.81-6.18 (m, 2H), 6.12 (d, J=16.7 Hz, 1H), 5.65 (dd, J=9.9, 7.4 Hz, 1H), 5.00-4.71 (m, 1H), 4.53 (d, J=28.5 Hz, 1H), 3.40 (d, J=9.3 Hz, 1H), 3.10 (d, J=10.0 Hz, 1H), 1.90 (d, J=32.0 Hz, 2H). Some peaks overlaps with solvent peak.

Example 170

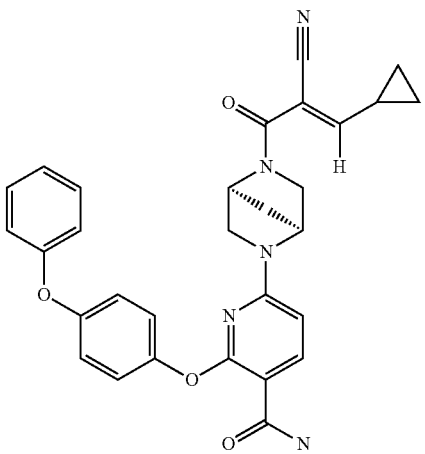 [SMILES: N#C/C(=C\C1CC1)C(=O)N1C[C@@H]2C[C@H]1CN2c1ccc(C(N)=O)c(Oc2ccc(Oc3ccccc3)cc2)n1]

6-((1S,4S)-5-((E)-2-cyano-3-cyclopropylacryloyl)-2,5-diazabicyclo[2.2.1]heptan-2-yl)-2-(4-phenoxyphenoxy)nicotinamide (190)

6-((1S,4S)-5-((E)-2-cyano-3-cyclopropylacryloyl)-2,5-diazabicyclo[2.2.1]heptan-2-yl)-2-(4-phenoxyphenoxy)nicotinamide was prepared from 2,6-dichloro-nicotinamide, 4-phenoxyphenol, (1S,4S)-tert-butyl 2,5-diazabicyclo[2.2.1]heptane-2-carboxylate and (E)-2-Cyano-3-cyclopropyl-acrylic acid with method 4A, 2B, 2C and 2D. HPLC: 99.9%, RT=4.82 min. MS: m/z=522 [M+H]+. $^1$H-NMR (DMSO-D6) δ 8.13 (m, 1H), 7.37 (m, 4H), 7.25 (m, 2H), 7.13 (m, 3H), 7.02 (m, 2H), 6.79 (m, 1H), 6.25 (m, 1H), 4.76 (m, 1H), 4.52 (m, 1H), 1.85 (m, 3H), 1.20 (m, 2H), 0.91 (m, 2H). Some peaks were overlapped with water peak.

Example 171

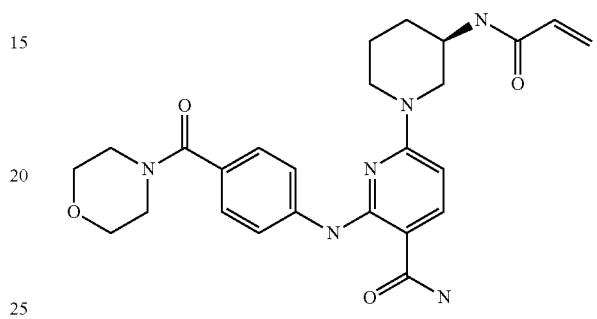

(R)-3-Acryloylamino-6'-[4-(morpholine-4-carbonyl)-phenylamino]-3,4,5,6-tetrahydro-2H-[1,2']bipyridinyl-5'-carboxylic acid amide (205)

(R)-3-Acryloylamino-6'-[4-(morpholine-4-carbonyl)-phenylamino]-3,4,5,6-tetrahydro-2H-[1,2']bipyridinyl-5'-carboxylic acid amide was prepared from 2,6-dichloro-nicotinamide, (4-aminophenyl)(morpholino)methanone, (R)-tert-butyl piperidin-3-ylcarbamate and acrylic acid with method 2A, 2B, 2C and 2D. HPLC: 97.5%, RT=2.94 min. MS: m/z=479 [M+H]+. $^1$H-NMR (DMSO-D6) δ 11.76 (s, 1H), 8.21 (d, 1H), 7.93 (d, 1H), 7.14 (d, 2H), 7.31 (d, 2H), 6.24 (m, 2H), 6.17 (d, 2H), 5.14 (d, 1H), 4.26 (d, 1H), 4.01 (d, 1H), 3.75 (m, 1H), 3.50 (d, 8H), 3.12 (m, 1H), 2.98 (m, 1H), 1.56 (d, 2H), 1.50 (m, 2H).

Example 173

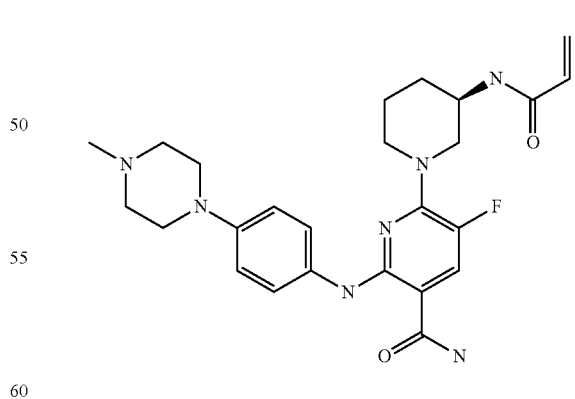

(R)-3-Acryloylamino-3'-fluoro-6'-[4-(4-methyl-piperazin-1-yl)-phenylamino]-3,4,5,6-tetrahydro-2H-[1,2']bipyridinyl-5'-carboxylic acid amide (226)

(R)-3-Acryloylamino-3'-fluoro-6'-[4-(4-methyl-piperazin-1-yl)-phenylamino]-3,4,5,6-tetrahydro-2H-[1,2']bipyridinyl-5'-carboxylic acid amide was prepared from 2,6-dichloro-5-fluoro-nicotinamide, 4-(4-methylpiperazin-1-yl)aniline, (R)-tert-butyl piperidin-3-ylcarbamate and acrylic acid with method 2A, 2B, 2C and 2D. HPLC: 98.7%, RT=2.72 min. MS: m/z=482 [M+H]+. ¹H-NMR (DMSO-D6) δ 11.10 (s, 1H), 8.20 (d, 1H), 7.80 (d, 1H), 7.41 (d, 2H), 6.77 (d, 2H), 6.25 (m, 1H), 6.13 (d, 1H), 5.17 (d, 1H), 4.20 (d, 1H), 4.0 (d, 1H), 3.90 (m, 2H), 3.12 (t, 1H), 3.00 (m, 4H), 2.91 (m, 1H), 2.44 (m, 4H), 2.25 (s, 3H), 1.94 (m, 1H), 1.80 (m, 1H), 1.0 (m, 1H). Some peaks were overlapped with water peak.

Example 174

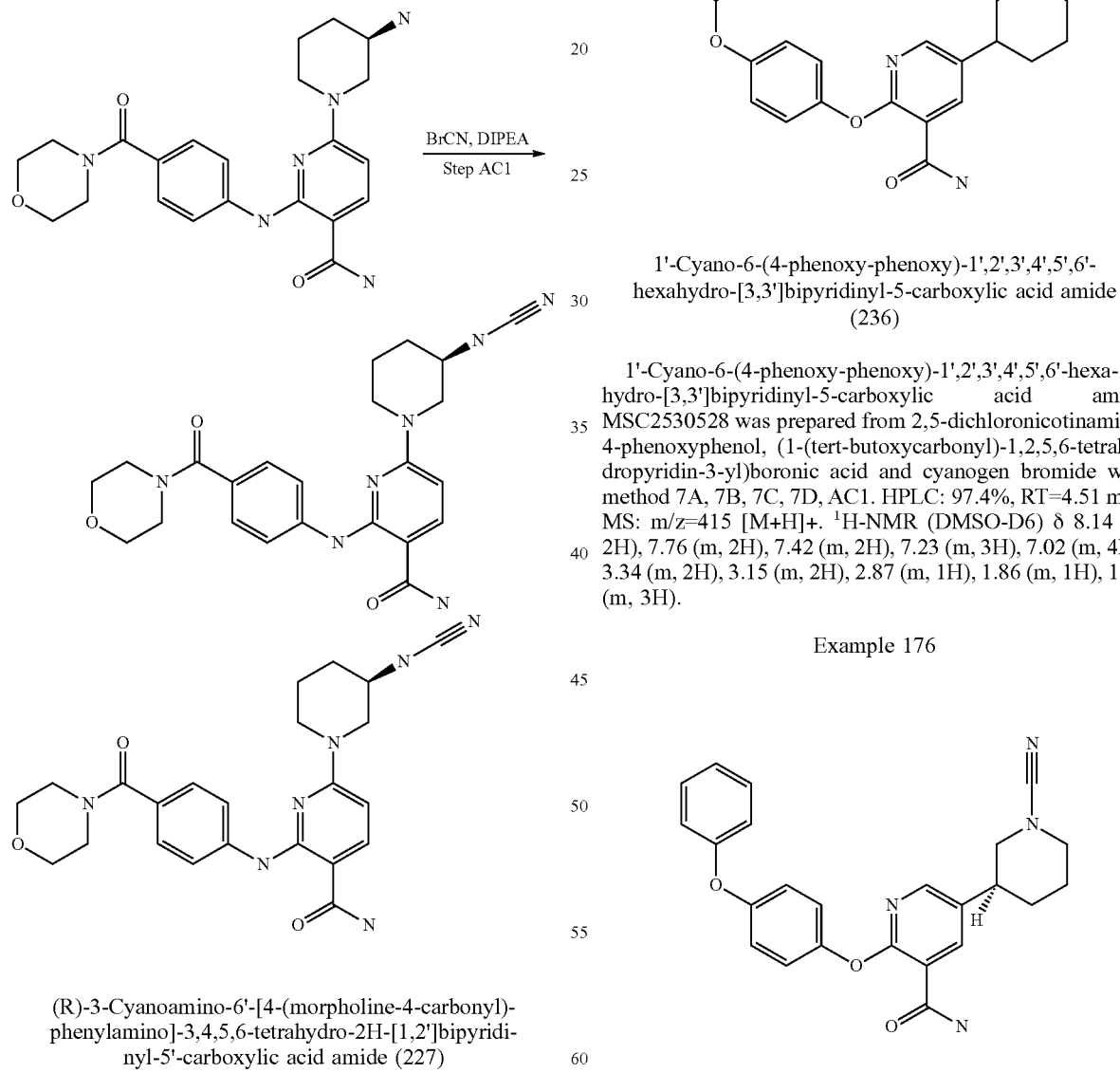

(R)-3-Cyanoamino-6'-[4-(morpholine-4-carbonyl)-phenylamino]-3,4,5,6-tetrahydro-2H-[1,2']bipyridinyl-5'-carboxylic acid amide (227)

In a rbf containing (R)-3-Amino-6'-[4-(morpholine-4-carbonyl)-phenylamino]-3,4,5,6-tetrahydro-2H-[1,2']bipyridinyl-5'-carboxylic acid amide hydrochloride (100.00 mg; 0.22 mmol; 1.00 eq.) in DCM (5.00 ml; 78.00 mmol; 359.56 eq.) was added DIPEA (0.22 ml; 1.30 mmol; 6.00 eq.) and cyanogen bromide (63.70 μl; 0.87 mmol; 4.00 eq.). The reaction was stirred at rt for 16 h before it was concentrated and purified under acidic conditions. The desired fractions were dried to afford the compound as a white solid (9.8 mg, 10%). HPLC: 97.2%, RT=3.00 min. MS: m/z=450 [M+H]+. ¹H-NMR (DMSO-D6) δ 11.80 (s, 1H), 8.01 (d, 1H), 7.20 (d, 2H), 7.44 (d, 2H), 7.03 (m, 1H), 6.27 (d, 1H), 4.46 (d, 1H), 3.97 (d, 1H), 3.50 (m, 8H), 3.03 (m, 4H), 2.0 (m, 1H), 1.75 (m, 1H), 1.5 (m, sH), 1.27 (m, 1H).

Example 175

1'-Cyano-6-(4-phenoxy-phenoxy)-1',2',3',4',5',6'-hexahydro-[3,3']bipyridinyl-5-carboxylic acid amide (236)

1'-Cyano-6-(4-phenoxy-phenoxy)-1',2',3',4',5',6'-hexahydro-[3,3']bipyridinyl-5-carboxylic acid amide MSC2530528 was prepared from 2,5-dichloronicotinamide, 4-phenoxyphenol, (1-(tert-butoxycarbonyl)-1,2,5,6-tetrahydropyridin-3-yl)boronic acid and cyanogen bromide with method 7A, 7B, 7C, 7D, AC1. HPLC: 97.4%, RT=4.51 min. MS: m/z=415 [M+H]+. ¹H-NMR (DMSO-D6) δ 8.14 (d, 2H), 7.76 (m, 2H), 7.42 (m, 2H), 7.23 (m, 3H), 7.02 (m, 4H), 3.34 (m, 2H), 3.15 (m, 2H), 2.87 (m, 1H), 1.86 (m, 1H), 1.70 (m, 3H).

Example 176

(S)-5-(1-cyanopiperidin-3-yl)-2-(4-phenoxyphenoxy)nicotinamide (240)

(S)-5-(1-cyanopiperidin-3-yl)-2-(4-phenoxyphenoxy)nicotinamide was obtained by the chiral separation of racemic 1'-cyano-6-(4-phenoxy-phenoxy)-1',2',3',4',5',6'-hexahydro-[3,3']bipyridinyl-5-carboxylic acid amide into its two enantiomers. Chiral separation method: 60% Isocratic system at 10 ml/min and 240 nm wavelength using the THAR (Technologies) SFC with the ODH column and MeOH mobile phase. HPLC: 100%, RT=4.51 min. MS: m/z=415 [M+H]+. Chiral HPLC: >98%, RT=7.0 min Example 177

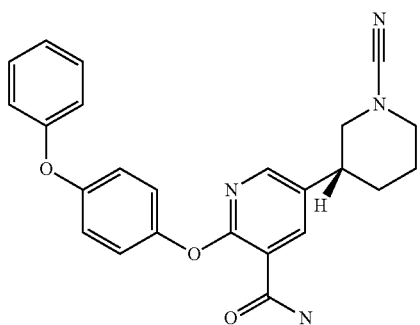 [SMILES: N#CN1CCC[C@H](c2cnc(Oc3ccc(Oc4ccccc4)cc3)c(C(N)=O)c2)C1]

(R)-5-(1-cyanopiperidin-3-yl)-2-(4-phenoxyphenoxy)nicotinamide (241)

(R)-5-(1-cyanopiperidin-3-yl)-2-(4-phenoxyphenoxy)nicotinamide was obtained by the chiral separation of 1'-cyano-6-(4-phenoxy-phenoxy)-1',2',3',4',5',6'-hexahydro-[3,3']bipyridinyl-5-carboxylic acid amide into its two enantiomers. Chiral separation method: 60% Isocratic system at 10 ml/min and 240 nm wavelength using the THAR (Technologies) SFC with the ODH column and MeOH mobile phase. HPLC: 100%, RT=4.51 min. MS: m/z=415 [M+H]+. Chiral HPLC: >98%, RT=8.6 min Example 178

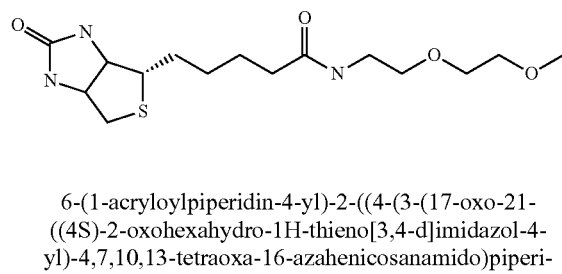

6-(1-acryloylpiperidin-4-yl)-2-((4-(3-(17-oxo-21-((4S)-2-oxohexahydro-1H-thieno[3,4-d]imidazol-4-yl)-4,7,10,13-tetraoxa-16-azahenicosanamido)piperidine-1-carbonyl)phenyl)amino)nicotinamide (191)

6-(1-acryloylpiperidin-4-yl)-2-((4-(3-(17-oxo-21-((4S)-2-oxohexahydro-1H-thieno[3,4-d]imidazol-4-yl)-4,7,10,13-tetraoxa-16-azahenicosanamido)piperidine-1-carbonyl)phenyl)amino)nicotinamide was prepared from 2,6-dichloro-nicotinamide, tert-butyl (1-(4-aminobenzoyl)piperidin-3-yl)carbamate, tert-butyl 4-(4,4,5,5-tetramethyl-1,3,2-dioxaborolan-2-yl)-5,6-dihydropyridine-1(2H)-carboxylate, 2,2-dimethyl-4-oxo-3,8,11,14,17-pentaoxa-5-azaicosan-20-oic acid, 5-((4S)-2-oxohexahydro-1H-thieno[3,4-d]imidazol-4-yl)pentanoic acid and acrylic acid with step 2A, 16A, 16B, 17C, 17D, 17E, 17F, 17G, 17F and 17G. HPLC: 98.8%, RT=2.84 min. MS: m/z=951 [M+H]+. $^1$H-NMR (DMSO-D6) δ 11.47 (s, 1H), 8.24 (s, 1H), 8.19 (d, 1H), 7.77 (m, 5H), 7.82 (m, 2H), 6.73 (m, 2H), 6.26 (d, 2H), 6.10 (d, 2H), 5.68 (d, 1H), 4.51 (m, 1H), 4.28 (m, 1H), 4.21 (m, 2H), 3.20 (m, 1H), 3.50 (m, 14H), 3.17 (m, 2H), 3.09 (m, 2H), 2.98 (m, 1H), 2.25 (m, 2H), 2.02 (m, 2H), 1.91 (m, 2H), 1.55 (m, 1H), 1.50 (m, 8H), 1.25 (m, 2H). Some peaks were overlapped with solvents peaks.

Example 179

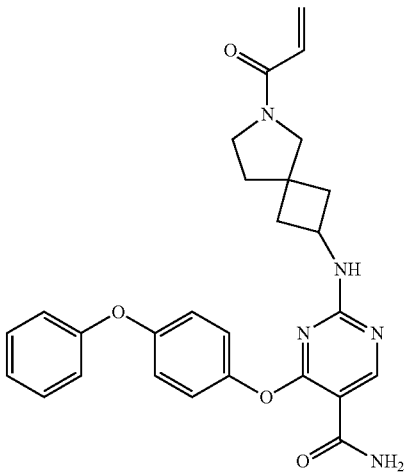 [SMILES: C=CC(=O)N1CCC2(CC(Nc3ncc(C(N)=O)c(Oc4ccc(Oc5ccccc5)cc4)n3)C2)C1]

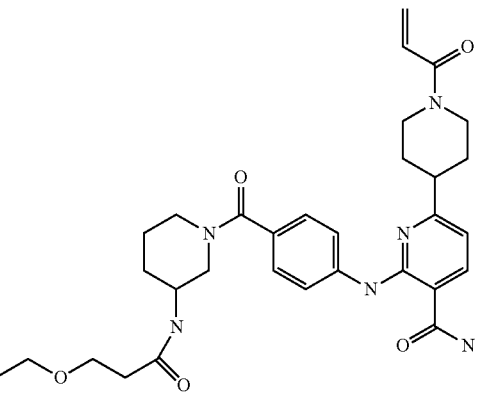

2-((6-acryloyl-6-azaspiro[3.4]octan-2-yl)amino)-4-(4-phenoxyphenoxy)pyrimidine-5-carboxamide (182)

2-((6-acryloyl-6-azaspiro[3.4]octan-2-yl)amino)-4-(4-phenoxyphenoxy)pyrimidine-5-carboxamide (31.0 mg; 28.2%) was prepared from 4,6-dichloro nicotinamide, 4-phenoxyphenol, N-Boc-6-azaspiro[3.4]octan-2-amine, and acrylic acid with methods 1A, 12A, 2C, 7D and 2D. HPLC-UV: 99.6% purity. LC/MS m/z=486.0 [M+H]+. $^1$H NMR (400 MHz, DMSO-d6) δ 8.99 (s, 1H), 7.82 (d, J=10.2 Hz, 2H), 7.55-6.79 (m, 10H), 6.61-6.49 (m, 1H), 5.81-5.53 (m, 2H), 4.50-4.40 (m, 1H), 4.00-3.70 (m, 4H), 2.14-1.60 (m, 6H).

Example 180

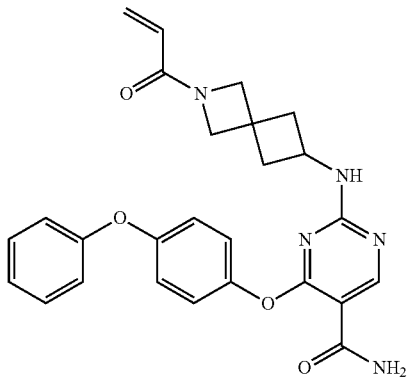 [SMILES: C=CC(=O)N1CC2(CC(Nc3ncc(C(N)=O)c(Oc4ccc(Oc5ccccc5)cc4)n3)C2)C1]

2-((2-acryloyl-2-azaspiro[3.3]heptan-6-yl)amino)-4-(4-phenoxyphenoxy)pyrimidine-5-carboxamide (183)

2-((2-acryloyl-2-azaspiro[3.3]heptan-6-yl)amino)-4-(4-phenoxyphenoxy)pyrimidine-5-carboxamide (13.0 mg; 12.8%) was prepared from 4,6-dichloro nicotinamide, 4-phenoxyphenol, N-Boc-2-azaspiro[3.3]heptan-6-amine, and acrylic acid with methods 1A, 12A, 2C, 7D and 2D. HPLC-UV: 93.1% purity. LC/MS m/z=472.0 [M+H]+. $^1$H NMR (400 MHz, Chloroform-d) δ 8.88 (s, 1H), 7.46-6.87 (m, 10H), 6.43-6.08 (m, 1H), 5.71 (d, J=10.3 Hz, 2H), 4.44-4.01 (m, 4H), 2.46-1.76 (m, 4H).

Example 181

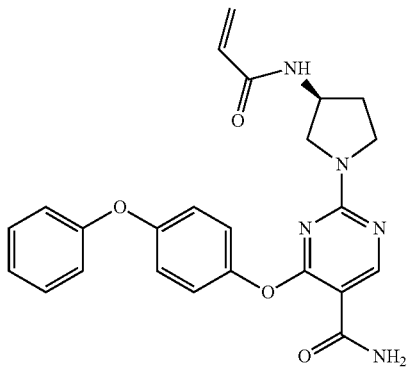 [SMILES: C=CC(=O)N[C@H]1CCN(c2ncc(C(N)=O)c(Oc3ccc(Oc4ccccc4)cc3)n2)C1]

(S)-2-(3-acrylamidopyrrolidin-1-yl)-4-(4-phenoxyphenoxy)pyrimidine-5-carboxamide (192)

(S)-2-(3-acrylamidopyrrolidin-1-yl)-4-(4-phenoxyphenoxy)pyrimidine-5-carboxamide (9.0 mg; 9.6%) was prepared from 4,6-dichloro nicotinamide, 4-phenoxyphenol, (S)-tert-butyl pyrrolidin-3-ylcarbamate, and acrylic acid with methods 1A, 12A, 2C, 7D and 2D. HPLC-UV: 93.1% purity. LC/MS m/z=446.0 [M+H]+. $^1$H NMR (400 MHz, Chloroform-d) δ 9.08 (s, 1H), 7.32-6.90 (m, 10H), 6.08 (dd, J=17.0, 10.2 Hz, 1H), 5.88-5.48 (m, 2H), 4.69-4.63 (m, 1H), 4.05-3.10 (m, 4H), 2.32-2.17 (m, 2H)

Example 182

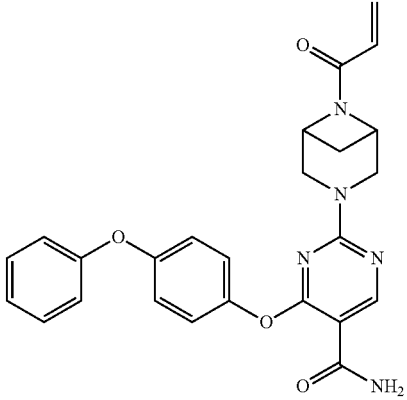 [SMILES: C=CC(=O)N1C2CC1CN(c1ncc(C(N)=O)c(Oc3ccc(Oc4ccccc4)cc3)n1)C2]

2-(6-acryloyl-3,6-diazabicyclo[3.1.1]heptan-3-yl)-4-(4-phenoxyphenoxy)pyrimidine-5-carboxamide (193)

2-(6-acryloyl-3,6-diazabicyclo[3.1.1]heptan-3-yl)-4-(4-phenoxyphenoxy)pyrimidine-5-carboxamide (11.0 mg; 11.8%) was prepared from 4,6-dichloro nicotinamide, 4-phenoxyphenol, tert-butyl 3,6-diazabicyclo[3.1.1]heptane-6-carboxylate, and acrylic acid with methods 1A, 12A, 2C, 7D and 2D. HPLC-UV: 99.6% purity. LC/MS m/z=458.0 [M+H]$^+$. $^1$H NMR (400 MHz, Chloroform-d) δ 9.09 (s, 1H), 7.41 (d, J=7.9 Hz, 2H), 7.25-6.83 (m, 7H), 6.53-6.05 (s, 2H), 5.66 (d, J=24.0 Hz, 1H), 4.56 (d, J=43.5 Hz, 2H), 4.18-3.79 (m, 2H), 3.67-3.24 (m, 2H), 2.81-2.73 (m, 2H).

Example 183

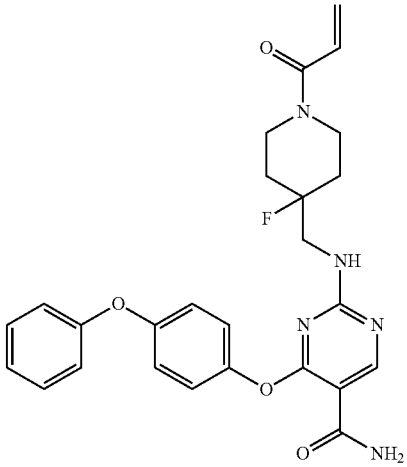 [SMILES: C=CC(=O)N1CCC(F)(CNc2ncc(C(N)=O)c(Oc3ccc(Oc4ccccc4)cc3)n2)CC1]

2-(((1-acryloyl-4-fluoropiperidin-4-yl)methyl) amino)-4-(4-phenoxyphenoxy)pyrimidine-5-carboxamide (194)

2-(((1-acryloyl-4-fluoropiperidin-4-yl)methyl)amino)-4-(4-phenoxyphenoxy)pyrimidine-5-carboxamide (9.0 mg; 9.6%) was prepared from 4,6-dichloro nicotinamide, 4-phenoxyphenol, tert-butyl 4-(aminomethyl)-4-fluoropiperidine-1-carboxylate, and acrylic acid with methods 1A, 12A, 2C, 7D and 2D. HPLC-UV: 91.6% purity. LC/MS m/z=492.0 [M+H]⁺. ¹H NMR (400 MHz, Chloroform-d) δ 9.04 (s, 1H), 7.39 (s, 2H), 7.27-6.81 (m, 7H), 6.54 (s, 1H), 6.29 (d, J=16.9 Hz, 1H), 6.12-5.60 (m, 2H), 4.39-4.19 (m, 2H), 3.75 (d, J=75.4 Hz, 2H), 3.40 (d, J=17.4 Hz, 2H), 1.91-1.76 (m, 2H).

Example 184

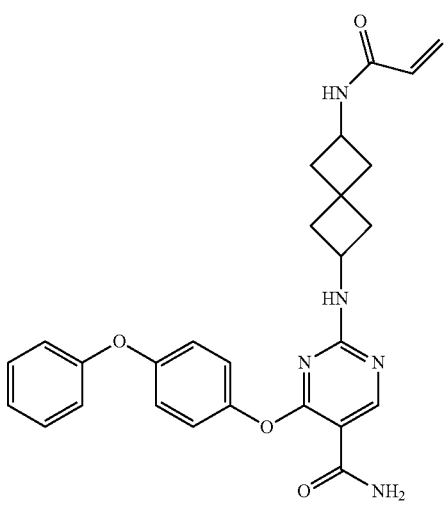 [SMILES: C=CC(=O)NC1CC2(C1)CC(Nc1ncc(C(N)=O)c(Oc3ccc(Oc4ccccc4)cc3)n1)C2]

2-((6-acrylamidospiro[3.3]heptan-2-yl)amino)-4-(4-phenoxyphenoxy)pyrimidine-5-carboxamide (195)

2-((6-acrylamidospiro[3.3]heptan-2-yl)amino)-4-(4-phenoxyphenoxy)pyrimidine-5-carboxamide (24.0 mg; 18.6%) was prepared from 4,6-dichloro nicotinamide, 4-phenoxyphenol, tert-butyl (6-aminospiro[3.3]heptan-2-yl)carbamate, and acrylic acid with methods 1A, 12A, 2C, 7D and 2D. HPLC-UV: 90.6% purity. LC/MS m/z=486.0 [M+H]⁺. ¹H NMR (400 MHz, Chloroform-d) δ 9.29-8.84 (m, 1H), 7.41-7.28 (m, 2H), 7.27-6.80 (m, 7H), 6.29 (d, J=17.1 Hz, 1H), 6.05 (dd, J=17.2, 10.4 Hz, 2H), 5.82-5.38 (m, 1H), 4.68-4.20 (m, 1H), 2.68-2.25 (m, 4H), 2.1-2.09 (m, 4H).

Example 185

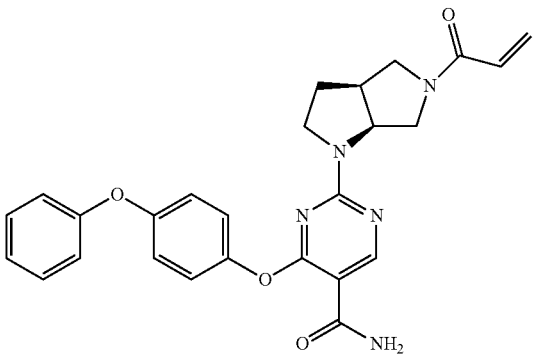 [SMILES: C=CC(=O)N1C[C@@H]2CCN(c3ncc(C(N)=O)c(Oc4ccc(Oc5ccccc5)cc4)n3)[C@@H]2C1]

2-((3aS,6aS)-5-acryloylhexahydropyrrolo[3,4-b]pyrrol-1(2H)-yl)-4-(4-phenoxyphenoxy)pyrimidine-5-carboxamide (203)

2-((3aS,6aS)-5-acryloylhexahydropyrrolo[3,4-b]pyrrol-1(2H)-yl)-4-(4-phenoxyphenoxy)pyrimidine-5-carboxamide (10.0 mg; 12.1%) was prepared from 4,6-dichloro nicotinamide, 4-phenoxyphenol, (3 aS,6aS)-tert-butyl hexahydropyrrolo[3,4-b]pyrrole-5(1H)-carboxylate, and acrylic acid with methods 1A, 12A, 2C, 7D and 2D. HPLC-UV: 98.7% purity. LC/MS m/z=472.0 [M+H]⁺. ¹H NMR (400 MHz, Chloroform-d) δ 9.08 (d, J=16.4 Hz, 1H), 7.73-6.96 (m, 10H), 6.39 (td, J=20.4, 18.8, 12.3 Hz, 1H), 6.15 (dd, J=16.9, 10.2 Hz, 2H), 5.69-5.61 (m, 2H), 4.71-4.63 (m, 2H), 4.44-4.20 (m, 2H), 1.88 (tt, J=17.4, 8.3 Hz, 2H).

Example 186

2-(3-acrylamidopiperidin-1-yl)-4-(4-phenoxyphenoxy)pyrimidine-5-carboxamide (204)

2-(3-acrylamidopiperidin-1-yl)-4-(4-phenoxyphenoxy) pyrimidine-5-carboxamide (10.0 mg; 12.1%) was prepared from 4,6-dichloro nicotinamide, 4-phenoxyphenol, (tert-butyl piperidin-3-ylcarbamate, and acrylic acid with methods 1A, 12A, 2C, 7D and 2D. HPLC-UV: 98.7% purity. LC/MS m/z=460.0 [M+H]⁺. ¹H NMR (400 MHz, Chloroform-d) δ 9.06 (d, J=1.1 Hz, 1H), 7.44, 7.32-7.29 (m, 2H), 6.88-6.77

(m, 7H), 6.24 (d, J=16.9 Hz, 1H), 6.00 (dd, J=16.9, 10.2 Hz, 1H), 5.62 (d, J=11.4 Hz, 1H), 4.07 (s, 1H), 3.70-3.64 (m, 4H), 1.81-1.77 (m, 4H).

m/z=500 [M+H]+ 3.71 min. $^1$H NMR (400 MHz, Chloroform-d) δ 9.05 (d, J=7.0 Hz, 1H), 7.50-7.26 (m, 4H), 7.18-6.80 (m, 5H), 6.71-6.22 (m, 3H), 5.83-5.50 (m, 2H), 4.61 (d, J=39.9 Hz, 2H), 4.27-3.55 (m, 3H), 3.21-2.83 (m, 3H), 2.51 (q, J=7.1 Hz, 2H), 1.66-1.12 (m, 4H).

Example 189

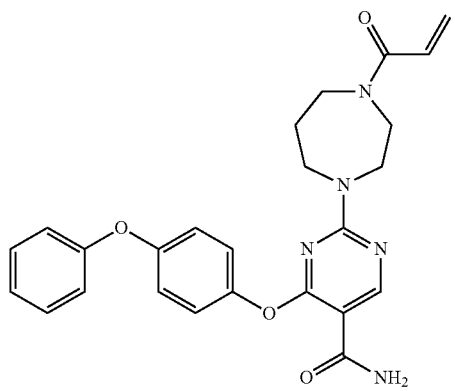 [SMILES: C=CC(=O)N1CCCN(c2ncc(C(N)=O)c(Oc3ccc(Oc4ccccc4)cc3)n2)CC1]

2-(4-acryloyl-1,4-diazepan-1-yl)-4-(4-phenoxyphenoxy)pyrimidine-5-carboxamide (206)

2-(4-acryloyl-1,4-diazepan-1-yl)-4-(4-phenoxyphenoxy)pyrimidine-5-carboxamide (15.0 mg; 16.2%) was prepared from 4,6-dichloro nicotinamide, 4-phenoxyphenol, tert-butyl 1,4-diazepane-1-carboxylate, and acrylic acid with methods 1A, 12A, 2C, 7D and 2D. HPLC-UV: 97.8% purity. LC/MS m/z=460.0 [M+H]$^+$. $^1$H NMR (400 MHz, Chloroform-d) δ 9.05 (d, J=10.6 Hz, 1H), 7.39 (q, J=7.2 Hz, 2H), 7.29-6.94 (m, 10H), 6.66-6.11 (m, 1H), 5.69 (td, J=18.5, 17.8, 10.2 Hz, 2H), 4.11-3.68 (m, 4H), 3.68-3.26 (m, 4H), 1.89-1.31 (m, 2H).

Example 188

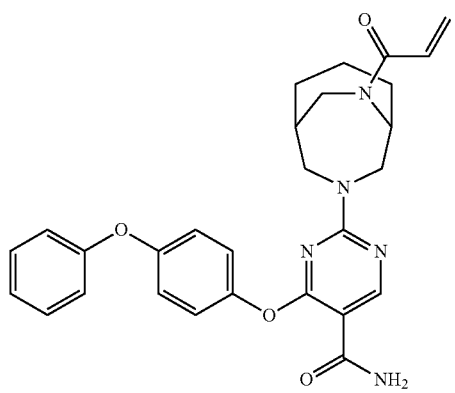

2-((1S,5R)-9-acryloyl-3,9-diazabicyclo[3.3.2]decan-3-yl)-4-(4-phenoxyphenoxy)pyrimidine-5-carboxamide (208)

2-((1S,5R)-9-acryloyl-3,9-diazabicyclo[3.3.2]decan-3-yl)-4-(4-phenoxyphenoxy)pyrimidine-5-carboxamide (15.0 mg; 16.2%) was prepared from 2,4-dichloropyrimidine-5-carboxamide, tert-butyl (1S,5R)-3,9-diazabicyclo[3.3.2]decane-9-carboxylate, and acryloyl chloride with methods 15A, 15B, 15C and 15D. HPLC: 91.3%, RT=4.21 min. MS:

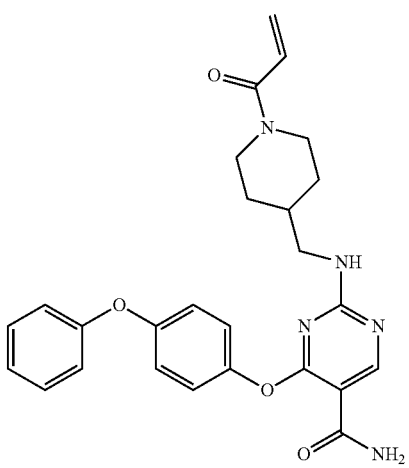 [SMILES: C=CC(=O)N1CCC(CNc2ncc(C(N)=O)c(Oc3ccc(Oc4ccccc4)cc3)n2)CC1]

2-(((1-acryloylpiperidin-4-yl)methyl)amino)-4-(4-phenoxyphenoxy)pyrimidine-5-carboxamide (209)

2-(((1-acryloylpiperidin-4-yl)methyl)amino)-4-(4-phenoxyphenoxy)pyrimidine-5-carboxamide (5.0 mg; 5.2%) was prepared from 2,4-dichloropyrimidine-5-carboxamide, 1-(4-(aminomethyl)piperidin-1-yl)prop-2-en-1-one, and acryloyl chloride with methods 15A, 15B, 15C and 15D. HPLC: 91.3%, RT=4.21 min. MS: m/z=474 [M+H]. $^1$H NMR (400 MHz, Chloroform-d) δ 9.21-8.95 (m, 1H), 7.39 (t, J=7.4 Hz, 2H), 7.18-6.92 (m, 7H), 6.63-6.20 (m, 1H), 5.95-5.58 (m, 2H), 4.12-3.76 (m, 2H), 3.65-3.30 (m, 2H), 2.10-1.58 (m, 2H), 1.56-1.50 (m, 5H).

Example 190

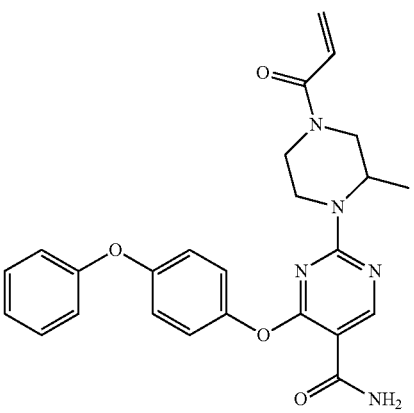 [SMILES: C=CC(=O)N1CCN(c2ncc(C(N)=O)c(Oc3ccc(Oc4ccccc4)cc3)n2)C(C)C1]

2-(4-acryloyl-2-methylpiperazin-1-yl)-4-(4-phenoxyphenoxy)pyrimidine-5-carboxamide (218)

2-(4-acryloyl-2-methylpiperazin-1-yl)-4-(4-phenoxyphenoxy)pyrimidine-5-carboxamide (8.0 mg; 8.6%) was prepared from 2,4-dichloropyrimidine-5-carboxamide, 1-(4-(aminomethyl)piperidin-1-yl)prop-2-en-1-one, and acryloyl chloride with methods 15A, 15B, 15C and 15D. HPLC: 91.3%, MS: m/z=460 [M+H]. $^1$H NMR (400 MHz, DMSO-d6) δ 9.21-8.95 (m, 1H), 7.56 (d, J=4.0 Hz, 2H), 6.92-6.43 (m, 7H), 6.06-5.47 (m, 1H), 4.85 (d, J=30.3 Hz, 1H), 4.23 (tt, J=9.4, 4.3 Hz, 1H), 3.89 (dd, J=95.8, 18.6 Hz, 2H), 3.58-3.35 (m, 2H), 2.33-1.83 (m, 2H), 1.83-1.63 (m, 3H).

Example 191

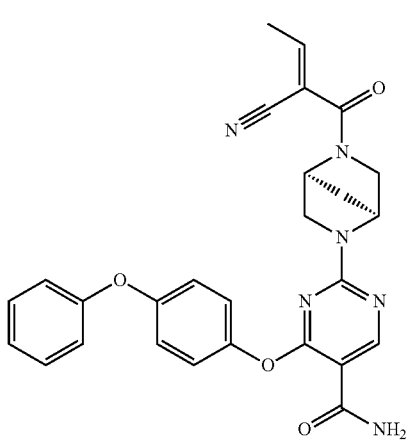 [SMILES: C/C=C(\C#N)C(=O)N1C[C@@H]2C[C@H]1CN2c1ncc(C(N)=O)c(Oc2ccc(Oc3ccccc3)cc2)n1]

2-((1S,4S)-5-((E)-2-cyanobut-2-enoyl)-2,5-diazabicyclo[2.2.1]heptan-2-yl)-4-(4-phenoxyphenoxy)pyrimidine-5-carboxamide (211)

24(1S,4S)-5-((E)-2-cyanobut-2-enoyl)-2,5-diazabicyclo[2.2.1]heptan-2-yl)-4-(4-phenoxyphenoxy)pyrimidine-5-carboxamide (6.0 mg; 3.7%) was prepared from 2,4-dichloropyrimidine-5-carboxamide, tert-butyl (1S,4S)-2,5-diazabicyclo[2.2.1]heptane-2-carboxylate, and (E)-2-cyanobut-2-enoic acid with methods 15A, 15B, 15C and 15D. HPLC: 91.3%, MS: m/z=497 [M+H]. 1H NMR (400 MHz, DMSO-d6) d 8.72 (d, J=3.9 Hz, 1H), 7.69-7.22 (m, 8H), 7.20-6.86 (m, 6H), 5.18-4.66 (m, 2H), 3.95-3.41 (m, 3H), 3.24-2.91 (m, 2H), 2.28-1.77 (m, 4H), 1.42-1.08 (m, 3H).

Example 192

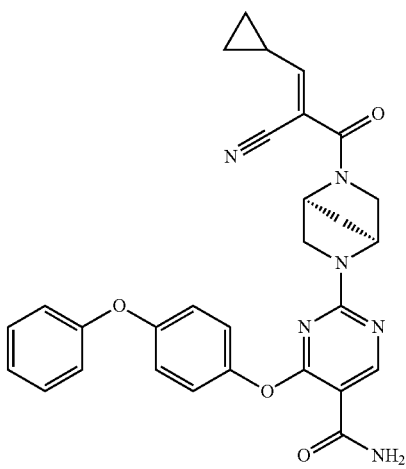 [SMILES: N#C/C(=C\C1CC1)C(=O)N1C[C@@H]2C[C@H]1CN2c1ncc(C(N)=O)c(Oc2ccc(Oc3ccccc3)cc2)n1]

2-((1S,4S)-5-((E)-2-cyano-3-cyclopropylacryloyl)-2,5-diazabicyclo[2.2.1]heptan-2-yl)-4-(4-phenoxyphenoxy)pyrimidine-5-carboxamide (210)

2-((1S,4S)-5-((E)-2-cyano-3-cyclopropylacryloyl)-2,5-diazabicyclo[2.2.1]heptan-2-yl)-4-(4-phenoxyphenoxy)pyrimidine-5-carboxamide was prepared from 2,4-dichloropyrimidine-5-carboxamide, tert-butyl (1S,4S)-2,5-diazabicyclo[2.2.1]heptane-2-carboxylate, and (E)-2-cyano-3-cyclopropylacrylic acid with methods 15A, 15B, 15C and 15D. HPLC: 93.3%, MS: m/z=523 [M+H]. 1H NMR (400 MHz, DMSO-d6) d 8.72 (s, 1H), 7.65-7.26 (m, 7H), 7.20-6.98 (m, 5H), 6.96-6.68 (m, 2H), 5.01 (d, J=10.2 Hz, 1H), 4.94-4.63 (m, 1H), 4.48-4.32 (m, 0H), 4.00-3.47 (m, 2H), 3.11 (d, J=10.8 Hz, 0H), 1.92 (d, J=11.3 Hz, 3H), 1.37-1.11 (m, 2H), 0.97 (d, J=16.7 Hz, 2H).

Example 193

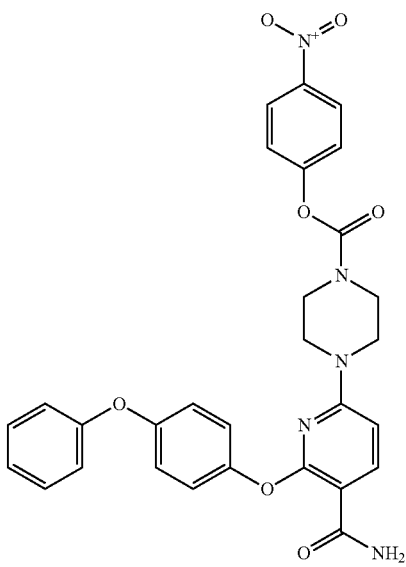

4-nitrophenyl 4-(5-carbamoyl-6-(4-phenoxyphenoxy)pyridin-2-yl)piperazine-1-carboxylate 2-(4-Phenoxy-phenoxy)-6-piperazin-1-yl-nicotinamide hydrochloride (0.25 mmol; 1.00 eq.; 105.00 mg) (synthesized by methods 15A, 15B, 15C) was combined with 4-nitro-phenylchloroformate (0.27 mmol; 1.10 eq.; 54.54 mg), and DIEA (0.74 mmol; 3.00 eq.; 95.37 mg; 0.13 ml) into DCM (62.40 mmol; 253.71 eq.; 5300.00 mg; 4.00 ml). The reaction was stirred at RT for 1 hour. Added 10 mL of DCM and washed with a solution of saturated bicarbonate. Organics were collected, dried over MgSO$_4$, filtered and concentrated to dryness to give the title compound which was used without additional purification (96.00 mg, 63%). MS: m/z=556 [M+H].

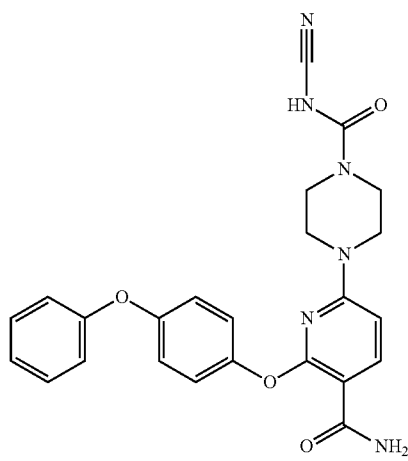 [SMILES: N#CNC(=O)N1CCN(c2ccc(C(N)=O)c(Oc3ccc(Oc4ccccc4)cc3)n2)CC1]

4-(5-carbamoyl-6-(4-phenoxyphenoxy)pyridin-2-yl)-N-cyanopiperazine-1-carboxamide (237)

Cyanamide (0.86 mmol; 5.00 eq.; 36.32 mg) was dissolved into THF (61.71 mmol; 357.13 eq.; 4450.00 mg; 5.00 ml) and then treated with Sodium hydride, 60% dispersion in mineraloil (0.43 mmol; 2.50 eq.; 17.28 mg). The mixture was stirred at RT for 21 minutes. 4-[5-Carbamoyl-6-(4-phenoxy-phenoxy)-pyridin-2-yl]-piperazine-1-carboxylic acid 4-nitro-phenyl ester (0.17 mmol; 1.00 eq.; 96.00 mg) in 2.5 mL of dry THF was then added drop wise. The reaction was then heated to reflux for 1 hour. Reaction was then quenched with 1.5 mL of water then purified directly on reverse phase using a gradient of 10-90% CH3CN/H2O (1% ammonium hydroxide) to give the title compound as an off white solid (22.00 mg; 27.8%). HPLC: 97.1%, MS: m/z=459 [M+H]. $^1$H NMR (400 MHz, DMSO-d6) δ 8.08 (d, J=8.6 Hz, 1H), 7.41 (t, J=7.8 Hz, 2H), 7.32-7.06 (m, 5H), 6.97 (d, J=8.1 Hz, 2H), 6.54 (d, J=8.6 Hz, 1H), 4.01 (s, 4H), 3.29 (h, J=4.3 Hz, 4H).

Example 194

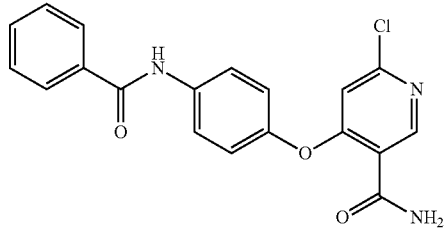 [SMILES: NC(=O)c1cnc(Cl)cc1Oc1ccc(NC(=O)c2ccccc2)cc1]

4-(4-Benzamidophenoxy)-6-chloronicotinamide

To a stirred solution of 4,6-dichloro-nicotinamide (500.00 mg; 2.59 mmol; 1.00 eq.) in DMF (5.00 ml; 10.00 V) was added N-(4-hydroxy-phenyl)-benzamide (669.79 mg; 3.11 mmol; 1.20 eq.) and cesium carbonate (2611.36 mg; 7.77 mmol; 3.00 eq.) at RT. The resulting reaction mixture was stirred for 5 h. The reaction completion was confirmed by TLC. After completion, the reaction mixture was quenched by the addition of water (20 mL). The solid was filtered and dried under vacuum. The solid was further triturated with acetonitrile (25 mL), filtered and dried under vacuum to afford 4-(4-benzoylamino-phenoxy)-6-chloro-nicotinamide (900.00 mg; 94.4%; off white solid). HPLC: 95.20% purity. MS: m/z=368.0 [M+H]$^+$.

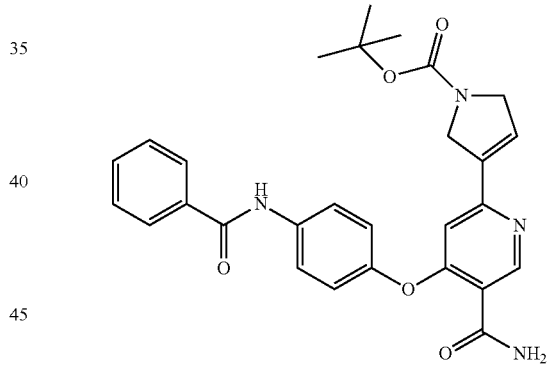

tert-Butyl 3-(4-(4-benzamidophenoxy)-5-carbamoylpyridin-2-yl)-2,5-dihydro-1H-pyrrole-1-carboxylate To a stirred solution of 4-(4-benzoylamino-phenoxy)-6-chloro-nicotinamide (900.00 mg; 2.33 mmol; 1.00 eq.) in mixture of 1,4-dioxane (8.10 ml; 9.00 V) and water (0.90 ml; 1.00 V) was added 3-(4,4,5,5-tetramethyl-[1,3,2]dioxaborolan-2-yl)-2,5-dihydro-pyrrole-1-carboxylic acid tert-butyl ester (1389.21 mg; 4.66 mmol; 2.00 eq.) and cesium carbonate (3.00 eq.) at RT under nitrogen atmosphere. The resulting reaction mixture was degassed with nitrogen for 20 min and to it was added bis(triphenylphosphine)palladium (II) dichloride (81.99 mg; 0.12 mmol; 0.05 eq.). The reaction mixture was heated to 90° C. for 14 h. The reaction completion was confirmed by TLC. After completion, the reaction mixture was cooled to RT, filtered through a Celite bed and washed with ethyl acetate (100 mL). The combined filtrate was washed with water (100 mL) and saturated brine solution (50 mL) and dried over Na₂SO₄. The organic solvent was concentrated under reduced pressure to afford the crude product, which was purified by column chromatography using silica gel (60-120 mesh) and 70-80% ethyl acetate in hexane as eluent to afford 3-[4-(4-benzoylamino-phenoxy)-5-carbamoyl-pyridin-2-yl]-2,5-dihydro-pyrrole-1-carboxylic acid tert-butyl ester (1000 mg; 69.7%; off-white solid). HPLC: 81.30% purity. MS: m/z=501.0 [M+H]⁺.

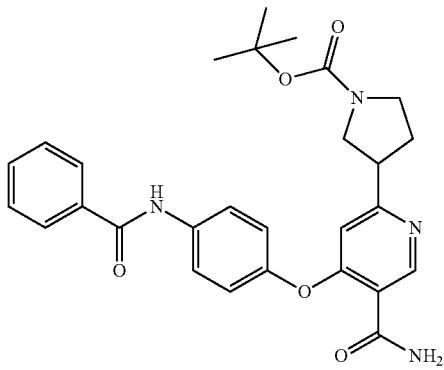 [SMILES: CC(C)(C)OC(=O)N1CCC(c2cc(Oc3ccc(NC(=O)c4ccccc4)cc3)c(C(N)=O)cn2)C1]

tert-Butyl 3-(4-(4-benzamidophenoxy)-5-carbamoylpyridin-2-yl)pyrrolidine-1-carboxylate To stirred solution of 3-[4-(4-Benzoylamino-phenoxy)-5-carbamoyl-pyridin-2-yl]-2,5-dihydro-pyrrole-1-carboxylic acid tert-butyl ester (1000.00 mg; 1.62 mmol; 1.00 eq.) in a mixture of methanol (5.00 ml; 5.00 V) and THF (5.00 ml; 5.00 V) was added palladium on carbon (10% w/w) (172.85 mg; 0.16 mmol; 0.10 eq.) under nitrogen atmosphere. The mixture was stirred at RT under 1 Kg H₂ pressure for 4 h. The reaction was monitored by TLC. The reaction mixture was filtered through a Celite bed. The Celite was washed with methanol and the filtrate was evaporated under reduced pressure to obtain 3-[4-(4-benzoylamino-phenoxy)-5-carbamoyl-pyridin-2-yl]-pyrrolidine-1-carboxylic acid tert-butyl ester (700.00 mg; 1.32 mmol; 81.5%; off-white solid; crude product). HPLC: 95.02% purity. MS: m/z=503.30 [M+H]⁺.

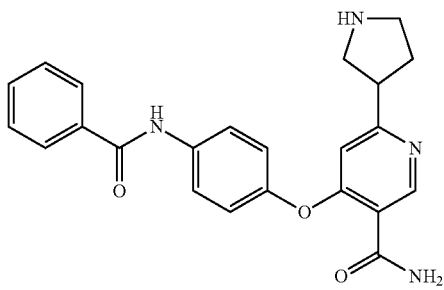 [SMILES: NC(=O)c1cnc(C2CCNC2)cc1Oc1ccc(NC(=O)c2ccccc2)cc1]

4-(4-Benzamidophenoxy)-6-(pyrrolidin-3-yl)nicotinamide

To a stirred solution of 3-[4-(4-benzoylamino-phenoxy)-5-carbamoyl-pyridin-2-yl]-pyrrolidine-1-carboxylic acid tert-butyl ester (700.00 mg; 1.32 mmol; 1.00 eq.) in 1,4-dioxane (3.50 ml; 5.00 V) was added HCl in dioxane (3.50 ml; 5.00 V) slowly at 0° C. The resulting mixture was stirred for 12 h at RT. The reaction completion was confirmed by TLC. The reaction mixture was evaporated under reduced pressure to get the residue. The residue was dissolved in water and basified with 10% NaHCO₃ solution and extracted with ethyl acetate. The organic layer was washed with water, dried over Na₂SO4 and evaporated under reduced pressure to get the crude product. The crude product was purified by column chromatography to afford 4-(4-Benzoylamino-phenoxy)-6-pyrrolidin-3-yl-nicotinamide (300.00 mg; 54.8%; off white solid). MS: m/z=403.30 [M+H]⁺. HPLC: 97.29% purity. ¹H NMR (400 MHz, DMSO-d6): δ10.39 (s, 1H), 8.68 (s, 1H), 7.97-7.95 (m, 2H), 7.90-7.88 (m, 2H), 7.70 (bs, 2H), 7.60-7.52 (m, 3H), 7.24-7.22 (m, 2H), 6.53 (s, 1H), 3.16-3.12 (m, 1H), 3.06-3.01 (m, 1H), 2.90-2.84 (m, 1H), 2.81-2.75 (m, 1H), 2.72-2.66 (m, 1H), 2.69-2.65 (m, 1H), 2.00-1.93 (m, 1H), 1.80-1.71 (m, 1H).

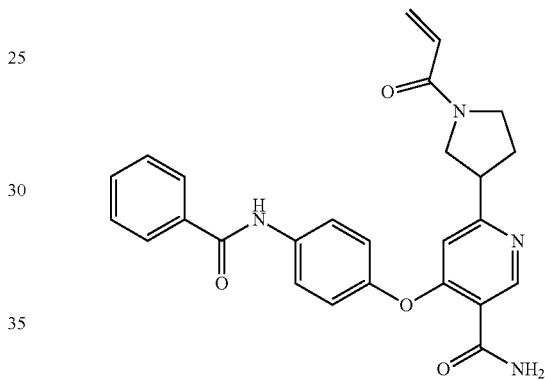

6-(1-Acryloylpyrrolidin-3-yl)-4-(4-benzamidophenoxy)nicotinamide (184)

To a stirred solution of 4-(4-benzoylamino-phenoxy)-6-pyrrolidin-3-yl-nicotinamide (150.00 mg; 0.36 mmol; 1.00 eq.) in DCM (1.50 ml; 10.00 V) was added ethyl-diisopropyl-amine (0.19 ml; 1.09 mmol; 3.00 eq.). To this reaction mixture was added acryloyl chloride (0.03 ml; 0.33 mmol; 0.90 eq.) dropwise at 0° C. The reaction mixture was stirred for 30 min at RT. The reaction completion was confirmed by TLC. The reaction mixture was quenched with ice water and extracted with DCM (1×30 ml). The organic layer was washed with water, brine solution, dried over Na₂SO₄ and evaporated under reduced pressure to get the crude product. The crude product was purified by column chromatography (60-120 mesh) using methanol (2-3%) in DCM as an eluent to afford 6-(1-acryloyl-pyrrolidin-3-yl)-4-(4-benzoylamino-phenoxy)-nicotinamide (50.00 mg; 29.9%; off-white solid). MS: m/z=457.20 [M+H]⁺. HPLC: 99.77% purity. ¹H NMR (400 MHz, DMSO-d6): 10.38 (s, 1H), 8.70 (d, J=2.00 Hz, 1H), 7.97-7.95 (m, 2H), 7.91-7.89 (m, 2H), 7.73 (s, 2H), 7.60-7.56 (m, 1H), 7.55-7.52 (m, 2H), 7.25-7.22 (m, 2H), 6.65-6.58 (m, 1H), 6.56-6.51 (m, 1H), 6.13-6.07 (m, 1H), 5.65-5.60 (m, 1H), 3.93-3.42 (m, 5H), 2.21-1.92 (m, 2H).

Example 195

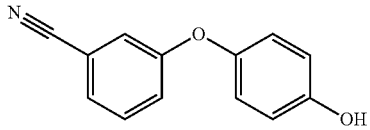 [SMILES: N#Cc1cccc(Oc2ccc(O)cc2)c1]

3-(4-Hydroxyphenoxy)benzonitrile

To a stirred solution of 3-[4-(4,4,5,5-tetramethyl-[1,3,2] dioxaborolan-2-yl)-phenoxy]-benzonitrile (1000.00 mg; 2.93 mmol; 1.00 eq.) in THF (10.00 ml; 10.00 V) at 0° C. was added first sodium hydroxide (117.06 mg; 2.93 mmol; 1.00 eq.), and then hydrogen peroxide (30% solution, 0.90 ml; 8.78 mmol; 3.00 eq.). The resulting reaction mixture was slowly warmed to room temperature for 3 h. Reaction progress was monitored by TLC. The reaction was slowly quenched by the addition of ice cold water and then extracted with ethyl acetate. The organic layer was with water, then brine, and then was dried over $Na_2SO_4$. The solvent was evaporated under reduced pressure to afford 3-(4-hydroxy-phenoxy)-benzonitrile (600.00 mg; 96.1%; off-white solid). $^1$H NMR (400 MHz, CDCl3): δ 7.41-7.37 (m, 1H), 7.33-7.32 (m, 1H), 7.31-7.27 (m, 2H), 7.20-7.14 (m, 2H), 6.96-6.86 (m, 2H), 5.23 (s, 1H).

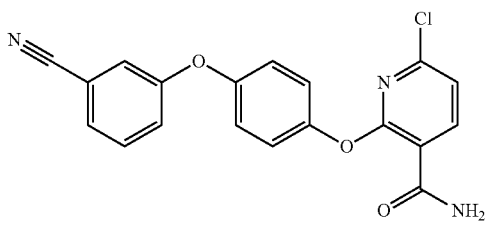 [SMILES: N#Cc1cccc(Oc2ccc(Oc3nc(Cl)ccc3C(N)=O)cc2)c1]

6-Chloro-2-(4-(3-cyanophenoxy)phenoxy)nicotinamide

To a stirred solution of 2,6-dichloro-nicotinamide (500.00 mg; 2.62 mmol; 1.00 eq.) in DMF (5.00 ml; 10.00 V) was added 3-(4-hydroxy-phenoxy)-benzonitrile (670.16 mg; 3.14 mmol; 1.20 eq.) and cesium carbonate (1722.97 mg; 5.24 mmol; 2.00 eq.) at RT. The resulting reaction mixture was stirred for 5 h. The reaction completion was confirmed by TLC. After completion of the reaction, the reaction mixture was quenched by the addition of water (20 mL). The solid was collected by filtration and dried under vacuum. The solid was further triturated with acetonitrile (25 mL) and filtered and dried under vacuum to afford 6-chloro-2-[4-(3-cyano-phenoxy)-phenoxy]-nicotinamide (800.00 mg; 83.6%; off white solid). HPLC: 98.06% purity. MS: m/z=364.0 [M+H]$^+$.

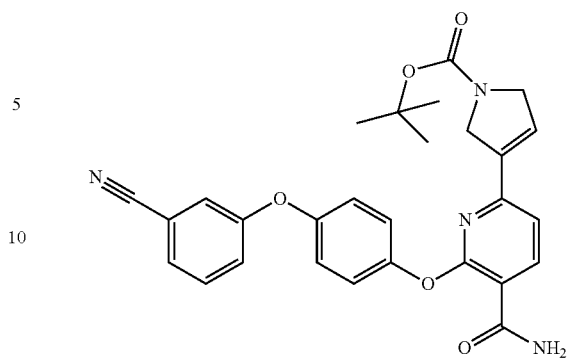

tert-Butyl 3-(5-carbamoyl-6-(4-(3-cyanophenoxy) phenoxy)pyridin-2-yl)-2,5-dihydro-1H-pyrrole-1-carboxylate To a stirred solution of 6-chloro-2-[4-(3-cyano-phenoxy)-phenoxy]-nicotinamide (800.00 mg; 2.14 mmol; 1.00 eq.) in a mixture of 1,4-dioxane (7.20 ml; 9.00 V) and water (0.80 ml; 1.00 V) was added 3-(4,4,5,5-tetramethyl-[1,3,2]dioxaborolan-2-yl)-2,5-dihydro-pyrrole-1-carboxylic acid tert-butyl ester (1278.96 mg; 4.29 mmol; 2.00 eq.) and then cesium carbonate (2117.57 mg; 6.43 mmol; 3.00 eq.) at RT under nitrogen atmosphere. The resulting reaction mixture was degassed with nitrogen for 20 min and then was treated with bis(triphenylphosphine)palladium(II) dichloride (153.61 mg; 0.21 mmol; 0.10 eq.). The reaction mixture was heated to 90° C. for 14 h. Reaction completion was confirmed by TLC. The reaction mixture was cooled to RT, filtered through a Celite bed and washed with ethyl acetate (200 mL). The combined filtrate was washed with water (100 mL) and then saturated brine (150 mL), and then was dried over $Na_2SO_4$. The organic solvent was concentrated under reduced pressure to afford 3-{5-carbamoyl-6-[4-(3-cyano-phenoxy)-phenoxy]-pyridin-2-yl}-2,5-dihydro-pyrrole-1-carboxylic acid tert-butyl ester (800.00 mg; 60.8%; off white solid). HPLC: 81.20% purity. MS: m/z=399.20 [M+H]$^+$.

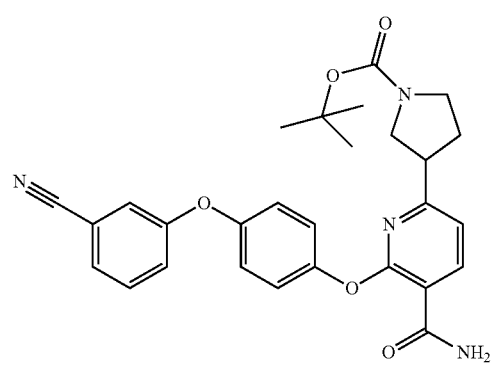 [SMILES: CC(C)(C)OC(=O)N1CCC(c2ccc(C(N)=O)c(Oc3ccc(Oc4cccc(C#N)c4)cc3)n2)C1]

tert-Butyl 3-(5-carbamoyl-6-(4-(3-cyanophenoxy) phenoxy)pyridin-2-yl)pyrrolidine-1-carboxylate To a stirred solution of 3-{5-carbamoyl-6-[4-(3-cyano-phenoxy)-phenoxy]-pyridin-2-yl}-2,5-dihydro pyrrole-1-carboxylic acid tert-butyl ester (800.00 mg; 1.30 mmol; 1.00 eq.) in a mixture of methanol (8.00 ml; 10.00 V) and THF (8.00 ml; 10.00 V) was added palladium on carbon (10% w/w) (138.67 mg; 0.13 mmol; 0.10 eq.) under nitrogen atmosphere. The mixture was stirred at RT under 1 Kg $H_2$ pressure for 4 h. The reaction was monitored by TLC. The reaction mixture was filtered through a Celite bed and washed with methanol. The filtrate was evaporated under vacuum to obtain 3-{5-carbamoyl-6-[4-(3-cyano-phenoxy)-phenoxy]-pyridin-2-yl}-pyrrolidine-1-carboxylic acid tert-butyl ester (600.00 mg; 78.2%; off white solid). HPLC: 85.01 purity. MS: m/z=401.20 $[M+H]^+$.

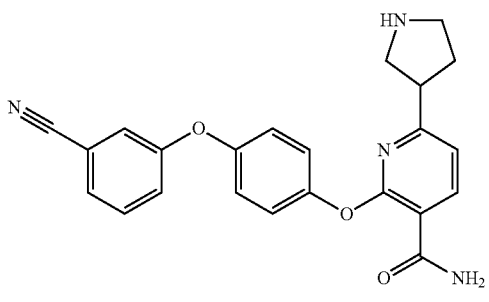 [SMILES: N#Cc1cccc(Oc2ccc(Oc3nc(C4CCNC4)ccc3C(N)=O)cc2)c1]

2-(4-(3-Cyanophenoxy)phenoxy)-6-(pyrrolidin-3-yl)nicotinamide

To a stirred solution of 3-{5-carbamoyl-6-[4-(3-cyano-phenoxy)-phenoxy]-pyridin-2-yl}-pyrrolidine-1-carboxylic acid tert-butyl ester (600.00 mg; 1.02 mmol; 1.00 eq.) in 1,4-dioxane (6.00 ml; 10.00 V) was added HCl in Dioxane (6.00 ml; 10.00 V) slowly dropwise at 0° C. Resulting mixture was stirred for 12 h at RT. The reaction completion was confirmed by TLC. The reaction mixture was evaporated under reduced pressure to provide the residue. The residue was dissolved in water and basified with 10% $NaHCO_3$ solution (up to pH 9), extracted with ethyl acetate, dried over $Na_2SO_4$ and evaporated under reduced pressure to provide the crude product. The crude was purified using flash chromatography to afford 2-[4-(3-Cyano-phenoxy)-phenoxy]-6-pyrrolidin-3-yl-nicotinamide as a light green solid (300 mg; 71.7%). MS: m/z=401.20 $[M+H]^+$. HPLC: 97.49% purity. $^1H$ NMR (400 MHz, DMSO-d6): 8.10-8.08 (m, 1H), 7.72 (s, 2H), 7.61-7.57 (m, 2H), 7.46-7.45 (m, 1H), 7.36-7.33 (m, 1H), 7.29-7.25 (m, 2H), 7.20-7.16 (m, 2H), 7.08 (d, J=7.68 Hz, 1H), 3.20-3.16 (m, 1H), 2.95-2.90 (m, 1H), 2.75-2.67 (m, 1H), 2.66-2.58 (m, 2H), 1.94-1.90 (m, 1H), 1.64-1.59 (m, 1H).

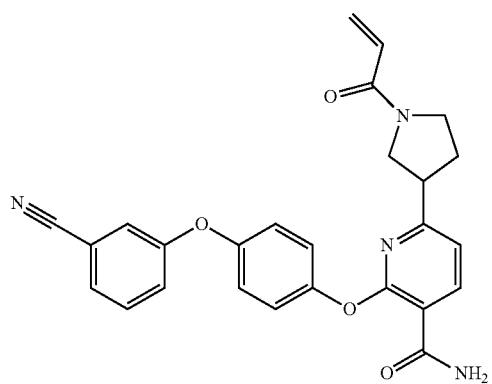 [SMILES: C=CC(=O)N1CCC(c2ccc(C(N)=O)c(Oc3ccc(Oc4cccc(C#N)c4)cc3)n2)C1]

6-(1-Acryloylpyrrolidin-3-yl)-2-(4-(3-cyanophenoxy)phenoxy)nicotinamide (185)

To a stirred solution of 2-[4-(3-cyano-phenoxy)-phenoxy]-6-pyrrolidin-3-yl-nicotinamide (200.00 mg; 0.49 mmol; 1.00 eq.) in DCM was added ethyl-diisopropyl-amine (0.26 ml; 1.46 mmol; 3.00 eq.). To this reaction mixture was added acryloyl chloride (0.04 ml; 0.44 mmol; 0.90 eq.) in drops at 0° C. The reaction mixture was stirred for 30 min at RT. Reaction completion was confirmed by TLC. The reaction was quenched by the addition of ice water and extracted with DCM (1×30 ml). The organic layer was washed with water, followed by brine, and then dried over $Na_2SO_4$. The solvent evaporated under reduced pressure to get the crude product. The crude product was purified by flash chromatography (60-120 mesh silica) using methanol (3-4%) in DCM as an eluent to afford 6-(1-acryloyl-pyrrolidin-3-yl)-2-[4-(3-cyano-phenoxy)-phenoxy]-nicotinamide (60.00 mg; 27.0%; off white solid). MS: m/z=455.30 $[M+H]^+$. HPLC: 99.44% purity. $^1H$ NMR (400 MHz, DMSO-d6): 8.14 (dd, J=4.08, 7.64 Hz, 1H), 7.61-7.58 (m, 2H), 7.53-7.49 (m, 1H), 7.34-7.32 (m, 2H), 7.26-7.23 (m, 1H), 7.20-7.10 (m, 2H), 6.46-6.40 (m, 1H), 6.07-6.05 (m, 1H), 5.62-5.56 (m, 1H), 3.84-3.63 (m, 1H), 3.56-3.37 (m, 3H), 3.35-3.30 (m, 2H), 2.21-2.08 (m, 1H), 1.95-1.81 (m, 1H).

Example 196

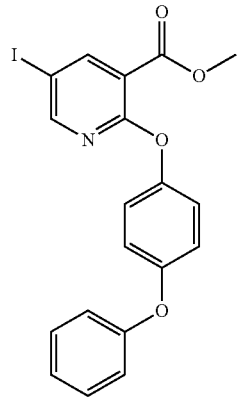

5-Iodo-2-(4-phenoxy-phenoxy)-nicotinic acid methyl ester

To a stirred solution of 2-chloro-5-iodo-nicotinic acid methyl ester (4.00 g; 12.77 mmol; 1.00 eq.) in DMF (40.00 ml; 10.00 V) were added potassium carbonate (3.60 g; 25.55 mmol; 2.00 eq.) and 4-phenoxy-phenol (2.64 g; 14.05 mmol; 1.10 eq.) at RT under nitrogen atmosphere. The reaction mixture was then heated to 90° C. for 2 h. After completion of the reaction (monitored by TLC and LC/MS), the reaction was first quenched by the addition of water (200 mL), and then extracted with diethyl ether (3×100 mL). The organic phases were combined, washed with water (2×100 mL), and then dried over $Na_2SO_4$. The solvent was evaporated under reduced pressure to afford 5-iodo-2-(4-phenoxy-phenoxy)-nicotinic acid methyl ester (4.00 g, 60.2%) as an off-white solid. HPLC: 86% purity. MS m/z=448 $[M+H]^+$. $^1H$ NMR (400 MHz, DMSO-d6) δ 8.83 (s, 1H), 8.56-8.49 (m, 1H), 7.42-7.38 (m, 2H), 7.16-7.12 (m, 3H), 7.05-7.02 (m, 4H), 3.9 (s, 3H).

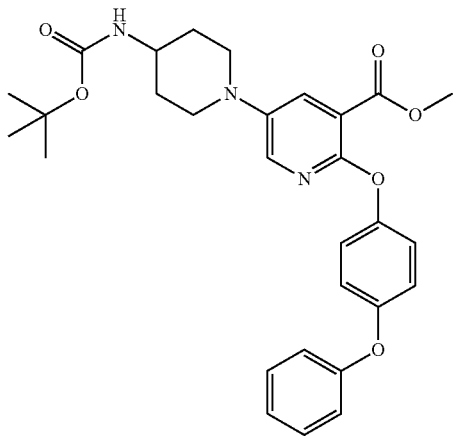 [SMILES: COC(=O)c1cc(N2CCC(NC(=O)OC(C)(C)C)CC2)cnc1Oc1ccc(Oc2ccccc2)cc1]

4-tert-Butoxycarbonylamino-6'-(4-phenoxy-phenoxy)-3,4,5,6-tetrahydro-2H-[1,3']bipyridinyl-5'-carboxylic acid methyl ester To a stirred solution of 5-iodo-2-(4-phenoxy-phenoxy)-nicotinic acid methyl ester (1.00 g; 1.92 mmol; 1.00 eq.) in 1,4-dioxane (20.00 ml; 20.00 V) were added piperidin-4-yl-carbamic acid tert-butyl ester (0.50 g; 2.31 mmol; 1.20 eq.) and cesium carbonate at RT under nitrogen atmosphere. The resulting reaction mixture was degassed with nitrogen for 20 min, and then treated with dicyclohexyl-(2',6'-diisopropoxy-biphenyl-2-yl)-phosphane (0.05 g; 0.10 mmol; 0.05 eq.) and tris(dibenzylideneacetone)dipalladium(0). The reaction mixture was heated in a sealed tube at 100° C. for 16 h. Upon completion of the reaction (as monitored by TLC), the reaction mixture was cooled to RT. The reaction mixture was filtered through a Celite bed, which was then washed with EtOAc (50 mL). The filtrate was washed with water (lx 50 mL) and brine (1×20 mL), and then dried over sodium sulphate. The solvent was concentrated under reduced pressure. The resulting residue was purified by flash chromatography using silica gel (60-120 mesh) and (3:7) EtOAc:Pet ether as an eluent to afford 4-tert-butoxycarbonylamino-6'-(4-phenoxy-phenoxy)-3,4,5,6-tetrahydro-2H-[1,3']bipyridinyl-5'-carboxylic acid methyl ester (800.00 mg, 66.7%) as a brown semi solid. HPLC 83.3% purity. MS m/z=520 [M+H]+. 1H NMR (400 MHz, DMSO-d6) δ 8.0 (s, 1H), 7.8 (s, 1H), 7.77-7.36 (m, 2H), 7.13-7.09 (t, J=7.4 Hz, 1H), 7.05-6.99 (m, 6H), 6.87-6.85 (d, J=7.7 Hz, 1H), 3.8 (s, 3H), 3.60-3.58 (d, J=12.6 Hz, 2H), 3.3 (s, 1H), 2.78-2.73 (t, J=11.8 Hz, 2H), 1.80-1.77 (d, J=10.2 Hz, 2H), 1.50-1.45 (m, 2H), 1.4 (s, 9H).

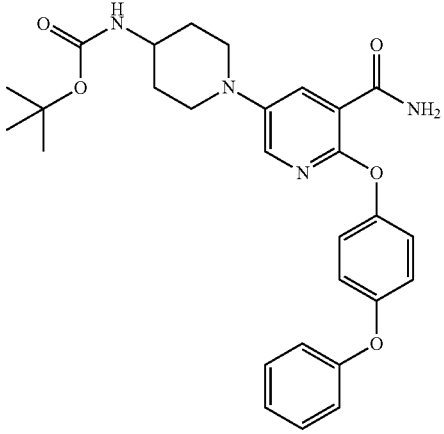 [SMILES: CC(C)(C)OC(=O)NC1CCN(c2cnc(Oc3ccc(Oc4ccccc4)cc3)c(C(N)=O)c2)CC1]

[5'-Carbamoyl-6'-(4-phenoxy-phenoxy)-3,4,5,6-tetrahydro-2H-[1,3']bipyridinyl-4-yl]-carbamic acid tert-butyl ester A solution of 4-tert-butoxycarbonylamino-6'-(4-phenoxy-phenoxy)-3,4,5,6-tetrahydro-2H-[1,3']bipyridinyl-5'-carboxylic acid methyl ester (800 mg; 1.28 mmol; 1.00 eq.) in methanolic ammonia (8.00 ml; 10.00 V) was heated to 60° C. for 16 h in sealed tube. The reaction progress was monitored by TLC. After completion of the reaction, the reaction mixture was concentrated under reduced pressure to afford [5'-carbamoyl-6'-(4-phenoxy-phenoxy)-3, 4, 5, 6-tetrahydro-2H-[1, 3'] bipyridinyl-4-yl]-carbamic acid tert-butyl ester (600.00 mg, 87.2%) as a yellow solid. HPLC 94.1% purity. MS m/z=505 [M+H]+. 1H NMR (400 MHz, DMSO-d6) δ 7.91 (s, 1H), 7.90 (s, 1H), 7.73-7.36 (m, 2H), 7.13-7.09 (m, 3H), 7.04-7.00 (m, 4H), 6.99-6.85 (m,1H), 3.59-3.56 (s, 2H), 3.31 (s, 1H), 2.76-2.71 (m, 2H), 1.80-1.77 (d, 2H), 1.55-1.50 (d, 2H), 1.45 (s, 9H).

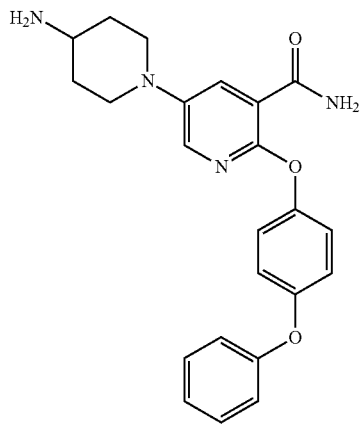 [SMILES: NC(=O)c1cc(N2CCC(N)CC2)cnc1Oc1ccc(Oc2ccccc2)cc1]

4-Amino-6'-(4-phenoxy-phenoxy)-3,4,5,6-tetrahydro-2H-[1,3']bipyridinyl-5'-carboxylic acid amide To a stirred solution of [5'-carbamoyl-6'-(4-phenoxy-phenoxy)-3,4,5,6-tetrahydro-2H-[1,3']bipyridinyl-4-yl]-carbamic acid tert-butyl ester (400 mg; 0.75 mmol; 1.00 eq.) in DCM (10.00 ml) was added 4N HCl in 1,4-dioxane (10.00 ml) dropwise at RT under nitrogen atmosphere. The reaction mixture was stirred at RT for 5 h. After completion of the reaction (monitored by TLC), the mixture was concentrated under reduced pressure. The residue was diluted with DCM (50 mL), neutralized by the addition of saturated aqueous sodium bicarbonate solution (20 mL), and extracted with DCM/15% MeOH (3×20 mL). The organic layer was washed with brine (20 mL), dried over sodium sulphate and concentrated under vacuum to afford 4-amino-6'-(4-phenoxy-phenoxy)-3,4,5,6-tetrahydro-2H-[1,3']bipyridinyl-5'-carboxylic acid amide (380.00 mg, 95.6%) as a light brown oil. HPLC: 75.9% purity. MS m/z=405 [M+H]$^+$. $^1$H NMR (400 MHz, DMSO-d6) δ 7.9 (s, 1H), 7.92-7.76 (m, 3H), 7.76-7.13 (m, 3H), 7.12-7.04 (m, 4H), 7.02-6.99 (m, 5H), 4.46-4.44 (t, J=5.2 Hz, 2H), 3.66-3.56 (m, 1H), 3.42-3.38 (m, 2H), 2.5 (s, 2H), 1.98-1.70 (m, 2H).

Example 197

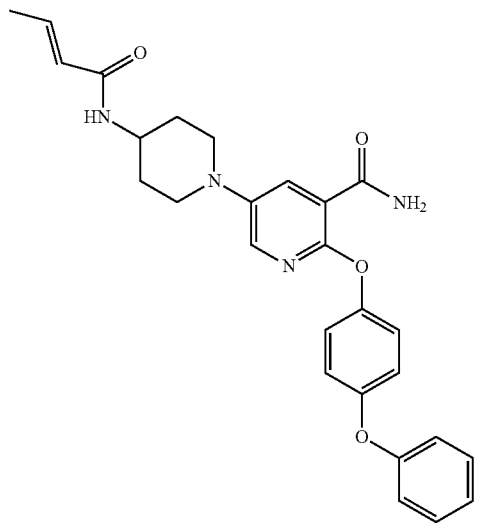 [SMILES: C/C=C/C(=O)NC1CCN(c2cnc(Oc3ccc(Oc4ccccc4)cc3)c(C(N)=O)c2)CC1]

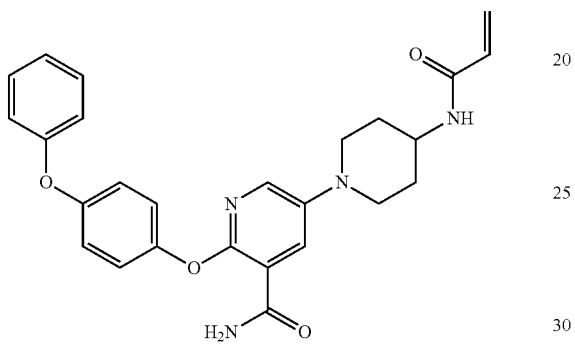

4-Acryloylamino-6'44-phenoxy-phenoxy)-3,4,5,6-tetrahydro-2H-[1,3']bipyridinyl-5'-carboxylic acid amide (197)

To a stirred solution of 4-amino-6'-(4-phenoxy-phenoxy)-3,4,5,6-tetrahydro-2H-[1,3']bipyridinyl-5'-carboxylic acid amide (170.00 mg; 0.32 mmol; 1.00 eq.) in dry DCM (5.10 ml; 30.00 V) at −10° C. under nitrogen was added N,N-diisopropylethylamine (0.17 ml; 0.96 mmol; 3.00 eq.) dropwise. The reaction mixture was stirred at −10° C. under nitrogen for 15 min. Acryloyl chloride (0.03 ml; 0.35 mmol; 1.10 eq.) was then added dropwise, and the mixture was stirred at −10° C. for another 30 min. After completion of the reaction (monitored by TLC), the reaction was quenched by the addition of water (50 mL) and extracted with DCM (3×30 mL). The organic layers were combined, washed with brine (1×20 mL), dried over sodium sulphate, and concentrated under reduced pressure. The residue was purified by flash chromatograpy over silica gel (60-120 mesh) using 0-2% DCM:MeOH as an eluent to afford 4-acryloylamino-6'-(4-phenoxy-phenoxy)-3,4,5,6-tetrahydro-2H-[1,3']bipyridinyl-5'-carboxylic acid amide (50.00 mg, 33.5%) as an off-white solid. HPLC: 98% purity. MS m/z=459 [M+H]$^+$ $^1$H NMR (400 MHz, DMSO-d6) δ 8.08-8.06 (d, J=7.6 Hz, 1H), 7.93-7.92 (d, J=3.1 Hz, 1H), 7.76-7.75 (d, J=3.1 Hz, 3H), 7.41-7.37 (m, 2H), 7.14-7.10 (m, 3H), 7.05-6.99 (m, 4H), 6.24-6.17 (m, 1H), 6.05-6.05 (m, 1H), 5.59-5.56 (m, 1H), 3.81-3.77 (m, 1H), 3.77-3.59 (m, 2H), 2.86-2.80 (m, 2H), 1.87-1.83 (m, 2H), 1.56-1.46 (m, 2H).

4-((E)-But-2-enoylamino)-6'-(4-phenoxy-phenoxy)-3,4,5,6-tetrahydro-2H-[1,3']bipyridinyl-5'-carboxylic acid amide (200)

To a stirred solution of 4-amino-6'-(4-phenoxy-phenoxy)-3,4,5,6-tetrahydro-2H-[1,3']bipyridinyl-5'-carboxylic acid amide (200.00 mg; 0.38 mmol; 1.00 eq.) in dry DCM (6.00 ml; 30.00 V) at −10° C. under nitrogen was added N,N-diisopropylethylamine (0.20 ml; 1.13 mmol; 3.00 eq.) dropwise. The reaction mixture was stirred at −10° C. for 15 min and then treated with (E)-but-2-enoyl chloride (0.04 g; 0.38 mmol; 1.00 eq.), dropwise. The reaction mixture was then stirred at −10° C. for 30 min. After completion of the reaction by TLC, the reaction was quenched by the addition of water (50 mL) and extracted with DCM (3×30 mL). The organic layers were combined, washed with brine (1×20 mL), dried over sodium sulphate and concentrated under reduced pressure. The crude product was purified by flash chromatography over silica gel (60-120 mesh) using DCM:MeOH (9.5:0.5) as an eluent to afford 4-((E)-but-2-enoylamino)-6'-(4-phenoxy-phenoxy)-3,4,5,6-tetrahydro-2H-[1,3']bipyridinyl-5'-carboxylic acid amide (70.00 mg, 37.7%) as an off-white solid. HPLC: 95.6% purity. MS m/z=473 [M+H]$^+$. $^1$H NMR (400 MHz, DMSO-d6) δ 7.92-7.86 (d, J=23.6 Hz, 1H), 7.84-7.75 (m, 1H), 7.75 (s, 3H), 7.41-7.37 (m, 2H), 7.14-7.11 (m, 3H), 7.04-6.99 (m, 4H), 6.62-6.56 (m, 1H), 5.90-5.85 (dd, J=15.3, 1.7 Hz, 1H), 3.62-3.59 (m, 3H), 2.83-2.78 (t, J=11.2 Hz, 2H), 1.83-1.76 (m, 5H), 1.50-1.47 (m, 2H).

Example 198

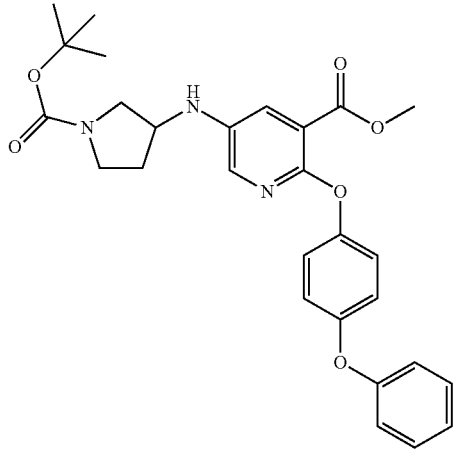 [SMILES: COC(=O)c1cc(NC2CCN(C(=O)OC(C)(C)C)C2)cnc1Oc1ccc(Oc2ccccc2)cc1]

5-(1-tert-Butoxycarbonyl-pyrrolidin-3-ylamino)-2-(4-phenoxy-phenoxy)-nicotinic acid methyl ester To a stirred solution of 5-iodo-2-(4-phenoxy-phenoxy)-nicotinic acid methyl ester (1.00 g; 1.92 mmol; 1.00 eq.) in 1,4-dioxane (15.00 ml; 15.00 V) was added 3-amino-pyrrolidine-1-carboxylic acid tert-butyl ester (0.44 g; 2.31 mmol; 1.20 eq.) at RT under nitrogen atmosphere. The resulting reaction mixture was degassed with nitrogen for 20 min. The reaction mixture was then treated with dicyclohexyl-(2',4',6'-triisopropoxy-4,6-dimethoxy-biphenyl-2-yl)-phosphane (0.06 g; 0.10 mmol; 0.05 eq.) and tris(dibenzylideneacetone)dipalladium(0) (181.54 mg; 0.19 mmol; 0.10 eq.). The reaction mixture was heated to 100° C. for 16 h. After completion of the reaction (monitored by TLC and LC/MS), the reaction mixture was cooled to RT. The reaction was quenched by the addition of water (100 mL) and extracted with EtOAc (3×50 mL). The organic layers were combined, washed with brine (1×50 mL), dried over sodium sulphate, and concentrated under reduced pressure. The residue was purified by flash chromatography over silica gel (60-120 mesh) using 25% EtOAc:Pet ether as an eluent to afford 5-(1-tert-butoxycarbonyl-pyrrolidin-3-ylamino)-2-(4-phenoxy-phenoxy)-nicotinic acid methyl ester (900.00 mg, 90.7%) as a brown semi solid. HPLC: 98% purity. MS m/z=506 [M+H]$^+$. $^1$H NMR (400 MHz, DMSO-d6) δ 7.76-7.75 (d, J=3.0 Hz, 1H), 7.50 (s, 1H), 7.40-7.30 (m, 2H), 7.12-7.08 (t, J=7.4 Hz, 1H), 6.99-6.97 (t, J=7.8 Hz, 5H), 6.18-6.17 (d, J=6.6 Hz, 1H), 4.01 (s, 1H), 3.79 (s, 3H), 3.54 (s, 1H), 3.32 (s, 1H), 3.07 (s, 2H), 2.11 (s, 1H), 1.79 (s, 1H), 1.39 (s, 9H).

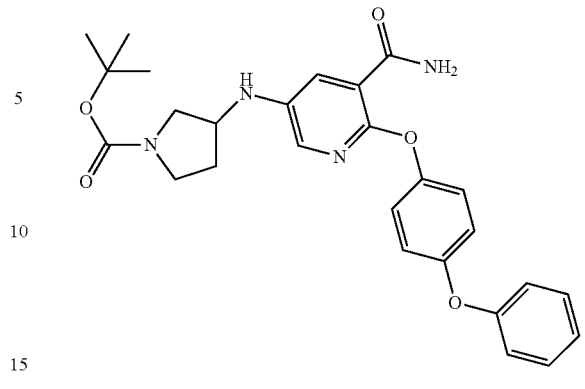

3-[5-Carbamoyl-6-(4-phenoxy-phenoxy)-pyridin-3-ylamino]-pyrrolidine-1-carboxylic acid tert-butyl ester A stirred solution of 5-(1-tert-butoxycarbonyl-pyrrolidin-3-ylamino)-2-(4-phenoxy-phenoxy)-nicotinic acid methyl ester (800.00 mg; 1.56 mmol; 1.00 eq.) in methanolic ammonia (24.00 ml; 30.00 V was heated to 60° C. for 16 h in sealed tube. The reaction monitored by TLC. After completion of the reaction, the reaction mixture was concentrated under reduced pressure to afford 3-[5-carbamoyl-6-(4-phenoxy-phenoxy)-pyridin-3-ylamino]-pyrrolidine-1-carboxylic acid tert-butyl ester (700.00 mg, 89.6%) as a yellow solid. HPLC 98% purity. MS m/z=435 [M+H] (cleavage of t-Butanol). $^1$H NMR (400 MHz, DMSO-d6) δ 7.69-7.67 (d, J=5.1 Hz, 2H), 7.62-7.61 (d, J=3.0 Hz, 1H), 7.45 (s, 1H), 7.40-7.36 (m, 2H), 7.13-7.06 (m, 3H), 7.03-6.98 (m, 4H), 6.06-6.04 (d, J=6.8 Hz, 1H), 3.52 (s, 1H), 3.35-3.32 (m, 3H), 3.08 (s, 1H), 1.78-1.74 (m, 2H), 1.39 (s, 9H).

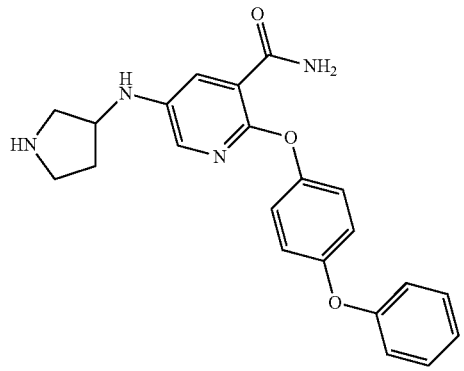 [SMILES: NC(=O)c1cc(NC2CCNC2)cnc1Oc1ccc(Oc2ccccc2)cc1]

2-(4-Phenoxy-phenoxy)-5-(pyrrolidin-3-ylamino)-nicotinamide

To a stirred solution of 3-[5-Carbamoyl-6-(4-phenoxy-phenoxy)-pyridin-3-ylamino]-pyrrolidine-1-carboxylic acid tert-butyl ester (600.00 mg; 1.21 mmol; 1.00 eq.) in DCM (10.00 ml) was added 4N HCl in 1,4-dioxane (10.00 ml) dropwise at RT under nitrogen atmosphere. The reaction mixture was stirred at RT for 5 h. After completion of the reaction mixture, it was concentrated under reduced pressure. The residue was diluted with DCM (50 mL), neutralized by the addition of saturated aqueous sodium bicarbonate (20 mL), and extracted with DCM/15% MeOH (3×20 mL). The organic layer was washed with brine (20 mL), dried over sodium sulphate and concentrated under reduced pressure to afford 2-(4-phenoxy-phenoxy)-5-(pyrrolidin-3-ylamino)-nicotinamide (400.00 mg, 68.9%) as a clear, colorless liquid. HPLC: 81.1% purity. MS m/z=390.44 [M+H].

Example 199

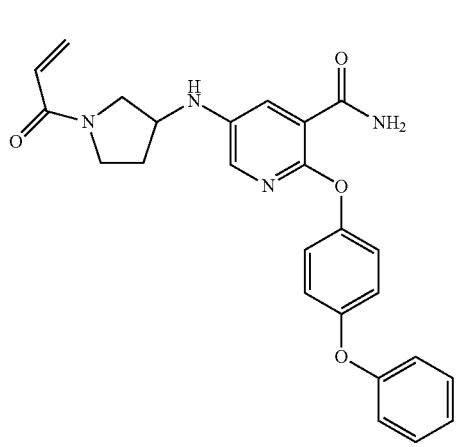 [SMILES: C=CC(=O)N1CCC(Nc2cnc(Oc3ccc(Oc4ccccc4)cc3)c(C(N)=O)c2)C1]

5-(1-Acryloyl-pyrrolidin-3-ylamino)-2-(4-phenoxy-phenoxy)-nicotinamide (201)

To a stirred solution of 2-(4-phenoxy-phenoxy)-5-(pyrrolidin-3-ylamino)-nicotinamide (200 mg; 0.41 mmol; 1.00 eq.) in dry DCM (6.00 ml; 30.00 V) was added N,N-disopropylethylamine (0.22 ml; 1.24 mmol; 3.00 eq.) dropwise at −10° C. under nitrogen. Stirring was continued at −10° C. under nitrogen for 15 minutes. Acryloyl chloride (0.03 ml; 0.41 mmol; 1.00 eq.) was then added dropwise and stirring was continued at −10° C. for 30 min. After completion of the reaction by TLC, the reaction was quenched by the addition of water (50 mL) and extracted with DCM (3×30 mL). The organic layers were combined, washed with brine (1×20 mL), dried over sodium sulphate, and concentrated under reduced pressure. The residue was purified by column chromatography over silica gel (60-120 mesh) using DCM:MeOH (0-2%) as an eluent to afford 5-(1-acryloyl-pyrrolidin-3-ylamino)-2-(4-phenoxy-phenoxy)-nicotinamide (50.00 mg, 27.0%) as an off-white solid. HPLC: 99.6% purity. MS m/z=445 [M+H]. $^1$H NMR (400 MHz, DMSO-d6) δ 7.69-7.63 (m, 3H), 7.47-7.44 (m, 1H), 7.40-7.36 (m, 2H), 7.13-7.06 (m, 3H), 7.02-6.98 (m, 4H), 6.58-6.54 (m, 1H), 6.16-6.07 (m, 2H), 5.68-5.65 (m, 1H), 4.07-3.89 (m, 1H), 3.88-3.45 (m, 4H), 2.22-2.09 (m, 1H), 1.92-1.77 (m, 1H).

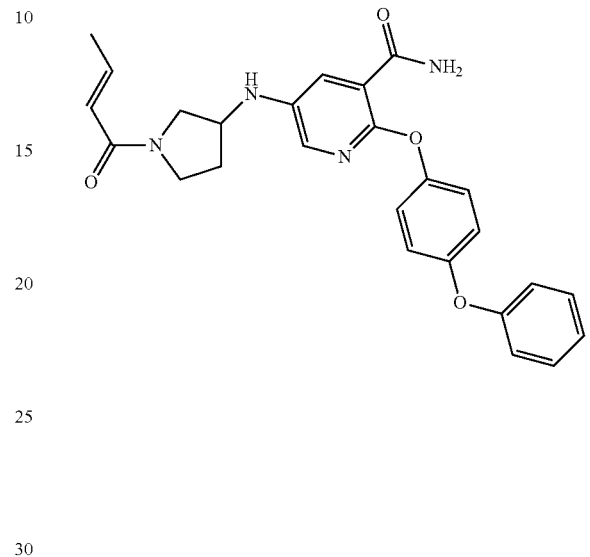

5-[1-((E)-But-2-enoyl)-pyrrolidin-3-ylamino]-2-(4-phenoxy-phenoxy)-nicotinamide (202)

To a stirred solution of 2-(4-phenoxy-phenoxy)-5-(pyrrolidin-3-ylamino)-nicotinamide (200.00 mg; 0.42 mmol; 1.00 eq) in dry DCM (6.00 ml; 30.00 V) was added N,N-diisopropylethylamine (0.22 ml; 1.25 mmol; 3.00 eq.) dropwise at −10° C. under nitrogen. Stirring at −10° C. under nitrogen was continued for 5 min. (E)-But-2-enoyl chloride (0.04 ml; 0.42 mmol; 1.00 eq.) was then added dropwise. The reaction mixture was then stirred at −10° C. for 30 min. After completion of the reaction (monitored by TLC), the reaction was quenched by the addition of water (50 mL) and extracted with DCM (3×30 mL). The organic layers were combined, washed with brine (1×20 mL), dried over sodium sulphate, and concentrated under reduced pressure. The residue was purified by flash chromatography over silica gel (60-120 mesh) by using DCM/MeOH (0-2%) as an eluent to afford 5-[1-((E)-but-2-enoyl)-pyrrolidin-3-ylamino]-2-(4-phenoxy-phenoxy)-nicotinamide (30.00 mg, 15.7%) as an off-white solid. HPLC: 95.58% purity. MS m/z=459 [M+H]. $^1$H NMR (400 MHz, DMSO-d6) δ7.69 (s, 2H), 7.63-7.62 (d, J=2.1 Hz, 1H), 7.46-7.44 (dd, J=7.1, 2.8 Hz, 1H), 7.40-7.36 (m, 2H), 7.13-7.07 (m, 3H), 7.03-6.98 (m, 4H), 6.70-6.63 (m, 1H), 6.29-6.11 (m 1H), 6.10-6.06 (m, 1H), 3.83 (s, 1H), 3.64-3.45 (m, 3H), 2.49-1.80 (m, 5H).

Example 200

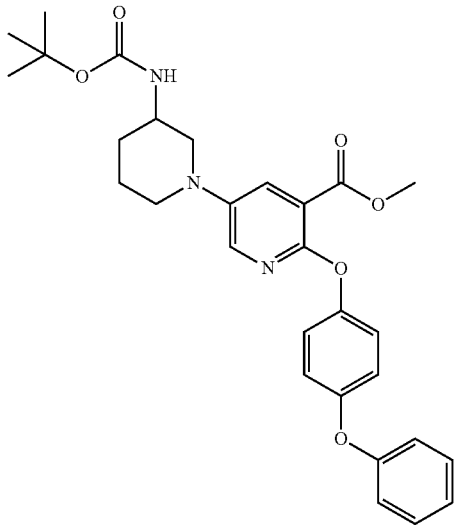 [SMILES: COC(=O)c1cc(N2CCCC(NC(=O)OC(C)(C)C)C2)cnc1Oc1ccc(Oc2ccccc2)cc1]

3-tert-Butoxycarbonylamino-6'-(4-phenoxy-phenoxy)-3,4,5,6-tetrahydro-2H-[1,3']bipyridinyl-5'-carboxylic acid methyl ester To a stirred solution of 5-iodo-2-(4-phenoxy-phenoxy)-nicotinic acid methyl ester (2.00 g; 3.85 mmol; 1.00 eq.) in 1,4-dioxane (40.00 ml; 20.00 V) were added piperidin-3-yl-carbamic acid tert-butyl ester (1.00 g; 4.62 mmol; 1.20 eq.) and cesium carbonate (2.58 g; 7.69 mmol; 2.00 eq.) at RT under nitrogen atmosphere. The resulting reaction mixture was degassed with nitrogen for 20 min, and then treated with dicyclohexyl-(2',6'-diisopropoxy-biphenyl-2-yl)-phosphane (0.09 g; 0.19 mmol; 0.05 eq.) and tris(dibenzylideneacetone)dipalladium(0) (0.36 g; 0.38 mmol; 0.10 eq.). The reaction mixture was heated in a sealed tube to 100° C. for 16 h. Upon completion of the reaction (monitored by TLC), the reaction mixture was cooled to RT, and filtered through Celite. The Celite was washed with EtOAc (50 mL). The filtrate was washed with water (1x 50 mL) and brine (1×20 mL), dried over sodium sulphate and then concentrated under reduced pressure. The residue was purified by flash chromatography over silica gel (60-120 mesh) by using (3:7) EtOAc:Pet ether as an eluent to afford 3-tert-butoxycarbonylamino-6'-(4-phenoxy-phenoxy)-3,4,5,6-tetrahydro-2H-[1,3']bipyridinyl-5'-carboxylic acid methyl ester (800.00 mg, 36.5%) as a yellow solid. HPLC: 91.1% purity. MS m/z=520 [M+H]. $^1$H NMR (400 MHz, DMSO-d6) δ 8.02 (s, 1H), 7.77-7.76 (d, J=3.1 Hz, 1H), 7.40-7.13 (m, 2H), 7.12-7.03 (m, 1H), 7.02-6.99 (m, 7H), 3.51 (s, 3H), 3.34 (s, 3H), 2.50 (s, 1H), 2.50 (s, 1H), 1.98 (s, 2H), 1.89 (s, 2H), 1.37 (s, 9H).

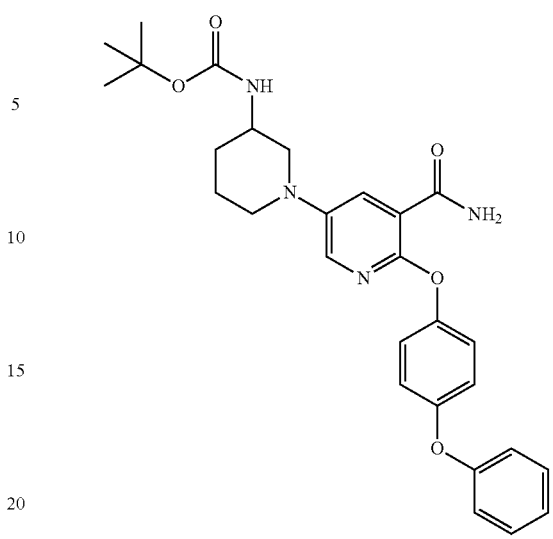

tert-butyl (1-(5-carbamoyl-6-(4-phenoxyphenoxy)pyridin-3-yl)piperidin-3-yl)carbamate A solution of 3-tert-butoxycarbonylamino-6'-(4-phenoxyphenoxy)-3,4,5,6-tetrahydro-2H-[1,3']bipyridinyl-5'-carboxylic acid methyl ester (800.00 mg; 1.40 mmol; 1.00 eq.) in methanolic ammonia (20.00 ml; 25.00 V) was heated to 60° C. for 16 h in sealed tube. The reaction progress was monitored by TLC. After completion of the reaction, the mixture was concentrated under reduced pressue to afford tert-butyl (1-(5-carbamoyl-6-(4-phenoxyphenoxy)pyridin-3-yl)piperidin-3-yl)carbamate (0.60 g, 76.3%) as a yellow solid. HPLC: 94.80% purity. MS m/z=505 [M+H].

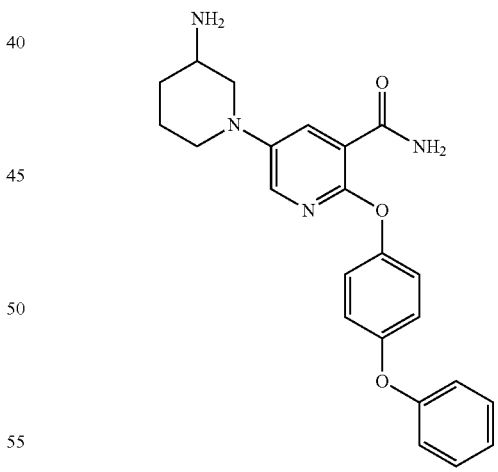

3-Amino-6'(4-phenoxy-phenoxy)-3,4,5,6-tetrahydro-2H-[1,3']bipyridinyl-5'-carboxylic acid amide To a stirred solution of [5'-carbamoyl-6'-(4-phenoxy-phenoxy)-3,4,5,6-tetrahydro-2H-[1,3']bipyridinyl-3-yl]-carbamic acid tert-butyl ester (600.00 mg; 1.07 mmol; 1.00 eq.) in DCM (6.00 ml; 10.00 V) was added 4N HCl in 1,4-dioxane (6.00 ml; 10.00 V) dropwise at RT under nitrogen atmosphere. The reaction mixture was stirred at RT for 5 h.

After completion of the reaction, the mixture was concentrated under reduced pressure. The residue was diluted with DCM (50 mL), neutralized by the addition of saturated aqueous sodium bicarbonate (20 mL), and extracted with DCM:15% MeOH (3×20 mL). The organic layer was washed with brine (20 mL), dried over sodium sulphate and concentrated under reduced pressure to afford 3-amino-6'-(4-phenoxy-phenoxy)-3,4,5,6-tetrahydro-2H-[1,3']bipyridinyl-5'-carboxylic acid amide (400.00 mg, 65.6%) as a light brown gum. HPLC: 71.20% purity. MS m/z=405 [M+H]. $^1$H NMR (400 MHz, DMSO-d6) δ 7.93-7.92 (d, J=3.2 Hz, 3H), 7.81-7.80 (t, J=10.9 Hz, 3H), 7.41-7.15 (m, 2H), 7.14-7.11 (m, 3H), 7.05-7.00 (m, 4H), 3.63-3.38 (m, 4H), 3.03-0.00 (m, 2H), 1.82 (s, 1H), 1.59 (d, J=8.1 Hz, 1H), 1.22 (d, J=3.8 Hz, 2H).

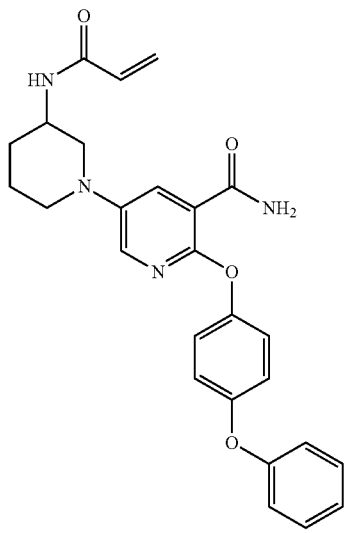 [SMILES: C=CC(=O)NC1CCCN(c2cnc(Oc3ccc(Oc4ccccc4)cc3)c(C(N)=O)c2)C1]

3-Acryloylamino-6'44-phenoxy-phenoxy)-3,4,5,6-tetrahydro-2H-[1,3']bipyridinyl-5'-carboxylic acid amide (198)

To a stirred solution of 3-amino-6'-(4-phenoxy-phenoxy)-3,4,5,6-tetrahydro-2H-[1,3']bipyridinyl-5'-carboxylic acid amide (100.00 mg; 0.18 mmol; 1.00 eq.) in dry DCM (3.00 ml; 30.00 V) was added N,N-diisopropylethylamine (0.09 ml; 0.53 mmol; 3.00 eq.) dropwise at −10° C. under nitrogen. Stirring at −10° C. was continued for 15 min. Acryloyl chloride (0.02 ml; 0.19 mmol; 1.10 eq.) was then added dropwise, and stirring at −10° C. continued for 30 min. After completion of the reaction by TLC, the reaction was quenched by the addition of water (50 mL) and extracted with DCM (3×30 mL). The combined organic layer was washed with brine (1×20 mL), dried over sodium sulphate and concentrated under vacuum. The crude product was purified by column chromatograpy over silica gel (60-120 mesh) using DCM:MeOH (9.5:0.5) as an eluent to afford 3-acryloylamino-6'-(4-phenoxy-phenoxy)-3,4,5,6-tetrahydro-2H-[1,3']bipyridinyl-5'-carboxylic acid amide (25.00 mg, 29.9%) as an off-white solid. HPLC: 97% purity. MS m/z=459[M+H]. $^1$H NMR (400 MHz, DMSO-d6): δ 8.15-8.13 (d, J=7.4 Hz, 1H), 7.92-7.91 (d, J=3.0 Hz, 1H), 7.8 (s, 1H), 7.729-7.722 (d, J=3.0 Hz, 2H), 7.40-7.36 (t, J=7.6 Hz, 2H), 7.13-7.10 (m, 3H), 7.04-6.99 (m, 4H), 6.28-6.21 (m, 1H), 6.11-6.07 (dd, J=17.1, 2.2 Hz, 1H), 5.60-5.57 (dd, J=10.1, 2.2 Hz, 1H), 3.86-3.85 (m, 1H), 3.57-3.45 (m, 2H), 2.84-2.79 (m, 1H), 2.67-2.61 (m, 1H), 1.85-1.76 (m, 2H), 1.65-1.56 (m, 1H), 1.46-1.38 (m, 1H).

Example 201

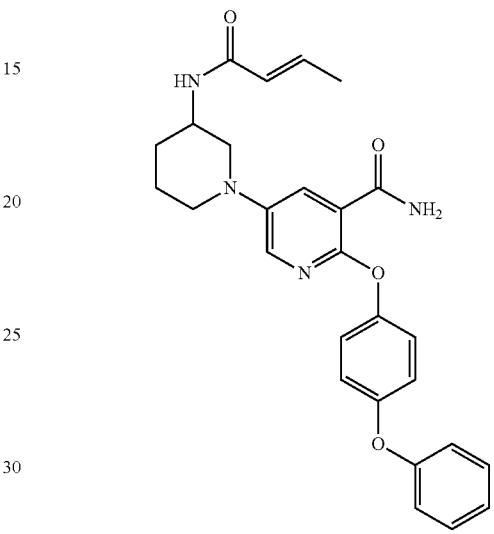

3-((E)-But-2-enoylamino)-6'-(4-phenoxy-phenoxy)-3,4,5,6-tetrahydro-2H-[1,3']bipyridinyl-5'-carboxylic acid amide (213)

To a stirred solution of 3-amino-6'-(4-phenoxy-phenoxy)-3,4,5,6-tetrahydro-2H-[1,3']bipyridinyl-5'-carboxylic acid amide (200.00 mg; 0.38 mmol; 1.00 eq.) in dry DCM (6.00 ml; 30.00 V) was added N,N-diisopropylethylamine (0.20 ml; 1.13 mmol; 3.00 eq.) dropwise at −10° C. under nitrogen. The reaction mixture was stirred at −10° C. for 15 min and then treated with (E)-but-2-enoyl chloride (39.63 mg; 0.38 mmol; 1.00 eq.), dropwise. Stirring at −10° C. was continued for 30 min. After completion of the reaction (monitored by TLC), the reaction was quenched by the addition of water (50 mL) and extracted with DCM (3×30 mL). The combined organic layer was washed with brine (1×20 mL), dried over sodium sulphate and concentrated under vacuum. The crude product was purified by flash chromatography over silica gel (60-120 mesh) using DCM:MeOH (9.5:0.5) as an eluent to afford 3-((E)-but-2-enoylamino)-6'-(4-phenoxy-phenoxy)-3,4,5,6-tetrahydro-2H-[1,3']bipyridinyl-5'-carboxylic acid amide (37.00 mg, 20.2%) as off-white solid. HPLC: 95.2% purity. MS m/z=473[M+H]$^+$. $^1$H NMR (400 MHz, DMSO-d6) δ 7.91-7.90 (d, J=3.2 Hz, 2H), 7.75-7.71 (t, J=12.8 Hz, 2H), 7.40-7.36 (m, 1H), 7.14-7.10 (m, 2H), 7.03-6.99 (m, 7H), 6.64-6.58 (m, 1H), 3.55-3.44 (m, 2H), 2.66 (s, 1H), 2.50-2.49 (m, 1H), 1.79-1.77 (m, 4H), 1.66-1.56 (m, 2H).

Example 202

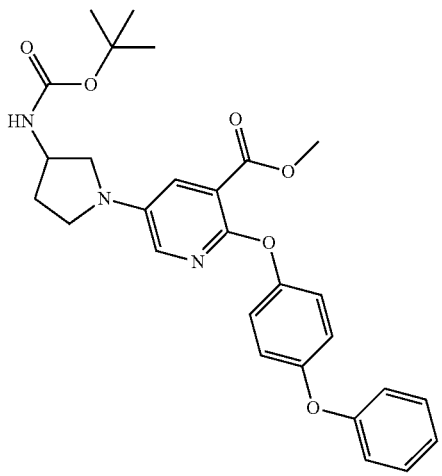 [SMILES: COC(=O)c1cc(N2CCC(NC(=O)OC(C)(C)C)C2)cnc1Oc1ccc(Oc2ccccc2)cc1]

5-(3-tert-Butoxycarbonylamino-pyrrolidin-1-yl)-2-(4-phenoxy-phenoxy)-nicotinic acid methyl ester To a stirred solution of 5-iodo-2-(4-phenoxy-phenoxy)-nicotinic acid methyl ester (2.00 g; 4.01 mmol; 1.00 eq.) in 1,4-dioxane (40.00 ml; 20.00 V) was added pyrrolidin-3-yl-carbamic acid tert-butyl ester (0.91 g; 4.81 mmol; 1.20 eq.) and cesium carbonate (2.69 g; 8.01 mmol; 2.00 eq.) at RT under nitrogen atmosphere. The resulting reaction mixture was degassed with nitrogen for 20 min and then treaed with tris(dibenzylideneacetone)dipalladium(0) and dicyclohexyl-(2',6'-diisopropoxy-biphenyl-2-yl)-phosphane (0.10 g; 0.20 mmol; 0.05 eq.). The reaction mixture was heated in sealed tube at 100° C. for 16 h. Reaction completion was confirmed by TLC. After completion, the reaction mixture was cooled to RT, and filtered through Celite. The Celite was washed with EtOAc (50 mL). The filtrate was washed with water (1x 50 mL) and brine (1×20 mL), dried over sodium sulphate and concentrated under vacuum. The residue was purified by column chromatography over silica gel (60-120 mesh) by using (3:7) EtOAc:Pet ether as an eluent to afford 5-(3-tert-butoxycarbonylamino-pyrrolidin-1-yl)-2-(4-phenoxy-phenoxy)-nicotinic acid methyl ester (1.20 g, 53.0%) as a yellow solid. HPLC: 84.42% purity. MS m/z=506[M+H]$^+$. $^1$H NMR (400 MHz, DMSO-d6) δ 7.699-7.692 (d, J=2.8 Hz, 1H), 7.39-7.32 (m, 3H), 7.22-7.21 (d, J=6.6 Hz, 1H), 7.12-7.08 (t, J=7.3 Hz, 1H), 7.01-6.97 (m, 6H), 4.15 (s, 1H), 3.80 (s, 3H), 3.50-3.46 (m, 1H), 3.37-3.25 (m, 2H), 3.07-3.04 (m, 1H), 2.16-2.11 (m, 1H), 1.91-1.86 (m, 1H), 1.38 (s, 9H).

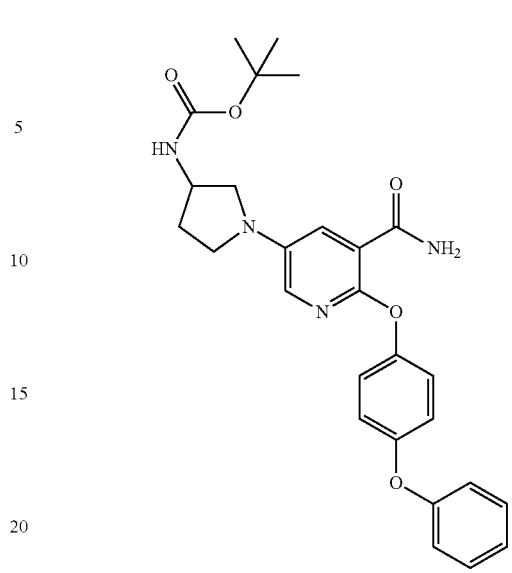

{1-[5-Carbamoyl-6-(4-phenoxy-phenoxy)-pyridin-3-yl]-pyrrolidin-3-yl}-carbamic acid tert-butyl ester A stirred solution of 5-(3-tert-butoxycarbonylamino-pyrrolidin-1-yl)-2-(4-phenoxy-phenoxy)-nicotinic acid methyl ester (1.20 g; 2.20 mmol; 1.00 eq.) in methanolic ammonia (36.00 ml; 30.00 V) was heated to 60° C. for 16 h in sealed tube. Reaction progress was monitored by TLC. After completion of the reaction, the reaction mixture was concentrated under vaccum to afford {1-[5-Carbamoyl-6-(4-phenoxy-phenoxy)-pyridin-3-yl]-pyrrolidin-3-yl}-carbamic acid tert-butyl ester (0.80 g, 68.7%) as a yellow solid. HPLC: 92.5% purity. MS m/z=491[M+H]$^+$. $^1$H NMR (400 MHz, DMSO-d6) δ 7.56-7.55 (d, J=3.1 Hz, 2H), 7.40-7.36 (m, 3H), 7.32 (d, J=3.1 Hz, 1H), 7.22-7.20 (d, J=6.7 Hz, 2H), 7.13-7.04 (m, 2H), 7.03-6.98 (m, 4H), 3.49-3.45 (m, 1H), 3.35 (s, 1H), 3.25-3.24 (m, 1H), 3.06-3.03 (m, 1H), 2.33 (s, 1H), 2.21 (s, 1H), 1.38 (s, 9H).

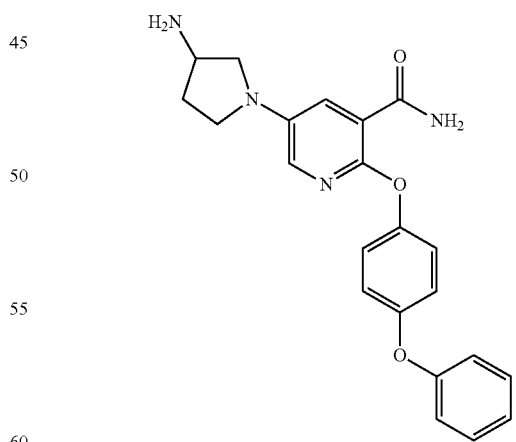

5-(3-Amino-pyrrolidin-1-yl)-2-(4-phenoxy-phenoxy)-nicotinamide

To a stirred solution of {1-[5-carbamoyl-6-(4-phenoxy-phenoxy)-pyridin-3-yl]-pyrrolidin-3-yl}-carbamic acid tert-butyl ester (800.00 mg; 1.50 mmol; 1.00 eq.) in DCM (8.00 ml; 10.00 V) was added 4N HCl in 1,4-dioxane (4.00 ml; 5.00 V) dropwise at RT under nitrogen atmosphere. The reaction mixture was stirred at RT for 5 h. After completion of the reaction, the mixture was concentrated under reduced pressure. The residue was diluted with DCM (50 mL), neutralized by the addition of saturated aqueous sodium bicarbonate (20 mL) and extracted with DCM:15% MeOH (3×20 mL). The organic layer was washed with brine (20 mL), dried over sodium sulphate, and concentrated under vaccum to afford 5-(3-amino-pyrrolidin-1-yl)-2-(4-phenoxy-phenoxy)-nicotinamide (500.00 mg, 78.2%) as a light yellow liquid. HPLC: 91.60% purity. MS m/z=391[M+H]$^+$.

Example 203

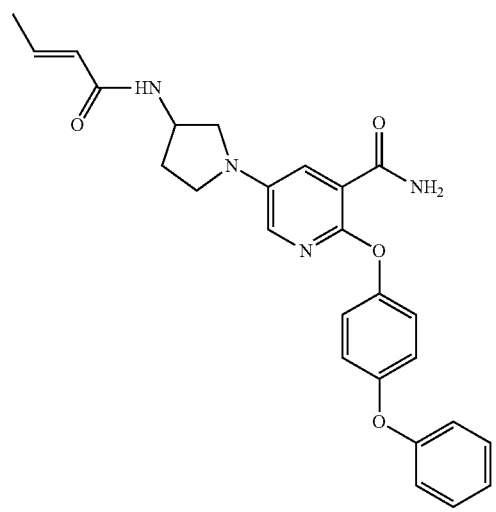

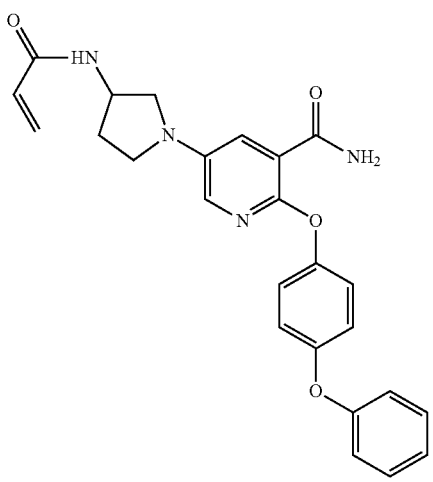 [SMILES: C=CC(=O)NC1CCN(c2cnc(Oc3ccc(Oc4ccccc4)cc3)c(C(N)=O)c2)C1]

5-[3-((E)-But-2-enoylamino)-pyrrolidin-1-yl]-2-(4-phenoxy-phenoxy)-nicotinamide (199)

5-(3-Acryloylamino-pyrrolidin-1-yl)-2-(4-phenoxy-phenoxy)-nicotinamide (196)

To a stirred solution of 5-(3-amino-pyrrolidin-1-yl)-2-(4-phenoxy-phenoxy)-nicotinamide (200.00 mg; 0.47 mmol; 1.00 eq.) in dry DCM (4.00 ml; 20.00 V) was added N,N-diisopropylethylamine (0.25 ml; 1.41 mmol; 3.00 eq.) dropwise at −10° C. under nitrogen. The reaction mixture was stirred at −10° C. for 15 min and then was treated with acryloyl chloride (0.04 ml; 0.47 mmol; 1.00 eq.) dropwise. Stirring at −10° C. was continued for another 30 min. After completion of the reaction by TLC, the reaction was quenched by the addition of water (50 mL) and extracted with DCM (3×30 mL). The combined organic layer was washed with brine (1×20 mL), dried over sodium sulphate and concentrated under vaccum. The crude product was purified by flash chromatograpy over silica gel (60-120 mesh) using DCM:MeOH (9.5:0.5) as an eluent to afford 5-(3-acryloylamino-pyrrolidin-1-yl)-2-(4-phenoxy-phenoxy)-nicotinamide (30.00 mg, 14.1%) as a light yellow solid. HPLC: 98.36% purity. MS m/z=445[M+H]$^+$. $^1$H NMR (400 MHz, DMSO-d6) δ 8.40-8.38 (d, J=8.0 Hz, 1H), 7.72 (s, 2H), 7.60-7.58 (d, J=3.2 Hz, 1H), 7.40-7.35 (m, 3H), 7.13-6.98 (m, 7H), 6.26-6.07 (m, 2H), 5.60-5.57 (dd, J=9.9, 2.2 Hz, 1H), 4.47-4.43 (m, 1H), 3.55-3.51 (m, 1H), 3.42-3.33 (m, 1H), 3.33-3.27 (m, 1H), 3.14-3.10 (m, 1H), 2.26-2.18 (m, 1H), 1.96-1.92 (m, 1H).

To a stirred solution of 5-(3-amino-pyrrolidin-1-yl)-2-(4-phenoxy-phenoxy)-nicotinamide (200 mg; 0.47 mmol; 1.00 eq.) in dry DCM (6.00 ml; 30.00 V) was added N,N-diisopropylethylamine (0.25 ml; 1.41 mmol; 3.00 eq.) dropwise at −10° C. under nitrogen. Stirring at −10° C. was continued for 15 min, and then the reaction mixture was treated with (E)-but-2-enoyl chloride (0.05 g; 0.47 mmol; 1.00 eq.), dropwise. The reaction mixture was then stirred at −10° C. for 30 min. After completion of the reaction by TLC, the reaction was quenched by the addition of water (50 mL), and extracted with DCM (3×30 mL). The organic layers were combined, ashed with brine (1×20 mL), dried over sodium sulphate and concentrated under vacuum. The crude product was purified by column chromatography over silica gel (60-120 mesh) by using DCM:MeOH (9.5:0.5) as an eluent to afford 5-[3-((E)-but-2-enoylamino)-pyrrolidin-1-yl]-2-(4-phenoxy-phenoxy)-nicotinamide (90.00 mg, 40.4%) as a light yellow solid. HPLC: 96.60% purity. MS m/z=459[M+H]$^+$. $^1$H NMR (400 MHz, DMSO-d6) 8.17 (s, 1H), 7.73 (s, 2H), 7.59 (d, J=3.1 Hz, 1H), 7.37-7.34 (m, 3H), 7.13-6.98 (m, 7H), 6.65-6.60 (m, 1H), 5.89 (dd, J=15.3, 1.6 Hz, 1H), 4.55 (s, 1H), 3.51 (s, 1H), 3.37 (s, 1H), 3.0 (s, 1H), 3.10 (s, 1H), 2.33-2.34 (m, 1H), 1.78-1.77 (m, 4H).

Example 204

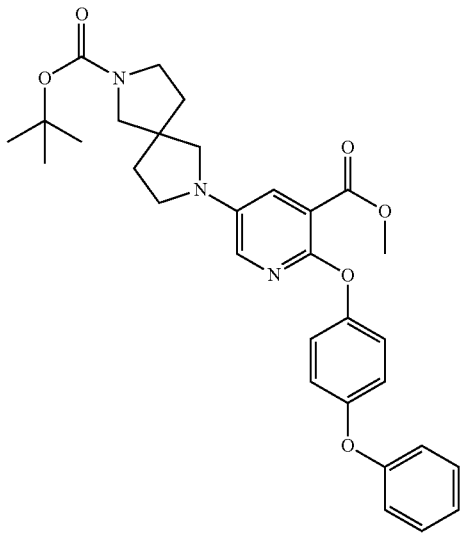 [SMILES: COC(=O)c1cc(N2CCC3(CCN(C(=O)OC(C)(C)C)C3)C2)cnc1Oc1ccc(Oc2ccccc2)cc1]

7-[5-Methoxycarbonyl-6-(4-phenoxy-phenoxy)-pyridin-3-yl]-2,7-diaza-spiro[4.4]nonane-2-carboxylic acid tert-butyl ester To a stirred solution of 5-iodo-2-(4-phenoxy-phenoxy)-nicotinic acid methyl ester (1.00 g; 1.92 mmol; 1.00 eq.) in 1,4-dioxane (20.00 ml; 20.00 V) were added 2,7-diaza-spiro[4.4]nonane-2-carboxylic acid tert-butyl ester (0.57 g; 2.31 mmol; 1.20 eq.) and cesium carbonate (1291.84 mg; 3.85 mmol; 2.00 eq.) at RT under nitrogen atmosphere. The resulting reaction mixture was degassed with nitrogen for 20 min and then treated with dicyclohexyl-(2',6'-diisopropoxy-biphenyl-2-yl)-phosphane (0.05 g; 0.10 mmol; 0.05 eq.) and tris(dibenzylideneacetone)dipalladium(0) (90.77 mg; 0.10 mmol; 0.05 eq.). The reaction mixture was heated in sealed tube to 100° C. for 16 h. Reaction completion was confirmed by TLC. After completion, the reaction mixture was cooled to RT and filtered through Celite. The Celite bed was washed with EtOAc (50 mL). The filtrate was washed with water (1x 50 mL) and brine (1×20 mL), dried over sodium sulphate and concentrated under vacuum. The residue was purified by flash chromatography over silica gel (60-120 mesh) using (3:7) EtOAc: Pet. ether as an eluent to afford 7-[5-methoxycarbonyl-6-(4-phenoxy-phenoxy)-pyridin-3-yl]-2,7-diaza-spiro[4.4]nonane-2-carboxylic acid tert-butyl ester (400.00 mg, 31.8%) as a brown semi solid. HPLC: 63.95% purity. MS m/z=546 [M+H]$^+$.

7-[5-Carbamoyl-6-(4-phenoxy-phenoxy)-pyridin-3-yl]-2,7-diaza-spiro[4.4]nonane-2-carboxylic acid tert-butyl ester A solution of 7-[5-methoxycarbonyl-6-(4-phenoxy-phenoxy)-pyridin-3-yl]-2,7-diaza-spiro[4.4]nonane-2-carboxylic acid tert-butyl ester (400.00 mg; 0.61 mmol; 1.00 eq.) in methanolic ammonia (4.00 ml; 10.00 V) was heated to 60° C. for 16 h in sealed tube. Reaction progress was monitored by TLC. After completion of the reaction, the mixture was concentrated under vacuum to afford 7-[5-carbamoyl-6-(4-phenoxy-phenoxy)-pyridin-3-yl]-2,7-diaza-spiro[4.4]nonane-2-carboxylic acid tert-butyl ester (300.00 mg, 41.7%) as a yellow solid. HPLC: 45% purity. MS m/z=531 [M+H]$^+$.

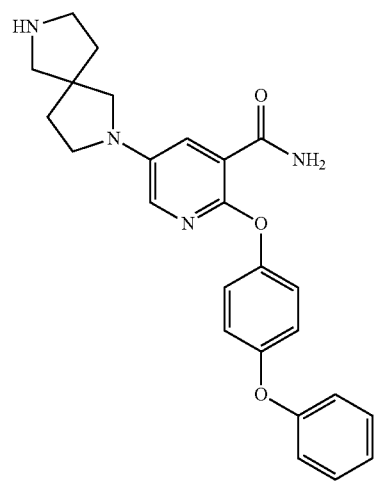 [SMILES: NC(=O)c1cc(N2CCC3(CCNC3)C2)cnc1Oc1ccc(Oc2ccccc2)cc1]

5-(2,7-Diaza-spiro[4.4]non-2-yl)-2-(4-phenoxy-phenoxy)-nicotinamide

To a stirred solution of 7-[5-carbamoyl-6-(4-phenoxy-phenoxy)-pyridin-3-yl]-2,7-diaza-spiro[4.4]nonane-2-carboxylic acid tert-butyl ester (400.00 mg; 0.75 mmol; 1.00 eq.) in DCM (10.00 ml) was added 4N HCl in 1,4-dioxane (10.00 ml) dropwise at RT under nitrogen atmosphere. The reaction mixture was stirred at RT for 5 h. After completion of the reaction (monitored by TLC), the mixture was concentrated under reduced pressure. The residue was diluted with DCM (50 mL), neutralized by the addition of saturated aqueous sodium bicarbonate solution (20 mL) and extracted with DCM:15% MeOH (3×20 mL). The organic layer was washed with brine (20 mL), dried over sodium sulphate and concentrated under vacuum. The crude product was purified by column chromatography over silica gel (60-120 mesh) using DCM:MeOH (9.5:0.5) as an eluent to afford 5-(2,7-diaza-spiro[4.4]non-2-yl)-2-(4-phenoxy-phenoxy)-nicotinamide (240.00 mg, 55.0%) as a light brown oil. HPLC: 73.60% purity. MS m/z=431 [M+H]$^+$.

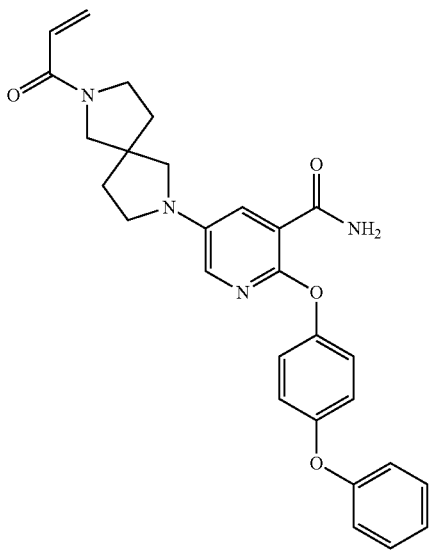 [SMILES: C=CC(=O)N1CCC2(CCN(c3cnc(Oc4ccc(Oc5ccccc5)cc4)c(C(N)=O)c3)C2)C1]

5-(7-Acryloyl-2,7-diaza-spiro[4.4]non-2-yl)-2-(4-phenoxy-phenoxy)-nicotinamide (224)

To a stirred solution of 5-(2,7-diaza-spiro[4.4] non-2-yl)-2-(4-phenoxy-phenoxy)-nicotinamide (100.00 mg; 0.18 mmol; 1.00 eq.) in dry DCM (3.00 ml; 30.00 V) was added N,N-diisopropylethylamine (0.09 ml; 0.53 mmol; 3.00 eq.) dropwise at −10° C. under nitrogen. The reaction mixture was stirred at −10° C. for 15 min and then was treated with acryloyl chloride (0.02 ml; 0.19 mmol; 1.10 eq.), dropwise. Stirring at −10° C. was continued for 30 min. After completion of the reaction (monitored by TLC), the reaction was quenched by the addition of water (50 mL) and extracted with DCM (3×30 mL). The organic layers were combined, washed with brine (1×20 mL), dried over sodium sulphate, and concentrated under vaccum. The residue was purified by flash chromatograpy over silica gel (60-120 mesh) using DCM:MeOH (0-2%) as an eluent to afford 5-(7-acryloyl-2,7-diaza-spiro[4.4]non-2-yl)-2-(4-phenoxy-phenoxy)-nicotinamide (15.00 mg, 17.2%) as a pale yellow solid. HPLC: 94.57% purity. MS m/z=485[M+H]$^+$. $^1$H NMR (400 MHz, DMSO-d6) δ 7.58-7.57 (d, J=1.2 Hz, 2H), 7.573-7.570 (d, J=1.2 Hz, 1H), 7.40-7.34 (m, 3H), 7.13-6.98 (m, 7H), 6.57-6.50 (dd, J=16.7, 10.3 Hz, 1H), 6.16-6.09 (m, 1H), 5.68-5.62 (m, 1H), 3.69-3.66 (t, J=7.0 Hz, 1H), 3.58-3.48 (m, 2H), 3.38-3.32 (m, 3H), 3.27-3.22 (m, 2H), 2.00-1.94 (m, 3H), 1.90-1.85 (m, 1H).

Example 205

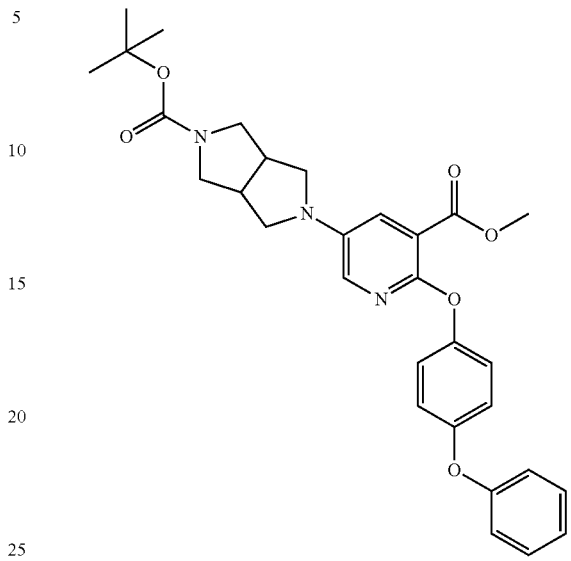

5-[5-Methoxycarbonyl-6-(4-phenoxy-phenoxy)-pyridin-3-yl]-hexahydro-pyrrolo[3,4-c]pyrrole-2-carboxylic acid tert-butyl ester To a stirred solution of 5-iodo-2-(4-phenoxy-phenoxy)-nicotinic acid methyl ester (2.00 g; 3.85 mmol; 1.00 eq.) in 1,4-dioxane (30.00 ml; 15.00 V) were added hexahydro-pyrrolo[3,4-c]pyrrole-2-carboxylic acid tert-butyl ester (1.06 g; 4.62 mmol; 1.20 eq.) and cesium carbonate (2.58 g; 7.69 mmol; 2.00 eq.) at RT under nitrogen atmosphere. The resulting reaction mixture was degassed with nitrogen for 20 min and then treated with dicyclohexyl-(2',6'-diisopropoxy-biphenyl-2-yl)-phosphane (0.09 g; 0.19 mmol; 0.05 eq.) and tris(dibenzylideneacetone)dipalladium(0) (0.18 g; 0.19 mmol; 0.05 eq.). The reaction mixture was heated in sealed tube to 100° C. for 16 h. Reaction completion was confirmed by TLC. After completion, the reaction mixture was cooled to RT, and filtered through Celite. The Celite bed was washed with EtOAc (50 mL). The organic phases were combined, washed with water (lx 50 mL) and brine (1×20 mL), dried over sodium sulphate and concentrated under vacuum. The residue was purified by flash chromatography over silica gel (60-120) mesh by using (3:7) EtOAc:Petether as an eluent to afford 5-[5-methoxycarbonyl-6-(4-phenoxy-phenoxy)-pyridin-3-yl]-hexahydro-pyrrolo[3,4-c]pyrrole-2-carboxylic acid tert-butyl ester (1.50 g, 67.4%) as a light orange solid. HPLC: 91.90% purity. MS m/z=532[M+H]$^+$. $^1$H NMR (400 MHz, DMSO-d6) δ 7.72-7.71 (d, J=3.1 Hz, 1H), 7.39-7.34 (m, 3H), 7.12-7.08 (m, 1H), 7.01-6.97 (m, 6H), 3.8 (s, 3H), 3.53-3.51 (t, J=10.4 Hz, 2H), 3.44-3.42 (d, J=7.5 Hz, 2H), 3.20-3.15 (m, 4H), 3.0 (s, 2H), 1.4 (s, 9H).

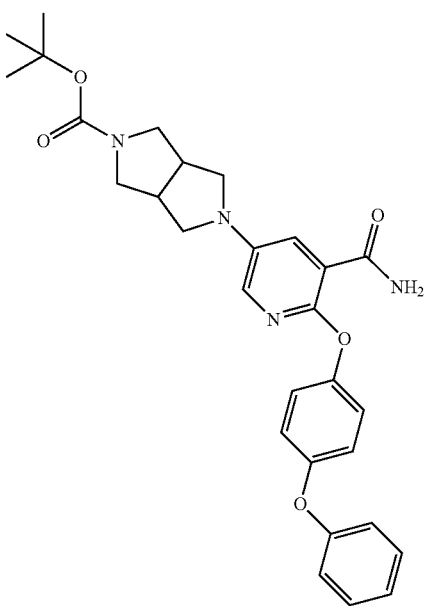 [SMILES: CC(C)(C)OC(=O)N1CC2CN(c3cnc(Oc4ccc(Oc5ccccc5)cc4)c(C(N)=O)c3)CC2C1]

5-[5-Carbamoyl-6-(4-phenoxy-phenoxy)-pyridin-3-yl]-hexahydro-pyrrolo[3,4-c]pyrrole-2-carboxylic acid tert-butyl ester A solution of 5-[5-methoxycarbonyl-6-(4-phenoxy-phenoxy)-pyridin-3-yl]-hexahydro-pyrrolo[3,4-c]pyrrole-2-carboxylic acid tert-butyl ester (1.50 g; 2.57 mmol; 1.00 eq.) in methanolic ammonia (30.00 ml; 20.00 V) was heated to 60° C. for 16 h in sealed tube. The reaction monitored by TLC. After completion of the reaction, the mixture was concentrated under vacuum to afford 5-[5-carbamoyl-6-(4-phenoxy-phenoxy)-pyridin-3-yl]-hexahydro-pyrrolo[3,4-c]pyrrole-2-carboxylic acid tert-butyl ester (1.30 g, 91.3%) as a yellow solid. HPLC: 93.20% purity. MS m/z=517 [M+H]$^+$. $^1$H NMR (400 MHz, DMSO-d6) δ 7.7 (s, 2H), 7.59-7.58 (d, J=3.1 Hz, 1H), 7.40-7.36 (m, 3H), 7.13-7.05 (m, 3H), 7.03-6.98 (m, 4H), 3.52-3.51 (d, J=5.0 Hz, 2H), 3.51-5.42 (d, J=35.5 Hz, 2H), 3.19-3.14 (m, 4H), 3.1 (s, 2H), 3.1 (s, 9H).

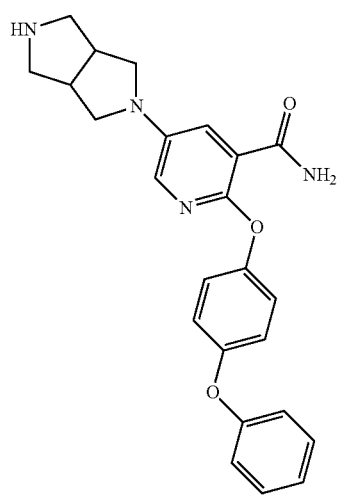 [SMILES: NC(=O)c1cc(N2CC3CNCC3C2)cnc1Oc1ccc(Oc2ccccc2)cc1]

5-(Hexahydro-pyrrolo[3,4-c]pyrrol-2-yl)-2-(4-phenoxy-phenoxy)-nicotinamide

To a stirred solution of 5-[5-carbamoyl-6-(4-phenoxy-phenoxy)-pyridin-3-yl]-hexahydro-pyrrolo[3,4-c]pyrrole-2-carboxylic acid tert-butyl ester (1.00 g; 1.80 mmol; 1.00 eq.) in DCM (10.00 ml) was added 4N HCl in 1,4-dioxane (10.00 ml) dropwise at RT under nitrogen atmosphere. The reaction mixture was stirred at RT for 5 h. After completion of the reaction (monitored by TLC), the mixture was concentrated under reduced pressure. The residue was diluted with DCM (50 mL), neutralized by the addition of saturated aqueous sodium bicarbonate solution (20 mL) and extracted with DCM:15% MeOH (3×20 mL). The organic layer was washed with brine (20 mL), dried over sodium sulphate and concentrated under vacuum to afford 5-(hexahydro-pyrrolo[3,4-c]pyrrol-2-yl)-2-(4-phenoxy-phenoxy)-nicotinamide (800.00 mg, 83.7%) as a colorless liquid. HPLC: 78.62% purity. MS m/z=417.30 [M+H]$^+$.

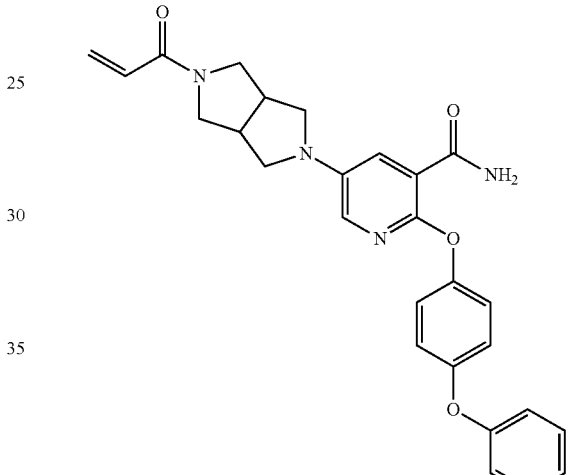

5-(5-Acryloyl-hexahydro-pyrrolo[3,4-c]pyrrol-2-yl)-2-(4-phenoxy-phenoxy)-nicotinamide (216)

To a stirred solution of 5-(hexahydro-pyrrolo[3,4-c]pyrrol-2-yl)-2-(4-phenoxy-phenoxy)-nicotinamide (420.00 mg; 0.77 mmol; 1.00 eq.) in dry DCM (12.60 ml; 30.00 V) was added N,N-diisopropylethylamine (0.41 ml; 2.30 mmol; 3.00 eq.) dropwise at −10° C. under nitrogen. The reaction mixture was stirred at −10° C. for 15 min and then treate with aryloyl chloride (0.07 ml; 0.84 mmol; 1.10 eq.), dropwise. Stirring was continued at −10° C. for 30 min. After completion of the reaction (monitored by TLC), the reaction was quenched by the addition of water (50 mL) and extracted with DCM (3×30 mL). The organic layers were combined, washed with brine (1×20 mL), dried over sodium sulphate, and concentrated under vacuum. The residue was purified by flash chromatography over silica gel (60-120 mesh) using DCM:MeOH (0-2%) as an eluent to afford 5-(5-acryloyl-hexahydro-pyrrolo[3,4-c]pyrrol-2-yl)-2-(4-phenoxy-phenoxy)-nicotinamide (130.00 mg, 35.4%) as a light yellow solid. HPLC: 97.86% purity. MS m/z=471

[M+H]⁺. ¹H NMR (400 MHz, DMSO-d6) δ 7.74 (s, 2H), 7.59-7.56 (m, 1H), 7.40-7.36 (m, 3H), 7.13-7.07 (m, 3H), 7.06-6.98 (m, 4H), 6.60-6.53 (m, 1H), 6.14-6.09 (m, 1H), 5.66-5.63 (m, 1H), 3.86-3.82 (m, 1H), 3.70-3.65 (m, 1H), 3.53-3.44 (m, 3H), 3.37-3.35 (m, 1H), 3.22-3.18 (m, 2H), 3.12-3.07 (m, 1H), 3.03-2.98 (m, 1H).

Example 206

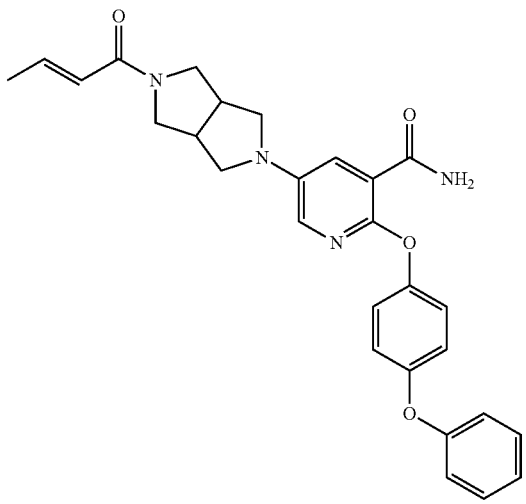 [SMILES: C/C=C/C(=O)N1CC2CN(c3cnc(Oc4ccc(Oc5ccccc5)cc4)c(C(N)=O)c3)CC2C1]

5-[5-((E)-But-2-enoyl)-hexahydro-pyrrolo[3,4-c]pyrrol-2-yl]-2-(4-phenoxy-phenoxy)-nicotinamide (217)

To a stirred solution of 5-(hexahydro-pyrrolo[3,4-c]pyrrol-2-yl)-2-(4-phenoxy-phenoxy)-nicotinamide (400.00 mg; 0.88 mmol; 1.00 eq.) in dry DCM (12.00 ml; 30.00 V) was added N,N-diisopropylethylamine (0.47 ml; 2.64 mmol; 3.00 eq.) dropwise at −10° C. under nitrogen. The reaction mixture was stirred at −10° C. for 15 min and then treated with (E)-but-2-enoyl chloride (0.09 g; 0.88 mmol; 1.00 eq.), dropwise. Stirring at −10° C. was continued for another 30 min. After completion of the reaction (monitored by TLC), the reaction mixture was quenched by the addition of water (50 mL) and extracted with DCM (3×30 mL). The organic layers were combined, washed with brine (1×20 mL), dried over sodium sulphate and concentrated under reduced pressure. The crude product was purified by flash chromatography over silica gel (60-120 mesh) using DCM:MeOH (9.5:0.5) as an eluent to afford 5-[5-((E)-but-2-enoyl)-hexahydro-pyrrolo[3,4-c]pyrrol-2-yl]-2-(4-phenoxy-phenoxy)-nicotinamide (115.00 mg; 26.1%) as a light yellow solid. HPLC: 95.07% purity. MS m/z=485 [M+H]⁺. ¹H NMR (400 MHz, DMSO-d6) δ 7.71 (s, 1H), 7.59-7.58 (d, J=3.12 Hz, 1H), 7.40-7.35 (m, 3H), 7.13-6.97 (m, 6H), 6.68-6.63 (m, 1H), 6.27-6.23 (m, 1H), 3.83-3.78 (m, 1H), 3.66-3.61 (m, 1H), 3.49-3.44 (m, 3H), 3.32 (m, 1H), 3.20-3.16 (m, 2H), 3.11-3.08 (m, 1H), 3.00-2.98 (m, 1H), 1.83-1.80 (m, 3H).

Example 207

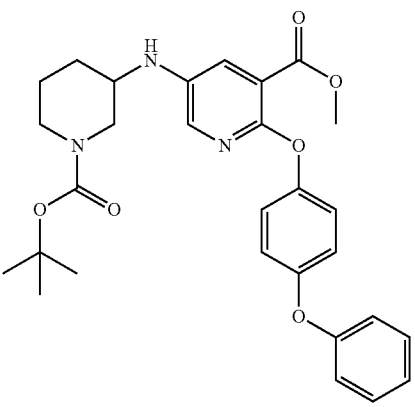 [SMILES: COC(=O)c1cc(NC2CCCN(C(=O)OC(C)(C)C)C2)cnc1Oc1ccc(Oc2ccccc2)cc1]

5-(1-tert-Butoxycarbonyl-piperidin-3-ylamino)-2-(4-phenoxy-phenoxy)-nicotinic acid methyl ester To a stirred solution of 5-iodo-2-(4-phenoxy-phenoxy)-nicotinic acid methyl ester (2.00 g; 3.85 mmol; 1.00 eq.) in 1,4-dioxane (40.00 ml; 20.00 V) were added 3-amino-piperidine-1-carboxylic acid tert-butyl ester (1.00 g; 4.62 mmol; 1.20 eq.) and cesium carbonate (2.58 g; 7.69 mmol; 2.00 eq.) at RT under nitrogen atmosphere. The resulting reaction mixture was degassed with nitrogen for 20 min and then treated with BrettPhos (0.11 g; 0.19 mmol; 0.05 eq.) and tris(dibenzylideneacetone)dipalladium(0) (0.36 g; 0.38 mmol; 0.10 eq.). The reaction mixture was heated in sealed tube to 100° C. for 16 h. Upon reaction completion (monitored by TLC), the reaction mixture was cooled to RT, and filtered through Celite. The Celite was washed with EtOAc (50 mL). The filtrate was washed with water (1x 50 mL) and brine (1×20 mL), dried over sodium sulphate and concentrated under vacuum. The residue was purified by flash chromatography over silica gel (60-120 mesh) by using (3:7) EtOAc:Pet ether as an eluent to afford 5-(1-tert-butoxycarbonyl-piperidin-3-ylamino)-2-(4-phenoxy-phenoxy)-nicotinic acid methyl ester (1.00 g; 45.2%) as a red solid. HPLC: 90.40% purity. MS m/z=464 [M+H]⁺. (Cleavage of t-Butanol). ¹H NMR (400 MHz, DMSO-d6) δ 7.5 (s, 1H), 7.39-7.35 (m, 2H), 7.12-7.09 (m, 1H), 7.01-6.97 (m, 6H), 3.8 (s, 3H), 3.7 (s, 1H), 3.5 (s, 1H), 3.3 (s, 1H), 3.0 (s, 2H), 1.9 (s, 1H), 1.7 (s, 1H), 1.43-1.16 (m, 11H).

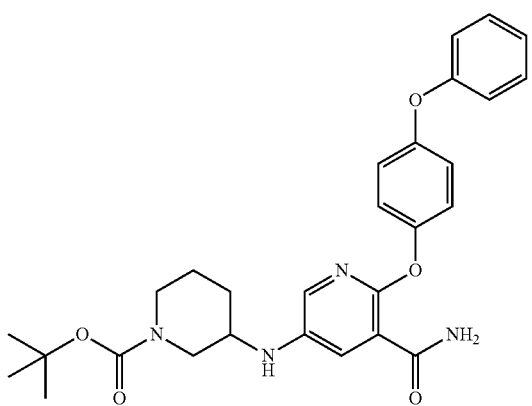 [SMILES: CC(C)(C)OC(=O)N1CCCC(Nc2cnc(Oc3ccc(Oc4ccccc4)cc3)c(C(N)=O)c2)C1]

3-[5-Carbamoyl-6-(4-phenoxy-phenoxy)-pyridin-3-ylamino]-piperidine-1-carboxylic acid tert-butyl ester A solution of 5-(1-tert-butoxycarbonyl-piperidin-3-ylamino)-2-(4-phenoxy-phenoxy)-nicotinic acid methyl ester (1.00 g; 1.74 mmol; 1.00 eq.) in ethanolic ammonia (20.00 ml; 407.56 mmol; 20.00 V) was heated to 60° C. for 16 h in sealed tube. The reaction progress was monitored by TLC. Upon completion of the reaction, the mixture was concentrated under vaccum to afford 3-[5-carbamoyl-6-(4-phenoxy-phenoxy)-pyridin-3-ylamino]-piperidine-1-carboxylic acid tert-butyl ester (800.00 mg, 82.5%) as a yellow solid. HPLC: 90.50% purity. MS m/z=505 [M+H]$^+$.

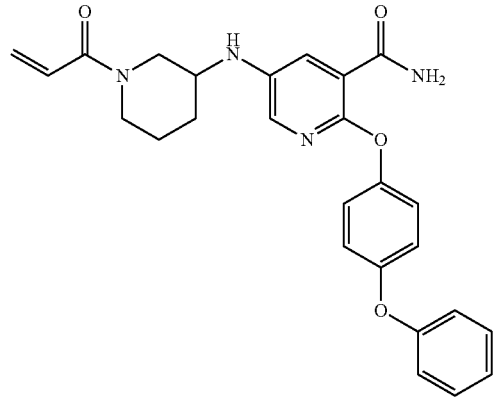

5-(1-Acryloyl-piperidin-3-ylamino)-2-(4-phenoxy-phenoxy)-nicotinamide (223)

To a stirred solution of 2-(4-phenoxy-phenoxy)-5-(piperidin-3-ylamino)-nicotinamide (200.00 mg; 0.32 mol; 1.00 eq.) in dry DCM (4.00 ml; 20.00 V) was added N,N-diisopropylethylamine (0.08 ml; 0.48 mmol; 1.50 eq.) drop-wise at −10° C. under nitrogen. Stirring was continued at −10° C. temperature for 15 min, and then acryloyl chloride (0.01 ml; 0.16 mmol; 0.50 eq.) was added, dropwise. Stirring at −10° C. was continued for another 30 min. After completion of the reaction (monitored by TLC), the reaction was quenched by the addition of water (50 mL) and extracted with DCM (3×30 mL). The organic layers were combined, washed with brine (1×20 mL), dried over sodium sulphate and concentrated under vacuum. The crude product was purified by flash chromatography over silica gel (60-120 mesh) by using DCM:MeOH (9:2) as an eluent to afford 5-(1-acryloyl-piperidin-3-ylamino)-2-(4-phenoxy-phenoxy)-nicotinamide (22.00 mg, 14.6%;) as a off-white solid. HPLC: 96.93% purity. MS m/z=459.20 [M+H]$^+$. $^1$H NMR (400 MHz, DMSO-d6) δ 7.66-7.64 (d, J=8.8 Hz, 3H), 7.48-7.47 (d, J=3.0 Hz, 1H), 7.40-7.35 (m, 2H), 7.13-7.07 (m, 3H), 7.03-6.99 (m, 4H), 6.82-6.53 (m, 1H), 6.13-6.00 (m, 1H), 5.86-5.82 (t, J=9.5 Hz, 1H), 5.68-5.56 (m, 1H), 4.39-3.81 (m, 2H), 3.17-3.13 (m, 2H), 2.59-2.56 (m, 1H), 1.99-1.98 (d, J=5.88 Hz, 1H), 1.75 (s, 1H), 1.47-1.43 (m, 2H).

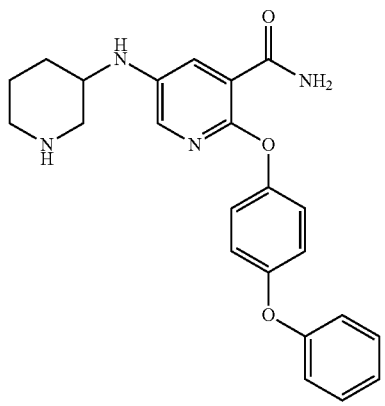 [SMILES: NC(=O)c1cc(NC2CCCNC2)cnc1Oc1ccc(Oc2ccccc2)cc1]

2-(4-Phenoxy-phenoxy)-5-(piperidin-3-ylamino)-nicotinamide

To a stirred solution of 3-[5-carbamoyl-6-(4-phenoxy-phenoxy)-pyridin-3-ylamino]-piperidine-1-carboxylic acid tert-butyl ester (800.00 mg; 1.49 mmol; 1.00 eq.) in DCM (10.00 ml) was added 4N HCl in 1,4-dioxane (10.00 ml) dropwise at RT under nitrogen atmosphere. The reaction mixture was stirred at RT for 5 h. After completion of the reaction (monitored by TLC), it was concentrated under reduced pressure. The residue was diluted with DCM (50 mL), neutralized by the addition of saturated aqueous sodium bicarbonate solution (20 mL) and extracted with DCM:15% MeOH (3×20 mL). The organic layer was washed with brine (20 mL), dried over sodium sulphate and concentrated under vacuum to afford 2-(4-phenoxy-phenoxy)-5-(piperidin-3-ylamino)-nicotinamide (620.00 mg, 79.7%) as a light brown oil. HPLC: 90.50% purity. MS m/z=405 [M+H]$^+$.

Example 208

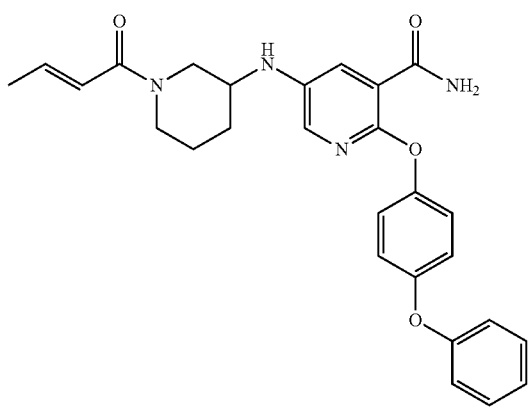 [SMILES: C/C=C/C(=O)N1CCCC(Nc2cnc(Oc3ccc(Oc4ccccc4)cc3)c(C(N)=O)c2)C1]

5-[1-((E)-But-2-enoyl)-piperidin-3-ylamino]-2-(4-phenoxy-phenoxy)-nicotinamide (215)

To a stirred solution of 2-(4-phenoxy-phenoxy)-5-(piperidin-3-ylamino)-nicotinamide (320 mg; 0.64 mmol; 1.00 eq.) in dry DCM (9.60 ml; 30.00 V) was added N,Ndiisopropylethylamine (0.34 ml; 1.92 mmol; 3.00 eq.) dropwise at −10° C. under nitrogen. Stirring was continued at −10° C. for 15 min, and then (E)-but-2-enoyl chloride (67.50 mg; 0.64 mmol; 1.00 eq.) was added, dropwise. Stirring at −10° C. was continued for another 30 min. After completion of the reaction (monitored by TLC), the reaction was quenched by the addition of water (50 mL) and extracted with DCM (3×30 mL). The organic layers were washed with brine (1×20 mL), dried over sodium sulphate and concentrated under vacuum. The crude product was purified by flash chromatography over silica gel (60-120 mesh) using DCM:MeOH (9.5:0.5) as an eluent to afford 5-[1-((E)-but-2-enoyl)-piperidin-3-ylamino]-2-(4-phenoxy-phenoxy)-nicotinamide (60.00 mg, 19.3%) as a off-white solid. HPLC: 95.03% purity. MS m/z=473 [M+H]$^+$. $^1$H NMR (400 MHz, DMSO-d6) δ 7.68-7.64 (m, 3H), 7.47 (d, J=2.9 Hz, 1H), 7.40-7.35 (m, 2H), 7.14-7.07 (m, 3H), 7.04-6.98 (m, 4H), 6.66-6.27 (m, 2H), 5.83-5.80 (m, 1H), 4.37 (d, J=11.3 Hz, 1H), 3.91-3.80 (m, 1H), 3.12 (s, 2H), 2.50 (s, 1H), 1.98 (s, 1H), 1.83-1.74 (m, 4H), 1.45 (d, J=8.40 Hz, 2H).

Example 209

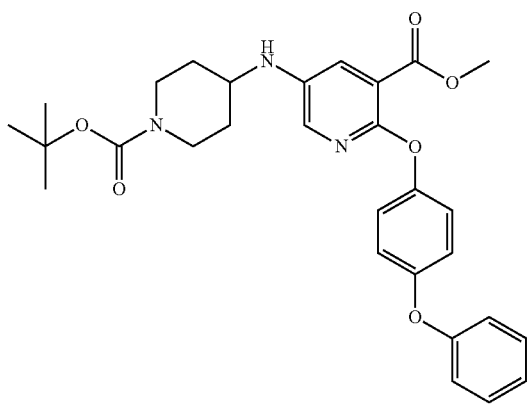 [SMILES: COC(=O)c1cc(NC2CCN(C(=O)OC(C)(C)C)CC2)cnc1Oc1ccc(Oc2ccccc2)cc1]

Methyl 5-((1-(tert-butoxycarbonyl)piperidin-4-yl)amino)-2-(4-phenoxyphenoxy)nicotinate To a stirred solution of 5-iodo-2-(4-phenoxy-phenoxy)-nicotinic acid methyl ester (2.00 g; 3.85 mmol; 1.00 eq.) in 1,4-dioxane (30.00 ml; 15.00 V) was added 4-amino-piperidine-1-carboxylic acid tert-butyl ester (0.94 g; 4.62 mmol; 1.20 eq.) at RT under nitrogen atmosphere. The resulting reaction mixture was degassed with nitrogen for 20 min and then treated with dicyclohexyl-(2',4',6'-triisopropoxy-4,6-dimethoxy-biphenyl-2-yl)-phosphane (0.11 g; 0.19 mmol; 0.05 eq.) and tris(dibenzylideneacetone)dipalladium(0) (0.36 g; 0.38 mmol; 0.10 eq.). The reaction mixture was heated to 100° C. for 16 h. After completion of the reaction (monitored by TLC), the reaction mixture was cooled to RT. The reaction was quenched by the addition of water (100 mL), and extracted with EtOAc (3×50 mL). The organic layers were combined, washed with brine (1×50 mL), dried over sodium sulphate, and concentrated under vaccum. The residue was purified by flash chromatography on silica gel (60-120 mesh) using 25% EtOAc:Petether as an eluent to afford 5-(1-tert-butoxycarbonyl-piperidin-4-ylamino)-2-(4-phenoxy-phenoxy)-nicotinic acid methyl ester (1.00 g; 48.0%; brown semi solid). HPLC: 95.86% purity. MS: m/z=520.20 [M+H]$^+$. $^1$H NMR (400 MHz, DMSO-d6) δ 7.94 (s, 1H), 7.76-7.75 (d, J=2.8 Hz, 1H), 7.48 (d, J=2.8 Hz, 2H), 7.39-7.35 (m, 1H), 7.12-6.97 (m, 6H), 5.86-5.84 (d, J=8.2 Hz, 1H), 4.02-4.00 (d, J=7.1 Hz, 2H), 3.85-3.78 (m, 3H), 3.45-3.32 (m, 1H), 3.32 (s, 1H), 2.92-2.88 (m, 2H), 1.39 (s, 9H).

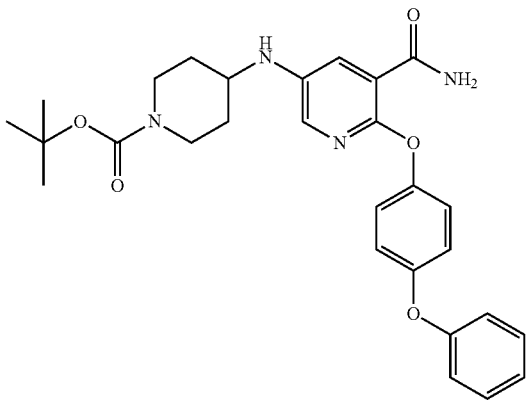 [SMILES: CC(C)(C)OC(=O)N1CCC(Nc2cnc(Oc3ccc(Oc4ccccc4)cc3)c(C(N)=O)c2)CC1]

tert-Butyl 4-((5-carbamoyl-6-(4-phenoxyphenoxy)pyridin-3-yl)amino)piperidine-1-carboxylate A solution of methyl 5-((1-(tert-butoxycarbonyl)piperidin-4-yl)amino)-2-(4-phenoxyphenoxy) nicotinate (0.90 g; 1.89 mmol; 1.00 eq.) in methanolic ammonia (12.00 ml; 13.33 V) was heated to 60° C. for 16 h in sealed tube. The reaction monitored by TLC. After completion of the reaction, the reaction mixture was concentrated under vacuum to afford 4-[5-carbamoyl-6-(4-phenoxy-phenoxy)-pyridin-3-ylamino]-piperidine-1-carboxylic acid tert-butyl ester (0.80 g; 79.0%). HPLC: 94.20% purity. MS: m/z=505.20 [M+H]$^+$. $^1$H NMR (400 MHz, DMSO-d6) δ 7.67-7.44 (m, 2H), 7.43-7.36 (m, 2H), 7.13-6.97 (m, 9H), 5.74-5.72 (d, J=8.3 Hz, 1H), 3.85-3.80 (t, J=13.0 Hz, 2H), 3.32 (s, 1H), 2.91 (s, 2H), 1.87-1.84 (t, J=10.1 Hz, 2H), 1.39 (s, 9H), 1.25-1.19 (m, 2H).

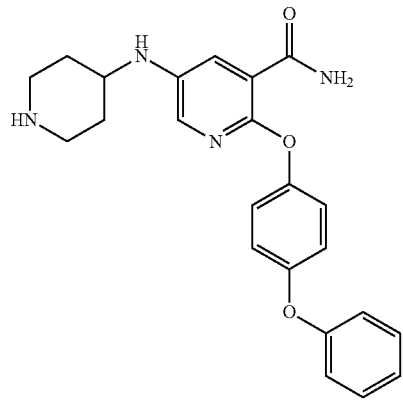 [SMILES: NC(=O)c1cc(NC2CCNCC2)cnc1Oc1ccc(Oc2ccccc2)cc1]

2-(4-phenoxyphenoxy)-5-(piperidin-4-ylamino)nicotinamide)

To a stirred solution of 4-[5-carbamoyl-6-(4-phenoxy-phenoxy)-pyridin-3-ylamino]-piperidine-1-carboxylic acid tert-butyl ester (900.00 mg; 1.62 mmol; 1.00 eq.) in DCM (9.00 ml; 10.00 V) was added 4N HCl in 1,4-dioxane (9.00 ml; 10.00 V) dropwise, at RT under nitrogen atmosphere. The reaction mixture was stirred at RT for 5 h. After completion of the reaction, the mixture was concentrated under reduced pressure. The residue was diluted with DCM (50 mL), neutralized by the addition of saturated aqueous sodium bicarbonate (20 mL), and extracted with DCM/15% MeOH (3×20 mL). The organic layer was washed with brine (20 mL), dried over sodium sulphate and concentrated under vacuum to afford 2-(4-phenoxy-phenoxy)-5-(piperidin-4-ylamino)-nicotinamide (600 mg; 69.5%; light brown gum). HPLC: 75.85% purity. MS: m/z=405.20 [M+H]$^+$. $^1$H NMR (400 MHz, DMSO-d6) δ 7.67-7.60 (m, 2H), 7.42-7.35 (m, 3H), 7.13-6.97 (m, 10H), 3.33 (s, 5H), 2.96-2.93 (d, J=12.5 Hz, 2H), 2.58-2.55 (d, J=12.0 Hz, 2H), 1.86-1.83 (d, J=10.5 Hz, 2H), 1.26-1.21 (m, 3H).

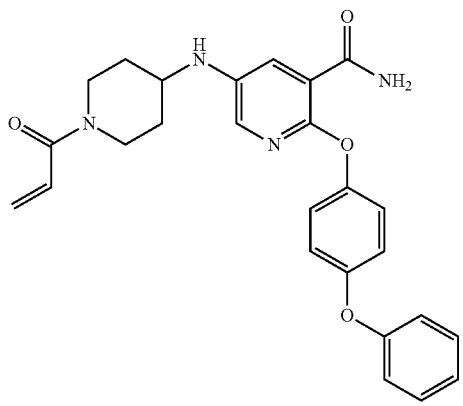 [SMILES: C=CC(=O)N1CCC(Nc2cnc(Oc3ccc(Oc4ccccc4)cc3)c(C(N)=O)c2)CC1]

5-(1-Acryloyl-piperidin-4-ylamino)-2-(4-phenoxy-phenoxy)-nicotinamide (252)

To a stirred solution of 2-(4-phenoxyphenoxy)-5-(piperidin-4-ylamino)nicotinamide in DCM (10.00 ml; 50.00 V) was added triethylamine (0.20 ml; 1.12 mmol; 3.00 eq.) and acryloyl chloride (0.03 ml; 0.41 mmol; 1.10 eq.). After the addition, the reaction mixture was stirred at RT under nitrogen for 1 h. Reaction progress was monitored by TLC. The reaction was quenched by the addition of water (20 mL) and extracted with DCM (2×50 mL). The organic layers were combined, washed with aq. solution of sodium bicarbonate (10%, 20 mL) and water (10 mL), dried over sodium sulfate and concentrated under reduced pressure. The crude product was purified by column chromatography over silica gel (230-400 mesh) using (1-2%) methanol in dichloromethane as an eluent. The product fractions were collected and concentrated under reduced pressure to afford 5-(1-acryloyl-piperidin-4-ylamino)-2-(4-phenoxy-phenoxy)-nicotinamide (30 mg, 16.5%) as a pale yellow solid. HPLC: 95.03% purity. MS m/z=459 [M+H]$^+$. $^1$H NMR (400 MHz, DMSO-d6) δ 7.68-7.64 (m, 3H), 7.46-7.36 (m, 3H), 7.13-6.79 (m, 8H), 6.08 (d, J=19.1 Hz, 1H), 5.71-5.69 (m, 1H), 4.35-4.22 (m, 1H), 4.11-4.10 (m, 1H), 3.80-3.33 (m, 3H), 2.48 (s, 2H), 1.23 (s, 2H).

Example 210

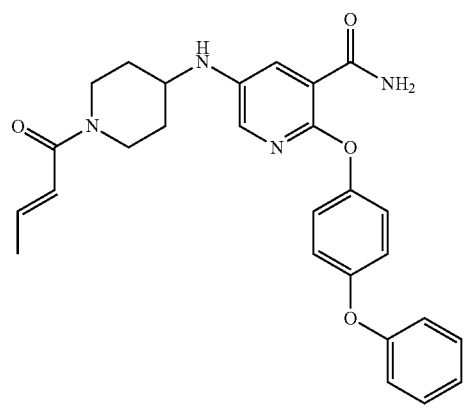 [SMILES: C/C=C/C(=O)N1CCC(Nc2cnc(Oc3ccc(Oc4ccccc4)cc3)c(C(N)=O)c2)CC1]

5-[1-((E)-But-2-enoyl)-piperidin-4-ylamino]-2-(4-phenoxy-phenoxy)-nicotinamide (234)

To a stirred solution of 2-(4-phenoxy-phenoxy)-5-(piperidin-4-ylamino)-nicotinamide (200.00 mg; 0.37 mmol; 1.00 eq.) in DCM (10.00 ml; 50.00 V) was added triethylamine (0.20 ml; 1.12 mmol; 3.00 eq.), and (E)-but-2-enoyl chloride (0.04 ml; 0.37 mmol; 1.00 eq.). After the addition, the reaction mixture was stirred at RT under nitrogen for 1 h. Reaction completion was assessed by TLC. The reaction was quenched by the addition of water (20 mL) and extracted with DCM (2×50 mL). The oragnic layers were combined, washed with aq. sodium bicarbonate (10%, 20 mL) and water (10 mL), dried over sodium sulfate and concentrated under reduced pressure. The crude product was purified by column chromatography over silica gel (230-400 mesh) using (1-2%) methanol in dichloromethane as an eluent. The resulting product fractions were collected and concentrated under vacuum to afford 5-[1-((E)-but-2-enoyl)-piperidin-4-ylamino]-2-(4-phenoxy-phenoxy)-nicotinamide (30.00 mg, 16.0%) as a pale yellow solid. HPLC: 96.6% purity. MS m/z=473 [M+H]$^+$. $^1$H NMR (400 MHz, DMSO-d6) δ 7.68-7.63 (m, 3H), 7.45-7.36 (m, 3H), 7.13-6.98 (m, 7H), 6.68-6.50 (m, 6H), 5.75 (s, 1H), 4.24 (d, J=10.8 Hz, 1H), 3.98 (d, J=11.2 Hz, 1H), 3.50 (s, 1H), 3.23-3.17 (m, 3H), 1.91-1.82 (m, 5H), 1.22 (s, 2H).

Example 211

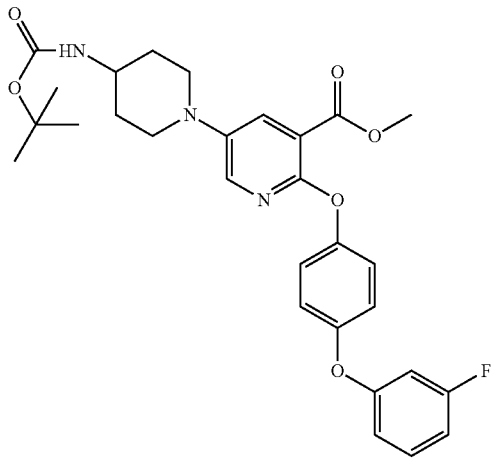 [SMILES: COC(=O)c1cc(N2CCC(NC(=O)OC(C)(C)C)CC2)cnc1Oc1ccc(Oc2cccc(F)c2)cc1]

4-tert-Butoxycarbonylamino-6'-[4-(3-fluoro-phenoxy)-phenoxy]-3,4,5,6-tetrahydro-2H-[1,3']bipyridinyl-5'-carboxylic acid methyl ester To a stirred solution of 2-[4-(3-fluoro-phenoxy)-phenoxy]-5-iodo-nicotinic acid methyl ester (1.50 g; 2.52 mmol; 1.00 eq.) in 1,4-dioxane (30.00 ml; 20.00 V) were added piperidin-4-yl-carbamic acid tert-butyl ester (0.66 g; 3.03 mmol; 1.20 eq.) and cesium carbonate (1.69 g; 5.05 mmol; 2.00 eq.) at RT under nitrogen atmosphere. The reaction mixture was degassed with nitrogen for 20 min and then treated with dicyclohexyl-(2',6'-diisopropoxy-biphenyl-2-yl)-phosphane (0.06 g; 0.13 mmol; 0.05 eq.) and tris(dibenzylideneacetone)dipalladium(0) (0.24 g; 0.25 mmol; 0.10 eq.). The reaction mixture was heated in a sealed tube to 100° C. for 16 h. Reaction progress was monitored by TLC. After completion, the reaction mixture was cooled to RT, and filtered through Celite. The Celite bed was washed with EtOAc (50 mL). The filtrate was washed with water (lx 50 mL) and brine (1×20 mL), dried over sodium sulphate and concentrated under vacuum. The residue was purified by flash chromatography on silica gel (60-120 mesh) using (3:7) EtOAc: Pet. ether as an eluent to afford 4-tert-butoxycarbonylamino-6'-[4-(3-fluoro-phenoxy)-phenoxy]-3,4,5,6-tetrahydro-2H-[1,3']bipyridinyl-5'-carboxylic acid methyl ester (1.00 g, 59.1%) as a red gum. HPLC: 80.22% purity. MS m/z=538 [M+H]$^+$. $^1$H NMR (400 MHz, DMSO-d6) δ 8.06-8.05 (d, J=3.1 Hz, 1H), 7.78-7.76 (t, J=3.1 Hz, 1H), 7.43-7.38 (m, 1H), 7.09-7.04 (m, 4H), 6.97-6.92 (m, 1H), 6.87-6.79 (m, 3H), 3.81 (s, 3H), 3.62-3.59 (d, J=12.8 Hz, 2H), 3.31 (s, 1H), 2.80-2.73 (m, 2H), 1.80-1.78 (d, J=10.6 Hz, 2H), 1.54-1.51 (m, 2H), 1.4 (s, 9H).

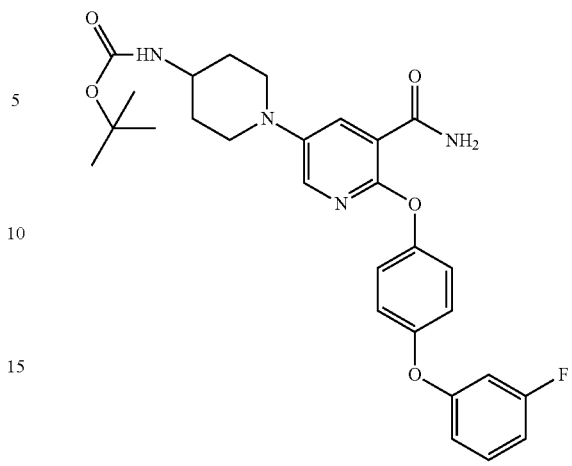

{5'-Carbamoyl-6'-[4-(3-fluoro-phenoxy)-phenoxy]-3,4,5,6-tetrahydro-2H-[1,3']bipyridinyl-4-yl}-carbamic acid tert-butyl ester A solution of 4-tert-butoxycarbonylamino-6'-[4-(3-fluoro-phenoxy)-phenoxy]-3,4,5,6-tetrahydro-2H-[1,3']bipyridinyl-5'-carboxylic acid methyl ester (1.00 g; 1.53 mmol; 1.00 eq.) in methanolic ammonia (20.00 ml; 20.00 V) was heated at 60° C. for 16 h in sealed tube. After completion of the reaction (monitored by TLC), the reaction mixture was concentrated under vacuum to afford {5'-carbamoyl-6'-[4-(3-fluoro-phenoxy)-phenoxy]-3,4,5,6-tetrahydro-2H-[1,3']bipyridinyl-4-yl}-carbamic acid tert-butyl ester (0.80 g, 96.4%) as a light orange solid. HPLC: 96.10% purity. MS m/z=523 [M+H]$^+$. $^1$H NMR (400 MHz, DMSO-d6) δ 7.91-7.74 (d, J=3.1 Hz, 1H), 7.75-7.72 (m, 3H), 7.44-7.38 (m, 1H), 7.16-7.10 (m, 2H), 7.10-7.08 (m, 2H), 6.98-6.93 (m, 1H), 6.87-6.82 (m, 3H), 3.61-3.56 (m, 2H), 3.4 (s, 2H), 2.77-2.72 (m, 2H), 1.81-1.75 (m, 2H), 1.54-1.46 (m, 2H), 1.4 (s, 9H).

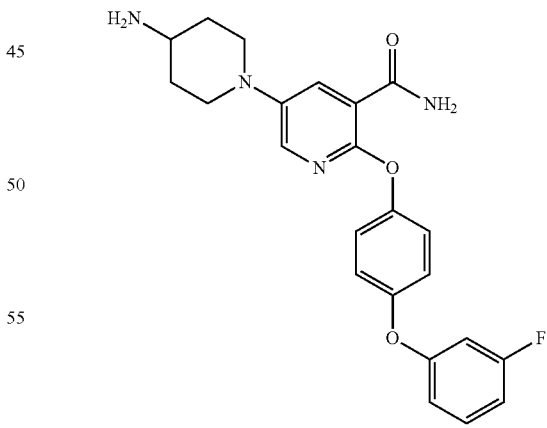

4-Amino-6'-[4-(3-fluoro-phenoxy)-phenoxy]-3,4,5,6-tetrahydro-2H-[1,3']bipyridinyl-5'-carboxylic acid amide To a stirred solution of {5'-carbamoyl-6'-[4-(3-fluoro-phenoxy)-phenoxy]-3,4,5,6-tetrahydro-2H-[1,3']bipyridinyl-4-yl}-carbamic acid tert-butyl ester (800.00 mg; 1.44 mmol; 1.00 eq.) in DCM (0.92 ml; 14.41 mmol; 10.00 eq.) was added 4N HCl in 1,4-dioxane (3.60 ml; 14.41 mmol; 10.00 eq.) dropwise at RT under nitrogen atmosphere. The reaction mixture was stirred at RT for 5 h. After completion of the reaction (monitored by TLC), it was concentrated under reduced pressure. The residue was diluted with DCM (50 mL), neutralized by the addition of saturated aq. sodium bicarbonate (20 mL) and extracted with DCM:15% MeOH (3×20 mL). The organic layer was washed with brine (20 mL), dried over sodium sulphate and concentrated under vacuum to afford 4-amino-6'-[4-(3-fluoro-phenoxy)-phenoxy]-3,4,5,6-tetrahydro-2H-[1,3']bipyridinyl-5'-carboxylic acid amide (600.00 mg,79.7%) light brown oil. HPLC: 96.10% purity. MS m/z=423 [M+H]$^+$.

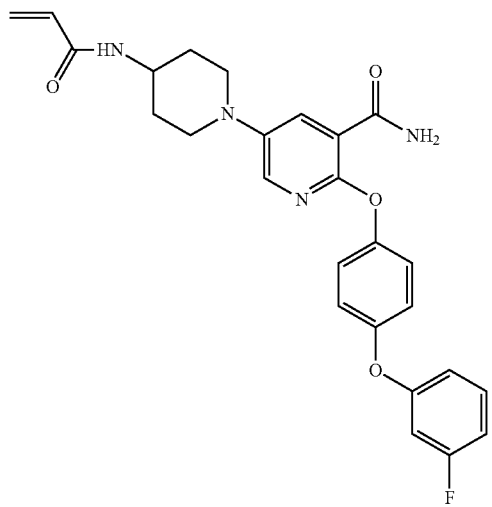 [SMILES: C=CC(=O)NC1CCN(c2cnc(Oc3ccc(Oc4cccc(F)c4)cc3)c(C(N)=O)c2)CC1]

4-Acryloylamino-6'-[4-(3-fluoro-phenoxy)-phenoxy]-3,4,5,6-tetrahydro-2H-[1,3']bipyridinyl-5'-carboxylic acid amide (212)

To a stirred solution of 4-amino-6'-(4-phenoxy-phenoxy)-3,4,5,6-tetrahydro-2H-[1,3']bipyridinyl-5'-carboxylic acid amide (350.00 mg; 0.70 mmol; 1.00 eq.) in dry DCM (10.50 ml; 30.00 V) was added N,N-diisopropylethylamine (0.37 ml; 2.10 mmol; 3.00 eq.) dropwise at −10° C. under nitrogen. Stirring was continued at −10° C. for 15 min and then acryloyl chloride (0.06 ml; 0.77 mmol; 1.10 eq.) was added dropwise. The reaction mixture was then stirred at −10° C. for 30 min. After completion of the reaction (monitored by TLC), the reaction was quenched by the addition of water (50 mL) and extracted with DCM (3×30 mL). The organic layers were combined, washed with brine (1×20 mL), dried over sodium sulphate and concentrated under vaccum. The crude product was purified by column chromatograpy over silica gel (60-120 mesh) using DCM:MeOH (9.5:0.5) as an eluent to afford 4-acryloylamino-6'-[4-(3-fluoro-phenoxy)-phenoxy]-3,4,5,6-tetrahydro-2H-[1,3']bipyridinyl-5'-carboxylic acid amide (192.00 mg, 55.8%) as an off-white solid. HPLC: 95.35% purity. MS m/z=477 [M+H]$^+$. $^1$H NMR (400 MHz, DMSO-d6) δ 8.07-8.06 (d, J=7.68 Hz, 1H), 7.94-7.93 (d, J=3.08 Hz, 1H), 7.76-7.74 (m, 3H), 7.44-7.38 (m, 1H), 7.12 (m, 2H), 6.98-6.93 (m, 1H), 6.87-6.80 (m, 2H), 6.24-6.17 (m, 1H), 6.10-6.05 (m, 1H), 5.59-5.56 (m, 1H), 3.81-3.78 (m, 1H), 3.62-3.60 (d, J=12.68 Hz, 2H), 2.83-2.80 (t, J=10.84 Hz, 2H), 1.86-1.84 (m, 2H), 1.56-1.46 (m, 2H).

Example 212

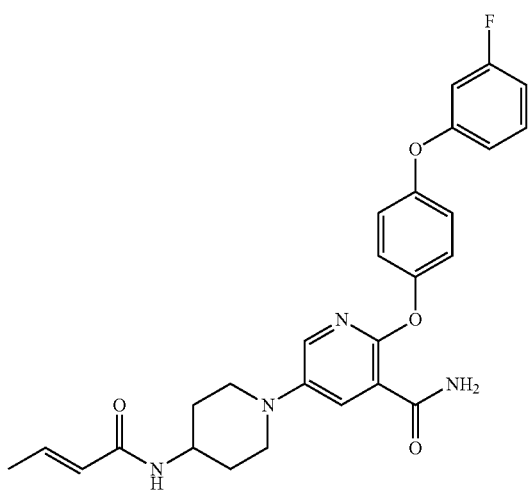 [SMILES: C/C=C/C(=O)NC1CCN(c2cnc(Oc3ccc(Oc4cccc(F)c4)cc3)c(C(N)=O)c2)CC1]

4-((E)-But-2-enoylamino)-6'-[4-(3-fluoro-phenoxy)-phenoxy]-3,4,5,6-tetrahydro-2H-[1,3']bipyridinyl-5'-carboxylic acid amide (214)

To a stirred solution of 4-amino-6'-[4-(3-fluoro-phenoxy)-phenoxy]-3,4,5,6-tetrahydro-2H-[1,3']bipyridinyl-5'-carboxylic acid amide (400.00 mg; 0.77 mmol; 1.00 eq.) in dry DCM (12.00 ml; 30.00 V) was added N,N-diisopropylethylamine (0.40 ml; 2.30 mmol; 3.00 eq.) dropwise at −10° C. under nitrogen. Stirring was continued at −10° C. for 15 min and then (E)-but-2-enoyl chloride (80.78 mg; 0.77 mmol; 1.00 eq.) was added dropwise. The reaction mixture was stirred at −10° C. for 30 min. Upon completion of the reaction (monitored by TLC), the reaction was quenched by the addition of water (50 mL) and extracted with DCM (3×30 mL). The oganic layers were combined, washed with brine (1×20 mL), dried over sodium sulphate and concentrated under reduced pressure. The crude product was purified by flash chromatograpy over silica gel (60-120 mesh) by using DCM:MeOH (9.5:0.5) as an eluent to afford 4-((E)-but-2-enoylamino)-6'-[4-(3-fluoro-phenoxy)-phenoxy]-3,4,5,6-tetrahydro-2H-[1,3']bipyridinyl-5'-carboxylic acid amide (213.00 mg, 55.1%) as an off-white solid. HPLC: 97% purity. MS m/z=491 [M+H]$^+$. $^1$H NMR (400 MHz, DMSO-d6) δ 7.94-7.93 (m, 1H), 7.84-7.83 (d, J=7.72 Hz, 1H), 7.76-7.74 (m, 2H), 7.44-7.38 (m, 1H), 7.16-7.13 (m, 2H), 7.11-7.08 (m, 2H), 6.98-6.93 (m, 1H), 6.87-6.87 (m, 2H), 6.80-6.57 (m, 1H), 5.88-5.86 (d, J=16.96 Hz, 1H), 3.80-3.73 (m, 1H), 3.62-3.59 (m, 2H), 2.82-2.79 (t, J=11.48 Hz, 2H), 1.84-1.76 (m, 5H), 1.54-1.44 (m, 2H).

Example 213

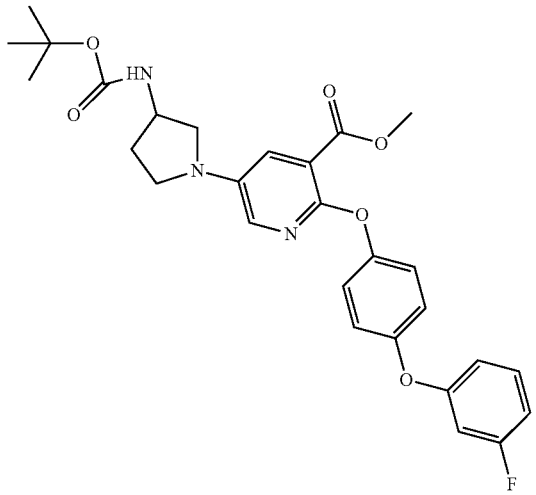 [SMILES: COC(=O)c1cc(N2CCC(NC(=O)OC(C)(C)C)C2)cnc1Oc1ccc(Oc2cccc(F)c2)cc1]

5-(3-tert-butoxycarbonylamino-pyrrolidin-1-yl)-2-[4-(3-fluoro-phenoxy)-phenoxy]-nicotinic acid methyl ester To a stirred solution of 2-[4-(3-fluoro-phenoxy)-phenoxy]-5-iodo-nicotinic acid methyl ester (2.00 g; 4.01 mmol; 1.00 eq.) in 1,4-dioxane (40.00 ml; 20.00 V) was added yrrolidin-3-yl-carbamic acid tert-butyl ester (0.91 g; 4.81 mmol; 1.20 eq.) and cesium carbonate (2.69 g; 8.01 mmol; 2.00 eq.) at RT under nitrogen atmosphere. The reaction mixture was degassed with nitrogen for 20 min and then treated with tris(dibenzylideneacetone)dipalladium(0) and dicyclohexyl-(2',6'-diisopropoxy-biphenyl-2-yl)-phosphane (0.10 g; 0.20 mmol; 0.05 eq.). The reaction mixture was heated in sealed tube to 100° C. for 16 h. Upon completion of the reaction (monitored by TLC), the reaction mixture was cooled to RT and filtered through Celite. The Celite bed was washed with EtOAc (50 mL). The filtrate was washed with water (lx 50 mL) and brine (1×20 mL), dried over sodium sulphate and concentrated under vacuum. The residue was purified by flash chromatography over silica gel (60-120 mesh) by using (3:7) EtOAc:Pet ether as an eluent to afford 5-(3-tert-butoxycarbonylamino-pyrrolidin-1-yl)-2-[4-(3-fluoro-phenoxy)-phenoxy]-nicotinic acid methyl ester (1.20 g, 44.9%) as a red gum. HPLC: 78.57% purity. MS m/z=524 [M+H]$^+$. $^1$H NMR (400 MHz, DMSO-d6) δ 7.72-7.70 (dd, J=3.3, −5.7 Hz, 1H), 7.42-7.31 (m, 1H), 7.21-7.20 (d, J=6.7 Hz, 1H), 7.07-7.04 (m, 1H), 7.02-6.98 (m, 2H), 6.96-6.91 (m, 3H), 4.15-4.13 (m, 1H), 3.8 (s, 3H), 3.51-3.32 (m, 3H), 3.08-3.04 (m, 1H), 2.18-2.10 (m, 1H), 1.93-1.86 (m, 1H), 1.4 (s, 9H).

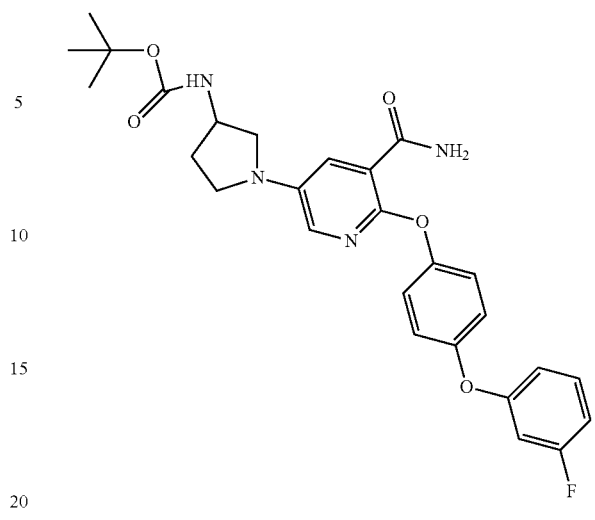

(1-{5-Carbamoyl-6-[4-(3-fluoro-phenoxy)-phenoxy]-pyridin-3-yl}-pyrrolidin-3-yl)-carbamic acid tert-butyl ester A stirred solution of 5-(3-tert-butoxycarbonylamino-pyrrolidin-1-yl)-2-[4-(3-fluoro-phenoxy)-phenoxy]-nicotinic acid methyl ester (1.20 g; 1.80 mmol; 1.00 eq.) in methanolic ammonia (36.00 ml; 30.00 V) and was heated at 60° C. for 16 h in sealed tube and cooled to ambient temperature. After completion of the reaction by TLC, the reaction mixture was concentrated under vacuum to afford (1-{5-carbamoyl-6-[4-(3-fluoro-phenoxy)-phenoxy]-pyridin-3-yl}-pyrrolidin-3-yl)-carbamic acid tert-butyl ester (0.90 g, 91.0%) as a yellow solid. HPLC: 93.5% purity. MS m/z=509 [M+H]$^+$. $^1$H NMR (400 MHz, DMSO-d6) δ 7.7 (s, 2H), 7.58-7.57 (d, J=3.1 Hz, 1H), 7.43-7.32 (m, 1H), 7.21-7.19 (d, J=6.6 Hz, 1H), 7.1 (s, 1H), 6.96-6.92 (m, 4H), 6.85-6.79 (m, 3H), 4.2 (s, 1H), 3.49-3.45 (m, 1H), 3.37-3.24 (m, 2H), 3.07-3.03 (m, 1H), 2.1 (s, 1H), 1.88-1.87 (d, J=5.6 Hz, 1H), 1.4 (s, 9H).

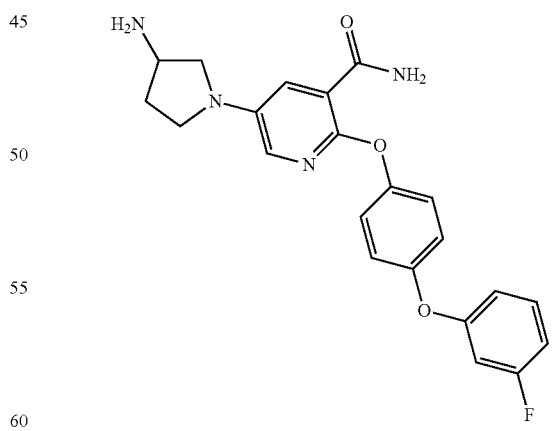

5-(3-Amino-pyrrolidin-1-yl)-2-[4-(3-fluoro-phenoxy)-phenoxy]-nicotinamide

To a stirred solution of (1-{5-carbamoyl-6-[4-(3-fluoro-phenoxy)-phenoxy]-pyridin-3-yl}-pyrrolidin-3-yl)-carbamic acid tert-butyl ester (800.00 mg; 1.45 mmol; 1.00 eq.) in DCM (8.00 ml; 10.00 V) was added 4N HCl in 1,4-dioxane (4.00 ml; 5.00 V) dropwise at RT under nitrogen atmosphere. The reaction mixture was stirred at RT for 5 h. After completion of the reaction mixture, it was concentrated under reduced pressure. The residue was diluted with DCM (50 mL), neutralized by the addition of saturated aq. sodium bicarbonate (20 mL), and extracted with DCM:15% MeOH (3×20 mL). The organic layer was washed with brine (20 mL), dried over sodium sulphate and concentrated under vacuum to afford 5-(3-amino-pyrrolidin-1-yl)-2-[4-(3-fluoro-phenoxy)-phenoxy]-nicotinamide (0.60 g, 93.0%) as a light brown gum. HPLC: 84.04% purity. MS m/z=409 [M+H]$^+$. $^1$H NMR (400 MHz, DMSO-d6) δ 7.71-7.70 (m, 2H), 7.55-7.54 (d, J=3.1 Hz, 1H), 7.43-7.37 (m, 1H), 7.30-7.29 (d, J=3.2 Hz, 1H), 7.1 (s, 4H), 6.96-6.91 (m, 1H), 6.85-6.78 (m, 2H), 3.6 (s, 1H), 3.42-3.24 (m, 3H), 2.9 (s, 1H), 2.08-1.98 (m, 2H), 1.73-1.68 (m, 1H).

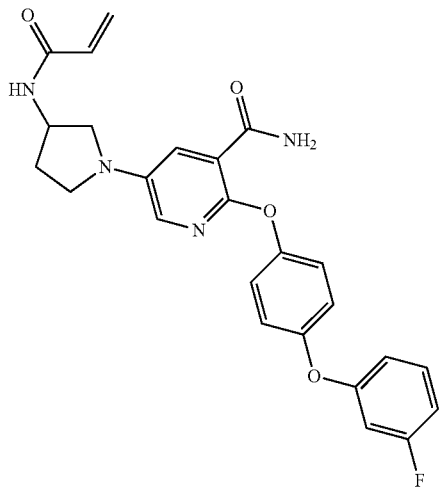 [SMILES: C=CC(=O)NC1CCN(c2cnc(Oc3ccc(Oc4cccc(F)c4)cc3)c(C(N)=O)c2)C1]

5-(3-Acryloylamino-pyrrolidin-1-yl)-2-[4-(3-fluoro-phenoxy)-phenoxy]-nicotinamide (219)

To a stirred solution of 5-(3-amino-pyrrolidin-1-yl)-2-[4-(3-fluoro-phenoxy)-phenoxy]-nicotinamide (300.00 mg; 0.67 mmol; 1.00 eq.) in dry DCM (6.00 ml; 20.00 V) was added N,N-diisopropylethylamine (0.36 ml; 2.02 mmol; 3.00 eq.) dropwise at −10° C. under nitrogen. Stirring was continued at −10° C. for 15 min and then acryloyl chloride (0.05 ml; 0.67 mmol; 1.00 eq.) was added dropwise. The reaction mixture was stirred at −10° C. for another 30 min. After completion of the reaction (monitored by TLC), the reaction was quenched with water (50 mL) and extracted with DCM (3×30 mL). The organic layers were combined, washed with brine (1×20 mL), dried over sodium sulphate and concentrated under vacuum. The crude product was purified by column chromatography over silica gel (60-120 mesh) using DCM:MeOH (9.5:0.5) as an eluent to afford 5-(3-acryloylamino-pyrrolidin-1-yl)-2-[4-(3-fluoro-phenoxy)-phenoxy]-nicotinamide (155.00 mg, 47.6%) as a off-white solid. HPLC: 95.50% purity. MS m/z=463 [M+H]$^+$. $^1$H NMR (400 MHz, DMSO-d6) δ 8.38 (s, 1H), 7.72-7.71 (d, J=2.6 Hz, 2H), 7.60-7.59 (d, J=3.1 Hz, 1H), 7.43-7.35 (m, 2H), 7.09 (s, 4H), 6.97-6.92 (m, 1H), 6.85-6.79 (m, 2H), 6.25-6.18 (m, 1H), 6.12-6.07 (dd, J=17.1, 2.4 Hz, 1H), 5.60-5.57 (dd, J=9.9, 2.4 Hz, 1H), 4.49-4.42 (m, 1H), 3.55-3.51 (m, 1H), 3.43-3.37 (m, 1H), 3.30 (s, 1H), 3.14-3.10 (dd, J=9.82, 4.16 Hz, 1H), 2.26-2.18 (m, 1H), 1.96-1.89 (m, 1H).

Example 214

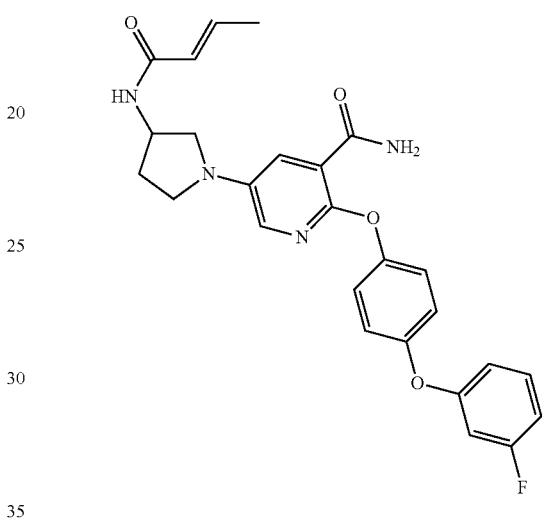

5-[3-((E)-But-2-enoylamino)-pyrrolidin-1-yl]-2-[4-(3-fluoro-phenoxy)-phenoxy]-nicotinamide (221)

To a stirred solution of in dry DCM (10.50 ml; 30.00 V) was added N,N-diisopropylethylamine (0.34 ml; 1.90 mmol; 3.00 eq.) dropwise at −10° C. under nitrogen. Stirring was continued at −10° C. for 15 min and then (E)-but-2-enoyl chloride (0.07 ml; 0.63 mmol; 1.00 eq.) was added. The reaction mixture was then stirred at −10° C. for another 30 min. After completion of the reaction (assessed by TLC), the reaction was quenched with water (50 mL) and extracted with DCM (3×30 mL). The organic layers were combined, washed with brine (1×20 mL), dried over sodium sulphate and concentrated under vacuum. The crude product was purified by column chromatograpy over silica gel (60-120 mesh) using DCM:MeOH (9.1) as an eluent to afford 5-[3-((E)-but-2-enoylamino)-pyrrolidin-1-yl]-2-[4-(3-fluoro-phenoxy)-phenoxy]-nicotinamide (155.00 mg, 49.6%) as an off-white solid. HPLC: 96.26% purity. MS m/z=477 [M+H]$^+$. $^1$H NMR (400 MHz, DMSO-d6) δ 8.17-8.16 (d, J=6.9 Hz, 1H), 7.72 (s, 2H), 7.59-7.58 (d, J=3.1 Hz, 1H), 7.43-7.37 (m, 1H), 7.35-7.34 (d, J=3.1 Hz, 1H), 7.09 (s, 4H), 6.97-6.92 (m, 1H), 6.85-6.79 (m, 2H), 6.65-6.59 (dd, J=11.1, 6.9 Hz, 1H), 5.91-5.87 (dd, J=15.3, 1.6 Hz, 1H), 4.45-4.41 (m, 1H), 3.54-3.50 (m, 1H), 3.40-3.38 (m, 2H), 3.11-3.08 (dd, J=9.78, 4.20 Hz, 1H), 2.22-2.17 (m, 1H), 1.94-1.88 (m, 1H), 1.78-1.76 (dd, J=6.9, 1.5 Hz, 3H).

Example 215

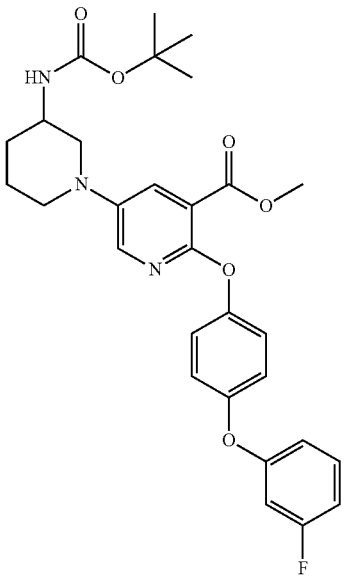 [SMILES: COC(=O)c1cc(N2CCCC(NC(=O)OC(C)(C)C)C2)cnc1Oc1ccc(Oc2cccc(F)c2)cc1]

tert-Butoxycarbonylamino-6'-[4-(3-fluoro-phenoxy)-phenoxy]-3,4,5,6-tetrahydro-2H-[1,3']bipyridinyl-5'-carboxylic acid methyl ester To a stirred solution of 2-[4-(3-fluoro-phenoxy)-phenoxy]-5-iodo-nicotinic acid methyl ester (1.50 g; 2.77 mmol; 1.00 eq.) in 1,4-dioxane (30.00 ml; 20.00 V) were added piperidin-3-yl-carbamic acid tert-butyl ester (0.72 g; 3.33 mmol; 1.20 eq.) and cesium carbonate (1.86 g; 5.55 mmol; 2.00 eq.) at RT under nitrogen atmosphere. The resulting reaction mixture was degassed with nitrogen for 20 min and then treated with dicyclohexyl-(2',6'-diisopropoxy-biphenyl-2-yl)-phosphane (0.07 g; 0.14 mmol; 0.05 eq.) and tris(dibenzylideneacetone)dipalladium(0) (0.26 g; 0.28 mmol; 0.10 eq.). The reaction mixture was heated in a sealed tube to 100° C. for 16 h. Upon completion of the reaction (monitored by TLC), the reaction mixture was cooled to RT and filtered through Celite. The Celite was washed with EtOAc (50 mL). The filtrate was washed with water (lx 50 mL) and brine (1×20 mL), dried over sodium sulphate and concentrated under vacuum. The residue was purified by column chromatograpy over silica gel (60-120 mesh) by using (3:7) EtoAc:Pet ether as an eluent to afford tert-butoxycarbonylamino-6'-[4-(3-fluoro-phenoxy)-phenoxy]-3,4,5,6-tetrahydro-2H-[1,3']bipyridinyl-5'-carboxylic acid methyl ester (1.20 g, 60.3%) as a yellow solid. HPLC: 74.91% purity. MS m/z=538 [M+H]$^+$. $^1$H NMR (400 MHz, DMSO-d6) δ 8.04-8.02 (d, J=4.3 Hz, 2H), 7.77-7.76 (d, J=3.1 Hz, 1H), 7.43-7.37 (m, 1H), 7.09-7.06 (m, 4H), 6.97-6.91 (m, 2H), 6.86-6.79 (m, 2H), 3.8 (s, 3H), 3.54-3.48 (m, 3H), 2.74-2.59 (m, 2H), 1.81-1.72 (m, 1H), 1.6 (s, 1H), 1.4 (s, 9H).

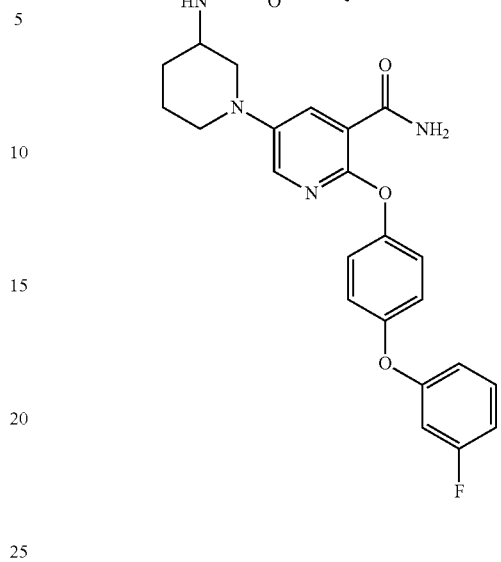

tert-butyl (1-(5-carbamoyl-6-(4-(3-fluorophenoxy)phenoxy)pyridin-3-yl)piperidin-3-yl)carbamate A solution of 3-tert-butoxycarbonylamino-6-[4-(3-fluoro-phenoxy)-phenoxy]-3,4,5,6-tetrahydro-2H-[1,3']bipyridi-nyl-5'-carboxylic acid methyl ester (1.20 g; 1.67 mmol; 1.00 eq.) in methanolic ammonia (20.00 ml; 16.67 V) was heated to 60° C. for 16 h in sealed tube. The reaction monitored by TLC. Upon completion of the reaction, the reaction mixture was concentrated under vacuum to afford tert-butyl (1-(5-carbamoyl-6-(4-(3-fluorophenoxy)phenoxy)pyridin-3-yl)piperidin-3-yl)carbamate (0.90 g, 96.8%) as a yellow solid. HPLC: 94.60% purity. MS m/z=523 [M+H]$^+$. $^1$H NMR (400 MHz, DMSO-d6) δ 7.90-7.89 (d, J=3.1 Hz, 1H), 7.76-7.70 (m, 3H), 7.44-7.38 (m, 1H), 7.16-7.11 (m, 2H), 7.10-7.08 (m, 2H), 6.97-6.90 (m, 2H), 6.87-6.80 (m, 2H), 3.56-3.47 (m, 3H), 2.70-2.65 (m, 1H), 2.57 (s, 1H), 1.81-1.72 (m, 2H), 1.56-1.54 (m, 1H), 1.38 (s, 10H).

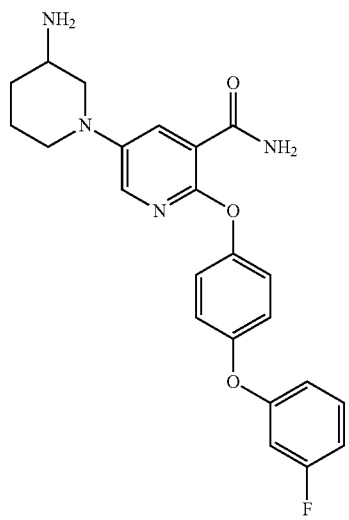 [SMILES: NC(=O)c1cc(N2CCCC(N)C2)cnc1Oc1ccc(Oc2cccc(F)c2)cc1]

3-Amino-6'-[4-(3-fluoro-phenoxy)-phenoxy]-3,4,5,6-tetrahydro-2H-[1,3']bipyridinyl-5'-carboxylic acid amid To a stirred solution of {5'-carbamoyl-6'-[4-(3-fluoro-phenoxy)-phenoxy]-3,4,5,6-tetrahydro-2H-[1,3']bipyridinyl-3-yl}-carbamic acid tert-butyl ester (900.00 mg; 1.62 mmol; 1.00 eq.) in DCM (9.00 ml; 10.00 V) was added 4N HCl in 1,4-dioxane (9.00 ml; 10.00 V) dropwise at RT under nitrogen atmosphere. The reaction mixture was stirred at RT for 5 h. After completion of the reaction, it was concentrated under reduced pressure. The residue was diluted with DCM (50 mL), neutralized by the addition of saturated aq. sodium bicarbonate (20 mL) and extracted with DCM:15% MeOH (3×20 mL). The organic layer was washed with brine (20 mL), dried over sodium sulphate and concentrated under vaccum to afford 3-amino-6'-[4-(3-fluoro-phenoxy)-phenoxy]-3,4,5,6-tetrahydro-2H-[1,3']bipyridinyl-5'-carboxylic acid amide (800.00 mg, 83.4%) light brown gum. LCMS: 71.3% purity. MS m/z=423 [M+H]$^+$.

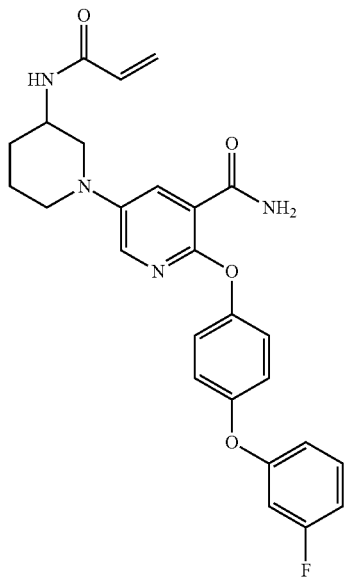 [SMILES: C=CC(=O)NC1CCCN(c2cnc(Oc3ccc(Oc4cccc(F)c4)cc3)c(C(N)=O)c2)C1]

3-Acryloylamino-6'-[4-(3-fluoro-phenoxy)-phenoxy]-3,4,5,6-tetrahydro-2H-[1,3']bipyridinyl-5'-carboxylic acid amide (220)

To a stirred solution of 3-amino-6'-[4-(3-fluoro-phenoxy)-phenoxy]-3,4,5,6-tetrahydro-2H-[1,3']bipyridinyl-5'-carboxylic acid amide (200.00 mg; 0.34 mmol; 1.00 eq.) in dry DCM (6.00 ml; 30.00 V) was added N,N-diisopropylethylamine (0.18 ml; 1.01 mmol; 3.00 eq.) dropwise at −10° C. under nitrogen. Stirring was continued at −10° C. for 15 min and then acryloyl chloride (0.03 ml; 0.37 mmol; 1.10 eq.) was added dropwise. The reaction mixture was stirred at −10° C. for 30 min. After completion of the reaction (monitored by TLC), the reaction was quenched by the addition of water (50 mL) and extracted with DCM (3×30 mL). The organic layers were combined, washed with brine (1×20 mL), dried over sodium sulphate and concentrated under vaccum. The crude product was purified by flash chromatograpy over silica gel (60-120 mesh) using DCM: MeOH (9:1) as an eluent to afford 3-acryloylamino-6'-[4-(3-fluoro-phenoxy)-phenoxy]-3,4,5,6-tetrahydro-2H-[1,3']bipyridinyl-5'-carboxylic acid amide (25.00 mg, 14.9%) as an off-white solid. HPLC: 95.76% purity. MS m/z=477 [M+H]$^+$. $^1$H NMR (400 MHz, DMSO-d6) δ 8.13 (s, 1H), 7.93-7.92 (d, J=3.1 Hz, 1H), 7.75-7.74 (dd, J=9.6, 6.2 Hz, 3H), 7.44-7.38 (m, 1H), 7.16-7.13 (m, 2H), 7.11-7.08 (m, 2H), 6.97-6.93 (m, 1H), 6.87-6.80 (m, 2H), 6.28-6.22 (dd, J=17.1, 10.0 Hz, 1H), 6.12-6.07 (dd, J=17.1, 2.2 Hz, 1H), 5.60-5.57 (dd, J=10.06, 2.28 Hz, 1H), 3.87-3.85 (m, 1H), 3.58-3.54 (m, 1H), 3.48-3.45 (m, 1H), 2.84-2.79 (t, J=9.84 Hz, 1H), 2.67-2.64 (m, 1H), 1.86-1.76 (m, 2H), 1.65-1.56 (m, 1H), 1.46-1.43 (m, 1H).

Example 216

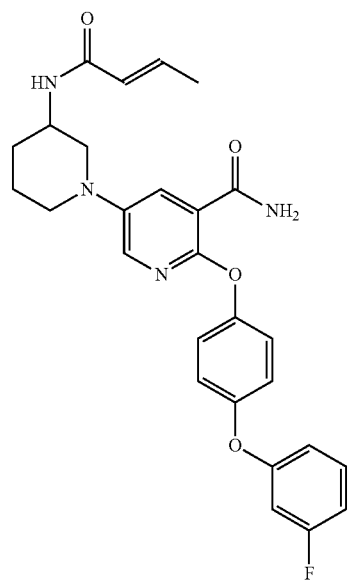 [SMILES: C/C=C/C(=O)NC1CCCN(c2cnc(Oc3ccc(Oc4cccc(F)c4)cc3)c(C(N)=O)c2)C1]

3-((E)-But-2-enoylamino)-6'-[4-(3-fluoro-phenoxy)-phenoxy]-3,4,5,6-tetrahydro-2H-[1,3']bipyridinyl-5'-carboxylic acid amide (222)

To a stirred solution of 3-amino-6'-[4-(3-fluoro-phenoxy)-phenoxy]-3,4,5,6-tetrahydro-2H-[1,3']bipyridinyl-5'-carboxylic acid amide (200.00 mg; 0.38 mmol; 1.00 eq.) in dry DCM (6.00 ml; 30.00 V) was added N,N-diisopropylethylamine (0.20 ml; 1.13 mmol; 3.00 eq.) dropwise at −10° C. under nitrogen. Stirring was continued at −10° C. for 15 min and (E)-but-2-enoyl chloride (39.63 mg; 0.38 mmol; 1.00 eq.) was added dropwise. The reaction mixture was stirred at −10° C. for 30 min. Upon completion of the reaction (monitored by TLC), the reaction was quenched by addition of water (50 mL) and extracted with DCM (3×30 mL). The organic layers were combined, washed with brine (1×20 mL), dried over sodium sulphate and concentrated under vacuum. The crude product was purified by column chromatography over silica gel (60-120 mesh) using DCM: MeOH (9.5:0.5) as an eluent to afford 3-((E)-but-2-enoylamino)-6'-[4-(3-fluoro-phenoxy)-phenoxy]-3,4,5,6-tetrahydro-2H-[1,3']bipyridinyl-5 carboxylic acid amide (50.00 mg, 26.4%) as a off-white solid. HPLC: 97.18% purity. MS m/z=491 [M+H]$^+$. $^1$H NMR (400 MHz, DMSO-d6) δ 7.91-7.89 (d, J=5.0 Hz, 2H), 7.76-7.74 (m, 3H), 7.43-7.37 (m, 1H), 7.16-7.13 (m, 2H), 7.11-7.07 (m, 2H), 6.97-6.96 (d, J=2.0 Hz, 1H), 6.95-6.93 (m, 1H), 6.87-6.80

(m, 2H), 6.62 (dd, J=15.2, 6.9, Hz, 1H), 5.95-5.90 (dd, J=15.3, 1.6 Hz, 1H), 3.83-3.79 (m, 1H), 3.56-3.46 (m, 1H), 2.83-2.77 (m, 1H), 2.67-2.58 (m, 1H), 1.83-1.75 (m, 5H), 1.63-1.55 (m, 1H), 1.44-1.41 (m, 1H).

Example 217

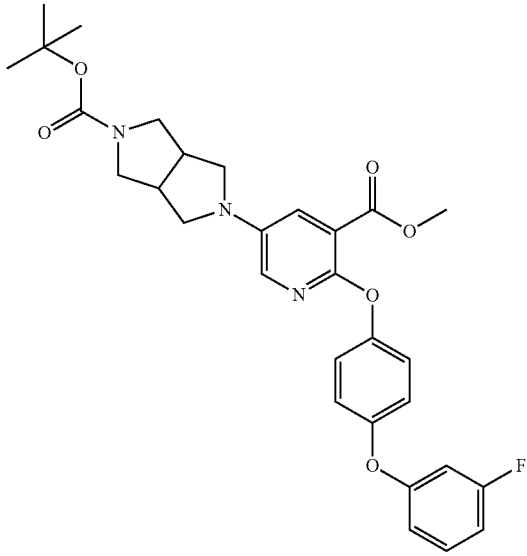 [SMILES: COC(=O)c1cc(N2CC3CN(C(=O)OC(C)(C)C)CC3C2)cnc1Oc1ccc(Oc2cccc(F)c2)cc1]

5-{6-[4-(3-Fluoro-phenoxy)-phenoxy]-5-methoxy-carbonyl-pyridin-3-yl}-hexahydro-pyrrolo[3,4-c]pyrrole-2-carboxylic acid tert-butyl ester To a stirred solution of 2-[4-(3-fluoro-phenoxy)-phenoxy]-5-iodo-nicotinic acid methyl ester (1.50 g; 2.77 mmol; 1.00 eq.) in 1,4-dioxane (30.00 ml; 20.00 V) were added hexahydro-pyrrolo[3,4-c]pyrrole-2-carboxylic acid tert-butyl ester (0.77 g; 3.33 mmol; 1.20 eq.) and cesium carbonate (1.86 g; 5.55 mmol; 2.00 eq.) at RT under nitrogen atmosphere. The resulting reaction mixture was degassed with nitrogen for 20 min and then treated with dicyclohexyl-(2',6'-diisopropoxy-biphenyl-2-yl)-phosphane (0.07 g; 0.14 mmol; 0.05 eq.) and tris(dibenzylideneacetone) dipalladium (0) (0.13 g; 0.14 mmol; 0.05 eq.). The reaction mixture was heated in a sealed tube at 100° C. for 16 h. The reaction progress was assessed by TLC. After completion, the reaction mixture was cooled to RT and filtered through Celite. The Celite bed was washed with EtOAc (50 mL). The filtrate was washed with water (1x 50 mL) and brine (1×20 mL), dried over sodium sulphate and concentrated under vacuum. The residue was purified by column chromatography over silica gel (60-120 mesh) by using (3:7) EtOAc:Pet ether as an eluent to afford 5-{6-[4-(3-fluoro-phenoxy)-phenoxy]-5-methoxycarbonyl-pyridin-3-yl}-hexahydro-pyrrolo[3,4-c] pyrrole-2-carboxylic acid tert-butyl ester (1.20 g, 72.4%) as a light orange solid. HPLC: 80.53% purity. MS m/z=550 [M+H]+. $^1$H NMR (400 MHz, DMSO-d6) δ 7.75-7.43 (m, 1H), 7.40-7.08 (m, 2H), 7.07-6.99 (m, 4H), 6.99-6.91 (m, 1H), 6.84-6.78 (m, 2H), 4.00 (s, 3H), 3.53-3.43 (m, 4H), 3.21-3.15 (m, 4H), 0.00 (s, 9H).

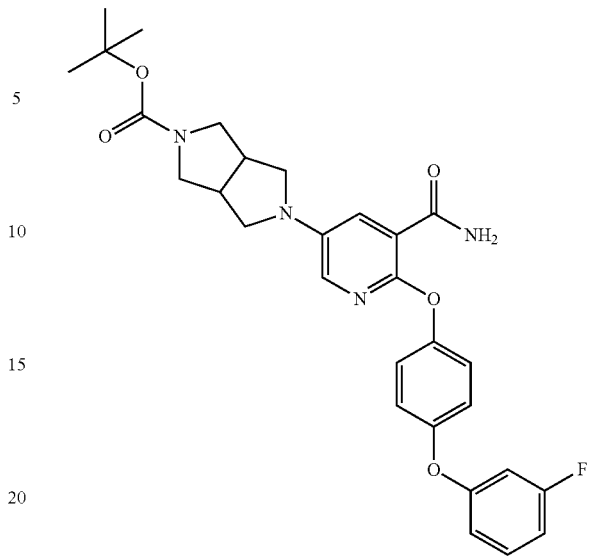

5-{5-Carbamoyl-6-[4-(3-fluoro-phenoxy)-phenoxy]-pyridin-3-yl}-hexahydro-pyrrolo[3,4-c]pyrrole-2-carboxylic acid tert-butyl ester A solution of 5-{6-[4-(3-fluoro-phenoxy)-phenoxy]-5-methoxycarbonyl-pyridin-3-yl}-hexahydro-pyrrolo[3,4-c] pyrrole-2-carboxylic acid tert-butyl ester (1.20 g; 1.99 mmol; 1.00 eq.) in methanolic ammonia (24.00 ml; 20.00 V) was heated at 60° C. for 16 h in a sealed tube. Upon completion of the reaction (monitored by TLC), the reaction mixture was concentrated under vacuum to afford 5-{5-carbamoyl-6-[4-(3-fluoro-phenoxy)-phenoxy]-pyridin-3-yl}-hexahydro-pyrrolo[3,4-c]pyrrole-2-carboxylic acid tert-butyl ester (0.90 g, 79.0%) as a yellow solid. HPLC: 98.70% purity. MS m/z=535.20 [M+H]+. $^1$H NMR (400 MHz, DMSO-d6) δ 7.72 (d, J=2.8 Hz, 2H), 7.59-7.58 (d, J=3.1 Hz, 1H), 7.43-7.36 (m, 2H), 7.08 (s, 4H), 6.96-6.92 (m, 1H), 3.52-3.51 (d, J=4.4 Hz, 2H), 3.45-3.41 (m, 2H), 3.19-3.14 (m, 4H), 1.38 (s, 9H).

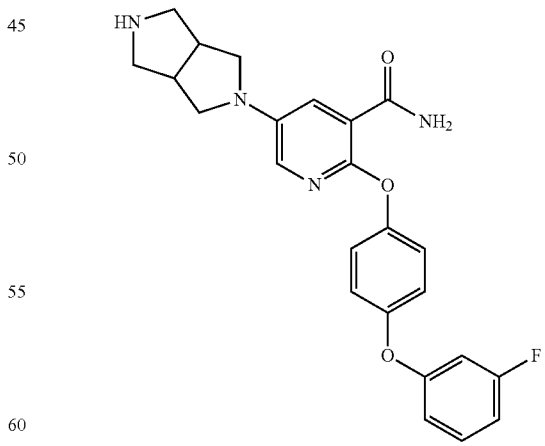

2-[4-(3-Fluoro-phenoxy)-phenoxy]-5-(hexahydro-pyrrolo[3,4-c]pyrrol-2-yl)-nicotinamide To a stirred solution of 5-{5-carbamoyl-6-[4-(3-fluoro-phenoxy)-phenoxy]-pyridin-3-yl}-hexahydro-pyrrolo[3,4- c]pyrrole-2-carboxylic acid tert-butyl ester (0.90 g; 1.57 mmol; 1.00 eq.) in DCM (10.00 ml) was added 4N HCl in 1,4-dioxane (10.00 ml) dropwise at RT under nitrogen atmosphere. The reaction mixture was stirred at RT for 5 h. After completion of the reaction (monitored by TLC), it was concentrated under reduced pressure. The residue was diluted with DCM (50 mL), neutralized with saturated sodium bicarbonate solution (20 mL) and extracted with DCM:15% MeOH (3×20 mL). The organic layer was washed with brine (20 mL), dried over sodium sulphate and concentrated under vacuum to afford 2-[4-(3-fluoro-phenoxy)-phenoxy]-5-(hexahydro-pyrrolo[3,4-c]pyrrol-2-yl)-nicotinamide (0.80 g, 92.2%) as a light brown oil. HPLC: 73.65% purity. MS m/z=435.20 [M+H]$^+$. $^1$H NMR (400 MHz, DMSO-d6) δ 7.72 (bs, 2H) 7.65-7.64 (d, J=3.1 Hz, 1H), 7.44-7.37 (m, 2H), 7.12-7.07 (m, 4H), 6.97-6.92 (m, 1H), 6.85-6.79 (m, 2H), 3.39-3.32 (m, 2H), 3.07-3.04 (m, 2H), 2.96-2.92 (m, 2H), 2.82 (s, 2H), 2.66-2.62 (m, 2H).

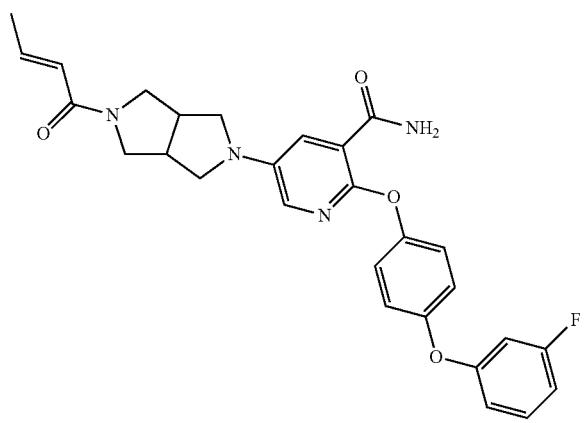 [SMILES: C/C=C/C(=O)N1CC2CN(c3cnc(Oc4ccc(Oc5cccc(F)c5)cc4)c(C(N)=O)c3)CC2C1]

5-[5-((E)-But-2-enoyl)-hexahydro-pyrrolo[3,4-c]pyrrol-2-yl]-2-[4-(3-fluoro-phenoxy)-phenoxy]-nicotinamide (235)

To a stirred solution of 2-[4-(3-fluoro-phenoxy)-phenoxy]-5-(hexahydro-pyrrolo[3,4-c]pyrrol-2-yl)-nicotinamide (400.00 mg; 0.84 mmol; 1.00 eq.) in dry DCM (8.00 ml; 20.00 V) was added N,N-diisopropylethylamine (0.45 ml; 2.53 mmol; 3.00 eq.) dropwise at −10° C. under nitrogen. Stirring was continued at −10° C. for 15 min and then (E)-but-2-enoyl chloride (0.06 ml; 0.67 mmol; 0.80 eq.) was added in dropwise. Stirring was continued at −10° C. for 30 min. After completion of the reaction (monitored by TLC), the reaction was quenched by addition of water (50 mL) and extracted with DCM (3×30 mL). The organic layer was combined, washed with brine (1×20 mL), dried over sodium sulphate and concentrated under vacuum. The crude product was purified by column chromatography over silica gel (60-120 mesh) using DCM:MeOH (9.5:0.5) as an eluent to afford 5-[5-((E)-but-2-enoyl)-hexahydro-pyrrolo[3,4-c]pyrrol-2-yl]-2-[4-(3-fluoro-phenoxy)-phenoxy]-nicotinamide (100.00 mg, 23.2%) as a pale yellow solid. HPLC: 98.44% purity. MS m/z=503.30 [M+H]$^+$. $^1$H NMR (400 MHz, DMSO-d6) δ 7.719-7.711 (d, J=3.0 Hz, 1H), 7.43-7.36 (m, 2H), 7.11-7.06 (m, 4H), 6.96-6.92 (m, 1H), 6.85-6.78 (m, 2H), 6.68-6.63 (m, 1H), 6.26-6.22 (d, J=15.0 Hz, 1H), 3.83-3.78 (m, 1H), 3.66-3.61 (m, 1H), 3.49-3.44 (m, 3H), 3.29 (s, 1H), 3.20-3.17 (m, 2H), 3.11-3.08 (m, 1H), 2.99-2.98 (m, 1H), 1.82-1.80 (m, 3H).

Example 218

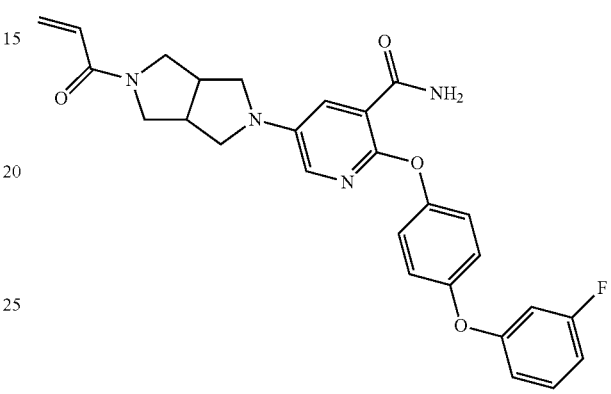

5-(5-Acryloyl-hexahydro-pyrrolo[3,4-c]pyrrol-2-yl)-2-[4-(3-fluoro-phenoxy)-phenoxy]-nicotinamide (238)

To a stirred solution of 2-[4-(3-fluoro-phenoxy)-phenoxy]-5-(hexahydro-pyrrolo[3,4-c]pyrrol-2-yl)-nicotinamide (400.00 mg; 0.66 mmol; 1.00 eq.) in dry DCM (12.00 ml; 30.00 V) was added N,N-diisopropylethylamine (0.35 ml; 1.97 mmol; 3.00 eq.) dropwise at −10° C. under nitrogen. Stirring was continued at −10° C. for 15 min. Acryloyl chloride (0.05 ml; 0.66 mmol; 1.00 eq.) was added dropwise and the reaction mixture was stirred at −10° C. for another 30 min. After completion of the reaction (assessed by TLC), the reaction was quenched with water (50 mL) and extracted with DCM (3×30 mL). The organic layers were combined, washed with brine (1×20 mL), dried over sodium sulphate and concentrated under vacuum. The crude was purified by column chromatography over silica gel (60-120 mesh) by using DCM:MeOH (9.5:0.5) as an eluent to afford 5-(5-acryloyl-hexahydro-pyrrolo[3,4-c]pyrrol-2-yl)-2-[4-(3-fluoro-phenoxy)-phenoxy]-nicotinamide (120.00 mg, 36.7%) as a pale yellow solid. HPLC: 94.57% purity. MS m/z=485.20 [M+H]$^+$. $^1$H NMR (400 MHz, DMSO-d6) δ 7.58-7.57 (d, J=1.2 Hz, 2H), 7.573-7.570 (d, J=1.2 Hz, 1H), 7.40-7.34 (m, 3H), 7.13-6.98 (m, 7H), 6.57-6.50 (dd, J=16.7, 10.3 Hz, 1H), 6.16-6.09 (m, 1H), 5.68-5.62 (m, 1H), 3.69-3.66 (t, J=7.0 Hz, 1H), 3.58-3.48 (m, 2H), 3.38-3.32 (m, 3H), 3.27-3.22 (m, 2H), 2.00-1.94 (m, 3H), 1.90-1.85 (m, 1H).

Example 219

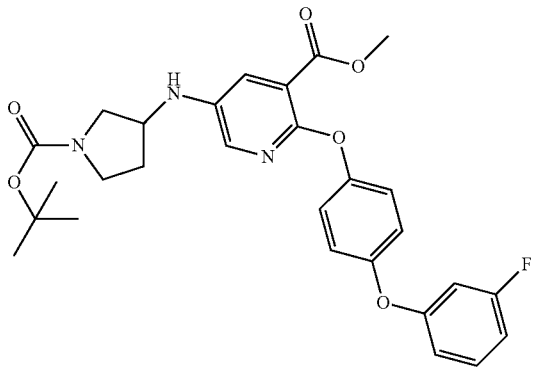 [SMILES: COC(=O)c1cc(NC2CCN(C(=O)OC(C)(C)C)C2)cnc1Oc1ccc(Oc2cccc(F)c2)cc1]

5-(1-tert-Butoxycarbonyl-pyrrolidin-3-ylamino)-2-[4-(3-fluoro-phenoxy)-phenoxy]-nicotinic acid methyl ester To a stirred solution of 2-[4-(3-fluoro-phenoxy)-phenoxy]-5-iodo-nicotinic acid methyl ester (1.50 g; 2.77 mmol; 1.00 eq.) in 1,4-dioxane (22.50 ml; 15.00 V) was added 3-amino-pyrrolidine-1-carboxylic acid tert-butyl ester (0.63 g; 3.33 mmol; 1.20 eq.) at RT under nitrogen atmosphere. The reaction mixture was degassed with nitrogen for 20 min and then treated with dicyclohexyl-(2',4',6'-triisopropoxy-4,6-dimethoxy-biphenyl-2-yl)-phosphane (0.08 g; 0.14 mmol; 0.05 eq.) and tris(dibenzylideneacetone)dipalladium(0) (261.77 mg; 0.28 mmol; 0.10 eq.). The reaction mixture was heated to 100° C. for 16 h. Upon completion of the reaction (monitored by TLC), the reaction mixture was cooled to RT. The reaction was quenched by addition of water (100 mL) and extracted with EtOAc (3×50 mL). The organic layers were combined, washed with brine (1×50 mL), dried over sodium sulphate, and concentrated under vacuum. The residue was purified by column chromatography over silica gel (60-120 mesh) by using 25% EtOAc:Petether as an eluent to afford 5-(1-tert-butoxycarbonyl-pyrrolidin-3-ylamino)-2-[4-(3-fluoro-phenoxy)-phenoxy]-nicotinic acid methyl ester (1.00 g, 67.0%) as a brown semi solid. HPLC 94.57% purity. MS m/z=524.30 [M+H]⁺. ¹H NMR (400 MHz, DMSO-d6) δ 7.77-7.76 (d, J=3.0 Hz, 1H), 7.50-7.37 (m, 2H), 7.07-7.00 (m, 4H), 6.95-6.91 (m, 1H), 6.84-6.78 (m, 2H), 6.20-6.19 (d, J=6.7 Hz, 1H), 4.01 (s, 1H), 3.79 (s, 3H), 3.53 (s, 1H), 3.32 (s, 1H), 3.11-3.06 (m, 2H), 2.11 (s, 1H), 1.76-1.75 (d, J=6.20 Hz, 1H), 1.39 (s, 9H).

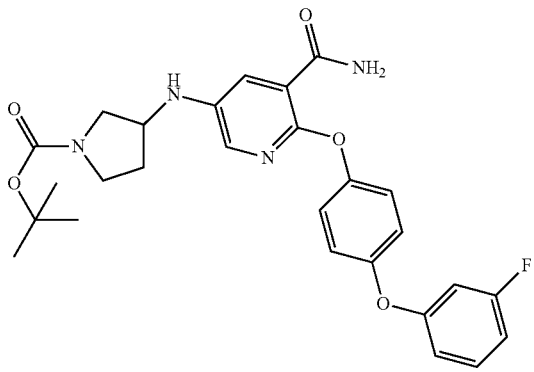 [SMILES: CC(C)(C)OC(=O)N1CCC(Nc2cnc(Oc3ccc(Oc4cccc(F)c4)cc3)c(C(N)=O)c2)C1]

3-{5-Carbamoyl-6-[4-(3-fluoro-phenoxy)-phenoxy]-pyridin-3-ylamino}-pyrrolidine-1-carboxylic acid tert-butyl ester A stirred solution of 5-(1-tert-butoxycarbonyl-pyrrolidin-3-ylamino)-2-[4-(3-fluoro-phenoxy) phenoxy]-nicotinic acid methyl ester (1.00 g; 1.88 mmol; 1.00 eq.) in methanolic ammonia (30.00 ml; 30.00 V) was heated to 60° C. for 16 h in a sealed tube. Upon completion of the reaction, the mixture was concentrated under vacuum to afford 3-{5-carbamoyl-6-[4-(3-fluoro-phenoxy)-phenoxy]-pyridin-3-ylamino}-pyrrolidine-1-carboxylic acid tert-butyl ester (0.80 g, 82.0%; yellow solid. HPLC: 98.16% purity. MS m/z=453 [M+H]+(cleavage of t-Butanol). ¹H NMR (400 MHz, DMSO-d6) δ 7.67-7.62 (m, 2H), 7.62-7.39 (m, 3H), 7.12-7.06 (m, 4H), 6.97-6.92 (m, 1H), 6.84-6.79 (m, 2H), 6.07-6.06 (d, J=6.8 Hz, 1H), 4.72 (s, 1H), 3.38-3.32 (m, 3H), 3.08 (s, 1H), 2.32 (s, 1H), 1.88 (s, 1H), 1.39 (s, 9H).

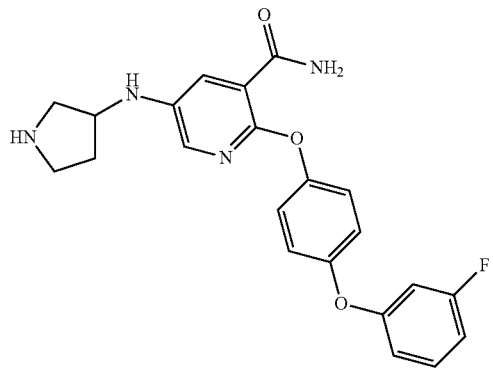 [SMILES: NC(=O)c1cc(NC2CCNC2)cnc1Oc1ccc(Oc2cccc(F)c2)cc1]

2-[4-(3-Fluoro-phenoxy)-phenoxy]-5-(pyrrolidin-3-ylamino)-nicotinamide

To a stirred solution of 3-{5-carbamoyl-6-[4-(3-fluoro-phenoxy)-phenoxy]-pyridin-3-ylamino}-pyrrolidine-1-carboxylic acid tert-butyl ester (800.00 mg; 1.55 mmol; 1.00 eq.) in DCM (10.00 ml) was added 4N HCl in 1,4-dioxane (10.00 ml) dropwise at RT under nitrogen atmosphere. The reaction mixture was stirred at RT for 5 h. After completion of the reaction mixture, it was concentrated under reduced pressure. The residue was diluted with DCM (50 mL), neutralized by the addition of saturated aq. sodium bicarbonate (20 mL), and extracted with DCM:15% MeOH (3×20 mL). The organic layer was washed with brine (20 mL), dried over sodium sulphate and concentrated under vaccum to afford 2-[4-(3-fluoro-phenoxy)-phenoxy]-5-(pyrrolidin-3-ylamino)-nicotinamide (600.00 mg, 76.8%) as a clear colorless liquid. HPLC 65.45% purity. MS m/z=409 [M+H]⁺. ¹H NMR (400 MHz, DMSO-d6) δ 7.67-7.43 (m, 2H), 7.42-7.37 (m, 4H), 7.11-7.08 (m, 5H), 7.06-6.34 (m, 3H), 5.91-5.90 (d, J=6.6 Hz, 1H), 3.85-3.78 (m, 1H), 3.63 (s, 1H), 3.02 (s, 1H), 2.88-2.32 (m, 3H), 1.53-1.52 (d, J=5.1 Hz, 1H).

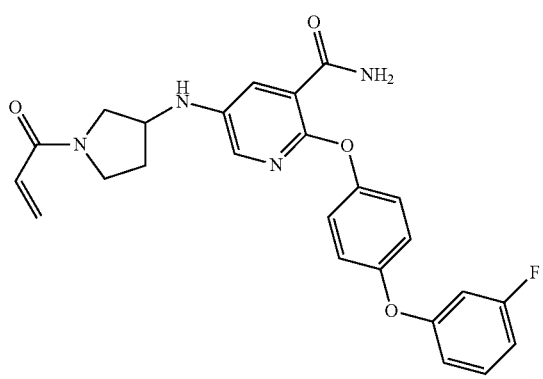 [SMILES: C=CC(=O)N1CCC(Nc2cnc(Oc3ccc(Oc4cccc(F)c4)cc3)c(C(N)=O)c2)C1]

5-(1-Acryloyl-pyrrolidin-3-ylamino)-2-[4-(3-fluoro-phenoxy)-phenoxy]-nicotinamide (253)

To a stirred solution of 2-[4-(3-fluoro-phenoxy)-phenoxy]-5-(pyrrolidin-3-ylamino)-nicotinamide (200.00 mg; 0.45 mmol; 1.00 eq.) in dry DCM (4.00 ml; 20.00 V) was added N,N-diisopropylethylamine (0.24 ml; 1.35 mmol; 3.00 eq.) dropwise at −10° C. under nitrogen. Stirring was continued at −10° C. for 15 min. Acryloyl chloride (0.05 ml; 0.66 mmol; 1.00 eq.) was added dropwise and the reaction mixture was stirred at −10° C. for another 30 min. After completion of the reaction (monitored by TLC), the reaction was quenched by addition of water (50 mL) and extracted with DCM (3×30 mL). The organic layers were combined, washed with brine (1×20 mL), dried over sodium sulphate and concentrated under vacuum. The crude product was purified by column chromatography over silica gel (60-120 mesh) by using DCM:MeOH (9:1) as an eluent to afford 5-(1-acryloyl-pyrrolidin-3-ylamino)-2-[4-(3-fluoro-phenoxy)-phenoxy]-nicotinamide (30.00 mg, 13.8%) as a pale brown solid. HPLC: 95.45% purity. MS m/z=463 [M+H]$^+$. $^1$H NMR (400 MHz, DMSO-d6) δ 7.68-7.47 (m, 3H), 7.46-7.39 (m, 1H), 7.12-7.07 (m, 5H), 6.94 (d, J=2.2 Hz, 1H), 6.85-6.79 (m, 2H), 6.58 (d, J=10.3 Hz, 1H), 6.16-6.08 (m, 2H), 5.66 (t, J=12.8 Hz, 1H), 3.66 (d, J=9.2 Hz, 3H), 3.32-3.15 (m, 2H), 2.49-1.23 (m, 2H).

Example 220

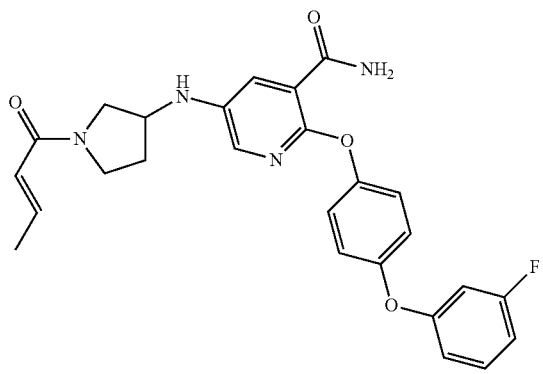 [SMILES: C/C=C/C(=O)N1CCC(Nc2cnc(Oc3ccc(Oc4cccc(F)c4)cc3)c(C(N)=O)c2)C1]

5-[1-((E)-But-2-enoyl)-pyrrolidin-3-ylamino]-2-[4-(3-fluoro-phenoxy)-phenoxy]-nicotinamide (229)

To a stirred solution of 2-[4-(3-fluoro-phenoxy)-phenoxy]-5-(pyrrolidin-3-ylamino)-nicotinamide (500.00 mg; 1.12 mmol; 1.00 eq.) in dry DCM (10.00 ml; 20.00 V) was added N,N-diisopropylethylamine (0.59 ml; 3.36 mmol; 3.00 eq.) dropwise at −10° C. under nitrogen. Stirring was continued for 15 min and then (E)-but-2-enoyl chloride (0.08 ml; 0.90 mmol; 0.80 eq.) was added dropwise. Stirring at −10° C. was continued for 30 min. After completion of the reaction (assessed by TLC), the reaction was quenched with water (50 mL) and extracted with DCM (3×30 mL). The organic layers were combined, washed with brine (1×20 mL), dried over sodium sulphate and concentrated under vacuum. The crude product was purified by column chromatography over silica gel (60-120 mesh) by using DCM:MeOH (9:1) as an eluent to afford 5-[1-((E)-but-2-enoyl)-pyrrolidin-3-ylamino]-2-[4-(3-fluoro-phenoxy)-phenoxy]-nicotinamide (100.00 mg; 0.21 mmol; 18.4%) as a pale brown solid. HPLC: 94.73% purity. MS m/z=477 [M+H]$^+$. $^1$H NMR (400 MHz, DMSO-d6) δ 7.68 (s, 2H), 7.64-7.63 (t, J=2.8 Hz, 1H), 7.47-7.39 (m, 2H), 7.12-7.06 (m, 4H), 6.97-6.92 (m, 1H), 6.85-6.79 (m, 2H), 6.70-6.63 (m, 1H), 6.29-6.25 (d, J=16.3 Hz, 1H), 6.12-6.06 (dd, J=16.7, 6.9 Hz, 1H), 4.06-3.97 (m, 1H), 3.86-3.42 (m, 4H), 2.21-2.07 (m, 1H), 1.91-1.76 (m, 4H).

Example 221

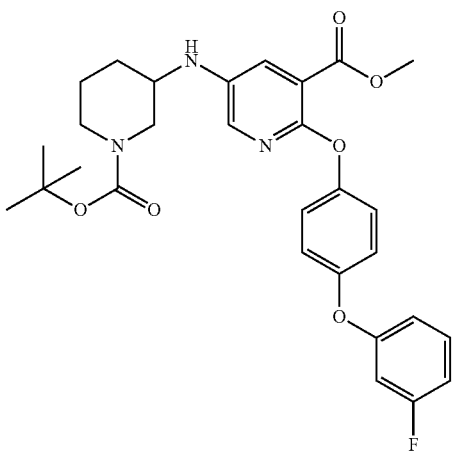 [SMILES: COC(=O)c1cc(NC2CCCN(C(=O)OC(C)(C)C)C2)cnc1Oc1ccc(Oc2cccc(F)c2)cc1]

5-(1-tert-Butoxycarbonyl-piperidin-3-ylamino)-2-[4-(3-fluoro-phenoxy)-phenoxy]-nicotinic acid methyl ester To a stirred solution of 2-[4-(3-fluoro-phenoxy)-phenoxy]-5-iodo-nicotinic acid methyl ester (1.50 g; 2.77 mmol; 1.00 eq.) in 1,4-dioxane (30.00 ml; 20.00 V) were added 3-amino-piperidine-1-carboxylic acid tert-butyl ester (0.72 g; 3.33 mmol; 1.20 eq.) and cesium carbonate (1.86 g; 5.55 mmol; 2.00 eq.) at RT under nitrogen atmosphere. The reaction mixture was degassed with nitrogen for 20 min and then treated with BrettPhos (0.08 g; 0.14 mmol; 0.05 eq.) and tris(dibenzylideneacetone)dipalladium(0) (0.26 g; 0.28 mmol; 0.10 eq.). The reaction mixture was heated in a sealed tube to 100° C. for 16 h. Upon completion of the reaction (monitored by TLC), the reaction mixture was cooled to RT and filtered through Celite. The Celite was then washed with EtOAc (50 mL). The filtrate was washed with water (1x 50 mL) and brine (1×20 mL), dried over sodium sulphate and concentrated under vacuum. The residue was purified by column chromatography over silica gel (60-120 mesh) using (3:7) EtOAc:Petether as an eluent to afford 5-(1-tert-butoxy-carbonyl-piperidin-3-ylamino)-2-[4-(3-fluoro-phenoxy)-phenoxy]-nicotinic acid methyl ester (1.30 g, 73.1%) as a red solid. HPLC: 83.85% purity. MS m/z=552 [M+H]$^+$.

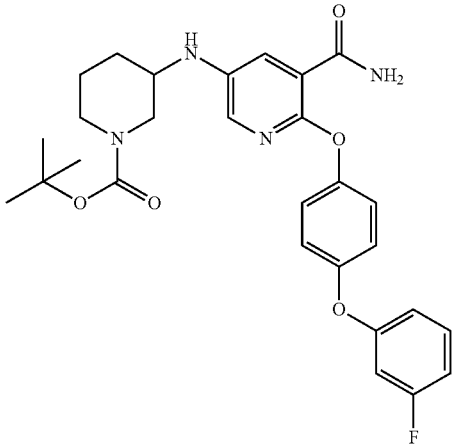 [SMILES: CC(C)(C)OC(=O)N1CCCC(Nc2cnc(Oc3ccc(Oc4cccc(F)c4)cc3)c(C(N)=O)c2)C1]

3-{5-Carbamoyl-6-[4-(3-fluoro-phenoxy)-phenoxy]-pyridin-3-ylamino}-piperidine-1-carboxylic acid tert-butyl ester A solution of 5-(1-tert-butoxycarbonyl-piperidin-3-ylamino)-2-[4-(3-fluoro-phenoxy)-phenoxy]-nicotinic acid methyl ester (1.30 g; 2.19 mmol; 1.00 eq.) in methanolic ammonia (20.00 ml; 407.56 mmol; 15.38 V) was heated to 60° C. for 16 h in a sealed tube. Reaction progress was monitored by TLC. Upon completion of the reaction, the mixture was concentrated under vaccum to afford 3-{5-carbamoyl-6-[4-(3-fluoro-phenoxy)-phenoxy]-pyridin-3-ylamino}-piperidine-1-carboxylic acid tert-butyl ester (1.10 g; 75.1%) as a yellow solid. HPLC: 78.04% purity. MS m/z=523 [M+H]$^+$.

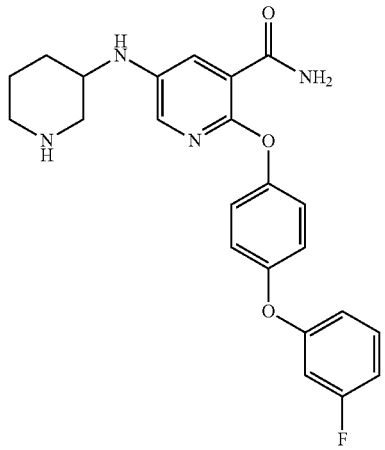 [SMILES: NC(=O)c1cc(NC2CCCNC2)cnc1Oc1ccc(Oc2cccc(F)c2)cc1]

2-[4-(3-Fluoro-phenoxy)-phenoxy]-5-(piperidin-3-ylamino)-nicotinamide)

To a stirred solution of 3-{5-carbamoyl-6-[4-(3-fluoro-phenoxy)-phenoxy]-pyridin-3-ylamino}-piperidine-1-carboxylic acid tert-butyl ester (1.00 g; 1.49 mmol; 1.00 eq.) in DCM (10.00 ml) was added 4N HCl in 1,4-dioxane (10.00 ml) dropwise at RT under nitrogen atmosphere. The reaction mixture was stirred at RT for 5 h. After completion of the reaction (monitored by TLC), it was concentrated under reduced pressure. The residue was diluted with DCM (50 mL), neutralized by the addition of saturated aq. sodium bicarbonate (20 mL) and extracted with DCM:15% MeOH (3×20 mL). The organic layer was washed with brine (20 mL), dried over sodium sulphate and concentrated under vacuum to afford 2-[4-(3-fluoro-phenoxy)-phenoxy]-5-(piperidin-3-ylamino)-nicotinamide (500.00 mg, 52.7%) as a light brown oil. HPLC: 66.40% purity. MS m/z=423.30 [M+H]$^+$.

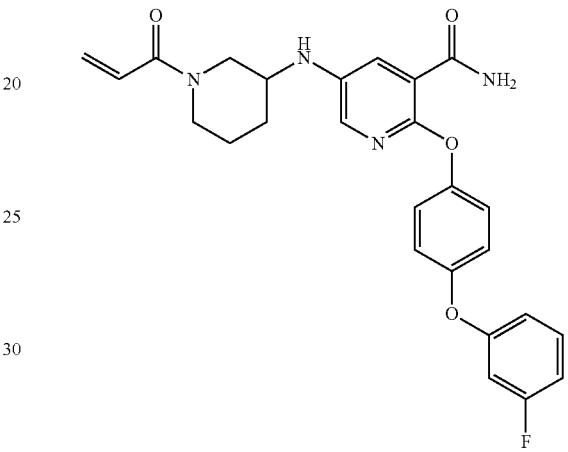

1'-Acryloyl-6-[4-(3-fluoro-phenoxy)-phenoxy]-1',2',3',4',5',6'-hexahydro-[3,3']bipyridinyl-5-carboxylic acid amide (251)

To a stirred solution of 2-[4-(3-fluoro-phenoxy)-phenoxy]-5-(piperidin-3-ylamino)-nicotinamide (200.00 mg; 0.31 mmol; 1.00 eq.) in DCM (10.00 ml; 50.00 V) was added triethylamine (0.17 ml; 0.94 mmol; 3.00 eq.) and acryloyl chloride (0.03 ml; 0.35 mmol; 1.10 eq.). After the addition, the reaction mixture was stirred at RT under nitrogen for 1 h. Reaction progress was monitored by TLC. The reaction was quenched by addition of water (20 mL) and extracted with DCM (2×50 mL). The organic layers were combined, washed with an aq. solution of sodium bicarbonate (10%, 20 mL) and water (10 mL), dried over sodium sulfate and then concentrated under reduced pressure. The crude product was purified by column chromatography over silica gel (230-400 mesh) using (1-2%) methanol in dichloromethane as an eluent. The resulting product fractions were combined and concentrated under vacuum to afford 1'-acryloyl-6-[4-(3-fluoro-phenoxy)-phenoxy]-1',2',3',4',5',6'-hexahydro-[3,3']bipyridinyl-5-carboxylic acid amide (30.00 mg, 20.2%) as a pale yellow solid. HPLC: 96.61% purity. MS m/z=477[M+H]$^+$. $^1$H NMR (400 MHz, DMSO-d6) δ 7.67-7.69 (d, J=17.1 Hz, 3H), 7.48-7.47 (d, J=2.8 Hz, 1H), 7.43-7.37 (m, 1H), 7.10-7.07 (m, 3H), 6.96-6.92 (m, 1H), 6.85-6.59 (m, 3H), 6.12-5.99 (m, 1H), 5.88-5.83 (d, J=17.4 Hz, 1H), 5.68-5.56 (m, 1H), 4.39-3.81 (m, 2H), 3.15 (s, 2H), 2.22 (s, 1H), 1.98 (s, 1H), 1.76 (s, 1H), 1.47-1.43 (m, 2H).

Example 222

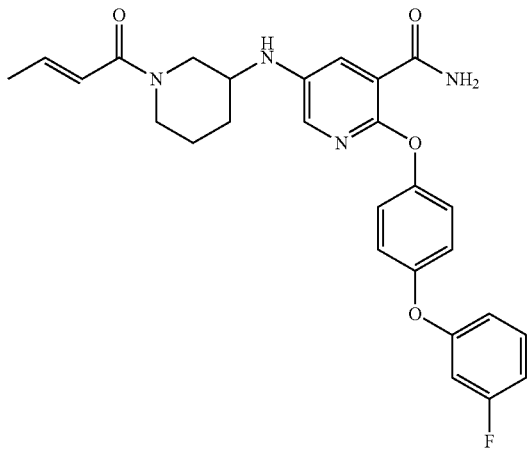 [SMILES: C/C=C/C(=O)N1CCCC(Nc2cnc(Oc3ccc(Oc4cccc(F)c4)cc3)c(C(N)=O)c2)C1]

(E)-5-((1-(but-2-enoyl)piperidin-3-yl)amino)-2-(4-(3-fluorophenoxy)phenoxy)nicotinamide (231)

To a stirred solution of 2-[4-(3-fluoro-phenoxy)-phenoxy]-5-(piperidin-3-ylamino)-nicotinamide (550.00 mg; 0.84 mmol; 1.00 eq.) in dry DCM (16.50 ml; 30.00 V) was added N,N-diisopropylethylamine (0.22 ml; 1.26 mmol; 1.50 eq.) dropwise at −10° C. under nitrogen. The reaction mixture was stirred at −10° C. for 15 min and then treated with (E)-but-2-enoyl chloride (44.33 mg; 0.42 mmol; 0.50 eq.), dropwise. The reaction mixture was then stirred at −10° C. for another 30 min. After completion of the reaction (monitored by TLC and LC/MS), the reaction was quenched by the addition of water (50 mL) and extracted with DCM (3×30 mL). The organic layers were combined, washed with brine (1×20 mL), dried over sodium sulphate and concentrated under vaccum. The crude product was purified by preparative HPLC (SUNFIRE C8 column (30×250), 10 micron; Mobile Phase A: 0.1% TFA in water, Mobile phase B: Acetonitrile; Flow: 20 ml/min). The product fractions were combined and concentrated. The residue was diluted with DCM (25 mL), washed with aq. NaHCO$_3$ solution (20 ml), water and brine, and then dried over Na$_2$SO$_4$. The solvent was concentrated under reduced pressure. The resulting yellow sticky solid was dried using a Genevac evaporator for 12 h to afford 5-[1-((E)-but-2-enoyl)-piperidin-3-ylamino]-2-[4-(3-fluoro-phenoxy)-phenoxy]-nicotinamide (65.00 mg, 15.5%;) as a pale yellow solid). HPLC 98.18% purity. MS m/z=491.20 [M+H]$^+$. $^1$H NMR (400 MHz, DMSO-d6) δ 7.68-7.48 (m, 3H), 7.47-7.37 (m, 2H), 7.13-7.06 (m, 4H), 6.97-6.92 (m, 1H), 6.85-6.79 (m, 2H), 6.68-6.27 (m, 2H), 5.84-5.74 (m, 1H), 4.39-3.80 (m, 2H), 3.17-3.12 (m, 2H), 2.50 (s, 1H), 1.98 (s, 1H), 1.83-1.74 (m, 4H), 1.46-1.39 (m, 2H).

Example 223

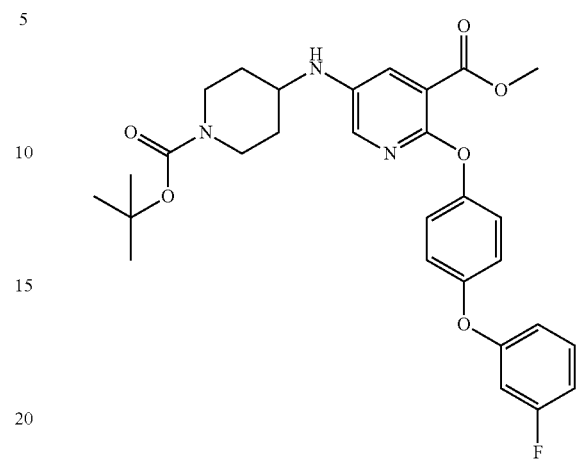

5-(1-tert-Butoxycarbonyl-piperidin-4-ylamino)-2-[4-(3-fluoro-phenoxy)-phenoxy]-nicotinic acid methyl ester To a stirred solution of 2-[4-(3-fluoro-phenoxy)-phenoxy]-5-iodo-nicotinic acid methyl ester (1.50 g; 2.77 mmol; 1.00 eq.) in 1,4-dioxane (22.50 ml; 15.00 V) was added 4-amino-piperidine-1-carboxylic acid tert-butyl ester (0.68 g; 3.33 mmol; 1.20 eq.) at RT under nitrogen atmosphere. The resulting reaction mixture was degassed with nitrogen for 20 min and then treated with dicyclohexyl-(2',4',6'-triisopropoxy-4,6-dimethoxy-biphenyl-2-yl)-phosphane (0.08 g; 0.14 mmol; 0.05 eq.) and tris(dibenzylideneacetone)dipalladium(0) (0.26 g; 0.28 mmol; 0.10 eq.). The reaction mixture was heated to 100° C. for 16 h. After completion of the reaction (as monitored by TLC), the reaction mixture was cooled to RT. The reaction was quenched by the addition of water (100 mL), and extracted with EtOAc (3×50 mL). The organic layers were combined, washed with brine (1×50 mL), dried over sodium sulphate, and concentrated under vacuum. The residue was purified by column chromatography on silica gel (60-120 mesh) using 25% EtOAc:Petether as an eluent to afford 5-(1-tert-butoxycarbonyl-piperidin-4-ylamino)-2-[4-(3-fluoro-phenoxy)-phenoxy]-nicotinic acid methyl ester (850.00 mg, 33.4%) as a brown semi solid. HPLC: 58.60% purity. MS m/z=537.70 [M+H]$^+$. $^1$H NMR (400 MHz, DMSO-d6) δ 7.77 (d, J=3.0 Hz, 1H), 7.49-7.48 (d, J=3.0 Hz, 1H), 7.43-7.37 (m, 1H), 7.07-6.91 (m, 5H), 6.83-6.78 (m, 2H), 5.89-5.87 (d, J=8.2 Hz, 1H), 3.78 (s, 3H), 3.42 (s, 2H), 1.87-1.85 (d, J=9.8 Hz, 2H), 1.39 (s, 9H), 1.25-1.17 (m, 3H).

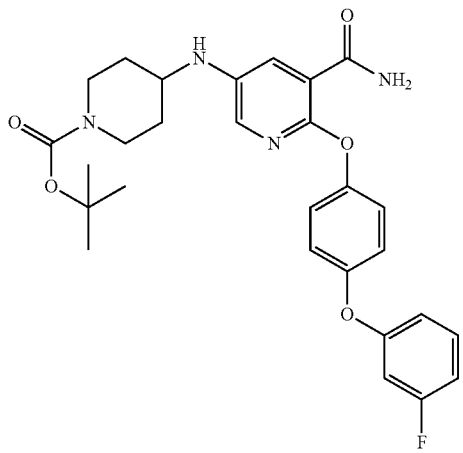 [SMILES: CC(C)(C)OC(=O)N1CCC(Nc2cnc(Oc3ccc(Oc4cccc(F)c4)cc3)c(C(N)=O)c2)CC1]

4-{5-Carbamoyl-6-[4-(3-fluoro-phenoxy)-phenoxy]-pyridin-3-ylamino}-piperidine-1-carboxylic acid tert-butyl ester A solution of 4-{5-carbamoyl-6-[4-(3-fluoro-phenoxy)-phenoxy]-pyridin-3-ylamino}-piperidine-1-carboxylic acid tert-butyl ester (900.00 mg; 0.98 mmol; 1.00 eq.) in methanolic ammonia (12.00 ml; 13.33 V) was heated to 60° C. for 16 h in a sealed tube. Reaction progress was monitored by TLC. After completion of the reaction, the mixture was concentrated under vacuum to afford 4-{5-carbamoyl-6-[4-(3-fluoro-phenoxy)-phenoxy]-pyridin-3-ylamino}-piperidine-1-carboxylic acid tert-butyl ester (600.00 mg, 80.4%). HPLC 68.75% purity. MS m/z=466.70 [M+H]$^+$. $^1$H NMR (400 MHz, DMSO-d6) δ 7.67-7.63 (m, 3H), 7.44-7.37 (m, 2H), 7.11-7.06 (m, 3H), 6.97-6.92 (m, 1H), 6.85-6.78 (m, 1H), 5.75-5.73 (d, J=8.3 Hz, 1H), 3.85-3.82 (d, J=12.7 Hz, 2H), 3.42 (s, 1H), 1.87-1.85 (d, J=10.0 Hz, 1H), 1.39 (s, 9H), 1.23-1.20 (m, 3H).

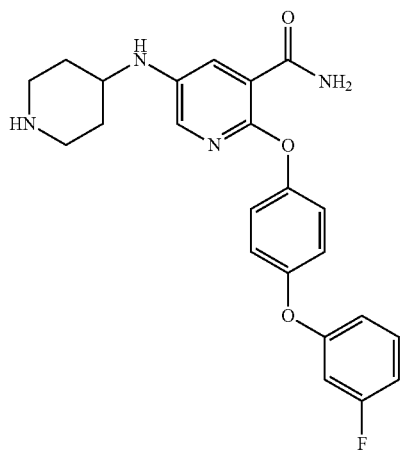 [SMILES: NC(=O)c1cc(NC2CCNCC2)cnc1Oc1ccc(Oc2cccc(F)c2)cc1]

2-[4-(3-Fluoro-phenoxy)-phenoxy]-5-(piperidin-4-ylamino)-nicotinamide

To a stirred solution of 4-{5-carbamoyl-6-[4-(3-fluoro-phenoxy)-phenoxy]-pyridin-3-ylamino}-piperidine-1-carboxylic acid tert-butyl ester (0.60 g; 1.08 mmol; 1.00 eq.) in DCM (6.00 ml; 10.00 V) was added 4N HCl in 1,4-dioxane (6.00 ml; 10.00 V) dropwise at RT under nitrogen atmosphere. The reaction mixture was stirred at RT for 5 h. After completion of the reaction, the mixture was concentrated under reduced pressure. The residue was diluted with DCM (50 mL), neutralized by the addition of saturated sodium bicarbonate (20 mL), and extracted with DCM:15% MeOH (3×20 mL). The organic layer was washed with brine (20 mL), dried over sodium sulphate and concentrated under vaccum to afford 2-[4-(3-fluoro-phenoxy)-phenoxy]-5-(piperidin-4-ylamino)-nicotinamide (0.50 g, 54.8%) as a light brown gum. HPLC: 68.75% purity. MS m/z=423.0 [M+H]$^+$.

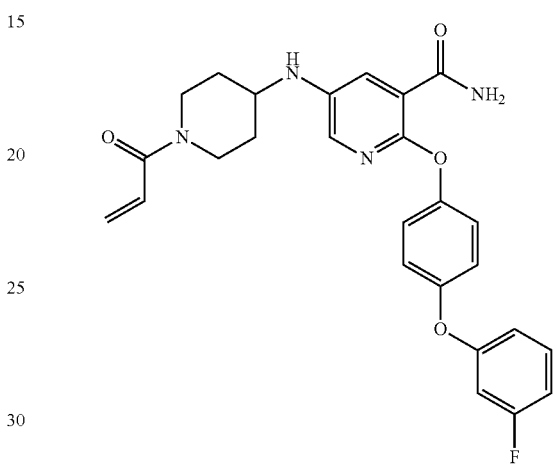

5-(1-Acryloyl-piperidin-4-ylamino)-2-[4-(3-fluoro-phenoxy)-phenoxy]-nicotinamide (228)

To a stirred solution of 2-[4-(3-fluoro-phenoxy)-phenoxy]-5-(piperidin-4-ylamino)-nicotinamide (200.00 mg; 0.24 mmol; 1.00 eq.) in dry DCM (6.00 ml; 30.00 V) was added N, N-diisopropylethylamine (0.13 ml; 0.71 mmol; 3.00 eq.) dropwise at −10° C. under nitrogen. The reaction mixture was stirred at −10° C. for 15 min and then treated with acryloyl chloride (0.02 ml; 0.24 mmol; 1.00 eq.) dropwise. Stirring at −10° C. was continued for 30 min. After completion of the reaction (monitored by TLC and LC/MS), the reaction was quenched by the addition of water (50 mL), and extracted with DCM (3×30 mL). The organic layers were combined, washed with brine (1×20 mL), dried over sodium sulphate, and concentrated under vacuum. The residue was purified by preparative HPLC (SUNFIRE C8 column, (30×250), 10 micron; Mobile Phase A: 0.1% TFA in water, B: Acetonitrile; Flow: 20 ml/min). The product fractions were combined and concentrated. The residue was diluted with DCM (25 mL), washed with aq. NaHCO$_3$ solution (20 ml), water and brine solution, and dried over Na$_2$SO$_4$. The solvent was concentrated under reduced pressure. The resulting yellow sticky solid was dried in a Genevac evaoporator for 12 h to afford 5-(1-acryloyl-piperidin-4-ylamino)-2-[4-(3-fluoro-phenoxy)-phenoxy]-nicotinamide (17.00 mg; 14.7%) as a pale yellow solid. HPLC: 97.08% purity. MS m/z=477 [M+H]$^+$. $^1$H NMR (400 MHz, DMSO-d6) δ 7.67-7.64 (m, 3H), 7.45-7.37 (m, 2H), 7.12-7.06 (m, 4H), 6.96-6.93 (m, J=7.2, 0.7 Hz, 1H), 6.86-6.79 (m, 3H), 6.10-6.06 (dd, J=16.7, 2.4 Hz, 1H), 5.78-5.76 (d, J=8.3 Hz, 1H), 5.67-5.64 (dd, J=10.4, 2.4 Hz, 1H), 4.26-4.23 (d, J=13.1 Hz, 1H), 4.00-3.96 (d, J=14.1 Hz, 1H), 3.56-3.50

(m, 1H), 3.25-3.19 (t, J=11.40 Hz, 1H), 2.94-2.88 (t, J=11.16 Hz, 1H), 1.92 (s, 2H), 1.24 (d, J=13.76 Hz, 2H).

Example 224

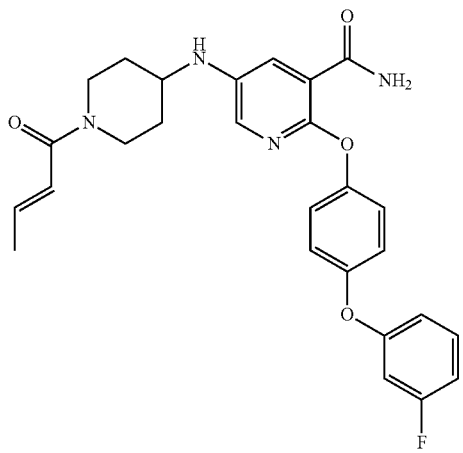 [SMILES: C/C=C/C(=O)N1CCC(Nc2cnc(Oc3ccc(Oc4cccc(F)c4)cc3)c(C(N)=O)c2)CC1]

5-[1-((E)-But-2-enoyl)-piperidin-4-ylamino]-2-[4-(3-fluoro-phenoxy)-phenoxy]-nicotinamide (230)

To a stirred solution of 2-[4-(3-fluoro-phenoxy)-phenoxy]-5-(piperidin-4-ylamino)-nicotinamide (300.00 mg; 0.54 mmol; 1.00 eq.) in dry DCM (9.00 ml; 30.00 V) was added N,N-diisopropylethylamine (0.29 ml; 1.62 mmol; 3.00 eq.) dropwise at −10° C. under nitrogen. Stirring at −10° C. was continued for 15 min and then (E)-But-2-enoyl chloride (56.91 mg; 0.54 mmol; 1.00 eq.) was added dropwise. The reaction mixture was stirred at −10° C. for another 30 min. After completion of the reaction (monitored by TLC), the reaction was quenched by the addition of water (50 mL), and extracted with DCM (3×30 mL). The organic layers were combined, washed with brine (1×20 mL), dried over sodium sulphate and concentrated under vacuum. The crude product was subjected to preparative HPLC (SUNFIRE C8 column (30×250), 10 micron; Mobile PhaseA: 0.1% TFA in water; Mobile Phase B: Acetonitrile; Flow: 20 ml/min). The product fractions were combined and concentrated. The residue was diluted with DCM (25 mL), washed with aq. NaHCO₃ solution (20 ml), water and brine solution, and then dried over Na₂SO₄. The solvent was evaporated under reduced pressure. The resulting yellow sticky solid was dried in a Genevac evaporator for 12 h) to afford 5-[1-((E)-but-2-enoyl)-piperidin-4-ylamino]-2-[4-(3-fluoro-phenoxy)-phenoxy]-nicotinamide (15.00 mg, 5.6%) as a pale yellow solid. HPLC 97.99% purity. MS m/z=491 [M+H]⁺. 1H NMR (400 MHz, DMSO-d6) δ 7.66-7.64 (m, 3H), 7.45-7.39 (m, 2H), 7.12-7.06 (m, 4H), 6.96-6.92 (m, 1H), 6.85-6.78 (m, 2H), 6.68-6.63 (m, 1H), 6.53-6.49 (dd, J=14.9, 1.6 Hz, 1H), 5.77-5.75 (d, J=8.3, Hz, 1H), 4.24-4.22 (d, J=11.4 Hz, 1H), 3.99-3.96 (d, J=12.5 Hz, 1H), 3.52-3.49 (d, J=8.36 Hz, 1H), 3.18 (s, 1H), 2.90-2.84 (m, 1H), 1.91 (s, 2H), 1.84-1.82 (m, 2H), 1.2 (s, 3H).

Example 225

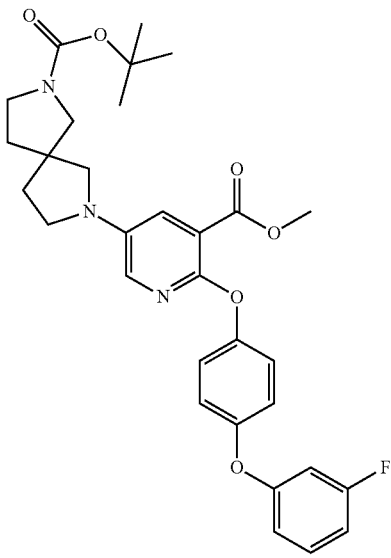 [SMILES: COC(=O)c1cc(N2CCC3(CCN(C(=O)OC(C)(C)C)C3)C2)cnc1Oc1ccc(Oc2cccc(F)c2)cc1]

tert-butyl 7-(6-(4-(3-fluorophenoxy)phenoxy)-5-(methoxycarbonyl)pyridin-3-yl)-2,7-diazaspiro[4.4]nonane-2-carboxylate To a stirred solution of 2-[4-(3-fluoro-phenoxy)-phenoxy]-5-iodo-nicotinic acid methyl ester (1.50 g; 2.77 mmol; 1.00 eq.) in 1,4-dioxane (30.00 ml; 20.00 V) were added 2,7-diaza-spiro[4.4]nonane-2-carboxylic acid tert-butyl ester (0.82 g; 3.33 mmol; 1.20 eq.) and cesium carbonate (1.86 g; 5.55 mmol; 2.00 eq.) at RT under nitrogen atmosphere. The resulting reaction mixture was degassed with nitrogen for 20 min and then treated with dicyclohexyl-(2′,6′-diisopropoxy-biphenyl-2-yl)-phosphane (0.07 g; 0.14 mmol; 0.05 eq.) and tris(dibenzylideneacetone)dipalladium (0) (0.13 g; 0.14 mmol; 0.05 eq.). The reaction mixture was heated in sealed tube at 100° C. for 16 h. Upon reaction completion (monitored by TLC), the mixture was cooled to RT, and filtered through Celite. The Celite bed was washed with EtOAc (50 mL). The filtrate was washed with water (1x 50 mL) and brine (1×20 mL), dried over sodium sulphate and concentrated under vacuum. The residue was purified by column chromatography over silica gel (60-120 mesh) by using (3:7) EtOAc:Pet ether as an eluent to afford 7-{6-[4-(3-fluoro-phenoxy)-phenoxy]-5-methoxycarbonyl-pyridin-3-yl}-2,7-diaza-spiro[4.4]nonane-2-carboxylic acid tert-butyl ester (0.70 g; 26.8%) as a brown semi solid. HPLC: 59.74% purity. MS: m/z=563.70 [M+H]⁺.

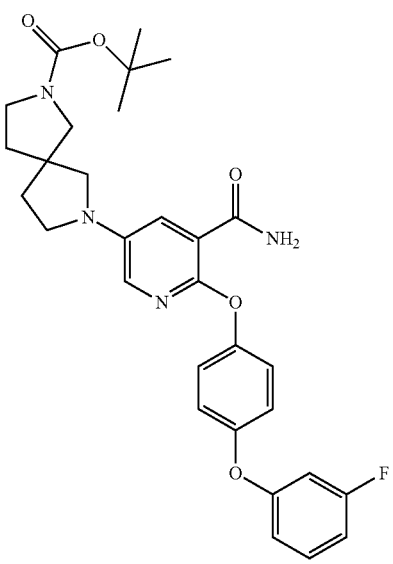 [SMILES: CC(C)(C)OC(=O)N1CCC2(CCN(c3cnc(Oc4ccc(Oc5cccc(F)c5)cc4)c(C(N)=O)c3)C2)C1]

tert-butyl 7-(5-carbamoyl-6-(4-(3-fluorophenoxy) phenoxy)pyridin-3-yl)-2,7-diazaspiro[4.4] nonane-2-carboxylate A solution of 7-{6-[4-(3-Fluoro-phenoxy)-phenoxy]-5-methoxycarbonyl-pyridin-3-yl}-2,7-diaza-spiro[4.4]nonane-2-carboxylic acid tert-butyl ester (0.70 g; 0.74 mmol; 1.00 eq.) in methanolic ammonia (14.00 ml; 20.00 V) was heated at 60° C. for 16 h in sealed tube. Reaction progress was monitored by TLC. After completion of the reaction, the mixture was concentrated under vacuum to afford 7-{5-carbamoyl-6-[4-(3-fluoro-phenoxy)-phenoxy]-pyridin-3-yl}-2,7-diaza-spiro[4.4]nonane-2-carboxylic acid tert-butyl ester (0.50 g; 99.6%) as a yellow solid. HPLC: 81.12% purity. MS: m/z=493.70 [M+H]+. ¹H NMR (400 MHz, DMSO-d6) δ 7.58 (bs, 1H), 7.57-7.37 (m, 1H), 7.34-7.30 (m, 1H), 7.08 (s, 4H), 6.96-6.92 (m, 1H), 6.82-6.78 (m, 2H), 3.36-3.32 (m, 4H), 3.22-3.20 (m, 4H), 1.98-1.93 (m, 2H), 1.87-1.84 (m, 2H), 1.38 (s, 9H).

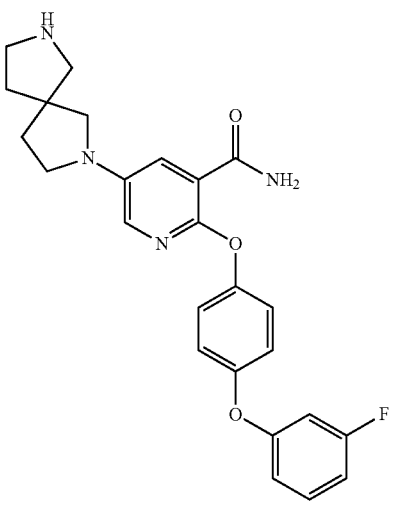 [SMILES: NC(=O)c1cc(N2CCC3(CCNC3)C2)cnc1Oc1ccc(Oc2cccc(F)c2)cc1]

2-(4-(3-Fluorophenoxy)phenoxy)-5-(2,7-diazaspiro [4.4]nonan-2-yl)nicotinamide

To a stirred solution of 7-{5-carbamoyl-6-[4-(3-fluoro-phenoxy)-phenoxy]-pyridin-3-yl}-2,7-diaza-spiro[4.4]nonane-2-carboxylic acid tert-butyl ester (400.00 mg; 0.69 mmol; 1.00 eq.) in DCM (10.00 ml) was added 4N HCl in 1,4-dioxane (10.00 ml) dropwise at RT under nitrogen atmosphere. The reaction mixture was stirred at RT for 5 h. After completion of the reaction (monitored by TLC), the mixture was concentrated under reduced pressure. The residue was diluted with DCM (50 mL), neutralized by the addition of saturated aqueous sodium bicarbonate solution (20 mL) and extracted with DCM:15% MeOH (3×20 mL). The organic layer was washed with brine (20 mL), dried over sodium sulphate and concentrated under vacuum. The crude product was purified by column chromatograpy over silica gel (60-120 mesh) by using DCM:MeOH (9.5:0.5) as an eluent to afford 5-(2,7-diaza-spiro[4.4]non-2-yl)-2-[4-(3-fluoro-phenoxy)-phenoxy]-nicotinamide (0.30 g; 44.4%; light brown oil). HPLC: 45.50% purity. MS: m/z=449.30 [M+H]+.

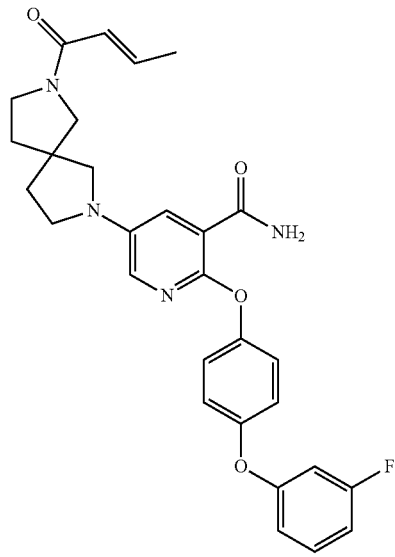 [SMILES: C/C=C/C(=O)N1CCC2(CCN(c3cnc(Oc4ccc(Oc5cccc(F)c5)cc4)c(C(N)=O)c3)C2)C1]

(E)-5-(7-(but-2-enoyl)-2,7-diazaspiro[4.4]nonan-2-yl)-2-(4-(3-fluorophenoxy) phenoxy) nicotinamide (232)

To a stirred solution of 5-(2,7-diaza-spiro[4.4]non-2-yl)-2-[4-(3-fluoro-phenoxy)-phenoxy]-nicotinamide (150.00 mg; 0.15 mmol; 1.00 eq.) in dry DCM (3.00 ml; 20.00 V) was added N,N-diisopropylethylamine (0.04 ml; 0.23 mmol; 1.50 eq.) dropwise at −10° C. under nitrogen. Stirring was maintained at −10° C. for 15 min and then (E)-but-2-enoyl chloride (0.01 ml; 0.08 mmol; 0.50 eq) was added in dropwise. Stirring was continued at −10° C. for 30 min. After completion of the reaction (monitored by TLC), the reaction was quenched by the addition of water (50 mL) and extracted with DCM (3×30 mL). The organic layers were combined, washed with brine (1×20 mL), dried over sodium sulphate and concentrated under vacuum. The crude product was purified by preparative HPLC (SUNFIRE C8 column (30×250), 10 micron; Mobile PhaseA: 0.1% TFA in water, Mobile Phase B: Acetonitrile; Flow: 20 ml/min). The product fractions were concentrated and the residue was diluted with DCM (25 mL). The DCM solution was washed with aq. NaHCO₃ solution (20 ml), water and brine solution, and then dried over Na₂SO₄. The solvent was evaporated under reduced pressure. The resulting yellow sticky solid was dried in a Genevac evaporator for 12 h to afford 5-[7-((E)-but-2-enoyl)-2,7-diaza-spiro[4.4]non-2-yl]-2-[4-(3-fluoro-phenoxy)-phenoxy]-nicotinamide (15.00 mg; 18.8%) as a pale yellow solid. HPLC: 99.70% purity MS: m/z=517.30 [M+H]⁺) ¹H NMR (400 MHz, DMSO-d6) δ 7.71 (s, 2H), 7.58-7.57 (t, J=2.8 Hz, 1H), 7.43-7.37 (m, 1H), 7.35-7.33 (m, 1H), 7.08 (s, 4H), 6.96-6.92 (m, 1H), 6.85-6.78 (m, 1H), 6.70-6.63 (m, 1H), 6.29-6.21 (m, 1H), 3.65-3.62 (t, J=7.0 Hz, 1H), 3.52-3.45 (m, 3H), 3.38-3.32 (m, 2H), 3.26-3.22 (m, 3H), 1.97-1.94 (m, 3H), 1.89-1.79 (m, 4H).

Example 226

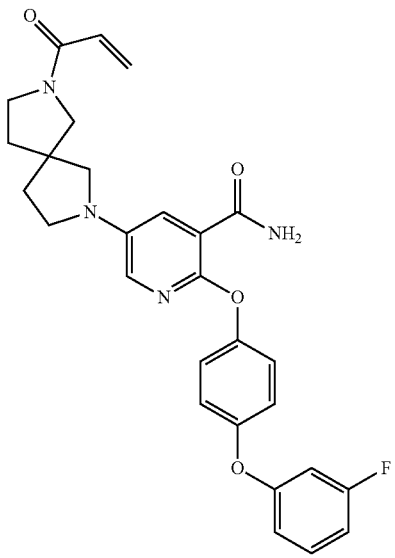 [SMILES: C=CC(=O)N1CCC2(CCN(c3cnc(Oc4ccc(Oc5cccc(F)c5)cc4)c(C(N)=O)c3)C2)C1]

5-(7-acryloyl-2,7-diazaspiro[4.4]nonan-2-yl)-2-(4-(3-fluorophenoxy)phenoxy)nicotinamide (233)

To a stirred solution of 5-(2,7-diaza-spiro[4.4]non-2-yl)-2-[4-(3-fluoro-phenoxy)-phenoxy]-nicotinamide (150.00 mg; 0.15 mmol; 1.00 eq.) in dry DCM (3.00 ml; 20.00 V) was added N,N-diisopropylethylamine (0.04 ml; 0.23 mmol; 1.50 eq.) dropwise at −10° C. under nitrogen. The reaction mixture was stirred at −10° C. for 15 min and then treated with acryloyl chloride (0.01 ml; 0.08 mmol; 0.50 eq.) dropwise. Stirring at −10° C. was continued for 30 min. After completion of the reaction (monitored by TLC and LC/MS), the reaction mixture was quenched by the addition of water (50 mL) and extracted with DCM (3×30 mL). The organic layers were combined, washed with brine (1×20 mL), dried over sodium sulphate and concentrated under vacuum. The crude product was purified by preparative HPLC (SUNFIRE C8 column (30×250), 10 micron; Mobile PhaseA: 0.1% TFA in water, Mobile Phase B: Acetonitrile; Flow: 20 ml/min). The product fractions were combined and concentrated. The residue was diluted with DCM (25 mL), washed with aq. NaHCO₃ solution (20 ml), water and brine, and then dried over Na₂SO₄. The solvent was then evaporated under reduced pressure. The resulting yellow sticky solid was dried in a Geneva evaporator for 12 h to afford 5-(7-acryloyl-2,7-diaza-spiro[4.4]non-2-yl)-2-[4-(3-fluoro-phenoxy)-phenoxy]-nicotinamide (15.00 mg) as a pale yellow solid. HPLC: 98.06% purity. MS: m/z=503.30 [M+H]⁺. ¹H NMR (400 MHz, DMSO-d6) δ 7.58-7.57 (dd, J=3.0, 1.2, Hz, 1H), 7.43-7.34 (m, 2H), 7.08 (s, 4H), 6.96-6.92 (m, 1H), 6.85-6.78 (m, 2H), 6.62-6.51 (m, 1H), 6.16-6.09 (m, 1H), 5.68-5.62 (m, 1H), 3.69-3.66 (t, J=7.1 Hz, 1H), 3.58-3.48 (m, 2H), 3.44-3.23 (m, 5H), 2.00-1.95 (m, 3H), 1.90-1.85 (m, 1H).

Example 227

Scheme 19

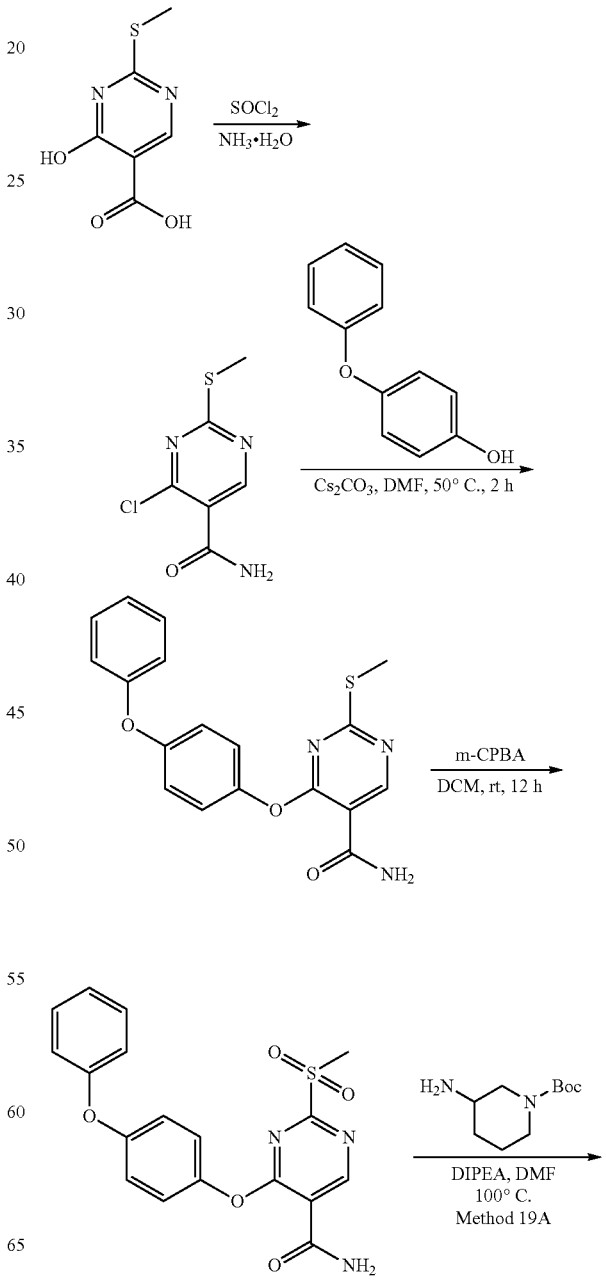

429

-continued

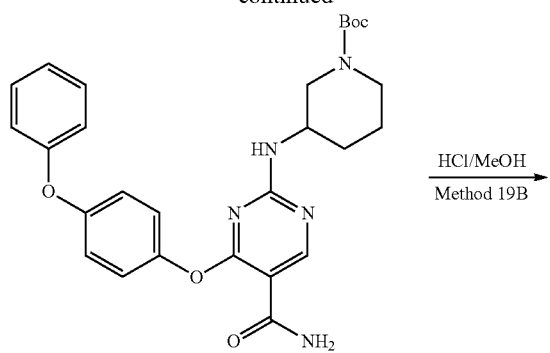

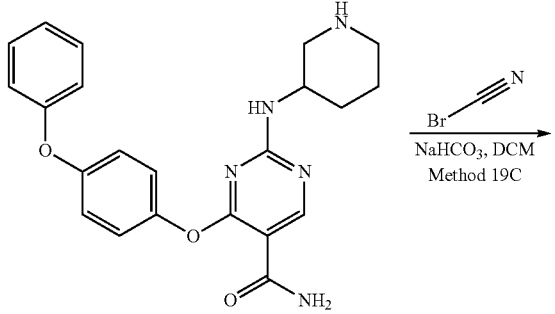

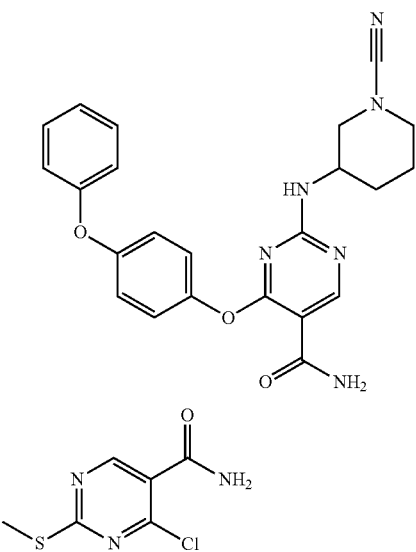

4-chloro-2-(methylsulfanyl)pyrimidine-5-carboxamide)

In a 250 mL round bottom flask with magnetic stir bar, 4-hydroxy-2-(methylsulfanyl)pyrimidine-5-carboxylic acid (12 g, 64.45 mmol, 1.00 eq.) was suspended in thionyl chloride (120 mL). The resulting solution was stirred for 18 h at 80° C., and then concentrated under reduced pressure to afford the acid chloride intermediate.

The acid chloride prepared above was dissolved in dioxane (10 mL), which was added dropwise to NH₃·H₂O (100 mL) slowly at 0° C. Precipitation happened, and then the solids were collected by filtration and the solid was dried in a IR dryer to yield 8 g (61%) of 4-chloro-2-(methylsulfanyl)pyrimidine-5-carboxamide as a white solid.

430

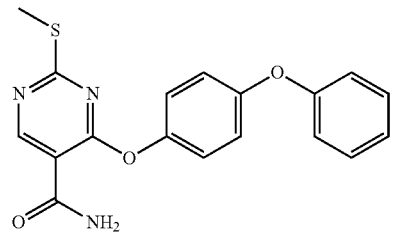 [SMILES: CSc1ncc(C(N)=O)c(Oc2ccc(Oc3ccccc3)cc2)n1]

2-(methylsulfanyl)-4-(4-phenoxyphenoxy)pyrimidine-5-carboxamide

In a 100 mL round bottom flask with magnetic stir bar, 4-chloro-2-(methylsulfanyl)pyrimidine-5-carboxamide (4.50 g, 22.10 mmol, 1.00 eq.) was dissolved in 45 mL N,N-dimethylformamide. To the stirring solution were added 4-phenoxyphenol (4.11 g, 22.07 mmol, 1.00 eq.) and Cs₂CO₃ (14.40 g, 44.20 mmol, 2.00 eq.) at RT. The resulting solution was stirred for 3 h at 50° C. The reaction was then quenched by the addition of 50 mL of water and the mixture was extracted with ethyl acetate (3×50 mL). The organic layers were combined, dried over anhydrous sodium sulfate and concentrated under reduced pressure. The residue was purified in a silica gel column eluting with methanol in dichloromethane (1% to 15% gradient) to afford 3 g (38%) of 2-(methylsulfanyl)-4-(4-phenoxyphenoxy)pyrimidine-5-carboxamide as a white solid.

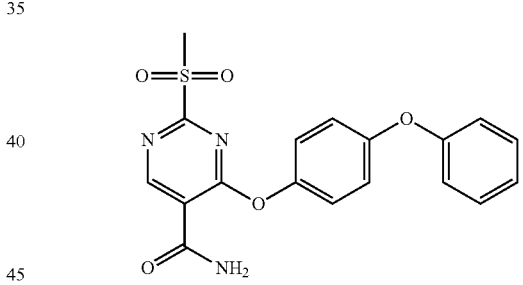

2-methanesulfonyl-4-(4-phenoxyphenoxy)pyrimidine-5-carboxamide

In a 250 mL round-bottom flask with magnetic stir bar, 2-(methylsulfanyl)-4-(4-phenoxyphenoxy)pyrimidine-5-carboxamide (2.00 g, 5.66 mmol, 1.00 eq.) was dissolved in 200 mL dichloromethane. To the stirring solution was added mCPBA (2.44 g, 14.14 mmol, 2.50 eq.) at 0° C. The reaction mixture was stirred at room temperature for 16 h. The reaction was quenched by the addition of sodium bicarbonate solution (100 mL) and the mixture was extracted with ethyl acetate (3×100 mL). The organic layers were combined, dried over anhydrous sodium sulfate and concentrated under reduced pressure to afford 2 g (92%, crude yield) of 2-methanesulfonyl-4-(4-phenoxyphenoxy)pyrimidine-5-carboxamide as a white solid.

Method 19A

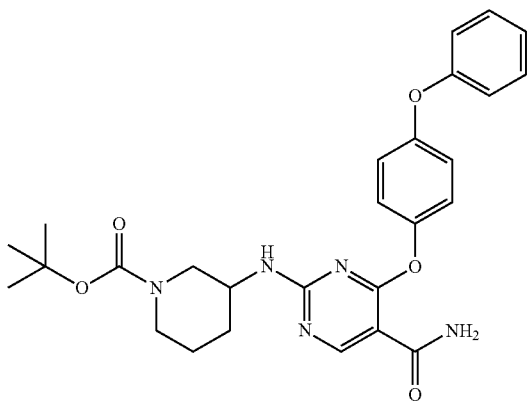 [SMILES: CC(C)(C)OC(=O)N1CCCC(Nc2ncc(C(N)=O)c(Oc3ccc(Oc4ccccc4)cc3)n2)C1]

tert-butyl 3-[[5-carbamoyl-4-(4-phenoxyphenoxy)pyrimidin-2-yl]amino]piperidine-1-carboxylate In a 50 mL round-bottom flask with magnetic stir bar, 2-methanesulfonyl-4-(4-phenoxyphenoxy)pyrimidine-5-carboxamide (500 mg, 1.3 mmol, 1.00 eq.) was dissolved in 10 mL N,N-dimethylformamide. To the stirring solution were added tert-butyl 3-aminopiperidine-1-carboxylate (390 mg, 1.9 mmol, 1.50 eq.) and DIEA (260 mg, 2.0 mmol, 1.60 eq.) at RT. The resulting solution was stirred for 2 h at 100° C. The reaction was then quenched by the addition of 10 mL water and the mixture was extracted with ethyl acetate (3×20 mL). The organic layers were combined, dried over anhydrous sodium sulfate and concentrated under reduced pressure. The residue was purified in a silica gel column eluting with methanol in dichloromethane (1% to 15% gradient) to afford 463 mg (61% for 2 steps) of tert-butyl 3-[[5-carbamoyl-4-(4-phenoxyphenoxy)pyrimidin-2-yl]amino]piperidine-1-carboxylate as a yellow solid.

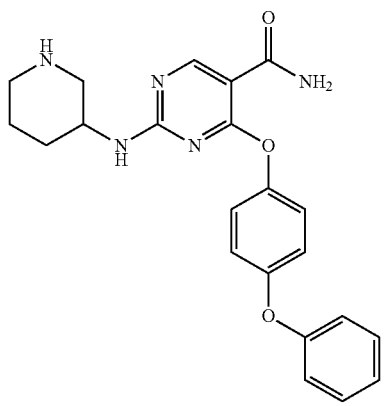 [SMILES: NC(=O)c1cnc(NC2CCCNC2)nc1Oc1ccc(Oc2ccccc2)cc1]

Method 19B 4-(4-phenoxyphenoxy)-2-[(piperidin-3-yl)amino]pyrimidine-5-carboxamide In a 25 mL round bottom flask with magnetic stir bar, tert-butyl 3-[[5-carbamoyl-4-(4-phenoxyphenoxy)pyrimidin-2-yl]amino]piperidine-1-carboxylate (140 mg, 0.28 mmol, 1.00 eq.) was dissolved in a solution of HCl in methanol (4N, 10 mL). The resulting mixture was stirred for 2 h at RT. The solvent was removed under reduced pressure to afford 120 mg (crude yield) of 4-(4-phenoxyphenoxy)-2-[(piperidin-3-yl)amino]pyrimidine-5-carboxamide as a yellow solid.

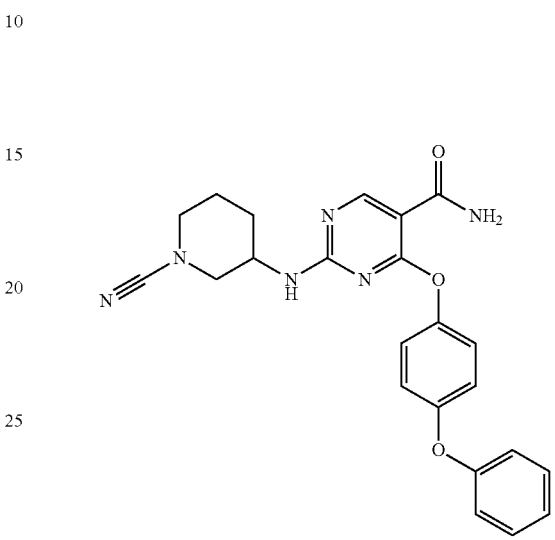

Method 19C

2-[(1-cyanopiperidin-3-yl)amino]-4-(4-phenoxyphenoxy)pyrimidine-5-carboxamide (239)

In a 25 mL round bottom flask with magnetic stir bar, 4-(4-phenoxyphenoxy)-2-[(piperidin-3-yl)amino]pyrimidine-5-carboxamide (50 mg, 0.12 mmol, 1.00 eq.) was dissolved in dichloromethane (4 mL) and water (1 mL), To the stirring solution were added cyanogen bromide (19.6 mg, 0.19 mmol, 1.50 eq.) and sodium bicarbonate (41 mg, 0.49 mmol, 4.00 eq.) at RT. The resulting mixture was stirred for 2 h at RT. The reaction mixture was then extracted with dichloromethane (3×5 mL) and the organic layers were combined, dried over anhydrous sodium sulfate and concentrated under reduced pressure. The residue (60 mg) was purified via prep-HPLC: column: XBridge Prep C18 OBD, 19×150 mm, 5um; mobile phases: MeCN in water (with 10 mM $NH_4HCO_3$); method: 30% to 75% gradient in 8 min. The product fractions were combined and lyophilized to afford 40 mg (75%) of 2-[(1-cyanopiperidin-3-yl)amino]-4-(4-phenoxyphenoxy)pyrimidine-5-carboxamide as a off-white solid. HPLC: 99.3% purity. MS: m/z=431.1 [M+H]+. VT $^1$H NMR (300 MHz, DMSO-d6, 353K, ppm): δ 8.68 (s, 1H), 7.41-7.35 (m, 3H), 7.29-7.23 (m, 2H), 7.15-7.02 (m, 7H), 3.55 (br s, 1H), 3.32-3.18 (m, 2H), 2.92-2.84 (m, 2H), 1.80-1.71 (m, 2H), 1.48-1.42 (m, 2H).

Example 228

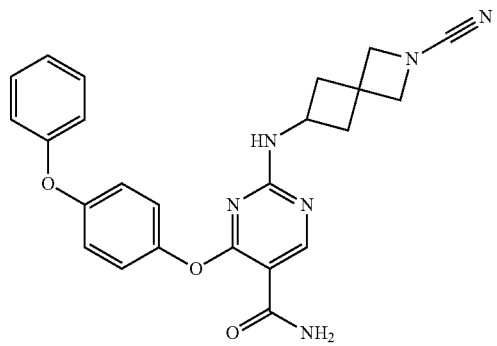 [SMILES: N#CN1CC2(CC(Nc3ncc(C(N)=O)c(Oc4ccc(Oc5ccccc5)cc4)n3)C2)C1]

2-[(2-cyano-2-azaspiro[3.3]heptan-6-yl]amino)-4-(4-phenoxyphenoxy)pyrimidine-5-carboxamide (242)

2-([2-cyano-2-azaspiro[3.3]heptan-6-yl]amino)-4-(4-phenoxyphenoxy)pyrimidine-5-carboxamide 17 mg (8%) was prepared from 2-methanesulfonyl-4-(4-phenoxyphenoxy)pyrimidine-5-carboxamide, tert-butyl 6-amino-2-azaspiro[3.3]heptane-2-carboxylate, HCl in MeOH (4N) and cyanogen bromide using method 19A, 19B, and 19C. HPLC: 99.0% purity. MS: m/z=443.1 [M+H]⁺. VT ¹H NMR (300 MHz, DMSO-d6, 353K, ppm): δ 8.64 (s, 1H), 7.55 (br s, 1H), 7.43-7.37 (m, 2H), 7.25-7.14 (m, 2H), 7.08-7.02 (m, 7H), 4.06-4.00 (m, 4H), 3.95 (m, 1H), 2.36 (br s, 2H), 2.11-2.09 (m, 2H).

Example 229

Scheme 20

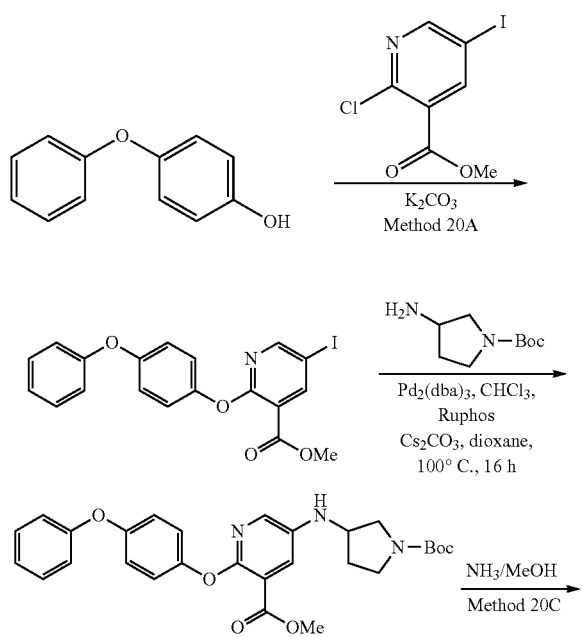

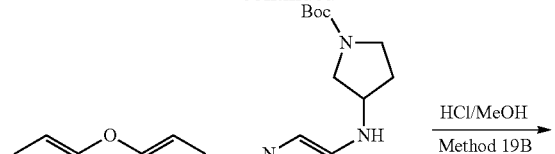

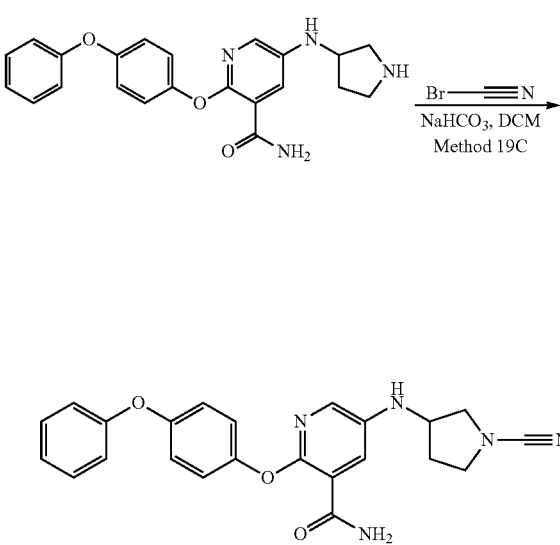

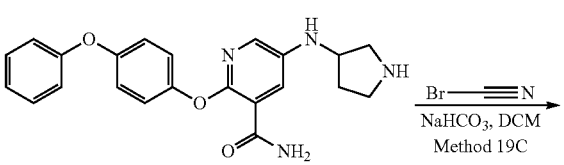

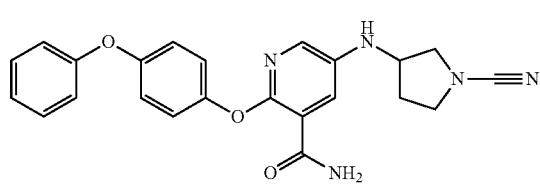

Method 20A

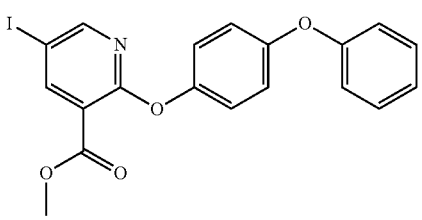 [SMILES: COC(=O)c1cc(I)cnc1Oc1ccc(Oc2ccccc2)cc1]

Methyl 5-iodo-2-(4-phenoxyphenoxy)pyridine-3-carboxylate

In a 250 mL round-bottom flask with magnetic stir bar, methyl 2-chloro-5-iodopyridine-3-carboxylate (5.00 g, 16.81 mmol, 1.00 eq.) was dissolved in N,N-dimethylformamide (100 mL) under N₂ atmosphere. To the stirring solution were added 4-phenoxyphenol (3.13 g, 16.81 mmol, 1.00 eq.) and potassium carbonate (4.65 g, 33.65 mmol, 2.00 eq.) at RT. The resulting mixture was stirred for 2 h at 90° C. Then the reaction mixture was cooled to RT and was quenched by 150 mL H₂O. Precipitation happened, and then the solids were collected by filtration and dried in an 100° C. oven under reduced pressure to afford 5 g (65%) of methyl 5-iodo-2-(4-phenoxyphenoxy)pyridine-3-carboxylate as a white solid.

Method 20 B

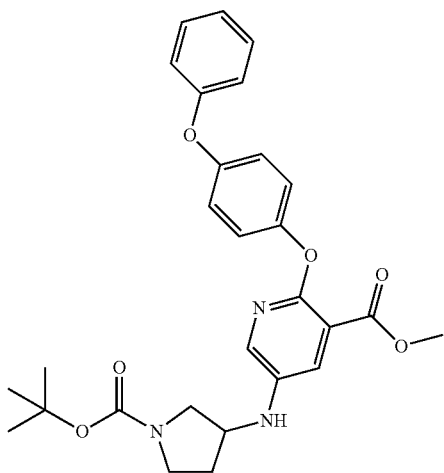 [SMILES: COC(=O)c1cc(NC2CCN(C(=O)OC(C)(C)C)C2)cnc1Oc1ccc(Oc2ccccc2)cc1]

Methyl 5-([1-[(tert-butoxy)carbonyl]pyrrolidin-3-yl]amino)-2-(4-phenoxyphenoxy)pyridine-3-carboxylate In a 25 mL round-bottom flask with magnetic stir bar, methyl 5-iodo-2-(4-phenoxyphenoxy)pyridine-3-carboxylate (447.00 mg, 1.00 mmol, 1.00 eq.) was dissolved in 5 mL dioxane. To the stirring solution were added tert-butyl 3-aminopyrrolidine-1-carboxylate (223.39 mg, 1.20 mmol, 1.20 eq.), Pd₂(dba)₃·CHCl₃ (51.73 mg, 0.05 mmol), RuPhos (46.64 mg, 0.10 mmol, 0.10 eq.) and Cs₂CO₃ (651.31 mg, 2.00 mmol, 2.00 eq.) under N₂ atmosphere at RT. The resulting mixture was degassed by N₂ flow for 5 min, and then stirred for 16 h at 90° C. The reaction mixture was diluted with 20 mL H₂O and extracted with ethyl acetate (3×10 mL). The organic layers were combined, dried over anhydrous sodium sulfate and concentrated under reduced pressure. The residue was purified in a silica gel column eluting with ethyl acetate in petroleum ether (5% to 30% gradient) to afford 70 mg (13%) of methyl 5-([1-[(tert-butoxy)carbonyl]pyrrolidin-3-yl]amino)-2-(4-phenoxyphenoxy)pyridine-3-carboxylate as brown oil.

Method 20C

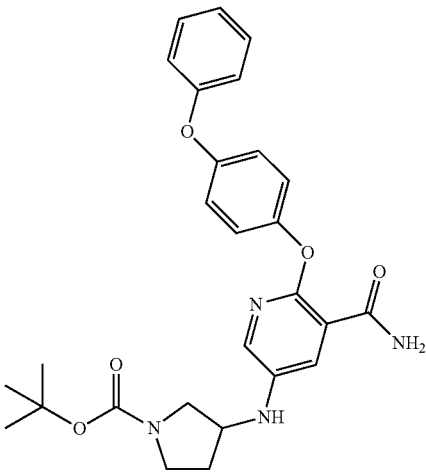 [SMILES: CC(C)(C)OC(=O)N1CCC(Nc2cnc(Oc3ccc(Oc4ccccc4)cc3)c(C(N)=O)c2)C1]

Tert-butyl 3-[[5-carbamoyl-6-(4-phenoxyphenoxy)pyridin-3-yl]amino]pyrrolidine-1-carboxylate In a 10-mL sealed tube with magnetic stir bar, methyl 5-([1-[(tert-butoxy)carbonyl]pyrrolidin-3-yl]amino)-2-(4-phenoxyphenoxy)pyridine-3-carboxylate (70 mg, 0.14 mmol, 1.00 eq.) was dissolved in a solution of NH₃ in methanol (10%, 2 mL) at RT. The resulting solution was then stirred for 16 h at 50° C. The reaction mixture was concentrated under reduced pressure to afford 55 mg (77%, crude yield) of tert-butyl 3-[[5-carbamoyl-6-(4-phenoxyphenoxy)pyridin-3-yl]amino]pyrrolidine-1-carboxylate as a yellow solid.

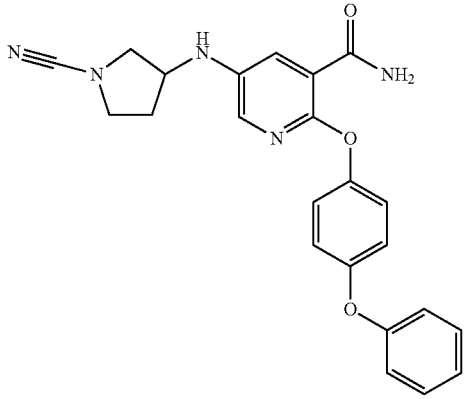 [SMILES: N#CN1CCC(Nc2cnc(Oc3ccc(Oc4ccccc4)cc3)c(C(N)=O)c2)C1]

5-[(1-cyanopyrrolidin-3-yl)amino]-2-(4-phenoxyphenoxy)pyridine-3-carboxamide (243)

5-[(1-cyanopyrrolidin-3-yl)amino]-2-(4-phenoxyphenoxy)pyridine-3-carboxamide 30 mg (65%) was prepared from tert-butyl 3-[[5-carbamoyl-6-(4-phenoxyphenoxy)pyridin-3-yl]amino]pyrrolidine-1-carboxylate, HCl in MeOH (4N) and cyanogen bromide using method 19B and 19C. HPLC: 99.4% purity. MS: m/z=416.1 [M+H]⁺. ¹H-NMR (400 MHz, DMSO-d6, ppm): δ 7.71-7.68 (m, 2H), 7.64 (s, 1H), 7.48-7.37 (m, 3H), 7.14-6.99 (m, 7H), 6.12 (d, J=6.6 Hz, 1H), 4.06-4.04 (m, 1H), 3.67-3.63 (m, 1H), 3.56-3.43 (m, 2H), 3.20-3.16 (m, 1H), 2.19-2.11 (m, 1H); 1.86-1.85 (m, 1H).

Example 230

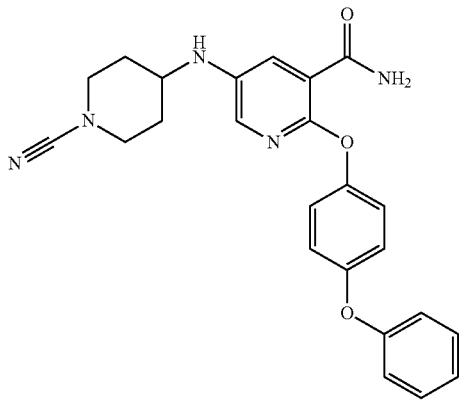 [SMILES: N#CN1CCC(Nc2cnc(Oc3ccc(Oc4ccccc4)cc3)c(C(N)=O)c2)CC1]

5-[(1-cyanopiperidin-4-yl)amino]-2-(4-phenoxyphenoxy)pyridine-3-carboxamide (246)

5-[(1-cyanopiperidin-4-yl)amino]-2-(4-phenoxyphenoxy) pyridine-3-carboxamide 30 mg (51%) was prepared from methyl 5-iodo-2-(4-phenoxyphenoxy)pyridine-3-carboxylate, tert-butyl 4-aminopiperidine-1-carboxylate, NH$_3$ in methanol (10%), HCl in MeOH (4N) and cyanogen bromide using method 20B, 20C, 19B, and 19C. HPLC: 99.4% purity. MS: m/z=430.2 [M+H]$^+$. $^1$H-NMR (400 MHz, DMSO-d6, ppm): δ 7.70-7.67 (m, 3H), 7.50 (m, 1H), 7.41-7.37 (m, 2H), 7.16-7.08 (m, 3H), 7.03-6.99 (m, 4H), 5.86 (d, J=6.6 Hz, 1H), 3.52-3.41 (m, 2H), 3.27-3.24 (m, 1H), 3.07-3.05 (m, 1H), 2.89-2.83 (m, 1H), 1.90-1.75 (m, 2H), 1.62-1.60 (m, 1H), 1.39-1.37 (m, 1H).

Example 231

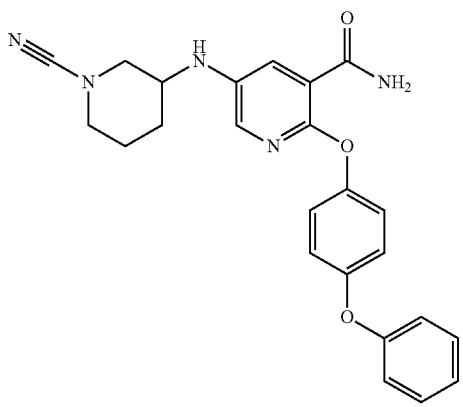 [SMILES: N#CN1CCCC(Nc2cnc(Oc3ccc(Oc4ccccc4)cc3)c(C(N)=O)c2)C1]

5-[(1-cyanopiperidin-3-yl)amino]-2-(4-phenoxyphenoxy)pyridine-3-carboxamide (247)

5-[(1-cyanopiperidin-3-yl)amino]-2-(4-phenoxyphenoxy) pyridine-3-carboxamide (20 mg) (62%) was prepared from methyl 5-iodo-2-(4-phenoxyphenoxy)pyridine-3-carboxylate, tert-butyl 3-aminopiperidine-1-carboxylate, NH$_3$ in methanol (10%), HCl in MeOH (4N) and cyanogen bromide using method 20B, 20C, 19B and 19C. HPLC: 99.8% purity. MS: m/z=430.2 [M+H]$^+$. $^1$H-NMR (400 MHz, DMSO-d6, ppm): δ 7.73-7.64 (m, 3H), 7.46-7.45 (m, 1H), 7.41-7.37 (m, 2H), 7.14-6.99 (m, 7H), 5.82 (d, J=6.6 Hz, 1H), 3.42-3.39 (m, 3H), 3.17-3.11 (m, 2H), 1.94-1.91 (m, 2H), 1.46-1.42 (m, 2H).

Example 232

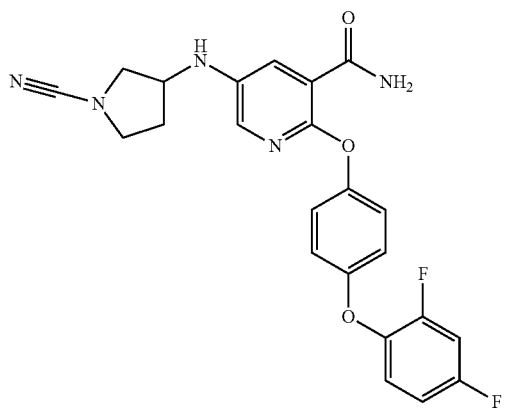 [SMILES: N#CN1CCC(Nc2cnc(Oc3ccc(Oc4ccc(F)cc4F)cc3)c(C(N)=O)c2)C1]

5-[(1-cyanopyrrolidin-3-yl)amino]-2-[4-(2,4-difluorophenoxy)phenoxy]pyridine-3-carboxamide (250)

5-[(1-cyanopyrrolidin-3-yl)amino]-2-[4-(2,4-difluorophenoxy)phenoxy]pyridine-3-carboxamide 20 mg (19%) was prepared from methyl 2-chloro-5-iodopyridine-3-carboxylate, 4-(2,4-difluorophenoxy)phenol, tert-butyl 3-aminopiperidine-1-carboxylate, NH3 in methanol (10%), HCl in MeOH (4N) and cyanogen bromide using method 20A, 20B, 20C, 19B and 19C. HPLC: 99.0% purity. MS: m/z=452.2 [M+H]$^+$. $^1$H-NMR (400 MHz, DMSO-d6, ppm): δ 7.69-7.67 (m, 2H), 7.61 (s, 1H), 7.51-7.45 (m, 2H), 7.27-7.25 (m, 1H), 7.16-7.13 (m, 1H), 7.08-7.05 (m, 2H), 6.99-6.95 (m, 2H), 6.11-6.10 (s, 1H), 4.03 (br s, 1H), 3.66-3.62 (m, 1H), 3.53-3.38 (m, 2H), 3.17-3.15 (m, 1H), 2.14-2.05 (m, 1H), 1.82-1.81 (m, 1H).

Example 233

Scheme 21

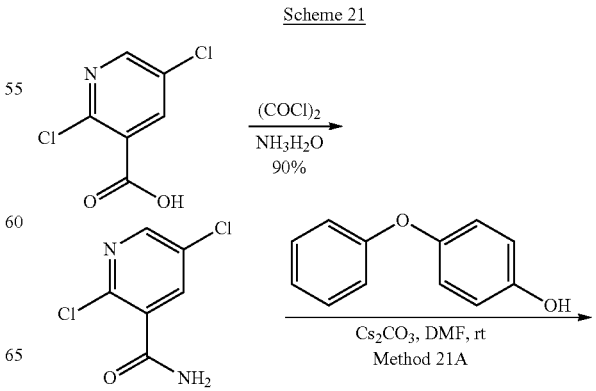

439

-continued

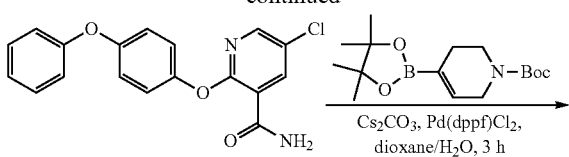

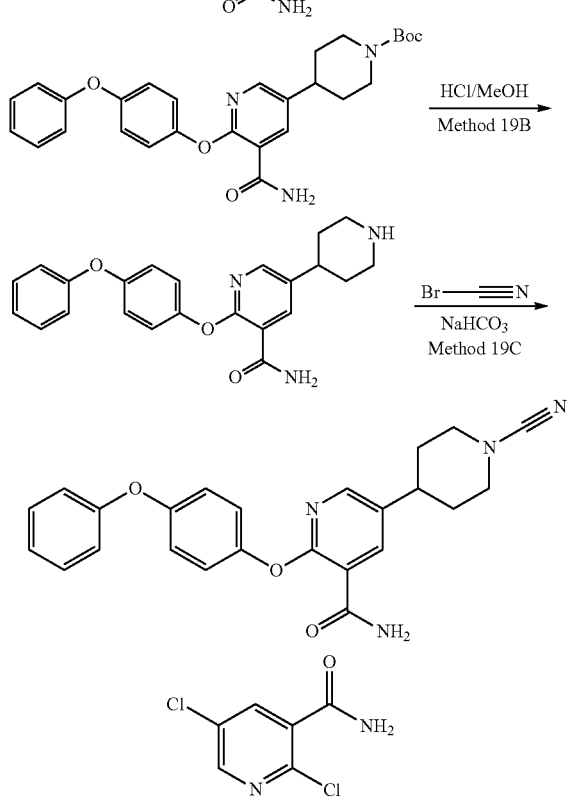

2,5-dichloropyridine-3-carboxamide

In a 250 mL round-bottom flask with magnetic stir bar, 2,5-dichloropyridine-3-carboxylic acid (10.00 g, 52.08 mmol, 1.00 eq.) was dissolved in 60 mL dichloromethane at 0° C. To the stirring solution was added a solution of oxalic dichloride (6.61 g, 52.08 mmol, 1.00 eq.) in N,N-dimethylformamide (0.56 mL) dropwise over 25 min period at 0° C. The resulting solution was stirred for 30 min at RT. The reaction mixture was then concentrated under reduced pressure to give the acid chloride intermediate.

The acid chloride prepared above was dissolved in dioxane (10 mL), which was added dropwise to 100 mL NH$_3$H$_2$O slowly at 0° C. The resulting mixture was then stirred for 10 min at 0° C. Precipitation happened, and then the solids were collected by filtration and The solid was dried in a IR dryer to give 9.6 g (94%) of 2,5-dichloropyridine-3-carboxamide as a off-white solid.

440

Method 21A

5-chloro-2-(4-phenoxyphenoxy)pyridine-3-carboxamide

In a 50-mL round-bottom flask with magnetic stir bar, 2,5-dichloropyridine-3-carboxamide (2.00 g, 10.47 mmol, 1.00 eq.) was dissolved in 10 mL N,N-dimethylformamide. To the stirring solution were added 4-phenoxyphenol (2.05 g, 11.01 mmol, 1.10 eq.) and Cs$_2$CO$_3$ (7.51 g, 23.05 mmol, 2.20 eq.). The resulting solution was stirred for 16 h at RT. The reaction mixture was then diluted with 5 mL H$_2$O and extracted with ethyl acetate (3×10 mL). The organic layers were combined, dried over anhydrous sodium sulfate and concentrated under reduced pressure. The residue was purified in a silica gel column eluting with ethyl acetate in petroleum ether (5% to 45% gradient) to yield 2.95 g (83%) of 5-chloro-2-(4-phenoxyphenoxy)pyridine-3-carboxamide as a white solid.

Method 21B

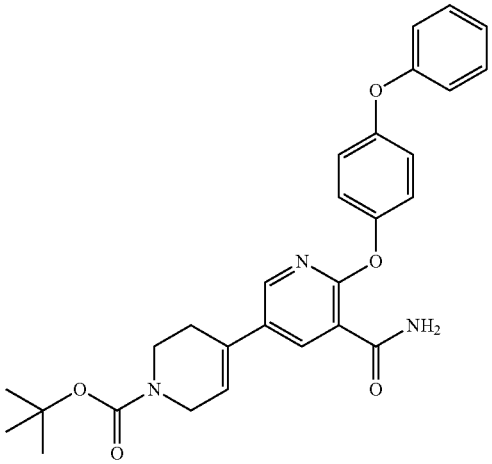 [SMILES: CC(C)(C)OC(=O)N1CC=C(c2cnc(Oc3ccc(Oc4ccccc4)cc3)c(C(N)=O)c2)CC1]

Tert-butyl 4-[5-carbamoyl-6-(4-phenoxyphenoxy)pyridin-3-yl]-1,2,3,6-tetrahydropyridine-1-carboxylate In a 30 mL microwave vial with magnetic stir bar, 5-chloro-2-(4-phenoxyphenoxy)pyridine-3-carboxamide (100.00 mg, 0.29 mmol, 1.00 eq.), tert-butyl 4-(tetramethyl-1,3,2-dioxaborolan-2-yl)-1,2,3,6-tetrahydropyridine-1-carboxylate (108.89 mg, 0.35 mmol, 1.20 eq.), Pd(dppf) Cl2CH$_2$Cl2 (23.97 mg, 0.03 mmol, 0.10 eq.) and Cs$_2$CO$_3$ (210.35 mg, 0.65 mmol, 2.20 eq.) were mixed in dioxane (2 mL) and water (0.2 mL). The resulting mixture was irradiated with microwave radiation for 3 h at 140° C. The reaction mixture was then diluted with 5 mL H₂O and extracted with ethyl acetate (3×10 mL). The organic layers were combined, dried over anhydrous sodium sulfate and concentrated under reduced pressure. The residue was purified in a silica gel column eluting with ethyl acetate in petroleum ether (5% to 45% gradient) to yield 105 mg (73%) of tert-butyl 4-[5-carbamoyl-6-(4-phenoxyphenoxy)pyridin-3-yl]-1,2,3,6-tetrahydropyridine-1-carboxylate as a light yellow solid.

Method 21C

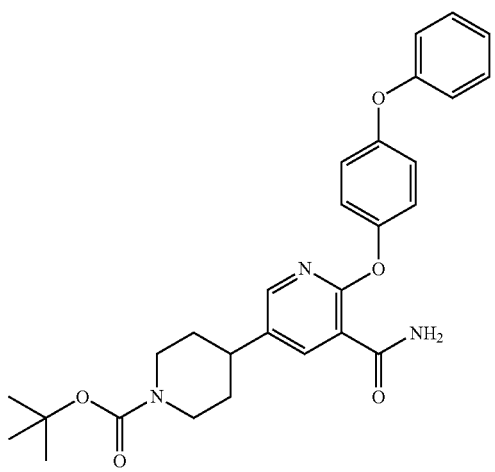 [SMILES: CC(C)(C)OC(=O)N1CCC(c2cnc(Oc3ccc(Oc4ccccc4)cc3)c(C(N)=O)c2)CC1]

Tert-butyl 4-[5-carbamoyl-6-(4-phenoxyphenoxy)pyridin-3-yl]piperidine-1-carboxylate In a 50-mL round-bottom flask with magnetic stir bar, tert-butyl 4-[5-carbamoyl-6-(4-phenoxyphenoxy)pyridin-3-yl]-1,2,3,6-tetrahydropyridine-1-carboxylate (623.00 mg, 1.28 mmol, 1.00 eq.) was dissolved in methanol (10 mL). To the stirring solution was added palladium on carbon (271.97 mg, 2.56 mmol, 2.00 eq.) under N₂ atmosphere. The round-bottom flask was then evacuated and charged with hydrogen. This procedure was repeated for 3 times. The reaction mixture was then stirred for 1.5 h at RT under H₂ atmosphere. The suspension was filtered through a Celite pad and the filtrate was concentrated under reduced pressure to yield 434 mg (69%, crude yield) of tert-butyl 4-[5-carbamoyl-6-(4-phenoxyphenoxy)pyridin-3-yl]piperidine-1-carboxylate as a white solid.

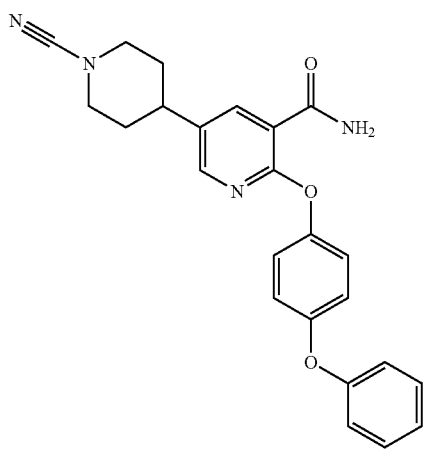 [SMILES: N#CN1CCC(c2cnc(Oc3ccc(Oc4ccccc4)cc3)c(C(N)=O)c2)CC1]

5-(1-cyanopiperidin-4-yl)-2-(4-phenoxyphenoxy)pyridine-3-carboxamide (244)

5-(1-cyanopiperidin-4-yl)-2-(4-phenoxyphenoxy)pyridine-3-carboxamide 30 mg (19%) was prepared from tert-butyl 4-[5-carbamoyl-6-(4-phenoxyphenoxy)pyridin-3-yl]piperidine-1-carboxylate, HCl in MeOH (4N) and cyanogen bromide using method 19B and 19C. HPLC: 99.4% purity. MS: m/z=415.0 [M+H]⁺. ¹H-NMR (300 MHz, DMSO-d6, ppm): δ 8.11-8.10 (m, 1H), 8.05-8.04 (m, 1H), 7.79-7.77 (m, 2H), 7.43-7.38 (t, J=7.8 Hz, 2H), 7.21-7.17 (m, 3H), 7.14-7.02 (m, 4H), 3.48-3.44 (m, 2H), 3.19-3.11 (m, 2H), 2.78 (m, 1H), 1.79-1.69 (m, 4H).

Example 234

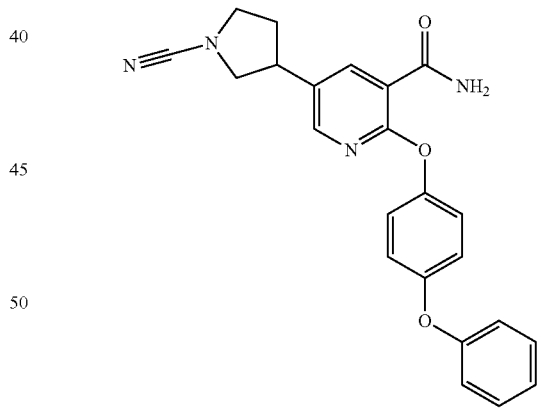

5-(1-cyanopyrrolidin-3-yl)-2-(4-phenoxyphenoxy)pyridine-3-carboxamide (245)

5-(1-cyanopyrrolidin-3-yl)-2-(4-phenoxyphenoxy)pyridine-3-carboxamide 25 mg (13%) was prepared from 5-chloro-2-(4-phenoxyphenoxy)pyridine-3-carboxamide, tert-butyl 3-(tetramethyl-1,3,2-dioxaborolan-2-yl)-2,5-dihydro-1H-pyrrole-1-carboxylate, Pd/C, HCl in MeOH (4N) and cyanogen bromide using method 21B, 21C, 19B and 19C. HPLC: 98.3% purity. MS: m/z=401.1 [M+H]⁺. ¹H-NMR (300 MHz, DMSO-d6, ppm): δ 8.15-8.09 (m, 2H), 7.80-7.78 (m, 2H), 7.43-7.38 (m, 2H), 7.21-7.14 (m, 3H), 7.12-7.02 (m, 4H), 3.79-3.74 (m, 5H), 2.25-2.22 (m, 1H), 2.03-1.99 (m, 1H).

Example 235

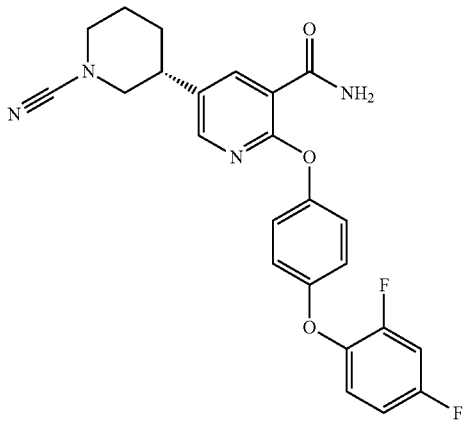 [SMILES: N#CN1CCC[C@H](c2cnc(Oc3ccc(Oc4ccc(F)cc4F)cc3)c(C(N)=O)c2)C1]

5-[(3R)-1-cyanopiperidin-3-yl]-2-[4-(2,4-difluorophenoxy)phenoxy]pyridine-3-carboxamide (248)

5-[(3R)-1-cyanopiperidin-3-yl]-2-[4-(2,4-difluorophenoxy)phenoxy]pyridine-3-carboxamide (20 mg, 13% overall yield was prepared from 2,5-dichloropyridine-3-carboxamide, 4-(2,4-difluorophenoxy)phenol, tert-butyl 5-(tetramethyl-1,3,2-dioxaborolan-2-yl)-1,2,3,6-tetrahydropyridine-1-carboxylate, Pd/C, HCl in MeOH (4N) and cyanogen bromide using method 21A, 21B, 21C, 19B and 19C. The racemic mixture was then was purified by chiral-HPLC to separate the enantiomers. HPLC: 98.6% purity. MS: m/z=451.1 [M+H]$^+$. $^1$H-NMR (300 MHz, DMSO-d6, ppm): δ 8.11-8.08 (m, 2H), 7.77 (m, 2H), 7.52-7.47 (m, 1H), 7.46-7.28 (m, 1H), 7.17-7.12 (m, 3H), 7.00-6.98 (m, 2H), 3.39-3.31 (m, 2H), 3.28-3.14 (m, 2H), 2.90-2.87 (m, 1H), 1.85-1.73 (m, 4H).

Example 236

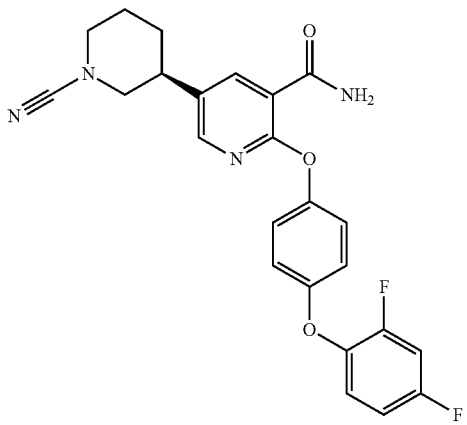 [SMILES: N#CN1CCC[C@@H](c2cnc(Oc3ccc(Oc4ccc(F)cc4F)cc3)c(C(N)=O)c2)C1]

5-[(3S)-1-cyanopiperidin-3-yl]-2-[4-(2,4-difluorophenoxy)phenoxy]pyridine-3-carboxamide (249)

5-[(3S)-1-cyanopiperidin-3-yl]-2-[4-(2,4-difluorophenoxy)phenoxy]pyridine-3-carboxamide (20 mg, 13% overall yield) was prepared from 2,5-dichloropyridine-3-carboxamide, 4-(2,4-difluorophenoxy)phenol, tert-butyl 5-(tetramethyl-1,3,2-dioxaborolan-2-yl)-1,2,3,6-tetrahydropyridine-1-carboxylate, Pd/C, HCl in MeOH (4N) and cyanogen bromide using method 21A, 21B, 21C, 19B and 19C. The racemic mixture was then was purified by chiral-HPLC to separate the enantiomers. PLC: 94.6% purity. MS: m/z=451.1 [M+H]$^+$. $^1$H-NMR (300 MHz, DMSO-d6, ppm): δ 8.12-8.09 (m, 2H), 7.78 (m, 2H), 7.50 (m, 1H), 7.32-7.31 (m, 1H), 7.18-7.15 (m, 3H), 7.01-6.99 (m, 2H), 3.38-3.29 (m, 2H), 3.14-3.12 (m, 2H), 2.91-2.85 (m, 1H), 1.85-1.80 (m, 1H), 1.75-1.60 (m, 3H).

Example 237

Assay A: BTK IC50 Enzyme Assay

The following describes a microfluidic, off-chip mobility shift kinase assay used to measure inherent potency of compounds against BTK enzyme. Compounds described by embodiments of the present invention were assayed using this protocol and the data from the same is recorded in Table 2 within the column labeled: "Time Dependent BTK Enzyme Assay IC$_{50}$". These IC$_{50}$ values are reported in ranges wherein: A<100 nM, B<1 uM, and C>1 uM.

2.5× stocks of full-length human BTK (08-080) from CarnaBio USA, Inc., Natick, Mass., 1.6×ATP and appropriate kinKDR peptide substrate (FITC-AHA-EEPLYWSF-PAKKK-NH2) were prepared in kinase reaction buffer consisting of 25 mM MgCl2, 0.015% Brij-35 (30%), 100 mM Hepes, pH 7.5, and 10 mM DTT.

5 uL of enzyme buffer and 7.5 uL of ATP/kinKDR peptide substrate mix were added to Matrix (#115304) 384-well, sterile, polypropylene plates (Thermo Fisher Scientific, Hudson, N.H.) with 125 nL of serially diluted compounds prepared in 100% DMSO, and incubated for 90 min. at 27 C. Following the incubation period, reactions were stopped by adding 60 uL stop buffer consisting of 100 mM Hepes, pH 7.5, 0.015% Brij-35 (30%), 0.277% Coating Reagent #3 (Caliper Life Sciences, Mountain View, Calif.), 5% DMSO. Stopped reactions were monitored at −2 PSI, −3000 V/−700 V in a LabChip 3000 plate reader from Caliper Life Sciences, a PerkinElmer Company (Hopkinton, Mass.), and the activity was measured by off-chip mobility shift assay measuring the charge/mass difference between substrate and product resulting from peptide phosphorilation. IC50 and efficacy were determined by plotting log [Inhibitor] vs. % Activity in GeneData Screener (Basel, Switzerland). Compounds described by embodiments of the present invention were assayed using this protocol and the data from the same is recorded in Table 2 within the column labeled: "Time Dependent PBMC BTK Enzyme Assay IC50." These IC50 values are reported in ranges wherein: A<100 nM, B<1 uM, and C>1 uM. I<1 uM and II>1 uM.

Assay B: Time Dependent PMBC IC50 Assay

Compounds described by embodiments of the present invention were assayed using a time dependent PMBC assay. The data from the same is recorded in Table 2 within the column labeled: "Time Dependent PBMC Assay IC50." These IC50 values are reported in ranges wherein: I<1 uM and II>1 uM.

Assay C: Time Dependent Human Whole Blood IC50 Assay

Compounds described by embodiments of the present invention were assayed using a human whole blood assay. The data from the same is recorded in Table 2 within the column labeled: "Time Dependent Human Whole Blood BTK Enzyme Assay IC$_{50}$". These IC$_{50}$ values are reported in ranges wherein: I<1 uM and II>1 uM.

The data is interpreted according to the following:

| Compound number | Assay A | Assay B | Assay C |
| --- | --- | --- | --- |
| 1 | ++++ | ++++ | +++ |
| 2 | +++ | | |
| 3 | ++++ | ++++ | ++++ |
| 4 | +++ | | |
| 5 | +++ | | |
| 6 | ++ | | |
| 7 | ++++ | ++++ | |
| 8 | ++++ | | |
| 9 | ++++ | ++++ | ++++ |
| 10 | ++++ | ++++ | |
| 11 | ++++ | ++++ | +++ |
| 12 | ++++ | ++++ | |
| 13 | ++++ | | |
| 14 | ++++ | ++++ | |
| 15 | ++++ | | |
| 16 | ++++ | ++++ | |
| 17 | ++++ | ++++ | |
| 18 | ++++ | ++++ | |
| 19 | ++++ | | |
| 20 | ++++ | ++++ | |
| 21 | ++++ | | |
| 22 | ++++ | ++++ | |
| 23 | ++++ | ++++ | +++ |
| 24 | ++++ | | |
| 25 | ++++ | | |
| 26 | ++++ | | |
| 27 | ++++ | | |
| 28 | ++++ | | |
| 29 | ++++ | | |
| 30 | ++++ | ++++ | |
| 31 | ++++ | +++ | |
| 32 | ++++ | | |
| 33 | ++++ | | |
| 34 | ++++ | | |
| 35 | ++++ | | |
| 36 | ++++ | | |
| 37 | ++++ | ++++ | +++ |
| 38 | ++++ | +++ | |
| 39 | ++++ | | |
| 40 | ++++ | +++ | |
| 41 | ++++ | | |
| 42 | ++++ | | |
| 43 | ++++ | | |
| 44 | ++++ | +++ | |
| 45 | ++++ | | +++ |
| 46 | ++++ | ++++ | ++ |
| 47 | ++++ | | |
| 48 | ++++ | | |
| 49 | ++++ | | |
| 50 | ++++ | | |
| 51 | ++++ | | |
| 52 | ++++ | | |
| 53 | ++++ | | |
| 54 | ++++ | | |
| 55 | ++++ | | |
| 56 | ++++ | | |
| 57 | ++++ | | |
| 58 | +++ | | |
| 59 | +++ | | |
| 60 | +++ | | |
| 61 | ++ | | |
| 62 | + | | |
| 63 | ++++ | | |
| 64 | ++++ | | |
| 65 | ++++ | ++++ | +++ |
| 66 | ++++ | | |
| 67 | ++++ | | |
| 68 | ++++ | ++++ | +++ |
| 69 | ++++ | ++++ | +++ |
| 70 | ++++ | | |
| 71 | ++++ | | |
| 72 | ++++ | ++++ | |
| 73 | ++++ | | |
| 74 | ++++ | | |
| 75 | ++++ | ++++ | |
| 76 | ++++ | | |
| 77 | ++++ | | |
| 78 | ++++ | | |
| 79 | ++++ | | |
| 80 | ++++ | | |
| 81 | ++++ | | |
| 82 | ++++ | | |
| 83 | ++++ | | |
| 84 | ++++ | | |
| 85 | +++ | | |
| 86 | +++ | | |
| 87 | +++ | | |
| 88 | +++ | | |
| 89 | +++ | | |
| 90 | +++ | | |
| 91 | +++ | | |
| 92 | +++ | | |
| 93 | +++ | | |
| 94 | +++ | | |
| 95 | +++ | | |
| 96 | ++ | | |
| 97 | ++ | | |
| 98 | ++ | | |
| 99 | ++ | | |
| 100 | + | | |
| 101 | + | | |
| 106 | ++++ | | |
| 107 | ++++ | | |
| 108 | ++++ | +++ | |
| 109 | ++++ | | |
| 110 | ++++ | | |
| 111 | ++++ | | |
| 112 | +++ | | |
| 113 | +++ | | |
| 114 | +++ | | |
| 115 | +++ | | |
| 116 | ++ | | |
| 117 | ++ | | |
| 123 | ++++ | | |
| 124 | ++++ | | |
| 125 | ++++ | | |
| 126 | ++++ | | |
| 127 | +++ | | |
| 132 | ++++ | | |
| 133 | ++ | | |
| 134 | ++++ | +++ | |
| 135 | ++ | | |
| 136 | ++ | | |
| 137 | + | | |
| 138 | + | | |
| 139 | ++++ | ++++ | ++++ |
| 140 | ++++ | | |
| 141 | +++ | | |
| 142 | +++ | | |
| 143 | +++ | | |
| 144 | +++ | | |
| 145 | ++ | | |
| 146 | + | | |
| 147 | ++++ | | |
| 148 | ++++ | | |
| 149 | ++++ | | |
| 150 | +++ | | |
| 151 | +++ | | |
| 152 | ++ | | |
| 153 | + | | |
| 154 | + | | |
| 155 | + | | |

| Compound number | Assay A | Assay B | Assay C |
|---|---|---|---|
| 156 | ++++ | | |
| 157 | ++++ | | |
| 158 | +++ | | |
| 159 | + | | |
| 160 | + | | |
| 161 | + | | |
| 162 | + | | |
| 163 | + | | |
| 164 | | | |
| 165 | + | | |
| 166 | + | | |
| 167 | ++ | | |
| 168 | ++ | | |
| 169 | ++ | | |
| 170 | + | | |
| 171 | + | | |
| 172 | + | | |
| 173 | ++++ | ++++ | |
| 174 | ++++ | ++++ | +++ |
| 175 | +++ | | |
| 176 | +++ | | |
| 177 | ++++ | + | |
| 178 | ++++ | | |
| 179 | ++++ | ++++ | |
| 180 | ++++ | ++++ | +++ |
| 181 | ++++ | | |
| 182 | ++ | | |
| 183 | +++ | | |
| 184 | ++ | | |
| 185 | ++++ | | |
| 186 | +++ | | |
| 187 | +++ | | |
| 188 | ++++ | ++++ | |
| 189 | ++++ | | |
| 190 | ++ | | |
| 191 | ++++ | + | |
| 192 | +++ | | |
| 193 | +++ | | |
| 194 | +++ | | |
| 195 | ++ | | |
| 196 | +++ | | |
| 197 | +++ | | |
| 198 | +++ | | |
| 199 | + | | |
| 200 | + | | |
| 201 | ++++ | | |
| 202 | ++ | | |
| 203 | +++ | | |
| 204 | ++ | | |
| 205 | ++++ | | |
| 206 | +++ | | |
| 208 | +++ | | |
| 209 | +++ | | |
| 210 | ++ | | |
| 211 | ++ | | |
| 212 | +++ | | |
| 213 | + | | |
| 214 | + | | |
| 215 | + | | |
| 216 | +++ | | |
| 217 | + | | |
| 218 | ++++ | | |
| 219 | +++ | | |
| 220 | ++ | | |
| 221 | + | | |
| 222 | + | | |
| 223 | +++ | | |
| 224 | +++ | | |
| 225 | ++++ | | |
| 226 | ++++ | | |
| 227 | +++ | + | |
| 228 | ++++ | | |
| 229 | ++ | | |
| 230 | ++ | | |
| 231 | ++ | | |
| 232 | ++ | | |
| 233 | +++ | | |
| 234 | ++ | | |
| 235 | + | | |
| 236 | ++++ | +++ | |
| 237 | ++ | | |
| 238 | +++ | | |
| 239 | ++ | | |
| 240 | +++ | | |
| 241 | ++++ | +++ | |
| 242 | + | | |
| 243 | +++ | | |
| 244 | ++ | | |
| 245 | ++ | | |
| 246 | + | | |
| 247 | ++ | | |
| 248 | ++ | | |
| 249 | + | | |
| 250 | ++ | | |
| 251 | +++ | | |
| 252 | ++++ | | |
| 253 | ++++ | | |

\+ >5 µm;
++ >1-5 µm;
+++ 0.1-1 µm;
++++ <0.1 µm.

Example 238

Pharmaceutical Preparations (A) Injection vials: A solution of 100 g of an active ingredient according to the invention and 5 g of disodium hydrogen phosphate in 3 l of bidistilled water is adjusted to pH 6.5 using 2 N hydrochloric acid, sterile filtered, transferred into injection vials, is lyophilized under sterile conditions and is sealed under sterile conditions. Each injection vial contains 5 mg of active ingredient.

(B) Suppositories: A mixture of 20 g of an active ingredient according to the invention is melted with 100 g of soy lecithin and 1400 g of cocoa butter, is poured into moulds and is allowed to cool. Each suppository contains 20 mg of active ingredient.

(C) Solution: A solution is prepared from 1 g of an active ingredient according to the invention, 9.38 g of $NaH_2PO_4.2H_2O$, 28.48 g of $Na_2HPO_4.12H_2O$ and 0.1 g of benzalkonium chloride in 940 ml of bidistilled water. The pH is adjusted to 6.8, and the solution is made up to 1 l and sterilized by irradiation. This solution could be used in the form of eye drops.

(D) Ointment: 500 mg of an active ingredient according to the invention is mixed with 99.5 g of Vaseline under aseptic conditions.

(E) Tablets: A mixture of 1 kg of an active ingredient according to the invention, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

(F) Coated tablets: Tablets are pressed analogously to Example E and subsequently are coated in a conventional manner with a coating of sucrose, potato starch, talc, tragacanth and dye.

(G) Capsules: 2 kg of an active ingredient according to the invention are introduced into hard gelatin capsules in a conventional manner in such a way that each capsule contains 20 mg of the active ingredient.

(H) Ampoules: A solution of 1 kg of an active ingredient according to the invention in 60 l of bidistilled water is sterile filtered, transferred into ampoules, is lyophilized under sterile conditions and is sealed under sterile conditions. Each ampoule contains 10 mg of active ingredient.

(I) Inhalation spray: 14 g of an active ingredient according to the invention are dissolved in 10 l of isotonic NaCl solution, and the solution is transferred into commercially available spray containers with a pump mechanism. The solution could be sprayed into the mouth or nose. One spray shot (about 0.1 ml) corresponds to a dose of about 0.14 mg.

While a number of embodiments of this invention are described herein, it is apparent that the basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A compound selected from the group consisting of

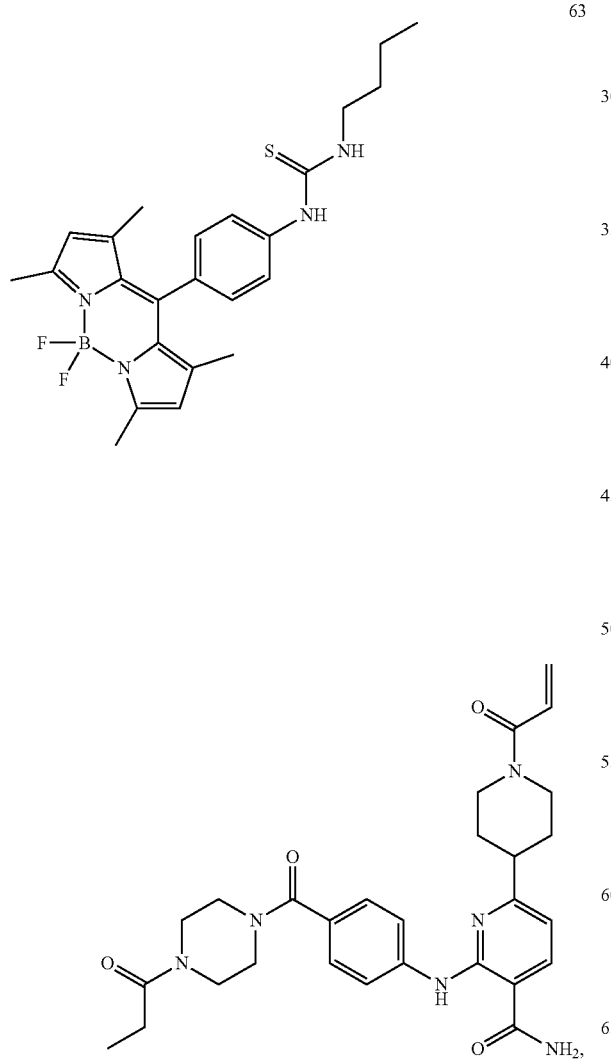

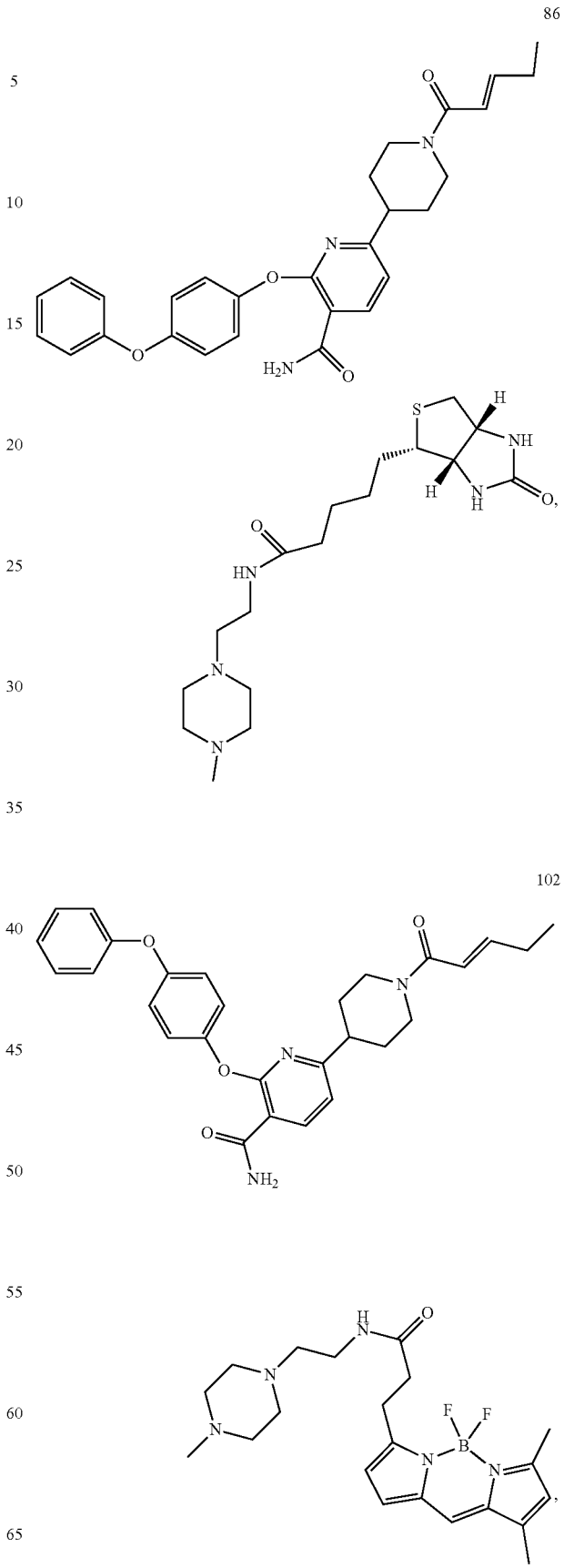

451
-continued

177

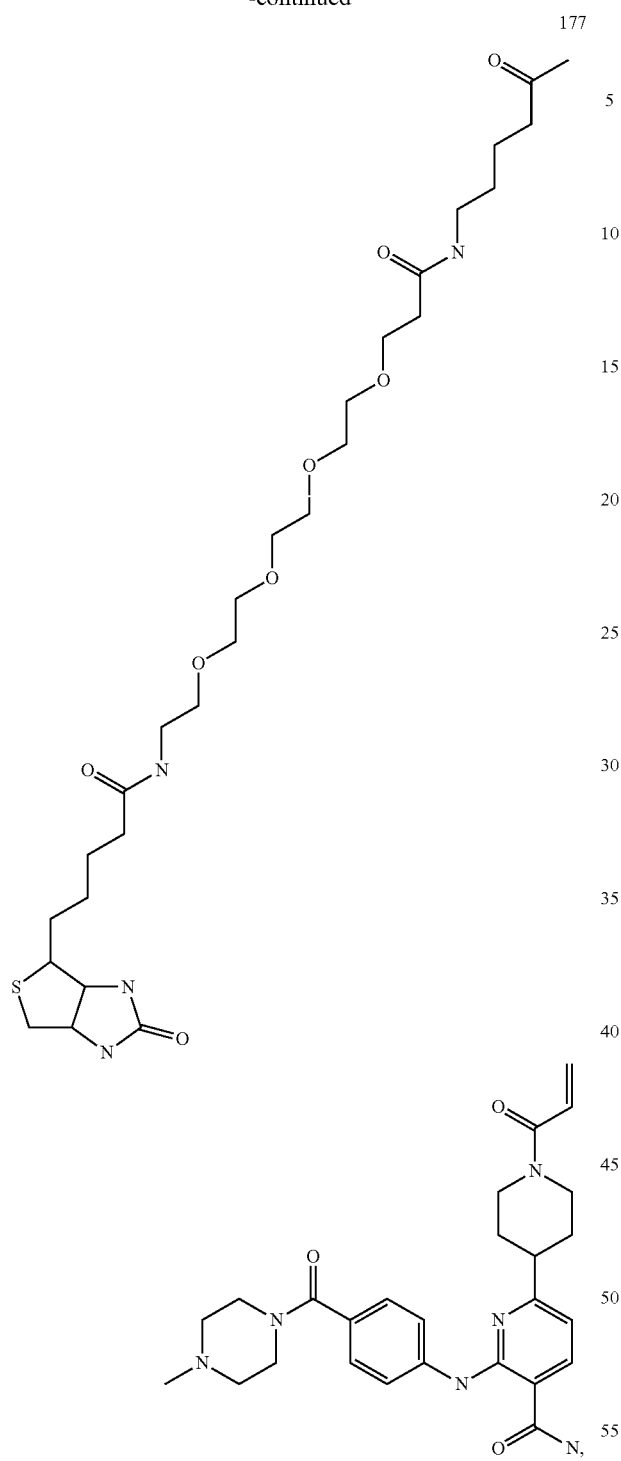

452
-continued

191

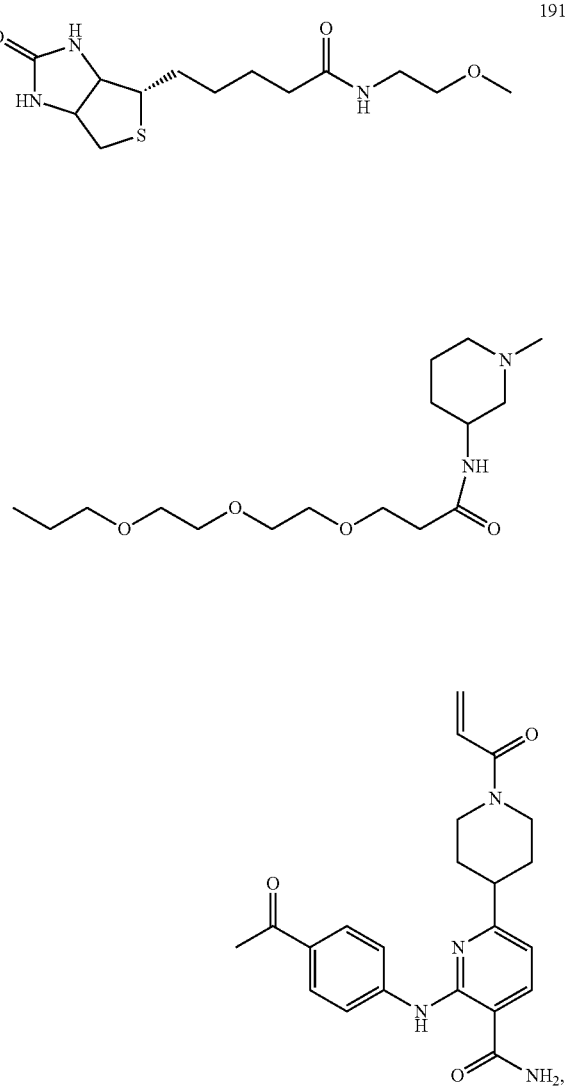

and
a pharmaceutically acceptable salt thereof.

2. A pharmaceutical composition, comprising:
a compound of claim 1, and
a pharmaceutically acceptable adjuvant, carrier, or vehicle.

3. A method for inhibiting BTK, or a mutant thereof, activity in a patient in need thereof or in a biological sample, comprising:
administering to said patient or contacting said biological sample with a compound of claim 1 or a physiologically acceptable salt thereof.

* * * * *

UNITED STATES PATENT AND TRADEMARK OFFICE
CERTIFICATE OF CORRECTION

PATENT NO. : 10,329,270 B2
APPLICATION NO. : 15/029420
DATED : June 25, 2019
INVENTOR(S) : Hui Qiu et al.

Page 1 of 3

It is certified that error appears in the above-identified patent and that said Letters Patent is hereby corrected as shown below:

In the Claims

Column 1 Lines 24-Column 2 Line 46. Claim 1 should be corrected as shown below:
1. A compound of the group consisting of:

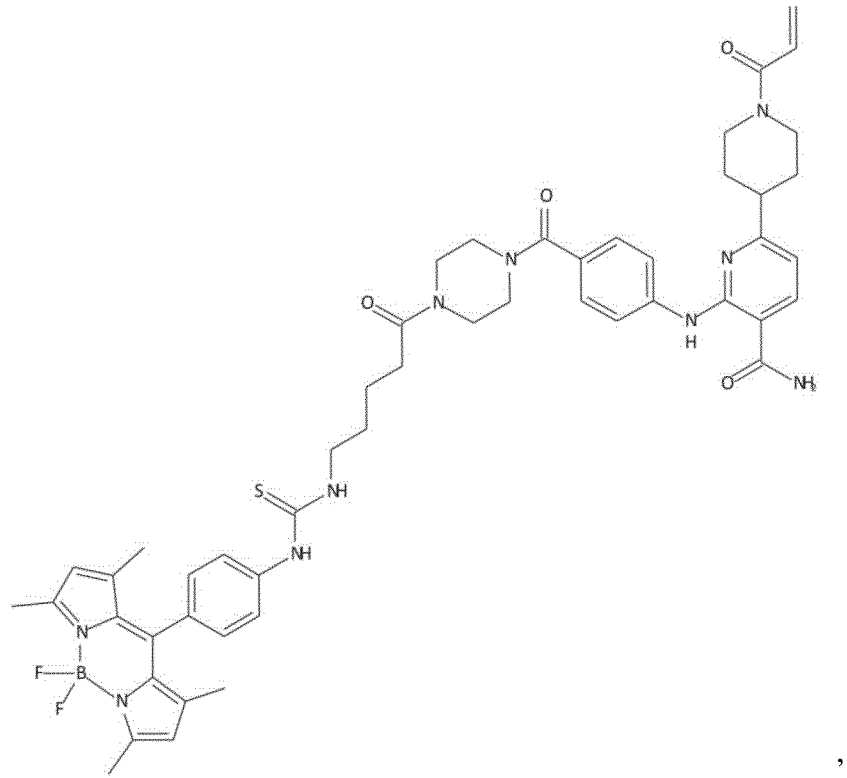

,

Signed and Sealed this
Nineteenth Day of November, 2019

Andrei Iancu
*Director of the United States Patent and Trademark Office*

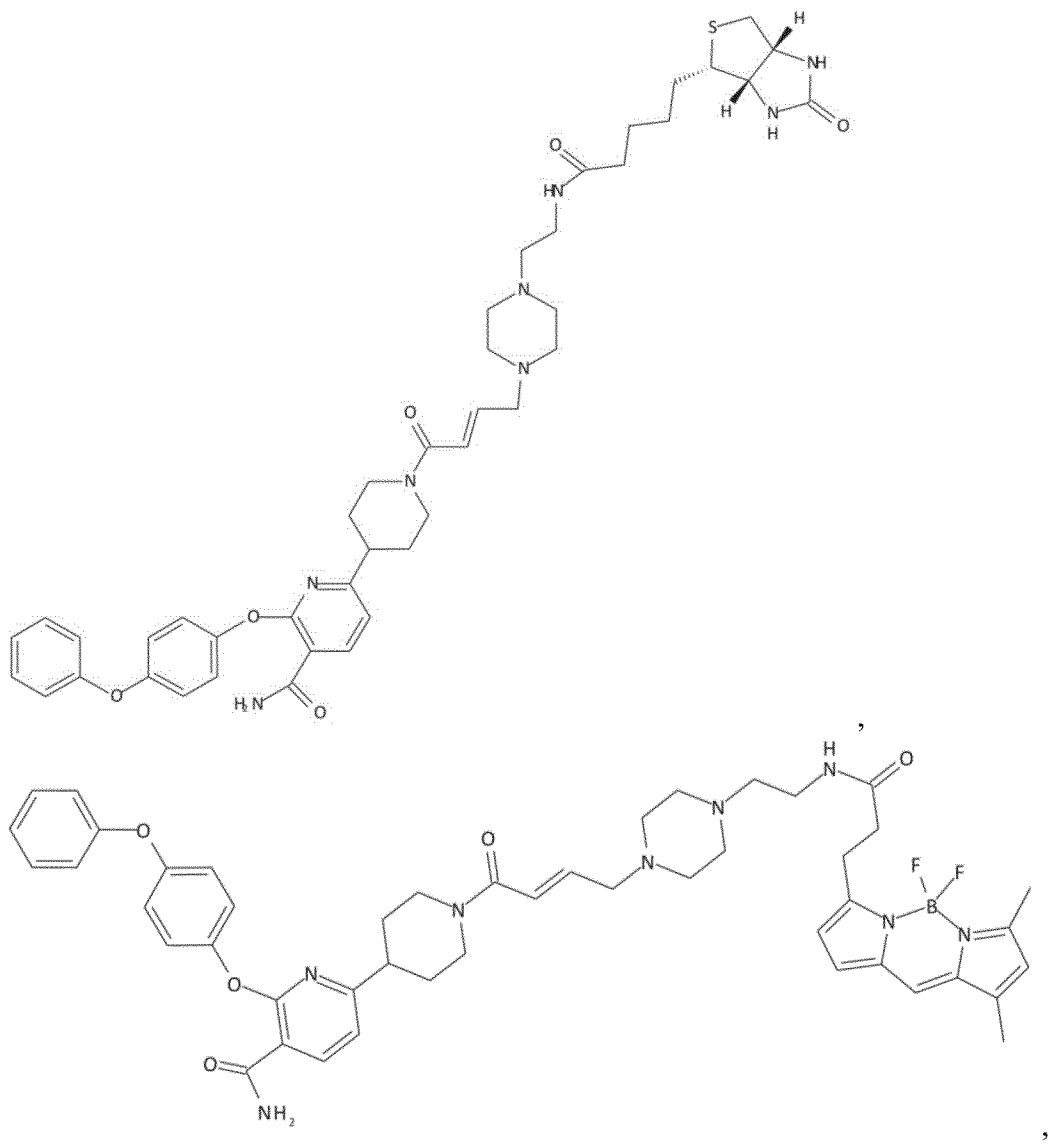

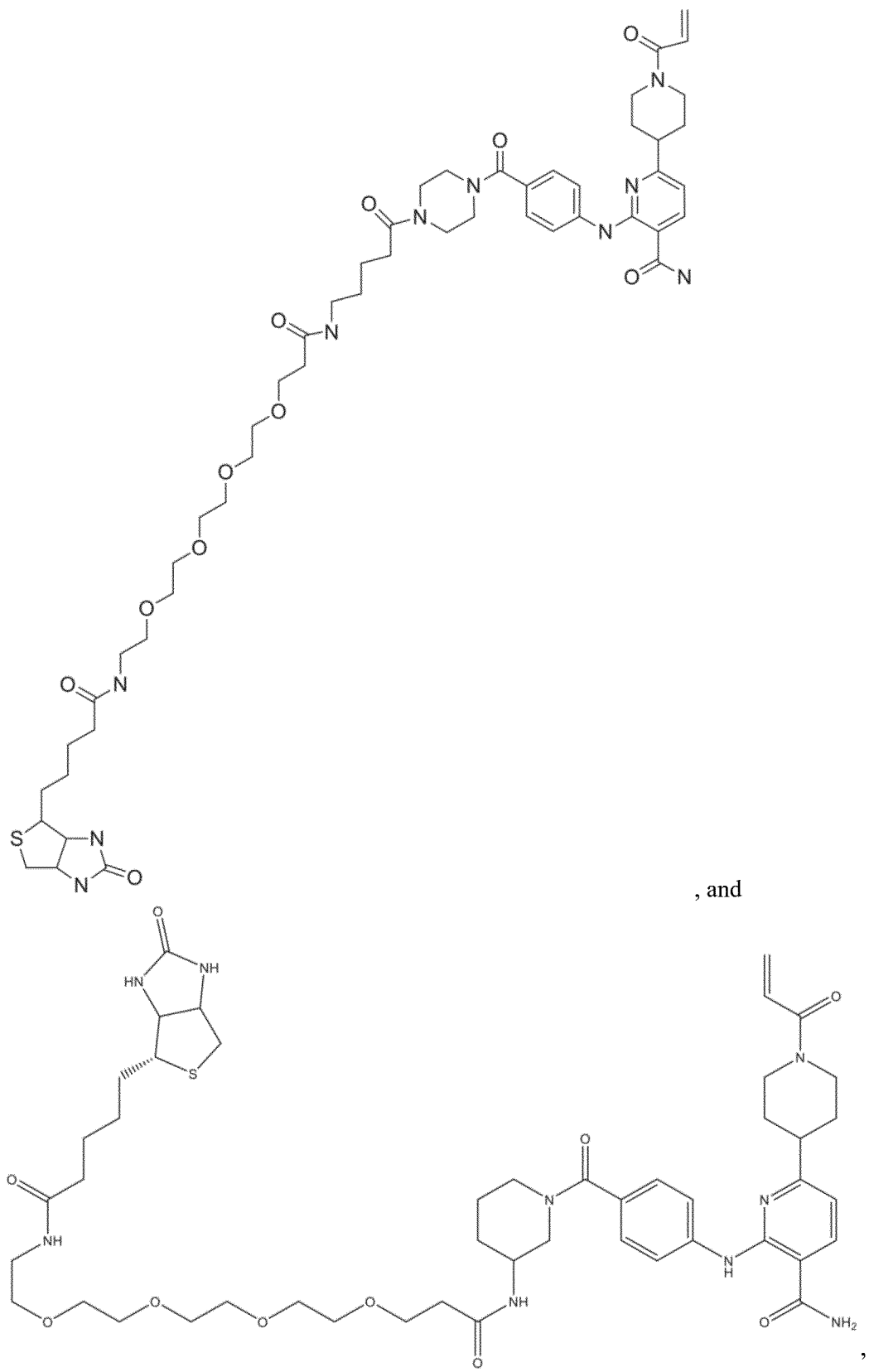
, and
or a pharmaceutically acceptable salt thereof.